US008524446B2

(12) United States Patent  (10) Patent No.: US 8,524,446 B2
Gao et al.  (45) Date of Patent: Sep. 3, 2013

(54) METHOD FOR DETECTING ADENO-ASSOCIATED VIRUS

(75) Inventors: Guangping Gao, West Borough, MA (US); James M Wilson, Glen Mills, PA (US); Mauricio R. Alvira, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/962,793

(22) Filed: Dec. 8, 2010

(65) Prior Publication Data

US 2011/0151434 A1    Jun. 23, 2011

Related U.S. Application Data

(63) Continuation of application No. 10/291,583, filed on Nov. 12, 2002, now abandoned.

(60) Provisional application No. 60/386,675, filed on Jun. 5, 2002, provisional application No. 60/377,066, filed on May 1, 2002, provisional application No. 60/341,117, filed on Dec. 17, 2001, provisional application No. 60/350,607, filed on Nov. 13, 2001.

(51) Int. Cl.
  *C12Q 1/70* (2006.01)
  *C12Q 1/68* (2006.01)
  *C07H 21/04* (2006.01)

(52) U.S. Cl.
  USPC ......... 435/5; 435/6.12; 536/23.72; 536/24.33

(58) Field of Classification Search
  None
  See application file for complete search history.

(56) References Cited

U.S. PATENT DOCUMENTS

| | | | |
|---|---|---|---|
| 5,412,073 A | 5/1995 | Kalsheker | |
| 5,866,552 A | 2/1999 | Wilson et al. | |
| 5,871,982 A | 2/1999 | Wilson et al. | |
| 6,039,942 A | 3/2000 | Lassen | |
| 6,156,303 A * | 12/2000 | Russell et al. | 424/93.2 |
| 6,251,677 B1 | 6/2001 | Wilson et al. | |
| 6,274,354 B1 | 8/2001 | Wilson et al. | |
| 6,312,957 B1 | 11/2001 | Einerhand et al. | |
| 6,365,394 B1 | 4/2002 | Gao et al. | |
| 6,376,237 B1 | 4/2002 | Colosi | |
| 6,387,368 B1 | 5/2002 | Wilson et al. | |
| 6,399,385 B1 | 6/2002 | Croyle et al. | |
| 6,428,988 B1 | 8/2002 | Wilson et al. | |
| 6,468,524 B1 | 10/2002 | Chiorini et al. | |
| 6,475,769 B1 | 11/2002 | Wilson et al. | |
| 6,482,634 B1 | 11/2002 | Wilson et al. | |
| 6,485,966 B2 | 11/2002 | Gao et al. | |
| 6,632,670 B1 | 10/2003 | Wadsworth et al. | |
| 6,759,237 B1 | 7/2004 | Wilson | |
| 6,943,019 B2 | 9/2005 | Wilson et al. | |
| 7,022,519 B2 | 4/2006 | Gao et al. | |
| 7,056,502 B2 | 6/2006 | Hildinger et al. | |
| 7,235,393 B2 | 6/2007 | Gao et al. | |
| 7,238,526 B2 | 7/2007 | Wilson et al. | |
| 7,282,199 B2 | 10/2007 | Gao et al. | |
| 7,790,449 B2 | 9/2010 | Gao et al. | |
| 2003/0138772 A1 | 7/2003 | Gao | |
| 2007/0036760 A1 | 2/2007 | Wilson | |
| 2008/0075740 A1 | 3/2008 | Gao | |
| 2009/0227030 A1 | 9/2009 | Gao | |

FOREIGN PATENT DOCUMENTS

| | | |
|---|---|---|
| CA | 2406745 | 1/2006 |
| EP | 1 310 571 A2 | 5/2003 |
| JP | 3958191 | 5/2007 |
| WO | WO 96/00587 A1 | 1/1996 |
| WO | WO 96/13598 A3 | 5/1996 |
| WO | WO 98/09657 A2 | 3/1998 |
| WO | WO 98/10086 A1 | 3/1998 |
| WO | WO 98/10088 A1 | 3/1998 |
| WO | WO 98/11244 A1 | 3/1998 |
| WO | WO 99/14354 A1 | 3/1999 |
| WO | WO 99/15677 A1 | 4/1999 |
| WO | WO 99/15685 A1 | 4/1999 |
| WO | WO 99/47691 A1 | 9/1999 |
| WO | WO 99/61601 A2 | 12/1999 |

(Continued)

OTHER PUBLICATIONS

"Minimal homology requirements for PCR primers," Sommer and Tautz, Nucleic Acids Research, 1989, vol. 17, No. 16, p. 6749.*
Bantel-Schaal, Human adeno-associated virus type 5 is only distantly related to other known primate helper-dependent parvoviruses, Journal of Virology, 73(2): 939-947, (Feb. 1999).
Calcedo et al, Serologic Characterization of Human and Non-Human Primate AAVs, Molecular Therapy, Abstract 102, 7(5):S41, (May 2003).
Chiorini et al, Cloning and Characterization of AAV5, Journal of Virology, 73(2):1309-1319, (Feb. 1999).
De et al, Therapeutic Levels for #945; 1-Antitrypsin Following Intrapleural Administration of a Non-Human Primate Serotype rh10 AAV Vector Expressing #945; 1-Antitrypsin, Abstract 338, 7th Annual Meeting of the American Society of Gene Therapy [Jun. 2-6, 2004] Minneapolis, Minnesota, (e-published May 2, 2004).
Forslund et al, A Broad Range of Human Papillomavirus Types Detected with a General PCR Method Suitable for Analysis of Cutaneous Tumours and Normal Skin, Journal of General Virology, 80(9):2437-2443, (Sep. 1999).

(Continued)

*Primary Examiner* — Bradley L Sisson
(74) *Attorney, Agent, or Firm* — Howson & Howson LLP; Cathy A. Kodroff

(57) ABSTRACT

A method for detecting and isolating AAV sequences in a sample of DNA obtained from tissue or cells is provided, which sample contains DNA and proviral AAV. The method involves subjecting the sample containing DNA to amplification via polymerase chain reaction (PCR) using a first set of primers which specifically amplify a first AAV region. The first AAV region is characterized by having at least 250 nucleotides of AAV capsid nucleic acid sequence, a variable sequence flanked by a sequence of at least 18 nucleotides at the 5' end of the first AAV region and a sequence of at least 18 nucleotides at the 3' end of the first AAV region. Each of the 5' and 3' at least 18 nucleotides is the same over at least 9 consecutive nucleotides relative to corresponding sequences in an alignment of at least two AAV serotypes. Each of the sets of primers consist of a 5' primer and a 3' primer. The method is further useful for identifying AAV sequences in the sample by the presence of amplified proviral AAV sequences.

9 Claims, 113 Drawing Sheets

(56) References Cited

FOREIGN PATENT DOCUMENTS

| WO | WO 00/28061 A3 | 5/2000 |
|---|---|---|
| WO | WO 00/75353 A1 | 12/2000 |
| WO | WO 01/14539 A | 3/2001 |
| WO | WO 01/23001 A2 | 4/2001 |
| WO | WO 01/23597 A3 | 4/2001 |
| WO | WO 01/40455 A3 | 6/2001 |
| WO | WO 01/68888 A | 9/2001 |
| WO | WO 01/70276 A2 | 9/2001 |
| WO | WO 01/83692 | 11/2001 |
| WO | WO 02/18659 A2 | 3/2002 |
| WO | WO 03/104392 A2 | 12/2003 |

OTHER PUBLICATIONS

Gao et al, Novel adeno-associated viruses from rhesus monkeys as vectors for human gene therapy, PNAS, 99(18):11854-11859, (Sep. 2002).

Gao et al, Clades of Adeno-Associated Viruses are Widely Disseminated in human Tissues, Journal of Virology, 78(12):6381-6388, (Jun. 2004).

Gao et al, Erythropoietin Gene Therapy leads to Autoimmune Anemia in Macaques, Blood, 103(9):3300-3302, (May 2004).

Gao et al, Adeno-Associated Viruses Undergo Substantial Evolution in Primates During Natural Infections, PNAS, 100(10): 6081-6086, (May 13, 2003).

Gao et al, Diversity of Latent AAV Genomes in Non-Human Primate and Human Tissues, Abstract 400, Molecular Therapy, 7(5): S158, (May 2003).

Gao et al, Autoimmune Anemia in Macaques Following Erythropoietin Gene Therapy, Abstract 341, 7th Annual Meeting of the American Society of Gene Therapy [Jun. 2-6, 2004] Minneapolis, Minnesota, (e-published May 2, 2004).

Herzog et al, Stable Gene Transfer and Expression of Human Blood Coagulation Factor IX After Intramuscular Injection of Recombinant Adeno- Associated Virus, Proc. Natl. Acad. USA, 94:5804-5807, (May 1997).

Kobinger et al, Pseudotyping HIV Vector with the Spike Envelope Protein of SARS-CoV for Studying Viral Tropism, Immunology and Gene Therapy Applications, Abstract 368, 7th Annual Meeting of The American Society of Gene Therapy [Jun. 2-6, 2004] Minneapolis, Minnesota, (e-published May 2, 2004).

Lebherz et al, Gene Therapy with Novel Adeno-Associated Virus Vectors Substantially Diminishes Atherosclerosis in a Murine Model of Familial Hypercholesterolemia, The Journal of Gene Medicine, 6(6):663-672, (Jun. 2004).

Limberis et al, A Novel AAV Vector for the Treatment of Cystic Fibrosis Airway Disease, Abstract 692, 7th Annual Meeting of the American Society of Gene Therapy [Jun. 2-6, 2004] Minneapolis, Minnesota, (e-published May 2, 2004).

Lu et al, Analysis of Homologous Recombination Between Different AAV Genomes in In Vitro co-Infections, Abstract 38, Molecular Therapy, 7(5): S15, (May 2003).

Mori et al, Two Novel Adeno-Associated Viruses from Cynomolgus Monkey: Pseudotyping Characterization of Capsid Protein, Virology, 330(2):375-383, (Dec. 20, 2004).

Mountz et al, Monkey See, Monkey Do, Gene Therapy, 10(3):194-196, (Feb. 2003).

Nucleic Acids Research, vol. 22, No. 15, Aug. 11, 1994, advertisement by Research Genetics for "Designer PCR".

Price et al, Targeted Gene Transfer to Lung Airway Epithelium Using Plasmid or Adenoviral Vectors Formulated with an Anti-Inflammatory Dexamathasone-Spermine conjugate, Abstract 498, 7th Annual Meeting of The American Society of Gene Therapy [Jun. 2-6, 2004] Minneapolis, Minnesota, (e-published May 2, 2004).

Rick et al, Congenital Bleeding Disorders, American Society of Hematology, pp. 559-574, (2003).

Rutledge et al, Infectious clones and vectors derived from adeno-associated virus (AAV) serotypes other than AAV type 2, Journal of Virology, 72(1):309-319, (Jan. 1998).

Sanmiguel et al, Real-time PCR as an Analytic Tool in Gene Therapy, Abstract 913, 7(5): 5352, (May 2003).

Tal J., Adeno-Associated Virus-Based Vectors in Gene Therapy, Journal of Biomedical Science, 7(4):279-291, (Jul. 2000).

Tobiasch, Discrimination Between Different Types of Human Adeno-Associated Viruses in Clinical Samples by PCR, Journal of Virological Methods, 71(1):17-25, (Mar. 1998).

Vandenberghe et al, Structure-Function Relationship of the Novel Non-Human Primate Adeno-associated Viruses, Abstract 99, Molecular Therapy, 7(5):S15, (May 2003).

Vandenberghe et al, AAV Clades: Their Ability to Recombine and Cross Species-Barriers, Abstract 88, 7th Annual Meeting of The American Society of Gene Therapy [Jun. 2-6, 2004] Minneapolis, Minnesota, (e-published May 2, 2004).

Wang et al, Production of AAV Vectors with Different Serotypes, Abstract 906, Molecular Therapy, 7(5):S350, (May 2003).

Xiao et al, Gene Therapy Vectors based on Adeno-Associated Virus Type 1, Journal of Virology, 73(5):3994-4003, (May 1999).

Xiao et al, Production of High-titer Recombinant Adeno-Associated Virus Vectors in the Absence of Helper Adenovirus, 72(3):2224-2232, (Mar. 1998).

Zhou et al, Direct Rescue and Cloning of Infectious Novel AAV Genomes From Non-Human Primate Tissues, Abstract 907, Molecular Therapy, 7(5):S350, (May 2003).

Zhou et al, Evaluation of Novel Gene Transfer Vectors Derived from Infectious Molecular Clones of Primate AAVs, Abstract 90, 7th Annual Meeting of the American Society of Gene Therapy [Jun. 2-6, 2004] Minneapolis, Minnesota, (e-published May 2, 2004).

Examination Report dated Feb. 11, 2009 issued in corresponding Indian patent application No. 1155/DELNP/2004.

Agent's correspondence dated Oct. 31, 2008 transmitting results of official action in corresponding Mexican patent application No. 04.055711 with confidential information redacted.

Office Action dated Aug. 11, 2003 issued in corresponding Canadian patent application No. 2,406,745.

Office Action dated Oct. 6, 2004 issued in corresponding Canadian patent application No. 2,406,745.

Office Action dated Oct. 26, 2010 issued in corresponding Korean patent application No. 10-2004-7007245.

Office Action dated Oct. 27, 2006 issued in corresponding Australian patent application No. 2002361573.

Office action dated Feb. 14, 2006 issued in corresponding Japanese patent application No. 328852/02, with confidential agent comments redacted.

Communication dated Dec. 30, 2003 issued in corresponding EP patent application No. 02257826.4.

Office Action dated Dec. 22, 2005 issued in parent U.S. Appl. No. 10/291,583.

Applicants' response filed May 15, 2006 to Office Action dated Dec. 22, 2005 issued in parent U.S. Appl. No. 10/291,583.

Office Action dated Feb. 16, 2007 issued in parent U.S. Appl. No. 10/291,583.

Applicants' response filed May 3, 2007 to Office Action dated Feb. 16, 2007 issued in parent U.S. Appl. No. 10/291,583.

Office Action dated Jun. 11, 2007 issued in parent U.S. Appl. No. 10/291,583.

Applicants' response filed Aug. 10, 2007 to Office Action dated Jun. 11, 2007 issued in parent U.S. Appl. No. 10/291,583.

Office Action dated Feb. 6, 2008 issued in parent U.S. Appl. No. 10/291,583.

Applicants' response filed Apr. 7, 2008 to Office Action dated Feb. 6, 2008 issued in parent U.S. Appl. No. 10/291,583.

Office Action dated May 1, 2008 issued in parent U.S. Appl. No. 10/291,583.

Applicants' response filed Sep. 29, 2008 to Office Action dated May 1, 2008 issued in parent U.S. Appl. No. 10/291,583.

Office Action dated Apr. 15, 2009 issued in parent U.S. Appl. No. 10/291,583.

Applicants' response filed Jul. 15, 2009 to Office Action dated Apr. 15, 2009 issued in parent U.S. Appl. No. 10/291,583.

Applicants' response filed Aug. 14, 2009 to Office Action dated Apr. 15, 2009 issued in parent U.S. Appl. No. 10/291,583.

Office Action dated Sep. 18, 2009 issued in parent U.S. Appl. No. 10/291,583.

Applicants' response filed Mar. 17, 2010 to Office Action dated Sep. 18, 2009 issued in parent U.S. Appl. No. 10/291,583.

Office Action dated Jun. 8, 2010 issued in parent U.S. Appl. No. 10/291,583.

* cited by examiner

FIG. 1A

```
               1                                                           50
    42_2      ..........  ..........  ..........  ..........  ..........
    42_8      ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
    42_4      ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      ..........  ..........  ..........  ..........  ..........
    43_1      ..........  ..........  ..........  ..........  ..........
    43_5      ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
    44_1      ..........  ..........  ..........  ..........  ..........
    44_5      ..........  ..........  ..........  ..........  ..........
  223_10      ..........  ..........  ..........  ..........  ..........
   223_2      ..........  ..........  ..........  ..........  ..........
   223_4      ..........  ..........  ..........  ..........  ..........
   223_5      ..........  ..........  ..........  ..........  ..........
   223_6      ..........  ..........  ..........  ..........  ..........
   223_7      ..........  ..........  ..........  ..........  ..........
    A3_4      ..........  ..........  ..........  ..........  ..........
    A3_5      ..........  ..........  ..........  ..........  ..........
    A3_7      ..........  ..........  ..........  ..........  ..........
    A3_3      ..........  ..........  ..........  ..........  ..........
   42_12      ..........  ..........  ..........  ..........  ..........
    AAV1      TTGCCCACTC  CCTCTCTGCG  CGCTCGCTCG  CTCGGTGGGG  CCTGCGGACC
    AAV2      TTGGCCACTC  CCTCTCTGCG  CGCTCGCTCG  CTCACTGAGG  CCGGGCGACC
    AAV3      TTGGCCACTC  CCTCTATGCG  CACTCGCTCG  CTCGGTGGGG  CCTGGCGACC
    AAV8      ..........  ..........  ..........  ..........  ..........
    AAV9      ..........  ..........  ..........  ..........  ..........
    AAV7      TTGGCCACTC  CCTCTATGCG  CGCTCGCTCG  CTCGGTGGGG  CCTGCGGACC
    44_2      ..........  ..........  ..........  ..........  ..........
```

FIG. 1C

```
                        101
Rep binding site                                                                        150
                              ┌──────────────  TRS
      42_2    ..........│.....│.....  ..........  ..........  ..........
      42_8    ..........│.....│.....  ..........  ..........  ..........
      42_15   ..........  ..........  ..........  ..........  ..........
      42_5b   ..........  ..........  ..........  ..........  ..........
      42_1b   ..........  ..........  ..........  ..........  ..........
      42_13   ..........  ..........  ..........  ..........  ..........
      42_3a   ..........  ..........  ..........  ..........  ..........
      42_4    ..........  ..........  ..........  ..........  ..........
      42_5a   ..........  ..........  ..........  ..........  ..........
      42_10   ..........  ..........  ..........  ..........  ..........
      42_3b   ..........  ..........  ..........  ..........  ..........
      42_11   ..........  ..........  ..........  ..........  ..........
      42_6b   ..........  ..........  ..........  ..........  ..........
      43_1    ..........  ..........  ..........  ..........  ..........
      43_5    ..........  ..........  ..........  ..........  ..........
      43_12   ..........  ..........  ..........  ..........  ..........
      43_20   ..........  ..........  ..........  ..........  ..........
      43_21   ..........  ..........  ..........  ..........  ..........
      43_23   ..........  ..........  ..........  ..........  ..........
      43_25   ..........  ..........  ..........  ..........  ..........
      44_1    ..........  ..........  ..........  ..........  ..........
      44_5    ..........  ..........  ..........  ..........  ..........
     223_10   ..........  ..........  ..........  ..........  ..........
     223_2    ..........  ..........  ..........  ..........  ..........
     223_4    ..........  ..........  ..........  ..........  ..........
     223_5    ..........  ..........  ..........  ..........  ..........
     223_6    ..........  ..........  ..........  ..........  ..........
     223_7    ..........  ..........  ..........  ..........  ..........
      A3_4    ..........  ..........  ..........  ..........  ..........
      A3_5    ..........  ..........  ..........  ..........  ..........
      A3_7    ..........  ..........  ..........  ..........  ..........
      A3_3    ..........  ..........  ..........  ..........  ..........
      42_12   ..........  ..........  ..........  ..........  ..........
      AAV1    GAGCGCGCAG  AGAGGGAGTG  GGCAACTCCA  TCACTAGGGG  TAATCGCGAA
      AAV2    GAGCGCGCAG  AGAGGGAGTG  GCCAACTCCA  TCACTAGGGG  TTC.......
      AAV3    GAGTGCGCAT  AGAGGGAGTG  GCCAACTCCA  TCACTAGAGG  T.........
      AAV8    .......CAG  AGAGGGAGTG  GCCAACTCCA  TCACTAGGGG  TAG.CGCGAA
      AAV9    .......CAG  AGAGGGAGTG  GCCAACTCCA  TCACTAGGGG  TAATCGCGAA
      AAV7    GAGCGCGCAT  AGAGGGAGTG  GCCAACTCCA  TCACTAGGGG  TA.CCGCGAA
      44_2    ..........│.....│.....  ..........  ..........  ..........
 ←Rep binding site                  TRS
```

FIG. 1D

```
          151                                                      200
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   GCGCCTCCCA  CGCTGCCGCG  TCAGCGCTGA  CGTAAATTAC  GTCATAGGGG
   AAV2   .......CTG  GAGGGGTGGA  GTCGTGACGT  GAATTACGTC  ATAGGGTTAG
   AAV3   .......ATG  GCAGTGACGT  AACGCGAAGC  GCGCGAAGCG  AGACCACGCC
   AAV8   GCGCCTCCCA  CGCTGCCGCG  TCAGCGCTGA  CGTAAATTAC  GTCATAGGGG
   AAV9   GCGCCTCCCA  CGCTGCCGCG  TCAGCGCTGA  CGTAGATTAC  GTCATAGGGG
   AAV7   GCGCCTCCCA  CGCTGCCGCG  TCAGCGCTGA  CGTAAATCAC  GTCATAGGGG
   44_2   ..........  ..........  ..........  ..........  ..........
```

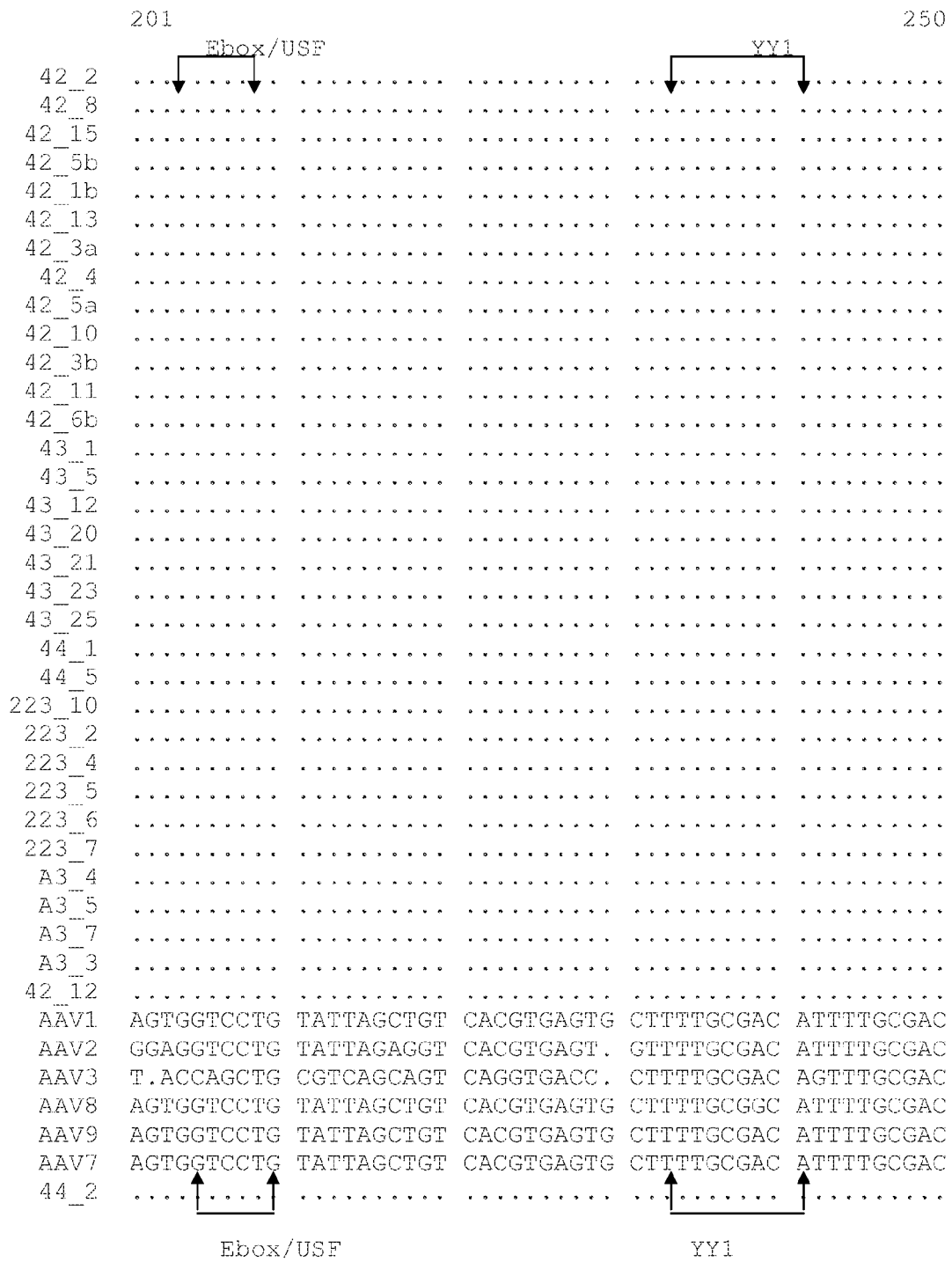

FIG. 1F 251                                                                              300

P5/TATA

42_2    ..........  .....↓....  ....↓.....  ..........  ....↓.....
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    ACCACGTGGC  CATTTAGGGT  ATATATGGCC  GAGTGAGC.G  AGCAGGATCT
AAV2    ACCATGTGGT  CACGCTGGGT  ATTTAAGCCC  GAGTGAGC.A  CGCAGGGTCT
AAV3    ACCACGTGGC  CGCTGAGGGT  ATATATTCTC  GAGTGAGCGA  ACCAGGAGCT
AAV8    ACCACGTGGC  CATTTGAGGT  ATATATGGCC  GAGTGAGC.G  AGCAGGATCT
AAV9    ACCACATGGC  CATTTGAGGT  ATATATGGCC  GAGTGAGC.G  AGCAGGATCT
AAV7    ACCACGTGGC  CATTTGAGGT  ATATATGGCC  GAGTGAGC.G  AGCAGGATCT
44_2    ..........  .....↑..↑.  ..........  ..........  ....↑.....
                         P5/TATA

FIG. 1H

```
              351                                                        400
  42_2        ..........  ..........  ..........  ..........  ..........
  42_8        ..........  ..........  ..........  ..........  ..........
  42_15       ..........  ..........  ..........  ..........  ..........
  42_5b       ..........  ..........  ..........  ..........  ..........
  42_1b       ..........  ..........  ..........  ..........  ..........
  42_13       ..........  ..........  ..........  ..........  ..........
  42_3a       ..........  ..........  ..........  ..........  ..........
  42_4        ..........  ..........  ..........  ..........  ..........
  42_5a       ..........  ..........  ..........  ..........  ..........
  42_10       ..........  ..........  ..........  ..........  ..........
  42_3b       ..........  ..........  ..........  ..........  ..........
  42_11       ..........  ..........  ..........  ..........  ..........
  42_6b       ..........  ..........  ..........  ..........  ..........
  43_1        ..........  ..........  ..........  ..........  ..........
  43_5        ..........  ..........  ..........  ..........  ..........
  43_12       ..........  ..........  ..........  ..........  ..........
  43_20       ..........  ..........  ..........  ..........  ..........
  43_21       ..........  ..........  ..........  ..........  ..........
  43_23       ..........  ..........  ..........  ..........  ..........
  43_25       ..........  ..........  ..........  ..........  ..........
  44_1        ..........  ..........  ..........  ..........  ..........
  44_5        ..........  ..........  ..........  ..........  ..........
 223_10       ..........  ..........  ..........  ..........  ..........
 223_2        ..........  ..........  ..........  ..........  ..........
 223_4        ..........  ..........  ..........  ..........  ..........
 223_5        ..........  ..........  ..........  ..........  ..........
 223_6        ..........  ..........  ..........  ..........  ..........
 223_7        ..........  ..........  ..........  ..........  ..........
  A3_4        ..........  ..........  ..........  ..........  ..........
  A3_5        ..........  ..........  ..........  ..........  ..........
  A3_7        ..........  ..........  ..........  ..........  ..........
  A3_3        ..........  ..........  ..........  ..........  ..........
  42_12       ..........  ..........  ..........  ..........  ..........
  AAV1        CGAGATCGTG  ATCAAGGTGC  CGAGCGACCT  GGACGAGCAC  CTGCCGGGCA
  AAV2        CGAGATTGTG  ATTAAGGTCC  CCAGCGACCT  TGACGGGCAT  CTGCCCGGCA
  AAV3        CGAGATTGTC  CTGAAGGTCC  CGAGTGACCT  GGACGAGCGC  CTGCCGGGCA
  AAV8        CGAGATCGTG  ATCAAGGTGC  CGAGCGACCT  GGACGAGCAC  CTGCCGGGCA
  AAV9        CGAGATTGTG  ATCAAGGTGC  CGAGCGACCT  GGACGAGCAC  CTGCCGGGCA
  AAV7        CGAGATCGTG  ATCAAGGTGC  CGAGCGACCT  GGACGAGCAC  CTGCCGGGCA
  44_2        ..........  ..........  ..........  ..........  ..........
```

FIG. 1I

```
         401                                                         450
   42_2  ..........  ..........  ..........  ..........  ..........
   42_8  ..........  ..........  ..........  ..........  ..........
  42_15  ..........  ..........  ..........  ..........  ..........
  42_5b  ..........  ..........  ..........  ..........  ..........
  42_1b  ..........  ..........  ..........  ..........  ..........
  42_13  ..........  ..........  ..........  ..........  ..........
  42_3a  ..........  ..........  ..........  ..........  ..........
   42_4  ..........  ..........  ..........  ..........  ..........
  42_5a  ..........  ..........  ..........  ..........  ..........
  42_10  ..........  ..........  ..........  ..........  ..........
  42_3b  ..........  ..........  ..........  ..........  ..........
  42_11  ..........  ..........  ..........  ..........  ..........
  42_6b  ..........  ..........  ..........  ..........  ..........
   43_1  ..........  ..........  ..........  ..........  ..........
   43_5  ..........  ..........  ..........  ..........  ..........
  43_12  ..........  ..........  ..........  ..........  ..........
  43_20  ..........  ..........  ..........  ..........  ..........
  43_21  ..........  ..........  ..........  ..........  ..........
  43_23  ..........  ..........  ..........  ..........  ..........
  43_25  ..........  ..........  ..........  ..........  ..........
   44_1  ..........  ..........  ..........  ..........  ..........
   44_5  ..........  ..........  ..........  ..........  ..........
 223_10  ..........  ..........  ..........  ..........  ..........
  223_2  ..........  ..........  ..........  ..........  ..........
  223_4  ..........  ..........  ..........  ..........  ..........
  223_5  ..........  ..........  ..........  ..........  ..........
  223_6  ..........  ..........  ..........  ..........  ..........
  223_7  ..........  ..........  ..........  ..........  ..........
   A3_4  ..........  ..........  ..........  ..........  ..........
   A3_5  ..........  ..........  ..........  ..........  ..........
   A3_7  ..........  ..........  ..........  ..........  ..........
   A3_3  ..........  ..........  ..........  ..........  ..........
  42_12  ..........  ..........  ..........  ..........  ..........
   AAV1  TTTCTGACTC  GTTTGTGAGC  TGGGTGGCCG  AGAAGGAATG  GGAGCTGCCC
   AAV2  TTTCTGACAG  CTTTGTGAAC  TGGGTGGCCG  AGAAGGAATG  GGAGTTGCCG
   AAV3  TTTCTAACTC  GTTTGTTAAC  TGGGTGGCCG  AGAAGGAATG  GGACGTGCCG
   AAV8  TTTCTGACTC  GTTTGTGAAC  TGGGTGGCCG  AGAAGGAATG  GGAGCTGCCC
   AAV9  TTTCTGACTC  TTTTGTGAAC  TGGGTGGCCG  AGAAGGAATG  GGAGCTGCCC
   AAV7  TTTCTGACTC  GTTTGTGAAC  TGGGTGGCCG  AGAAGGAATG  GGAGCTGCCC
   44_2  ..........  ..........  ..........  ..........  ..........
```

FIG. 1J

```
              451                                                          500
    42_2      ..........  ..........  ..........  ..........  ..........
    42_8      ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
    42_4      ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      ..........  ..........  ..........  ..........  ..........
    43_1      ..........  ..........  ..........  ..........  ..........
    43_5      ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
    44_1      ..........  ..........  ..........  ..........  ..........
    44_5      ..........  ..........  ..........  ..........  ..........
  223_10      ..........  ..........  ..........  ..........  ..........
   223_2      ..........  ..........  ..........  ..........  ..........
   223_4      ..........  ..........  ..........  ..........  ..........
   223_5      ..........  ..........  ..........  ..........  ..........
   223_6      ..........  ..........  ..........  ..........  ..........
   223_7      ..........  ..........  ..........  ..........  ..........
    A3_4      ..........  ..........  ..........  ..........  ..........
    A3_5      ..........  ..........  ..........  ..........  ..........
    A3_7      ..........  ..........  ..........  ..........  ..........
    A3_3      ..........  ..........  ..........  ..........  ..........
   42_12      ..........  ..........  ..........  ..........  ..........
    AAV1      CCGGATTCTG  ACATGGATCT  GAATCTGATT  GAGCAGGCAC  CCCTGACCGT
    AAV2      CCAGATTCTG  ACATGGATCT  GAATCTGATT  GAGCAGGCAC  CCCTGACCGT
    AAV3      CCGGATTCTG  ACATGGATCC  GAATCTGATT  GAGCAGGCAC  CCCTGACCGT
    AAV8      CCGGATTCTG  ACATGGATCG  GAATCTGATC  GAGCAGGCAC  CCCTGACCGT
    AAV9      CCGGATTCTG  ACATGGATCG  GAATCTGATC  GAGCAGGCAC  CCCTGACCGT
    AAV7      CCGGATTCTG  ACATGGATCT  GAATCTGATC  GAGCAGGCAC  CCCTGACCGT
    44_2      ..........  ..........  ..........  ..........  ..........
```

FIG. 1K

```
           501                                                      550
    42_2   ..........  ..........  ..........  ..........  ..........
    42_8   ..........  ..........  ..........  ..........  ..........
   42_15   ..........  ..........  ..........  ..........  ..........
   42_5b   ..........  ..........  ..........  ..........  ..........
   42_1b   ..........  ..........  ..........  ..........  ..........
   42_13   ..........  ..........  ..........  ..........  ..........
   42_3a   ..........  ..........  ..........  ..........  ..........
    42_4   ..........  ..........  ..........  ..........  ..........
   42_5a   ..........  ..........  ..........  ..........  ..........
   42_10   ..........  ..........  ..........  ..........  ..........
   42_3b   ..........  ..........  ..........  ..........  ..........
   42_11   ..........  ..........  ..........  ..........  ..........
   42_6b   ..........  ..........  ..........  ..........  ..........
    43_1   ..........  ..........  ..........  ..........  ..........
    43_5   ..........  ..........  ..........  ..........  ..........
   43_12   ..........  ..........  ..........  ..........  ..........
   43_20   ..........  ..........  ..........  ..........  ..........
   43_21   ..........  ..........  ..........  ..........  ..........
   43_23   ..........  ..........  ..........  ..........  ..........
   43_25   ..........  ..........  ..........  ..........  ..........
    44_1   ..........  ..........  ..........  ..........  ..........
    44_5   ..........  ..........  ..........  ..........  ..........
  223_10   ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
    A3_4   ..........  ..........  ..........  ..........  ..........
    A3_5   ..........  ..........  ..........  ..........  ..........
    A3_7   ..........  ..........  ..........  ..........  ..........
    A3_3   ..........  ..........  ..........  ..........  ..........
   42_12   ..........  ..........  ..........  ..........  ..........
    AAV1   GGCCGAGAAG  CTGCAGCGCG  ACTTCCTGGT  CCAATGGCGC  CGCGTGAGTA
    AAV2   GGCCGAGAAG  CTGCAGCGCG  ACTTTCTGAC  GGAATGGCGC  CGTGTGAGTA
    AAV3   GGCCGAAAAG  CTTCAGCGCG  AGTTCCTGGT  GGAGTGGCGC  CGCGTGAGTA
    AAV8   GGCCGAGAAG  CTGCAGCGCG  ACTTCCTGGT  CCAATGGCGC  CGCGTGAGTA
    AAV9   GGCCGAGAAG  CTGTAGCGCG  ACTTCCTGGT  CCAATGGCGC  CGCGTGAGTA
    AAV7   GGCCGAGAAG  CTGCAGCGCG  ACTTCCTGGT  CCAATGGCGC  CGCGTGAGTA
    44_2   ..........  ..........  ..........  ..........  ..........
```

FIG. 1L

```
           551                                                              600
  42_2     ..........  ..........  ..........  ..........  ..........
  42_8     ..........  ..........  ..........  ..........  ..........
 42_15     ..........  ..........  ..........  ..........  ..........
 42_5b     ..........  ..........  ..........  ..........  ..........
 42_1b     ..........  ..........  ..........  ..........  ..........
 42_13     ..........  ..........  ..........  ..........  ..........
 42_3a     ..........  ..........  ..........  ..........  ..........
  42_4     ..........  ..........  ..........  ..........  ..........
 42_5a     ..........  ..........  ..........  ..........  ..........
 42_10     ..........  ..........  ..........  ..........  ..........
 42_3b     ..........  ..........  ..........  ..........  ..........
 42_11     ..........  ..........  ..........  ..........  ..........
 42_6b     ..........  ..........  ..........  ..........  ..........
  43_1     ..........  ..........  ..........  ..........  ..........
  43_5     ..........  ..........  ..........  ..........  ..........
 43_12     ..........  ..........  ..........  ..........  ..........
 43_20     ..........  ..........  ..........  ..........  ..........
 43_21     ..........  ..........  ..........  ..........  ..........
 43_23     ..........  ..........  ..........  ..........  ..........
 43_25     ..........  ..........  ..........  ..........  ..........
  44_1     ..........  ..........  ..........  ..........  ..........
  44_5     ..........  ..........  ..........  ..........  ..........
223_10     ..........  ..........  ..........  ..........  ..........
 223_2     ..........  ..........  ..........  ..........  ..........
 223_4     ..........  ..........  ..........  ..........  ..........
 223_5     ..........  ..........  ..........  ..........  ..........
 223_6     ..........  ..........  ..........  ..........  ..........
 223_7     ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
 42_12     ..........  ..........  ..........  ..........  ..........
  AAV1     AGGCCCCGGA  GGCCCTCTTC  TTTGTTCAGT  TCGAGAAGGG  CGAGTCCTAC
  AAV2     AGGCCCCGGA  GGCCCTTTTC  TTTGTGCAAT  TTGAGAAGGG  AGAGAGCTAC
  AAV3     AGGCCCCGGA  GGCCCTCTTT  TTTGTCCAGT  TCGAAAAGGG  GGAGACCTAC
  AAV8     AGGCCCCGGA  GGCCCTCTTC  TTTGTTCAGT  TCGAGAAGGG  CGAGAGCTAC
  AAV9     AGGCCCCGGA  GGCCCTCTTC  TTTGTTCAGT  TCGAGAAGGG  CGAGAGCTAC
  AAV7     AGGCCCCGGA  GGCCCTGTTC  TTTGTTCAGT  TCGAGAAGGG  CGAGAGCTAC
  44_2     ..........  ..........  ..........  ..........  ..........
```

FIG. 1M

```
            601                                                              650
    42_2    ..........  ..........  ..........  ..........  ..........
    42_8    ..........  ..........  ..........  ..........  ..........
   42_15    ..........  ..........  ..........  ..........  ..........
   42_5b    ..........  ..........  ..........  ..........  ..........
   42_1b    ..........  ..........  ..........  ..........  ..........
   42_13    ..........  ..........  ..........  ..........  ..........
   42_3a    ..........  ..........  ..........  ..........  ..........
    42_4    ..........  ..........  ..........  ..........  ..........
   42_5a    ..........  ..........  ..........  ..........  ..........
   42_10    ..........  ..........  ..........  ..........  ..........
   42_3b    ..........  ..........  ..........  ..........  ..........
   42_11    ..........  ..........  ..........  ..........  ..........
   42_6b    ..........  ..........  ..........  ..........  ..........
    43_1    ..........  ..........  ..........  ..........  ..........
    43_5    ..........  ..........  ..........  ..........  ..........
   43_12    ..........  ..........  ..........  ..........  ..........
   43_20    ..........  ..........  ..........  ..........  ..........
   43_21    ..........  ..........  ..........  ..........  ..........
   43_23    ..........  ..........  ..........  ..........  ..........
   43_25    ..........  ..........  ..........  ..........  ..........
    44_1    ..........  ..........  ..........  ..........  ..........
    44_5    ..........  ..........  ..........  ..........  ..........
  223_10    ..........  ..........  ..........  ..........  ..........
   223_2    ..........  ..........  ..........  ..........  ..........
   223_4    ..........  ..........  ..........  ..........  ..........
   223_5    ..........  ..........  ..........  ..........  ..........
   223_6    ..........  ..........  ..........  ..........  ..........
   223_7    ..........  ..........  ..........  ..........  ..........
    A3_4    ..........  ..........  ..........  ..........  ..........
    A3_5    ..........  ..........  ..........  ..........  ..........
    A3_7    ..........  ..........  ..........  ..........  ..........
    A3_3    ..........  ..........  ..........  ..........  ..........
   42_12    ..........  ..........  ..........  ..........  ..........
    AAV1    TTCCACCTCC  ATATTCTGGT  GGAGACCACG  GGGGTCAAAT  CCATGGTGCT
    AAV2    TTCCACATGC  ACGTGCTCGT  GGAAACCACC  GGGGTGAAAT  CCATGGTTTT
    AAV3    TTCCACCTGC  ACGTGCTGAT  TGAGACCATC  GGGGTCAAAT  CCATGGTGGT
    AAV8    TTTCACCTGC  ACGTTCTGGT  CGAGACCACG  GGGGTCAAGT  CCATGGTGCT
    AAV9    TTTCACCTGC  ACGTTCTGGT  CGAGACCACG  GGGGTCAAGT  CCATGGTGCT
    AAV7    TTCCACCTTC  ACGTTCTGGT  GGAGACCACG  GGGGTCAAGT  CCATGGTGCT
    44_2    ..........  ..........  ..........  ..........  ..........
```

FIG. 1N

```
           651                                                    700
   42_2    .......... .......... .......... .......... ..........
   42_8    .......... .......... .......... .......... ..........
  42_15    .......... .......... .......... .......... ..........
  42_5b    .......... .......... .......... .......... ..........
  42_1b    .......... .......... .......... .......... ..........
  42_13    .......... .......... .......... .......... ..........
  42_3a    .......... .......... .......... .......... ..........
   42_4    .......... .......... .......... .......... ..........
  42_5a    .......... .......... .......... .......... ..........
  42_10    .......... .......... .......... .......... ..........
  42_3b    .......... .......... .......... .......... ..........
  42_11    .......... .......... .......... .......... ..........
  42_6b    .......... .......... .......... .......... ..........
   43_1    .......... .......... .......... .......... ..........
   43_5    .......... .......... .......... .......... ..........
  43_12    .......... .......... .......... .......... ..........
  43_20    .......... .......... .......... .......... ..........
  43_21    .......... .......... .......... .......... ..........
  43_23    .......... .......... .......... .......... ..........
  43_25    .......... .......... .......... .......... ..........
   44_1    .......... .......... .......... .......... ..........
   44_5    .......... .......... .......... .......... ..........
 223_10    .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    .......... .......... .......... .......... ..........
   A3_5    .......... .......... .......... .......... ..........
   A3_7    .......... .......... .......... .......... ..........
   A3_3    .......... .......... .......... .......... ..........
  42_12    .......... .......... .......... .......... ..........
   AAV1    GGGCCGCTTC CTGAGTCAGA TTAGGGACAA GCT.GGTGCA GACCATCTAC
   AAV2    GGGACGTTTC CTGAGTCAGA TTCGCGAAAA ACT..GATTC AGAGAATTTA
   AAV3    CGGCCGCTAC GTGAGCCAGA TTAAAGAGAA GCT..GGTGA CCCGCATCTA
   AAV8    AGGCCGCTTC CTGAGTCAGA TTCGGGAAAA GCTTGGTCCA GACCATCTAC
   AAV9    AGGCCGCTTC CTGAGTCAGA TTCGGGAGAA GCT.GGTCCA GACCATCTAC
   AAV7    AGGCCGCTTC CTGAGTCAGA TTCGGGAGAA GCT....G.. GTCCAGACCA
   44_2    .......... .......... .......... .......... ..........
```

FIG. 10

```
        701                                                           750
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  ..........  ..........  ..........  ..........  ..........
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   C.GCGGGATC  GAGCCG.ACC  CTGCCCAACT  GGTTCGCGGT  GACCAA.GAC
 AAV2   CCGCGGGATC  GAGCCG.ACT  TTGCCAAACT  GGTTCGCGGT  CACAAA...G
 AAV3   CCGCGGGGTC  GAGCCG.CAG  CTTCCGAACT  GGTTCGCGGT  GACCAA...A
 AAV8   CCGCGGGGTC  GAGCCCCACC  TTGCCCAACT  GGTTCGCGGT  GACCAAAGAC
 AAV9   C.GCGGGATC  GAGCCG.ACC  CTGCCCAACT  GGTTCGCGGT  GACCAA.GAC
 AAV7   TCTACCGCGG  GGTCGAGCCC  ACGCTGCCCA  ACTGGTTCGC  GGTGACCAAG
 44_2   ..........  ..........  ..........  ..........  ..........
```

FIG. 1P

```
          751                                                      800
  42_2    ..........  ..........  ..........  ..........  ..........
  42_8    ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
  42_4    ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
  43_1    ..........  ..........  ..........  ..........  ..........
  43_5    ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
  44_1    ..........  ..........  ..........  ..........  ..........
  44_5    ..........  ..........  ..........  ..........  ..........
 223_10   ..........  ..........  ..........  ..........  ..........
 223_2    ..........  ..........  ..........  ..........  ..........
 223_4    ..........  ..........  ..........  ..........  ..........
 223_5    ..........  ..........  ..........  ..........  ..........
 223_6    ..........  ..........  ..........  ..........  ..........
 223_7    ..........  ..........  ..........  ..........  ..........
  A3_4    ..........  ..........  ..........  ..........  ..........
  A3_5    ..........  ..........  ..........  ..........  ..........
  A3_7    ..........  ..........  ..........  ..........  ..........
  A3_3    ..........  ..........  ..........  ..........  ..........
  42_12   ..........  ..........  ..........  ..........  ..........
  AAV1    GCG.TAATGG  CGCCGGAGGG  GGG.AACAAG  GTGGTGGACG  AGTGCTACAT
  AAV2    ACCAGAAATG  GCGCCGGAGG  CGGGAACAAG  GTGGTGGATG  AGTGCTACAT
  AAV3    ACGCGAAATG  GCGCCGGGGG  CGGGAACAAG  GTGGTGGACG  ACTGCTACAT
  AAV8    GCGGTAATGG  CGCCGGCGGG  GGGGAACAAG  GTGGTGGACG  AGTGCTACAT
  AAV9    GCG.TAATGG  CGCCGGCGGG  GGG.AACAAG  GTGGTGGACG  AGTGCTACAT
  AAV7    ACGCGTAATG  GCGCCGGCGG  GGGGAACAAG  GTGGTGGACG  AGTGCTACAT
  44_2    ..........  ..........  ..........  ..........  ..........
```

FIG. 1Q

```
        801                                                              850
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   CCCCAACTAC  CTCCTGCCCA  AGACTCAGCC  CGAGCTGCAG  TGGGCGTGGA
  AAV2   CCCCAATTAC  TTGCTCCCCA  AAACCCAGCC  TGAGCTCCAG  TGGGCGTGGA
  AAV3   CCCCAACTAC  CTGCTCCCCA  AGACCCAGCC  CGAGCTCCAG  TGGGCGTGGA
  AAV8   CCCCAACTAC  CTCCTGCCCA  AGACTCAGCC  CGAGCTGCAG  TGGGCGTGGA
  AAV9   CCCCAACTAC  CTCCTGCCCA  AGACTCAGCC  CGAGCTGCAG  TGGGCGTGGA
  AAV7   CCCCAACTAC  CTCCTGCCCA  AGACCCAGCC  CGAGCTGCAG  TGGGCGTGGA
  44_2   ..........  ..........  ..........  ..........  ..........
```

FIG. 1S

```
            901                                                          950
    42_2    ..........  ..........  ..........  ..........  ..........
    42_8    ..........  ..........  ..........  ..........  ..........
   42_15    ..........  ..........  ..........  ..........  ..........
   42_5b    ..........  ..........  ..........  ..........  ..........
   42_1b    ..........  ..........  ..........  ..........  ..........
   42_13    ..........  ..........  ..........  ..........  ..........
   42_3a    ..........  ..........  ..........  ..........  ..........
    42_4    ..........  ..........  ..........  ..........  ..........
   42_5a    ..........  ..........  ..........  ..........  ..........
   42_10    ..........  ..........  ..........  ..........  ..........
   42_3b    ..........  ..........  ..........  ..........  ..........
   42_11    ..........  ..........  ..........  ..........  ..........
   42_6b    ..........  ..........  ..........  ..........  ..........
    43_1    ..........  ..........  ..........  ..........  ..........
    43_5    ..........  ..........  ..........  ..........  ..........
   43_12    ..........  ..........  ..........  ..........  ..........
   43_20    ..........  ..........  ..........  ..........  ..........
   43_21    ..........  ..........  ..........  ..........  ..........
   43_23    ..........  ..........  ..........  ..........  ..........
   43_25    ..........  ..........  ..........  ..........  ..........
    44_1    ..........  ..........  ..........  ..........  ..........
    44_5    ..........  ..........  ..........  ..........  ..........
  223_10    ..........  ..........  ..........  ..........  ..........
   223_2    ..........  ..........  ..........  ..........  ..........
   223_4    ..........  ..........  ..........  ..........  ..........
   223_5    ..........  ..........  ..........  ..........  ..........
   223_6    ..........  ..........  ..........  ..........  ..........
   223_7    ..........  ..........  ..........  ..........  ..........
    A3_4    ..........  ..........  ..........  ..........  ..........
    A3_5    ..........  ..........  ..........  ..........  ..........
    A3_7    ..........  ..........  ..........  ..........  ..........
    A3_3    ..........  ..........  ..........  ..........  ..........
   42_12    ..........  ..........  ..........  ..........  ..........
    AAV1    CGGCTCGTGG  CGCAGCACCT  GACCCACGTC  AGCCAGACCC  AGGAGCAGAA
    AAV2    CGGTTGGTGG  CGCAGCATCT  GACGCACGTG  TCGCAGACGC  AGGAGCAGAA
    AAV3    CGGCTGGTGG  CGCAGCATCT  GACGCACGTG  TCGCAGACGC  AGGAGCAGAA
    AAV8    CGGCTCGTGG  CGCAGCACCT  GACCCACGTC  AGCCAGACGC  AGGAGCAGAA
    AAV9    CGGCTCGTGG  CGCAGCACCT  GACCCACGTC  AGCCAGACGC  AGGAGCAGAA
    AAV7    CGGCTCGTGG  CGCAGCACCT  GACCCACGTC  AGCCAGACGC  AGGAGCAGAA
    44_2    ..........  ..........  ..........  ..........  ..........
```

FIG. 1T

```
         951                                                    1000
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   CAAGGAGAAT  CTGAACCCCA  ATTCTGACGC  GCCTGTCATC  CGGTCAAAAA
  AAV2   CAAAGAGAAT  CAGAATCCCA  ATTCTGATGC  GCCGGTGATC  AGATCAAAAA
  AAV3   CAAAGAGAAT  CAGAACCCCA  ATTCTGACGC  GCCGGTCATC  AGGTCAAAAA
  AAV8   CAAGGAGAAT  CTGAACCCCA  ATTCTGACGC  GCCCGTGATC  AGGTCAAAAA
  AAV9   CAAGGAGAAT  CTGAACCCCA  ATTCTGACGC  GCCCGTGATC  AGGTCAAAAA
  AAV7   CAAGGAGAAT  CTGAACCCCA  ATTCTGACGC  GCCCGTGATC  AGGTCAAAAA
  44_2   ..........  ..........  ..........  ..........  ..........
```

FIG. 1U 1001                                                                   1050
                      Rep52/40 start codon
                                ↓  ↓
    42_2      ..........  ..........  ..........  ..........  ..........
    42_8      ..........  ..........  ..........  ..........  ..........
    42_15     ..........  ..........  ..........  ..........  ..........
    42_5b     ..........  ..........  ..........  ..........  ..........
    42_1b     ..........  ..........  ..........  ..........  ..........
    42_13     ..........  ..........  ..........  ..........  ..........
    42_3a     ..........  ..........  ..........  ..........  ..........
    42_4      ..........  ..........  ..........  ..........  ..........
    42_5a     ..........  ..........  ..........  ..........  ..........
    42_10     ..........  ..........  ..........  ..........  ..........
    42_3b     ..........  ..........  ..........  ..........  ..........
    42_11     ..........  ..........  ..........  ..........  ..........
    42_6b     ..........  ..........  ..........  ..........  ..........
    43_1      ..........  ..........  ..........  ..........  ..........
    43_5      ..........  ..........  ..........  ..........  ..........
    43_12     ..........  ..........  ..........  ..........  ..........
    43_20     ..........  ..........  ..........  ..........  ..........
    43_21     ..........  ..........  ..........  ..........  ..........
    43_23     ..........  ..........  ..........  ..........  ..........
    43_25     ..........  ..........  ..........  ..........  ..........
    44_1      ..........  ..........  ..........  ..........  ..........
    44_5      ..........  ..........  ..........  ..........  ..........
    223_10    ..........  ..........  ..........  ..........  ..........
    223_2     ..........  ..........  ..........  ..........  ..........
    223_4     ..........  ..........  ..........  ..........  ..........
    223_5     ..........  ..........  ..........  ..........  ..........
    223_6     ..........  ..........  ..........  ..........  ..........
    223_7     ..........  ..........  ..........  ..........  ..........
    A3_4      ..........  ..........  ..........  ..........  ..........
    A3_5      ..........  ..........  ..........  ..........  ..........
    A3_7      ..........  ..........  ..........  ..........  ..........
    A3_3      ..........  ..........  ..........  ..........  ..........
    42_12     ..........  ..........  ..........  ..........  ..........
    AAV1      CCTCCGCGCG  CTACATGGAG  CTGGTCGGGT  GGCTGGTGGA  CCGGGGCATC
    AAV2      CTTCAGCCAG  GTACATGGAG  CTGGTCGGGT  GGCTCGTGGA  CAAGGGGATT
    AAV3      CCTCAGCCAG  GTACATGGAG  CTGGTCGGGT  GGCTGGTGGA  CCGCGGGATC
    AAV8      CCTCCGCGCG  CTATATGGAG  CTGGTCGGGT  GGCTGGTGGA  CCGGGGCATC
    AAV9      CCTCCGCGCG  CTACATGGAG  CTGGTCGGGT  GGCTGGTGGA  CCGGGGCATC
    AAV7      CCTCCGCGCG  CTACATGGAG  CTGGTCGGGT  GGCTGGTGGA  CCGGGGCATC
    44_2      ..........  ..........  ..........  ..........  ..........
                                ↑  ↑
                          Rep 52/40 start

FIG. 1V

```
           1051                                                    1100
   42_2    .......... .......... .......... .......... ..........
   42_8    .......... .......... .......... .......... ..........
  42_15    .......... .......... .......... .......... ..........
  42_5b    .......... .......... .......... .......... ..........
  42_1b    .......... .......... .......... .......... ..........
  42_13    .......... .......... .......... .......... ..........
  42_3a    .......... .......... .......... .......... ..........
   42_4    .......... .......... .......... .......... ..........
  42_5a    .......... .......... .......... .......... ..........
  42_10    .......... .......... .......... .......... ..........
  42_3b    .......... .......... .......... .......... ..........
  42_11    .......... .......... .......... .......... ..........
  42_6b    .......... .......... .......... .......... ..........
   43_1    .......... .......... .......... .......... ..........
   43_5    .......... .......... .......... .......... ..........
  43_12    .......... .......... .......... .......... ..........
  43_20    .......... .......... .......... .......... ..........
  43_21    .......... .......... .......... .......... ..........
  43_23    .......... .......... .......... .......... ..........
  43_25    .......... .......... .......... .......... ..........
   44_1    .......... .......... .......... .......... ..........
   44_5    .......... .......... .......... .......... ..........
 223_10    .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    .......... .......... .......... .......... ..........
   A3_5    .......... .......... .......... .......... ..........
   A3_7    .......... .......... .......... .......... ..........
   A3_3    .......... .......... .......... .......... ..........
  42_12    .......... .......... .......... .......... ..........
   AAV1    ACCTCCGAGA AGCAGTGGAT CCAGGAGGAC CAGGCCTCGT ACATCTCCTT
   AAV2    ACCTCGGAGA AGCAGTGGAT CCAGGAGGAC CAGGCCTCAT ACATCTCCTT
   AAV3    ACGTCAGAAA AGCAATGGAT TCAGGAGGAC CAGGCCTCGT ACATCTCCTT
   AAV8    ACCTCCGAGA AGCAGTGGAT CCAGGAGGAC CAGGCCTCGT ACATCTCCTT
   AAV9    ACCTCCGAGA AGCAGTGGAT CCAGGAGGAC CAGGCCTCGT ACATCTCCTT
   AAV7    ACCTCCGAGA AGCAGTGGAT CCAGGAGGAC CAGGCCTCGT ACATCTCCTT
   44_2    .......... .......... .......... .......... ..........
```

FIG. 1W

```
         1101                                                  1150
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
223_10   ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   CAACGCCGCT  TCCAACTCGC  GGTCCCAGAT  CAAGGCCGCT  CTGGACAATG
  AAV2   CAATGCGGCC  TCCAACTCGC  GGTCCCAAAT  CAAGGCTGCC  TTGGACAATG
  AAV3   CAACGCCGCC  TCCAACTCGC  GGTCCCAGAT  CAAGGCCGCG  CTGGACAATG
  AAV8   CAACGCCGCC  TCCAACTCGC  GGTCCCAGAT  CAAGGCCGCG  CTGGACAATG
  AAV9   CAACGCCGCC  TCCAACTCGC  GGTCCCAGAT  CAAGGCCGCG  CTGGACAATG
  AAV7   CAACGCCGCC  TCCAACTCGC  GGTCCCAGAT  CAAGGCCGCG  CTGGACAATG
  44_2   ..........  ..........  ..........  ..........  ..........
```

FIG. 1X

```
       1151                                                        1200
 42_2  ..........  ..........  ..........  ..........  ..........
 42_8  ..........  ..........  ..........  ..........  ..........
42_15  ..........  ..........  ..........  ..........  ..........
42_5b  ..........  ..........  ..........  ..........  ..........
42_1b  ..........  ..........  ..........  ..........  ..........
42_13  ..........  ..........  ..........  ..........  ..........
42_3a  ..........  ..........  ..........  ..........  ..........
 42_4  ..........  ..........  ..........  ..........  ..........
42_5a  ..........  ..........  ..........  ..........  ..........
42_10  ..........  ..........  ..........  ..........  ..........
42_3b  ..........  ..........  ..........  ..........  ..........
42_11  ..........  ..........  ..........  ..........  ..........
42_6b  ..........  ..........  ..........  ..........  ..........
 43_1  ..........  ..........  ..........  ..........  ..........
 43_5  ..........  ..........  ..........  ..........  ..........
43_12  ..........  ..........  ..........  ..........  ..........
43_20  ..........  ..........  ..........  ..........  ..........
43_21  ..........  ..........  ..........  ..........  ..........
43_23  ..........  ..........  ..........  ..........  ..........
43_25  ..........  ..........  ..........  ..........  ..........
 44_1  ..........  ..........  ..........  ..........  ..........
 44_5  ..........  ..........  ..........  ..........  ..........
223_10 ..........  ..........  ..........  ..........  ..........
223_2  ..........  ..........  ..........  ..........  ..........
223_4  ..........  ..........  ..........  ..........  ..........
223_5  ..........  ..........  ..........  ..........  ..........
223_6  ..........  ..........  ..........  ..........  ..........
223_7  ..........  ..........  ..........  ..........  ..........
 A3_4  ..........  ..........  ..........  ..........  ..........
 A3_5  ..........  ..........  ..........  ..........  ..........
 A3_7  ..........  ..........  ..........  ..........  ..........
 A3_3  ..........  ..........  ..........  ..........  ..........
42_12  ..........  ..........  ..........  ..........  ..........
 AAV1  CCGGCAAGAT  CATGGCGCTG  ACCAAATCCG  CGCCCGACTA  CCTGGTAGGC
 AAV2  CGGGAAAGAT  TATGAGCCTG  ACTAAAACCG  CCCCCGACTA  CCTGGTGGGC
 AAV3  CCTCCAAGAT  CATGAGCCTG  ACAAAGACGG  CTCCGGACTA  CCTGGTGGGC
 AAV8  CCGGCAAGAT  CATGGCGCTG  ACCAAATCCG  CGCCCGACTA  CCTGGTGGGG
 AAV9  CCGGCAAGAT  CATGGCGCTG  ACCAAATCCG  CGCCCGACTA  CCTGGTAGGC
 AAV7  CCGGCAAGAT  CATGGCGCTG  ACCAAATCCG  CGCCCGACTA  CCTGGTGGGG
 44_2  ..........  ..........  ..........  ..........  ..........
```

FIG. 1Y

```
         1201                                                      1250
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ........GA  ATTCGCCCTT  TCTACGGCTG
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   CCCGCTCCGC  CCGCGGACAT  TAAAACCAAC  CGCATCTACC  GCATCCTGGA
  AAV2   CAGCAGCCCG  TGGAGGACAT  TTCCAGCAAT  CGGATTTATA  AAATTTTGGA
  AAV3   AGCAACCCGC  CGGAGGACAT  TACCAAAAAT  CGGATCTACC  AAATCCTGGA
  AAV8   CCCTCGCTGC  CCGCGGACAT  TACCCAGAAC  CGCATCTACC  GCATCCTCGC
  AAV9   CCTTCACTTC  CGGTGGACAT  TACGCAGAAC  CGCATCTACC  GCATCCTGCA
  AAV7   CCCTCGCTGC  CCGCGGACAT  TAAAACCAAC  CGCATCTACC  GCATCCTGGA
  44_2   ..........  ..........  ..........  ..........  ..........
```

FIG. 12

```
           1251                                                    1300
   42_2    ..........  ..........  ..........  ..........  ..........
   42_8    ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
   42_4    ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    CGTCAACTGG  ACCAATGAGA  ACTTTCCCTT  CAACGATTGC  GTCGACAAGA
   43_1    ..........  ..........  ..........  ..........  ..........
   43_5    ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
   44_1    ..........  ..........  ..........  ..........  ..........
   44_5    ..........  ..........  ..........  ..........  ..........
 223_10    ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
  42_12    ..........  ..........  ..........  ..........  ..........
   AAV1    GCTGAACGGC  TACGAACCTG  CCTACGCCGG  CTCCGTCTTT  CTCGGCTGGG
   AAV2    ACTAAACGGG  TACGATCCCC  AATATGCGGC  TTCGTCTTT   CTGGGATGGG
   AAV3    GCTGAACGGG  TACGATCCGC  AGTACGCGGC  CTCCGTCTTC  CTGGGCTGGG
   AAV8    TCTCAACGGC  TACGACCTG   CCTACGCCGG  CTCCGTCTTT  CTCGGCTGGG
   AAV9    GCTCAACGGC  TACGACCCTG  CCTACGCCGG  CTCCGTCTTT  CTCGGCTGGG
   AAV7    GCTGAACGGG  TACGATCCTG  CCTACGCCGG  CTCCGTCTTT  CTCGGCTGGG
   44_2    ..........  ..........  ..........  ..........  ..........
```

FIG. 1AA

```
        1301                                                        1350
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  TGGTGATCTG  GTGGGAGGAG  GGCAAGATGA  CGGCCAAGGT  CGTGGAGTCC
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
 223_10 ..........  ..........  ..........  ..........  ..........
 223_2  ..........  ..........  ..........  ..........  ..........
 223_4  ..........  ..........  ..........  ..........  ..........
 223_5  ..........  ..........  ..........  ..........  ..........
 223_6  ..........  ..........  ..........  ..........  ..........
 223_7  ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   CCCAGAAAAG  GTTCGGGAAG  CGCAACACCA  TCTGGCTGTT  TGGGCCGGCC
 AAV2   CCACGAAAAA  GTTCGGCAAG  AGGAACACCA  TCTGGCTGTT  TGGGCCTGCA
 AAV3   CGCAAAAGAA  GTTCGGGAAG  AGGAACACCA  TCTGGCTCTT  TGGGCCGGCC
 AAV8   CTCAGAAAAA  GTTCGGGAAA  CGCAACACCA  TCTGGCTGTT  TGGACCCGCC
 AAV9   CACAAAAGAA  GTTCGGGAAA  CGCAACACCA  TCTGGCTGTT  TGGGCCGGCC
 AAV7   CCCAGAAAAA  GTTCGGGAAG  CGCAACACCA  TCTGGCTGTT  TGGGCCCGCC
 44_2   ..........  ..........  ..........  ..........  ..........
```

FIG. 1AB

```
             1351                                                    1400
    42_2     ..........  ..........  ..........  .......GAA  TTCGCCCTTT
    42_8     ..........  ..........  ..........  .......GAA  TTCGCCCTTT
    42_15    ..........  ..........  ..........  .......GAA  TTCGCCCTTT
    42_5b    ..........  ..........  ..........  .......GAA  TTCGCCCTTT
    42_1b    ..........  ..........  ..........  ..........  ..........
    42_13    ..........  ..........  ..........  .......GAA  TTCGCCCTTT
    42_3a    ..........  ..........  ..........  .......GAA  TTCGCCCTTT
    42_4     ..........  ..........  ..........  ..........  ..........
    42_5a    ..........  ..........  ..........  ........GA  ATTCGCCCTT
    42_10    ..........  ..........  ..........  ..........  ..........
    42_3b    ..........  ..........  ..........  ..........  ..........
    42_11    ..........  ..........  ..........  .......GAA  TTCGCCCTTT
    42_6b    GCCAAGGCCA  TTCTCGGCGG  CAGCAAGGTG  CGCGTGGACC  AAAAGTGCAA
    43_1     ..........  ..........  ..........  .......GAA  TTCGCCCTTT
    43_5     ..........  ..........  ..........  .......GAA  TTCGCCCTTT
    43_12    ..........  ..........  ..........  .......GAA  TTCGCCCTT.
    43_20    ..........  ..........  ..........  .......GAA  TTCGCCCTTT
    43_21    ..........  ..........  ..........  .......GAA  TTCGCCCTT.
    43_23    ..........  ..........  ..........  .......GAA  TTCGCCCTT.
    43_25    ..........  ..........  ..........  .......GAA  TTCGCCCTTT
    44_1     ..........  ..........  ..........  .......GAA  TTCGCCCTTT
    44_5     ..........  ..........  ..........  .......GAA  TTCGCCCTTT
   223_10    ..........  ..........  ..........  ..........  ..........
   223_2     ..........  ..........  ..........  ..........  ..........
   223_4     ..........  ..........  ..........  ..........  ..........
   223_5     ..........  ..........  ..........  ..........  ..........
   223_6     ..........  ..........  ..........  ..........  ..........
   223_7     ..........  ..........  ..........  ..........  ..........
    A3_4     ..........  ..........  ..........  ........GA  ATTCGCCCTT
    A3_5     ..........  ..........  ..........  ........GA  ATTCGCCCTT
    A3_7     ..........  ..........  .........A  GCGGCCGCGA  ATTCGCCCTT
    A3_3     ..........  ..........  ..........  ........GA  ATTCGCCCTT
    42_12    ..........  ..........  ..........  .......GAA  TTCGCCCTTT
    AAV1     ACCACGGGCA  AGACCAACAT  CGCGGAAGCC  ATCGCCCACG  CCGTGCCCTT
    AAV2     ACTACCGGGA  AGACCAACAT  CGCGGAGGCC  ATAGCCCACA  CTGTGCCCTT
    AAV3     ACGACGGGTA  AAACCAACAT  CGCGGAAGCC  ATCGCCCACG  CCGTGCCCTT
    AAV8     ACCACCGGCA  AGACCAACAT  TGCGGAAGCC  ATCGCCCACG  CCGTGCCCTT
    AAV9     ACCACGGGAA  AGACCAACAT  CGCAGAAGCC  ATTGCCCACG  CCGTGCCCTT
    AAV7     ACCACCGGCA  AGACCAACAT  TGCGGAAGCC  ATCGCCCACG  CCGTGCCCTT
    44_2     ..........  ..........  ..........  ........GA  ATTCGCCCTT
```

FIG. 1AC

```
         1401                                                      1450
42_2    .CTACGGCTG CGTCAACTGG ACCAATGAGA ACTTTCCCTT CAACGATTGC
42_8    .CTACGGCTG CGTCAACTGG ACCAATGAGA ACTTTCCCTT CAACGATTGC
42_15   .CTACGGCTG CGTCAACTGG ACCAATGAGA ACTTTCCCTT CAACGATTGC
42_5b   .CTACGGCTG CGTCAACTGG ACCAATGAGA ACTTTCCCTT CAACGATTGC
42_1b   .......... .......... .......... .......... ..........
42_13   .CTACGGCTG CGTCAACTGG ACCAATGAGA ACTTTCCCTT CAACGATTGC
42_3a   .CTACGGCTG CGTCAACTGG ACCAATGAGA ACTTTCCCTT CAACGATTGC
42_4    .......... .......... .......... .......... ..........
42_5a   .CTACGGCTG CGTCAACTGG ACCAATGAGA ACTTTCCCTT CAACGATTGC
42_10   .......... .......... .......... .......... ..........
42_3b   .......... .......... .......... .......... ..........
42_11   .CTACGGCTG CGTCAACTGG ACCAATGAGA ACTTTCCCTT CAACGATTGC
42_6b   .GTCTTCCGC CCAGATCGAT CCCACCCCCG TGATCGTCAC TTCCAACACC
43_1    .CTACGGCTG CATCAACTGG ACCAATGAGA ACTTTCCCTT CAACGATTGC
43_5    .CTACGGCTG CGTCAACTGG ACCAATGAGA ACTTTCCCTT CAACGATTGC
43_12   .....GGCTG CGTCAACTGG ACCAATGAGA ACTTTCCCTT CAACGATTGC
43_20   .CTACGGCTG CGTCAACTGG ACCAATGAGA ACTTTCCCTT CAACGATTGC
43_21   .....GGCTG CGTCAACTGG ACCAATGAGA ACTTTCCCTT CAACGATTGC
43_23   .CTACGGCTG CGTCAACTGG ACCAATGAGA ACTTTCCCTT CAACGATTGC
43_25   .CTACGGCTG CGTCAACTGG ACCAATGAGA ACTTTCCCTT CAACGATTGC
44_1    .CTACGGCTG CGTCAACTGG ACCAATGAGA ACTTTCCCTT CAACGATTGC
44_5    .CTACGGCTG CGTCAACTGG ACCAATGAGA ACTTTCCCTT CAACGATTGC
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
A3_4    TCTACGGCTG CGTCAACTGG ACCAATGAAA ACTTTCCCTT CAACGATTGC
A3_5    TCTACGGCTG CGTCAACTGG ACCAATGAAA ACTTTCCCTT CAACGATTGC
A3_7    TCTACGGCTG CGTCAACTGG ACCAATGAAA ACTTTCCCTT CAACGATTGC
A3_3    TCTACGGCTG CGTCAACTGG ACCAATGAAA ACTTTCCCTT CAACGATTGC
42_12   .CTACGGCTG CGTCAACTGG ACCAATGAGA ACTTTCCCTT CAACGATTGC
AAV1    .CTACGGCTG CGTCAACTGG ACCAATGAGA ACTTTCCCTT CAATGATTGC
AAV2    .CTACGGGTG CGTAAACTGG ACCAATGAGA ACTTTCCCTT CAACGACTGT
AAV3    .CTACGGCTG CGTAAACTGG ACCAATGAGA ACTTTCCCTT CAACGATTGC
AAV8    .CTACGGCTG CGTCAACTGG ACCAATGAGA ACTTTCCCTT CAATGATTGC
AAV9    .CTACGGCTG CGTCAACTGG ACCAATGAGA ACTTTCCCTT CAACGATTGC
AAV7    .CTACGGCTG CGTCAACTGG ACCAATGAGA ACTTTCCCTT CAACGATTGC
44_2    TCTACGGCTG CGTCAACTGG ACCAATGAGA ACTTTCCCTT CAACGATTGC
```

FIG. 1AD

```
           1451                                                      1500
  42_2    GTCGACAAGA TGGTGATCTG GTGGGAGGAG GGCAAGATGA CGGCCAAGGT
  42_8    GTCGACAAGA TGGTGATCTG GTGGGAGGAG GGCAAGATGA CGGCCAAGGT
  42_15   GTCGACAAGA TGGTGATCTG GTGGGAGGAG GGCAAGATGA CGGCCAAGGT
  42_5b   GTCGACAAGA TGGTGATCTG GTGGGAGGAG GGCAAGATGA CGGCCAAGGT
  42_1b   .......... .......... .......... .......... ..........
  42_13   GTCGACAAGA TGGTGATCTG GTGGGAGGAG GGCAAGATGA CGGCCAAGGT
  42_3a   GTCGACAAGA TGGTGATCTG GTGGGAGGAG GGCAAGATGA CGGCCAAGGT
  42_4    .......... .......... .......... .......... ..........
  42_5a   GTCGACAAGA TGGTGATCTG GTGGGAGGAG GGCAAGATGA CGGCCAAGGT
  42_10   .......... .......... .......... .......... ..........
  42_3b   .......... .......... .......... .......... ..........
  42_11   GTCGACAAGA TGGTGATCTG GTGGGAGGAG GGCAAGATGA CGGCCAAGGT
  42_6b   AACATGTGCG CCGTGATTGA CGGGAACAGC ACCACCTTCG AGCACCAGCA
  43_1    GTCGACAAGA TGGTGATCTG GTGGGAGGAG GGCAAGATGA CGGCCAAGGT
  43_5    GTCGACAAGA TGGTGATCTG GTGGGAGGAG GGCAAGATGA CGGCCAAGGT
  43_12   GTCGACAAGA TGGTGATCTG GTGGGAGGAG GGCAAGATGA CGGCCAAGGT
  43_20   GTCGACAAGA TGGTGATCTG GTGGGAGGAG GGCAAGATGA CGGCCAAGGT
  43_21   GTCGACAAGA TGGTGATCTG GTGGGAGGAG GGCAAGATGA CGGCCAAGGT
  43_23   GTCGACAAGA TGGTGATCTG GTGGGAGGAG GGCAAGATGA CGGCCAAGGT
  43_25   GTCGACAAGA TGGTGATCTG GTGGGAGGAG GGCAAGATGA CGGCCAAGGT
  44_1    GTCGACAAGA TGTTGATCTG GTGGGAGGAG GGCAAGATGA CGGCCAAGGT
  44_5    GTCGACAAGA TGGTGATCTG GTGGGAGGAG GGCAAGATGA CGGCCAAGGT
 223_10   .......... .......... .......... .......... ..........
 223_2    .......... .......... .......... .......... ..........
 223_4    .......... .......... .......... .......... ..........
 223_5    .......... .......... .......... .......... ..........
 223_6    .......... .......... .......... .......... ..........
 223_7    .......... .......... .......... .......... ..........
  A3_4    GTCGACAAGA TGGTGATCTG GTGGGAGGAG GGAAAGATGA CCGCCAAGGT
  A3_5    GTCGACAAGA TGGTGATCTG GTGGGAGGAG GGAAAGATGA CCGCCAAGGT
  A3_7    GTCGACAAGA TGGTGATCTG GTGGGAGGAG GGAAAGATGA CCGCCAAGGT
  A3_3    GTCGACAAGA TGGTGATCTG GTGGGAGGAG GGAAAGATGA CCGCCAAGGT
  42_12   GTCGACAAGA TGGTGATCTG GTGGGAGGAG GGCAAGATGA CGGCCAAGGT
  AAV1    GTCGACAAGA TGGTGATCTG GTGGGAGGAG GGCAAGATGA CGGCCAAGGT
  AAV2    GTCGACAAGA TGGTGATCTG GTGGGAGGAG GGGAAGATGA CCGCCAAGGT
  AAV3    GTCGACAAGA TGGTGATCTG GTGGGAGGAG GGCAAGATGA CGGCCAAGGT
  AAV8    GTCGACAAGA TGGTGATCTG GTGGGAGGAG GGCAAGATGA CGGCCAAGGT
  AAV9    GTCGACAAGA TGGTGATCTG GTGGGAGGAG GGCAAGATGA CGGCCAAGGT
  AAV7    GTCGACAAGA TGGTGATCTG GTGGGAGGAG GGCAAGATGA CGGCCAAGGT
  44_2    GTCGACAAGA TGGTGATCTG GTGGGAGGAG GGCAAGATGA CGGCCAAGGT
```

FIG. 1AE

```
         1501                                                    1550
  42_2   CGTGGAGTCC GCCAAGGCCA TTCTCGGCGG CAGCAAGGTG CGCGTGGACC
  42_8   CGTGGAGTCC GCCAAGGCCA TTCTCGGCGG CAGCAAGGTG CGCGTGGACC
 42_15   CGTGGAGTCC GCCAAGGCCA TTCTCGGCGG CAGCAAGGTG CGCGTGGACC
 42_5b   CGTGGAGTCC GCCAAGGCCA TTCTCGGCGG CAGCAAGGTG CGCGTGGACC
 42_1b   .......... .......... .......... .......... ..........
 42_13   CGTGGAGTCC GCCAAGGCCA TTCTCGGCGG CAGCAAGGTG CGCGTGGACC
 42_3a   CGTGGAGTCC GCCAAGGCCA TTCTCGGCGG CAGCAAGGTG CGCGTGGACC
  42_4   .......... .......... .......... .......... ..........
 42_5a   CGTGGAGTCC GCCAAGGCCA TTCTCGGCGG CAGCAAGGTG CGCGTGGACC
 42_10   .......... .......... .......... .......... ..........
 42_3b   .......... .......... .......... .......... ..........
 42_11   CGTGGAGTCC GCCAAGGCCA TTCTCGGCGG CAGCAAGGTG CGCGTGGACC
 42_6b   GCCGTTGCAG GACCGGATGT TCAAATTTGA ACTCACCCGC CGTCTGGAGC
  43_1   CGTGGAGTCC GCCAAGGCCA TTCTCGGCGG CAGCAAGGTG CGCGTGGACC
  43_5   CGTGGAGTCC GCCAAGGCCA TTCTCGGCGG CAGCAAGGTG CGCGTGGACC
 43_12   CGTGGAGTCC GCCAAGGCCA TTCTCGGCGG CAGCAAGGTG CGCGTGGACC
 43_20   CGTGGAGTCC GCCAAGGCCA TTCTCGGCGG CAGCAAGGTG CGTGTGGACC
 43_21   CGTGGAGTCC GCCAAGGCCA TTCTCGGCGG CAGCAAGGTG CGTGTGGACC
 43_23   CGTGGAGTCC GCCAAGGCCA TTCTCGGCGG CAGCAAGGTG CGTGTGGACC
 43_25   CGTGGAGTCC GCCAAGGCCA TTCTCGGCGG CAGCAAGGTG CGTGTGGACC
  44_1   CGTGGAGTCC GCCAAGGCCA TTCTCGGCGG CAGCAAAGTG CGCGTGGACC
  44_5   CGTGGAGTCC GCCAAGGCCA TTCTCGGCGG CAGCAAAGTG CGCGTGGACC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   CGTGGAATCT GCCAAAGCCA TTCTGGGTGG AAGCAAGGTT CGTGTGGACC
  A3_5   CGTGGAATCT GCCAAAGCCA TTCTGGGTGG AAGCAAGGTT CGTGTGGACC
  A3_7   CGTGGAATCT GCCAAAGCCA TTCTGGGTGG AAGCAAGGTT CGTGTGGACC
  A3_3   CGTGGAATCT GCCAAAGCCA TTCTGGGTGG AGGCAAGGTT CGTGTGGACC
 42_12   CGTGGAGTCC GCCAAGGCCA TTCTCGGCGG CAGCAAGGTG CGCGTGGACC
  AAV1   CGTGGAGTCC GCCAAGGCCA TTCTCGGCGG CAGCAAGGTG CGCGTGGACC
  AAV2   CGTGGAGTCG GCCAAAGCCA TTCTCGGAGG AAGCAAGGTG CGCGTGGACC
  AAV3   CGTGGAGAGC GCCAAGGCCA TTCTGGGCGG AAGCAAGGTG CGCGTGGACC
  AAV8   CGTGGAGTCC GCCAAGGCCA TTCTCGGCGG CAGCAAGGTG CGCGTGGACC
  AAV9   CGTGGAGTCC GCCAAGGCCA TTCTCGGCGG CAGCAAGGTG CGCGTGGACC
  AAV7   CGTGGAGTCC GCCAAGGCCA TTCTCGGCGG CAGCAAGGTG CGCGTGGACC
  44_2   CGTGGAGTCC GCCAAGGCCA TTCTCGGCGG CAGCAAAGTG CGCGTGGACC
```

FIG. 1AF

```
            1551                                                      1600
  42_2     AAAAGTGCAA GTCTTCCGCC CAGATCGATC CCACCCCCGT GATCGTCACT
  42_8     AAAAGTGCAA GTCTTCCGCC CAGATCGATC CCACCCCCGT GATCGTCACT
  42_15    AAAAGTGCAA GTCGTCCGCC CAGATCGACC CCACCCCCGT GATCGTCACC
  42_5b    AAAAGTGCAA GTCGTCCGCC CAGATCGACC CCACCCCCGT GATCGTCACC
  42_1b    .......... .......... .......... .......... ..........
  42_13    AAAAGTGCAA GTCGTCCGCC CAGATCGATC CCACCCCCGT GATCGTCACT
  42_3a    AAAAGTGCAA GTCGTCCGCC CAGATCGATC CCACCCCCGT GATCGTCACT
  42_4     .......... .......... .......... .......... ..........
  42_5a    AAAAGTGCAA GTCGTCCGCC CAGATCGACC CCACCCCCGT GATCGTCACC
  42_10    .......... .......... .......... .......... ..........
  42_3b    .......... .......... .......... .......... ..........
  42_11    AAAAGTGCAA GTCTTCCGCC CAGATCGATC CCACCCCCGT GATCGTCACT
  42_6b    ATGACTTTGG CAAGGTGACA AAGCAGGAAG TCAAAGAGTT CTTCCGCTGG
  43_1     AAAAGTGCAA GTCGTCCGCC CAGATCGACC CCACCCCCGT GATCGTCACC
  43_5     AAAAGTGCAA GTCGTCCGCC CAGATCGACC CCACCCCCGT GATCGTCACC
  43_12    AAAAGTGCAA GTCGTCCGCC CAGATCGACC CCACCCCCGT GATCGTCACC
  43_20    AAAAGTGCAA GTCTTCCGCC CAGATCGATC CCACCCCCGT GATCGTCACC
  43_21    AAAAGTGCAA GTCTTCCGCC CAGATCGATC CCACCCCCGT GATCGTCACC
  43_23    AAAAGTGCAA GTCTTCCGCC CAGATCGATC CCACCCCCGT GATCGTCACC
  43_25    AAAAGTGCAA GTCTTCCGCC CAGATCGATC CCACCCCCGT GATCGTCACC
  44_1     AAAAGTGCAA GCCGTCCGCC CAGATCGACC CCACCCCCGT GATCGTCACC
  44_5     AAAAGTGCAA GTCGTCCGCC CAGATCGACC CCACCCCCGT GATCGTCACC
 223_10    .......... .......... .......... .......... ..........
 223_2     .......... .......... .......... .......... ..........
 223_4     .......... .......... .......... .......... ..........
 223_5     .......... .......... .......... .......... ..........
 223_6     .......... .......... .......... .......... ..........
 223_7     .......... .......... .......... .......... ..........
  A3_4     AGAAATGCAA GTCTTCGGCC CAGATCGACC CGACTCCGGT GATTGTCACC
  A3_5     AGAAATGCAA GTCTTCGGCC CAGATCGACC CGACTCCGGT GATTGTCACC
  A3_7     AGAAATGCAG GTCTTCGGCC CAGATCGACC CGACTCCGGT GATTGTCACC
  A3_3     AGAAATGCAA GTCTTCGGCC CAGATCGACC CGACTCCGGT GATTGTCACC
  42_12    AAAAGTGCAA GTCGTCCGCC CAGATCGACC CCACCCCCGT GATCGTCACC
  AAV1     AAAAGTGCAA GTCGTCCGCC CAGATCGACC CCACCCCCGT GATCGTCACC
  AAV2     AGAAATGCAA GTCCTCGGCC CAGATAGACC CGACTCCCGT GATCGTCACC
  AAV3     AAAAGTGCAA GTCATCGGCC CAGATCGAAC CCACTCCCGT GATCGTCACC
  AAV8     AAAAGTGCAA GTCGTCCGCC CAGATCGACC CCACCCCCGT GATCGTCACC
  AAV9     AAAAGTGCAA GTCGTCCGCC CAGATCGACC CCACTCCCGT GATCGTCACC
  AAV7     AAAAGTGCAA GTCGTCCGCC CAGATCGACC CCACCCCCGT GATCGTCACC
  44_2     AAAAGTGCAA GTCGTCCGCC CAGATCGACC CCACCCCCGT GATCGTCACC
```

FIG. 1AG

```
          1601                                                    1650
 42_2   TCCAACACCA ACATGTGCGC TGTGATTGAC GGGAACAGCA CCACCTTCGA
 42_8   TCCAACACCA ACATGTGCGC CGTGATTGAC GGGAACAGCA CCACCTTCGA
 42_15  TCCAACACCA ACATGTGCGC CGTGATTGAC GGGAACAGCA CCACCTTCGA
 42_5b  TCCAACACCA ACATGTGCGC CGTGATTGAC GGGAACAGCA CCACCTTCGA
 42_1b  .......... .......... .......... .......... ..........
 42_13  TCCAACACCA ACATGTGCGC CGTGATTGAC GGGAACAGCA CCACCTTCGA
 42_3a  TCCAACACCA ACATGTGCGC CGTGATTGAC GGGAACAGCA CCACCTTCGA
 42_4   .......... .......... .......... .......... ..........
 42_5a  TCCAACACCA ACATGTGCGC CGTGATTGAC GGGAACAGCA CCACCTTCGA
 42_10  .......... .......... .......... .......... ..........
 42_3b  .......... .......... .......... .......... ..........
 42_11  TCCAACACCA ACATGTGCGC CGTGATTGAC GGGAACAGCA CCACCTTCGA
 42_6b  GCGCAGGATC ACGTGACCGA GGTGGCGCAT GAGTTCTACG TCAGAAAGGG
 43_1   TCCAACACCA ACATGTGCGC CGTGATTGAC GGGAACAGCA CCACCTTCGA
 43_5   TCCAACACCA ACATGTGCGC CGTGATTGAC GGGAACAGCA CCACCTTCGA
 43_12  TCCAACACCA ACATGTGCGC CGTGATTGAC GGGAACAGCA CCACCTTCGA
 43_20  TCCAACACCA ACATGTGCGC CGTGATTGAC GGGAACAGCG CCACCTTCGA
 43_21  TCCAACACCA ACATGTGCGC CGTGATTGAC GGGAACAGCA CCACCTTCGA
 43_23  TCCAACACCA ACATGTGCGC CGTGATTGAC GGGAACAGCA CCACCTTCGA
 43_25  TCCAACACCA ACATGTGCGC CGTGATTGAC GGGAACAGCA CCACCTTCGA
 44_1   TCCAACACCA ACATGTGCGC CGTGATTGAC GGGAACAGCA CCACCTTCGA
 44_5   TCCAACACCA ACATGTGCGC CGTGATTGAC GGGAACAGCA CCACCTTCGA
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   TCTAACACCA ACATGTGCGC CGTGATTGAC GGAAACTCGA CCACCTTCGA
 A3_5   TCTAACACCA ACATGTGCGC CGTGATTGAC GGAAACTCGA CCACCTTCGA
 A3_7   TCTAACACCA ACATGTGCGC CGTGATTGAC GGAAACTCGA CCACCTTCGA
 A3_3   TCTAACACCA ACATGTGCGC CGTGATTGAC GGAAACTCGA CCACCTTCGA
 42_12  TCCAACACCA ACATGTGCGC CGTGATTGAC GGGAACAGCA CCACCTTCGA
 AAV1   TCCAACACCA ACATGTGCGC CGTGATTGAC GGGAACAGCA CCACCTTCGA
 AAV2   TCCAACACCA ACATGTGCGC CGTGATTGAC GGGAACTCAA CGACCTTCGA
 AAV3   TCCAACACCA ACATGTGCGC CGTGATTGAC GGGAACAGCA CCACCTTCGA
 AAV8   TCCAACACCA ACATGTGCGC CGTGATTGAC GGGAACAGCA CCACCTTCGA
 AAV9   TCCAACACCA ACATGTGCGC CGTGATTGAC GGGAACAGCA CCACCTTCGA
 AAV7   TCCAACACCA ACATGTGCGC CGTGATTGAC GGGAACAGCA CCACCTTCGA
 44_2   TCCAACACCA ACATGTGCGC CGTGATTGAC GGGAACAGCA CCACCTTCGA
```

FIG. 1AH

```
         1651                                                          1700
  42_2   GCACCAGCAG CCGTTACAAG ACCGGATGTT CAAATTTGAA CTCACCCGCC
  42_8   GCACCAGCAG CCGTTACAAG ACCGGATGTT CAAATTTGAA CTCACCCGCC
  42_15  GCACCAGCAG CCGTTGCAGG ACCGGATGTT CAAATTTGAA CTCACCCGCC
  42_5b  GCACCAGCAG CCGTTACAAG ACCGGATGTT CAAATTTGAA CTCACCCGCC
  42_1b  .......... .......... .......... .......... ..........
  42_13  GCACCAGCAG CCGTTACAAG ACCGGATGTT CAAATTTGAA CTCACCCGCC
  42_3a  GCACCAGCAG CCGTTACAAG ACCGGATGTT CAAATTTGAA CTCACCCGCC
  42_4   .......... .......... .......... .......... ..........
  42_5a  GCACCAGCAG CCGTTGCAGG ACCGGATGTT CAAATTTGAA CTCACCCGCC
  42_10  .......... .......... .......... .......... ..........
  42_3b  .......... .......... .......... .......... ..........
  42_11  GCACCAGCAG CCGTTACAAG ACCGGATGTT CAAATTTGAA CTCACCCGCC
  42_6b  TGGAGCCAAC AAGAGACCCG CCCCCGATGA CGCGGATAAA AGCGAGCCCA
  43_1   GCACCAGCAG CCGTTGCAGG ACCGGATGTT CAAGTTCGAA CTCACCCGCC
  43_5   GCACCAGCAG CCGTTGCAGG ACCGGATGTT CAAGTTCGAA CTCACCCGCC
  43_12  GCACCAGCAG CCGTTGCAGG ACCGGATGTT CAAGTTCGAA CTCACCCGCC
  43_20  GCACCAGCAG CCGTTGCAGG ACCGGATGTT CAAATTTGAA CTCACCCGCC
  43_21  GCACCAGCAG CCGTTGCAGG ACCGGATGTT CAAATTTGAA CTCACCCGCC
  43_23  GCACCAGCAG CCGTTGCAGG ACCGGATGTT CAAATTTGAA CTCACCCGCC
  43_25  GCACCAGCAG CCGTTGCAGG ACCGGATGTT CAAATTTGAA CTCACCCGCC
  44_1   GCACCAGCAG CCGTTGCGGG ACCGGATGTT CAAGTTTGAA CTCACCCGCC
  44_5   GCACCAGCAG CCGTTGCAGG ACCGGATGTT CAAGTTTGAA CTCACCCGCC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   GCACCAGCAG CCGTTGCAAG ACCGGATGTT CAAATTTGAA CTTACCCGCC
  A3_5   GCACCAGCAG CCGTTGCAAG ACCGGATGTT CAAATTTGAA CTTACCCGCC
  A3_7   GCACCAGCAG CCGTTGCAAG ACCGGATGTT CAAATTTGAA CTTACCCGCC
  A3_3   GCACCAGCAG CCGTTGCAAG ACCGGATGTT CAAATTTGAA CTTACCCGCC
  42_12  GCACCAGCAG CCGTTACAAG ACCGGATGTT CAAATTTGAA CTCACCCGCC
  AAV1   GCACCAGCAG CCGTTGCAGG ACCGGATGTT CAAATTTGAA CTCACCCGCC
  AAV2   ACACCAGCAG CCGTTGCAAG ACCGGATGTT CAAATTTGAA CTCACCCGCC
  AAV3   GCATCAGCAG CCGCTGCAGG ACCGGATGTT TGAATTTGAA CTTACCCGCC
  AAV8   GCACCAGCAG CCTCTCCAGG ACCGGATGTT TAAGTTCGAA CTCACCCGCC
  AAV9   GCACCAGCAG CCTCTCCAGG ACCGGATGTT TAAGTTCGAA CTCACCCGCC
  AAV7   GCACCAGCAG CCGTTGCAGG ACCGGATGTT CAAATTTGAA CTCACCCGCC
  44_2   GCACCAGCAG CCGTTGCAGG ACCGGATGTT CAAGTTTGAA CTCACCCGCC
```

FIG. 1AI

```
         1701                                                     1750
 42_2    GTCTGGAGCA CGACTTTGGC AAGGTGACAA AGCAGGAAGT CAAAGAGTTC
 42_8    GTCTGGAGCA CGACTTTGGC AAGGTGACAA AGCAGGAAGT CAAAGAGTTC
 42_15   GTCTGGAGCA TGACTTTGGC AAGGTGACAA AGCAGGAAGT CAAAGAGTTC
 42_5b   GTCTGGAGCA CGACTTTGGC AAGGTGACAA AGCAGGAAGT CAAAGAGTTC
 42_1b   .......... .......... .......... .......... ..........
 42_13   GTCTGGAGCA TGACTTTGGC AAGGTGACAA AGCAGGAAGT CAAAGAGTTC
 42_3a   GTCTGGAGCA TGACTTTGGC AAGGTGACAA AGCAGGAAGT CAAAGAGTTC
 42_4    .......... .......... .......... .......... ..........
 42_5a   GTCTGGAGCA TGACTTTGGC AAGGCGACAA AGCAGGAAGT CAAAGAGTTC
 42_10   .......... .......... .......... .......... ..........
 42_3b   .......... .......... .......... .......... ..........
 42_11   GTCTGGAGCA CGACTTTGGC AAGGTGACAA AGCAGGAAGT CAAAGAGTTC
 42_6b   AGCGGGCCTG CCCCTCAGTC GCGGATCCAT CGACGTCAGA CGCGGAAGGA
 43_1    GTCTGGAGCA CGACTTTGGC AAGGTGACCA AGCAGGAAGT CAAAGAGTTC
 43_5    GTCTGGAGCA CGACTTTGGC AAGGTGACCA AGCAGGAAGT CAAAGAGTTC
 43_12   GTCTGGAGCA CGACTTTGGC AAGGTGACCA AGCAGGAAGT CAAAGAGTTC
 43_20   GTCTGGAGCA TGACTTTGGC AAGGTGACGA AGCAGGAAGT CAAAGAGTTC
 43_21   GTCTGGAGCA TGACTTTGGC AAGGTGACGA AGCAGGAAGT CAAAGAGTTC
 43_23   GTCTGGAGCA TGACTTTGGC AAGGTGACGA AGCAGGAAGT CAAAGAGTTC
 43_25   GTCTGGAGCA TGACTTTGGC AAGGTGACGA AGCAGGAAGT CAAAGGGTTC
 44_1    GTCTGGAGCA CGACTTTGGC AAGGTGACAA AGCAGGAAGT CAGAGAGTTC
 44_5    GTCTGGAGCA CGACTTTGGC AAGGTGACAA AGCAGGAAGT CAGAGAGTTC
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    GTTTGGATCA TGACTTTGGG AAGGTCACCA AGCAGGAAGT CAAAGACTTT
 A3_5    GTTTGGATCA TGACTTTGGG AAGGTCACCA AGCAGGAAGT CAAAGACTTT
 A3_7    GTTTGGATCA TGACTTTGGG AAGGTCACCA AGCAGGAAGT CAAAGACTTT
 A3_3    GTTTGGATCA TGACTTTGGG AAGGTCACCA AGCAGGAAGT CAAAGACTTT
 42_12   GTCTGGAGCA CGACTTTGGC AAGGTGACAA AGCAGGAAGT CAAAGAGTTC
 AAV1    GTCTGGAGCA TGACTTTGGC AAGGTGACAA AGCAGGAAGT CAAAGAGTTC
 AAV2    GTCTGGATCA TGACTTTGGG AAGGTCACCA AGCAGGAAGT CAAAGACTTT
 AAV3    GTTTGGACCA TGACTTTGGG AAGGTCACCA AACAGGAAGT AAAGGACTTT
 AAV8    GTCTGGAGCA CGACTTTGGC AAGGTGACAA AGCAGGAAGT CAAAGAGTTC
 AAV9    GTCTGGAGCA CGACTTTGGC AAGGTGACAA AGCAGGAAGT CAAAGAGTTC
 AAV7    GTCTGGAGCA CGACTTTGGC AAGGTGACGA AGCAGGAAGT CAAAGAGTTC
 44_2    GTCTGGAGCA CGACTTTGGC AAGGTGACAA AGCAGGAAGT CAGAGAGTTC
```

FIG. 1AJ

```
             1751                                                        1800
   42_2     TTCCGCTGGG CGCAGGATCA CGTGACCGAG GTGGCGCATG AGTTCTACGT
   42_8     TTCCGCTGGG CGCAGGATCA CGTGACCGAG GTGGCGCATG AGTTCTACGT
   42_15    TTCCGCTGGG CGCAGGATCA CGTGACCGAG GTGGCGCATG AGTTCTACGT
   42_5b    TTCCGCTGGG CGCAGGATCA CGTGACCGAG GTGGCGCATG AGTTCTACGT
   42_1b    .......... .......... .......... .......... ..........
   42_13    TTCCGCTGGG CGCAGGATCA CGTGACCGAG GTGGCGCATG AGTTCTACGT
   42_3a    TTCCGCTGGG CGCAGGATCA CGTGACCGAG GTGGCGCATG AGTTCTACGT
   42_4     .......... .......... .......... .......... ..........
   42_5a    TTCCGCTGGG CGCAGGATCA CGTGACCGAG GTGGCGCATG AGTTCTACGT
   42_10    .......... .......... .......... .......... ..........
   42_3b    .......... .......... .......... .......... ..........
   42_11    TTCCGCTGGG CGCAGGATCA CGTGACCGAG GTGGCGCATG AGTTCTACGT
   42_6b    GCTCCGGTGG ACTTTGCCGA CAGGTACCAA AACAAATGTT CTCGTCACGC
   43_1     TTCCGCTGGG CGCAGGATCA CGTGACCGAG GTGGCGCATG AGTTCTACGT
   43_5     TTCCGCTGGG CGCAGGATCA CGTGACCGAG GTGGCGCATG AGTTCTACGT
   43_12    TTCCGCTGGG CGCAGGATCA CGTGACCGAG GTGGCGCATG AGTTCTACGT
   43_20    TTCCGCTGGG CGCAGGATCA CGTGACCGAG GTGGCGCATG AGTTCCACGT
   43_21    TTCCGCTGGG CGCAGGATCA CGTGACCGAG GTGGCGCATG AGTTCCACGT
   43_23    TTCCGCTGGG CGCAGGATCA CGTGACCGAG GTGGCGCATG AGTTCCACGT
   43_25    TTCCGCTGGG CGCAGGATCA CGTGACCGAG GTGGCGCATG AGTTCCACGT
   44_1     TTCCGCTGGG CGCAGGATCA CGTGACCGAG GTGGCGCACG AGTTCTACGT
   44_5     TTCCGCTGGG CGCAGGATCA CGTGACCGAG GTGGCGCACG AGTTCTACGT
  223_10    .......... .......... .......... .......... ..........
  223_2     .......... .......... .......... .......... ..........
  223_4     .......... .......... .......... .......... ..........
  223_5     .......... .......... .......... .......... ..........
  223_6     .......... .......... .......... .......... ..........
  223_7     .......... .......... .......... .......... ..........
   A3_4     TTCCGGTGGG CTCAAGATCA CGTGACTGAG GTGGAGCATG AGTTCTACGT
   A3_5     TTCCGGTGGG CTCAAGATCA CGTGACTGAG GTGGAGCATG AGTTCTACGT
   A3_7     TTCCGGTGGG CTCAAGATCA CGTGACTGAG GTGGAGCATG AGTTCTACGT
   A3_3     TTCCGGTGGG CTCAAGATCA CGTGACTGAG GTGGAGCATG AGTTCTACGT
   42_12    TTCCGCTGGG CGCAGGATCA CGTGACCGAG GTGGCGCATG AGTTCTACGT
   AAV1     TTCCGCTGGG CGCAGGATCA CGTGACCGAG GTGGCGCATG AGTTCTACGT
   AAV2     TTCCGGTGGG CAAAGGATCA CGTGGTTGAG GTGGAGCATG AATTCTACGT
   AAV3     TTCCGGTGGG CTTCCGATCA CGTGACTGAC GTGGCTCATG AGTTCTACGT
   AAV8     TTCCGCTGGG CCAGTGATCA CGTGACCGAG GTGGCGCATG AGTTTTACGT
   AAV9     TTCCGCTGGG CCAGTGATCA CGTGACCGAG GTGGCGCATG AGTTTTACGT
   AAV7     TTCCGCTGGG CCAGTGATCA CGTGACCGAG GTGGCGCATG AGTTCTACGT
   44_2     TTCCGCTGGG CGCAGGATCA CGTGACCGAG GTGGCGCACG AGTTCTACGT
```

FIG. 1AK

```
        1801                                                            1850
                                                             P40/TATA
 42_2   CAGAAAGGGT GGAGCCAACA AGAGACCCGC CCCCGATGAC GCGGATAAAA
 42_8   CAGAAAGGGT GGAGCCAACA AGAGACCCGC CCCCGATGAC GCGGATAAAA
 42_15  CAGAAAGGGT GGAGCCAACA AGAGACCCGC CCCCGATGAC GCGGATAAAA
 42_5b  CAGAAAGGGT GGAGCCAACA AGAGACCCGC CCCCGATGAC GCGGATAAAA
 42_1b  .......... .......... .......... .......... ..........
 42_13  CAGAAAGGGT GGAGCCAACA AGAGACCCGC CCCCGATGAC GCGGATAAAA
 42_3a  CAGAAAGGGT GGAGCCAACA AGAGACCCGC CCCCGATGAC GCGGATAAAA
 42_4   .......... .......... .......... .......... ..........
 42_5a  CAGAAAGGGT GGAGCCAACA AGAGACCCGC CCCCGATGAC GCGGATAAAA
 42_10  .......... .......... .......... .......... ..........
 42_3b  .......... .......... .......... .......... ..........
 42_11  CAGAAAGGGT GGAGCCAACA AGAGACCCGC CCCCGATGAC GCGGATAAAA
 42_6b  GGGCATAGCG CTGACGTAAA TCACGTCATA GGGGAGTGGT CCTGTATTAG
 43_1   CAGAAAGGGC GGAGCCAGCA AAAGACCCGC CCCCGATGAC GCGGATATAA
 43_5   CAGAAAGGGC GGAGCCAGCA AAAGACCCGC CCCCGATGAC GCGGATATAA
 43_12  CAGAAAGGGC GGAGCCAGCA AAAGACCCGC CCCCGATGAC GCGGATATAA
 43_20  CAGAAAGGGT GGAGCCAACA AGAGACCCGC CCCCGATGAC GCGGATATAA
 43_21  CAGAAAGGGT GGAGCCAACA AGAGACCCGC CCCCGATGAC GCGGATATAA
 43_23  CAGAAAGGGT GGCGCCAACA AGAGACCCGC CCCCGATGAC GCGGATATAA
 43_25  CAGAAAGGGT GGAGCCAACA AGAGACCCGC CCCCGATGAC GCGGATATAA
 44_1   CAGAAAGGGT GGAGCCAACA AGAGACCCGC CCCCGATGAC GCGGATAAAA
 44_5   CAGAAAGGGT GGAGCCAACA AGAGACCCGC CCCCGATGAC GCGGATAAAA
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   CAAAAAGGGT GGAGCCAAGA AAAGGCCCGC CCCCGATGAT GTATATATAA
 A3_5   CAAAAAGGGT GGAGCCAAGA AAAGGCCCGC CCCCGATGAT GTATATATAA
 A3_7   CAAAAAGGGT GGAGCCAAGA AAAGGCCCGC CCCCGATGAT GTATATATAA
 A3_3   CAAAAAGGGT GGAGCCAAGA AAAGGCCCGC CCCCGATGAT GTATATATAA
 42_12  CAGAAAGGGT GGAGCCAACA AGAGACCCGC CCCCGATGAC GCGGATAAAA
 AAV1   CAGAAAGGGT GGAGCCAACA AAAGACCCGC CCCCGATGAC GCGGATAAAA
 AAV2   CAAAAAGGGT GGAGCCAAGA AAAGACCCGC CCCAGTGAC  GCAGATATAA
 AAV3   CAGAAAGGGT GGAGCTAAGA AACGCCCGC  CTCCAATGAC GCGGATGTAA
 AAV8   CAGAAAGGGC GGAGCCAGCA AAAGACCCGC CCCCGATGAC GCGGATAAAA
 AAV9   CAGAAAGGGC GGAGCCAGCA AAAGACCCGC CCCCGATGAC GCGGATAAAA
 AAV7   CAGAAAGGGC GGAGCCAGCA AAAGACCCGC CCCCGATGAC GCGGATATAA
 44_2   CAGAAAGGGT GGAGCCAACA AGAGACCCGC CCCCGATGAC GCGGATAAAA
                                                             P40/TATA
```

FIG. 1AL

```
            1851                                                              1900
                                          P40 RNA
    42_2    GCGAGCCCAA GCGGGCCTGC CCCTCAGTCG CGGATCCATC GACGTCAGAC
    42_8    GCGAGCCCAA GCGGGCCTGC CCCTCAGTCG CGGATCCATC GACGTCAGAC
   42_15    GCGAGCCCAA GCGGGCCTGC CCCTCAGTCG CGGATCCATC GACGTCAGAC
   42_5b    GCGAGCCCAA GCGGGCCTGC CCCTCAGTCG CGGATCCATC GACGTCAGAC
   42_1b    .......... .......... .......... .......... ..........
   42_13    GCGAGCCCAA GCGGGCCTGC CCCTCAGTCG CGGATCCATC GACGTCAGAC
   42_3a    GCGAGCCCAA GCGGGCCTGC CCCTCAGTCG CGGATCCATC GACGTCAGAC
    42_4    .......... .......... .......... .......... ..........
   42_5a    GCGAGCCCAA GCGGGCCCGC CCCTCAGTCG CGGATCCATC GACGTCAGAC
   42_10    .......... .......... .......... .......... ..........
   42_3b    .......... .......... .......... .......... ..........
   42_11    GCGAGCCCAA GCGGGCCTGC CCCTCAGTCG CGGATCCATC GACGTCAGAC
   42_6b    CTGTCACGTG AGTGCTTTTG CGACATTTTG C..ATCCATC GACGTCAGAC
    43_1    GCGAGCCCAA GCGGGCCTGC CCCTCAGTCG CGGATCCATC GACGTCAGAC
    43_5    GCGAGCCCAA GCGGGCCTGC CCCTCAGTCG CGGATCCATC GACGTCAGAC
   43_12    GCGAGCCCAA GCGGGCCTGC CCCTCAGTCG CGGATCCATC GACGTCAGAC
   43_20    GCGAGCCCAA GCGGGCCTGC CCCTCAGTCG CGGATCCATC GACGTCAGAC
   43_21    GCGAGCCCAA GCGGGCCTGC CCCTCAGTCG CGGATCCATC GACGTCAGAC
   43_23    GCGAGCCCAA GCGGGCCTGC CCCTCAGTCG CGGATCCATC GACGTCAGAC
   43_25    GCGAGCCCAA GCGGGCCTGC CCCTCAGTCG CGGATCCATC GACGTCAGAC
    44_1    GCGAGCCCAA GCGGGCCTGC CCCTCAGTCG CGGATCCATC GACGTCAGAC
    44_5    GCGAGCCCAA GCGGGCCTGC CCCTCAGTCG CGGATCCATC GACGTCAGAC
  223_10    .......... .......... .......... .......... ..........
   223_2    .......... .......... .......... .......... ..........
   223_4    .......... .......... .......... .......... ..........
   223_5    .......... .......... .......... .......... ..........
   223_6    .......... .......... .......... .......... ..........
   223_7    .......... .......... .......... .......... ..........
    A3_4    ATGAGCCCAA GCGGGCGCGC GAGTCAGTTG CGCAGCCATC GACGTCAGAC
    A3_5    ATGAGCCCAA GCGGGCGCGC GAGTCAGTTG CGCAGCCATC GACGTCAGAC
    A3_7    ATGAGCCCAA GCGGGCGCGC GAGTCAGTTG CGCAGCCATC GACGTCAGAC
    A3_3    ATGAGCCCAA GCGGGCGCGC GAGTCAGTTG CGCAGCCATC GACGTCAGAC
   42_12    GCGAGCCCAA GCGGGCCTGC CCCTCAGTCG CGGATCCATC GACGTCAGAC
    AAV1    GCGAGCCCAA GCGGGCCTGC CCCTCAGTCG CGGATCCATC GACGTCAGAC
    AAV2    GTGAGCCCAA ACGGGTGCGC GAGTCAGTTG CGCAGCCATC GACGTCAGAC
    AAV3    GCGAGCCAAA ACGGGAGTGC ACGTCACTTG CGCAGCCGAC AACGTCAGAC
    AAV8    GCGAGCCCAA GCGGGCCTGC CCCTCAGTCG CGGATCCATC GACGTCAGAC
    AAV9    GCGAGCCCAA GCGGGCCTGC CCCTCAGTCG CGGATCCATC GACGTCAGAC
    AAV7    GCGAGCCCAA GCGGGCCTGC CCCTCAGTCG CGGATCCATC GACGTCAGAC
    44_2    GCGAGCCCAA GCGGGCCTGC CCCTCAGTCG CGGATCCATC GACGTCAGAC
                                                   P40 RNA
```

FIG. 1AM

```
        1901                                                    1950
  42_2   GCGGAAGGAG CTCCGGTGGA CTTTGCCGAC AGGTACCAAA ACAAATGTTC
  42_8   GCGGAAGGAG CTCCGGTGGA CTTTGCCGAC AGGTACCAAA ACAAATGTTC
  42_15  GCGGAAGGAG CTCCGGTGGA CTTTGCCGAC AGGTACCAAA ACAAATGTTC
  42_5b  GCGGAAGGAG CTCCGGTGGA CTTTGCCGAC AGGTACCAAA ACAAATGTTC
  42_1b  .......... .......... .......... .......... ..........
  42_13  GCGGAAGGAG CTCCGGTGGA CTTTGCCGAC AGGTACCAAA ACAAATGTTC
  42_3a  GCGGAAGGAG CTCCGGTGGA CTTTGCCGAC AGGTACCAAA ACAAATGTTC
  42_4   .......... .......... .......... .......... ..........
  42_5a  GCGGAAGGAG CTCCGGTGGA CTTTGCCGAC AGGTACCAAA ACAAATGTTC
  42_10  .......... .......... .......... .......... ..........
  42_3b  .......... .......... .......... .......... ..........
  42_11  GCGGAAGGAG CTCCGGTGGA CTTTGCCGAC AGGTACCAAA ACAAATGTTC
  42_6b  GCGGAAGGAG CTCCGGTGGA CTTTGCCGAC AGGTACCAAA ACAAGTGTTC
  43_1   GCGGAAGGAG CTCCGGTGGA CTTTGCCGAC AGGTACCAAA ACAAATGTTC
  43_5   GCGGAAGGAG CTCCGGTGGA CTTTGCCGAC AGGTACCAAA ACAAATGTTC
  43_12  GCGGAAGGAG CTCCGGTGGA CTTTGCCGAC AGGTACCAAA ACAAATGTTC
  43_20  GCGGAAGGAG CTCCGGTGGA CTTTGCCGAC AGGTACCAAA ACAAATGTTC
  43_21  GCGGAAGGAG CTCCGGTGGA CTTTGCCGAC AGGTACCAAA ACAAATGTTC
  43_23  GCGGAAGGAG CTCCGGTGGA CTTTGCCGAC AGGTACCAAA ACAAATGTTC
  43_25  GCGGAAGGAG CTCCGGTGGA CTTTGCCGAC AGGTACCAAA ACAAATGTTC
  44_1   GCGGAAGGAG CTCCGGTGGA CTTTGCCGAC AGGTACCAAA ACAAATGTTC
  44_5   GCGGAAGGAG CTCCGGTGGA CTTTGCCGAC AGGTACCAAA ACAAATGTTC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   GCGGA...AG CTTCGATAAA CTACGCGGGC AGGTACCAAA ACAAATGTTC
  A3_5   GCGGA...AG CTTCGATAAA CTACGCGGAC AGGTACCAAA ACAAATGTTC
  A3_7   GCGGA...AG CTTCGATAAA CTACGCGGAC AGGTACCAAA ACAAATGTTC
  A3_3   GCGGA...AG CTTCGATAAA CTACGCGGAC AGGTACCAAA ACAAATGTTC
  42_12  GCGGAAGGAG CTCCGGTGGA CTTTGCCGAC AGGTACCAAA ACAAATGTTC
  AAV1   GCGGAAGGAG CTCCGGTGGA CTTTGCCGAC AGGTACCAAA ACAAATGTTC
  AAV2   GCGGA...AG CTTCGATCAA CTACGCAGAC AGGTACCAAA ACAAATGTTC
  AAV3   GCGGA...AG CACCGGCGGA CTACGCGGAC AGGTACCAAA ACAAATGTTC
  AAV8   GCGGAAGGAG CTCCGGTGGA CTTTGCCGAC AGGTACCAAA ACAAATGTTC
  AAV9   GCGGAAGGAG CTCCGGTGGA CTTTGCCGAC AGGTACCAAA ACAAATGTTC
  AAV7   GCGGAAGGAG CTCCGGTGGA CTTTGCCGAC AGGTACCAAA ACAAATGTTC
  44_2   GCGGAAGGAG CTCCGGTGGA CTTTGCCGAC AGGTACCAAA ACAAATGTTC
```

FIG. 1AN

```
          1951                                                    2000
 42_2    TCGTCACGCG GGCATGCTTC AGATGCTGTT TCCCTG.CAA GACATGCGAG
 42_8    TCGTCACGCG GGCATGCTTC AGATGCTGTT TCCCTG.CAA GACATGCGAG
 42_15   TCGTCACGCG GGCATGCTTC AGATGCTGTT TCCCTG.CAA GACATGCGAG
 42_5b   TCGTCACGCG GGCATGCTTC AGATGCTGTT TCCCTG.CAA GACATGCGAG
 42_1b   .......... .......... ....GAATTC GCCCTT.... .GGCTGCGTC
 42_13   TCGTCACGCG GGCATGCTTC AGATGCTGTT TCCCTG.CAA GACATGCGAG
 42_3a   TCGTCACGCG GGCATGCTTC AGATGCTGCT TCCCTG.CAA GACATGCGAG
 42_4    .......... .......... ....GAATTC GCCCTTTCTA CGGCTGCGTC
 42_5a   TCGTCACGCG GGCATGCTTC AGATGCTGTT TCCCTG.CAA AACATGCGAG
 42_10   .......... .......... ....GAATTC GCCCTTTCTA CGGCTGCGTC
 42_3b   .......... .......... ....GAATTC GCCCTTTCTA CGGCTGCGTC
 42_11   TCGTCACGCG GGCATGCTTC AGATGCTGTT TCCCTG.CAA GACATGCGAG
 42_6b   TCGTCACGCG GGCATGCTTC AGATGCTGTT TCCCTG.CAA GACATGCGAG
 43_1    TCGTCACGCG GGCATGCTTC AGATGCTGTT TCCCTG.CAA AACGTGCGAG
 43_5    TCGTCACGCG GGCATGCTTC AGACGCTGTT TCCCTG.CAA AACGTGCGAG
 43_12   TCGTCACGCG GGCATGCTCC AGATGCTGTT TCCCTG.CAA AACGTGCGAG
 43_20   TCGTCACGCG GGCATGCTTC AGATGCTGTT TCCCTG.CAA GACATGCGAG
 43_21   TCGTCACGCG GGCATGCTTC AGATGCTGTT TCCCTG.CAA GACATGCGAG
 43_23   TCGTCACGCG GGCATGCTTC AGATGCTGTT TCCCTG.CAA GACATGCGAG
 43_25   TCGTCACGCG GGCATGCTTC AGATGCTGTT TCCCTG.CAA GACATGCGAG
 44_1    TCGTCACGCG GGCATGCTTC AGATGCTGTT TCCCTG.CAA AACATGCGAG
 44_5    TCGTCACGCG GGCATGCTTC AGATGCTGTT TCCCTG.CAA AACATGCGAG
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    TCGTCACGTG GGCATGAATC TGATGCTGTT TCCCTG.TCG ACAATGCGAA
 A3_5    TCGTCACGTG GGCATGAATC TGATGCTGTT TCCCTG.TCG ACAATGCGAA
 A3_7    TCGTCACGTG GGCATGAATC TGATGCTGTT TCCCTG.TCG ACAATGCGAA
 A3_3    TCGTCACGTG GGCATGAATC TGATGCTGTT TCCCTG.TCG ACAATGCGAA
 42_12   TCGTCACGCG GGCATGCTTC AGATGCTGTT TCCCTG.CAA GACATGCGAG
 AAV1    TCGTCACGCG GGCATGCTTC AGATGCTGTT TCCCTG.CAA GACATGCGAG
 AAV2    TCGTCACGTG GGCATGAATC TGATGCTGTT TCCCTG.CAG ACAATGCGAG
 AAV3    TCGTCACGTG GGCATGAATC TGATGCTTTT TCCCTG.TAA ACATGCGAG
 AAV8    TCGTCACGCG GGCATGCTTC AGATGCTGTT TCCCTG.CAA AACGTGCGAG
 AAV9    TCGTCACGCG GGCATGCTTC AGATGCTGCT TCCCTG.CAA AACGTGCGAG
 AAV7    TCGTCACGCG GGCATGATTC AGATGCTGTT TCCCTG.CAA AACGTGCGAG
 44_2    TCGTCACGCG GGCATGCTTC AGATGCTGTT TCCCTG.CAA AACATGCGAG
```

FIG. 1AO

```
             2001                                                       2050
    42_2     AGAATGAATC AGAATTTCAA CATTTGCTTC ACGCACGGGA CCAGAGACTG
    42_8     AGAATGAATC AGAATTTCAA CATTTGCTTC ACGCACGGGA CCAGAGACTG
   42_15     AGAATGAATC AGAATTTCAA CATTTGCTTC ACGCGCGGGA CCAGAGACTG
   42_5b     AGAATGAATC AGAATTTCAA CATTTGCTTC ACGCACGGGA CCAGAGACTG
   42_1b     A.ACTGGACC A..ATGAGAA CTTTCCCTTC A........A CGATTGCGTC
   42_13     AGAATGAATC AGAATTTCAA CATTTGCTTC ACGCACGGGA CCAGAGACTG
   42_3a     AGAATGAATC AGAATTTCAG CATTTGCTTC ACGCACGGGA CCAGAGACTG
    42_4     A.ACTGGACC A..ATGAGAA CTTTCCCTTC A........A CGATTGCGTC
   42_5a     AGAATGAATC AGAATTTCAA CATTTGCTTC ACGCACGGGA CCAGAGACTG
   42_10     A.ACTGGACC A..ATGAGAA CTTTCCCTTC A........A CGATTGCGTC
   42_3b     A.ACTAGACC A..ATGAGAA CTTTCCCTTC A........A CGATTGCGTC
   42_11     AGAATGAATC AGAATTTCAA CATTTGCTTC ACGCACGGGA CCGGAGACTG
   42_6b     AGAATGAATC AGAATTTCAA CATTTGCTTC ACGCACGGGA CCAGAGACTG
    43_1     AAAATGAATC AGAATTTCAA CATTTGCTTC ACGCACGGGG TCAGAGACTG
    43_5     AGAATGAATC AGAATTTCAA CATTTGCTTC ACGCACGGGG TCAGAGACTG
   43_12     AGAATGAATC AGAATTTCAA CATTTGCTTC ACGCACGGGG TCAGAGACTG
   43_20     AGAATGAATC AGAATTTCAA CATTTGCTTC ACGCACGGGA CCAGAGACTG
   43_21     AGAATGAATC AGAATTTCAA CATTTGCTTC ACGCACGGGA CCAGAGACTG
   43_23     AGAATGAATC AGAATTTCAA CATTTGCTTC ACGCACGGGA CCAGAGACTG
   43_25     AGAATGAATC AGAATTTCAA CATTTGCTTC ACGCACGGGA CCAGAGACTG
    44_1     AGAATGAATC AGAATTTCAA CATTTGCTTC ACGCACGGGA CCAGAGACTG
    44_5     AGAATGAATC AGAATTTCAA CATTTGCTTC ACGCACGGGA CCAGAGACTG
  223_10     .......... .......... .......... .......... ..........
   223_2     .......... .......... .......... .......... ..........
   223_4     .......... .......... .......... .......... ..........
   223_5     .......... .......... .......... .......... ..........
   223_6     .......... .......... .......... .......... ..........
   223_7     .......... .......... .......... .......... ..........
    A3_4     AGAATGAATC AGAATTCAAA TATCTGCTTC ACACACGGGC AAAAAGACTG
    A3_5     AGAATGAATC AGAATTCAAA TATCTGCTTC ACACACGGGC AAAAAGACTG
    A3_7     AGAATGAATC AGAATTCAAA TATCTGCTTC ACACACGGGC AAAAAGACTG
    A3_3     AGAATGAATC AGAATTCAAA TATCTGCTTC ACACACGGGC AAAAAGACTG
   42_12     AGAATGAATC AGAATTTCAA CATTTGCTTC ACGCACGGGA CCAGAGACTG
    AAV1     AGAATGAATC AGAATTTCAA CATTTGCTTC ACGCACGGGA CGAGAGACTG
    AAV2     AGAATGAATC AGAATTCAAA TATCTGCTTC ACTCACGGAC AGAAAGACTG
    AAV3     AGAATGAATC AAATTTCCAA TGTCTGTTTT ACGCATGGTC AAAGAGACTG
    AAV8     AGAATGAATC AGAATTTCAA CATTTGCTTC ACACACGGGG TCAGAGACTG
    AAV9     AGAATGAATC AGAATTTCAA CATTTGCTTC ACACACGGGG TCAGAGACTG
    AAV7     AGAATGAATC AGAATTTCAA CATTTGCTTC ACACACGGGG TCAGAGACTG
    44_2     AGAATGAATC AGAATTTCAA CATTTGCTTC ACGCACGGGA CCAGAGACTG
```

FIG. 1AP

```
           2051                                                  2100
 42_2     TTCAGAATGT TTCCCCGGCG TGTCAGAATC TCAACC.... ..GGTCGTCA

42_8     TTCAGAATGT TTCCCCGGCG TGTCAGAATC TCAACC.... ..GGTCGTCA
 42_15    TTCAGAATGT TTCCCGGGCG TGTCAGAATC TCAACC.... ..GGTCGTCA
 42_5b    TTCAGAATGT TTCCCCGGCG TGTCAGAATC TCAACC.... ..GGTCGTCA
 42_1b    GACAAGATGG TGATCTGGTG GG..AGGAGG GCAAGA.... ..TGACGGCC
 42_13    TTCAGAATGT TTCCCCGGCG TGTCAGAATC TCAACC.... ..GGTCGTCA
 42_3a    TTCAGAATGT TTCCCCGGCG TGTCAGAATC TCAACC.... ..GGTCGTCA
 42_4     GACAAGATGG TGATCTGGTG GG..AGGAGG GCAAGA.... ..TGACGGCC
 42_5a    TTCAGAATGT TTCCCCGGCG TGTCAGAATC TCAACC.... ..GGTCGTCA
 42_10    GACAAGATGG TGATCTGGTG GG..AGGAGG GCAAGA.... ..TGACGGCC
 42_3b    GACAAGATGG TGATCTGGTG GG..AGGAGG GCAAGA.... ..TGACGGCC
 42_11    TTCAGAATGT TTCCCCGGCG TGTCAGAATC TCAACC.... ..GGTCGTCA
 42_6b    TTCAGAATGT TTCCCCGGCG TGTCAGAATC TCAACC.... ..GGTCGTCA
 43_1     CTCAGAATGT TTCCCCGGTG CATCAGAATC TCAACC.... ..GGTCGTCA
 43_5     CTCAGAATGT TTCCCCGGTG CATCAGAATC TCAACC.... ..GGTCGTCA
 43_12    CTCAGAATGT TTCCCCGGTG CATCAGAATC TCAACC.... ..GGTCGTCA
 43_20    TTCAGAATGT TTCCCCGGCG TGTCAGAATC TCAACC.... ..GGTCGTCA
 43_21    TTCAGAATGT TTCCCCGGCG TGTCAGAATC TCAACC.... ..GGTCGTCA
 43_23    TTCAGAATGT TTCCCCGGCG TGTCAGAATC TCAACC.... ..GGTCGTCA
 43_25    TTCAGAATGT TTCCCCGGCG TGTCAGAATC TCAACC.... ..GGTCGTCA
 44_1     TTCAGAATGT TTCCCCGGCG TGTCAGAATC TCAACC.... ..GGTCGTCA
 44_5     TTCAGAATGT TTCCCCGGCG TGTCAGAATC TCAACC.... ..GGTTGTCA
223_10    .......... .......... .......... .......... ..........
223_2     .......... .......... .......... .......... ..........
223_4     .......... .......... .......... .......... ..........
223_5     .......... .......... .......... .......... ..........
223_6     .......... .......... .......... .......... ..........
223_7     .......... .......... .......... .......... ..........
 A3_4     TTTGGAATGC TTTCCCG... TGTCAGAATC TCAACCCGTT TCTGTCGTCA
 A3_5     TTTGGAATGC TTTCCCG... TGTCAGAATC TCAACCCGTT CCTGTCGTCA
 A3_7     TTTGGAATGC TTTCCCG... TGTCAGAATC TCAACCCGTT TCTGTCGTCA
 A3_3     TTTGGAATGC TTTCCCG... TGTCAGAATC TCAACCCGTT TCTGTCGTCA
 42_12    TTCAGAATGT TTCCCCGGCG TGTCAGAATC TCAACC.... ..GGTCGTCA
 AAV1     TTCAGAGTGC TTCCCCGGCG TGTCAGAATC TCAACC.... ..GGTCGTCA
 AAV2     TTTAGAGTGC TTTCCCG... TGTCAGAATC TCAACCCGTT TCTGTCGTCA
 AAV3     TGGGGAATGC TTCCCTGGAA TGTCAGAATC TCAACCCGTT TCTGTCGTCA
 AAV8     CTCAGAGTGT TTCCCCGGCG TGTCAGAATC TCAACC.... ..GGTCGTCA
 AAV9     CTCAGAGTGT TTCCCCGGCG TGTCAGAATC TCAACC.... ..GGTCGTCA
 AAV7     TTTAGAGTGT TTCCCCGGCG TGTCAGAATC TCAACC.... ..GGTCGTCA
 44_2     TTCAGAATGT TTCCCCGGCG TGTCAGAATC TCAACC.... ..GGTCGTCA
```

FIG. 1AQ

```
         2101                                                    2150
  42_2   GAAAGAGGAC GTATCGGAAA CTCTGTGCCA TTCATCATCT GCTGGGG.CG

42_8   GAAAGAGGAC GTATCGGAAA CTCTGTGCCA TTCATCATCT GCTAGGG.CG
 42_15   GAAAGAGGAC GTATCGGAAA CTCTGTGCCA TTCATCATCT GCTGGGG.CG
 42_5b   GAAAGAGGAC GTATCGGAAA CTCTGTGCCA TTCATCATCT GCTGGGG.CG
 42_1b   .AAGGTCGTG GAGTCCGCCA AG....GCCA TTCATCATCT GCTGGGG.CG
 42_13   GAAAGAGGAC GTATCGGAAA CTCTGTGCCA TTCATCATCT GCTGGGG.CG
 42_3a   GAAAGAGGAC GTATCGGAAA CTCTGTGCCA TTCATCATCT GCTGGGG.CG
  42_4   .AAGGTCGTG GAGTCCGCCA AG....GCCA TTCATCATCT GCTGGGG.CG
 42_5a   GAAAGAGGAC GTATCGGAAA CTCTGTGCCA TTCATCATCT GCTGGGG.CG
 42_10   AA....GGTC GTGAAGTCCG CCAAG.GCCA TTCATCATCT GCTGGGG.CG
 42_3b   AA....GGTC GTGGAGTCCG CCAAG.GCCA TTCATCATCT GCTGGGG.CG
 42_11   GAAAGAGGAC GTATCGGAAA CTCTGTGCCA TTCATCATCT GCTGGGG.CG
 42_6b   GAAAGAGGAC GTATCGGAAA CTCTGTGCCA TTCATCATCT GCTGGGG.CG
  43_1   GAAAAAAAC GTATCAGAAA CTGTGTGCCA TTCATCATCT GCTGGGG.CG
  43_5   GAAAAAAAC GTATCAGAAA CTGTGTGCCA TTCATCATCT GCTGGGG.CG
 43_12   GAAAAAAAC GTATCAGAAA CTGTGTGCCA TTCATCATCT GCTGGGG.CG
 43_20   GAAAGAGGAC GTATCGGAAA CTCTGTGCGA TTCATCATCT GCTGGGG.CG
 43_21   GAAAGAGGAC GTATCGGAAA CTCTGTGCGA TTCATCATCT GCTGGGG.CG
 43_23   GAAAGAGGAC GTATCGGAAA CTCTGTGCGA TTCATCATCT GCTGGGG.CG
 43_25   GAAAGAGGAC GTATCGGAAA CTCTGTGCGA TTCATCATCT GCTGGGG.CG
  44_1   GAAAAAAGAC GTATCGGAAA CTCTGTGCGA TTCATCATCT GCTGGGG.CG
  44_5   GAAAAAAGAC GTATCGGAAA CTCTGTGCGA TTCATCATCT GCTGGGG.CG
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   GAAAAACG.. .TATCAGAAA CTTTGTTACA TTCATCATAT CATGGGA.AA
  A3_5   GAAAAACG.. .TATCAGAAA CTTTGTTACA TTCATCATAT CATGGGA.AA
  A3_7   GAAAAACG.. .TATCAGAAA CTTTGTTACA TTCATCATAT CATGGGA.AA
  A3_3   GAAAAACG.. .TATCAGAAA CTTTGTTACA TTCATCATAT CATGGGA.AA
 42_12   GAAAGAGGAC GTATCGGAAA CTCTGTGCCA TTCATCATCT GCTGGGG.CG
  AAV1   GAAAGAGGAC GTATCGGAAA CTCTGTGCCA TTCATCATCT GCTGGGG.CG
  AAV2   AAAAGGCG.. .TATCAGAAA CTGTGCTACA TTCATCATAT CATGGGA.AA
  AAV3   AAAAGAAGAC TTATCAGAAA CTGTGTCCAA TTCATCATAT CCTGGGA.AG
  AAV8   GAAAGAGGAC GTATCGGAAA CTCTGTGCGA TTCATCATCT GCTGGGG.CG
  AAV9   GAAAGAGGAC GTATCGGAAA CTCTGTGCGA TTCATCATCT GCTGGGG.CG
  AAV7   GAAAAAAGAC GTATCGGAAA CTCTGCGCGA TTCATCATCT GCTGGGG.CG
  44_2   GAAAAAAGAC GTATCGGAAA CTCTGTGCGA TTCATCATCT GCTGGGGGCG
```

FIG. 1AR

```
       2151                                                    2200
 42_2   GGCTCCCGAG ATTGCTTGCT CGGCCTGCGA TCTGGTCAAC GTGGACCTGG
 42_8   GGCTCCCGAG ATTGCTTGCT CGGCCTGCGA TCTGGTCAAC GTGGACCTGG
42_15   GGCTCCCGAG ATTGCTTGCT CGGCCTGCGA TCTGGTCAAC GTGGACCTGG
42_5b   GGCTCCCGAG ATTGCTTGCT CGGCCTGCGA TCTGGTCAAC GTGGACCTGG
42_1b   GGCTCCCGAG ATTGCTTGCT CGGCCTGCGA TCTGGTCAAC GTGGACCTGG
42_13   GGCTCCCGAG ATTGCTTGCT CGGCCTGCGA TCTGGTCAAC GTGGACCTGG
42_3a   GGCTCCCGAG ATTGCTTGCT CGGCCTGCGA TCTGGTCAAC GTGGACCTGG
 42_4   GGCTCCCGAG ATTGCTTGCT CGGCCTGCGA TCTGGTCAAC GTGGACCTGG
42_5a   GGCTCCCGAG ATTGCTTGCT CGGCCTGCGA TCTGGTCAAC GTGGACCTGG
42_10   GGCTCCCGAG ATTGCTTGCT CGGCCTGCGA TCTGGTCAAC GTGGACCTGG
42_3b   GGCTCCCGAG ATTGCTTGCT CGGCCTGCGA TCTGGTCAAC GTGGACCTGG
42_11   GGCTCCCGAG ATTGCTTGCT CGGCCTGCGA TCTGGTCAAC GTGGACCTGG
42_6b   GGCTCCCGAG ATTGCTTGCT CGGCCTGCGA TCTGGTCAAC GTGGACCTGG
 43_1   GGCACCCGAG ATTGCTTGCT CGGCCTGCGA TCTGGTCAAC GTGGACCTGG
 43_5   GGCACCCGAG ATTGCTTGCT CGGCCTGCGA TCTGGTCAAC GTGGACCTGG
43_12   GGCACCCGAG ATTGCTTGCT CGGCCTGCGA TCTGGTCAAC GTGGACCTGG
43_20   GGCTCCCGAG ATTGCTTGCT CGGCCTGCGA TCTGGTCAAC GTGGACCTGG
43_21   GGCTCCCGAG ATTGCTTGCT CGGCCTGCGA TCTGGTCAAC GTGGACCTGG
43_23   GGCTCCCGAG ATTGCTTGCT CGGCCTGCGA TCTGGTCAAC GTGGACCTGG
43_25   GGCTCCCGAG ATTGCTTGCT CGGCCTGCGA TCTGGTCAAC GTGGACCTGG
 44_1   GGCACCCGAG ATTGCTTGCT CGGCCTGCGA TCTGGTCAAC GTGGACCTAG
 44_5   GGCACCCGAG ATTGCTTGCT CGGCCTGCGA TCTGGTCAAC GTGGACCTAG
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   AGAACCAGAC ...GCCTGCA CTGCCTGCGA CCTGGTAAAT GTGGACTTGG
 A3_5   AGTACCAGAC ...GCCTGCA CTGCCTGCGA CCTGGTAAAT GTGGACTTGG
 A3_7   AGTACCAGAC ...GCCTGCA CTGCCTGCGA CCTGGTAAAT GTGGACTTGG
 A3_3   AGTACCAGAC ...GCCTGCA CTGCCTGCGA CCTGGTAAAT GTGGACTTGG
42_12   GGCTCCCGAG ATTGCTTGCT CGGCCTGCGA TCTGGTCAAC GTGGACCTGG
 AAV1   GGCTCCCGAG ATTGCTTGCT CGGCCTGCGA TCTGGTCAAC GTGGACCTGG
 AAV2   GGTGCCAGAC ...GCTTGCA CTGCCTGCGA TCTGGTCAAT GTGGATTTGG
 AAV3   GGCACCCGAG ATTGCCTGTT CGGCCTGCGA TTTGGCCAAT GTGGACTTGG
 AAV8   GGCTCCCGAG ATTGCTTGCT CGGCCTGCGA TCTGGTCAAC GTGGACCTGG
 AAV9   GGCTCCCGAG ATTGCTTGCT CGGCCTGCGA TCTGGTCAAC GTGGACCTGG
 AAV7   GGCGCCCGAG ATTGCTTGCT CGGCCTGCGA CCTGGTCAAC GTGGACCTGG
 44_2   GGCACCCGAG ATTGCTTGCT CGGCCTGCGA TCTGGTCAAC GTGGACCTAG
```

FIG. 1AS

```
             2201                                                    2250
                         Rep 78 stop      vp1 start
     42_2   ATGACCGTGT TTCTGAGCAA TAAATGACTT AAACCAGGTA TGGCTGCCGA
     42_8   ATGACTGTGT TTCTGAGCAA TAAATGACTT AAACCAGGTA TGGCTGCCGA
    42_15   ATGACTGTGT TTCTGAGCAA TAAATGACTT AAACCAGGTA TGGCTGCCGA
    42_5b   ATGACTGTGT TTCTGAGCAA TAAATGACTT AAACCAGGTA TGGCTGCCGA
    42_1b   ATGACTGTGT TTCTGAGCAA TAAATGACTT AAACCAGGTA TGGCTGCCGA
    42_13   ATGACTGTGT TTCTGAGCAA TAAATGACTT AAACCAGGTA TGGCTGCCGA
    42_3a   ATGACTGTGT TTCTGAGCAA TAAATGACTT AAACCAGGTA TGGCTGCCGA
     42_4   ATGACTGTGT TTCTGAGCAA TAAATGACTT AAACCAGGTA TGGCTGCCGA
    42_5a   ATGACTGTGT TTCTGAGCAA TAAATGACTT AAACCAGGTA TGGCTGCCGA
    42_10   ATGACTGTGT TTCTGAGCAA TAAATGACTT AAACCAGGTA TGGCTGCCGA
    42_3b   ATGACTGTGT TTCTGAGCAA TAAATGACTT AAACCAGGTA TGGCTGCCGA
    42_11   ATGACTGTGT TTCTGAGCAA TAAATGACTT AAACCAGGTA TGGCTGCCGA
    42_6b   ATGACTGTGT TTCTGAGCAA TAAATGACTT AAACCAGGTA TGGCTGCCGA
     43_1   ACGACTGTGT TTCTGAGCAA TAAATGACTT AAACCAGGTA TGGCTGCCGA
     43_5   ACGACTGTGT TTCTGAGCAA TAAATGACTT AAACCAGGTA TGGCTGCCGA
    43_12   ACGACTGTGT TTCTGAGCAA TAAATGACTT AAACCAGGTA TGGCTGCCGA
    43_20   ATGACTGTGT TTCTGAGCAA TAAATGACTT AAACCAGGTA TGGCTGCCGA
    43_21   ATGACTGTGT TTCTGAGCAA TAAATGACTT AAACCAGGTA TGGCTGCCGA
    43_23   ATGACTGTGT TTCTGAGCAA TAAATGACTT AAACCAGGTA TGGCTGCCGA
    43_25   ATGACTGTGT TTCTGAGCAA TAAATGACTT AAACCAGGTA TGGCTGCCGA
     44_1   ATGACTGTGT TTCTGAGCAA TAAATGACTT AAACCAGGTA TGGCTGCCGA
     44_5   ATGACTGTGT TTCTGAGCAA TAAATGACTT AAACCAGGTA TGGCTGCCGA
   223_10   .......... .......... .......... .......... ..........
    223_2   .......... .......... .......... .......... ..........
    223_4   .......... .......... .......... .......... ..........
    223_5   .......... .......... .......... .......... ..........
    223_6   .......... .......... .......... .......... ..........
    223_7   .......... .......... .......... .......... ..........
     A3_4   ATGACTGTAT TTCTGAGCAA TAAATGACTT AAATCAGGTA TGGCTGCTGA
     A3_5   ATGACTGTAT TTCTGAGCAA TAAATGACTT AAATCAGGTA TGGCTGCTGA
     A3_7   ATGACTGTAT TTCTGAGCAA TAAATGACTT AAATCAGGTA TGGCTGCTGA
     A3_3   ATGACTGTAT TTCTGAGCAA TAAATGACTT AAATCAGGTA TGGCTGCTGA
    42_12   ATGACTGTGT TTCTGAGCAA TAAATGACTT AAACCAGGTA TGGCTGCCGA
     AAV1   ATGACTGTGT TTCTGAGCAA TAAATGACTT AAACCAGGTA TGGCTGCCGA
     AAV2   ATGACTGCAT CTTTGAACAA TAAATGATTT AAATCAGGTA TGGCTGCCGA
     AAV3   ATGACTGTGT TTCTGAGCAA TAAATGACTT AAACCAGGTA TGGCTGCTGA
     AAV8   ATGACTGTGT TTCTGAGCAA TAAATGACTT AAACCAGGTA TGGCTGCCGA
     AAV9   ATGACTGTGT TTCTGAGCAA TAAATGACTT AAACCAGGTA TGGCTGCCGA
     AAV7   ACGACTGCGT TTCTGAGCAA TAAATGACTT AAACCAGGTA TGGCTGCCGA
     44_2   ATGACTGTGT TTCTGAGCAA TAAATGACTT AAACCAGGTA TGGCTGCCGA
                         Rep78 stop                    vp1 start
```

FIG. 1AT

```
           2251                                                              2300
                                                    Rep68 stop
   42_2    TGGTTATCTT CCAGATTGGC TCGAGGACAA CCTCTCTGAG GGCATTCGCG
   42_8    TGGTTATCTT CCAGATTGGC TCGAGGACAA CCTCTCTGAG GGCATTCGCG
  42_15    TGGTTATCTT CCAGATTGGC TCGAGGACAA CCTCTCTGAG GGCATTCGCG
  42_5b    TGGTTATCTT CCAGATTGGC TCGAGGACAA CCTCTCTGAG GGCATTCGCG
  42_1b    TGGTTATCTT CCAGATTGGC TCGAGGACAA CCTCTCTGAG GGCATTCGCG
  42_13    TGGTTATCTT CCAGATTGGC TCGAGGACAA CCTCTCTGAG GGCATTCGCG
  42_3a    TGGTCATCTT CCAGATTGGC TCGAGGACAA CCTCTCTGAG GGCATTCGCG
   42_4    TGGTTATCTT CCAGATTGGC TCGAGGACAA CCTCTCTGAG GGCATTCGCG
  42_5a    TGGTTATCTT CCAGATTGGC TCGAGGACAA CCTCTCTGAG GGCATTCGCG
  42_10    TGGTTATCTT CCAGATTGGC TCGAGGACAA CCTCTCTGAG GGCATTCGCG
  42_3b    TGGTTATCTT CCAGATTGGC TCGAGGACAA CCTCTCTGAG GGCATTCGCG
  42_11    TGGTTATCTT CCAGATTGGC TCGAGGACAA CCTCTCTGAG GGCATTCGCG
  42_6b    TGGTTATCTT CCAGATTGGC TCGAGGACAA CCTCTCTGAG GGCATTCGCG
   43_1    TGGTTATCTT CCAGATTGGC TTGAGGACAA CCTCTCTGAG GGCATTCGCG
   43_5    TGGTTATCTT CCAGATTGGC TTGAGGACAA CCTCTCTGAG GGCATTCGCG
  43_12    TGGTTATCTT CCAGATTGGC TTGAGGACAA CCTCTCTGAG GGCATTCGCG
  43_20    TGGTTATCTT CCAGATTGGC TCGAGGACAA CCTCTCTGAG GGCATTCGCG
  43_21    TGGTTATCTT CCAGATTGGC TCGAGGACAA CCTCTCTGAG GGCATTCGCG
  43_23    TGGTTATCTT CCAGATTGGC TCGAGGACAA CCTCTCTGAG GGCATTCGCG
  43_25    TGGTTATCTT CCAGATTGGC TCGAGGACAA CCTCTCTGAG GGCATTCGCG
   44_1    TGGTTATCTT CCAGATTGGC TCGAGGACAA CCTCTCTGAG GGCATTCGCG
   44_5    TGGTTATCTT CCAGATTGGC TCGAGGACAA CCTCTCTGAG GGCATTCGCG
  223_10   .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    CGGTTATCTT CCAGATTGGC TCGAGGACAC TCTCTCTGAA GGAATCAGAC
   A3_5    CGGTTATCTT CCAGATTGGC TCGAGGACAC TCTCTCTGAA GGAATCAGAC
   A3_7    CGGTTATCTT CCAGATTGGC TCGAGGACAC TCTCTCTGAA GGAATCAGAC
   A3_3    CGGTTATCTT CCAGATTGGC TCGAGGACAC TCTCTCTGAA GGAATCAGAC
  42_12    TGGTTATCTT CCAGATTGGC TCGAGGACAA CCTCTCTGAG GGCATCCGCG
   AAV1    TGGTTATCTT CCAGATTGGC TCGAGGACAA CCTCTCTGAG GGCATTCGCG
   AAV2    TGGTTATCTT CCAGATTGGC TCGAGGACAC TCTCTCTGAA GGAATAAGAC
   AAV3    CGGTTATCTT CCAGATTGGC TCGAGGACAA CCTTTCTGAA GGCATTCGTG
   AAV8    TGGTTATCTT CCAGATTGGC TCGAGGACAA CCTCTCTGAG GGCATTCGCG
   AAV9    TGGTTATCTT CCAGATTGGC TCGAGGACAA CCTCTCTGAG GGCATTCGCG
   AAV7    TGGTTATCTT CCAGATTGGC TCGAGGACAA CCTCTCTGAG GGCATTCGCG
   44_2    TGGTTATCTT CCAGATTGGC TCGAGGACAA CCTCTCTGAG GGCATTCGCG
                                                    Rep 68 stop
```

FIG. 1AU

```
         2301                                                   2350
   42_2  AGTGGTGGGA CTTGAAACCT GGAGCCCCGA AACCCAAAGC CAACCAGCAA

42_8  AGTGGTGGGA CTTGAAACCT GGAGCCCCGA AACCCAAAGC CAACCAGCAA
  42_15  AGTGGTGGGA CTTGAAACCT GGAGCCCCGA AACCCAAAGC CAACCAGCAA
  42_5b  AGTGGTGGGA CTTGAAACCT GGAGCCCCGA AACCCAAAGC CAACCAGCAA
  42_1b  AGTGGTGGGA CTTGAGACCT GGAGCCCCGA AACCCAAAGC CAACCAGCAA
  42_13  AGTGGTGGGA CTTGAAACCT GGAGCCCCGA AACCCAAAGC CAACCAGCAA
  42_3a  AGTGGTGGGA CTTGAAACCT GGAGCCCCGA AACCCAAAGC CAACCAGCAA
   42_4  AGTGGTGGGA CTTGAAACCT GGAGCCCCGA AACCCAAAGC CAACCAGCAA
  42_5a  AGTGGTGGGA CTTGAAACCT GGAGCCCCGA AACCCAAAGC CAACCAGCAA
  42_10  AGTGGTGGGA CTTGAAACCT GGAGCCCCGA AACCCAAAGC CAACCAGCAA
  42_3b  AGTGGTGGGA CTTGAAACCT GGAGCCCCGA AACCCAAAGC CAACCAGCAA
  42_11  AGTGGTGGGA CTTGAAACCT GGAGCCCCGA AACCCAAAGC CAACCAGCAA
  42_6b  AGTGGTGGGA CTTGAAACCT GGAGCCCCGA AACCCAAAGC CAACCAGCAA
   43_1  AGTGGTGGGA CCTGAAACCT GGAGCCCCGA AACCCAAAGC CAACCAGCAA
   43_5  AGTGGTGGGA CCTGAAACCT GGAGCCCCGA AACCCAAAGC CAACCAGCAA
  43_12  AGTGGTGGGA CCTGAAACCT GGAGCCCCGA AACCCAAAGC CAACCAGCAA
  43_20  AGTGGTGGGA CTTGAAACCT GGAGCCCCGA AACCCAAAGC CAACCAGCAA
  43_21  AGTGGTGGGA CTTGAAACCT GGAGCCCCGA AACCCAAAGC CAACCAGCAA
  43_23  AGTGGTGGGA CTTGAAACCT GGAGCCCCGA AACCCAAAGC CAACCAGCAA
  43_25  AGTGGTGGGA CTTGAAACCT GGAGCCCCGA AACCCAAAGC CAACCAGCAA
   44_1  AGTGGTGGGA CTTGAAACCT GGAGCCCCGA AACCCAAAGC CAACCAGCAA
   44_5  AGTGGTGGGA CTTGAAACCT GGAGCCCCGA AACCCAAAGC CAACCAGCAA
 223_10  .......... .......... .......... .......... ..........
  223_2  .......... .......... .......... .......... ..........
  223_4  .......... .......... .......... .......... ..........
  223_5  .......... .......... .......... .......... ..........
  223_6  .......... .......... .......... .......... ..........
  223_7  .......... .......... .......... .......... ..........
   A3_4  AGTGGTGGAA GCTCAAACCT GGCCCACCAC CGCCGAAACC TAACCAACAA
   A3_5  AGTGGTGGAA GCTCAAACCT GGCCCACCAC CGCCGAAACC TAACCAACAA
   A3_7  AGTGGTGGAA GCTCAAACCT GGCCCACCAC CGCCGAAACC TAACCAACAA
   A3_3  AGTGGTGGAA GCTCAAACCT GGCCCACCAC CGCCGAAACC TAACCAACAA
  42_12  AGTGGTGGGA CTTGAAACCT GGAGCCCCGA AACCCAAAGC CAACCAGCAA
   AAV1  AGTGGTGGGA CTTGAAACCT GGAGCCCCGA AGCCCAAAGC CAACCAGCAA
   AAV2  AGTGGTGGAA GCTCAAACCT GGCCCACCAC CACCAAAGCC CGCAGAGCGG
   AAV3  AGTGGTGGGC TCTGAAACCT GGAGTCCCTC AACCCAAAGC GAACCAACAA
   AAV8  AGTGGTGGGC GCTGAAACCT GGAGCCCCGA AGCCCAAAGC CAACCAGCAA
   AAV9  AGTGGTGGGC GCTGAAACCT GGAGCCCCGA AGCCCAAAGC CAACCAGCAA
   AAV7  AGTGGTGGGA CCTGAAACCT GGAGCCCCGA AACCCAAAGC CAACCAGCAA
   44_2  AGTGGTGGGA CTTGAAACCT GGAGCCCCGA AACCCAAAGC CAACCAGCAA
```

FIG. 1AV

```
           2351                                                    2400
   42_2    AAGCAGGACG ACGGCCGGGG TCTGGTGCTT CCTGGCTACA AGTACCTCGG
   42_8    AAGCAGGACG ACGGCCGGGG TCTGGTGCTT CCTGGCTACA AGTACCTCGG
  42_15    AAGCAGGACG ACGGCCGGGG TCTGGTGCTT CCTGGCTACA AGTACCTCGG
  42_5b    AAGCAGGACG ACGGCCGGGG TCTGGTGCTT CCTGGCTACA AGTACCTCGG
  42_1b    AAGCAGGACG ACGGCCGGGG TCTGGTGCTT CCTGGCTACA AGTACCTCGG
  42_13    AAGCAGGACG ACGGCCGGGG TCTGGTGCTT CCTGGCTACA AGTACCTCGG
  42_3a    AAGCAGGACG ACGGCCGGGG TCTGGTGCTT CCTGGCTACA AGTACCTCGG
   42_4    AAGCAGGACG ACGGCCGGGG TCTGGTGCTT CCTGGCTACA AGTACCTCGG
  42_5a    AAGCAGGACG ACGGCCGGGG TCTGGTGCTT CCTGGCTACA AGTACCTCGG
  42_10    AAGCAGGACG ACGGCCGGGG TCTGGTGCTT CCTGGCTACA AGTACCTCGG
  42_3b    AAGCAGGACG ACGGCCGGGG TCTGGTGCTT CCTGGCTACA AGTACCTCGG
  42_11    AAGCAGGACG ACGGCCGGGG TCTGGTGCTT CCTGGCTACA AGTACCTCGG
  42_6b    AAGCAGGACG ACGGCCGGGG TCTGGTGCTT CCTGGCTACA AGTACCTCGG
   43_1    AAGCAGGACG ACGGCCGGGG TCTGGTGCTT CCTGGCTACA AGTACCTCGG
   43_5    AAGCAGGACG ACGGCCGGGG TCTGGTGCTT CCTGGCTACA AGTACCTCGG
  43_12    AAGCAGGACG ACGGCCGGGG TCTGGTGCTT CCTGGCTACA AGTACCTCGG
  43_20    AAGCAGGACG ACGGCCGGGG TCTGGTGCTT CCTGGCTACA AGTACCTCGG
  43_21    AAGCAGGACG ACGGCCGGGG TCTGGTGCTT CCTGGCTACA AGTACCTCGG
  43_23    AAGCAGGACG ACGGCCGGGG TCTGGTGCTT CCTGGCTACA AGTACCTCGG
  43_25    AAGCAGGACG ACGGCCGGGG TCTGGTGCTT CCTGGCTACA AGTACCTCGG
   44_1    AAGCAGGACG ACGGCCGGGG TCTGGTGCTT CCTGGCTACA AGTACCTCGG
   44_5    AAGCAGGACG ACGGCCGGGG TCTGGTGCTT CCTGGCTACA AGTACCTCGG
 223_10    .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    CACCGGGACG ACAGTAGGGG TCTTGTGCTT CCTGGGTACA AGTACCTCGG
   A3_5    CACCGGGACG ACAGTAGGGG TCTTGTGCTT CCTGGGTACA AGTACCTCGG
   A3_7    CACCGGGACG ACAGTAGGGG TCTTGTGCTT CCTGGGTACA AGTACCTCGG
   A3_3    CACCGGGACG ACAGTAGGGG TCTTGTGCTT CCTGGGTACA AGTACCTCGG
  42_12    AAGCAGGACG ACGGCCGGGG TCTGGTGCTT CCTGGCTACA AGTACCTCGG
   AAV1    AAGCAGGACG ACGGCCGGGG TCTGGTGCTT CCTGGCTACA AGTACCTCGG
   AAV2    CATAAGGACG ACAGCAGGGG TCTTGTGCTT CCTGGGTACA AGTACCTCGG
   AAV3    CACCAGGACA ACCGTCGGGG TCTTGTGCTT CCGGGTTACA AATACCTCGG
   AAV8    AAGCAGGACG ACGGCCGGGG TCTGGTGCTT CCTGGCTACA AGTACCTCGG
   AAV9    AAGCAGGACG ACGGCCGGGG TCTGGTGCTT CCTGGCTACA AGTACCTCGG
   AAV7    AAGCAGGACA ACGGCCGGGG TCTGGTGCTT CCTGGCTACA AGTACCTCGG
   44_2    AAGCAGGACG ACGGCCGGGG TCTGGTGCTT CCTGGCTACA AGTACCTCGG
```

FIG. 1AW

```
           2401                                                    2450
 42_2      ACCCTTCAAC GGACTCGACA AGGGAGAGCC GGTCAACGAG GCAGACGCCG
 42_8      ACCCTTCAAC GGACTCGACA AGGGGGAGCC CGTCAACGCG GCGGACGCAG
 42_15     ACCCTTCAAC GGACTCGACA AGGGGGAGCC CGTCAACGCG GCGGACGCAG
 42_5b     ACCCTTCAAC GGACTCGACA AGGGAGAGCC GGTCAACGAG GCAGACGCCG
 42_1b     ACCCTTCAAC GGACTCGACA AGGGAGAGCC GGTCAACGAG GCAGACGCCG
 42_13     ACCCTTCAAC GGACTCGACA AGGGGGAGCC CGTCAACGCG GCGGACGCAG
 42_3a     ACCCTTCAAC GGACTCGACA AGGGGGAGCC CGTCAACGCG GCGGACGCAG
 42_4      ACCCTTCAAC GGACTCGACA AGGGAGAGCC GGTCAACGAG GCAGACGCCG
 42_5a     ACCCTTCAAC GGACTCGACA AGGGAGAGCC GGTCAACGAG GCAGACGCCG
 42_10     ACCCTTCAAC GGACTCGACA AGGGAGAGCC GGTCAACGAG GCAGACGCCG
 42_3b     ACCCTTCAAC GGACTCGACA AGGGAGAGCC GGTCAACGAG GCAGACGCCG
 42_11     ACCCTTCAAC GGACTCGACA AGGGAGAGCC GGTCAACGCG GCGGACGCAG
 42_6b     ACCCTTCAAC GGACTCGACA AGGGAGAGCC GGTCAACGAG GCAGACGCCG
 43_1      ACCCTTCAAC GGACTCGACA AGGGGGAGCC CGTCAACGCG GCGGACGCAG
 43_5      ACCCTTCAAC GGACTCGACA AGGGGGAGCC CGTCAACGCG GCGGACGCAG
 43_12     ACCCTTCAAC GGACTCGACA AGGGGGAGCC CGTCAACGCG GCGGACGCAG
 43_20     ACCCTTCAAC GGACTCGACA AGGGGGAGCC CGTCAACGCG GCGGACGCAG
 43_21     ACCCTTCAAC GGACTCGACA AGGGGGAGCC CGTCAACGCG GCGGACGCAG
 43_23     ACCCTTCAAC GGACTCGACA AGGGGGAGCC CGTCAACGCG GCGGACGCAG
 43_25     ACCCTTCAAC GGACTCGACA AGGGGGAGCC CGTCAACGCG GCGGACGCAG
 44_1      ACCCTTCAAC GGACTCGACA AGGGGGAGCC CGTCAACGCG GCGGACGCAG
 44_5      ACCCTTCAAC GGACTCGACA AGGGGGAGCC CGTCAACGCG GCGGACGCAG
223_10     .......... .......... .......... .......... ..........
223_2      .......... .......... .......... .......... ..........
223_4      .......... .......... .......... .......... ..........
223_5      .......... .......... .......... .......... ..........
223_6      .......... .......... .......... .......... ..........
223_7      .......... .......... .......... .......... ..........
 A3_4      ACCCTTCAAC GGACTCGACA AAGGAGAGCC GGTCAACGAG GCAGACGCCG
 A3_5      ACCCTTCAAC GGACTCGACA AAGGAGAGCC GGTCAACGAG GCAGACGCCG
 A3_7      ACCCTTCAAC GGACTCGACA AAGGAGAGCC GGTCAACGAG GCAGACGCCG
 A3_3      ACCCTTCAAC GGACTCGACA AAGGAGAGCC GGTCAACGAG GCAGACGCCG
 42_12     ACCCTTCAAC GGACTCGACA AGGGAGAGCC GGTCAACGAG GCAGACGCCG
 AAV1      ACCCTTCAAC GGACTCGACA AGGGGGAGCC CGTCAACGCG GCGGACGCAG
 AAV2      ACCCTTCAAC GGACTCGACA AGGGAGAGCC GGTCAACGAG GCAGACGCCG
 AAV3      ACCCGGTAAC GGACTCGACA AAGGAGAGCC GGTCAACGAG GCGGACGCGG
 AAV8      ACCCTTCAAC GGACTCGACA AGGGGGAGCC CGTCAACGCG GCGGACGCAG
 AAV9      ACCCTTCAAC GGACTCGACA AGGGGGAGCC CGTCAACGCG GCGGACGCAG
 AAV7      ACCCTTCAAC GGACTCGACA AGGGGGAGCC CGTCAACGCG GCGGACGCAG
 44_2      ACCCTTCAAC GGACTCGACA AGGGGGAGCC CGTCAACGCG GCGGACGCAG
```

FIG. 1AX

```
            2451                                                    2500
   42_2     CGGCCCTCGA GCACG.ACAA GGCCTACGAC AAGCAGCTCG AGCAGGGGGA
   42_8     CGGCCCTCGA GCACG.ACAA GGCCTACGAC CAGCAGCTCA AAGCGGGTGA
   42_15    CGGCCCTCGA GCACG.ACAA GGCCTACGAC CAGCAGCTCA AAGCGGGTGA
   42_5b    CGGCCCTCGA GCACG.ACAA GGCCTACGAC AAGCAGCTCG AGCAGGGGGA
   42_1b    CGGCCCTCGA GCACG.ACAA GGCCTACGAC AAGCAGCTCG AGCAGGGGGA
   42_13    CGGCCCTCGA GCACG.ACAA GGCCTACGAC CAGCAGCTCA AAGCGGGTGA
   42_3a    CGGCCCTCGA GCACG.ACAA GGCCTACGAC CAGCAGCTCA AAGCGGGTGA
   42_4     CGGCCCTCGA GCACG.ACAA GGCCTACGAC AAGCAGCTCG AGCAGGGGGA
   42_5a    CGGCCCTCGA GCACG.ACAA GGCCTACGAC AAGCAGCTCG AGCAGGGGGA
   42_10    CGGCCCTCGA GCACG.ACAA GGCCTACGAC AAGCAGCTCG AGCAGGGGGA
   42_3b    CGGCCCTCGA GCACG.ACAA GGCCTACGAC AAGCAGCTCG AGCAGGGGGA
   42_11    CGGCCCTCGA GCACG.ACAA GGCCTACGAC CAGCAGCTCA AAGCGGGTGA
   42_6b    CGGCCCTCGA GCACG.ACAA GGCCTACGAC AAGCAGCTCG AGCAGGGGGA
   43_1     CGGCCCTCGA GCACG.ACAA GGCCTACGAC CAGCAGCTCA AAGCGGGTGA
   43_5     CGGCCCTCGA GCACG.ACAA GGCCTACGAC CAGCAGCTCA AAGCGGGTGA
   43_12    CGGCCCTCGA GCACG.ACAA GGCCTACGAC CAGCAGCTCA AAGCGGGTGA
   43_20    CGGCCCTCGA GCACG.ACAA AGCCTACGAC CAGCAGCTCA AAGCGGGTGA
   43_21    CGGCCCTCGA GCACG.ACAA AGCCTACGAC CAGCAGCTCA AAGCGGGTGA
   43_23    CGGCCCTCGA GCACG.ACAA AGCCTACGAC CAGCAGCTCA AAGCGGGTGA
   43_25    CGGCCCTCGA GCACG.ACAA AGCCTACGAC CAGCAGCTCA AAGCGGGTGA
   44_1     CGGCCCTCGA GCACG.ACAA GGCCTACGAC CAGCAGCTCA AAGCGGGTGA
   44_5     CGGCCCTCGA GCACG.ACAA GGCCTACGAC CAGCAGCTCA AAGCGGGTGA
  223_10    .......... .......CAA GGCCTACGAC CAGCAGCTCA AAGCGGGTGA
  223_2     .......... .......CAA GGCCTACGAC CAGCAGCTCA AAGCGGGTGA
  223_4     .......... .......CAA GGCCTACGAC CAGCAGCTCA AAGCGGGTGA
  223_5     .......... .......CAA GGCCTACGAC CAGCAGCTCA AAGCGGGTGA
  223_6     .......... .......CAA GGCCTACGAC CAGCAGCTCA AAGCGGGTGA
  223_7     .......... .......CAA GGCCTACGAC CAGCAGCTCA AAGCGGGTGA
   A3_4     CGGCCCTCGA GCACG.ACAA AGCCTACGAC CACCAGCTCA AGCAAGGGGA
   A3_5     CGGCCCTCGA GCACG.ACAA AGCCTACGAC CACCAGCTCA AGCAAGGGGA
   A3_7     CGGCCCTCGA GCACG.ACAA AGCCTACGAC CACCAGCTCA AGCAAGGGGA
   A3_3     CGGCCCTCGA GCACG.ACAA AGCCTACGAC CACCAGCTCA AGCAAGGGGA
   42_12    CGGCCCTCGA GCACG.ACAA GGCCTACGAC AAGCAGCTCG AGCAGGGGGA
   AAV1     CGGCCCTCGA GCACG.ACAA GGCCTACGAC CAGCAGCTCA AAGCGGGTGA
   AAV2     CGGCCCTCGA GCACGTACAA AGCCTACGAC CGGCAGCTCG ACAGCGGAGA
   AAV3     CAGCCCTCGA ACACG.ACAA AGCTTACGAC CAGCAGCTCA AGGCCGGTGA
   AAV8     CGGCCCTCGA GCACG.ACAA GGCCTACGAC CAGCAGCTGC AGGCGGGTGA
   AAV9     CGGCCCTCGA GCACG.GCAA GGCCTACGAC CAGCAGCTGC AGGCGGGTGA
   AAV7     CGGCCCTCGA GCACG.ACAA GGCCTACGAC CAGCAGCTCA AAGCGGGTGA
   44_2     CGGCCCTCGA GCACG.ACAA GGCCTACGAC CAGCAGCTCA AAGCGGGTGA
```

FIG. 1AY

```
         2501                                                    2550
  42_2   CAACCCGTAC CTCAAGTACA ACCACGCCGA CGCCGAGTTT CAGGAGCGTC
  42_8   CAATCCGTAC CTGCGGTATA ACCACGCCGA CGCCGAGTTT CAGGAGCGTC
  42_15  CAATCCGTAC CTGCGGTATA ACCACGCCGA CGCCGAGTTT CAGGAGCGTC
  42_5b  CAACCCGTAC CTCAAGTACA ACCACGCCGA CGCCGAGTTT CAGGAGCGTC
  42_1b  CAACCCGTAC CTCAAGTACA ACCACGCCGA CGCCGAGTTT CAGGAGCGTC
  42_13  CAATCCGTAC CTGCGGTATA ACCACGCCGA CGCCGAGTTT CAGGAGCGTC
  42_3a  CAATCCGTAC CTGCGGTATA ACCACGCCGA CGCCGAGTTT CAGGAGCGTC
  42_4   CAACCCGTAC CTCAAGTACA ACCACGCCGA CGCCGAGTTT CAGGAGCGTC
  42_5a  CAACCCGTAC CTCAAGTACA ACCACGCCGA CGCCGAGTTT CAGGAGCGTC
  42_10  CAACCCGTAC CTCAAGTACA ACCACGCCGA CGCCGAGTTT CAGGAGCGTC
  42_3b  CAACCCGTAC CTCAAGTACA ACCACGCCGA CGCCGAGTTT CAGGAGCGTC
  42_11  CAATCCGTAC CTGCGGTATA ACCACGCCGA CGCCGAGTTT CAGGAGCGTC
  42_6b  CAACCCGTAC CTCAAGTACA ACCACGCCGA CGCCGAGTTT CAGGAGCGTC
  43_1   CAATCCGTAC CTGCGGTATA ACCACGCCGA CGCCGAGTTT CAGGAGCGTC
  43_5   CAATCCGTAC CTGCGGTATA ACCACGCCGA CGCCGAGTTT CAGGAGCGTC
  43_12  CAATCCGTAC CTGCGGTATA ACCACGCCGA CGCCGAGTTT CAGGAGCGTC
  43_20  CAATCCGTAC CTGCGGTATA ATCACGCCGA CGCCGAGTTT CAGGAGCGTC
  43_21  CAATCCGTAC CTGCGGTATA ATCACGCCGA CGCCGAGTTT CAGGAGCGTC
  43_23  CAATCCGTAC CTGCGGTATA ATCACGCCGA CGCCGAGTTT CAGGAGCGTC
  43_25  CAATCCGTAC CTGCGGTATA ATCACGCCGA CGCCGAGTTT CAGGAGCGTC
  44_1   CAATCCGTAC CTGCGGTATA ACCACGCCGA CGCCGAGTTT CAGGAGCGTC
  44_5   CAATCCGTAC CTGCGGTATA ACCACGCCGA CGCCGAGTTT CAGGAGCGTC
 223_10  CAATCCGTAC CTGCGGTATA ACCACGCCGA CGCCGAGTTT CAGGAGCGTC
 223_2   CAATCCGTAC CTGCGGTATA ACCACGCCGA CGCCGAGTTT CAGGAGTGTC
 223_4   CAATCCGTAC CTGCGGTATA ACCACGCCGA CGCCGAGTTT CAGGAGCGTC
 223_5   CAATCCGTAC CTGCGGTATA ACCACGCCGA CGCCGAGTTT CAGGAGCGTC
 223_6   CAATCCGTAC CTGCGGTATA ACCACGCCGA CGCCGAGTTT CAGGAGCGTC
 223_7   CAATCCGTAC CTGCGGTATA ACCACGCCGA CGCCGAGTTT CAGGAGCGTC
  A3_4   CAACCCGTAC CTCAAATACA ACCACGCGGA CGCTGAATTT CAGGAGCGTC
  A3_5   CAACCCGTAC CTCAAATACA ACCACGCGGA CGCTGAATTT CAGGAGCGTC
  A3_7   CAACCCGTAC CTCAAATACA ACCACGCGGA CGCTGAATTT CAGGAGCGTC
  A3_3   CAACCCGTAC CTCAAATACA ACCACGCGGA CGCTGAATTT CAGGAGCGTC
  42_12  CAACCCGTAC CTCAAGTACA ACCACGCCGA CGCCGAGTTT CAGGAGCGTC
  AAV1   CAATCCGTAC CTGCGGTATA ACCACGCCGA CGCCGAGTTT CAGGAGCGTC
  AAV2   CAACCCGTAC CTCAAGTACA ACCACGCCGA CGCGGAGTTT CAGGAGCGCC
  AAV3   CAACCCGTAC CTCAAGTACA ACCACGCCGA CGCCGAGTTT CAGGAGCGTC
  AAV8   CAATCCGTAC CTGCGGTATA ACCACGCCGA CGCCGAGTTT CAGGAGCGTC
  AAV9   CAATCCGTAC CTGCGGTATA ACCACGCCGA CGCCGAGTTT CAGGAGCGTC
  AAV7   CAATCCGTAC CTGCGGTATA ACCACGCCGA CGCCGAGTTT CAGGAGCGTC
  44_2   CAATCCGTAC CTGCGGTATA ACCACGCCGA CGCCGAGTTT CAGGAGCGTC
```

FIG. 1AZ

```
          2551                                                    2600
   42_2   TTCAAGAAGA TACGTCTTTT GGGGGCAACC TCGGGCGAGC AGTCTTCCAG
   42_8   TGCAAGAAGA TACGTCTTTT GGGGGCAACC TCGGGCGAGC AGTCTTCCAG
  42_15   TGCAAGAAGA TACGTCTTTT GGGGGCAACC TCGGGCGAGC AGTCTTCCAG
  42_5b   TTCAAGAAGA TACGTCTTTT GGGGGCAACC TCGGGCGAGC AGTCTTCCAG
  42_1b   TTCAAGAAGA TACGTCTTTT GGGGGCAACC TCGGGCGAGC AGTCTTCCAG
  42_13   TTCAAGAAGA TACGTCTTTT GGGGGCAACC TCGGGCGAGC AGTCTTCCAG
  42_3a   TTCAAGAAGA TACGTCTTTT GGGGGCAACC TCGGGCGAGC AGTCTTCCAG
   42_4   TTCAAGAAGA TACGTCTTTT GGGGGCAACC TCGGGCGAGC AGTCTTCCAG
  42_5a   TTCAAGAAGA TACGTCTTTT GGGGGCAACC TCGGGCGAGC AGTCTTCCGG
  42_10   TTCAAGAAGA TACGTCTTTT GGGGGCAACC TCGGGCGAGC AGTCTTCCAG
  42_3b   TTCAAGAAGA TACGTCTTTT GGGGGCAACC TCGGGCGAGC AGTCTTCCAG
  42_11   TTCAAGAAGA TACGTCTTTT GGGGGCAACC TCGGGCGAGC AGTCTTCCAG
  42_6b   TTCAAGAAGA TACGTCTTTT GGGGGCAACC TCGGGCGAGC AGTCTTCCAG
   43_1   TGCAAGAAGA TACGTCTTTT GGGGGCAACC TCGGGCGAGC AGTCTTCCAG
   43_5   TGCAAGAAGA TACGTCTTTT GGGGGCAACC TCGGGCGAGC AGTCTTCCAG
  43_12   TGCAAGAAGA TACGTCTTTT GGGGGCAACC TCGGGCGAGC AGTCTTCCAG
  43_20   TGCAAGAAGA TACGTCTTTT GGGGGCAACC TCGGGCGAGC AGTCTTCCAG
  43_21   TGCAAGAAGA TACGTCTTTT GGGGGCAACC TCGGGCGAGC AGTCTTCCAG
  43_23   TGCAAGAAGA TACGTCCTTT GGGGGCAACC TCGGGCGAGC AGTCTTCCAG
  43_25   TGCAAGAAGA TACGTCTTTT GGGGGCAACC TCGGGCGAGC AGTCTTCCAG
   44_1   TGCAAGAAGA TACGTCTTTT GGGGGCAACC TCGGGCGAGC AGTCTTCCAG
   44_5   TGCAAGAAGA TACGTCTTTT GGGGGCAACC TCGGGCGAGC AGTCTTCCAG
  223_10  TTCAAGAAGA TACGTCTTTT GGGGGCAACC TCGGGCGAGC AGTCTTCCAG
  223_2   TTCAAGAAGA TACGTCTTTT GGGGGCAACC TCGGGCGAGC AGTCTTCCAG
  223_4   TTCAAGAAGA TACGTCTTTT GGGGGCAACC TCGGGCGAGC AGTCTTCCAG
  223_5   TTCAAGAAGA TACGTCTTTT GGGGGCAACC TCGGGCGAGC AGTCTTCCAG
  223_6   TTCAAGAAGA TACGTCTTTT GGGGGCAACC TCGGGCGAGC AGTCTTCCAG
  223_7   TTCAAGAAGA TACGTCTTTT GGGGGCAACC TCGGGCGAGC AGTCTTCCAG
   A3_4   TTCAAGAAGA TACGTCTTTC GGGGGCAACC TCGGGCGAGC AGTCTTCCAG
   A3_5   TTCAAGAAGA TACGTCTTTC GGGGGCAACC TCGGGCGAGC AGTCTTCCAG
   A3_7   TTCAAGAAGA TACGTCTTTC GGGGGCAACC TCGGGCGAGC AGTCTTCCAG
   A3_3   TTCAAGAAGA TACGTCTTTC GGGGGCAACC TCGGGCGAGC AGTCTTCCAG
  42_12   TTCAAGAAGA TACGTCTTTT GGGGGCAACC TCGGGCGAGC AGTCTTCCAG
   AAV1   TGCAAGAAGA TACGTCTTTT GGGGGCAACC TCGGGCGAGC AGTCTTCCAG
   AAV2   TTAAGAAGA  TACGTCTTTT GGGGGCAACC TCGGACGAGC AGTCTTCCAG
   AAV3   TTCAAGAAGA TACGTCTTTT GGGGGCAACC TTGGCAGAGC AGTCTTCCAG
   AAV8   TGCAAGAAGA TACGTCTTTT GGGGGCAACC TCGGGCGAGC AGTCTTCCAG
   AAV9   TGCAAGAAGA TACGTCTTTT GGGGGCAACC TCGGGCGAGC AGTCTTCCAG
   AAV7   TGCAAGAAGA TACGTCATTT GGGGGCAACC TCGGGCGAGC AGTCTTCCAG
   44_2   TGCAAGAAGA TACGTCTTTT GGGGGCAACC TCGGGCGAGC AGTCTTCCAG
```

FIG. 1AAA

```
           2601                                                    2650
   42_2    GCCAAGAAGC GGGTTCTCGA ACCTCTCGGT CTGGTTGAGG AAGGCGCTAA
   42_8    GCCAAGAAGC GGGTTCTCGA ACCTCTCGGT CTGGTTGAGG AAGGCGCTAA
  42_15    GCCAAGAAGC GGGTTCTCGA ACCTCTCGGT CTGGTTGAGG AAGGCGCTAA
  42_5b    GCCAAGAAGC GGGTTCTCGA ACCTCTCGGT CTGGTTGAGG AAGGCGCTAA
  42_1b    GCCAAGAAGC GGGTTCTCGA ACCTCTCGGT CTGGTTGAGG AAGGCGCTAA
  42_13    GCCAAGAAGC GGGTTCTCGA ACCTCTCGGT CTGGTTGAGG AAGGCGCTAA
  42_3a    GCCAAGAAGC GGGTTCTCGA ACCTCTCGGT CTGGTTGAGG AAGGCGCTAA
   42_4    GCCAAGAAGC GGGTTCTCGA ACCTCTCGGT CTGGTTGAGG AAGGCGCTAA
  42_5a    GCCAAGAAGC GGGTTCTCGA ACCTCTCGGT CTGGTTGAGG AAGGCGCTAA
  42_10    GCCAAGAAGC GGGTTCTCGA ACCTCTCGGT CTGGTTGAGG AAGGCGCTAA
  42_3b    GCCAAGAAGC GGGTTCTCGA ACCTCTCGGT CTGGTTGAGG AAGGCGCTAA
  42_11    GCCAAGAAGC GGGTTCTCGA ACCTCTCGGT CTGGTTGAGG AAGGCGCTAA
  42_6b    GCCAAGAAGC GGGTTCTCGA ACCTCTCGGT CTGGTTGAGG AAGGCGCTAA
   43_1    GCCAAGAAGC GGGTTCTCGA ACCTCTCGGT CTGGTTGAGG AAGGCGCTAA
   43_5    GCCAAGAAGC GGGTTCTCGA ACCTCTCGGT CTGGTTGAGG AAGGCGCTAA
  43_12    GCCAAGAAGC GGGTTCTCGA ACCTCTCGGT CTGGTTGAGG AAGGCGCTAA
  43_20    GCCAAGAAGC GGGTTCTCGA ACCTCTCGGT CTGGTTGAGG AAGGCGCTAA
  43_21    GCCAAGAAGC GGGTTCTCGA ACCTCTCGGT CTGGTTGAGG AAGGCGCTAA
  43_23    GCCAAGAAGC GGGTTCTCGA ACCTCTCGGT CTGGTTGAGG AAGGCGCTAA
  43_25    GCCAAGAAGC GGGTTCTCGA ACCTCTCGGT CTGGTTGAGG AAGGCGCTAA
   44_1    GCCAAGAAGC GGGTTCTCGA ACCTCTCGGT CTGGTTGAGG AAGGCGCTAA
   44_5    GCCAAGAAGC GGGTTCTCGA ACCTCTCGGT CTGGTTGAGG AAGGCGCTAA
 223_10    GCCAAAAAGC GGGTTCTCGA ACCTCTTGGT CTGGTTGAGA CGCCAGCTAA
  223_2    GCCAAAAAGC GGGTTCTCGA ACCTCTTGGT CTGGTTGAGA CGCCAGCTAA
  223_4    GCCAAAAAGC GGGTTCTCGA ACCTCTTGGT CTGGTTGAGA CGCCAGCTAA
  223_5    GCCAAAAAGC GGGTTCTCGA ACCTCTTGGT CTGGTTGAGA CGCCAGCTAA
  223_6    GCCAAAAAGC GGGTTCTCGA ACCTCTTGGT CTGGTTGAGA CGCCAGCTAA
  223_7    GCCAAAAAGC GGGTTCTCGA ACCTCTTGGT CTGGTTGAGA CGCCAGCTAA
   A3_4    GCCAAAAAGA GGGTACTCGA GCCTCTTGGT CTGGTTGAGG AAGCTGTTAA
   A3_5    GCCAAAAAGA GGGTACTCGA GCCTCTTGGT CTGGTTGAGG AAGCTGTTAA
   A3_7    GCCAAAAAGA GGGTACTCGA GCCTCTTGGT CTGGTTGAGG AAGCTGTTAA
   A3_3    GCCAAAAAGA GGGTACTCGA GCCTCTTGGT CTGGTTGAGG AAGCTGTTAA
  42_12    GCCAAGAAGC GGGTTCTCGA ACCTCTCGGT CTGGTTGAGG AAGGCGCTAA
   AAV1    GCCAAGAAGC GGGTTCTCGA ACCTCTCGGT CTGGTTGAGG AAGGCGCTAA
   AAV2    GCGAAAAAGA GGGTTCTTGA ACCTCTGGGC CTGGTTGAGG AACCTGTTAA
   AAV3    GCCAAAAAGA GGATCCTTGA GCCTCTTGGT CTGGTTGAGG AAGCAGCTAA
   AAV8    GCCAAGAAGC GGGTTCTCGA ACCTCTCGGT CTGGTTGAGG AAGGCGCTAA
   AAV9    GCCAAGAAGC GGGTTCTCGA ACCTCTCGGT CTGGTTGAGG AAGGCGCTAA
   AAV7    GCCAAGAAGC GGGTTCTCGA ACCTCTCGGT CTGGTTGAGG AAGGCGCTAA
   44_2    GCCAAGAAGC GGGTTCTCGA ACCTCTCGGT CTGGTTGAGG AAGGCGCTAA
```

FIG. 1AAB 2651                                                                                             2700

```
         vp2 start
 42_2    GACGGCTCCT GGAAAGAAGA GACCCATAGA ...ATCCCCC ..........
 42_8    GACGGCTCCT GGAAAGAAGA GACCGGTAGA GCCATCACCC CAGCGTTCTC
 42_15   GACGGCTCCT GGAAAGAAGA GACCGGTAGA GCCATCACCC CAGCGTTCTC
 42_5b   GACGGCTCCT GGAAAGAAGA GACCGGTAGA GCCATCACCC CAGCGTTCTC
 42_1b   GACGGCTCCT GGAAAGAAGA GACCCATAGA ...ATCCCCC ..........
 42_13   GACGGCTCCT GGAAAGAAGA GACCCATAGA ...ATCCCCC ..........
 42_3a   GACGGCTCCT GGAAAGAAGA GACCCATAGA ...ATCCCCC ..........
 42_4    GACGGCTCCT GGAAAGAAGA GACCCATAGA ...ATCCCCC ..........
 42_5a   GACGGCTCCT GGAAAGAAGA GACCCATAGA ...ATCCCCC ..........
 42_10   GACGGCTCCT GGAAAGAAGA GACCCATAGA ...ATCCCCC ..........
 42_3b   GACGGCTCCT GGAAAGAAGA GACCCATAGA ...ATCCCCC ..........
 42_11   GACGGCTCCT GGAAAGAAGA GACCCATAGA ...ATCCCCC ..........
 42_6b   GACGGCTCCT GGAAAGAAGA GACCGGTAGA GCCATCACCC CAGCGTTCTC
 43_1    GACGGCTCCT GGAAAGAAGA GACCGGTAGA GCCATCACCT CAGCGTTCCC
 43_5    GACGGCTCCT GGAAAGAAGA GACCGGTAGA GCCATCACCT CAGCGTTCCC
 43_12   GACGGCTCCT GGAAAGAAGA GACCGGTAGA GCCATCACCT CAGCGTTCCC
 43_20   GACGGCTCCT GGAAAGAAGA GACTGGTAGA GCAGTCGCCA CAAGAG...C
 43_21   GACGGCTCCT GGAAAGAAGA GACCGGTAGA GCAGTCGCCA CAAGAG...C
 43_23   GACGGCTCCT GGAAAGAAGA GACCGGTAGA GCAGTCGCCA CAAGAG...C
 43_25   GACGGCTCCT GGAAAGAAGA GACCGGTAGA GCAGTCGCCA CAAGAG...C
 44_1    GACGGCTCCT GGAAAGAAGA GACCGGTAGA GCCATCACCC CAGCGTTCTC
 44_5    GACGGCTCCT GGAAAGAAGA GACCGGTAGA GCCATCACCC CAGCGTTCTC
223_10   GACGGCACCT GGAAAGAAGC GACCGGTAGA CTCGCCA... ..........
223_2    GACGGCACCT GGAAAGAAGC GACCGGTAGA CTCGCCA... ..........
223_4    GACGGCACCT GGAAAGAAGC GACCGGTAGA CTCGCCA... ..........
223_5    GACGGCACCT GGAAAGAAGC GACCGGTAGA CTCGCCA... ..........
223_6    GACGGCACCT GGAAAGAAGC GACCGGTAGA CTCGCCA... ..........
223_7    GACGGCACCT GGAAAGAAGC GACCGGTAGA CTCGCCA... ..........
 A3_4    GACGGCTCCT GGAAAAAAGA GACCTATAGA GCAGTCTCCT GCAGAA...C
 A3_5    GACGGCTCCT GGAAAAAAGA GACCTATAGA GCAGTCTCCT GCAGAA...C
 A3_7    GACGGCTCCT GGAAAAAAGA GACCTATAGA GCAGTCTCCT GCAGAA...C
 A3_3    GACGGCTCCT GGAAAAAAGA GACCTATAGA GCAGTCTCCT GCAGAA...C
 42_12   GACGGCTCCT GGAAAGAAGA GACCGGTAGA GCCATCACCC CAGCGTTCTC
 AAV1    GACGGCTCCT GGAAAGAAAC GTCCGGTAGA GCAGTCGCCA CAAGAG...C
 AAV2    GACGGCTCCG GGAAAAAAGA GGCCGGTAGA GCACTCTCCT GTGGAG...C
 AAV3    AACGGCTCCT GGAAAGAAGG GGGCTGTAGA TCAGTCTCCT CAGGAA...C
 AAV8    GACGGCTCCT GGAAAGAAGA GACCGGTAGA GCCATCACCC CAGCGTTCTC
 AAV9    GACGGCTCCT GGAAAGAAGA GACCGGTAGA GCCATCACCC CAGCGTTCTC
 AAV7    GACGGCTCCT GCAAAGAAGA GACCGGTAGA GCCGTCACCT CAGCGTTCCC
 44_2    GACGGCTCCT GGAAAGAAGA GACCGGTAGA GCCATCACCC CAGCGTTCTC
         vp2 start
```

FIG. 1AAC

```
             2701                                                    2750
   42_2    ..GACTCCTC CACGGGCATC GGCAAGAAAG GCCAGCAGCC CGCTAAAAAG
   42_8    CAGACTCCTC TACGGGCATC GGCAAGACAG GCCAGCAGCC CGCGAAAAAG
   42_15   CAGACTCCTC TACGGGCATC GGCAAGACAG GCCAGCAGCC CGCGAAAAAG
   42_5b   CAGACTCCTC TACGGGCATC GGCAAGACAG GCCAGCAGCC CGCGAAAAAG
   42_1b   ..GACTCCTC CACGGGCATC GGCAAGAAAG GCCAGCAGCC CGCTAAAAAG
   42_13   ..GACTCCTC CACGGGCATC GGCAAGAAAG GCCAGCAGCC CGCTAAAAAG
   42_3a   ..GACTCCTC CACGGGCATC GGCAAGAAAG GCCAGCAGCC CGCTAAAAAG
   42_4    ..GACTCCTC CACGGGCATC GGCAAGAAAG GCCAGCAGCC CGCTAAAAAG
   42_5a   ..GACTCCTC CACGGGCATC GGCAAGAAAG GCCAGCAGCC CGCTAAAAAG
   42_10   ..GACTCCTC CACGGGCATC GGCAGGAAAG GCCAGCAGCC CGCTAAAAAG
   42_3b   ..GACTCCTC CACGGGCATC GGCAAGAAAG GCCAGCAGCC CGCTAAAAAG
   42_11   ..GACTCCTC CACGGGCATC GGCAAGAAAG GCCAGCAGCC CGCTAAAAAG
   42_6b   CAGACTCCTC TACGGGCATC GGCAAGACAG GCCAGCAGCC CGCGAAAAAG
   43_1    CCGACTCCTC CACGGGCATC GGCAAGAAAG GCCACCAGCC CGCGAGAAAG
   43_5    CCGACTCCTC CACGGGCATC GGCAAGAAAG GCCACCAGCC CGCGAGAAAG
   43_12   CCGACTCCTC CACGGGCATC GGCAAGAAAG GCCACCAGCC CGCGAGAAAG
   43_20   CAGACTCCTC CTCGGGCATC GGCAAGACAG GCCAGCAGCC CGCTAAAAAG
   43_21   CAGACTCCTC CTCGGGCATC GGCAAGACAG GCCAGCAGCC CGCTAAAAAG
   43_23   CAGACTCCTC CTCGGGCATC GGCAAGACAG GCCAGCAGCC CGCTAAAAAG
   43_25   CAGACTCCTC CTCGGGCATC GGCAAGACAG GCCAGCAGCC CGCTAAAAAG
   44_1    CAGACTCCTC TACGGGCATC GGCAAGAAAG GCCAGCAGCC CGCGAAAAAG
   44_5    CAGACTCCTC TACGGGCATC GGCAAGAAAG GCCAGCAGCC CGCGAAAAAG
   223_10  ..GACTCCAC CTCGGGCATC GGCAAGAAAG GCCAGCAGCC CGCGAAAAAG
   223_2   ..GACTCCAC CTCGGGCATC GGCAAGAAAG GCCAGCAGCC CGCGAAAAAG
   223_4   ..GACTCCAC CTCGGGCATC GGCAAGAAAG GCCAGCAGCC CGCGAAAAAG
   223_5   ..GACTCCAC CTCGGGCATC GGCAAGAAAG GCCAGCAGCC CGCGAAAAAG
   223_6   ..GACTCCAC CTCGGGCATC GGCAAGAAAG GCCAGCAGCC CGCGAAAAAG
   223_7   ..GACTCCAC CTCGGGCATC GGCAAGAAAG GCCAGCAGCC CGCGAAAAAG
   A3_4    CGGACTCTTC CTCGGGCATC GGCGAATCAG GCCAGCAGCC CGCTAAGAAA
   A3_5    CGGACTCTTC CTCGGGCATC GGCAAATCAG GCCAGCAGCC CGCTAAGAAA
   A3_7    CGGACTCTTC CTCGGGCATC GGCAAATCAG GCCAGCAGCC CGCTAAGAAA
   A3_3    CGGACTCTTC CTCGGGCATC GGCAAATCAG GCCAGCAGCC CGCTAAGAAA
   42_12   CAGACTCCTC TACGGGCATC GGCAAGACAG GCCAGCAGCC CGCGAAAAAG
   AAV1    CAGACTCCTC CTCGGGCATC GGCAAGACAG GCCAGCAGCC CGCTAAAAAG
   AAV2    CAGACTCCTC CTCGGGAACC GGAAAGGCGG GCCAGCAGCC TGCAAGAAAA
   AAV3    CGGACTCATC ATCTGGTGTT GGCAAATCGG GCAAACAGCC TGCCAGAAAA
   AAV8    CAGACTCCTC TACGGGCATC GGCAAGAAAG GCCAACAGCC CGCCAGAAAA
   AAV9    CAGACTCCTC TACGGGCATC GGCAAGAAAG GCCAACAGCC CGCCAGAAAA
   AAV7    CCGACTCCTC CACGGGCATC GGCAAGAAAG GCCAGCAGCC CGCCAGAAAG
   44_2    CAGACTCCTC TACGGGCATC GGCAAGAAAG GCCAGCAGCC CGCGAAAAAG
```

FIG. 1AAD

```
        2751                                                    2800
  42_2   AAGCTCAACT TTGGGCAGAC TGGCGACTCA GAGTCAGTGC CCGACCCCCA
  42_8   AGACTCAACT TTGGGCAGAC TGGCGACTCA GAGTCAGTGC CCGACCCTCA
 42_15   AGACTCAACT TTGGGCAGAC TGGCGACTCA GAGTCAGTGC CCGACCCTCA
 42_5b   AGACTCAACT TTGGGCAGAC TGGCGACTCA GAGTCAGTGC CCGACCCTCA
 42_1b   AGACTCAACT TTGGGCAGAC TGGCGACTCA GAGTCAGTGC CCGACCCTCA
 42_13   AAGCTCAACT TTGGGCAGAC TGGCGACTCA GAGTCAGTGC CCGACCCTCA
 42_3a   AAGCTCAACT TTGGGCAGAC TGGCGACTCA GAGTCAGTGC CCGACCCTCA
  42_4   AAGCTCAACT TTGGGCAGAC TGGCGACTCA GAGTCAGTGC CCGACCCTCA
 42_5a   AAGCTCAACT TTGGGCAGAC TGGCGACTCA GAGTCAGTGC CCGACCCCCA
 42_10   AAGCTCAACT TTGGGCAGAC TGGCGACTCA GAGTCAGTGC CCGACCCTCA
 42_3b   AAGCTCAACT TTGGGCAGAC TGGCGACTCA GAGTCAGTGC CCGACCCTCA
 42_11   AAGCTCAACT TTGGGCAGAC TGGCGACTCA GAGTCAGTGC CCGACCCTCA
 42_6b   AGACTCAACT TTGGGCAGAC TGGCGACTCA GAGTCAGTGC CCGACCCTCA
  43_1   AGACTGAACT TTGGGCAGAC TGGCGACTCG GAGTCAGTCC CCGACCCTCA
  43_5   AGACTGAACT TTGGGCAGAC TGGCGACTCG GAGTCAGTCC CCGACCCTCA
 43_12   AGACTGAACT TTGGGCAGAC TGGCGACTCG GAGTCAGTCC CCGACCCTCA
 43_20   AGACTCAATT TTGGTCAGAC TGGCGACTCA GAGTCAGTCC CCGACCCACA
 43_21   AGACTCAATT TTGGTCAGAC TGGCGACTCA GAGTCAGTCC CCGACCCACA
 43_23   AGACTCAATT TTGGTCAGAC TGGCGACTCA GAGTCAGTCC CCGACCCACA
 43_25   AGACTCAATT TTGGTCAGAC TGGCGACTCA GAGTCAGTCC CCGACCCACA
  44_1   AGACTCAACT TTGGGCAGAC TGGCGACTCA GAGTCAGTGC CCGACCCTCA
  44_5   AGACTCAACT TTGGGCAGAC TGGCGACTCA GAGTCAGTGC CCGACCCTCA
 223_10  AGACTCAACT TTGGGCAGAC TGGCGACTCA GAGTCAGTCC CCGACCCTCA
 223_2   AGACTCAACT TTGGGCAGAC TGGCGACTCA GAGTCAGTCC CCGACCCTCA
 223_4   AGACTCAACT TTGGGCAGAC TGGCGACTCA GAGCCAGTCC CCGACCCTCA
 223_5   AGACTCAACT TTGGGCAGAC TGGCGACTCA GAGCCAGTCC CCGACCCTCA
 223_6   AGACTCAACT TTGGGCAGAC TGGCGACTCA GAGTCAGTCC CCGACCCTCA
 223_7   AGACTCAACT TTGGGCAGAC TGGCGACTCA GAGTCAGTCC CCGACCCTCA
  A3_4   AGACTCAATT TTGGTCAGAC TGGCGACACA GAGTCAGTCC CAGACCCTCA
  A3_5   AGACTCAATT TTGGTCAGAC TGGCGACACA GAGTCAGTCC CAGACCCTCA
  A3_7   AGACTCAATT TTGGTCAGAC TGGCGACACA GAGTCAGTCC CAGACCCTCA
  A3_3   AGACTCAATT TTGGTCAGAC TGGCGACACA GAGTCAGTCC CAGGCCCTCA
 42_12   AGACTCAACT TTGGGCAGAC TGGCGACTCA GAGTCAGTGC CCGACCCTCA
  AAV1   AGACTCAATT TTGGTCAGAC TGGCGACTCA GAGTCAGTCC CCGATCACA
  AAV2   AGATTGAATT TTGGTCAGAC TGGAGACGCA GACTCAGTAC CTGACCCCCA
  AAV3   AGACTAAATT TCGGTCAGAC TGGAGACTCA GAGTCAGTCC CAGACCCTCA
  AAV8   AGACTCAATT TTGGTCAGAC TGGCGACTCA GAGTCAGTTC CAGACCCTCA
  AAV9   AGACTCAATT TTGGTCAGAC TGGCGACTCA GAGTCAGTTC CAGACCCTCA
  AAV7   AGACTCAATT TCGGTCAGAC TGGCGACTCA GAGTCAGTCC CCGACCCTCA
  44_2   AGACTCAACT TTGGGCAGAC TGGCGACTCA GAGTCAGTGC CCGACCCTCA
```

FIG. 1AAE

```
              2801                                                    2850
                                                                        vp3
start
   42_2    ACCTCTCGGA GAACCTCCCG CCGCGCCCTC AGGTCTGGGA TCTGGTACAA
   42_8    ACCAATCGGA GAACCCCCCG CAGGCCCCTC TGGTCTGGGA TCTGGTACAA
   42_15   ACCAATCGGA GAACCCCCCG CAGGCCCCTC TGGTCTGGGA TCTGGTACAA
   42_5b   ACCAATCGGA GAACCCCCCG CAGGCCCCTC TGGTCTGGGA TCTGGTACAA
   42_1b   ACCAATCGGA GAACCCCCCG CAGGCCCCTC TGGTCTGGGA TCTGGCACAA
   42_13   ACCAATCGGA GAACCCCCCG CAGGCCCCTC TGGTCTGGGA TCTGGTACAA
   42_3a   ACCAATCGGA GAACCCCCCG CAGGCCCCTC TGGTCTGGGA TCTGGTACAA
   42_4    ACCAATCGGA GAACCCCCCG CAGGCCCCTC TGGTCTGGGA TCTGGTACAA
   42_5a   ACCTCTCGGA GAACCTCCCG CCGCGCCCTC AGGTCTGGGA TCTGGTACAA
   42_10   ACCAATCGGA GAACCCCCCG CAGGCCCCTC TGGTCTGGGA TCTGGTACAA
   42_3b   ACCAATCGGA GAACCCCCCG CAGGCCCCTC TGGTCTGGGA TCTGGTACAA
   42_11   ACCAATCGGA GAACCCCCCG CAGGCCCCTC TGGTCTGGGA TCTGGTACAA
   42_6b   ACCAATCGGA GAACCCCCCG CAGGCCCCTC TGGTCTGGGA TCTGGTACAA
   43_1    ACCAATCGGA GAACCACCAG CAGGCCCCTC TGGTCTGGGA TCTGGTACAA
   43_5    ACCAATCGGA GAACCACCAG CAGGCCCCTC TGGTCTGGGA TCTGGTACAA
   43_12   ACCAATCGGA GAACCACCAG CAGGCCCCTC TGGTCTGGGA TCTGGTACAA
   43_20   ACCTCTCGGA GAACCTCCAG CAGCCCCCTC AGGTCTGGGA CCTAATACAA
   43_21   ACCTCTCGGA GAACCTCCAG CAGCCCCCTC AGGTCTGGGA CCTAATACAA
   43_23   ACCTCTCGGA GAACCTCCAG CAGCCCCCTC AGGTCTGGGA CCTAATACAA
   43_25   ACCTCTCGGA GAACCTCCAG CAGCCCCCTC AGGTCTGGGA CCTAATACAA
   44_1    ACCAATCGGA GAACCCCCCG CAGGCCCCTC TGGTCTGGGA TCTGGTACAA
   44_5    ACCAATCGGA GAACCCCCCG CAGGCCCCTC TGGTCTGGGA TCTGGTACAA
  223_10   ACCAATCGGA GAACCACCAG CAGGCCCCTC TGGTCTGGGA TCTGGTACAA
  223_2    ACCAATCGGA GAACCACCAG CAGGCCCCTC TGGTCTGGGA TCTGGTACAA
  223_4    ACCAATCGGA GAACCACCAG CAGGCCCCTC TGGTCTGGGA TCTGGTACAA
  223_5    ACCAATCGGA GAACCACCAG CAGGCCCCTC TGGTCTGGGA TCTGGTACAA
  223_6    ACCAATCGGA GAACCACCAG CAGGCCCCTC TGGTCTGGGA TCTGGTACAA
  223_7    ACCAATCGGA GAACCACCAG CAGGCCCCTC TGGTCTGGGA TCTGGTACAA
   A3_4    ACCAATCGGA GAACCCCCCG CAGCCCCCTC TGGTGTGGGA TCTAATACAA
   A3_5    ACCAATCGGA GAACCCCCCG CAGCCCCCTC TGGTGTGGGA TCTAATACAA
   A3_7    ACCAATCGGA GAACCCCCCG CAGCCCCCTC TGGTGTGGGA TCTAATACAA
   A3_3    ACCAATCGGA GAACCCCCCG CAGCCCCCTC TGGTGTGGGA TCTAATACAA
   42_12   ACCAATCGGA GAACCCCCCG CAGGCCCCTC TGGTCTGGGA TCTGGTACAA
   AAV1    ACCTCTCGGA GAACCTCCAG CAACCCCGC  TGCTGTGGGA CCTACTACAA
   AAV2    GCCTCTCGGA CAGCCACCAG CAGCCCCCTC TGGTCTGGGA ACTAATACGA
   AAV3    ACCTCTCGGA GAACCACCAG CAGCCCCCAC AAGTTTGGGA TCTAATACAA
   AAV8    ACCTCTCGGA GAACCTCCAG CAGCCCCCTC TGGTGTGGGA CCTAATACAA
   AAV9    ACCTCTCGGA GAACCTCCAG CAGCGCCCTC TGGTGTGGGA CCTAATACAA
   AAV7    ACCTCTCGGA GAACCTCCAG CAGCGCCCTC TAGTGTGGGA TCTGGTACAG
   44_2    ACCAATCGGA GAACCCCCCG CAGGCCCCTC TGGTCTGGGA TCTGGTACAA
                                                              vp3
                                                             start
```

FIG. 1AAF

```
          2851                                                        2900
        vp3 start codon
 42_2   TGGCTGCAGG CGGTGGCGCA CCAATGGCAG ACAATAACGA AGGCGCCGAC
 42_8   TGGCTGCAGG CGGTGGCGCT CCAATGGCAG ACAATAACGA AGGCGCCGAC
 42_15  TGGCTGCAGG CGGTGGCGCT CCAATGGCAG ACAATAACGA AGGCGCCGAC
 42_5b  TGGCTGCAGG CGGTGGCGCT CCAATGGCAG ACAATAACGA AGGCGCCGAC
 42_1b  TGGCTGCAGG CGGTGGCGCT CCAATGGCAG ACAATAACGA AGGCGCCGAC
 42_13  TGGCTGCAGG CGGTGGCGCT CCAATGGCAG ACAATAACGA AGGCGCCGAC
 42_3a  TGGCTGCAGG CGGTGGCGCT CCAATGGCAG ACAATAACGA AGGCGCCGAC
 42_4   TGGCTGCAGG CGGTGGCGCT CCAATGGCAG ACAATAACGA AGGCGCCGAC
 42_5a  TGGCTGCAGG CGGTGGCGCA CCAATGGCAG ACAATAACGA AGGCGCCGAC
 42_10  TGCCTGCAGG CGGTGGCGCT CCAATGGCAG ACAATAACGA AGGCGCCGAC
 42_3b  TGGCTGCAGG CGGTGGCGCT CCAATGGCAG ACAATAACGA AGGCGCCGAC
 42_11  TGGCTGCAGG CGGTGGCGCT CCAATGGCAG ACAATAACGA AGGCGCCGAC
 42_6b  TGGCTGCAGG CGGTGGCGCT CCAATGGCAG ACAATAACGA AGGCGCCGAC
 43_1   TGGCTGCAGG CGGTGGCGCT CCAATGGCAG ACAATAACGA AGGCGCCGAC
 43_5   TGGCTGCAGG CGGTGGCGCT CCAATGGCAG ACAATAACGA AGGCGCCGAC
 43_12  TGGCTGCAGG CGGTGGCGCT CCAATGGCAG ACAATAACGA AGGCGCCGAC
 43_20  TGGCTTCAGG CGGTGGCGCT CCAATGGCAG ACAATAACGA AGGCGCCGAC
 43_21  TGGCTTCAGG CGGTGGCGCT CCAATGGCAG ACAATAACGA AGGCGCCGAC
 43_23  TGGCTTCAGG CGGTGGCGCT CCAATGGCAG ACAATAACGA AGGCGCCGAC
 43_25  TGGCTTCAGG CGGTGGCGCT CCAATGGCAG ACAATAACGA AGGCGCCGAC
 44_1   TGGCTGCAGG CGGTGGCGCT CCAATGGCAG ACAATAACGA AGGCGCCGAC
 44_5   TGGCTGCAGG CGGTGGCGCT CCAATGGCAG ACAATAACGA AGGCGCCGAC
223_10  TGGCTGCAGG CGGTGGCGCA CCAATGGCTG ACAATAACGA GGGCGCCGAC
223_2   TGGTTGCAGG CGGTGGCGCA CCAATGGCTG ACAATAACGA GGGCGCCGAC
223_4   TGGCTGCAGG CGGTGGCGCA CCAATGGCTG ACAATAACGA GGGCGCCGAC
223_5   TGGCTGCAGG CGGTGGCGCA CCAATGGCTG ACAATAACGA GGGCGCCGAC
223_6   TGGCTGCAGG CGGTGGCGCA CCAATGGCTG ACAATAGCGA GGGCGCCGAC
223_7   TGGCTGCAGG CGGTGGCGCA CCAATGGCTG ACAATAACGA GGGCGCCGAC
 A3_4   TGGCTTCAGG CGGTGGGGCA CCAATGGCAG ACGATAACGA AGGCGCCGAC
 A3_5   TGGCTTCAGG CGGTGGGGCA CCAATGGCAG ACAATAACGA AGGCGCCGAC
 A3_7   TGGCTTCAGG CGGTGGGGCA CCAATGGCAG ACAATAACGA AGGCGCCGAC
 A3_3   TGGCTTCAGG CGGTGGGGCA CCAATGGCAG ACAATAACGA AGGCGCCGAC
 42_12  TGGCTGCAGG CGGTGGCGCT CCAATGGCAG ACAATAACGA AGGCGCCGAC
 AAV1   TGGCTTCAGG CGGTGGCGCA CCAATGGCAG ACAATAACGA AGGCGCCGAC
 AAV2   TGGCTACAGG CAGTGGCGCA CCAATGGCAG ACAATAACGA GGGCGCCGAC
 AAV3   TGGCTTCAGG CGGTGGCGCA CCAATGGCAG ACAATAACGA GGGTGCCGAT
 AAV8   TGGCTGCAGG CGGTGGCGCA CCAATGGCAG ACAATAACGA AGGCGCCGAC
 AAV9   TGGCTGCAGG CGGTGGCGCA CCAATGGCAG ACAATAACGA AGGCGCCGAC
 AAV7   TGGCTGCAGG CGGTGGCGCA CCAATGGCAG ACAATAACGA AGGTGCCGAC
 44_2   TGGCTGCAGG CGGTGGCGCT CCAATGGCAG ACAATAACGA AGGCGCCGAC
        vp3 start codon (cont'd)
```

FIG. 1AAG

```
        2901                                                        2950
  42_2   GGAGTGGGTA ATGCCTCCGG AAATTGGCAT TGCGATTCCA CATGGCTGGG
  42_8   GGAGTGGGTA GTTCCTCAGG AAATTGGCAT TGCGATTCCA CATGGCTGGG
 42_15   GGAGTGGGTA GTTCCTCAGG AAATTGGCAT TGCGATTCCA CATGGCTGGG
 42_5b   GGAGTGGGTA GTTCCTCAGG AAATTGGCAT TGCGATTCCA CATGGCTGGG
 42_1b   GGAGTGGGTA GTTCCTCAGG AAATTGGCAT TGCGATTCCA CATGGCTGGG
 42_13   GGAGTGGGTA GTTCCTCAGG AAATTGGCAT TGCGATTCCA CATGGCTGGG
 42_3a   GGAGTGGGTA GTTCCTCAGG AAATTGGCAT TGCGATTCCA CATAGCTGGG
  42_4   GGAGTGGGTA ATGCCTCCGG AAATTGGCAT TGCGATTCCA CATGGCTGGG
 42_5a   GGAGTGGGTA ATGCCTCCGG AAATTGGCAT TGCGATTCCA CATGGCTGGG
 42_10   GGAGTGGGTA ATGCCTCCGG AAATTGGCAT TGCGATTCCA CATGGCTGGG
 42_3b   GGAGTGGGTA ATGCCTCCGG AAATTGGCAT TGCGATTCCA CATGGCTGGG
 42_11   GGAGTGGGTA ATGCCTCCGG AAATTGGCAT TGCGATTCCA CATGGCTGGG
 42_6b   GGAGTGGGTA GTTCCTCAGG AAATTGGCAT TGCGATTCCA CATGGCTGGG
  43_1   GGAGTGGGTA GTTCCTCAGG AAATTGGCAT TGCGATTCCA CATGGCTGGG
  43_5   GGAGTGGGTA GTTCCTCAGG AAATTGGCAT TGCGATTCCA CATGGCTGGG
 43_12   GGAGTGGGTA GTTCCTCAGG AAATTGGCAT TGCGATTCCA CATGGCTGGG
 43_20   GGAGTGGGTA ATTCCTCGGG AAATTGGCAT TGCGATTCCA CATGGCTGGG
 43_21   GGAGTGGGTA ATTCCTCGGG AAATTGGCAT TGCGATTCCA CATGGCTGGG
 43_23   GGAGTGGGTA ATTCCTCGGG AAATTGGCAT TGCGATTCCA CATGGCTGGG
 43_25   GGAGTGGGTA ATTCCTCGGG AAATTGGCAT TGCGATTCCA CATGGCTGGG
  44_1   GGAGTGGGTA GTTCCTCAGG AAATTGGCAT TGCGATTCCA CATGGCTGGG
  44_5   GGAGTGGGTA GTTCCTCAGG AAATTGGCAT TGCGATTCCA CATGGCTGGG
 223_10  GGAGTGGGTA ATGCCTCAGG AAATTGGCAT TGCGATTCCA CATGGCTGGG
 223_2   GGAGTGGGTA ATGCCTCAGG AAATTGGCAT TGCGATTCCA CATGGCTGGG
 223_4   GGAGTGGGTA ATGCCTCAGG AAATTGGCAT TGCGATTCCA CACGGCTGGG
 223_5   GGAGTGGGTA ATGCCTCAGG AAATTGGCAT TGCGATTCCA CACGGCTGGG
 223_6   GGAGTGGGTA ATGCCTCAGG AAATTGGCAT TGCGATTCCA CATGGCTGGG
 223_7   GGAGTGGGTA ATGCCTCAGG AAATTGGCAT TGCGATTCCA CATGGCTGGG
  A3_4   GGAGTGGGTA ATTCCTCGGG AAATTGGCAT TGCGATTCCA CATGGATGGG
  A3_5   GGAGTGGGTA ATTCCTCGGG AAATTGGCAT TGCGATTCCA CATGGATGGG
  A3_7   GGAGTGGGTA ATTCCTCGGG AAATTGGCAT TGCGATTCCA CATGGATGGG
  A3_3   GGAGTGGGTA ATTCCTCGGG AAATTGGCAT TGCGATTCCA CATGGATGGG
 42_12   GGAGTGGGTA GTTCCTCAGG AAATTGGCAT TGCGATTCCA CATGGCTGGG
  AAV1   GGAGTGGGTA ATGCCTCAGG AAATTGGCAT TGCGATTCCA CATGGCTGGG
  AAV2   GGAGTGGGTA ATTCCTCCGG AAATTGGCAT TGCGATTCCA CATGGATGGG
  AAV3   GGAGTGGGTA ATTCCTCAGG AAATTGGCAT TGCGATTCCC AATGGCTGGG
  AAV8   GGAGTGGGTA GTTCCTCGGG AAATTGGCAT TGCGATTCCA CATGGCTGGG
  AAV9   GGAGTGGGTA ATTCCTCGGG AAATTGGCAT TGCGATTCCA CATGGCTGGG
  AAV7   GGAGTGGGTA ATGCCTCAGG AAATTGGCAT TGCGATTCCA CATGGCTGGG
 AAV10          GGTA ATTCCTCCGG AAATTGGCAT TGCGATTCCA CATGGCTGGG
 AAV11          GGTA ATTCCTCCGG AAATTGGCAT TGCGATTCCA CATGGCTGGG
 AAV12          GGTA ATTCCTCCGG AAATTGGCAT TGCGATTCCA CATGGCTGGG
  44_2   GGAGTGGGTA GTTCCTCAGG AAATTGGCAT TGCGATTCCA CATGGCTGGG
```

FIG. 1AAH

```
          2951                                                    3000
   42_2   CGACAGAGTC ATCACCACCA GCACCCGCAC CTGGGCCCTG CCCACCTACA
   42_8   CGACAGAGTC ATCACCACCA GCACCCGAAC CTGGGCCCTC CCCACCTACA
  42_15   CGACAGAGTC ATCACCACCA GCACCCGAAC CTGGGCCCTC CCCACCTACA
  42_5b   CGACAGAGTC ATCACCACCA GCACCCGAAC CTGGGCCCTC CCCACCTACA
  42_1b   CGACAGAGTC ATCACCACCA GCACCCGAAC CTGGGCCCTC CCCACCTACA
  42_13   CGACAGAGTC ATCACCACCA GCACCCGAAC CTGGGCCCTC CCCACCTACA
  42_3a   CGACAGAGTC ATCACCACCA GCACCCGAAC CTGGGCCCTC CCCACCTACA
   42_4   CGACAGAGTC ATCACCACCA GCACCCGCAC CTGGGCCCTG CCCACCTACA
  42_5a   CGACAGAGTC ATCACCACCA GCACCCGCAC CTGGGCCCTG CCCACCTACA
  42_10   CGACAGAGTC ATCACCACCA GCACCCGCAC CTGGGCCCTG CCCACCTACA
  42_3b   CGACAGAGTC ATCACCACCA GCACCCGCAC CTGGGCCCTG CCCACCTACA
  42_11   CGACAGAGTC ATCACCACCA GCACCCGCAC CTGGGCCCTG CCCACCTACA
  42_6b   CGACAGAGTC ATCACCACCA GCACCCGAAC CTGGGCCCTC CCCACCTACA
   43_1   CGACAGAGTC ATCACCACCA GCACCCGAAC CTGGGCCCTG CCCACCTACA
   43_5   CGACAGAGTC ATCACCACCA GCACCCGAAC CTGGGCCCTG CCCACCTACA
  43_12   CGACAGAGTC ATCACCACCA GCACCCGAAC CTGGGCCCTG CCCACCTACA
  43_20   GGACAGAGTC ATCACCACCA GCACCCGAAC CTGGGCCCTG CCCACCTACA
  43_21   GGACAGAGTC ATCACCACCA GCACCCGAAC CTGGGCCCTG CCCACCTACA
  43_23   GGACAGAGTC ATCACCACCA GCACCCGAAC CTGGGCCCTG CCCACCTACA
  43_25   GGACAGAGTC ATCACCACCA GCACCCGAAC CTGGGCCCTG CCCACCTACA
   44_1   CGACAGAGTC ATCACCACCA GCACCCGAAC CTGGGCCCTC CCCACCTACA
   44_5   CGACAGAGTC ATCACCACCA GCACCCGAAC CTGGGCCCTC CCCACCTACA
  223_10  CGACAGAGTC ATCACCACCA GCACCCGAAC CTGGGCCCTG CCCACCTACA
  223_2   CGACAGAGTC ATCACCACCA GCACCCGAAC CTGGGCCCTG CCCACCTACA
  223_4   CGACAGAGTC ATCACCACCA GCACCCGAAC CTGGGCCCTG CCCACCTACA
  223_5   CGACAGAGTC ATCACCACCA GCACCCGAAC CTGGGCCCTG CCCACCTACA
  223_6   CGACAGAGTC ATCACCACCA GCACCCGAAC CTGGGCCCTG CCCACCTACA
  223_7   CGACAGAGTC ATCACCACCA GCACCCGAAC CTGGGCCCTG CCCACCTACA
   A3_4   CGACAGAGTT ATCACCACCA GCACAAGAAC CTGGGCCCTC CCCACCTACA
   A3_5   CGACAGAGTT ATCACCACCA GCACAAGAAC CTGGGCCCTC CCCACCTACA
   A3_7   CGACAGAGTT ATCACCACCA GCACAAGAAC CTGGGCCCTC CCCACCTACA
   A3_3   CGACAGAGTT ATCACCACCA GCACAAGAAC CTGGGCCCTC CCCACCTACA
  42_12   CGACAGAGTC ATCACCACCA GCACCCGAAC CTGGGCCCTC CCCACCTACA
   AAV1   CGACAGAGTC ATCACCACCA GCACCCGCAC CTGGGCCTTG CCCACCTACA
   AAV2   CGACAGAGTC ATCACCACCA GCACCCGAAC CTGGGCCCTG CCCACCTACA
   AAV3   CGACAGAGTC ATCACCACCA GCACCAGAAC CTGGGCCCTG CCCACTTACA
   AAV8   CGACAGAGTC ATCACCACCA GCACCCGAAC CTGGGCCCTG CCCACCTACA
   AAV9   GGACAGAGTC ATCACCACCA GCACCCGAAC CTGGGCATTG CCCACCTACA
   AAV7   CGACAGAGTC ATTACCACCA GCACCCGAAC CTGGGCCCTG CCCACCTACA
   AAV10  CGACAGAGTC ATCACCACCA GCACCCGAAC CTGGTCCTG CCCACCTACA
   AAV11  CGACAGAGTC ATCACCACCA GCACCCGAAC CTGGGCCCTG CCAACCTACA
   AAV12  CGACCGAGTC ATTACCACCA GCACCCGGAC TTGGGCCCTG CCCACCTACA
   44_2   CGACAGAGTC ATCACCACCA GCACCCGAAC CTGGGCCCTC CCCACCTACA
```

FIG. 1AAI

```
              3001                                                          3050
    42_2     ACAACCACCT CTACAAGCAG ATATCAA..G TCAGAGCGGG GCT....ACC
    42_8     ACAACCACCT CTACAAGCAA ATCTCCAACG GGACATCGGG AGGAAGCACC
    42_15    ACAACCACCT CTACAAGCAA ATCTCCAACG GGACATCGGG AGGAAGCACC
    42_5b    ACAACCACCT CTACAAGCAA ATCTCCAACG GGACATCGGG AGGAAGCACC
    42_1b    ACAACCACCT CTACAAGCAA ATCTCCAACG GGACATCGGG AGGAAGCACC
    42_13    ACAACCACCT CTACAAGCAA ATCTCCAACG GGACATCGGG AGGAAGCACC
    42_3a    ACAACCACCT CTACAAGCAA ATCTCCAACG GGACATCGGG AGGAAGCACC
    42_4     ACAACCACCT CTACAAGCAG ATATCAA... .GTCAGAGCG GGGC..TACC
    42_5a    ACAACCACCT CTACAAGCAG ATATCAA... .GTCAGAGCG GGGC..TACC
    42_10    ACAACCACCT CTACAAGCAG ATATCAA..G TCAGAGCGGG GCTA....CC
    42_3b    ACAACCACCT CTACAAGCAG ATATCAA..G TCAGAGCGGG GCTA....CC
    42_11    ACAACCACCT CTACAAGCAG ATATCAA..G TCAGAGCGGG GCTA....CC
    42_6b    ACAACCACCT CTACAAGCAA ATCTCCAACG GGACATCGGG AGGAAGCACC
    43_1     ACAACCATCT CTACAAGCAA ATCTCCAACG GGACATCGGG AGGAAGCACT
    43_5     ACAACCATCT CTACAAGCAA ATCTCCAACG GGACATCGGG AGGAAGCACT
    43_12    ACAACCATCT CTACAAGCAA ATCTCCAACG GGACATCGGG AGGAAGCACT
    43_20    ACAACCACCT CTACAAGCAA ATCTCCAACG GCACCTCGGG AGGAAGCACC
    43_21    ACAACCACCT CTACAAGCAA ATCTCCAACG GCACCTCGGG AGGAAGCACC
    43_23    ACAACCACCT CTACAAGCAA ATCTCCAACG GCACCTCGGG AGGAAGCACC
    43_25    ACAACCACCT CTACAAGCAA ATCTCCAACG GCACCTCGGG AGGAAGCACC
    44_1     ACAACCACCT CTACAAGCAA ATCTCCAACG GGACTTCGGG AGGAAGCACC
    44_5     ACAACCACCT CTACAAGCAA ATCTCCAACG GGACTTCGGG AGGAAGCACC
   223_10    ACAACCACCT CTACAAGCAA ATCTCCAGTC AGTCAGCAGG GAG...CACC
   223_2     ACAACCACCT CTACAAGCAA ATCTCCAGTC AGTCAGCAGG GAG...CACC
   223_4     ACAACCACCT CTACAAGCAA ATCTCCAGTC AGTCAGCAGG GAG...CACC
   223_5     ACAACCACCT CTACAAGCAA ATCTCCAGTC AGTCAGCAGG GAG...CACC
   223_6     ACAACCACCT CTACAAGCAA ATCTCCAGTC AGTCAGCAGG GAG...CACC
   223_7     ACAACCACCT CTACAAGCAA ATCTCCAGTC AGTCAGCAGG GAG...CACC
    A3_4     ATAATCACCT CTACAAGCAA ATCTCCA... GCGAATCGGG AGC...CACC
    A3_5     ATAATCACCT CTACAAGCAA ATCTCCA... GCGAATCGGG AGC...CACC
    A3_7     ATAATCGCCT CTACAAGCAA ATCTCCA... GCGAATCGGG AGC...CACC
    A3_3     ATAATCACCT CTACAAGCAA ATCTCCA... GCGAATCGGG AGC...CACC
    42_12    ACAACCACCT CTACAAGCAA ATCTCCAACG GGACATCGGG AGGAAGCACC
    AAV1     ATAACCACCT CTACAAGCAA ATCTCCAGTG CTTCAACGGG .GG..CCAGC
    AAV2     ACAACCACCT CTACAAACAA ATTTCCA... GCCAATCAGG AGC...CTCG
    AAV3     ACAACCATCT CTACAAGCAA ATCTCCA... GCCAATCAGG AGC...TTCA
    AAV8     ACAACCACCT CTACAAGCAA ATCTCCAACG GGACATCGGG AGGAGCCACC
    AAV9     ACAACCACCT CTACAAGCAA ATCTCCAATG GAACATCGGG AGGAAGCACC
    AAV7     ACAACCACCT CTACAAGCAA ATCTCCAGTG AAACTGCAGG TAG...TACC
    AAV10    ACAACCACAT CTACAAGCAA ATCTCCAGCG AGACAGGAGC CACCAACGAC
    AAV11    ACAACCACCT CTACAAACAA ATCTCCAGCG CTTCAACGGG GGCCAGCAAC
    AAV12    ACAACCACCT CTACAAGCAA ATCTCCAGCC AATCGGGTGC CACCAACGAC
    44_2     ACAACCACCT CTACAAGCAA ATCTCCAACG GGACTTCGGG AGGAAGCACC
```

FIG. 1AAJ

```
           3051                                                    3100
  42_2     AACGACAACC ACTTCTTCGG CTACAGCACC CCCTGGGGCT ATTTTGACTT
  42_8     AACGACAACA CCTACTTCGG CTACAGCACC CCCTGGGGGT ATTTTGACTT
  42_15    AACGACAACA CCTACTTCGG CTACAGCACC CCCTGGGGGT ATTTTGACTT
  42_5b    AACGACAACA CCTACTTCGG CTACAGCACC CCCTGGGGGT ATTTTGACTT
  42_1b    AACGACAACA CCTACTTCGG CTACAGCACC CCCTGGGGGT ATTTTGACTT
  42_13    AACGACAACA CCTACTTCGG CTACAGCACC CCCTGGGGGT ATTTTGACTT
  42_3a    AACGACAACA CCTACTTCGG CTACAGCACC CCCTGGGGGT ATTTTGACTT
  42_4     AACGACAACC ACTTCTTCGG CTACAGCACC CCCTGGGGCT ATTTTGACTT
  42_5a    AACGACAACC ACTTCTTCGG CTACAGCACC CCCTGGGGCT ATTTTGACTT
  42_10    AACGACAACC ACTTCTTCGG CTACAGCACC CCCTGGGGCT ATTTTGACTT
  42_3b    AACGACAACC ACTTCTTCGG CTACAGCACC CCCTGGGGCT ATTTTGACTT
  42_11    AACGACAACC ACTTCTTCGG CTACAGCACC CCCTGGGGCT ATTTTGACTT
  42_6b    AACGACAACA CCTACTTCGG CTACAGCACC CCCTGGGGGT ATTTTGACTT
  43_1     AACGACAACA CCTACTTTGG CTACAGCACC CCCTGGGGGT ATTTTGACTT
  43_5     AACGACAACA CCTACTTTGG CTACAGCACC CCCTGGGGGT ATTTTGACTT
  43_12    AACGACAACA CCTACTTTGG CTACAGCACC CCCTGGGGGT ATTTTGACTT
  43_20    AACGACAACA CCTATTTTGG CTACAGCACC CCCTGGGGGT ATTTTGACTT
  43_21    AACGACAACA CCTATTTTGG CTACAGCACC CCCTGGGGGT ATTTTGACTT
  43_23    AACGACAACA CCTATTTTGG CTACAGCACC CCCTGGGGGT ATTTTGACTT
  43_25    AACGACAACA CCTATTTTGG CTACAGCACC CCCTGGGGGT ATTTTGACTT
  44_1     AACGACAACA CCTACTTCGG CTACAGCACC CCCTGGGGGT ATTTTGACTT
  44_5     AACGACAACA CCTACTTCGG CTACAGCACC CCCTGGGGGT ATTTTGACTT
 223_10    AACGATAACG TCTATTTCGG CTACAGCACC CCCTGGGGGT ATTTTGACTT
 223_2     AACGATAACG TCTATTTCGG CTACAGCACC CCCTGGGGGT ATTTTGACTT
 223_4     AACGATAACG TCTATTTCGG CTACAGCACC CCCTGGGGGT ATTTTGACTT
 223_5     AACGATAACG TCTATTTCGG CTACAGCACC CCCTGGGGGT ATTTTGACTT
 223_6     AACGATAACG TCTATTTCGG CTACAGCACC CCCTGGGGGT ATTTTGACTT
 223_7     AACGATAACG TCTATTTCGG CTACAGCACC CCCTGGGGGT ATTTTGACTT
  A3_4     AACGACAACC ACTACTTCGG CTACAGCACC CCCTGGGGGT ATTTTGACTT
  A3_5     AACGACAACC ACTACTTCGG CTACAGCACC CCCTGGGGGT ATTTTGACTT
  A3_7     AACGACAACC ACTACTTCGG CTACAGCACC CCCTGGGGGT ATTTTGACTT
  A3_3     AACGACAACC ACTACTTCGG CTACAGCACC CCCTGGGGGT ATTTTGACTT
  42_12    AACGACAACA CCTACTTCGG CTACAGCACC CCCTGGGGGT ATTTTGACTT
  AAV1     AACGACAACC ACTACTTCGG CTACAGCACC CCCTGGGGGT ATTTTGATTT
  AAV2     AACGACAATC ACTACTTTGG CTACAGCACC CCTTGGGGGT ATTTTGACTT
  AAV3     AACGACAACC ACTACTTTGG CTACAGCACC CCTTGGGGCT ATTTTGACTT
  AAV8     AACGACAACA CCTACTTCGG CTACAGCACC CCCTGGGGGT ATTTTGACTT
  AAV9     AACGACAACA CCTACTTTGG CTACAGCACC CCCTGGGGGT ATTTTGACTT
  AAV7     AACGACAACA CCTACTTCGG CTACAGCACC CCCTGGGGGT ATTTTGACTT
  AAV10    AACCACTACT TCGGCTACAG C......ACC CCCTGGGGGT ATTTTGACTT
  AAV11    ...GACAACC ACTACTTTGG CTACAGCACC CCCTGGGGGT ATTTTGACTT
  AAV12    AACCACTACT TCGGCTA... ...CAGCACC CCTTGGGGGT ATTTTGATTT
  44_2     AACGACAACA CCTACTTCGG CTACAGCACC CCCTGGGGGT ATTTTGACTT
```

FIG. 1AAK

```
           3101                                                    3150
    42_2   TAACAGATTC CACTGCCACT TCTCACCACG TGACTGGCAG CGACTCATCA
    42_8   TAACAGATTC CACTGCCACT TCTCACCACG TGACTGGCAG CGACTCATCA
   42_15   TAACAGATTC CACTGCCACT TCTCACCACG TGACTGGCAG CGACTCATCA
   42_5b   TAACAGATTC CACTGCCACT TCTCACCACG TGACTGGCAG CGACTCATCA
   42_1b   TAACAGATTC CACTGCCACT TCTCACCACG TGACTGGCAG CGACTCATCA
   42_13   TAACAGATTC CACTGCCACT TCTCACCACG TGACTGGCAG CGACTCATCA
   42_3a   TAACAGATTC CACTGCCACT TCTCACCACG TGACTGGCAG CGACTCATCA
    42_4   CAACAGATTC CACTGCCACT TCTCATCACG TGACTGGCAG CGACTCATCA
   42_5a   CAACAGATTC CACTGCCACT TCTCACCACG TGACTGGCAG CGACTCATCA
   42_10   CAACAGATTC CACTGCCACT TCTCACCACG TGACTGGCAG CGACTCATCA
   42_3b   CAACAGATTC CACTGCCACT TCTCACCACG TGACTGGCAG CGACTCATCA
   42_11   CAACAGATTC CACTGCCACT TCTCACCACG TGACTGGCAG CGACTCATCA
   42_6b   TAACAGATTC CACTGCCACT TCTCACCACG TGACTGGCAG CGACTCATCA
    43_1   CAACAGATTC CACTGCCACT TCTCACCACG TGACTGGCAG CGACTCATCA
    43_5   CAACAGATTC CACTGCCACT TCTCACCACG TGACTGGCAG CGACTCATCA
   43_12   CAACAGATTC CACTGCCACT TCTCACCACG TGACTGGCAG CGACTCATCA
   43_20   CAACAGATTC CACTGTCACT TTTCACCACG TGACTGGCAA CGACTCATCA
   43_21   CAACAGATTC CACTGTCACT TTTCACCACG TGACTGGCAA CGACTCATCA
   43_23   CAACAGATTC CACTGTCACT TTTCACCACG TGACTGGCAA CGACTCATCA
   43_25   CAACAGATTC CACTGTCACT TTTCACCACG TGACTGGCAA CGACTCATCA
    44_1   TAACAGATTC CACTGCCACT TCTCACCACG TGACTGGCAG CGACTCATCA
    44_5   TAACAGATTC CACTGCCACT TCTCACCACG TGACTGGCAG CGACTCATCA
  223_10   CAACAGATTC CATTGCCACT TCTCACCACG TGACTGGCAG CGACTTATCA
   223_2   CAACAGATTC CATTGCCACT TCTCACCACG TGACTGGCAG CGACTTATCA
   223_4   CAACAGATTC CATTGCCACT TCTCACCACG TGACTGGCAG CGACTTATCA
   223_5   CAACAGATTC CATTGCCACT TCTCACCACG TGACTGGCAG CGACTTATCA
   223_6   CAACAGATTC CATTGCCACT TCTCACCACG TGACTGGCAG CGACTTATCA
   223_7   CAACAGATTC CATTGCCACT TCTCACCACG TGACTGGCAG CGACTTATCA
    A3_4   TAACAGATTC CACTGTCACT TCTCACCACG TGACTGGCAG CGACTCATCA
    A3_5   TAACAGATTC CACTGTCACT TCTCACCACG TGACTGGCAG CGACTCATCA
    A3_7   TAACAGATTC CACTGTCACT TCTCACCACG TGACTGGCAG CGACTCATCA
    A3_3   TAACAGATTC CACTGTCACT TCTCACCACG TGACTGGCAG CGACTCATCA
   42_12   TAACAGATTC CACTGCCACT TCTCACCACG TGACTGGCAG CGACTCATCA
    AAV1   CAACAGATTC CACTGCCACT TTTCACCACG TGACTGGCAG CGACTCATCA
    AAV2   CAACAGATTC CACTGCCACT TTTCACCACG TGACTGGCAA AGACTCATCA
    AAV3   TAACAGATTC CACTGCCACT TCTCACCACG TGACTGGCAG CGACTCATTA
    AAV8   TAACAGATTC CACTGCCACT TTTCACCACG TGACTGGCAG CGACTCATCA
    AAV9   CAACAGATTC CACTGCCACT TCTCACCACG TGACTGGCAG CGACTCATCA
    AAV7   TAACAGATTC CACTGCCACT TCTCACCACG TGACTGGCAG CGACTCATCA
   AAV10   TAACAGATTC CACTGCCACT TTTCACCACG TGACTGGCAG CGACTCATCA
   AAV11   TAACAGATTC CACTGCCACT TCTCACCACG TGACTGGCAG CGACTCATCA
   AAV12   CAACAGATTC CACTGCCATT TCTCACCACG TGACTGGCAG CGACTCATCA
    44_2   TAACAGATTC CACTGCCACT TCTCACCACG TGACTGGCAG CGACTCATCA
```

FIG. 1AAL

```
           3151                                                          3200
  42_2     ACAACAACTG GGGATTCCGG CCCAGAAAGC TGCGGTTCAA GTTGTTCAAC
  42_8     ACAACAACTG GGGATTCCGG CCCAAGAGAC TCAACTTCAA GCTCTTCAAC
  42_15    ACAACAACTG GGGATTCCGG CCCAAGAGAC TCAACTTCAA GCTCTTCAAC
  42_5b    ACAACAACTG GGGATTCCGG CCCAAGAGAC TCAACTTCAA GCTCTTCAAC
  42_1b    ACAACAACTG GGGATTCCGG CCCAAGAGAC TCAACTTCAA GCTCTTCAAC
  42_13    ACAACAACTG GGGATTCCGG CCCAAGAGAC TCAACTTCAA GCTCTTCAAC
  42_3a    ACAACAGCTG GGGATTCCGG CCCAAGAGAC TCAACTTCAA GCTCTTCAAC
  42_4     ACAACAACTG GGGATTCCGG CCCAAGAGAC TCAACTTCAA GCTCTTCAAC
  42_5a    ACAACAACCG GGGATTCCGG CCCAGAAAGC TGCGGTTCAA GTTGTTCAAC
  42_10    ACAACAACTG GGGATTCCGG CCCAGAAAGC TGCGGTTCAA GTTGTTCAAC
  42_3b    ACAACAACTG GGGATTCCGG CCCAGAAAGC TGCGGTTCAA GTTGTTCAAC
  42_11    ACAACAACTG GGGATTCCGG CCCAGAAAGC TGCGGTTCAA GTTGTTCAAC
  42_6b    ACAACAACTG GGGATTCCGG CCCAGAAAGC TGCGGTTCAA GTTGTTCAAC
  43_1     ACAATAACTG GGGATTCCGG CCCAAGAGAC TCAACTTCAA GCTCTTCAAC
  43_5     ACAATAACTG GGGATTCCGG CCCAAGAGAC TCAACTTCAA GCTCTTCAAC
  43_12    ACAATAACTG GGGATTCCGG CCCAAGAGAC TCAACTTCAA GCTCTTCAAC
  43_20    ACAACAATTG GGGATTCCGG CCCAAAAGAC TCAACTTCAA GCTGTTCAAC
  43_21    ACAACAATTG GGGATTCCGG CCCAAAAGAC TCAACTTCAA GCTGTTCAAC
  43_23    ACAACAATTG GGGATTCCGG CCCAAAAGAC TCAACTTCAA GCTGTTCAAC
  43_25    ACAACAATTG GGGATTCCGG CCCAAAAGAC TCAACTTCAA GCTGTTCAAC
  44_1     ACAACAACTG GGGATTCCGG CCCAAGAGAC TCAACTTCAA GCTCTTCAAC
  44_5     ACAACAACTG GGGATTCCGG CCCAAGAGAC CCAACTTCAA GCTCTTCAAC
 223_10    ACAACAACTG GGGATTCCGG CCCAAGAAGC TCAACTTCAA GCTCTTCAAC
 223_2     ACAACAACTG GGGATTCCGG CCCAAGAAGC TCAACTTCAA GCTCTTCAAC
 223_4     ACAACAACTG GGGATTCCGG CCCAAGAAGC TCAACTTCAA GCTCTTCAAC
 223_5     ACAACAACTG GGGATTCCGG CCCAAGAAGC TCAACTTCAA GCTCTTCAAC
 223_6     ACAACAACTG GGGATTCCGG CCCAAGAAGC TCAACTTCAA GCTCTTCAAC
 223_7     ACAACAACTG GGGATTCCGG CCCAAGAAGC TCAACTTCAA GCTCTTCAAC
  A3_4     ACAACAACTG GGGATTTAGA CCCAAGAAAC TCAATTTCAA GCTCTTCAAC
  A3_5     ATAACAACTG GGGATTTAGA CCCAAGAAAC TCAATTTCAA GCTCTTCAAC
  A3_7     ACAACAACTG GGGATTTAGA CCCAAGAAAC TCAATTTCAA GCTCTTCAAC
  A3_3     ACAACAACTG GGGATTTAGA CCCAAGAAAC TCAATTTCAA GCTCTTCAAC
  42_12    ACAACAACTG GGGATTCCGG CCCAAGAGAC TCAACTTCAA GCTCTTCAAC
  AAV1     ACAACAATTG GGGATTCCGG CCCAAGAGAC TCAACTTCAA ACTCTTCAAC
  AAV2     ACAACAACTG GGGATTCCGA CCCAAGAGAC TCAACTTCAA GCTCTTTAAC
  AAV3     ACAACAACTG GGGATTCCGG CCCAAGAAAC TCAGCTTCAA GCTCTTCAAC
  AAV8     ACAACAACTG GGGATTCCGG CCCAAGAGAC TCAGCTTCAA GCTCTTCAAC
  AAV9     ACAACAACTG GGGATTCCGG CCAAAGAGAC TCAACTTCAA GCTGTTCAAC
  AAV7     ACAACAACTG GGGATTCCGG CCCAAGAAGC TGCGGTTCAA GCTCTTCAAC
  AAV10    ACAACAACTG GGGATTC
  AAV11    ACAACAACTG GGGATTC
  AAV12    ACAACAACTG GGGATTC
  44_2     ACAACAACTG GGGATTCCGG CCCAAGAGAC TCAACTTCAA GCTCTTCAAC
```

FIG. 1AAM

```
       3201                                                    3250
 42_2  ATCCAGGTCA AGGAGGTCAC GACGAACGAC GGCGTTACGA CCATCGCTAA
 42_8  ATCCAGGTCA AGGAGGTCAC GCAGAATGAA GGCACCAAGA CCATCGCCAA
 42_15 ATCCAGGTCA AGGAGGTCAC GCAGAATGAA GGCACCAAGA CCATCGCCAA
 42_5b ATCCAGGTCA AGGAGGTCAC GCAGAATGAA GGCACCAAGA CCATCGCCAA
 42_1b ATCCAGGTCA AGGAGGTCAC GCAGAATGAA GGCACCAAGA CCATCGCCAA
 42_13 ATCCAGGTCA AGGAGGTCAC GCAGAATGAA GGCACCAAGA CCATCGCCAA
 42_3a ATCCAGGTCA AGGAGGTCAC GCAGAATGAA GGCACCAAGA CCATCGCCAA
 42_4  ATCCAGGTCA AGGAGGTCAC GCAGAATGAA GGCACCAAGA CCATCGCCAA
 42_5a ATCCAGGTCA AGGAGGTCAC GACGAACGAC GGCGTTACGA CCATCGCTAA
 42_10 ATCCAGGTCA AGGAGGTCAC GACGAACGAC GGCGTTACGA CCATCGCTAA
 42_3b ATCCAGGTCA AGGAGGTCAC GACGAACGAC GGCGTTACGA CCATCGCTAA
 42_11 ATCCAGGTCA AGGAGGTCAC GACGAACGAC GGCGTTACGA CCATCGCTAA
 42_6b ATCCAGGTCA AGGAGGTCAC GACGGACGAC GGCGTTACGA CCATCGCTAA
 43_1  ATCCAGGTCA AGGAGGTCAC GCAGAATGAA GGCACCAAGA CCATCGCCAA
 43_5  ATCCAGGTCA AGGAGGTCAC GCAGAATGAA GGCACCAAGA CCATCGCCAA
 43_12 ATCCAGGTCA AGGAGGTCAC GCAGAATGAA GGCACCAAGA CCATCGCCAA
 43_20 ATCCAGGTCA AGGAAGTCAC GACGAACGAA GGCACCAAGA CCATCGCCAA
 43_21 ATCCAGGTCA AGGAAGTCAC GACGAACGAA GGCACCAAGA CCATCGCCAA
 43_23 ATCCAGGTCA AGGAAGTCAC GACGAACGAA GGCACCAAGA CCATCGCCAA
 43_25 ATCCAGGTCA AGGAAGTCAC GACGAACGAA GGCACCAAGA CCATCGCCAA
 44_1  ATCCAGGTCA AGGAGGTCAC GCAGAATGAA GGCACCAAGA CCATCGCCAA
 44_5  ATCCAGGTCA AGGAGGTCAC GCAGAATGAA GGCACCAAGA CCATCGCCAA
223_10 ATCCAGGTCA AGGAGGTCAC GACGAATGAC GGTGTCACAA CCATCGCTAA
223_2  ATCCAGGTCA AGGAGGTCAC GACGAATGAC GGTGTCACAA CCATCGCTAA
223_4  ATCCAGGTCA AGGAGGTCAC GACGAATGAC GGCGTCACAA CCATCGCTAA
223_5  ATCCAGGTCA AGGAGGTCAC GACGAATGAC GGCGTCACAA CCATCGCTAA
223_6  ATCCAGGTCA AGGAGGTCAC GACGAATGAC GGTGTCACAA CCATCGCTAA
223_7  ATCCAGGTCA AGGAGGTCAC GACGAATGAC GGCGTCACAA CCATCGCTAA
 A3_4  ATCCAAGTCA AGGAGGTCAC GCAGAATGAT GGAACCACGA CCATCGCCAA
 A3_5  ATCCAAGTCA AGGAGGTCAC GCAGAATGAT GGAACCACGA CCATCGCCAA
 A3_7  ATCCAAGTCA AGGAGGTCAC GCAGAATGAT GGAACCACGA CCATCGCCAA
 A3_3  ATCCAAGTCA AGGAGGTCAC GCAGAATGAT GGAACCACGA CCATCGCCAA
 42_12 ATCCAGGTCA AGGAGGTCAC GCAGAATGAA GGCACCAAGA CCATCGCCAA
 AAV1  ATCCAAGTCA AGGAGGTCAC GACGAATGAT GGCGTCACAA CCATCGCTAA
 AAV2  ATTCAAGTCA AAGAGGTCAC GCAGAATGAC GGTACGACGA CGATTGCCAA
 AAV3  ATCAAGTTA CAGGGTCAC GCAGAACGAT GGCACGACGA CTATTGCCAA
 AAV8  ATCCAAGTCA AGGAGGTCAC GCAGAATGAA GGCACCAAGA CCATCGCCAA
 AAV9  ATCCAGGTCA AGGAGGTTAC GACGAACGAA GGCACCAAGA CCATCGCCAA
 AAV7  ATCCAGGTCA AGGAGGTCAC GACGAATGAC GGCGTTACGA CCATCGCTAA
 44_2  ATCCAGGTCA AGGAGGTCAC GCAGAATGAA GGCACCAAGA CCATCGCCAA
```

FIG. 1AAN

```
          3251                                                      3300
   42_2   TAACCTTACC AGCACGATTC AGGTCTTCTC GGACTCGGAG TACCAACTGC
   42_8   TAACCTTACC AGCACGATTC AGGTCTTTAC GGACTCGGAA TACCAGCTCC
  42_15   TAACCTTACC AGCACGATTC AGGTCTTTAC GGACTCGGAA TACCAGCTCC
  42_5b   TAACCTTACC AGCACGATTC AGGTCTTTAC GGACTCGGAA TACCAGCTCC
  42_1b   TAACCTTACC AGCACGATTC AGGTCTTTAC GGACTCGGAA TACCAGCTCC
  42_13   TAACCTTACC AGCACGATTC AGGTCTTTAC GGACTCGGAA TACCAGCTCC
  42_3a   TAACCTTACC AGCACGATTC AGGTCTTTAC GGACTCGGAA TACCAGCTCC
   42_4   TAACCTTACC AGCACGATTC AGGTCTTTAC GGACTCGGAA TACCGGCTCC
  42_5a   TAACCTTACC AGCACGATTC AGGTCTTCTC GGACTCGGAG TACCAACTGC
  42_10   TAACCTTACC AGCACGATTC AGGTCTTCTC GGACTCGGAG TACCAACTGC
  42_3b   TAACCTTACC AGCACGATTC AGGTCTTCTC GGACTCGGAG TACCAACTGC
  42_11   TAACCTTACC AGCACGATTC AGGTCTTCTC GGACTCGGAG TACCAACTGC
  42_6b   TAACCTTACC AGCACGATTC AGGTCTTCTC GGACTCGGAG TACCAACTGC
   43_1   TAACCTTACC AGCACGATTC AGGTGTTTAC GGACTCGGAA TACCAGCTCC
   43_5   TAACCTTACC AGCACGATTC AGGTGTTTAC GGACTCGGAA TACCAGCTCC
  43_12   TAACCTTACC AGCACGATTC AGGTGTTTAC GGACTCGGAA TACCAGCTCC
  43_20   TAATCTCACC AGCACCGTGC AGGTCTTTAC GGACTCGGAG TACCAGTTAC
  43_21   TAATCTCACC AGCACCGTGC GGGTCTTTAC GGACTCGGAG TACCAGTTAC
  43_23   TAATCTCACC AGCACCGTGC AGGTCTTTAC GGACTTGGAG TACCAGTTAC
  43_25   TAATCTCACC AGCACCGTGC AGGTCTTTAC GGACTCGGAG TACCAGTTAC
   44_1   TAACCTTACC AGCACGATTC AGGTCTTTAC GGACTCGGAA TACCAGCTCC
   44_5   TAACCTTACC AGCACGATTC AGGTCTTTAC GGACTCGGAA TACCAGCTCC
  223_10  TAACCTTACC AGCACGGTTC AGGTCTTTTC GGACTCGGAA TATCAACTGC
  223_2   TAACCTTACC AGCACGGTTC AGGTCTTTTC GGACTCGGAA TATCAACTGC
  223_4   TAACCTTACC AGCACGGTTC AGGTCTTTTC GGACTCGGAA TATCAACTGC
  223_5   TAACCTTACC AGCACGGTTC AGGTCTTTTC GGACTCGGAA TATCAACTGC
  223_6   TAACCTTACC AGCACGGTTC AGGTCTTTTC GGACTCGGAA TATCAACTGC
  223_7   TAACCTTACC AGCACGGTTC AGGTCTTTTC GGACCCGGAA TATCAACTGC
   A3_4   TAACCTTACC AGCACGGTGC AGGTCTTCAC AGACTCTGAG TACCAGCTGC
   A3_5   TAACCTTACC AGCACGGTGC AGGTCTTCAC AGACTCTGAG TACCAGCTGC
   A3_7   TAACCTTACC AGCACGGTGC AGGTCTTCAC AGACTCTGAG TACCAGCTGC
   A3_3   TAACCTTACC AGCGCGGTGC AGGTCTTCAC AGACTCTGAG TACCAGCTGC
  42_12   TAACCTTACC AGCACGATTC AGGTCTTTAC GGACTCGGAA TACCAGCTCC
   AAV1   TAACCTTACC AGCACGGTTC AAGTCTTCTC GGACTCGGAG TACCAGCTTC
   AAV2   TAACCTTACC AGCACGGTTC AGGTGTTTAC TGACTCGGAG TACCAGCTCC
   AAV3   TAACCTTACC AGCACGGTTC AAGTGTTTAC GGACTCGGAG TATCAGCTCC
   AAV8   TAACCTCACC AGCACCATCC AGGTGTTTAC GGACTCGGAG TACCAGCTGC
   AAV9   TAACCTTACC AGCACCGTCC AGGTCTTTAC GGACTCGGAG TACCAGCTAC
   AAV7   TAACCTTACC AGCACGATTC AGGTATTCTC GGACTCGGAA TACCAGCTGC
   44_2   TAACCTTACC AGCACGATTC AGGTCTTTAC GGACTCGGAA TACCAGCTCC
```

FIG. 1AAO

```
         3301                                                    3350
  42_2   CGTACGTCCT CGGCTCTGCG CACCAGGGCT GCCTCCCTCC GTTCCCTGCG
  42_8   CGTACGTCCT CGGCTCTGCG CACCAGGGCT GCCTGCCTCC GTTCCCGGCG
 42_15   CGTACGTCCT CGGCTCTGCG CACCAGGGCT GCCCGCCTCC GTTCCCGGCG
 42_5b   CGTACGTCCT CGGCTCTGCG CACCAGGGCT GCCTGCCTCC GTTCCCGGCG
 42_1b   CGTACGTCCT CGGCTCTGCG CACCAGGGCT GCCTGCCTCC GTTCCCGGCG
 42_13   CGTACGTCCT CGGCTCTGCG CACCAGGGCT GCCTGCCTCC GTTCCCGGCG
 42_3a   CGTACGTCCT CGGCTCTGCG CACCAGGGCT GCCTGCCTCC GTTCCCGGCG
  42_4   CGTACGTCCT CGGCTCTGCG CACCAGGGCT GCCTGCCTCC GTTCCCGGCG
 42_5a   CGTACGTCCT CGGCTCTGCG CACCAGGGCT GCCTCCCTCC GTTCCCTGCG
 42_10   CGTACGTCCT CGGCTCTGCG CACCAGGGCT GCCTCCCTCC GTTCCCTGCG
 42_3b   CGTACGTCCT CGGCTCTGCG CACCAGGGCT GCCTCCCTCC GTTCCCTGCG
  42_1   CGTACGTCCT CGGCTCTGCG CACCAGGGCT GCCTCCCTCC GTTCCCTGCG
 42_6b   CGTACGTCCT CGGCTCTGCG CACCAGGGCT GCCTCCCTCC GTTCCCTGCG
  43_1   CGTACGTCCC CGGCTCTGCG CACCAGGGCT GCCTCCCTCC GTTCCCGGCG
  43_5   CGTACGTCCC CGGCTCTGCG CACCAGGGCT GCCTCCCTCC GTTCCCGGCG
 43_12   CGTACGTCCT CGGCTCTGCG CACCAGGGCT GCCTCCCTCC GTTCCCGGCG
 43_20   CGTACGTGCT AGGATCCGCT CACCAGGGAT GTCTGCCTCC GTTCCCGGCG
 43_21   CGTACGTGCT AGGATCCGCT CACCAGGGAT GTCTGCCTCC GTTCCCGGCG
 43_23   CGTACGTGCT AGGATCCGCT CACCAGGGAT GTCTGCCTCC GTTCCCGGCG
 43_25   CGTACGTGCT AGGATCCGCT CACCAGGGAT GTCTGCCTCC GTTCCCGGCG
  44_1   CGTACGTCCT CGGCTCTGCG CACCAGGGCT GCCTGCCTCC GTTCCCGGCG
  44_5   CGTACGTCCT CGGCTCTGCG CACCAGGGCT GCCTGCCTCC GTTCCCGGCG
 223_10  CGTACGTCCT CGGCTCCGCG CACCAGGGCT GCCTGCCTCC GTTCCCGGCA
 223_2   CGTACGTCCT CGGCTCCGCG CACCAGGGCT GCCTGCCTCC GTTCCCGGCA
 223_4   CGTACGTCCT CGGCTCCGCG CACCAGGGCT GCCTGCCTCC GTTCCCGGCA
 223_5   CGTACGTCCT CGGCTCCGCG CACCAGGGCT GCCTGCCTCC GTTCCCGGCA
 223_6   CGTACGTCCT CGGCTCCGCG CACCAGGGCT GCCTGCCTCC GTTCCCGGCA
 223_7   CGTACGTCCT CGGCTCCGCG CACCAGGGCT GCCTGCCTCC GTTCCCGGCA
  A3_4   CCTACGTCCT CGGTTCGGCT CACCAGGGCT GCCTTCCGCC GTTCCCAGCA
  A3_5   CCTACGTCCT CGGTTCGGCT CACCAGGGCT GCCTTCCGCC GTTCCCAGCA
  A3_7   CCTACGTCCT CGGTTCGGCT CACCAGGGCT GCCTTCCGCC GTTCCCAGCA
  A3_3   CCTACGTCCT CGGTTCGGCT CACCAGGGCT GCCTTCCGCC GTTCCCAGCA
 42_12   CGTACGTCCT CGGCTCTGCG CACCAGGGCT GCCTGCCTCC GTTCCCGGCG
  AAV1   CGTACGTCCT CGGCTCTGCG CACCAGGGCT GCCTCCCTCC GTTCCCGGCG
  AAV2   CGTACGTCCT CGGCTCGGCG CATCAAGGAT GCCTCCCGCC GTTCCCAGCA
  AAV3   CGTACGTGCT CGGGTCGGCG CACCAAGGCT GTCTCCCGCC GTTTCCAGCG
  AAV8   CGTACGTTCT CGGCTCTGCC CACCAGGGCT GCCTGCCTCC GTTCCCGGCG
  AAV9   CGTACGTCCT AGGCTCTGCC CACCAAGGAT GCCTGCCACC GTTTCCTGCA
  AAV7   CGTACGTCCT CGGCTCTGCG CACCAGGGCT GCCTGCCTCC GTTCCCGGCG
  44_2   CGTACGTCCT CGGCTCTGCG CACCAGGGCT GCCTGCCTCC GTTCCCGGCG
```

FIG. 1AAP

```
            3351                                                    3400
     42_2   GACGTGTTCA TGATTCCTCA GTACGGATAT CTGACTCTAA ACAACGGCAG
     42_8   GACGTCTTCA TGATTCCTCA GTACGGGTAC CTGACTCTGA ACAACGGCAG
    42_15   GACGTCTTCA TGATTCCTCA GTACGGGTAC CTGACTCTGA ACAACGGCAG
    42_5b   GACGTCTTCA TGATTCCTCA GTACGGGTAC CTGACTCTGA ACAACGGCAG
    42_1b   GACGTCTTCA TGATTCCTCA GTACGGGTAC CTGACTCTGA ACAACGGCAG
    42_13   GACGTCTTCA TGATTCCTCA GTACGGGTAC CTGACTCTGA ACAACGGCAG
    42_3a   GACGTCTTCA TGATTCCTCA GTACGGGTAC CTGACTCTGA ACAACGGCAG
     42_4   GACGTCTTCA TGATTCCTCA GTACGGGTAC CTGACTCTGA ACAACGGCAG
    42_5a   GACGTGTTCA TGATTCCTCA GTACGGATAT CTGACTCTAA ACAACGGCAG
    42_10   GACGTGTTCA TGATTCCTCA GTACGGATAT CTGACTCTAA ACAACGGCAG
    42_3b   GACGTGTTCA TGATTCCTCA GTACGGATAT CTGACTCTAA ACAACGGCAG
     42_1   GACGTGTTCA TGATTCCTCA GTACGGATAT CTGACTCTAA ACAACGGCAG
    42_6b   GACGTGTTCA TGATTCCTCA GTACGGATAT CTGACTCTAA ACAACGGCAG
     43_1   GACGTCTTCA TGATTCCTCA GTACGGGTAT CTGACCCTAA ACAATGGCAG
     43_5   GACGTCTTCA TGATTCCTCA GTACGGGTAT CTGACCCTAA ACAATGGCAG
    43_12   GACGTCTTCA TGATTCCTCA GTACGGGTAT CTGACCCTAA ACAATGGCAG
    43_20   GACGTCTTCA CGGTTCCTCA GTACGGCTAT TTAACTTTAA ACAATGGAAG
    43_21   GACGTCTTCA TGGTTCCTCA GTACGGCTAT TTAACTTTAA ACAATGGAAG
    43_23   GACGTCTTCA TGGTTCCTCA GTACGGCTAT TTAACTTTAA ACAATGGAAG
    43_25   GACGTCTTCA TGGTTCCTCA GTACGGCTAT TTAACTTTAA ACAATGGAAG
     44_1   GACGTCTTCA TGATTCCTCA GTACGGGTAC CTGACTCTGA ACAATGGCAG
     44_5   GACGTCTTCA TGATTCCTCA GTACGGGTAC CTGACTCTGA ACAATGGCAG
   223_10   GACGTGTTCA TGATTCCGCA GTACGGATAC CTGACTCTGA ACAATGGCAG
    223_2   GACGTGTTCA TGATTCCGCA GTACGGATAC CTGACTCTGA ACAATGGCAG
    223_4   GACGTGTTCA TGATTCCGCA GTACGGATAC CTGACTCTGA ACAATGGCAG
    223_5   GACGTGTTCA TGATTCCGCA GTACGGATAC CTGACTCTGA ACAATGGCAG
    223_6   GACGTGTTCA TGATTCCGCA GTACGGATAC CTGACTCTGA ACAATGGCAG
    223_7   GACGTGTTCA TGATTCCGCA GTACGGATAC CTGACTCTGA ACAATGGCAG
     A3_4   GACGTCTTCA TGATTCCTCA GTACGGCTAC TTGACTCTGA ACAATGGCAG
     A3_5   GACGTCTTCA TGATTCCTCA GTACGGCTAC TTGACTCTGA ACAATGGCAG
     A3_7   GACGTCTTCA TGATTCCTCA GTACGGCTAC TTGACTCTGA ACAATGGCAG
     A3_3   GACGTCTTCA TGATTCCTCA GTACGGCTAC TTGACTCTGA ACAATGGCAG
    42_12   GACGTCTTCA TGATTCCTCA GTACGGGTAC CTGACTCTGA ACAACGGCAG
     AAV1   GACGTGTTCA TGATTCCGCA ATACGGCTAC CTGACGCTCA ACAATGGCAG
     AAV2   GACGTCTTCA TGGTGCCACA GTATGGATAC CTCACCCTGA ACAACGGGAG
     AAV3   GACGTCTTCA TGGTCCCTCA GTATGGATAC CTCACCCTGA ACAACGGAAG
     AAV8   GACGTGTTCA TGATTCCCCA GTACGGCTAC CTAACACTCA ACAACGGTAG
     AAV9   GACGTCTTCA TGGTTCCTCA GTACGGCTAC CTGACGCTCA ACAATGGAAG
     AAV7   GACGTCTTCA TGATTCCTCA GTACGGCTAC CTGACTCTCA ACAATGGCAG
     44_2   GACGTCTTCA TGATTCCTCA GTACGGGTAC CTGACTCTGA ACAATGGCAG
```

FIG. 1AAQ

```
          3401                                                    3450
  42_2    TCAGTCTGTG GGACGTTCCT CCTTCTACTG CCTGGAGTAC TTTCCTTCTC
  42_8    TCAGGCCGTG GGCCGTTCCT CCTTCTACTG CCTGGAGTAC TTTCCTTCTC
  42_15   TCAGGCCGTG GGCCGTTCCT CCTTCTACTG CCTGGAGTAC TTTCCTTCTC
  42_5b   TCAGGCCGTG GGCCGTTCCT CCTTCTACTG CCTGGAGTAC TTTCCTTCTC
  42_1b   TCAGGCCGTG GGCCGTTCCT CCTTCTACTG CCTGGAGTAC TTTCCTTCTC
  42_13   TCAGGCCGTG GGCCGTTCCT CCTTCTACTG CCTGGAGTAC TTTCCTTCTC
  42_3a   TCAGGCCGTG GGCCGTTCCT CCTTCTACTG CCTGGAGTAC TTTCCTTCTC
  42_4    TCAGGCCGTG GGCCGTTCCT CCTTCTACTG CCTGGAGTAC TTTCCTTCTC
  42_5a   TCAGTCTGTG GGACGTTCCT CCTTCTACTG CCTGGAGTAC TTTCCTTCTC
  42_10   TCAGTCTGTG GGACGTTCCT CCTTCTACTG CCTGGAGTAC TTTCCTTCTC
  42_3b   TCAGTCTGTG GGACGTTCCT CCTTCTACTG CCTGGAGTAC TTTCCTTCTC
  42_11   TCAGTCTGTG GGACGTTCCT CCTTCTACTG CCTGGAGTAC TTTCCTTCTC
  42_6b   TCAGTCTGTG GGACGTTCCT CCTTCTACTG CCTGGAGTAC TTTCCTTCTC
  43_1    TCAGGCTGTG GGCCGTTCCT CCTTCTACTG CCTGGAATAC TTCCCTTCTC
  43_5    TCAGGCTGTG GGCCGTTCCT CCTTCTACTG CCTGGAATAC TTCCCTTCTC
  43_12   TCAGGCTGTG GGCCGTTCCT CCTTCTACTG CCTGGAATAC TTCCCTTCTC
  43_20   CCAAGCCCTG GGACGTTCCT CCTTCTACTG TCTGGAGTAT TTCCCATCGC
  43_21   CCAAGCCCTG GGACGTTCCT CCTTCTACTG TCTGGAGTAT TTCCCATCGC
  43_23   CCAAGCCCTG GGACGTTCCT CCTTCTACTG TCTGGAGTAT TTCCCATCGC
  43_25   CCAAGCCCTG GGACGTTCCT CCTTCTACTG TCTGGAGTAT TTCCCATCGC
  44_1    TCAGGCCGTG GGCCGTTCCT CCTTCTACTG CCTGGAGTAC TTTCCTTCTC
  44_5    TCAGGCCGTG GGCCGTTCCT CCTTCTACTG CCTGGAGTAC TTTCCTTCTC
 223_10   CCAATCGGTA GGCCGTTCCT CCTTCTACTG CCTGGAGTAC TTTCCTTCTC
 223_2    CCAATCGGTA GGCCGTTCCT CCTTCTACTG CCTGGAGTAC TTTCCTTCTC
 223_4    CCAATCGGTA GGCCGTTCCT CCTTCTACTG CCTGGAGTAC TTTCCTTCTC
 223_5    CCAATCGGTA GGCCGTTCCT CCTTCTACTG CCTGGAGTAC TTTCCTTCTC
 223_6    CCAATCGGTA GGCCGTTCCT CCTTCTACTG CCTGGAGTAC TTTCCTTCTC
 223_7    CCAATCGGTA GGCCGTTCCT CCTTCTACTG CCTGGAGTAC TTTCCTTCTC
  A3_4    CCAAGCGGTA GGACGTTCTT CATTCTACTG TCTAGAGTAT TTTCCCTCTC
  A3_5    CCAAGCGGTA GGACGTTCTT CATTCTACTG TCTAGAGTAT TTTCCCTCTC
  A3_7    CCAAGCGGTA GGACGTTCTT CATTCTACTG TCTAGAGTAT TTTCCCTCTC
  A3_3    CCAAGCGGTA GGACGTTCTT CATTCTACTG TCTAGAGTAT TTTCCCTCTC
  42_12   TCAGGCCGTG GGCCGTTCCT CCTTCTACTG CCTGGAGTAC TTTCCTTCTC
  AAV1    CCAAGCCGTG GGACGTTCAT CCTTTTACTG CCTGGAATAT TTCCCTTCTC
  AAV2    TCAGGCAGTA GGACGCTCTT CATTTTACTG CCTGGAGTAC TTTCCTTCTC
  AAV3    TCAAGCGGTG GGACGCTCAT CCTTTTACTG CCTGGAGTAC TTCCCTTCGC
  AAV8    TCAGGCCGTG GGACGCTCCT CCTTCTACTG CCTGGAATAC TTTCCTTCGC
  AAV9    TCAAGCGTTA GGACGTTCTT CTTTCTACTG TCTGGAATAC TTCCCTTCTC
  AAV7    TCAGTCTGTG GGACGTTCCT CCTTCTACTG CCTGGAGTAC TTCCCCTCTC
  44_2    TCAGGCCGTG GGCCGTTCCT CCTTCTACTG CCTGGAGTAC TTTCCTTCTC
```

FIG. 1AAR

```
         3451                                                    3500
  42_2   AGATGCTGAG AACGGGCAAT AACTTTGAAT TCAGCTACAC CTTTGAGGAA
  42_8   AAATGCTGAG AACGGGCAAC AACTTTGAGT TCAGCTACCA GTTTGAGGAC
 42_15   AAATGCGGAG AACGGGCAAC AACTTTGAGT TCAGCTACCA GTTTGAGGAC
 42_5b   AAATGCTGAG AACGGGCAAC AACTTTGAGT TCAGCTACCA GTTTGAGGAC
 42_1b   AAATGCTGAG AACGGGCAAC AACTTTGAGT TCAGCTACCA GTTTGAGGAC
 42_13   AAATGCTGAG AACGGGCAAC AACTTTGAGT TCAGCTACCA GTTTGAGGAC
 42_3a   AAATGCTGAG AACGGGCAAC AACTTTGAGT TCAGCTACCA GTTTGAGGAC
  42_4   AAATGCTGAG AACGGGCAAC AACTTTGAGT TCAGCTACCA GTTTGAGGAC
 42_5a   AGATGCTGAG AACGGGCAAT AACTTTGAAT TCAGCTACCA GTTTGAGGAC
 42_10   AGATGCTGAG AACGGGCAAT AACTTTGAAT TCAGCTACAC CTTTGAGGAA
 42_3b   AGATGCTGAG AACGGGCAAT AACTTTGAAT TCAGCTACAC CTTTGAGGAA
 42_11   AGATGCTGAG AACGGGCAAT AACTTTGAAT TCAGCTACAC CTTTGAGGAA
 42_6b   AGATGCTGAG AACGGGCAAT AACTTTGAAT TCAGCTACAC CTTTGAGGAA
  43_1   AAATGCTGAG GACGGGCAAC AACTTTGAAT TCAGCTACAC CTTCGAGGAC
  43_5   AAATGCTGAG GACGGGCAAC AACTTTGAAT TCAGCTACAC CTTCGAGGAC
 43_12   AAATGCTGAG GACGGGCAAC AACTTTGAAT TCAGCTACAC CTTCGAGGAC
 43_20   AGATGCTGAG AACCGGCAAC AACTTTCAGT TCAGCTACAC CTTCGAGGAC
 43_21   AGATGCTGAG AACCGGCAAC AACTTTCAGT TCAGCTACAC CTTCGAGGAC
 43_23   AGATGCCGAG AACCGGCAAC AACTTTCAGT TCAGCTACAC CTTCGAGGAC
 43_25   AGATGCTGAG AACCGGCAAC AACTTTCAGT TCAGCTACAC CTTCGAGGAC
  44_1   AAATGCTGAG AACGGGCAAC AACTTTGAGT TCAGCTACCA GTTTGAGGAC
  44_5   AAATGCTGAG AACGGGCAAC AACTTTGAGT TCAGCTACCA GTTTGAGGAC
 223_10  AGATGCTGAG AACGGGCAAC AACTTCACCT TTAGCTACAC CTTCGAGGAC
 223_2   AGATGCTGAG AACGGGCAAC AACTTCACCT TTAGCTACAC CTTCGAGGAC
 223_4   AGATGCTGAG AACGGGCAAC AACTTCACCT TTAGCTACAC CTTCGAGGAC
 223_5   AGATGCTGAG AACGGGCAAC AACTTCACCT TTAGCTACAC CTTCGAGGAC
 223_6   AGATGCTGAG AACGGGCAAC AACTTCACCT TTAGCTACAC CTTCGAGGAC
 223_7   AGATGCTGAG AACGGGCAAC AACTTCACCT TTAGCTACAC CTTCGAGGAC
  A3_4   AGATGCTGAG GACGGGAAAC AACTTCACCT TCAGCTACAC TTTTGAAGAC
  A3_5   AGATGCTGAG GACGGGAAAC AACTTCACCT TCAGCTACAC TTTTGAAGAC
  A3_7   AGATGCTGAG GACGGGAAAC AACTTCACCT TCAGCTACAC TTTTGAAGAC
  A3_3   AGATGCTGAG GACGGGAAAC AACTTCACCT TCAGCTACAC TTTTGAAGAC
 42_12   AAATGCTGAG AACGGGCAAC AACTTTGAGT TCAGCTACCA GTTTGAGGAC
  AAV1   AGATGCTGAG AACGGGCAAC AACTTTACCT TCAGCTACAC CTTTGAGGAA
  AAV2   AGATGCTGCG TACCGGAAAC AACTTTACCT TCAGCTACAC TTTTGAGGAC
  AAV3   AGATGCTAAG GACTGGAAAT AACTTCCAAT TCAGCTATAC CTTCGAGGAT
  AAV8   AGATGCTGAG AACCGGCAAC AACTTCCAGT TTACTTACAC CTTCGAGGAC
  AAV9   AGATGCTGAG AACCGGCAAC AACTTTCAGT TCAGCTACAC TTTCGAGGAC
  AAV7   AGATGCTGAG AACGGGCAAC AACTTTGAGT TCAGCTACAG CTTCGAGGAC
  44_2   AAATGCTGAG AACGGGCAAC AACTTTGAGT TCAGCTACCA GTTTGAGGAC
```

FIG. 1AAS

```
          3501                                                    3550
   42_2   GTGCCTTTCC ACAGCAGCTA TGCGCACAGC CAGAGCCTGG ACCGGCTGAT
   42_8   GTGCCTTTTC ACAGCAGCTA CGCGCACAGC CAAAGCCTGG ACCGGCTGAT
  42_15   GTGCCTTTTC ACAGCAGCTA CGCGCATAGC CAAAGCCTGG ACCGGCTGAT
  42_5b   GTGCCTTTTC ACAGCAGCTA CGCGCACAGC CAAAGCCTGG ACCGGCTGAT
  42_1b   GTGCCTTTTC ACAGCAGCTA TGCGCACAGC CAAAGCCTGG ACCGGCTGAT
  42_13   GTGCCTTTTC ACAGCAGCTA TGCGCACAGC CAAAGCCTGG ACCGGCTGAT
  42_3a   GTGCCTTTTC ACAGCAGCTA CGCGCACAGC CAAAGCCTGG ACCGGCTGAT
   42_4   GTGCCTTTTC ACAGCAGCTA CGCGCACAGC CAAAGCCTGG ACCGGCTGAT
  42_5a   GTGCCTTTC  ACAGCAGCTA CGCGCACAGC CAAAGCCTGG ACCGGCTGAT
  42_10   GTGCCTTTCC ACAGCAGCTA TGCGCACAGC CAGAGCCTGG ACCGGCTGAT
  42_3b   GTGCCTTTCC ACAGCAGCTA TGCGCACAGC CAGAGCCTGG ACCGGCTGAT
  42_11   GTGCCTTTCC ACAGCAGCTA TGCGCACAGC CAGAGCCTGG ACCGGCTGAT
  42_6b   GTGCCTTTCC ACAGCAGCTA TGCGCATAGC CAGAGCCTGG ACCGGCTGAT
   43_1   GTGCCTTTCC ACAGCAGCTA CGCGCACAGC CAGAGCCTGG ACCGGCTGAT
   43_5   GTGCCTTTCC ACAGCAGCTA CGCGCACAGC CAGAGCCTGG ACCGGCTGAT
  43_12   GTGCCTTTCC ACAGCAGCTA CGCGCACAGC CAGAGCCTGG ACCGGCTGAT
  43_20   GTGCCTTTCC ACAGCAGCTA CGCGCACAGC CAGAGCCTGG ACAGGCTGAT
  43_21   GTGCCTTTCC ACAGCAGCTA CGCGCACAGC CAGAGCCTGG ACAGGCTGAT
  43_23   GTGCCTTTCC ACAGCAGCTA CGCGCACAGC CAGAGCCTGG ACAGGCTGAT
  43_25   GTGCCTTTCC ACAGCAGCTA CGCGCACAGC CAGAGCCTGG ACAGGCTGAT
   44_1   GTGCCTTTTC ACAGCAGCTA CGCGCACAGC CAAAGCCTGG ACCGGCTGAT
   44_5   GTGCCTTTTC ACAGCAGCTA CGCGCACAGC CAAAGCCTGG ACCGGCTGAT
  223_10  GTGCCTTTCC ACAGCAGCTA CGCGCACAGC CAGAGTCTGG ACCGGCTGAT
  223_2   GTGCCTTTCC ACAGCAGCTA CGCGCACAGC CAGAGTCTGG ACCGGCTGAT
  223_4   GTGCCTTTCC ACAGCAGCTA CGCGCACAGC CAGAGTCTGG GCCGGCTGAT
  223_5   GTGCCTTTCC ACAGCAGCTA CGCGCACAGC CAGAGTCTGG GCCGGCTGAT
  223_6   GTGCCTTTCC ACAGCAGCTA CGCGCACAGC CAGAGTCTGG ACCGGCTGAT
  223_7   GTGCCTTTCC ACAGCAGCTA CGCGCACAGC CAGAGTCTGG ACCGGCTGAT
   A3_4   GTGCCTTTCC ACAGCAGCTA CGCGCACAGC CAGAGTCTGG ATCGGCTGAT
   A3_5   GTGCCTTTCC ACAGCAGCTA CGCGCACAGC CAGAGTCTGG ATCGGCTGAT
   A3_7   GTGCCTTTCC ACAGCAGCTA CGCGCACAGC CAGAGTCTGG ATCGGCTGAT
   A3_3   GTGCCTTTCC ACAGCAGCTA CGCGCACAGC CAGAGTCTGG ATCGGCTGAT
  42_12   GTGCCTTTTC ACAGCAGCTA CGCGCACAGC CAAAGCCTGG ACCGGCTGAC
   AAV1   GTGCCTTTCC ACAGCAGCTA CGCGCACAGC CAGAGCCTGG ACCGGCTGAT
   AAV2   GTTCCTTTCC ACAGCAGCTA CGCTCACAGC CAGAGTCTGG ACCGTCTCAT
   AAV3   GTACCTTTTC ACAGCAGCTA CGCTCACAGC CAGAGTTTGG ATCGCTTGAT
   AAV8   GTGCCTTTCC ACAGCAGCTA CGCCCACAGC CAGAGCTTGG ACCGGCTGAT
   AAV9   GTGCCTTTCC ACAGCAGCTA CGCACACAGC CAGAGTCTAG ATCGACTGAT
   AAV7   GTGCCTTTCC ACAGCAGCTA CGCACACAGC CAGAGCCTGG ACCGGCTGAT
   44_2   GTGCCTTTTC ACAGCAGCTA CGCGCACAGC CAAAGCCTGG ACCGGCTGAT
```

FIG. 1AAT

```
            3551                                                    3600
  42_2    GAATCCCCTC ATCGACCAGT ACCTGTACTA CCTGGCCCGG ACCCAGAGCA
  42_8    GAACCCCCTC ATCGACCAGT ACCTGTACTA CCTGTCTCGG ACTCAGTCCA
  42_15   GAACCCCCTC ATCGACCAGT ACCTGTACTA CCTGTCTCGG ACTCAGTCCA
  42_5b   GAACCCCCTC ATCGACCAGT ACCTGTACTA CCTGTCTCGG ACTCAGTCCA
  42_1b   GAACCCCCTC ATCGACCAGT ACCTGTACTA CCTGTCTCGG ACTCAGTCCA
  42_13   GAACCCCCTC ATCGACCAGT ACCTGTACTA CCTGTCTCGG ACTCAGTCCA
  42_3a   GAACCCCCTC ATCGACCAGT ACCTGTACTA CCTGTCTCGG ACTCAGTCCA
  42_4    GAACCCCCTC ATCGACCAGT ACCTGTACTA CCTGTCTCGG ACTCAGTCCA
  42_5a   GAACCCCCTC ATCGACCAGT ACCTGTACTA CCTGTCTCGG ACTCAGTCCA
  42_10   GAATCCCCTC ATCGACCAGT ACCTGTACTA CCTGGCCCGG ACCCAGAGCA
  42_3b   GAATCCCCTC ATCGACCAGT ACCTGTACTA CCTGGCCCGG ACCCAGAGCA
  42_11   GAATCCCCTC ATCGACCAGT ACCTGTACTA CCTGGCCCGG ACCCAGAGCA
  42_6b   GAATCCCCTC ATCGACCAGT ACCTGTACTA CCTGGCCCGG ACCCAGAGCA
  43_1    GAACCCTCTC ATCGACCAGT ACCTGTATTA CTTATCCAGA ACTCAGTCCA
  43_5    GAACCCTCTC ATCGACCAGT ACCTGTATTA CTTATCCAGA ACTCAGTCCA
  43_12   GAACCCTCTC ATCGACCAGT ACCTGTATTA CTTATCCAGA ACTCAGTCCA
  43_20   GAATCCCCTC ATCGACCAGT ACCTGTACTA CCTGGTCAGA ACGCAAACGA
  43_21   GAATCCCCTC ATCGACCAGT ACCTGTACTA CCTGGTCAGA ACGCAAACGA
  43_23   GAATCCCCTC ATCGACCAGT ACCTGTACTA CCTGGTCAGA ACGCAAACGA
  43_25   GAATCCCCTC ATCGACCAGT ACCTGTACTA CCTGGTCAGA ACGCAAACGA
  44_1    GAACCCCCTC ATCGACCAGT ACCTGTACTA CCTGTCTCGG ACTCAGTCCA
  44_5    GAACCCCCTC ATCGACCAGT ACCTGTACTA CCTGTCTCGG ACTCAGTCCA
 223_10   GAATCCCCTC ATCGACCAGT ACCTGTACTA CTTGGCCAGA ACACAGAGCA
 223_2    GAATCCCCTC ATCGACCAGT ACCTGTACTA CTTGGCCAGA ACACAGAGCA
 223_4    GAATCCCCTC ATCGACCAGT ACCTGTACTA CTTGGCCAGA ACACAGAGCA
 223_5    GAATCCCCTC ATCGACCAGT ACCTGTACTA CTTGGCCAGA ACACAGAGCA
 223_6    GAATCCCCTC ATCGACCAGT ACCTGTACTA CTTGGCCAGA ACACAGAGCA
 223_7    GAATCCCCTC ATCGACCAGT ACCTGTACTA CTTGGCCAGA ACACAGAGCA
  A3_4    GAATCCTCTC ATTGACCAGT ACCTGTATTA CCTGAGCAAA ACTCAGGGTA
  A3_5    GAATCCTCTC ATTGACCAGT ACCTGTATTA CCTGAGCAAA ACTCAGGGTA
  A3_7    GAATCCTCTC ATTGACCAGT ACCTGTATTA CCTGAGCAAA ACTCAGGGTA
  A3_3    GAATCCTCTC ATTGACCAGT ACCTGTATTA CCTGAGCAAA ACTCAGGGTA
  42_12   GAACCCCCTC ATCGACCAGT ACCTGTACTA CCTGGCCCGG ACCCAGAGCA
  AAV1    GAATCCTCTC ATCGACCAAT ACCTGTATTA CCTGAACAGA ACTCAAA.AT
  AAV2    GAATCCTCTC ATCGACCAGT ACCTGTATTA CTTGAGCAGA ACAAACACTC
  AAV3    GAATCCTCTT ATTGATCAGT ATCTGTACTA CCTGAACAGA ACGCAAGGAA
  AAV8    GAATCCTCTG ATTGACCAGT ACCTGTACTA CTTGTCTCGG ACTCAAACAA
  AAV9    GAACCCCCTC ATCGACCAGT ACCTATACTA CCTGGTCAGA ACACAGACAA
  AAV7    GAATCCCCTC ATCGACCAGT ACTTGTACTA CCTGGCCAGA ACACAGAGTA
  44_2    GAACCCCCTC ATCGACCAGT ACCTGTACTA CCTGTCTCGG ACTCAGTCCA
```

FIG. 1AAU

```
         3601                                                    3650
  42_2   CTACGG..GG TCCACAAGGG AGCTGCA.GT TCCA...... TCAGGCTGGG
  42_8   CGGGA...GG TACCGCAGGA ACTCAGCAGT TGCTATTTTC TCAGGCCGGG
  42_15  CGGGA...GG TACCGCAGGA ACTCAGCAGT TGCTATTTTC TCAGGCCGGG
  42_5b  CGGGA...GG TACCGCAGGA ACTCAGCAGT TGCTATTTTC TCAGGCCGGG
  42_1b  CGGGA...GG TACCGCAGGA ACTCAGCAGT TGCTATTTTC TCAGGCCGGG
  42_13  CGGGA...GG TACCGCAGGA ACTCAGCAGT TGCTATTTTC TCAGGCCGGG
  42_3a  CGGGA...GG TACCGCAGGA ACTCAGCAGT TGCTATTTTC TCAGGCCGGG
  42_4   CGGGA...GG TACCGCAGGA ACTCAGCAGT TGCTATTTTC TCAGGCCGGG
  42_5a  CGGGA...GG TACCGCAGGA ACTCAGCAGT TGCTATTTTC TCAGGCCGGG
  42_10  CTACG...GG GTCCACAAGG GAGCTGCAGT TCCA...... TCAGGCTGGG
  42_3b  CTACG...GG GTCCACAAGG GAGCTGCAGT TCCA...... TCAGGCTGGG
  42_11  CTACG...GG GTCCACAAGG GAGCTGCAGT TCCA...... TCAGGCTGGG
  42_6b  CTACG...GG GTCCACAAGG GAGCTGCAGT TCCA...... TCAGGCTGGG
  43_1   CAGGA...GG AACTCAAGGT ACTCAGCAAT TGTTATTTTC TCAAGCCGGG
  43_5   CAGGA...GG AACTCAAGGT ACTCAGCAAT TGTTATTTTC TCAAGCCGGG
  43_12  CAGGA...GG AACTCAAGGT ACTCAGCAAT TGTTATTTTC TCAAGCCGGG
  43_20  CT......GG AACTGGAGGG ACGCAGACTC TGGCATTCAG CCAAGCGGGT
  43_21  CT......GG AACTGGAGGG ACGCAGACTC TGGCATTCAG CCAAGCGGGT
  43_23  CT......GG AACTGGAGGG ACGCAGACTC TGGCATTCAG CCAAGCGGGT
  43_25  CT......GG AACTGGAGGG ACGCAGACTC TGGCATTCAG CCAAGCGGGT
  44_1   CGGGA...GG TACCGCAGGA ACTCAGCAGT TGCTATTTTC TCAGGCCGGG
  44_5   CGGGA...GG TACCGCAGGA ACTCAGCAGT TGCTATTTTC TCAGGCCGGG
 223_10  ACGCAGGAGG TACTGCTGGC AATCGGGAAC TGCAGTTTTA TCAGGGCGGA
 223_2   ACGCAGGAGG TACTGCTGGC AATCGGGAAC TGCAGTTTTA TCAGGGCGGA
 223_4   ACGCAGGAGG TACTGCTGGC AATCGGGAAC TGCAGTTTTA TCAGGGCGGA
 223_5   ACGCAGGAGG TACTGCTGGC AATCGGGAAC TGCAGTTTTA TCAGGGCGGA
 223_6   ACGCAGGAGG TACTGCTGGC AATCGGGAAC TGCAGTTTTA TCAGGGCGGA
 223_7   ACGCAGGAGG TACTGCTGGC AATCGGGAAC TGCAGTTTTA TCAGGGCGGA
  A3_4   CAAG...TGG AACAACGCAG CAATCGAGAC TGCAGTTCAG CCAAGCTGGG
  A3_5   CAAG...TGG AACAACGCAG CAATCGAGAC TGCAGTTCAA CCAAGCTGGG
  A3_7   CAAG...TGG AACAACGCAG CAATCGAGAC TGCAGTTCAG CCAAGCTGGG
  A3_3   CAAG...TGG AACAACGCAG CAATCGAGAC TGCAGTTCAG CCAAGCTGGG
  42_12  CTACG...GG GTCCACAAGG GGGCTGCAGT TCCA...... TCAGGCTGGG
  AAV1   CAGTCC..GG AAGTGCCCAA ACAAGGACT TGCTGTTTAG CCGTGGGTCT
  AAV2   CAAG...TGG AACCACCACG CAGTCAAGGC TTCAGTTTTC TCAGGCCGGA
  AAV3   CAACCTCTGG AACAACCAAC CAATCACGGC TGCTTTTTAG CCAGGCTGGG
  AAV8   CAGGAG..GC .ACGGCAAAT ACGCAGACTC TGGGCTTCAG CCAAGGTGGG
  AAV9   CTGGA...... .ACTGGGGGA ACTCAAACTT TGGCATTCAG CCAAGCAGGC
  AAV7   ACCCAGGAGG CACAGCTGGC AATCGGGAAC TGCAGTTTTA CCAGGGCGGG
  44_2   CGGGA...GG TACCGCAGGA ACTCAGCAGT TGCTATTTTC TCAGGCCGGG
```

FIG. 1AAV

```
         3651                                                    3700
 42_2    CCCAACACCA TGGCCGAGCA ATCAAAGAAC TGGCTGCCCG GACCCTGTTA
 42_8    CCTAATAACA TGTCGGCTCA GGCCAAAAAC TGGCTACCCG GGCCCTGCTA
 42_15   CCTAATAACA TGTCGGCTCA GGCCAAAAAC TGGCTACCCG GGCCCTGCTA
 42_5b   CCTAATAACA TGTCGGCTCA GGCCAAAAAC TGGCTACCCG GGCCCTGCTA
 42_1b   CCTAATAACA TGTCGGCTCA GGCCAAAAAC TGGCTACCCG GGCCCTGCTA
 42_13   CCTAATAACA TGTCGGCTCA GGCCAAAAAC TGGCTACCCG GGCCCTGCTA
 42_3a   CCTAATAACA TGTCGGCTCA GGCCAAAAAC TGGCTACCCG GGCCCTGCTA
 42_4    CCTAATAACA TGTCGGCTCA GGCCAAAAAC TGGCTACCCG GGCCCTGCTA
 42_5a   CCTAATAACA TGTCGGCTCA GGCCAAAAAC TGGCTACCCG GGCCCTGCTA
 42_10   CCCAACACCA TGGCCGAGCA ATCAAAGAAC TGGCTGCCCG GACCCTGTTA
 42_3b   CCCAACACCA TGGCCGAGCA ATCAAAGAAC TGGCTGCCCG GACCCTGTTA
 42_11   CCCAACACCA TGGCCGAGCA ATCAAAGAAC TGGCTGCCCG GACCCTGTTA
 42_6b   CCCAACACCA TGGCCGAGCA ATCAAAGAAC TGGCTGCCCG GACCCTGTTA
 43_1    CCCGCAAACA TGTCGGCTCA GGCCAAGAAC TGGCTACCTG GACCGTGTTA
 43_5    CCCGCAAACA TGTCGGCTCA GGCCAAGAAC TGGCTACCTG GACCGTGTTA
 43_12   CCCGCAAACA TGTCGGCTCA GGCCAAGAAC TGGCTACCTG GACCGTGTTA
 43_20   CCTAGCTCAA TGGCCAACCA GGCTAGAAAT TGGGTGCCCG GACCTTGCTA
 43_21   CCTAGCTCAA TGGCCAACCA GGCTAGAAAT TGGGTGCCCG GACCTTGCTA
 43_23   CCTAGCTCAA TGGCCAACCA GGCTAGAAAT TGGGTGCCCG GACCTTGCTA
 43_25   CCTAGCTCAA TGGCCAACCA GGCTAGAAAT TGGGTGCCCG GACCTTGCTA
 44_1    CCTAATAACA TGTCGGCTCA GGCCAAAAAC TGGCTACCCG GGCCCTGCTA
 44_5    CCTAATAACA TGTCGGCTCA GGCCAAAAAC TGGCTACCCG GGCCCTGCTA
 223_10  CCTACCACCA TGGCCGAACA AGCAAAGAAC TGGCTGCCCG GACCTTGCTT
 223_2   CCTACCACCA TGGCCGAACA AGCAAAGAAC TGGCTGCCCG GACCTTGCTT
 223_4   CCTACCACCA TGGCCGAACA AGCAAAGAAC TGGCTGCCCG GACCTTGCTT
 223_5   CCTACCACCA TGGCCGAACA AGCAAAGAAC TGGCTGCCCG GACCTTGCTT
 223_6   CCTACCACCA TGGCCGAACA AGCAAAGAAC TGGCTGCCCG GACCTTGCTT
 223_7   CCTACCACCA TGGCCGAACA AGCAAAGAAC TGGCTGCCCG GACCTTGCTT
 A3_4    CCTAGCTCCA TGGCTCAGCA GGCCAAAAAC TGGCTACCGG GACCCAGCTA
 A3_5    CCTAGCTCCA TGGCTCAGCA GGCCAAAAAC TGGCTACCGG GACCCAGCTA
 A3_7    CCTAGCTCCA TGGCTCAGCA GGCCAAAAAC TGGCTACCGG GACCCAGCTA
 A3_3    CCTAGCTCCA TGGCTCAGCA GGCCAAAAAC TGGCTACCGG GACCCAGCTA
 42_12   CCCAACACCA TGGCCGAGCA ATCAAAGAAC TGGCTGCCCG GACCCTGTTA
 AAV1    CCAGCTGGCA TGTCTGTTCA GCCCAAAAAC TGGCTACCTG GACCCTGTTA
 AAV2    GCGAGTGACA TTCGGGACCA GTCTAGGAAC TGGCTTCCTG GACCCTGTTA
 AAV3    CCTCAGTCTA TGTCTTTGCA GGCCAGAAAT TGGCTACCTG GGCCCTGCTA
 AAV8    CCTAATACAA TGGCCAATCA GGCAAGAAC  TGGCTGCCAG GACCCTGTTA
 AAV9    CCTAGCTCAA TGGCCAATCA GGCTAGAAAC TGGGTACCCG GGCCTTGCTA
 AAV7    CCTTCAACTA TGGCCGAACA AGCCAAGAAT TGGTTACCTG GACCTTGCTT
 44_2    CCTAATAACA TGTCGGCTCA GGCCAAAAAC TGGCTACCCG GGCCCTGCTA
```

FIG. 1AAW

```
          3701                                                    3750
   42_2   TCGGCAGCAG AGACTGTCAA AAAACATAGA CAGCAACAAC AACAGTAACT
   42_8   CCGGCAGCAA CGCGTCTCCA CGACACTGTC GCAAAATAAC AACAGCAACT
   42_15  CCGGCAGCAA CGCGTCTCCA CGACACTGTC GCAAAATAAC AACAGCAACT
   42_5b  CCGGCAGCAA CGCGTCTCCA CGACACTGTC GCAAAATAAC AACAGCAACT
   42_1b  CCGGCAGCAA CGCGTCTCCA CGACAGTGTC GCAAAATAAC AACAGCAACT
   42_13  CCGGCAGCAA CGCGTCTCCA CGACAGTGTC GCAAAATAAC AACAGCAACT
   42_3a  CCGGCAGCAA CGCGTCTCCA CGACACTGTC GCAAAATAAC AACAGCAACT
   42_4   CCGGCAGCAA CGCGTCTCCA CGACACTGTC GCAAAATAAC AACAGCAACT
   42_5a  CCGGCAGCAA CGCGTCTCCA CGACACTGTC GCAAAATAAC AACAGCAACT
   42_10  TCGGCAGCAG AGACTGTCAA AAAACATAGA CAGCAACAAC AACAGTAACT
   42_3b  TCGGCAGCAG AGACTGTCAA AAAACATAGA CAGCAACAAC ACCAGTAACT
   42_11  TCGGCGGCAG AGACTGTCAA AAGACATAGA CAGCAACAAC AACAGTAACT
   42_6b  TCGGCAGCAG AGACTGTCAA AAAACATAGA CAGCAACAAC AACAGTAACT
   43_1   CCGTCAGCAA CGAGTTTCCA CGACACTGTC GCAAAACAAC AACAGCAATT
   43_5   CCGTCAGCAA CGAGTTTCCA CGACACTGTC GCAAAACAAC AACAGCAATT
   43_12  CCGTCAGCAA CGAGTTTCCA CGACACTGTC GCAAAACAAC AACAGCAATT
   43_20  CCGGCAGCAG CGCGTCTCCA CGACAACCAA CCAGAACAAC AACAGCAACT
   43_21  CCGGCAGCAG CGCGTCTCCA CGACAACCAA CCAGAGCAAC AACAGCAACT
   43_23  CCGGCAGCAG CGCGTCTCCA CGACAACCAA CCAGAACAAC AACAGCAACT
   43_25  CCGGCAGCAG CGCGTCTCCA CGACAACCAA CCAGAACAAC AACAGCAACT
   44_1   CCGGCAGCAA CGCGTCTCCA CGACACTGTC GCAAAATAAC AACAGCAACT
   44_5   CCGGCAGCAA CGCGTCTCCA CGACACTGTC GCAAAATAAC AACAGCAACT
  223_10  CCGGCAACAG AGAGTATCCA AGACGCTGGA TCAAAATAAC AACAGCAACT
  223_2   CCGGCAACAG AGAGTATCCA AGACGCTGGA TCAAAATAAC AACAGCAACT
  223_4   CCGGCAACAG AGAGTATCCA AGACGCTGGA TCAAAATAAC AACAGCAACT
  223_5   CCGGCAACAG AGAGTATCCA AGACGCTGGA TCAAAATAAC AACAGCAACT
  223_6   CCGGCAACAG AGAGTATCCA AGACGCTGGA TCAAAATAAC AACAGCAACT
  223_7   CCGGCAACAG AGAGTATCCA AGACGCTGGA TCAAAATAAC AACAGCAACT
   A3_4   CCGACAGCAG CGAATGTCTA AGACGGCTAA TGACAACAAC AACAGTGAAT
   A3_5   CCGACAGCAG CGAATGTCTA AGACGGCTAA TGACAACAAC AACAGTGAAT
   A3_7   CCGACAGCAG CGAATGTCTA AGACGGCTAA TGACAACAAC AACAGTGAAT
   A3_3   CCGACAGCAG CGAATGTCTA AGACGGCTAA TGACAACAAC AACAGTGAAT
   42_12  TCGGCAGCAG AGACTGTCAA AAAACATAGA CAGCAACAAC AACAGTAACT
   AAV1   TCGGCAGCAG CGCGTTTCTA AAACAAAAAC AGACAACAAC AACAGCAATT
   AAV2   CCGCCAGCAG CGAGTATCAA AGACATCTGC GGATAACAAC AACAGTGAAT
   AAV3   CCGGCAACAG AGACTTTCAA AGACTGCTAA CGACAACAAC AACAGTAACT
   AAV8   CCGCCAACAA CGCGTCTCAA CGACAACCGG GCAAACAAC AATAGCAACT
   AAV9   CCGTCAGCAG CGCGTCTCCA CAACCACCAA CCAAAATAAC AACAGCAACT
   AAV7   CCGGCAACAA AGAGTCTCCA AAACGCTGGA TCAAACAAC AACAGCAACT
   44_2   CCGGCAGCAA CGCGTCTCCA CGACACTGTC GCAAAATAAC AACAGCAACT
```

FIG. 1AAX

```
         3751                                                      3800
  42_2   TTGCCTGGAC CGGGGCCACT AAATACCATC TGAATGGTAG AAATTCATTA
  42_8   TTGCTTGGAC CGGTGCCACC AAGTATCATC TGAATGGCAG AGACTCTCTG
 42_15   TTGCTTGGAC CGGTGCCACC AAGTATCATC TGAATGGCAG AGACTCTCTG
 42_5b   TTGCTTGGAC CGGTGCCACC AAGTATCATC TGAATGGCAG AGACTCTCTG
 42_1b   TTGCTTGGAC CGGTGCCACC AAGTATCATC TGAATGGCAG AGACTCTCTG
 42_13   TTGCTTGGAC CGGTGCCACC AAGTATCATC TGAATGGCAG AGACTCTCTG
 42_3a   TTGCTTGGAC CGGTGCCACC AAGTATCATC TGAATGGCAG AGACTCTCTG
  42_4   TTGCTTGGAC CGGTGCCACC AAGTATCATC TGAATGGCAG AGACTCTCTG
 42_5a   TTGCTTGGAC CGGTGCCACC AAGTATCATC TGAATGGCAG AGACTCTCTG
 42_10   TTGCCTGGAC CGGGGCCACT AAATACCATC TGAATGGTAG AAATTCATTA
 42_3b   TTGCCTGGAC CGGGGCCACT AAATACCATC TGAATGGTAG AAATTCATTA
 42_11   TTGCCTGGAC CGGGGCCACT AAATACCATC TGAATGGTAG AAATTCATTA
 42_6b   TTGCCTGGAC CGGGGCCACT AAATACCATC TGAATGGTAG AAATTCATTA
  43_1   TTGCTTGGAC CGGTGCCACC AAGTATCACC TGAATGGCAG AGACTCCCTG
  43_5   TTGCTTGGAC CGGTGCCACC AAGTATCACC TGAATGGCAG AGACTCCCTG
 43_12   TTGCTTGGAC CGGTGCCACC AAGTATCACC TGAATGGCAG AGACTCCCTG
 43_20   TTGCCTGGAC GGGAGCTGCC AAGTTTAAGC TGAACGGCCG AGACTCTCTA
 43_21   TTGCCTGGAC GGGAGCTGCC AAGTTTAAGC TGAACGGCCG AGACTCTCTA
 43_23   TTGCCTGGAC GGGAGCTGCC AAGTTTAAGC TGAACGGCCG AGACTCTCTA
 43_25   TTGCCTGGAC GGGAGCTGCC AAGTTTAAGC TGAACGGCCG AGACTCTCTA
  44_1   TTGCCTGGAC CGGTGCCACC AAGTATCATC TGAATGGCAG AGACTCTCTG
  44_5   TTGCCTGGAC CGGTGCCACC AAGTATCATC TGAATGGCAG AGACTCTCTG
 223_10  TTGCCTGGAC TGGTGCCACA AAATACCATT TAAATGNAAG AAATTCATTG
  223_2  TTGCCTGGAC TGGTGCCACA AAATACCATT TAAATGGAAG AAATTCATTG
  223_4  TTGCCTGGAC TGGTGCCACA AAATACCATT TAAATGGAAG AAATTCATTG
  223_5  TTGCCTGGAC TGGTGCCACA AAATACCATT TAAATGGAAG AAATTCATTG
  223_6  TTGCCTGGAC TGGTGCCACA AAATACCATT TAAATGGAAG AAATTCATTG
  223_7  TTGCCTGGAC TGGTGCCACA AAATACCATT TAAATGGAAG AAATTCATTG
   A3_4  TTGCTTGGAC TGCAGCCACC AAATATTACC TGAATGGAAG AAATTCTCTG
   A3_5  TTGCTTGGAC TGCAGCCACC AAATATTACC CGAATGGAAG AAATTCTCTG
   A3_7  TTGCTTGGAC TGCAGCCACC AAATATTACC TGAATGGAAG AAATTCTCTG
   A3_3  TTGCTTGGAC TGCAGCCACC AAATATTACC TGAATGGAAG AAATTCTCTG
  42_12  TTGCCTGGAC CGGGGCCACT AAATACCATC TGAATGGTAG AAATTCATTA
   AAV1  TTACCTGGAC TGGTGCTTCA AAATATAACC TCAATGGGCG TGAATCCATC
   AAV2  ACTCGTGGAC TGGAGCTACC AAGTACCACC TCAATGGCAG AGACTCTCTG
   AAV3  TTCCTTGGAC AGCGGCCAGC AAATATCATC TCAATGGCCG CGACTCGCTG
   AAV8  TTGCCTGGAC TGCTGGGACC AAATACCATC TGAATGGAAG AAATTCATTG
   AAV9  TTGCGTGGAC GGGAGCTGCT AAATTCAAGC TGAACGGGAG AGACTCGCTA
   AAV7  TTGCTTGGAC TGGTGCCACC AAATATCACC TGAACGGCAG AAACTCGTTG
   44_2  TTGCCTGGAC CGGTGCCACC AAGTATCATC TGAATGGCAG AGACTCTCTG
```

FIG. 1AAY

```
          3801                                                      3850
   42_2   ACCAACCCGG GCGTAGCCAT GGCCACCAAC AAGGACGACG AGGACCAGTT
   42_8   GTAAATCCCG GTGTCGCTAT GGCAACGCAC AAGGACGACG AAGAGCGATT
  42_15   GTAAATCCCG GTGTCGCTAT GGCAACGCAC AAGGACGACG AAGAGCGATT
  42_5b   GTAAATCCCG GTGTCGCTAT GGCAACGCAC AAGGACGACG AAGAGCGATT
  42_1b   GTAAATCCCG GTGTCGCTAT GGCAACGCAC AAGGGCGACG AAGAGCGATT
  42_13   GTAAATCCCG GTGTCGCTAT GGCAACGCAC AAGGGCGACG AAGAGCGATT
  42_3a   GTAAATCCCG GTGTCGCTAT GGCAACGCAC AAGGACGACG AAGAGCGATT
   42_4   GTAAATCCCG GTGTCGCTAT GGCAACGCAC AAGGACGACG AAGAGCGATT
  42_5a   GTAAATCCCG GTGTCGCTAT GGCAACGCAC AAGGACGACG AAGAGCGATT
  42_10   ACCAACCCGG GCGTAGCCAT GGCCACCAAC AAGGACGACG AGGACCAGTT
  42_3b   ACCAACCCGG GCGTAGCCAT GGCCACCAAC AAGGACGACG AGGACCAGTT
  42_11   ACCAACCCGG GCGTAGCCAT GGCCACCAAC AAGGACGACG AGGACCAGTT
  42_6b   ACCAACCCGG GCGTAGCCAT GGCCACCAAC AAGGACGACG AGGACCAGTT
   43_1   GTTAATCCCG GCGTTGCCAT GGCTACCCAC AAGGACGACG AGGAGCGCTT
   43_5   GTTAATCCCG GCGTTGCCAT GGCTACCCAC AAGGACGACG AGGAGCGCTT
  43_12   GTTAATCCCG GCGTTGCCAT GGCTACCCAC AAGGACGACG AGGAGCGCTT
  43_20   ATGAATCCGG GCGTGGCAAT GGCTTCCCAC AAGGATGACG ACGACCGCTT
  43_21   ATGAATCCGG GCGTGGCAAT GGCTTCCCAC AAGGATGACG ACGACCGCTT
  43_23   ATGAATCCGG GCGTGGCAAT GGCTTCCCAC AAGGATGACG ACGACCGCTT
  43_25   ATGAATCCGG GCGTGGCAAT GGCTTCCCAC AAGGATGACG ACGACCGCTT
   44_1   GTAAATCCCG GTGTCGCTAT GGCAACCCAC AAGGACGACG AAGAGCGATT
   44_5   GTAAATCCCG GTGTCGCTAT GGCAACCCAC AAGGACGACG AAGAGCGATT
  223_10  GTTAATCCCG GTGTCGCCAT GGCAACCCAC AAGGACGACG AGGAACGCTT
  223_2   GTTAATCCCG GTGTCGCCAT GGCAACCCAC AAGGACGACG AGGAACGCTT
  223_4   GTTAATCCCG GTGTCGCCAT GGCAACCCAC AAGGACGACG AGGAACGCTT
  223_5   GTTAATCCCG GTGTCGCCAT GGCAACCCAC AAGGACGACG AGGAACGCTT
  223_6   GTTAATCCCG GTGTCGCCAT GGCAACCCAC AAGGACGACG AGGAACGCTT
  223_7   GTTAATCCCG GTGTCGCCAT GGCAACCCAC AAGGACGACG AGGAACGCTT
   A3_4   GTCAATCCCG GGCCCCCAAT GGCCAGTCAC AAGGACGATG AGGAAAAGTA
   A3_5   GTCAATCCCG GGCCCCCAAT GGCCAGTCAC AAGGACGATG AGGAAAAGTA
   A3_7   GTCAATCCCG GGCCCCCAAT GGCCAGTCAC AAGGACGATG AGGAAAAGTA
   A3_3   GTCAATCCCG GGCCCCCAGT GGCCAGTCAC AAGGACGATG AGGAAAAGTA
  42_12   ACCAACCCGG GCGTAGCCAT GGCCACCAAC AAGGACGACG AGGACCAGTT
   AAV1   ATCAACCCTG GCACTGCTAT GGCCTCACAC AAAGACGACG AAGACAAGTT
   AAV2   GTGAATCC.. GGCC....AT GGCAAGCCAC AAGGACGATG AAGAAAAGTT
   AAV3   GTGAATCCAG GACCACCTAT GGCCAGTCAC AAGGACGATG AAGAAAAATT
   AAV8   GCTAATCCTG GCATCGCTAT GGCAACACAC AAAGACGACG AGGAGCGTTT
   AAV9   ATGAATCCTG GCGTGGCTAT GGCATCGCAC AAAGACGACG AGGACCGCTT
   AAV7   GTTAATCCCG GCGTCGCCAT GGCAACTCAC AAGGACGACG AGGACCGCTT
   44_2   GTAAATCCCG GTGTCGCTAT GGCAACCCAC AAGGACGACG AAGAGCGATT
```

FIG. 1AAZ

```
          3851                                                    3900
  42_2    CTTTCCCATC AACGGAGTGC TGGTTTTTGG CGAAACGGGG GCTGCCAACA
  42_8    TTTTCCATCC AGCGGAGTCT TGATGTTTGG GAAACAGGGA GCTGGAAA..
  42_15   TTTTCCATCC AGCGGAGTCT TGATGTTTGG GAAACAGGGA GCTGGAAA..
  42_5b   TTTTCCATCC AGCGGAGTCT TGATGTTTGG GAAACAGGGA GCTGGAAA..
  42_1b   TTTTCCATCC AGCGGAGTCT TGATGTTTGG GAAACAGGGA GCTGGAAA..
  42_13   TTTTCCATCC AGCGGAGTCT TGATGTTTGG GAAACAGGGA GCTGGAAA..
  42_3a   TTTTCCATCC AGCGGAGTCT TGATGTTTGG GAAACAGGGA GCTGGAAA..
  42_4    TTTTCCATCC AGCGGAGTCT TGATGTTTGG GAAACAGGGA GCTGGAAA..
  42_5a   TTTTCCATCC AGCGGAGTCT TGATGTTTGG GAAACAGGGA GCTGGAAA..
  42_10   CTTTCCCATC AACGGAGTGC TGGTTTTTGG CAAAACGGGG GCTGCCAACA
  42_3b   CTTTCCCATC AACGGAGTGC TGGTTTTTGG CAAAACGGGG GCTGCCAACA
  42_11   CTTTCCCATC AACGGAGTGC TGGTTTTTGG CAAAACGGGG GCTGCCAACA
  42_6b   CTTTCCCATC AACGGAGTGC TGGTTTTTGG CAAAACGGGG GCTGCCAACA
  43_1    CTTCCCGTCA AGCGGAGTTC TAATGTTTGG CAAGCAGGGG GCTGGAAA..
  43_5    CTTCCCGTCA AGCGGAGTTC TAATGTTTGG CAAGCAGGGG GCTGGAAA..
  43_12   CTTCCCGTCA AGCGGAGTTC TAATGTTTGG CAAGCAGGGG GCTGGAAA..
  43_20   CTTCCCTTCG AGCGGGGTCC TGATTTTTGG CAAGCAAGGA GCCGGGAA..
  43_21   CTTCCCTTCG AGCGGGGTCC TGATTTTTGG CAAGCAAGGA GCCGGGAA..
  43_23   CTTCCCTTCG AGCGGGGTCC TGATTTTTGG CAAGCAAGGA GCCGGGAA..
  43_25   CTTCCCTTCG AGCGGGGTCC TGATTTTTGG CAAGCAAGGA GCCGGGAA..
  44_1    TTTTCCGTCC AGCGGAGTCT TAATGTTTGG GAAACAGGGA GCTGGAAA..
  44_5    TTTTCCGTCC AGCGGAGTCT TAATGTTTGG GAAACAGGGA GCTGGAAA..
 223_10   CTTCCCTTCG AGCGGAGTTC TAATTTTTGG CAAAACTGGA GCAGCTAATA
 223_2    CTCCCCTTCG AGCGGAGTTC TAATTTTTGG CAAAACTGGA GCAGCTAATA
 223_4    CTTCCCTTCG AGCGGAGTTC TAATTTTTGG CAAAACTGGA GCAGCTAATA
 223_5    CTTCCCTTCG AGCGGAGTTC TAATTTTTGG CAAAACTGGA GCAGCTAATA
 223_6    CTTCCCTTCG AGCGGAGTTC TAATTTTTGG CAAAACTGGA GCAGCTAATA
 223_7    CTTCCCTTCG AGCGGAGTTC TAATTTTTGG CAAAACTGGA GCAGCTAATA
  A3_4    TTTCCCCATG CACGGAAATC TCATCTTTGG AAAACAAGGC ACAGGAAC..
  A3_5    TTTCCCCATG CACGGAAATC TCATCTTTGG AAAACAAGGC ACAGGAAC..
  A3_7    TTTCCCCATG CACGGAAATC TCATCTTTGG AAAACAAGGC ACAGGAAC..
  A3_3    TTTCCCCATG CACGGAAATC TCATCTTTGG AAAACAAGGC ACAGGAAC..
  42_12   CTTTCCCATC AACGGAGTGC TGGTTTTTGG CAAAACGGGG GCTGCCAACA
  AAV1    CTTTCCCATG AGCGGTGTCA TGATTTTTGG AAAAGAGAGC GCCGGAGC..
  AAV2    TTTTCCTCAG AGCGGGGTTC TCATCTTTGG GAAGCAAGGC TCAGAGAA..
  AAV3    TTTCCCTATG CACGGCAATC TAATATTTGG CAAAGAAGGG ACAACGGC..
  AAV8    TTTTCCCAGT AACGGGATCC TGATTTTTGG CAAACAAAAT GCTGCCAG..
  AAV9    CTTTCCATCA AGTGGCGTTC TCATATTTGG CAAGCAAGGA GCCGGGAA..
  AAV7    TTTCCCATCC AGCGGAGTCC TGATTTTTGG AAAAACTGGA GCAACTAACA
  44_2    TTTTCCGTCC AGCGGAGTCT TAATGTTTGG GAAACAGGGA GCTGGAAA..
```

FIG. 1AAAA

```
            3901                                                      3950
   42_2    AGACAACGCT GGAA...... AACGTGCTAA TGACCAGCGA GGAGGAGATC
   42_8    AGACAACG.T GGACTATAGC AGCGTTATGC TAACCAGTGA GGAAGAAATC
   42_15   AGACAACG.T GGACTATAGC AGCGTTATGC TAACCAGTGA GGAAGAAATC
   42_5b   AGACAACG.T GGACTATAGC AGCGTTATGC TAACCAGTGA GCAAGAAATC
   42_1b   AGACAACG.T AGACTATAGC AGCGTTATGC TAACCAGTGA GGAAGAAATC
   42_13   AGACAACG.T GGACTATAGC AGCGTTATGC TAACCAGTGA GGAAGAAATC
   42_3a   AGACAACG.T GGACTATAGC AGCGTTATGC TAACCAGTGA GGAAGAAATC
   42_4    AGACAACG.T GGACTATAGC AGCGTTATGC TAACCAGTGA GGAAGAAATC
   42_5a   AGACAACG.T GGACTATAGC AGCGTTATGC TAACCAGTGA GGAAGAAATC
   42_10   AGACAACGCT GGAA...... AACGTGCTAA TGACCAGCGA GGAGGAGATC
   42_3b   AGACAACGCT GGAA...... AACGTGCTAA TGACCAGCGA GGAGGAGATC
   42_11   AGACAACGCT GGAA...... AACGTGCTAA TGACCAGCGA GGAGGAGATC
   42_6b   AGACAACGCT GGAA...... AACGTGCTAA TGACCAGCGA GGAGGAGATC
   43_1    AGACAATG.T GGACTACAGC AGCGTGATGC TCACCAGCGA AGAAGAAATT
   43_5    AGACAATG.T GGACTACAGC AGCGTGATGC TCACCAGCGA AGAAGAAATT
   43_12   AGACAATG.T GGACTACAGC AGCGTGATGC TCACCAGCGA AGAAGAAATT
   43_20   CGATGGAG.T GGATTACAGC CAAGTGCTGA TTACAGATGA GGAAGAAATC
   43_21   CGATGGAG.T GGATTACAGC CAAGTGCTGA TTACAGATGA GGAAGAAATC
   43_23   CGATGGAG.T GGATTACAGC CAAGTGCTGA TTACAGATGA GGAAGAAATC
   43_25   CGATGGAG.T GGATTACAGC CAAGTGCTGA TTACAGATGA GGAAGAAATC
   44_1    AGACAACG.T GGACTATAGC AGCGTTATGC TAACCAGTGA GGAAGAAATT
   44_5    AGACAACG.T GGACTATAGC AGCGTTATGC TAACCAGTGA GGAAGAAATT
  223_10   AAACTACATT AGAA...... AACGTGCTCA TGACAAATGA AGAAGAAATT
  223_2    AAACTACATT AGAA...... AACGTGCTCA TGACAAATGA AGAAGAAATT
  223_4    AAACTACATT AGAA...... AACGTGCTCA TGACAAATGA AGAAGAAATT
  223_5    AAACTACATT AGAA...... AACGTGCTCA TGACAAATGA AGAAGAAATT
  223_6    AAACTACATT AGAA...... AACGTGCTCA TGACAAATGA AGAAGAAATT
  223_7    AAACTACATT AGAA...... AACGTGCTCA TGACAAATGA AGAAGAAATT
   A3_4    TACCAATG.T GGACATTGAA TCAGTGCTTA TTACAGACGA AGAAGAAATC
   A3_5    TACCAATG.T GGACATTGAA TCAGTGCTTA TTACAGACGA ACAAGAAATC
   A3_7    TACCAATG.T GGACATTGAA TCAGTGCTTA TTACAGACGA AGAAGAAATC
   A3_3    TACCAATG.T GGACATTGAA TCAGTGCTTA TTACAGACGA AGAAGAAATC
   42_12   AGACAACGCT GGAA...... AACGTGCTAA TGACCAGCGA GGAGGAGATC
   AAV1    TTCAAACA.C TGCATTGGAC AATGTCATGA TTACAGACGA AGAGGAAATT
   AAV2    AACAAATG.T GAACATTGAA AAGGTCATGA TTACAGACGA AGAGGAAATC
   AAV3    AAGTAACG.C AGAATTAGAT AATGTAATGA TTACGGATGA AGAAGAGATT
   AAV8    AGACAATG.C GGATTACAGC GATGTCATGC TCACCAGCGA GGAAGAAATC
   AAV9    CGATGGAG.T CGACTACAGC CAGGTGCTGA TTACAGATGA GGAAGAAATT
   AAV7    AAACTACATT GGAA...... AATGTGTTAA TGACAAATGA AGAAGAAATT
   44_2    AGACAACG.T GGACTATAGC AGCGTTATGC TAACCAGTGA GGAAGAAATT
```

FIG. 1AAAB

```
            3951                                                    4000
  42_2    AAAACCACCA ATCCCGTGGC TACAGAAGAA TACGGTGTGG TCTCCAGCAA
  42_8    AAAACCACCA ACCCAGTGGC CACAGAACAG TACGGCGTGG TGGCCGATAA
  42_15   AAAACCACCA ACCCAGTGGC CACAGAACAG TACGGCGTGG TGGCCGATAA
  42_5b   AAAACCACCA ACCCAGTGGC CACAGAACAG TACGGCGTGG TGGCCGATAA
  42_1b   AAAACCACCA ACCCAGTGGC CACAGAACAG TACGGCGTGG TGGCCGATAA
  42_13   AAAACCACCA ACCCAGTGGC CACAGAACAG TACGGCGTGG TGGCCGATAA
  42_3a   AAAACCACCA ACCCAGTGGC CACAGAACAG TACGGCGTGG TGGCCGATAA
  42_4    AAAACCACCA ACCCAGTGGC CACAGAACAG TACGGCGTGG TGGCCGATAA
  42_5a   AAAACCACCA ACCCAGTGGC CACAGAACAG TACGGCGTGG TGGCCGATAA
  42_10   AAAACCACCA ATCCCGTGGC TACAGAAGAA TACGGTGTGG TCTCCAGCAA
  42_3b   AAAACCACCA ATCCCGTGGC TACAGAACAG TACGGTGTGG TCTCCAGCAA
  42_11   AAAACCACCA ATCCCGTGGC TACAGAAGAA TACGGTGTGG TCTCCAGCAA
  42_6b   AAAACCACCA ATCCCGTGGC TACAGAAGAA TACGGTGTGG TCTCCAGCAA
  43_1    AAAACTACTA ACCCAGTGGC TACAGAGCAG TATGGTGTGG TGGCAGACAA
  43_5    AAAACTACTA ACCCAGTGGC TACAGAGCAG TATGGTGTGG TGGCAGACAA
  43_12   AAAACTACTA ACCCAGTGGC TACAGAGCAG TATGGTGTGG TGGCAGACAA
  43_20   AAGGCTACCA ACCCCGTGGC CACAGAAGAA TATGGAGCAG TGGCCATCAA
  43_21   AAGGCTACCA ACCCCGTGGC CACAGAAGAA TATGGAGCAG TGGCCATCAA
  43_23   AAGGCTACCA ACCCCGTGGC CACAGAAGAA TATGGAGCAG TGGCCATCAA
  43_25   AAGGCTACCA ACCCCGTGGC CACAGAAGAA TATGGAGCAG TGGCCATCAA
  44_1    AAAACCACCA ACCCAGTGGC CACGGAACAG TACGGCGTGG TGGCCGATAA
  44_5    AAAACCACCA ACCCAGTGGC CACAGAACAG TACGGCGTGG TGGCCGATAA
  223_10  CGTCCTACCA ACCCGGTAGC TACCGAGGAA TACGGGATTG TAAGCAGCAA
  223_2   CGTCCTACCA ACCCGGTAGC TACCGAGGAA TACGGGATTG TAAGCAGCAA
  223_4   CGTCCTACCA ACCCGGTAGC TACCGAGGAA TACGGGATTG TAAGCAGCAA
  223_5   CGTCCTACCA ACCCGGTAGC TACCGAGGAA TACGGGATTG TAAGCAGCAA
  223_6   CGTCCTACCA ACCCGGTAGC TACCGAGGAA TACGGGATTG TAAGCAGCAA
  223_7   CGTCCTACCA ACCCGGTAGC TACCGAGGAA TACGGGATTG TAAGCAGCAA
  A3_4    AGAACAACTA ATCCTGTGGC TACAGAACAA TACGGACAGG TTGCCACCAA
  A3_5    AGAACGACTA ATCCTGTGGC TACAGAACAA TACGGACAGG TTGCCACCAA
  A3_7    AGAACAACTA ATCCTGTGGC TACAGAACAA TACGGACAGG TTGCCACCAA
  A3_3    AGAACAACTA ATCCTGTGGC TACAGAACAA TACGGACAGG TTGCCACCAA
  42_12   AAAACCACCA ATCCCGTGGC TACAGAAGAA TACGGTGTGG TCTCCAGCAA
  AAV1    AAAGCCACTA ACCCTGTGGC CACCGAAAGA TTTGGGACCG TGGCAGTCAA
  AAV2    GGAACAACCA ATCCCGTGGC TACGGAGCAG TATGGTTCTG TATCTACCAA
  AAV3    CGTACCACCA ATCCTGTGGC AACAGAGCAG TATGGAACTG TGGCAAATAA
  AAV8    AAAACCACTA ACCCTGTGGC TACAGAGGAA TACGGTATCG TGGCAGATAA
  AAV9    AAAGCCACCA ACCCTGTAGC CACAGAGGAA TACGGAGCAG TGGCCATCAA
  AAV7    CGTCCTACTA ATCCTGTAGC CACGGAAGAA TACGGGATAG TCAGCAGCAA
  44_2    AAAACCACCA ACCCAGTGGC CACAGAACAG TACGGCGTGG TGGCCGATAA
```

FIG. 1AAAC

```
         4001                                                    4050
  42_2   CCTGCAATCG TCTACGGCCG GACCCCAGAC ACAGACTGTC AACAGCCAGG
  42_8   CCTGCAACAG CAAAACGCCG CTCCTATTGT AGGGGCCGTC AACAGTCAAG
 42_15   CCTGCAACAG CAAAACGCCG CTCCTATTGT AGGGGCCGTC AACAGTCAAG
 42_5b   CCTGCAACAG CAAAACGCCG CTCCTATTGT AGGGGCCGTC AACAGTCAAG
 42_1b   CCTGCAACAG CAAAACGCCG CTCCTATTGT AGGGGCCGTC AACAGTCAAG
 42_13   CCTGCAACAG CAAAACGCCG CTCCTATTGT AGGGGCCGTC AACAGTCAAG
 42_3a   CCTGCAACAG CAAAACGCCG CTCCTATTGT AGGGGCCGTC AACAGTCAAG
  42_4   CCTGCAACAG CAAAACGCCG CTCCTATTGT AGGGGCCGTC AACAGTCAAG
 42_5a   CCTGCAACAG CAAAACGCCG CTCCTATTGT AGGGGCCGTC AACAGTCAAG
 42_10   CCTGCAATCG TCTACGGCCG GACCCCAGAC ACAGACTGTC AACAGCCAGG
 42_3b   CCTGCAATCG TCTACGGCCG GACCCCAGAC ACAGACTGTC AACAGCCAGG
 42_11   CCTGCAATCG TCTACGGCCG GACCCCAGAC ACAGACTGTC AACAGCCAGG
 42_6b   CCTGCAATCG TCTACGGCCG GACCCCAGAC ACAGACTGTC AACAGCCAGG
  43_1   CCTGCAGCAG ACCAACGGAG CTCCCATTGT GGGAACTGTC AACAGCCAGG
  43_5   CCTGCAGCAG ACCAACGGAG CTCCCATTGT GGGAACTGTC AACAGCCAGG
 43_12   CCTGCAGCAG ACCAACGGAG CTCCCATTGT GGGAACTGTC AACAGCCAGG
 43_20   CAACCAGGCC GCCAATACGC AGGCGCAGAC CGGACTCGTG CACAACCAGG
 43_21   CAACCAGGCC GCCAATACGC AGGCGCAGAC CGGACTCGTG CACAACCAGG
 43_23   CAACCAGGCC GCCAATACGC AGGCGCAGAC CGGACTCGTG CACAACCAGG
 43_25   CAACCAGGCC GCCAATACGC AGGCGCAGAC CGGACTCGTG CACAACCAGG
  44_1   CCTGCAACAG CAAAACGCCG CTCCTATTGT AGGGGCCGTC AACAGTCAAG
  44_5   CCTGCAACAG CAAAACGCCG CTCCTATTGT AGGGGCCGTC AACAGTCAAG
 223_10  CTTGCAGGCG GCTAGCACCG CAGCCCAGAC ACAAGTTGTT AACAACCAGG
 223_2   CTTGCAGGCG GCTAGCACCG CAGCCCAGAC ACAAGTTGTT AACAACCAGG
 223_4   CTTGCAGGCG GCTAGCACCG CAGCCCAGAC ACAAGTTGTT AACAACCAGG
 223_5   CTTGCAGGCG GCTAGCACCG CAGCCCAGAC ACAAGTTGTT AACAACCAGG
 223_6   CTTGCAGGCG GCTAGCACCG CAGCCCAGAC ACAAGTTGTT AACAACCAGG
 223_7   CTTGCAGGCG GCTAGCACCG CAGCCCAGAC ACAAGTTGTT AACAACCAGG
  A3_4   CCATCAGAGT CAGGACACCA CAGCTTCCTA TGGAAGTGTG GACAGCCAGG
  A3_5   CCGTCAGAGT CAGAACACCA CAGCTTCCTA TGGAAGTGTG GACAGCCAGG
  A3_7   CCATCAGAGT CAGAACACCA CAGCTTCCTA TGGAAGTGTG GACAGCCAGG
  A3_3   CCATCAGAGT CAGAACACCA CAGCTTCCTA TGGAAGTGTG GACAGCCAGG
 42_12   CCTGCAATCG TCTACGGCCG GACCCCAGAC ACAGACTGTC AACAGCCAGG
  AAV1   TTTCCAGAGC AGCAGCACAG ACCCTGCGAC CGGAGATGTG CATGCTATGG
  AAV2   CCTCCAGAGA GGCAACAGAC AAGCAGCTAC CGCAGATGTC AACACACAAG
  AAV3   CTTGCAGAGC TCAAATACAG CTCCCACGAC TGGAACTGTC AATCATCAGG
  AAV8   CTTGCAGCAG CAAAACACGG CTCCTCAAAT TGGAACTGTC AACAGCCAGG
  AAV9   CAACCAGGCC GCTAACACGC AGGCGCAAAC TGGACTTGTG CATAACCAGG
  AAV7   CTTACAAGCG GCTAATACTG CAGCCCAGAC ACAAGTTGTC AACAACCAGG
  44_2   CCTGCAACAG CAAAACGCCG CTCCTATTGT AGGGGCCGTC AACAGTCAAG
```

FIG. 1AAAD

```
              4051                                                      4100
    42_2     GGGCTCTGCC CGGCATGGTC TGGCAGAACC GGGACGTGTA CCTGCAGGGT
    42_8     GAGCCTTACC TGGCATGGTC TGGCAGAACC GGGACGTGTA CCTGCAGGGT
    42_15    GAGCCTTACC TGGCATGGTC TGGCAGAACC GGGACGTGTA CCTGCAGGGT
    42_5b    GAGCCTTACC TGGCATGGTC TGGCAGAACC GGGACGTGTA CCTGCAGGGT
    42_1b    GAGCCTTACC TGGCATGGTC TGGCAGAACC GGGACGTGTA CCTGCAGGGT
    42_13    GAGCCTTACC TGGCATGGTC TGGCAGAACC GGGACGTGTA CCTGCAGGGT
    42_3a    GAGCCTTACC TGGCATGGTC TGGCAGAACC GGGACGTGTA CCTGCAGGGT
    42_4     GAGCCTTACC TGGCATGGTC TGGCAGAACC GGGACGTGTA CCTGCAGGGT
    42_5a    GAGCCTTACC TGGCATGGCC TGGCAGAACC GGGACGTGTA CCTGCAGGGT
    42_10    GGGCTCTGCC CGGCATGGTC TGGCAGAACC GGGACGTGTA CCTGCAGGGT
    42_3b    GGGCTCTGCC CGGCATGGTC TGGCAGAACC GGGACGTGTA CCTGCAGGGT
    42_11    GGGCTCTGCC CGGCATGGTC TGGCAGAACC GGGACGTGTA CCTGCAGGGT
    42_6b    GGGCTCTGCC CGGCATGGTC TGGCAGAACC GGGACGTGTA CCTGCAGGGT
    43_1     GGGCCTTACC TGGTATGGTC TGGCAAAACC GGGACGTGTA CCTGCAGGGC
    43_5     GGGCCTTACC TGGTATGGTC TGGCAAAACC GGGACGTGTA CCTGCAGGGC
    43_12    GGGCCTTACC TGGTATGGTC TGGCAAAACC GGGACGTGTA CCTGCAGGGC
    43_20    GGGTGATTCC CGGCATGGTG TGGCAGAATA GAGACGTGTA CCTGCAGGGT
    43_21    GGGTGATTCC CGGCATGGTG TGGCAGAATA GAGACGTGTA CCTGCAGGGT
    43_23    GGGTGATTCC CGGCATGGTG TGGCAGAATA GAGACGTGTA CCTGCAGGGT
    43_25    GGGTGATTCC CGGCATGGTG TGGCAGAATA GAGACGTGTA CCTGCAGGGT
    44_1     GAGCCTTACC TGGCATGGTC TGGCAGAACC GGGACGTGTA CCTGCAGGGT
    44_5     GAGCCTTACC TGGCATGGTC TGGCAGAACC GGGACGTGTA CCTGCAGGGT
   223_10    GAGCCTTACC TGGCATGGTC TGGCAGAACC GGGACGTGTA CCTGCAAGGT
   223_2     GAGCCTTACC TGGCATGGTC TGGCAGAACC GGGACGTGTA CCTGCAAGGT
   223_4     GAGCCTTACC TGGCATGGTC TGGCAGAACC GGGACGTGTA CCTGCAAGGT
   223_5     GAGCCTTACC TGGCATGGTC TGGCAGAACC GGGACGTGTA CCTGCAAGGT
   223_6     GAGCCTTACC TGGCATGGTC TGGCAGAACC GGGACGTGTA CCTGCAAGGT
   223_7     GAGCCTTACC TGGCATGGTC TGGCAGAACC GGGACGTGTA CCTGCAAGGT
    A3_4     GAATCTTACC TGGAATGGTG TGGCAGGACC GCGATGTCTA TCTTCAAGGT
    A3_5     GAATCTTACC TGGAATGGTG TGGCAGGACC GCGATGTCTA TCTTCAAGGT
    A3_7     GAATCTTACC TGGAATGGTG TGGCAGGACC GCGATGTCTA TCTTCAAGGT
    A3_3     GAATCTTACC TGGAATGGTG TGGCAGGACC GCGATGTCTA TCTTCAAGGT
    42_12    GGGCTCTGCC CGGCATGGTC TGGCAGAACC GGGACGTGTA CCTGCAGGGT
    AAV1     GAGCATTACC TGGCATGGTG TGGCAAGATA GAGACGTGTA CCTGCAGGGT
    AAV2     GCGTTCTTCC AGGCATGGTC TGGCAGGACA GAGATGTGTA CCTTCAGGGG
    AAV3     GGGCCTTACC TGGCATGGTG TGGCAAGATC GTGACGTGTA CCTTCAAGGA
    AAV8     GGGCCTTACC CGGTATGGTC TGGCAGAACC GGGACGTGTA CCTGCAGGGT
    AAV9     GAGTTATTCC TGGTATGGTC TGGCAGAACC GGGACGTGTA CCTGCAGGGC
    AAV7     GAGCCTTACC TGGCATGGTC TGGCAGAACC GGGACGTGTA CCTGCAGGGT
    44_2     GAGCCTTACC TGGCATGGTC TGGCAGAACC GGGACGTGTA CCTGCAGGGT
```

FIG. 1AAAE

```
          4101                                                      4150
 42_2    CCC.ATCTGG GCCAAAATTC CTCACACGGA CGGCAACTTT CACCCGTCTC
 42_8    CCT.ATCTGG GCCAAGATTC CTCACACGGA CGGCAACTTT CATCCTTCGC
 42_15   CCT.ATCTGG GCCAAGATTC CTCACACGGA CGGCAACTTT CATCCTTCGC
 42_5b   CCT.ATCTGG GCCAAGATTC CTCACACGGA CGGCAACTTT CATCCTTCGC
 42_1b   CCT.ATCTGG GCCAAGATTC CTCACACGGA CGGCAACTTT CATCCTTCGC
 42_13   CCT.ATCTGG GCCAAGATTC CTCACACGGA CGGCAACTTT CATCCTTCGC
 42_3a   CCT.ATCTGG GCCAAGATTC CTCACACGGA CGGCAACTTT CATCCTTCGC
 42_4    CCT.ATCTGG GCCAAGATTC CTCACACGGA CGGCAACTTT CATCCTTCGC
 42_5a   CCT.ATCTGG GCCAAGATTC CTCACACGGA CGGCAACTTT CATCCTTCGC
 42_10   CCC.ATCTGG GCCAAAATTC CTCACACGGA CGGCAACTTT CACCCGTCTC
 42_3b   CCC.ATCTGG GCCAAAATTC CTCACACGGA CGGCAACTTT CACCCGTCTC
 42_11   CCC.ATCTGG GCCAAAATTC CTCACACGGA CGGCAACTTT CACCCGTCTC
 42_6b   CCC.ATCTGG GCCAAAATTC CTCACACGGA CGGCAACTTT CACCCGTCTC
 43_1    CCC.ATCTGG GCCAAAATTC CTCACACGGA CGGCAACTTT CATCCTTCGC
 43_5    CCC.ATCTGG GCCAAAATTC CTCACACGGA CGGCAACTTT CATCCTTCGC
 43_12   CCC.ATCTGG GCCAAAATTC CTCACACGGA CGGCAACTTT CATCCTTCGC
 43_20   CCC.ATCTGG GCCAAAATTC CTCACACGGA CGGCAACTTT CACCCGTCTC
 43_21   CCC.ATCTGG GCCAAAATTC CTCACACGGA CGGCAACTTT CACCCGTCTC
 43_23   CCC.ATCTGG GCCAAAATTC CTCACACGGA CGGCAACTTT CACCCGTCTC
 43_25   CCC.ATCTGG GCCAAAATTC CTCACACGGA CGGCAACTTT CACCCGTCTC
 44_1    CCT.ATCTGG GCCAAGATTC CTCACACGGA CGGAAACTTT CATCCCTCGC
 44_5    CCT.ATCTGG GCCAAGATTC CTCACACGGA CGGAAACTTT CATCCCTCGC
223_10   CCC.ATTTGG GCCAAGATTC CTCACACGGA CGGCAACTTT CACCCGTCTC
223_2    CCC.ATTTGG GCCAAGATTC CTCACACGGA CGGCAACTTT CACCCGTCTC
223_4    CCC.ATTTGG GCCAAGATTC CTCACACGGA CGGCAACTTT CACCCGTCTC
223_5    CCC.ATTTGG GCCAAGATTC CTCACACGGA CGGCAACTTT CACCCGTCTC
223_6    CCC.ATTTGG GCCAAGATTC CTCACACGGA CGGCAACTTT CACCCGTCTC
223_7    CCC.ATTTGG GCCAAGATTC CTCACACGGA CGGCAACTTT CACCCGTCTC
 A3_4    CCC.ATTTGG GCCAAAACTC CTCACACGGA CGGACACTTT CATCCTTCTC
 A3_5    CCC.ATTTGG GCCAAAACTC CTCACACGGA CGGACACTTT CATCCTTCTC
 A3_7    CCC.ATTTGG GCCAAAACTC CTCACACGGA CGGACACTTT CATCCTTCTC
 A3_3    CCC.ATTTGG GCCAAAACTC CTCACACGGA CGGACACTTT CATCCTTCTC
 42_12   CCC.ATCTGG GCCAAAATTC CTCACACGGA CGGCAACTTT CACCCGTCTC
 AAV1    CCC.ATTTGG GCCAAAATTC CTCACACAGA TGGACACTTT CACCCGTCTC
 AAV2    CCC.ATCTGG GCAAGATTC  CACACACGGA CGGACATTTT CACCCCTCTC
 AAV3    CCT.ATCTGG GCAAGATTC  CTCACACGGA TGGACACTTT CATCCTTCTC
 AAV8    CCC.ATCTGG GCCAAGATTC CTCACACGGA CGGCAACTTC CACCCGTCTC
 AAV9    CCCTATTTGG GCTAAAATAC CTCACACAGA TGGCAACTTT CACCCGTCTC
 AAV7    CCC.ATCTGG GCCAAGATTC CTCACACGGA TGGCAACTTT CACCCGTCTC
 44_2    CCT.ATCTGG GCCAAGATTC CTCACACGGA CGGAAACTTT CATCCCTCGC
```

FIG. 1AAAF

```
              4151                                                        4200
   42_2    CCCTGATGGG CGGATTTGGA CTCAAACACC CGCCTCCTCA AATTCTCATC
   42_8    CGCTGATGGG AGGCTTTGGA CTGAAACACC CGCCTCCTCA GATCCTGATT
   42_15   CGCTGATGGG AGGCTTTGGA CTGAAACACC CGCCTCCTCA GATCCTGATT
   42_5b   CGCTGATGGG AGGCTTTGGA CTGAAACACC CGCCTCCTCA GATCCTGATT
   42_1b   CGCTGATGGG AGGCTTTGGA CTGAAACACC CGCCTCCTCA GATCCTGATT
   42_13   CGCTGATGGG AGGCTTTGGA CTGAAACACC CGCCTCCTCA GATCCTGATT
   42_3a   CGCTGATGGG AGGCTTTGGA CTGAAACACC CGCCTCCTCA GATCCTGATT
   42_4    CGCTGATGGG AGGCTTTGGA CTGAAACACC CGCCTCCTCA GATCCTGATT
   42_5a   CGCTGATGGG AGGCTTTGGA CTGAAACACC CGCCTCCTCA GATCCTGATT
   42_10   CCCTGATGGG CGGATTTGGA CTCAAACACC CGCCTCCTCA AATTCTCATC
   42_3b   CCCTGATGGG CGGATTTGGA CTCAAACACC CGCCTCCTCA AATTCTCATC
   42_11   CCCTGATGGG CGGATTTGGA CTCAAACACC CGCCTCCTCA AATTCTCATC
   42_6b   CCCTGATGGA CGGATTTGGA CTCAAACACC CGCCTCCTCA AATTCTCATC
   43_1    CGCTGATGGG AGGCTTTGGA CTGAAACACC CGCCTCCTCA GATCCTGGTG
   43_5    CGCTGATGGG AGGCTTTGGA CTGAAACACC CGCCTCCTCA GATCCTGGTG
   43_12   CGCTGATGGG AGGCTTTGGA CTGAAACACC CGCCTCCTCA GATCCTGGTG
   43_20   CCCTGATGGG CGGCTTTGGA CTGAAGCACC CGCCTCCTCA AATTCTCATC
   43_21   CCCTGATGGG CGGCTTTGGA CTGAAGCACC CGCCTCCTCA AATTCTCATC
   43_23   CCCTGATGGG CGGCTTTGGA CTGAAGCACC CGCCTCCTCA AATTCTCATC
   43_25   CCCTGATGGG CGGCTTTGGA CTGAAGCACC CGCCTCCTCA AATTCTCATC
   44_1    CGCTGATGGG AGGCTTTGGA CTGAAACACC CGCCTCCTCA GATCCTGATT
   44_5    CGCTGATGGG AGGCTTTGGA CTGAAACACC CGCCTCCTCA GATCCTGATT
  223_10   CTCTAATGGG TGGCTTTGGA CTGAAACACC CGCCTCCCCA GATCCTGATC
  223_2    CTCTAATGGG TGGCTTTGGA CTGAAACACC CGCCTCCCCA GATCCTGATC
  223_4    CTCTAATGGG TGGCTTTGGA CTGAAACACC CGCCTCCCCA GATCCTGATC
  223_5    CTCTAATGGG TGGCTTTGGA CTGAAACACC CGCCTCCCCA GATCCTGATC
  223_6    CTCTAATGGG TGGCTTTGGA CTGAAACACC CGCCTCCCCA GATCCTGATC
  223_7    CTCTAATGGG TGGCTTTGGA CTGAAACACC CGCCTCCCCA GATCCTGATC
   A3_4    CGCTCATGGG AGGCTTTGGA CTGAAACACC CTCCTCCCCA GATCCTGATC
   A3_5    CGCTCATGGG AGGCTTTGGA CTGAAACACC CTCCTCCCCA GATCCTGATC
   A3_7    CGCTCATGGG AGGCTTTGGA CTGAAACACC CTCCTCCCCA GATCCTGATC
   A3_3    CGCTCATGGG AGGCTTTGGA CTGAAACACC CTCCTCCCCA GATCCTGATC
   42_12   CCCTGATGGG CGGATTTGGA CTCAAACACC CGCCTCCTCA AATTCTCATC
   AAV1    CTCTTATGGG CGGCTTTGGA CTCAAGAACC CGCCTCCTCA GATCCTCATC
   AAV2    CCCTCATGGG TGGATTCGGA CTTAAACACC CTCCTCCACA GATTCTCATC
   AAV3    CTCTGATGGG AGGCTTTGGA CTGAAACATC CGCCTCCTCA AATCATGATC
   AAV8    CGCTGATGGG CGGCTTTGGC CTGAAACATC CTCCGCCTCA GATCCTGATC
   AAV9    CTCTGATGGG TGGATTTGGA CTGAAACACC CACCTCCACA GATTCTAATT
   AAV7    CTTTGATGGG CGGCTTTGGA CTTAAACATC CGCCTCCTCA GATCCTGATC
   44_2    CGCTGATGGG AGGCTTTGGA CTGAAACACC CGCCTCCTCA GATCCTGATT
```

FIG. 1AAAG

```
            4201                                                        4250
   42_2     AAAAACACCC CGGTACCTGC TAATCCTCCA GAGGTGTTTA CTCCTGCCAA
   42_8     AAGAATACAC CTGTTCCCGC GGATCCTCCA ACTACCTTCA GTCAAGCCAA
   42_15    AAGAATACAC CTGTTCCCGC GGATCCTCCA ACTACCTTCA GTCAAGCCAA
   42_5b    AAGAATACAC CTGTTCCCGC GGATCCTCCA ACTACCTTCA GTCAAGCCAA
   42_1b    AAGAATACAC CTGTTCCCGC GGATCCTCCA ACTACCTTCA GTCAAGCCAA
   42_13    AAGAATACAC CTGTTCCCGC GGATCCTCCA ACTACCTTCA GTCAAGCCAA
   42_3a    AAGAATACAC CTGTTCCCGC GGATCCTCCA ACTACCTTCA GTCAAGCCAA
   42_4     AAGAATACAC CTGTTCCCGC GGATCCTCCA ACTACCTTCA GTCAAGCCAA
   42_5a    AAGAATACAC CTGTTCCCGC GGATCCTCCA ACTACCTTCA GTCAAGCCAA
   42_10    AAAAACACCC CGGTACCTGC TAATCCTCCA GAGGTGTTTA CTCCTGCCAA
   42_3b    AAAAACACCC CGGTACCTGC TAATCCTCCA GAGGTGTTTA CTCCTGCCAA
   42_11    AAAAACACCC CGGTACCTGC TAATCCTCCA GAGGTGTTTA CTCCTGCCAA
   42_6b    AAAAACACCC CGGTACCTGC TAATCCTCCA GAGGTGTTTA CTCCTGCCAA
   43_1     AAAAACACTC CTGTTCCTGC GGATCCTCCG ACCACCTTCA GCCAGGCCAA
   43_5     AAAAACACTC CTGTTCCTGC GGATCCTCCG ACCACCTTCA GCCAGGCCAA
   43_12    AAAAACACTC CTGTTCCTGC GGATCCTCCG ACCACCTTCA GCCAGGCCAA
   43_20    AAGAACACAC CGGTTCCAGC GGACCCGCCG CTTACCTTCA ACCAGGCCAA
   43_21    AAGAACACAC CGGTTCCAGC GGACCCGCCG CTTACCTTCA ACCAGGCCAA
   43_23    AAGAACACAC CGGTTCCAGC GGACCCGCCG CTTACCTTCA ACCAGGCCAA
   43_25    AAGAACACAC CGGTTCCAGC GGACCCGCCG CTTACCTTCA ACCAGGCCAA
   44_1     AAGAATACAC CTGTTCCCGC GGATCCTCCA ACTACCTTCA GTCAAGCTAA
   44_5     AAGAATACAC CTGTTCCCGC GGATCCTCCA ACTACCTTCA GTCAAGCTAA
   223_10   AAAAACACAC CGGTACCTGC TAATCCTCCA GAAGTGTTTA CTCCTGCCAA
   223_2    AAAAACACGC CGGTACCTGC TAATCCTCCA GAAGTGTTTA CTCCTGCCAA
   223_4    AAAAACACAC CGGTACCTGC TAATCCTCCA GAAGTGTTTA CTCCTGCCAA
   223_5    AAAAACACAC CGGTACCTGC TAATCCTCCA GAAGTGTTTA CTCCTGCCAA
   223_6    AAAAACACAC CGGTACCTGC TAATCCTCCA GAAGTGTTTA CTCCTGCCAA
   223_7    AAAAACACAC CGGTACCTGC TAATCCTCCA GAAGTGTTTA CTCCTGCCAA
   A3_4     AAAAACACAC CTGTGCCAGC GAATCCCGCG ACCACTTTCA CTCCTGGAAA
   A3_5     AAAAACACAC CTGTGCCAGC GAATCCCGCG ACCACTTTCA CTCCTGGAAA
   A3_7     AAAAACACAC CTGTGCCAGC GAATCCCGCG ACCACTTTCA CTCCTGGAAA
   A3_3     AAAAACACAC CTGTGCCAGC GAATCCCGCG ACCACTTTCA CTCCTGGAAA
   42_12    A...A..... .......... .......... .......... ..........
   AAV1     AAAAACACGC CTGTTCCTGC GAATCCTCCG GCGGAGTTTT CAGCTACAAA
   AAV2     AAGAACACCC CGGTACCTGC GAATCCTTCG ACCACCTTCA GTGCGGCAAA
   AAV3     AAAAATACTC CGGTACCGGC AAATCCTCCG ACGACTTTCA GCCCGGCCAA
   AAV8     AAGAACACGC CTGTACCTGC GGATCCTCCG ACCACCTTCA ACCAGTCAAA
   AAV9     AAAAATACAC CAGTGCCGGC AGATCCTCCT CTTACCTTCA ATCAAGCCAA
   AAV7     AAGAACACTC CCGTTCCCGC TAATCCTCCG GAGGTGTTTA CTCCTGCCAA
   44_2     AAGAATACAC CTGTTCCCGC GGATCCTCCA ACTACCTTCA GTCAAGCTAA
```

FIG. 1AAAH

```
              4251                                                       4300
     42_2    GTTTGCCTCA TTTATCACGC AGTACAGCAC CGGCCA.GGT CAGCGTGGAG
     42_8    GCTGGCGTCG TTCATCACGC AGTACAGCAC CGGACA.GGT CAGCGTGGAA
     42_15   GCTGGCGTCG TTCATCACGC AGTACAGCAC CGGACA.GGT CAGCGTGGAA
     42_5b   GCTGGCGTCG TTCATCACGC AGTACAGCAC CGGACA.GGT CAGCGTGGAA
     42_1b   GCTGGCGTCG TTCATCACGC AGTACAGCAC CGGACA.GGT CAGCGTGGAA
     42_13   GCTGGCGTCG TTCATCACGC AGTACAGCAC CGGACA.GGT CAGCGTGGAA
     42_3a   GCTGGCGTCG TTCATCACGC AGTACAGCAC CGGACA.GGT CAGCGTGGAA
     42_4    GCCGGCGTCG TTCATCACGC AGTACAGCAC CGGACA.GGT CAGCGTGGAA
     42_5a   GCTGGCGTCG TTCATCACGC AGTACAGCAC CGGACA.GGT CAGCGTGGAA
     42_10   GTTTGCCTCA TTTATCACGC AGTACAGCAC CGGCCA.GGT CAGCGTGGAG
     42_3b   GTTTGCCTCA TTTATCACGC AGTACAGCAC CGGCCA.GGT CAGCGTGGAG
     42_11   GTTTGCCTCA TTTATCACGC AGTACAGCAC CGGCCA.GGT CAGCGTGGAG
     42_6b   GTTTGCCTCA TTTATCACGC AGTACAGCAC CGGCCA.GGT CAGCGTGGAG
     43_1    GCTGGCTTCT TTTATCACGC AGTACAGCAC CGGACA.GGT CAGCGTGGAA
     43_5    GCTGGCTTCT TTTATCACGC AGTACAGCAC CGGACA.GGT CAGCGTGGAA
     43_12   GCTGGCTTCT TTTATCACGC AGTACAGCAC CGGACA.GGT CAGCGTGGAA
     43_20   GCTGAACTCT TTCATCACGC AGTACAGCAC CGGACA.GGT CAGCGTGGAA
     43_21   GCTGAACTCT TTCATCACGC AGTACAGCAC CGGACA.GGT CAGCGTGGAA
     43_23   GCTGAACTCT TTCATCACGC AGTACAGCAC CGGACA.GGT CAGCGTGGAA
     43_25   GCTGAACTCT TTCATCACGC AGTACAGCAC CGGACA.GGT CAGCGTGGAA
     44_1    GCTGGCGTCG TTCATCACGC AGTACAGCAC CGGACA.GGT CAGCGTGGAA
     44_5    GCTGGCGTCG TTCATCACGC AGTACAGCAC CGGACA.GGT CAGCGTGGAA
    223_10   GTTTGCTTCC TTCATCACGC AGTACAGCAC CGGGCA.AGT CAGCGTTGAG
    223_2    GTTTGCTTCC TTCATCACGC AGTACAGCAC CGGGCA.AGT CAGCGTTGAG
    223_4    GTTTGCTTCC TTCATCACGC AGTACAGCAC CGGGCA.AGT CAGCGTTGAG
    223_5    GTTTGCTTCC TTCATCACGC AGTACAGCAC CGGGCA.AGT CAGCGTTGAG
    223_6    GCTTGCTTCC TTCATCACGC AGTACAGCAC CGGGCA.AGT CAGCGTTGAG
    223_7    GATTGCTTCC TTCATCACGC AGTACAGCAC CGGGCA.AGT CAGCGTTGAG
     A3_4    GTTTGCTTCG TTCATTACCC AGTATTCCAC CGGACA.GGT CAGCGTGGAA
     A3_5    GTTTGCTTCG TTCATTACCC AGTATTCCAC CGGACA.GGT CAGCGTGGAA
     A3_7    GTTTGCTTCG TTCATTACCC AGTATTCCAC CGGACA.GGT CAGCGTGGAA
     A3_3    GTTTGCTTCG TTCATTACCC AGTATTCCAC CGGACA.GGT CAGCGTGGAA
     42_12   .......... .......... .......... .......... ..........
     AAV1    GTTGCTTCA TTCATCACCC AATACTCCAC AGGACA.AGT GAGTGTGGAA
     AAV2    GTTGCTTCC TTCATCACAC AGTACTCCAC GGGACACGGT CAGCGTGGAG
     AAV3    GTTGCTTCA TTTATCACTC AGTACTCCAC TGGACA.GGT CAGCGTGGAA
     AAV8    GCTGAACTCT TTCATCACGC AATACAGCAC CGGACA.GGT CAGCGTGGAA
     AAV9    GCTGAACTCT TTCATCACGC AGTACAGCAC GGGACA.AGT CAGCGTGGAA
     AAV7    GTTTGCTTCG TTCATCACAC AGTACAGCAC CGGACA.AGT CAGCGTGGAA
     44_2    GCTGGCGTCG TTCATCACGC AGTACAGCAC CGGACA.GGT CAGCGTGGAA
```

FIG. 1AAAI

```
            4301                                                   4350
   42_2     ATCGAGTGGG AACTGCAGAA AGAAAACAGC AAACGCTGGA ATCCAGAGAT
   42_8     ATTGAATGGG AGCTGCAGAA AGAGAACAGC AAGCGCTGGA ACCCAGAGAT
   42_15    ATTGAATGGG AGCTGCAGAA AGAGAACAGC AAGCGCTGGA ACCCAGAGAT
   42_5b    ATTGAATGGG AGCTGCAGAA AGAGAACAGC AAGCGCTGGA ACCCAGAGAT
   42_1b    ATTGAATGGG AGCTGCAGAA AGAGAACAGC AAGCGCTGGA ACCCAGAGAT
   42_13    ATTGAATGGG AGCTGCAGAA AGAGAACAGC AAGCGCTGGA ACCCAGAGAT
   42_3a    ATTGAATGGG AGCTGCAGAA AGAGAACAGC AAGCGCTGGA ACCCAGAGAT
   42_4     ATTGAATGGG AGCTGCAGAA AGAGAACAGC AAGCGCTGGA ACCCAGAGAT
   42_5a    ATTGAATGGG AGCTGCAGAA AGAGAACAGC AAGCGCTGGA ACCCAGAGAT
   42_10    ATCGAGTGGG AACTGCAGAA AGAAAACAGC AAACGCTGGA ATCCAGAGAT
   42_3b    ATCGAGTGGG AACTGCAGAA AGAAAACAGC AAACGCTGGA ATCCAGAGAT
   42_11    ATCGAGTGGG AACTGCAGAA AGAGAACAGC AAACGCTGGA ATCCAGAGAT
   42_6b    ATCGAGTGGG AACTGCAGAA AGAAAACAGC AAACGCTGGA ATCCAGAGAT
   43_1     ATCGAATGGG AGCTGCAGAA AGAAAACAGC AAGCGCTGGA ACCCAGAGAT
   43_5     ATCGAATGGG AGCTGCAGAA AGAAAACAGC AAGCGCTGGA ACCCAGAGAT
   43_12    ATCGAATGGG AGCTGCAGAA AGAAAACAGC AAGCGCTGGA ACCCAGAGAT
   43_20    ATCGAGTGGG AGCTGCAGAA AGAAAACAGC AAACGCTGGA ATCCAGAGAT
   43_21    ATCGAGTGGG AGCTGCAGAA AGAAAACAGC AAACGCTGGA ATCCAGAGAT
   43_23    ATCGAGTGGG AGCTGCAGAA AGAAAACAGC AAACGCTGGA ATCCAGAGAT
   43_25    ATCGAGTGGG AGCTGCAGAA AGAAAACAGC AAACGCTGGA ATCCAGAGAT
   44_1     ATTGAATGGG AGCTGCAGAA AGAAAACAGC AAACGCTGGA ACCCAGAGAT
   44_5     ATTGAATGGG AGCTGCAGAA AGAAAACAGC AAACGCTGGA ACCCAGAGAT
  223_10    ATCGAGTGGG AGCTGCAGAA AGAGAACAGC AAGCGCTGGA ACCCAGAGAT
  223_2     ATCGAGTGGG AGCTGCAGAA AGAGAACAGC AAGCGCTGGA ACCCAGAGAT
  223_4     ATCGAATGGG AGCTGCAGAA AGAGAACAGC AAGCGCTGGA ACCCAGAGAT
  223_5     ATCGAATGGG AGCTGCAGAA AGAGAACAGC AAGCGCTGGA ACCCAGAGAT
  223_6     ATCGAGTGGG AGCTGCAGAA AGAGAACAGC AAGCGCTGGA ACCCAGAGAT
  223_7     ATCGAGTGGG AGCTGCAGAA AGAGAACAGC AAGCGCTGGA ACCCAGAGAT
   A3_4     ATAGAGTGGG AGCTGCAGAA AGAAAACAGC AAACGCTGGA ACCCAGAAAT
   A3_5     ATAGAGTGGG AGCTGCAGAA AGAAAACAGC AAACGCTGGA ACCCGGAAAT
   A3_7     ATAGAGTGGG AGCTGCAGAA AGAAAACAGC AAACGCTGGA ACCCAGAAAT
   A3_3     ATAGAGTGGG AGCTGCAGAA AGAAAACAGC AAACGCTGGA ACCCAGAAAT
   42_12    .......... .......... .......... .......... ..........
   AAV1     ATTGAATGGG AGCTGCAGAA AGAAAACAGC AAGCGCTGGA ATCCCGAAGT
   AAV2     ATCGAGTGGG AGCTGCAGAA GGAAAACAGC AAACGCTGGA ATCCCGAAAT
   AAV3     ATTGAGTGGG AGCTACAGAA AGAAAACAGC AAACGTTGGA ATCCAGAGAT
   AAV8     ATTGAATGGG AGCTGCAGAA GGAAAACAGC AAGCGCTGGA ACCCCGAGAT
   AAV9     ATCGAGTGGG AGCTGCAGAA AGAAAACAGC AAGCGCTGGA ATCCAGAGAT
   AAV7     ATCGAGTGGG AGCTGCAGAA GGAAAACAGC AAGCGCTGGA ACCCGGAGAT
   44_2     ATTGAATGGG AGCTGCAGAA AGAAAACAGC AAACGCTGGA ACCCAGAGAT
```

FIG. 1AAAJ

```
           4351                                                    4400
   42_2    TCAGTACACC TCAAATTATG CCAAGTCTAA TAAT.GTGGA ATTTGCTGTC
   42_8    TCAGTATACT TCCAACTACT ACAAATCTAC AAAT.GTGGA CTTTGCTGTC
  42_15    TCAGTATACT TCCAACTACT ACAAATCTAC AAAT.GTGGA CTTTGCTGTC
  42_5b    TCAGTATACT TCCAACTACT ACAAATCTAC AAAT.GTGGA CTTTGCTGTC
  42_1b    TCAGTATACT TCCAACTACT ACAAATCTAC AAAT.GTGGA CTTTGCTGTC
  42_13    TCAGTATACT TCCAACTACT ACAAATCTAC AAAT.GTGGA CTTTGCTGTC
  42_3a    TCAGTATACT TCCAACTACT ACAAATCTAC AAAT.GTGGA CTTTGCTGTC
   42_4    TCAGTATACT TCCAACTACT ACAAATCTAC AAAT.GTGGA CTTTGCTGTC
  42_5a    TCAGTATACT TCCAACTACT ACAAATCTAC AAAT.GTGGA CTTTGCTGTC
  42_10    TCAGTACACC TCAAATTATG CCAAGTCTAA TAAT.GTGGA ATTTGCTGTC
  42_3b    TCAGTACACC TCAAATTATG CCAAGTCTAA TAAT.GTGGA ATTTGCTGTC
  42_11    TCAGTACACC TCAAATTATG CCAAGTCTAA TAAT.GTGGA ATTTGCTGTC
  42_6b    TCAGTACACC TCAAATTATG CCAAGTCTAA TAAT.GTGGA ATTTGCTGTC
   43_1    TCAGTATACT TCCAACTACT ACAAATCTAC AAAT.GTGGA CTTTGCTGTC
   43_5    TCAGTATACT TCCAACTACT ACAAATCTAC AAAT.GTGGA CTTTGCTGTC
  43_12    TCAGTATACT TCCAACTACT ACAAATCTAC AAAT.GTGGA CTTTGCTGTC
  43_20    TCAATACACT TCCAACTACT ACAAATCTAC AAAT.GTGGA CTTTGCTGTC
  43_21    TCAATACACT TCCAACTACT ACAAATCTAC AAAT.GTGGA CTTTGCTGTC
  43_23    TCAATACACT TCCAACTACT ACAAATCTAC AAAT.GTGGA CTTTGCTGTC
  43_25    TCAATACACT TCCAACTACT ACAAATCTAC AAAT.GTGGA CTTTGCTGTC
   44_1    TCAATACACT TCCAACTACT ACAAATCTAC AAAT.GTGGA CTTCGCTGTT
   44_5    TCAATACACT TCCAACTACT ACAAATCTAC AAAT.GTGGA CTTTGCTGTT
  223_10   TCAGTACACC TCCAACTTTG ACAAACAGAC TGGA.GTGGA CTTTGCTGTT
  223_2    TCAGTACACC TCCAACTTTG ACAAACAGAC TGGA.GTGGA CTTTGCTGTT
  223_4    TCAGTACACC TCCAACTTTG ACAAACAGAC TGGA.GTGGA CTTTGCTGTT
  223_5    TCAGTACACC TCCAACTTTG ACAAACAGAC TGGA.GTGGA CTTTGCTGTT
  223_6    TCAGTACACC TCCAACTTTG ACAAACAGAC TGGA.GTGGA CTTTGCTGTT
  223_7    TCAGTACACC TCCAACTTTG ACAAACAGAC TGGA.GTGGA CTTTGCTGTT
   A3_4    TCAGTACACC TCCAACTACA ACAAGTCGGT GAAT.GTGGA GTTTACCGTG
   A3_5    TCAGTACACC TCCAACTACA ACAAGTCGGT GAAT.GTGGA GTTTACCGTG
   A3_7    TCAGTACACC TCCAACTACA ACAAGTCGGT GAAT.GTGGA GTTTACCGTG
   A3_3    TCAGTACACC TCCAACTACA ACAAGTCGGT GAAT.GTGGA GTTTACCGTG
  42_12    ...GTATACT TCCAACTACT ACAAATCTAC AAAT.GTGGA CTTTGCTGTC
   AAV1    GCAGTACACA TCCAATTATG CAAAATCTGC CAAC.GTTGA TTTTACTGTG
   AAV2    TCAGTACACT TCCAACTACA ACAAGTCTGT TAATCGTGGA CTT.ACCGTG
   AAV3    TCAGTACACT TCCAACTACA ACAAGTCTGT TAAT.GTGGA CTTTACTGTA
   AAV8    CCAGTACACC TCCAACTACT ACAAATCTAC AAGT.GTGGA CTTTGCTGTT
   AAV9    CCAGTATACT TCAAACTACT ACAAATCTAC AAAT.GTGGA CTTTGCTGTC
   AAV7    TCAGTACACC TCCAACTTTG AAAAGCAGAC TGGT.GTGGA CTTTGCCGTT
   44_2    TCAATACACT TCCAACTACT ACAAATCTAC AAAT.GTGGA CTTTGCTGTT
```

FIG. 1AAAK

```
            4401                                                    4450
  42_2    AACAACGAAG GGGTTTATAC TGAGCCTCGC CCCATTGGCA CCCGTTACCT
  42_8    AATACTGAGG GTACTTATTC AGAGCCTCGC CCCATTGGCA CCCGTTACCT
  42_15   AATACTGAGG GTACTTATTC AGAGCCTCGC CCCATTGGCA CCCGTTACCT
  42_5b   AATACTGAGG GTACTTATTC AGAGCCTCGC CCCATTGGCA CCCGTTACCT
  42_1b   AATACTGAGG GTACTTATTC AGAGCCTCGC CCCATTGGCA CCCGTTACCT
  42_13   AATACTGAGG GTACTTATTC AGAGCCTCGC CCCATTGGCA CCCGTTACCT
  42_3a   AATACTGAGG GTACTTATTC AGAGCCTCGC CCCATTGGCA CCCGTTACCT
  42_4    AATACTGAGG GTACTTATTC AGAGCCTCGC CCCATTGGCA CCCGTTACCT
  42_5a   AATACTGAGG GTACTTATTC AGAGCCTCGC CCCATTGGCA CCCGTTACCT
  42_10   AACAACGAAG GGGTTTATAC TGAGCCTCGC CCCATTGGCA CCCGTTACCT
  42_3b   AACAACGAAG GGGTTTATAC TGAGCCTCGC CCCATTGGCA CCCGTTACCT
  42_11   AACAACGAAG GGGTTTATAC TGAGCCTCGC CCCATTGGCA CCCGTTACCT
  42_6b   AACAACGAAG GGGTTTATAC TGAGCCTCGC CCCATTGGCA CCCGTTACCT
  43_1    AATACTGAGG GTACTTATTC AGAGCCTCGC CCCATTGGCA CTCGTTATCT
  43_5    AATACCGAGG GTACTTATTC AGAGCCTCGC CCCATTGGCA CTCGTTATCT
  43_12   AATACTGAGG GTACTTATTC AGAGCCTCGC CCCATTGGCA CTCGTTATCT
  43_20   AACACGAAG  GAGTTTATAG CGAGCCTCGC CCCATTGGCA CCCGTTACCT
  43_21   AACACGGAAG GAGTTTATAG CGAGCCTCGC CCCATTGGCA CCCGTTACCT
  43_23   AACACGGAAG GAGTTTATAG CGAGCCTCGC CCCATTGGCA CCCGTTACCT
  43_25   AACACGGAGG GGGTTTATAG CGAGCCTCGC CCCATTGGCA CCCGTTACCT
  44_1    AACACAGATG GCACTTATTC TGAGCCTCGC CCCATTGGCA CCCGTTACCT
  44_5    AACACAGATG GCACTTATTC TGAGCCTCGC CCCATTGGCA CCCGTTACCT
 223_10   GACAGCCAGG GTGTTTACTC TGAGCCT... .......... ..........
 223_2    GACAGCCAGG GTGTTTACTC TGAGCCT... .......... ..........
 223_4    GACAGCCAGG GTGTTTACTC TGAGCCT... .......... ..........
 223_5    GACAGCCAGG GTGTTTACTC TGAGCCT... .......... ..........
 223_6    GACAGCCAGG GTGTTTACTC TGAGCCT... .......... ..........
 223_7    GACAGCCAGG GTGTTTACTC TGAGCCT... .......... ..........
  A3_4    GACGCAAACG GTGTTTATTC TGAACCCCGC CCTATTGGCA CTCGTTACCT
  A3_5    GACGCAAACG GTGTTTATTC TGAACCCCGC CCTATTGGCA CTCGTTACCT
  A3_7    GACGCAAACG GTGTTTATTC TGAACCCCGC CCTATTGGCA CTCGTTACCT
  A3_3    GACGCAAACG GTGTTTATTC TGAACCCCGC CCTATTGGCA CTCGTTACCT
  42_12   AATACTGAGG GTACTTATTC AGAGCCTCGC CCCATTGGCA CCCGTTACCT
  AAV1    GACAACAATG GACTTTATAC TGAGCCTCGC CCCATTGGCA CCCGTTACCT
  AAV2    GATACTAATG GCGTGTATTC AGAGCCTCGC CCCATTGGCA CCAGATACCT
  AAV3    GACACTAATG GTGTTTATAG TGAACCTCGC CCTATTGGAA CCCGGTATCT
  AAV8    AATACAGAAG GCGTGTACTC TGAACCCCGC CCCATTGGCA CCCGTTACCT
  AAV9    AATACCGAAG GTGTTTACTC TGAGCCTCGC CCATTGGTA  CTCGTTACCT
  AAV7    GACAGCCAGG GTGTTTACTC TGAGCCTCGC CCTATTGGCA CTCGTTACCT
  44_2    AACACAGATG GCACTTATTC TGAGCCTCGC CCCATCGGCA CCCGTTACCT
```

FIG. 1AAAL

```
       4451                                                    4500
                 VP1-3 stop     Poly A signal
  42_2    CACCCGTAAC CTGTAATTGC CTGTTAATCA ATAAACCGGT TAATTCGTTT
  42_8    CACCCGTAAC CTGTAATTGC CTGTTAATCA ATAAACCGGC TAATTCGTTT
  42_15   CACCCGTAAC CTGTAATTGC CTGTTAATCA ATAAACCGGT TAATTCGTTT
  42_5b   CACCCGTAAC CTGTAATTGC CTGTTAATCA ATAAACCGGT TAATTCGTTT
  42_1b   CACCCGTAAC CTGTAATTGC CTGTTAATCA ATAAACCGGT TGATTCGTTT
  42_13   CACCCGTAGC CTGTAATTGC CTGTTAATCA ATAAACCGGT TGATTCGTTT
  42_3a   CACCCGTAAC CTGTAATTGC CTGTTAATCA ATAAACCGGT TAATTCGTTT
  42_4    CACCCGTAAC CTGTAATTGC CTGTTAATCA ATAAACCGGT TAATTCGTTT
  42_5a   CACCCGTAAC CTGTAATTGC CTGTTAATCA ATAAACCGGT TAATTCGTTT
  42_10   CACCCGTAAC CTGTAATTGC CTGTTAATCA ATAAACCGGT TAATTCGTTT
  42_3b   CACCCGTAAC CTGTAATTGC CTGTTAATCA ATAAACCGGT TAATTCGTTT
  42_11   CACCCGTAAC CTGTAATTAC TTGTTAATCA ATAAACCGGT TGATTCGTTT
  42_6b   CACCCGTAAC CTGTAATTGC CTGTTAATCA ATAAACCGGT TAATTCGTTT
  43_1    CACCCGTAAT CTGTAATTGC TTGTTAATCA ATAAACCGGT ..........
  43_5    CACCCGTAAT CTGTAATTGC TTGTTAATCA ATAAACCGGT TAATTCGTTT
  43_12   CACCCGTAAT CTGTAATTGC TTGTTAATCA ATAAACCGGT TAATTCGTTT
  43_20   CACCCGCAAC CTGTAATTAC ATGTTAATCA ATAAACCGGT TAATTCGTTT
  43_21   CACCCGCAAC CTGTAATTAC ATGTTAATCA ATAAACCGGT TAATTCGTTT
  43_23   CACCCGCAAC CTGTAATTAC ATGTTAATCA ATAAACCGGT TAATTCGTTT
  43_25   CACCCGCAAC CTGTAATTAC ATGTTAATCA ATAAACCGGT TAATTCGTTT
  44_1    CACCCGTAAT CTGTAATTGC TCGTTAATCA ATAAACCGGT TGATTCGTTT
  44_5    CACCCGTAAT CTGTAATTGC TTGTTAATCA ATAAACCGGT TGATTCGTTT
 223_10   .......... .......... .......... .......... ..........
 223_2    .......... .......... .......... .......... ..........
 223_4    .......... .......... .......... .......... ..........
 223_5    .......... .......... .......... .......... ..........
 223_6    .......... .......... .......... .......... ..........
 223_7    .......... .......... .......... .......... ..........
  A3_4    TACCCGGAAC TTGTAATTTC CTGTTAATGA ATAAACCGAT TTATGCGTTT
  A3_5    TACCCGGAAC TTGTAATTTC CTGTTAATGA ATAAACCGAT TTATGCGTTT
  A3_7    TACCCGGAAC TTGTAATTTC CTGTTAATGA ATAAACCGAT TTATGCGTTT
  A3_3    TACCCGGAAC TTGTAATTTC CTGTTAATGA ATAAGCCGAT TTATGCGTTT
  42_12   CACCCGTAAC CTGTAATTGC CTGTTAATCA ATAAACCGGT TAATTCGTTT
  AAV1    TACCCGTCCC CTGTAATTAC GTGTTAATCA ATAAACCGGT TGATTCGTTT
  AAV2    GACTCGTAAT CTGTAATTGC TTGTTAATCA ATAAACCGTT TAATTCGTTT
  AAV3    CACACGAAAC TTGTGAATCC TGGTTAATCA ATAAACCGTT TAATTCGTTT
  AAV8    CACCCGTAAT CTGTAATTGC CTGTTAATCA ATAAACCGGT TGATTCGTTT
  AAV9    CACCCGTAAT TTGTAATTGC CTGTTAATCA ATAAACCGGT TAATTCGTTT
  AAV7    CACCCGTAAT CTGTAATTGC ATGTTAATCA ATAAACCGGT TGATTCGTTT
  44_2    CACCCGTAAT CTGTAATTGC TTGTTAATCA ATAAACCGGT TGATTCGTTT
                 vp1-3 stop      PolyA signal
```

FIG. 1AAAM

```
             4501                                              4550
   42_2    CAGTTGAACT TTGGTCTC.T GCGAAGGGCG AATTC..... ..........
   42_8    CAGTTGAACT TTGGTCTC.T GCGAAGGGCG AATTC..... ..........
  42_15    CAGTTGAACT TTGGTCTC.T GCGAAGGGCG AATTC..... ..........
  42_5b    CAGTTGAACT TTGGTCTC.T GCGAAGGGCG AATTCGTTTA AACCTGCAGG
  42_1b    CAGTTGAACT TTGGTCTC.. ...AAGGGCG AATTC..... ..........
  42_13    CAGTTGAACT TTGGTCTC.T GCGAAGGGCG AATTC..... ..........
  42_3a    CAGTTGAACT TTGGTCTC.T GCGAAGGGCG AATTC..... ..........
   42_4    CAGTTGAACT TTGGTCTC.T GCGAAGGGCG AATTC..... ..........
  42_5a    CAGTTGAACT TTGGTCTC.T GCGAAGGGCG AATTC..... ..........
  42_10    CAGTTGAACT TTGGTC.... ...AAGGGCG AATTC..... ..........
  42_3b    CAGTTGAACT TTGGTCTC.T GCGAAGGGCG AATTC..... ..........
  42_11    CAGTTGAACT TTGGTCTC.T GCGAAGGGCG AATTC..... ..........
  42_6b    CAGTTGAACT TTGGTCTC.T GCGAAGGGCG AATTC..... ..........
   43_1    .......... .......... .......... .......... ..........
   43_5    CAGTTGAACT TTGGTCTC.T GCGAAGGGCG AATTCGTTTA AACCTGCAGG
  43_12    CAGTTGAACT TTGGTCTC.T GCGAAGGGCG AATTC..... ..........
  43_20    CAGTTGAACT TTGGTCTC.T GCGAAGGGCG AATTC..... ..........
  43_21    CAGTTGAACT TTGGTCTC.T GCGAAGGGCG AATTC..... ..........
  43_23    CAGTTGAACT TTGGTCTC.T GCGAAGGGCG AATTC..... ..........
  43_25    CAGTTGAACT TTGGTCTC.T GCGAAGGGCG AATTC..... ..........
   44_1    CAGTTGAACT TTGGTCTC.T GCGAAGGGCG AATTC..... ..........
   44_5    CAGTTGAACT TTGGTCTC.T GCGAAGGGCG AATTC..... ..........
 223_10    .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    CAGTTGAACT TTGGTCTC.T GCGAAGGGCG AATTCGC.GG CCGCTA....
   A3_5    CAGTTGAACT TTGGTCTC.T GCGAAGGGCG AATTC..... ..........
   A3_7    CAGTTGAACT TTGGTCTC.T GCGAAGGGCG AATTC..... ..........
   A3_3    CAGTTGAACT TTGGTCTC.T GCGAAGGGCG AATTCGT.TT AAACCT....
  42_12    CAGTTGAACT TTGGTCTC.T GCGAAGGGCG AATTC..... ..........
   AAV1    CAGTTGAACT TTGGTCTCCT GTCCTTCTTA TCTTATCGGT TACCATGGTT
   AAV2    CAGTTGAACT TTGGTCTC.T GCGTATTTCT ..TTCTT.AT CTAGTTTCCA
   AAV3    CAGTTGAACT TTGGCTCT.T GTGCACTTCT TTATCTTTAT CTTGTTTCCA
   AAV8    CAGTTGAACT TTGGTCTC.T GCG....... .......... ..........
   AAV9    CAGTTGAACT TTGGTCTC.T GCG....... .......... ..........
   AAV7    CAGTTGAACT TTGGTCTCCT GTGCTTCTTA TCTTATCGGT TTCCATAGCA
   44_2    CAGTTGAACT TTGGTCTC.T GCGAAGGGCG AATTC..... ..........
```

FIG. 1AAAN

```
         4551                                                      4600
  42_2   ..........  ..........  ..........  ..........  ..........
  42_8   ..........  ..........  ..........  ..........  ..........
 42_15   ..........  ..........  ..........  ..........  ..........
 42_5b   ACTAGTCCCT  TTAGTGAGGG  TTAATTCTGA  G.........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   AC........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   ATAGCTTACA  CATTAACTGC  TTGGTTGCGC  T.........  ..........
  AAV2   TGGCTAC...  GTAGATAAGT  AGC.......  ..........  ..........
  AAV3   TGGCTACTGC  GTAGATAAGC  AGCGGCCTGC  GGCGCTTGCG  CTTCGCGGTT
  AAV8   ..........  ..........  ..........  ..........  ..........
  AAV9   ..........  ..........  ..........  ..........  ..........
  AAV7   ACTGGTTACA  CATTAACTGC  TTGGGTGCGC  TTCACGATAA  GAACACTGAC
  44_2   ..........  ..........  ..........  ..........  ..........
```

```
                            FIG. 1AAAO 4601                                                    4650
  42_2   ..........  ..........  ..........  ..........  ..........
  42_8   ..........  ..........  ..........  ..........  ..........
 42_15   ..........  ..........  ..........  ..........  ..........
 42_5b   ....CTTGGC  GTAATCATGG  GTCATAG...  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   ....TCGCGA  TAAAAGACTT  ACGTCATCGG  GTTACCCCTA  GTGATGGAGT
  AAV2   ....ATGGCG  GGTTAATCAT  TAACTACAAG  GA.ACCCCTA  GTGATGGAGT
  AAV3   TACAACTGCT  GGTTAATATT  TAACTCTCGC  CATACCTCTA  GTGATGGAGT
  AAV8   ..........  ..........  ..........  ..........  ..........
  AAV9   ..........  ..........  ..........  ..........  ..........
  AAV7   ..........  ..........  ...GTCACCGC  GGTACCCCTA  GTGATGGAGT
  44_2   ..........  ..........  ..........  ..........  ..........
```

FIG. 1AAAP

```
            4651                                                              4700
   42_2     ..........  ..........  ..........  ..........  ..........
   42_8     ..........  ..........  ..........  ..........  ..........
  42_15     ..........  ..........  ..........  ..........  ..........
  42_5b     ..........  ..........  ..........  ..........  ..........
  42_1b     ..........  ..........  ..........  ..........  ..........
  42_13     ..........  ..........  ..........  ..........  ..........
  42_3a     ..........  ..........  ..........  ..........  ..........
   42_4     ..........  ..........  ..........  ..........  ..........
  42_5a     ..........  ..........  ..........  ..........  ..........
  42_10     ..........  ..........  ..........  ..........  ..........
  42_3b     ..........  ..........  ..........  ..........  ..........
  42_11     ..........  ..........  ..........  ..........  ..........
  42_6b     ..........  ..........  ..........  ..........  ..........
   43_1     ..........  ..........  ..........  ..........  ..........
   43_5     ..........  ..........  ..........  ..........  ..........
  43_12     ..........  ..........  ..........  ..........  ..........
  43_20     ..........  ..........  ..........  ..........  ..........
  43_21     ..........  ..........  ..........  ..........  ..........
  43_23     ..........  ..........  ..........  ..........  ..........
  43_25     ..........  ..........  ..........  ..........  ..........
   44_1     ..........  ..........  ..........  ..........  ..........
   44_5     ..........  ..........  ..........  ..........  ..........
 223_10     ..........  ..........  ..........  ..........  ..........
  223_2     ..........  ..........  ..........  ..........  ..........
  223_4     ..........  ..........  ..........  ..........  ..........
  223_5     ..........  ..........  ..........  ..........  ..........
  223_6     ..........  ..........  ..........  ..........  ..........
  223_7     ..........  ..........  ..........  ..........  ..........
   A3_4     ..........  ..........  ..........  ..........  ..........
   A3_5     ..........  ..........  ..........  ..........  ..........
   A3_7     ..........  ..........  ..........  ..........  ..........
   A3_3     ..........  ..........  ..........  ..........  ..........
  42_12     ..........  ..........  ..........  ..........  ..........
   AAV1     TGCCCACTCC  CTCTCTGCGC  GCTCGCTCGC  TCGGTGGGGC  CTGCGGACCA
   AAV2     TGGCCACTCC  CTCTCTGCGC  GCTCGCTCGC  TCACTGAGGC  CGGGCGACCA
   AAV3     TGGCCACTCC  CTCTATGCGC  ACTCGCTCGC  TCGGTGGGGC  CTGGCGACCA
   AAV8     ..........  ..........  ..........  ..........  ..........
   AAV9     ..........  ..........  ..........  ..........  ..........
   AAV7     TGGCCACTCC  CTCTATGCGC  GCTCGCTCGC  TCGGTGGGGC  CTGCGGACCA
   44_2     ..........  ..........  ..........  ..........  ..........
```

FIG. 1AAAQ

```
            4701                                                      4750
   42_2     ..........  ..........  ..........  ..........  ..........
   42_8     ..........  ..........  ..........  ..........  ..........
  42_15     ..........  ..........  ..........  ..........  ..........
  42_5b     ..........  ..........  ..........  ..........  ..........
  42_1b     ..........  ..........  ..........  ..........  ..........
  42_13     ..........  ..........  ..........  ..........  ..........
  42_3a     ..........  ..........  ..........  ..........  ..........
   42_4     ..........  ..........  ..........  ..........  ..........
  42_5a     ..........  ..........  ..........  ..........  ..........
  42_10     ..........  ..........  ..........  ..........  ..........
  42_3b     ..........  ..........  ..........  ..........  ..........
  42_11     ..........  ..........  ..........  ..........  ..........
  42_6b     ..........  ..........  ..........  ..........  ..........
   43_1     ..........  ..........  ..........  ..........  ..........
   43_5     ..........  ..........  ..........  ..........  ..........
  43_12     ..........  ..........  ..........  ..........  ..........
  43_20     ..........  ..........  ..........  ..........  ..........
  43_21     ..........  ..........  ..........  ..........  ..........
  43_23     ..........  ..........  ..........  ..........  ..........
  43_25     ..........  ..........  ..........  ..........  ..........
   44_1     ..........  ..........  ..........  ..........  ..........
   44_5     ..........  ..........  ..........  ..........  ..........
 223_10     ..........  ..........  ..........  ..........  ..........
  223_2     ..........  ..........  ..........  ..........  ..........
  223_4     ..........  ..........  ..........  ..........  ..........
  223_5     ..........  ..........  ..........  ..........  ..........
  223_6     ..........  ..........  ..........  ..........  ..........
  223_7     ..........  ..........  ..........  ..........  ..........
   A3_4     ..........  ..........  ..........  ..........  ..........
   A3_5     ..........  ..........  ..........  ..........  ..........
   A3_7     ..........  ..........  ..........  ..........  ..........
   A3_3     ..........  ..........  ..........  ..........  ..........
  42_12     ..........  ..........  ..........  ..........  ..........
   AAV1     AAGGTCCGCA  GACGGCAGAG  CTCTGCTCTG  CCGGCCCCAC  CGAGCGAGCG
   AAV2     AAGGTCGCCC  GACGCCCGGG  CTTTGCCCGG  GCGGCCTCAG  TGAGCGAGCG
   AAV3     AAGGTCGCCA  GACGGACGTG  CTTTGCACGT  CCGGCCCCAC  CGAGCGAGCG
   AAV8     ..........  ..........  ..........  ..........  ..........
   AAV9     ..........  ..........  ..........  ..........  ..........
   AAV7     AAGGTCCGCA  GACGGCAGAG  CTCTGCTCTG  CCGGCCCCAC  CGAGCGAGCG
   44_2     ..........  ..........  ..........  ..........  ..........
```

FIG. 1AAAR

```
          4751                    4774
  42_2    ..........  ..........  ....
  42_8    ..........  ..........  ....
  42_15   ..........  ..........  ....
  42_5b   ..........  ..........  ....
  42_1b   ..........  ..........  ....
  42_13   ..........  ..........  ....
  42_3a   ..........  ..........  ....
  42_4    ..........  ..........  ....
  42_5a   ..........  ..........  ....
  42_10   ..........  ..........  ....
  42_3b   ..........  ..........  ....
  42_11   ..........  ..........  ....
  42_6b   ..........  ..........  ....
  43_1    ..........  ..........  ....
  43_5    ..........  ..........  ....
  43_12   ..........  ..........  ....
  43_20   ..........  ..........  ....
  43_21   ..........  ..........  ....
  43_23   ..........  ..........  ....
  43_25   ..........  ..........  ....
  44_1    ..........  ..........  ....
  44_5    ..........  ..........  ....
 223_10   ..........  ..........  ....
 223_2    ..........  ..........  ....
 223_4    ..........  ..........  ....
 223_5    ..........  ..........  ....
 223_6    ..........  ..........  ....
 223_7    ..........  ..........  ....
  A3_4    ..........  ..........  ....
  A3_5    ..........  ..........  ....
  A3_7    ..........  ..........  ....
  A3_3    ..........  ..........  ....
  42_12   ..........  ..........  ....
  AAV1    AGCGCGCAGA  GAGGGAGTGG  GCAA
  AAV2    AGCGCGCAGA  GAGGGAGTGG  CCAA
  AAV3    AGTGCGCATA  GAGGGAGTGG  CCAA
  AAV8    ..........  ..........  ....
  AAV9    ..........  ..........  ....
  AAV7    AGCGCGCATA  GAGGGAGTGG  CCAA
  44_2    ..........  ..........  ....
```

```
                         10        20        30        40        50        60
                  ....|....|....|....|....|....|....|....|....|....|....|....|
C1\VP1            MAADGYLPDWLEDNLSEGIREWWDLKPGAPKPKANQQKQDDGRGLVLPGYKYLGPFNGLD
C2\VP1            MAADGYLPDWLEDNLSEGIREWWDLKPGAPKLKANQQKQDDGRGLVLPGYKYLGPFHGLD
C5\VP1@2          MAADGYLPDWLEDNLSEGIREWWDLKPGAPKPKANQQKQDDGRGLVLPGYEYLGPFNGLD
AAV4\VP1          -MTDGYLPDWLEDNLSEGVREWWALQPGAPKPKANQQHQDNARGLVLPGYKYLGPGNGLD
AAV1              MAADGYLPDWLEDNLSEGIREWWDLKPGAPKPKANQQKQDDGRGLVLPGYKYLGPFNGLD
AAV6\VP1          MAADGYLPDWLEDNLSEGIREWWDLKPGAPKPKANQQKQDDGRGLVLPGYKYLGPFNGLD
A3_3              MAADGYLPDWLEDTLSEGIRQWWKLKPGPPPPKPNQQHRDDSRGLVLPGYKYLGPFNGLD
A3_7              MAADGYLPDWLEDTLSEGIRQWWKLKPGPPPPKPNQQHRDDSRGLVLPGYKYLGPFNGLD
A3_4              MAADGYLPDWLEDTLSEGIRQWWKLKPGPPPPKPNQQHRDDSRGLVLPGYKYLGPFNGLD
A3_5              MAADGYLPDWLEDTLSEGIRQWWKLKPGPPPPKPNQQHRDDSRGLVLPGYKYLGPFNGLD
AAV2              MAADGYLPDWLEDTLSEGIRQWWKLKPGPPPPKPAERHKDDSRGLVLPGYKYLGPFNGLD
AAV3              MAADGYLPDWLEDNLSEGIREWWALKPGVPQPKANQQHQDNRRGLVLPGYKYLGPGNGLD
13.3b\VP1         MAADGYLPDWLEDNLSEGIREWWDLKPGAPKPKANQQKQDNGRGLVLPGYKYLGPFNGLD
AAV7              MAADGYLPDWLEDNLSEGIREWWDLKPGAPKPKANQQKQDNGRGLVLPGYKYLGPFNGLD
223_4             ------------------------------------------------------------
223_5             ------------------------------------------------------------
223_10            ------------------------------------------------------------
223_2             ------------------------------------------------------------
223_7             ------------------------------------------------------------
223_6             ------------------------------------------------------------
44_1              MAADGYLPDWLEDNLSEGIREWWDLKPGAPKPKANQQKQDDGRGLVLPGYKYLGPFNGLD
44_5              MAADGYLPDWLEDNLSEGIREWWDLKPGAPKPKANQQKQDDGRGLVLPGYKYLGPFNGLD
44_2              MAADGYLPDWLEDNLSEGIREWWDLKPGAPKPKANQQKQDDGRGLVLPGYKYLGPFNGLD
29.3\VP1          MAADGYLPDWLEDNLSEGIREWWALKPGAPKPKANQQKQDDGRGLVLPGYKYLGPFNGLD
29.5\VP1          MAADGYLPDWLEDNLSEGIREWWALKPGAPKPKANQQKQDDGRGLVLPGYKYLGPFNGLD
42_15             MAADGYLPDWLEDNLSEGIREWWDLKPGAPKPKANQQKQDDGRGLVLPGYKYLGPFNGLD
42_8              MAADGYLPDWLEDNLSEGIREWWDLKPGAPKPKANQQKQDDGRGLVLPGYKYLGPFNGLD
42_13             MAADGYLPDWLEDNLSEGIREWWDLKPGAPKPKANQQKQDDGRGLVLPGYKYLGPFNGLD
42_3A             MAADGHLPDWLEDNLSEGIREWWDLKPGAPKPKANQQKQDDGRGLVLPGYKYLGPFNGLD
42_4              MAADGYLPDWLEDNLSEGIREWWDLKPGAPKPKANQQKQDDGRGLVLPGYKYLGPFNGLD
42_5A             MAADGYLPDWLEDNLSEGIREWWDLKPGAPKPKANQQKQDDGRGLVLPGYKYLGPFNGLD
42_1B             MAADGYLPDWLEDNLSEGIREWWDLRPGAPKPKANQQKQDDGRGLVLPGYKYLGPFNGLD
42_5B             MAADGYLPDWLEDNLSEGIREWWDLKPGAPKPKANQQKQDDGRGLVLPGYKYLGPFNGLD
43_1              MAADGYLPDWLEDNLSEGIREWWDLKPGAPKPKANQQKQDDGRGLVLPGYKYLGPFNGLD
43_12             MAADGYLPDWLEDNLSEGIREWWDLKPGAPKPKANQQKQDDGRGLVLPGYKYLGPFNGLD
43_5              MAADGYLPDWLEDNLSEGIREWWDLKPGAPKPKANQQKQDDGRGLVLPGYKYLGPFNGLD
AAV8              MAADGYLPDWLEDNLSEGIREWWALKPGAPKPKANQQKQDDGRGLVLPGYKYLGPFNGLD
43_21             MAADGYLPDWLEDNLSEGIREWWDLKPGAPKPKANQQKQDDGRGLVLPGYKYLGPFNGLD
43_25             MAADGYLPDWLEDNLSEGIREWWDLKPGAPKPKANQQKQDDGRGLVLPGYKYLGPFNGLD
43_23             MAADGYLPDWLEDNLSEGIREWWDLKPGAPKPKANQQKQDDGRGLVLPGYKYLGPFNGLD
43_20             MAADGYLPDWLEDNLSEGIREWWDLKPGAPKPKANQQKQDDGRGLVLPGYKYLGPFNGLD
AAV_9             MAADGYLPDWLEDNLSEGIREWWDLKPGAPKPKANQQKQDDGRGLVLPGYKYLGPFNGLD
24.1              MAADGYLPDWLEDNLSEGIREWWDLKPGAPKPKANQQKQDDGRGLVLPGYKYLRPFNGLD
42.2REAL          MAADGYLPDWLEDNLSEGIREWWDLKPGAPKPKANQQKQDDGRGLVLPGYKYLGPFNGLD
7.2\VP1           MAADGYLPDWLEGNLSEGIREWWDLKPGAPKPKANQQKQDDGRGLVLPGYRYLGPFNGLD
27.3\VP1          MAADGYLPDWLEDNLSEGIREWWDLKPGAPKPKANQQKQDDGRGLVLPGYKYLGPFNGLD
16.3\VP1          MAADGYLPDWLEDNLSEGIREWWDLKPGAPKPKANQQKQDDGRGLVLPGYKYLGPFNGLD
42_10             MAADGYLPDWLEDNLSEGIREWWDLKPGAPKPKANQQKQDDGRGLVLPGYKYLGPFNGLD
42_3B             MAADGYLPDWLEDNLSEGIREWWDLKPGAPKPKANQQKQDDGRGLVLPGYKYLGPFNGLD
42_11             MAADGYLPDWLEDNLSEGIREWWDLKPGAPKPKANQQKQDDGRGLVLPGYKYLGPFNGLD
F1\VP1            MAADGYLPDWLEDNLSEGIREWWDLKPGAPKPKANQQKQDDGRGLVLPGYKYLGPFNGLD
F5\VP1@3          MAADGYLPDWLEDNLSEGIREWWDLKPGAPKPKANQQKQDDGRGLVLPGYKYLGPFNGLD
F3\VP1            MAADGYLPDWLEDNLSEGIREWWDLKPGAPKPKANQQKQDDGRGLVLPGYKYLGPFNGLD
42_6B             MAADGYLPDWLEDNLSEGIREWWDLKPGAPKPKANQQKQDDGRGLVLPGYKYLGPFNGLD
42_12             MAADGYLPDWLEDNLSEGIREWWDLKPGAPKPKANQQKQDDGRGLVLPGYKYLGPFNGLD
AAV5\CAP          MSFVDHPPDWLEE--VGEGLREFLGLEAGPPKPKPNQQHQDQARGLVLPGYNYLGPGNGLD
```

FIG. 2A

```
                        70        80        90       100       110       120
                   ....|....|....|....|....|....|....|....|....|....|....|....|
C1\VP1             KGEPVNAADAAALEHDKAYDQQLKAGDNPYLRYNHADAEFQERLQEDTSFGGNLGRAVFQ
C2\VP1             KGEPVNAADAAALEHDKAYDQQLKAGDNPYLRYNHADAEFQERLQEDTSFGGNLGRAVFQ
C5\VP1@2           KGEPVNAADAAALEHDKAYDQQLKAGDNPYLRYNHADAEFQERLQEDTSFGGNLGRAVFQ
AAV4\VP1           KGEPVNAADAAALEHDKAYDQQLKAGDNPYLKYNHADAEFQQRLQGDTSFGGNLGRAVFQ
AAV1               KGEPVNAADAAALEHDKAYDQQLKAGDNPYLRYNHADAEFQERLQEDTSFGGNLGRAVFQ
AAV6\VP1           KGEPVNAADAAALEHDKAYDQQLKAGDNPYLRYNHADAEFQERLQEDTSFGGNLGRAVFQ
A3_3               KGEPVNEADAAALEHDKAYDHQLKQGDNPYLKYNHADAEFQERLQEDTSFGGNLGRAVFQ
A3_7               KGEPVNEADAAALEHDKAYDHQLKQGDNPYLKYNHADAEFQERLQEDTSFGGNLGRAVFQ
A3_4               KGEPVNEADAAALEHDKAYDHQLKQGDNPYLKYNHADAEFQERLQEDTSFGGNLGRAVFQ
A3_5               KGEPVNEADAAALEHDKAYDHQLKQGDNPYLKYNHADAEFQERLQEDTSFGGNLGRAVFQ
AAV2               KGEPVNEADAAALEHDKAYDRQLDSGDNPYLKYNHADAEFQERLKEDTSFGGNLGRAVFQ
AAV3               KGEPVNEADAAALEHDKAYDQQLKAGDNPYLKYNHADAEFQERLQEDTSFGGNLGRAVFQ
13.3b\VP1          KGEPVNAADAAALEHDKAYDQQLNAGDNPYLRYNHADAEFQERLQEDTSFGGNLGRAVFQ
AAV7               KGEPVNAADAAALEHDKAYDQQLKAGDNPYLRYNHADAEFQERLQEDTSFGGNLGRAVFQ
223_4              ------------------KAYDQQLKAGDNPYLRYNHADAEFQERLQEDTSFGGNLGRAVFQ
223_5              ------------------KAYDQQLKAGDNPYLRYNHADAEFQERLQEDTSFGGNLGRAVFQ
223_10             ------------------KAYDQQLKAGDNPYLRYNHADAEFQERLQEDTSFGGNLGRAVFQ
223_2              ------------------KAYDQQLKAGDNPYLRYNHADAEFQECLQEDTSFGGNLGRAVFQ
223_7              ------------------KAYDQQLKAGDNPYLRYNHADAEFQERLQEDTSFGGNLGRAVFQ
223_6              ------------------KAYDQQLKAGDNPYLRYNHADAEFQERLQEDTSFGGNLGRAVFQ
44_1               KGEPVNAADAAALEHDKAYDQQLKAGDNPYLRYNHADAEFQERLQEDTSFGGNLGRAVFQ
44_5               KGEPVNAADAAALEHDKAYDQQLKAGDNPYLRYNHADAEFQERLQEDTSFGGNLGRAVFQ
44_2               KGEPVNAADAAALEHDKAYDQQLKAGDNPYLRYNHADAEFQERLQEDTSFGGNLGRAVFQ
29.3\VP1           KGEPVNAADAAALEHDKAYDQQLKAGDNPYLRYNHADAEFQERLQEDTSFGGNLGRAVFQ
29.5\VP1           KGEPVNAADAAALEHDKAYDQQLKAGDNPYLRYNHADAEFQERLQEDTSFGGNLGRAVFQ
42_15              KGEPVNAADAAALEHDKAYDQQLKAGDNPYLRYNHADAEFQERLQEDTSFGGNLGRAVFQ
42_8               KGEPVNAADAAALEHDKAYDQQLKAGDNPYLRYNHADAEFQERLQEDTSFGGNLGRAVFQ
42_13              KGEPVNAADAAALEHDKAYDQQLKAGDNPYLRYNHADAEFQERLQEDTSFGGNLGRAVFQ
42_3A              KGEPVNAADAAALEHDKAYDQQLKAGDNPYLRYNHADAEFQERLQEDTSFGGNLGRAVFQ
42_4               KGEPVNEADAAALEHDKAYDKQLEQGDNPYLKYNHADAEFQERLQEDTSFGGNLGRAVFQ
42_5A              KGEPVNEADAAALEHDKAYDKQLEQGDNPYLKYNHADAEFQERLQEDTSFGGNLGRAVFR
42_1B              KGEPVNEADAAALEHDKAYDKQLEQGDNPYLKYNHADAEFQERLQEDTSFGGNLGRAVFQ
42_5B              KGEPVNEADAAALEHDKAYDKQLEQGDNPYLKYNHADAEFQERLQEDTSFGGNLGRAVFQ
43_1               KGEPVNAADAAALEHDKAYDQQLKAGDNPYLRYNHADAEFQERLQEDTSFGGNLGRAVFQ
43_12              KGEPVNAADAAALEHDKAYDQQLKAGDNPYLRYNHADAEFQERLQEDTSFGGNLGRAVFQ
43_5               KGEPVNAADAAALEHDKAYDQQLKAGDNPYLRYNHADAEFQERLQEDTSFGGNLGRAVFQ
AAV8               KGEPVNAADAAALEHDKAYDQQLQAGDNPYLRYNHADAEFQERLQEDTSFGGNLGRAVFQ
43_21              KGEPVNAADAAALEHDKAYDQQLKAGDNPYLRYNHADAEFQERLQEDTSFGGNLGRAVFQ
43_25              KGEPVNAADAAALEHDKAYDQQLKAGDNPYLRYNHADAEFQERLQEDTSFGGNLGRAVFQ
43_23              KGEPVNAADAAALEHDKAYDQQLKAGDNPYLRYNHADAEFQERLQEDTSFGGNLGRAVFQ
43_20              KGEPVNAADAAALEHDKAYDQQLKAGDNPYLRYNHADAEFQERLQEDTSFGGNLGRAVFQ
AAV_9              KGEPVNAADAAALEHDKAYDQQLKAGDNPYLRYNHADAEFQERLQEDTSFGGNLGRAVFQ
24.1               KGEPVNEADAAALEHDKAYDKQLEQGDNPYLKYNHADAEFQERLQEDTSFGGNLGRAVFQ
42.2REAL           KGEPVNEADAAALEHDKAYDKQLEQGDNPYLKYNHADAEFQERLQEDTSFGGNLGRAVFQ
7.2\VP1            KGEPVNEADAAALEHDKAYDKQLEQGDNPYLKYNHADAEFQERLQEDTSFGGNLGRAVFQ
27.3\VP1           KGEPVNEADAAALEHDKAYDKQLEQGDNPYLKYNHADAEFQERLQEDTSFGGNLGRAVFQ
16.3\VP1           KGEPVNEADAAALEHDKAYDKQLEQGDNPYLKYNHADAEFQERLQEDTSFGGNLGRAVFQ
42_10              KGEPVNEADAAALEHDKAYDKQLEQGDNPYLKYNHADAEFQERLQEDTSFGGNLGRAVFQ
42_3B              KGEPVNEADAAALEHDKAYDKQLEQGDNPYLKYNHADAEFQERLQEDTSFGGNLGRAVFQ
42_11              KGEPVNAADAAALEHDKAYDQQLKAGDNPYLRYNHADAEFQERLQEDTSFGGNLGRAVFQ
F1\VP1             KGEPVNAADAAALEHDKAYDQQLKAGDNPYLRYNHADAEFQERLQEDTSFGGNLGRAVFQ
F5\VP1@3           KGEPVNAADAAALEHDKAYDQQLKAGDNPYLRYNHADAEFQERLQEDTSFGGNLGRAVFQ
F3\VP1             KGEPVNAADAAALEHDKAYDQQLKAGDNPYLRYNHADAEFQERLQEDTSFGGNLGRAVFQ
42_6B              KGEPVNEADAAALEHDKAYDKQLEQGDNPYLKYNHADAEFQERLQEDTSFGGNLGRAVFQ
42_12              KGEPVNEADAAALEHDKAYDKQLEQGDNPYLKYNHADAEFQERLQEDTSFGGNLGRAVFQ
AAV5\CAP           RGEPVNRADEVAREHDISYNEQLEAGDNPYLKYNHADAEFQEKLADDTSFGGNLGKAVFQ
```

FIG. 2B

```
                   130       140       150       160       170       180
            ....|....|....|....|....|....|....|....|....|....|....|....|
C1\VP1      AKKRVLEPLGLVEEGAKTAPGKKRP-LESPQ-EPDSSSGIGKKGKQPAKKRLNFEEDTGA
C2\VP1      AKKRVLEPLGLVEEGAKTAPGKKRP-LESPQ-EPDSSSGIGKKGKQPAKKRLNFEEDTGA
C5\VP1@2    AKKRVLEPLGLVEEGAKTAPGKKRP-LESPQ-EPDSSSGIGKKGKQPAKKRLNFEEDTGA
AAV4\VP1    AKKRVLEPLGLVEQAGETAPGKKRPLIESPQ-QPDSSTGIGKKGKQPAKKKLVFEDETGA
AAV1        AKKRVLEPLGLVEEGAKTAPGKKRPVEQSPQ-EPDSSSGIGKTGQQPAKKRLNFGQTGDS
AAV6\VP1    AKKRVLEPFGLVEEGAKTAPGKKRPVEQSPQ-EPDSSSGIGKTGQQPAKKRLNFGQTGDS
A3_3        AKKRVLEPLGLVEEAVKTAPGKKRPIEQSPA-EPDSSSGIGKSGQQPAKKRLNFGQTGDT
A3_7        AKKRVLEPLGLVEEAVKTAPGKKRPIEQSPA-EPDSSSGIGKSGQQPAKKRLNFGQTGDT
A3_4        AKKRVLEPLGLVEEAVKTAPGKKRPIEQSPA-EPDSSSGIGESGQQPAKKRLNFGQTGDT
A3_5        AKKRVLEPLGLVEEAVKTAPGKKRPIEQSPA-EPDSSSGIGKSGQQPAKKRLNFGQTGDT
AAV2        AKKRVLEPLGLVEEPVKTAPGKKRPVEHSPV-EPDSSSGTGKAGCQPARKRLNFGQTGDA
AAV3        AKKRILEPLGLVEEAAKTAPGKKGAVDQSPQ-EPDSSSGVGKSGKQPARKRLNFGQTGDS
13.3b\VP1   AKKRVLEPLGLVEEGAKTAPAKKRPVEPSPQRSPDSSTGIGKKGQQPARKRLNFGQTGDS
AAV7        AKKRVLEPLGLVEEGAKTAPAKKRPVEPSPQRSPDSSTGIGKKGQQPARKRLNFGQTGDS
223_4       AKKRVLEPLGLVETPAKTAPGKKRPVD-----SPDSTSGIGKKGQQPAKKRLNFGQTGDS
223_5       AKKRVLEPLGLVETPAKTAPGKKRPVD-----SPDSTSGIGKKGQQPAKKRLNFGQTGDS
223_10      AKKRVLEPLGLVETPAKTAPGKKRPVD-----SPDSTSGIGKKGQQPAKKRLNFGQTGDS
223_2       AKKRVLEPLGLVETPAKTAPGKKRPVD-----SPDSTSGIGKKGQQPAKKRLNFGQTGDS
223_7       AKKRVLEPLGLVETPAKTAPGKKRPVD-----SPDSTSGIGKKGQQPAKKRLNFGQTGDS
223_6       AKKRVLEPLGLVETPAKTAPGKKRPVD-----SPDSTSGIGKKGQQPAKKRLNFGQTGDS
44_1        AKKRVLEPLGLVEEGAKTAPGKKRPVEPSPQRSPDSSTGIGKKGQQPAKKRLNFGQTGDS
44_5        AKKRVLEPLGLVEEGAKTAPGKKRPVEPSPQRSPDSSTGIGKKGQQPAKKRLNFGQTGDS
44_2        AKKRVLEPLGLVEEGAKTAPGKKRPVEPSPQRSPDSSTGIGKKGQQPAKKRLNFGQTGDS
29.3\VP1    AKKRVLEPLGLVEEGAKTAPGKKRPVEPSPQRSPDSTTGIGKKGQQPAKKRLNFGQTGDS
29.5\VP1    AKKRVLEPLGLVEEGAKTAPGKKRPVEPSPQRSPDSSTGIGKKGQQPAKKRLNFGQTGDS
42_15       AKKRVLEPLGLVEEGAKTAPGKKRPVEPSPQRSPDSSTGIGKTGQQPAKKRLNFGQTGDS
42_8        AKKRVLEPLGLVEEGAKTAPGKKRPVEPSPQRSPDSSTGIGKTGQQPAKKRLNFGQTGDS
42_13       AKKRVLEPLGLVEEGAKTAPGKKRPIE-----SPDSSTGIGKKGQQPAKKKLNFGQTGDS
42_3A       AKKRVLEPLGLVEEGAKTAPGKKRPIE-----SPDSSTGIGKKGQQPAKKKLNFGQTGDS
42_4        AKKRVLEPLGLVEEGAKTAPGKKRPIE-----SPDSSTGIGKKGQQPAKKKLNFGQTGDS
42_5A       AKKRVLEPLGLVEEGAKTAPGKKRPIE-----SPDSSTGIGKKGQQPAKKKLNFGQTGDS
42_1B       AKKRVLEPLGLVEEGAKTAPGKKRPIE-----SPDSSTGIGKKGQQPAKKKLNFGQTGDS
42_5B       AKKRVLEPLGLVEEGAKTAPGKKRPVEPSPQRSPDSSTGIGKTGQQPAKKRLNFGQTGDS
43_1        AKKRVLEPLGLVEEGAKTAPGKKRPVEPSPQRSPDSSTGIGKKGHQPARKRLNFGQTGDS
43_12       AKKRVLEPLGLVEEGAKTAPGKKRPVEPSPQRSPDSSTGIGKKGHQPARKRLNFGQTGDS
43_5        AKKRVLEPLGLVEEGAKTAPGKKRPVEPSPQRSPDSSTGIGKKGHQPARKRLNFGQTGDS
AAV8        AKKRVLEPLGLVEEGAKTAPGKKRPVEPSPQRSPDSSTGIGKKGQQPARKRLNFGQTGDS
43_21       AKKRVLEPLGLVEEGAKTAPGKKRPVEQSPQ-EPDSSSGIGKTGQQPAKKRLNFGQTGDS
43_25       AKKRVLEPLGLVEEGAKTAPGKKRPVEQSPQ-EPDSSSGIGKTGQQPAKKRLNFGQTGDS
43_23       AKKRVLEPLGLVEEGAKTAPGKKRPVEQSPQ-EPDSSSGIGKTGQQPAKKRLNFGQTGDS
43_20       AKKRVLEPLGLVEEGAKTAPGKKRLVEQSPQ-EPDSSSGIGKTGQQPAKKRLNFGQTGDS
AAV_9       AKKRVLEPLGLVEEGAKTAPGKKRPVEQSPQ-EPDSSSGIGKSGQQPAKKRLNFGQTGDS
24.1        AKKRVLEPLGLVEEVAKTAPGKKRPIE-----SPDSSTGIGKKGQQPAKKKLNFGQTGDS
42.2REAL    AKKRVLEPLGLVEEGAKTAPGKKRPIE-----SPDSSTGIGKKGQQPAKKKLNFGQTGDS
7.2\VP1     AKKRVLEPLGLVEEGAKTAPGKKRPIE-----SPDSSTGIGKNGQPPAKKKLNFGQTGDS
27.3\VP1    AKKRVLEPLGLVEEGAKTASGKKRPIE-----SPDSSTGIGKKGQQPAKKKLNFGQTGDS
16.3\VP1    AKKRVLEPLGLVEEGAKTAPGKKRPIE-----SPDSSTGIGKKGQQPAKKKLNFGQTGDS
42_10       AKKRVLEPLGLVEEGAKTAPGKKRPIE-----SPDSSTGIGRKGQQPAKKKLNFGQTGDS
42_3B       AKKRVLEPLGLVEEGAKTAPGKKRPIE-----SPDSSTGIGKKGQQPAKKKLNFGQTGDS
42_11       AKKRVLEPLGLVEEGAKTAPGKKRPIE-----SPDSSTGIGKKGQQPAKKKLNFGQTGDS
F1\VP1      AKKRVLEPLGLVEEGAKTAPGKKRPID-----SPDSSTGIGKKGQQPAKKKLNFGQTGDS
F5\VP1@3    AKKRVLEPLGLVEEGAKTAPGKKRPID-----SPDSSTGIGKKGQQPAKKKLNFGQTGDS
F3\VP1      AKKRVLEPLGLVEEGAKTAPGKKRPIG-----SPDSSTGIGKKGQQPAKKKLNFGQTGDS
42_6B       AKKRVLEPLGLVEEGAKTAPGKKRPVEPSPQRSPDSSTGIGKTGQQPAKKRLNFGQTGDS
42_12       AKKRVLEPLGLVEEGAKTAPGKKRPVEPSPQRSPDSSTGIGKTGQQPAKKRLNFGQTGDS
AAV5\CAP    AKKRVLEPFGLVEEGAKTAPTGKR----------IDDHFPKRKKARTEEDSKP---STSSDA
```

FIG. 2C

```
                          190       200       210       220       230       240
                   ....|....|....|....|....|....|....|....|....  ....|....|....|
   C1\VP1          GDGP----PEGSDTSAMS--SDIEMRAAPGGNAVDAGQGSDGVGNASGDWHCDSTWSEGK
   C2\VP1          GDGP----PEGSDTSAMS--SDIEMRAAPGGNAVDAGQGSDGVGNASGDWHCDSTWSEGK
   C5\VP1@2        GDGP----PEGSDTSAMS--SDIEMRAAPGGNAVDAGQGSDGVGNASGDWHCDSTWSEGK
   AAV4\VP1        GDGP-----PEGSTSGAMS--DDSEMRAAAGGAAVEGGQGADGVGNASGDWHCDSTWSEGH
   AAV1            ESVPD-PQPLGEPPATPAAVGPTTMASGGGAPMADNNEGADGVGNASGNWHCDSTWLGDR
   AAV6\VP1        ESVPD-PQPLGEPPATPAAVGPTTMASGGGAPMADNNEGADGVGNASGNWHCDSTWLGDR
   A3_3            ESVPG-PQPIGEPPAAPSGVGSNTMASGGGAPMADNNEGADGVGNSSGNWHCDSTWMGDR
   A3_7            ESVPD-PQPIGEPPAAPSGVGSNTMASGGGAPMADNNEGADGVGNSSGNWHCDSTWMGDR
   A3_4            ESVPD-PQPIGEPPAAPSGVGSNTMASGGGAPMADDNEGADGVGNSSGNWHCDSTWMGDR
   A3_5            ESVPD-PQPIGEPPAAPSGVGSNTMASGGGAPMADNNEGADGVGNSSGNWHCDSTWMGDR
   AAV2            DSVPD-PQPLGQPPAAPSGLGTNTMATGSGAPMADNNEGADGVGNSSGNWHCDSTWMGDR
   AAV3            ESVPD-PQPLGEPPAAPTSLGSNTMASGGGAPMADNNEGADGVGNSSGNWHCDSQWLGDR
   13.3b\VP1       ESVPD-PQPLGEPPAAPSSVGSGTVAAGGGAPMADNNEGADGVGNASGNWHCDSTWLGDR
   AAV7            ESVPD-PQPLGEPPAAPSSVGSGTVAAGGGAPMADNNEGADGVGNASGNWHCDSTWLGDR
   223_4           EPVPD-PQPIGEPPAGPSGLGSGTMAAGGGAPMADNNEGADGVGNASGNWHCDSTRLGDR
   223_5           EPVPD-PQPIGEPPAGPSGLGSGTMAAGGGAPMADNNEGADGVGNASGNWHCDSTRLGDR
   223_10          ESVPD-PQPIGEPPAGPSGLGSGTMAAGGGAPMADNNEGADGVGNASGNWHCDSTWLGDR
   223_2           ESVPD-PQPIGEPPAGPSGLGSGTMVAGGGAPMADNNEGADGVGNASGNWHCDSTWLGDR
   223_7           ESVPD-PQPIGEPPAGPSGLGSGTMAAGGGAPMADNNEGADGVGNASGNWHCDSTWLGDR
   223_6           ESVPD-PQPIGEPPAGPSGLGSGTMAAGGGAPMADNSEGADGVGNASGNWHCDSTWLGDR
   44_1            ESVPD-PQPIGEPPAGPSGLGSGTMAAGGGAPMADNNEGADGVGSSSGNWHCDSTWLGDR
   44_5            ESVPD-PQPIGEPPAGPSGLGSGTMAAGGGAPMADNNEGADGVGSSSGNWHCDSTWLGDR
   44_2            ESVPD-PQPIGEPPAGPSGLGSGTMAAGGGAPMADNNEGADGVGSSSGNWHCDSTWLGDR
   29.3\VP1        ESVPD-PQPIGEPPAGPSGLGSGTMAAGGGAPMADNNEGADGVGSSSGNWHCDSTWLGDR
   29.5\VP1        ESVPD-PQPIGEPPAGPSGLGSGTMAAGGGAPMADNNEGADGVGSSSGNWHCDSTWLGDG
   42_15           ESVPD-PQPIGEPPAGPSGLGSGTMAAGGGAPMADNNEGADGVGSSSGNWHCDSTWLGDR
   42_8            ESVPD-PQPIGEPPAGPSGLGSGTMAAGGGAPMADNNEGADGVGSSSGNWHCDSTWLGDR
   42_13           ESVPD-PQPIGEPPAGPSGLGSGTMAAGGGAPMADNNEGADGVGSSSGNWHCDSTWLGDR
   42_3A           ESVPD-PQPIGEPPAGPSGLGSGTMAAGGGAPMADNNEGADGVGSSSGNWHCDSTWLGDR
   42_4            ESVPD-PQPIGEPPAGPSGLGSGTMAAGGGAPMADNNEGADGVGNASGNWHCDSTWLGDR
   42_5A           ESVPD-PQPLGEPPAAPSGLGSGTMAAGGGAPMADNNEGADGVGSSSGNWHCDSTWLGDR
   42_1B           ESVPD-PQPIGEPPAGPSGLGSGTMAAGGGAPMADNNEGADGVGSSSGNWHCDSTWLGDR
   42_5B           ESVPD-PQPIGEPPAGPSGLGSGTMAAGGGAPMADNNEGADGVGSSSGNWHCDSTWLGDR
   43_1            ESVPD-PQPIGEPPAGPSGLGSGTMAAGGGAPMADNNEGADGVGSSSGNWHCDSTWLGDR
   43_12           ESVPD-PQPIGEPPAGPSGLGSGTMAAGGGAPMADNNEGADGVGSSSGNWHCDSTWLGDR
   43_5            ESVPD-PQPIGEPPAGPSGLGSGTMAAGGGAPMADNNEGADGVGSSSGNWHCDSTWLGDR
   AAV8            ESVPD-PQPLGEPPAAPSGVGPNTMAAGGGAPMADNNEGADGVGSSSGNWHCDSTWLGDR
   43_21           ESVPD-PQPLGEPPAAPSGLGPNTMASGGGAPMADNNEGADGVGNSSGNWHCDSTWLGDR
   43_25           ESVPD-PQPLGEPPAAPSGLGPNTMASGGGAPMADNNEGADGVGNSSGNWHCDSTWLGDR
   43_23           ESVPD-PQPLGEPPAAPSGLGPNTMASGGGAPMADNNEGADGVGNSSGNWHCDSTWLGDR
   43_20           ESVPD-PQPLGEPPAAPSGLGPNTMASGGGAPMADNNEGADGVGNSSGNWHCDSTWLGDR
   AAV_9           ESVPD-PQPLGEPPEAPSGLGPNTMASGGGAPMADNNEGADGVGNSSGNWHCDSTWLGDR
   24.1            ESVPD-PQPLGEPPAAPSGLGSGTMAAGGGAPMADNNEGADGVGNASGNWHCDSTWLGDR
   42.2REAL        ESVPD-PQPLGEPPAAPSGLGSGTMAAGGGAPMADNNEGADGVGNASGNWHCDSTWLGDR
   7.2\VP1         ESVPD-PQPLGEPPAAPSGLGSGTMAAGGGAPMADNNEGADGVGNASGNWHCDSTWLGDR
   27.3\VP1        ESVPD-PQPLGEPPAAPSGLGSGTMAAGGGAPMADNNEGADGVGNASGNWHCDSTWLGDR
   16.3\VP1        ESVPD-PQPLGEPPAAPSGLGSGTMAAGGGAPMADNNEGADGVGNASGNWHCDSTWLGDR
   42_10           ESVPD-PQPIGEPPAGPSGLGSGTMAAGGGAPMADNNEGADGVGNASGNWHCDSTWLGDR
   42_3B           ESVPD-PQPIGEPPAGPSGLGSGTMAAGGGAPMADNNEGADGVGSSSGNWHCDSTWLGDR
   42_11           ESVPD-PQPIGEPPAGPSGLGSGTMAAGGGAPMADNNEGADGVGSSSGNWHCDSTWLGDR
   F1\VP1          ESVPD-PQPLGEPPAAPSSVGSGTMAAGGGAPMADNNEGADGVGNASGNWHCDSTWLGDR
   F5\VP1@3        ESVPD-PQPLGEPPAAPSSVGSGTMAAGGGAPTADNNEGADGVGNASGNWHCDSTWLGDR
   F3\VP1          ESVPD-PQPLGEPPAAPSSVGSGTMAAGGGAPMADNNEGADGVGNASGNWHCDSTWLGDR
   42_6B           ESVPD-PQPIGEPPAGPSGLGSGTMAAGGGAPMADNNEGADGVGSSSGNWHCDSTWLGDR
   42_12           ESVPD-PQPIGEPPAGPSGLGSGTMAAGGGAPMADNNEGADGVGSSSGNWHCDSTWLGDR
   AAV5\CAP        EAGPSGSQQLQIPAQPASSLGADTMSAGGGGPLGDNNQGADGVGNASGDWHCDSTWMGDR
```

FIG. 2D

```
                   250        260        270        280        290        300
              ....|....|....|....|....|....|....|....|....|....|....|....|
C1\VP1        VTTTSTRTWVLPTYNNHLYLRLG-----TTSNSNTYNGFSTPWGYFDFNRFHCHFSPRDW
C2\VP1        VTTTSTRTWVLPTYNNHLYLRLG-----TTSNSNTYNGFSTPWGYFDFNRFHCHFSPRDW
C5\VP1@2      VTTTSTRTWVLPTYNNHLYLRLG-----TTSNSNTYNGFSTPWGYFDFNRFHCHFSPRDW
AAV4\VP1      VTTTSTRTWVLPTYNNHLYKRLG-----ESLQSNTYNGFSTPWGYFDFNRFHCHFSPRDW
AAV1          VITTSTRTWALPTYNNHLYKQIS-SASTGASNDNHYFGYSTPWGYFDFNRFHCHFSPRDW
AAV6\VP1      VITTSTRTWALPTYNNHLYKQIS-SASTGASNDNHYFGYSTPWGYFDFNRFHCHFSPRDW
A3_3          VITTSTRTWALPTYNNHLYKQIS--SESGATNDNHYFGYSTPWGYFDFNRFHCHFSPRDW
A3_7          VITTSTRTWALPTYNNRLYKQIS--SESGATNDNHYFGYSTPWGYFDFNRFHCHFSPRDW
A3_4          VITTSTRTWALPTYNNHLYKQIS--SESGATNDNHYFGYSTPWGYFDFNRFHCHFSPRDW
A3_5          VITTSTRTWALPTYNNHLYKQIS--SESGATNDNHYFGYSTPWGYFDFNRFHCHFSPRDW
AAV2          VITTSTRTWALPTYNNHLYKQIS--SQSGASNDNHYFGYSTPWGYFDFNRFHCHFSPRDW
AAV3          VITTSTRTWALPTYNNHLYKQIS--SQSGASNDNHYFGYSTPWGYFDFNRFHCHFSPRDW
13.3b\VP1     VITTSTRTWALPTYNNHLYEQIS-SETAGSTNDNTYFGYSTPWGYFDFNRFHCHFSPRDW
AAV7          VITTSTRTWALPTYNNHLYKQIS-SETAGSTNDNTYFGYSTPWGYFDFNRFHCHFSPRDW
223_4         VITTSTRTWALPTYNNHLYKQIS-SQSAGSTNDNVYFGYSTPWGYFDFNRFHCHFSPRDW
223_5         VITTSTRTWALPTYNNHLYKQIS-SQSAGSTNDNVYFGYSTPWGYFDFNRFHCHFSPRDW
223_10        VITTSTRTWALPTYNNHLYKQIS-SQSAGSTNDNVYFGYSTPWGYFDFNRFHCHFSPRDW
223_2         VITTSTRTWALPTYNNHLYKQIS-SQSAGSTNDNVYFGYSTPWGYFDFNRFHCHFSPRDW
223_7         VITTSTRTWALPTYNNHLYKQIS-SQSAGSTNDNVYFGYSTPWGYFDFNRFHCHFSPRDW
223_6         VITTSTRTWALPTYNNHLYKQIS-SQSAGSTNDNVYFGYSTPWGYFDFNRFHCHFSPRDW
44_1          VITTSTRTWALPTYNNHLYKQISNGTSGGSTNDNTYFGYSTPWGYFDFNRFHCHFSPRDW
44_5          VITTSTRTWALPTYNNHLYKQISNGTSGGSTNDNTYFGYSTPWGYFDFNRFHCHFSPRDW
44_2          VITTSTRTWALPTYNNHLYKQISNGTSGGSTNDNTYFGYSTPWGYFDFNRFHCHFSPRDW
29.3\VP1      VITTSTRTWALPTYNNHLYKQISNGTSGGSTNDNTYFGYSTPWGYFDFNRFHCHFSPRDW
29.5\VP1      VITTSTRTWALPTYNNHLYKQISNGTSGGSTNDNTYFGYSTPWGYFDFNRFHCHFSPRDW
42_15         VITTSTRTWALPTYNNHLYKQISNGTSGGSTNDNTYFGYSTPWGYFDFNRFHCHFSPRDW
42_8          VITTSTRTWALPTYNNHLYKQISNGTSGGSTNDNTYFGYSTPWGYFDFNRFHCHFSPRDW
42_13         VITTSTRTWALPTYNNHLYKQISNGTSGGSTNDNTYFGYSTPWGYFDFNRFHCHFSPRDW
42_3A         VITTSTRTWALPTYNNHLYKQISNGTSGGSTNDNTYFGYSTPWGYFDFNRFHCHFSPRDW
42_4          VITTSTRTWALPTYNNHLYKQIS--SQSGATNDNHFFGYSTPWGYFDFNRFHCHFSSRDW
42_5A         VITTSTRTWALPTYNNHLYKQIS--SQSGATNDNHFFGYSTPWGYFDFNRFHCHFSPRDW
42_1B         VITTSTRTWALPTYNNHLYKQISNGTSGGSTNDNTYFGYSTPWGYFDFNRFHCHFSPRDW
42_5B         VITTSTRTWALPTYNNHLYKQISNGTSGGSTNDNTYFGYSTPWGYFDFNRFHCHFSPRDW
43_1          VITTSTRTWALPTYNNHLYKQISNGTSGGSTNDNTYFGYSTPWGYFDFNRFHCHFSPRDW
43_12         VITTSTRTWALPTYNNHLYKQISNGTSGGSTNDNTYFGYSTPWGYFDFNRFHCHFSPRDW
43_5          VITTSTRTWALPTYNNHLYKQISNGTSGGSTNDNTYFGYSTPWGYFDFNRFHCHFSPRDW
AAV8          VITTSTRTWALPTYNNHLYKQISNGTSGGATNDNTYFGYSTPWGYFDFNRFHCHFSPRDW
43_21         VITTSTRTWALPTYNNHLYKQISNGTSGGSTNDNTYFGYSTPWGYFDFNRFHCHFSPRDW
43_25         VITTSTRTWALPTYNNHLYKQISNGTSGGSTNDNTYFGYSTPWGYFDFNRFHCHFSPRDW
43_23         VITTSTRTWALPTYNNHLYKQISNGTSGGSTNDNTYFGYSTPWGYFDFNRFHCHFSPRDW
43_20         VITTSTRTWALPTYNNHLYKQISNGTSGGSTNDNTYFGYSTPWGYFDFNRFHCHFSPRDW
AAV_9         VITTSTRTWALPTYNNHLYKQISNGTSGGSTNDNTYFGYSTPWGYFDFNRFHCHFSPRDW
24.1          VITTSTRTWALPTYNNHLYKQIS-SQS-GATNDNHFFSYSTPWGYFDFNRFHCHFSPRDW
42.2REAL      VITTSTRTWALPTYNNHLYKQIS-SQS-GATNDNHFFGYSTPWGYFDFNRFHCHFSPRDW
7.2\VP1       VITTSTRTWALPTYNNHLYKQIS-SQS-GATNDNHFFGYSTPWGYFDFNRFHCHFSPRDW
27.3\VP1      VITTSTRTWALPTYNNHLYKQIS-SQS-GATNDNHFFGYSTPWGYFDFNRFHCHFSPRDW
16.3\VP1      VITTSTRTWALPTYNNHLYKQIS-SQS-GATNDNHFFGYSTPWGYFDFNRFHCHFSPRDW
42_10         VITTSTRTWALPTYNNHLYKQIS-SQS-GATNDNHFFGYSTPWGYFDFNRFHCHFSPRDW
42_3B         VITTSTRTWALPTYNNHLYKQIS-SQS-GATNDNHFFGYSTPWGYFDFNRFHCHFSPRDW
42_11         VITTSTRTWALPTYNNHLYKQIS-SQS-GATNDNHFFGYSTPWGYFDFNRFHCHFSPRDW
F1\VP1        VITTSTRTWALPTYNNHLYKQIS-SSSGATNDNHYFGYSTPWGYFDFNRFHCHFSPRDW
F5\VP1@3      VITTSTRTWALPTYNNHLYKQIS-SSSGATNDNHYFGYSTPWGYFDFNRFHCHFSPRDW
F3\VP1        VITTSTRTWALPTYNNHLYKQIS-SSSGATNDNHYFGYSTPWGYFDFNRFHCHFSPRDW
42_6B         VITTSTRTWALPTYNNHLYKQISNGTSGGSTNDNTYFGYSTPWGYFDFNRFHCHFSPRDW
42_12         VITTSTRTWALPTYNNHLYKQISNGTSGGSTNDNTYFGYSTPWGYFDFNRFHCHFSPRDW
AAV5\CAP      VVTKSTRTWVLPSYNNHQYREIK-SGSVDGSNANAYFGYSTPWGYFDFNRFHSHWSPRDW
```

FIG. 2E

```
                    310        320        330        340        350        360
              ....|....|....|....|....|....|....|....|....|....|....|....|
C1\VP1        QRLINNNWGLRPKAMRVKIFNIQVKEVTTSNGETTVANNLTSTVQIFADSSYELPYVMDA
C2\VP1        QRLINNNWGLRPKAMRVKIFNIQVKEVTTSNGETTVANNLTSTVQIFADSSYELPYVMDA
C5\VP1@2      QRLINNNWGLRPKAMRVKIFNIQVKEVTTSNGETTVANNLTSTVQIFADSSYELPYVMDA
AAV4\VP1      QRLINNNWGMRPKAMRVKIFNIQVKEVTTSNGETTVANNLTSTVQIFADSSYELPYVMDA
AAV1          QRLINNNWGFRPKRLNFKLFNIQVKEVTTNDGVTTIANNLTSTVQVFSDSEYQLPYVLGS
AAV6\VP1      QRLINNNWGFRPKRLNFKLFNIQVKEVTTNDGVTTIANNLTSTVQVFSDSEYQLPYVLGS
A3_3          QRLINNNWGFRPKKLNFKLFNIQVKEVTQNDGTTTIANNLTSAVQVFTDSEYQLPYVLGS
A3_7          QRLINNNWGFRPKKLNFKLFNIQVKEVTQNDGTTTIANNLTSTVQVFTDSEYQLPYVLGS
A3_4          QRLINNNWGFRPKKLNFKLFNIQVKEVTQNDGTTTIANNLTSTVQVFTDSEYQLPYVLGS
A3_5          QRLINNNWGFRPKKLNFKLFNIQVKEVTQNDGTTTIANNLTSTVQVFTDSEYQLPYVLGS
AAV2          QRLINNNWGFRPKRLNFKLFNIQVKEVTQNDGTTTIANNLTSTVQVFTDSEYQLPYVLGS
AAV3          QRLINNNWGFRPKKLSFKLFNIQVRGVTQNDGTTTIANNLTSTVQVFTDSEYQLPYVLGS
13.3b\VP1     QRLINNNWGFRPKKLRFKLFNIQVKEVTTNDGVTTIANNLTSTIQVFSDSEYQLPYVLGS
AAV7          QRLINNNWGFRPKKLRFKLFNIQVKEVTTNDGVTTIANNLTSTIQVFSDSEYQLPYVLGS
223_4         QRLINNNWGFRPKKLNFKLFNIQVKEVTTNDGVTTIANNLTSTVQVFSDSEYQLPYVLGS
223_5         QRLINNNWGFRPKKLNFKLFNIQVKEVTTNDGVTTIANNLTSTVQVFSDSEYQLPYVLGS
223_10        QRLINNNWGFRPKKLNFKLFNIQVKEVTTNDGVTTIANNLTSTVQVFSDSEYQLPYVLGS
223_2         QRLINNNWGFRPKKLNFKLFNIQVKEVTTNDGVTTIANNLTSTVQVFSDSEYQLPYVLGS
223_7         QRLINNNWGFRPKKLNFKLFNIQVKEVTTNDGVTTIANNLTSTVQVFSDPEYQLPYVLGS
223_6         QRLINNNWGFRPKKLNFKLFNIQVKEVTTNDGVTTIANNLTSTVQVFSDSEYQLPYVLGS
44_1          QRLINNNWGFRPKRLNFKLFNIQVKEVTQNEGTKTIANNLTSTIQVFTDSEYQLPYVLGS
44_5          QRLINNNWGFRPKRPNFKLFNIQVKEVTQNEGTKTIANNLTSTIQVFTDSEYQLPYVLGS
44_2          QRLINNNWGFRPKRLNFKLFNIQVKEVTQNEGTKTIANNLTSTIQVFTDSEYQLPYVLGS
29.3\VP1      QRLINNNWGFRPKRLNFKLFNIQVKEVTQNEGTKTIANNLTSTIQVFTDSEYQLPYVLGS
29.5\VP1      QRLINNNWGFRPKSLNFKLFNIQVKEVTQNEGTKTIANNLTSTIQVFTDSEYQLPYVLGS
42_15         QRLINNNWGFRPKRLNFKLFNIQVKEVTQNEGTKTIANNLTSTIQVFTDSEYQLPYVLGS
42_8          QRLINNNWGFRPKRLNFKLFNIQVKEVTQNEGTKTIANNLTSTIQVFTDSEYQLPYVLGS
42_13         QRLINNNWGFRPKRLNFKLFNIQVKEVTQNEGTKTIANNLTSTIQVFTDSEYQLPYVLGS
42_3A         QRLINNSWGFRPKRLNFKLFNIQVKEVTQNEGTKTIANNLTSTIQVFTDSEYQLPYVLGS
42_4          QRLINNNWGFRPKRLNFKLFNIQVKEVTQNEGTKTIANNLTSTIQVFTDSEYRLPYVLGS
42_5A         QRLINNNRGFRPRKLRFKLFNIQVKEVTTNDGVTTIANNLTSTIQVFSDSEYQLPYVLGS
42_1B         QRLINNNWGFRPKRLNFKLFNIQVKEVTQNEGTKTIANNLTSTIQVFTDSEYQLPYVLGS
42_5B         QRLINNNWGFRPKRLNFKLFNIQVKEVTQNEGTKTIANNLTSTIQVFTDSEYQLPYVLGS
43_1          QRLINNNWGFRPKRLNFKLFNIQVKEVTQNEGTKTIANNLTSTIQVFTDSEYQLPYVPGS
43_12         QRLINNNWGFRPKRLNFKLFNIQVKEVTQNEGTKTIANNLTSTIQVFTDSEYQLPYVLGS
43_5          QRLINNNWGFRPKRLNFKLFNIQVKEVTQNEGTKTIANNLTSTIQVFTDSEYQLPYVLGS
AAV8          QRLINNNWGFRPKRLSFKLFNIQVKEVTQNEGTKTIANNLTSTIQVFTDSEYQLPYVLGS
43_21         QRLINNNWGFRPKRLNFKLFNIQVKEVTTNEGTKTIANNLTSTVRVFTDSEYQLPYVLGS
43_25         QRLINNNWGFRPKRLNFKLFNIQVKEVTTNEGTKTIANNLTSTVQVFTDSEYQLPYVLGS
43_23         QRLINNNWGFRPKRLNFKLFNIQVKEVTTNEGTKTIANNLTSTVQVFTDLEYQLPYVLGS
43_20         QRLINNNWGFRPKRLNFKLFNIQVKEVTTNEGTKTIANNLTSTVQVFTDSEYQLPYVLGS
AAV_9         QRLINNNWGFRPKRLNFKLFNIQVKEVTTNEGTKTIANNLTSTVQVFTDSEYQLPYVLGS
24.1          QRLINNNWGFRPRKLRFKLFNIQVKEVTTNDGVTTIANNLTSTIQVFSDSEYQLPYVLGS
42.2REAL      QRLINNNWGFRPRKLRFKLFNIQVKEVTTNDGVTTIANNLTSTIQVFSDSEYQLPYVLGS
7.2\VP1       QRLINNNWGFRPKKLRFKLFNIQVKEVTTNDGVTTIANNLTSTIQVFSDSEYQLPYVLGS
27.3\VP1      QRLINNNWGFRPRKLRFKLFNIQVKEVTTNDGVTTIANNLTSTIQVFSDSEYQLPYVLGS
16.3\VP1      QRLINNNWGFRPKKLRFKLFNIQVKEVTTNDGVTTIANNLTSTIQVFSDSEYQLPYVLGS
42_10         QRLINNNWGFRPKKLRFKLFNIQVKEVTTNDGVTTIANNLTSTIQVFSDSEYQLPYVLGS
42_3B         QRLINNNWGFRPKKLRFKLFNIQVKEVTTNDGVTTIANNLTSTIQVFSDSEYQLPYVLGS
42_11         QRLINNNWGFRPRKLRFKLFNIQVKEVTTNDGVTTIANNLTSTIQVFSDSEYQLPYVLGS
F1\VP1        QRLINNNWGFRPKKLRFKLFNIQVKEVTTNDGVTTIANNLTSTVQVFSDSEYQLPYVLGS
F5\VP1@3      QRLINNNWGFRPKKLRFKLFNIQVKEVTTNDGVTTIANNLTSTVQVFSDSEYQLPYVLGS
F3\VP1        QRLINNNWGFRPKKLRFKLLNIQVKEVTTNDGVTTIANNLTSTVQVFSDSEYQLPYVLGS
42_6B         QRLINNNWGFRPRKLRFKLFNIQVKEVTTDDGVTTIANNLTSTIQVFSDSEYQLPYVLGS
42_12         QRLINNNWGFRPKRLNFKLFNIQVKEVTQNEGTKTIANNLTSTIQVFTDSEYQLPYVLGS
AAV5\CAP      QRLINNYWGFRPRSLRVKIFNIQVKEVTVQDSTTTIANNLTSTVQVFTDDDYQLPYVVGN
```

FIG. 2F

```
                         370        380        390        400        410        420
                    ....|....|....|....|....|....|....|....|....|....|....|....|
C1\VP1              GQEGSLSPFPNDVFMVPQYGYCGIVTG-ENQNQTDRNAFYCLEYFPSQMLRTGNNFEMAY
C2\VP1              GQEGSLPPFPNDVFMVPQYGYCGIVTG-ENQNQTDRNAFYCLEYFPSQMLRTGNNFEMAY
C5\VP1@2            GQEGSLPPFPNDVFMVPQYGYCGIVTG-ENQNQTDRNAFYCLEYFPSQMLRTGNNFETAY
AAV4\VP1            GQEGSLPPFPNDVFMVPQYGYCGLVTGNTSQQQTDRNAFYCLEYFPSQMLRTGNNFEITY
AAV1                AHQGCLPPFPADVFMIPQYGYLTLNNG---SQAVGRSSFYCLEYFPSQMLRTGNNFTFSY
AAV6\VP1            AHQGCLPPFPADVFMIPQYGYLTLNNG---SQAVGRSSFYCLEYFPSQMLRTGNNFTFSY
A3_3                AHQGCLPPFPADVFMIPQYGYLTLNNG---SQAVGRSSFYCLEYFPSQMLRTGNNFTFSY
A3_7                AHQGCLPPFPADVFMIPQYGYLTLNNG---SQAVGRSSFYCLEYFPSQMLRTGNNFTFSY
A3_4                AHQGCLPPFPADVFMIPQYGYLTLNNG---SQAVGRSSFYCLEYFPSQMLRTGNNFTFSY
A3_5                AHQGCLPPFPADVFMIPQYGYLTLNNG---SQAVGRSSFYCLEYFPSQMLRTGNNFTFSY
AAV2                AHQGCLPPFPADVFMVPQYGYLTLNNG---SQAVGRSSFYCLEYFPSQMLRTGNNFTFSY
AAV3                AHQGCLPPFPADVFMVPQYGYLTLNNG---SQAVGRSSFYCLEYFPSQMLRTGNNFQFSY
13.3b\VP1           AHQGCLPPFPADVFMIPQYGYLTLNNG---SQSVGRSSFYCLEYFPSQMLRTGNNFEFSY
AAV7                AHQGCLPPFPADVFMIPQYGYLTLNNG---SQSVGRSSFYCLEYFPSQMLRTGNNFEFSY
223_4               AHQGCLPPFPADVFMIPQYGYLTLNNG---SQSVGRSSFYCLEYFPSQMLRTGNNFTFSY
223_5               AHQGCLPPFPADVFMIPQYGYLTLNNG---SQSVGRSSFYCLEYFPSQMLRTGNNFTFSY
223_10              AHQGCLPPFPADVFMIPQYGYLTLNNG---SQSVGRSSFYCLEYFPSQMLRTGNNFTFSY
223_2               AHQGCLPPFPADVFMIPQYGYLTLNNG---SQSVGRSSFYCLEYFPSQMLRTGNNFTFSY
223_7               AHQGCLPPFPADVFMIPQYGYLTLNNG---SQSVGRSSFYCLEYFPSQMLRTGNNFTFSY
223_6               AHQGCLPPFPADVFMIPQYGYLTLNNG---SQSVGRSSFYCLEYFPSQMLRTGNNFTFSY
44_1                AHQGCLPPFPADVFMIPQYGYLTLNNG---SQAVGRSSFYCLEYFPSQMLRTGNNFEFSY
44_5                AHQGCLPPFPADVFMIPQYGYLTLNNG---SQAVGRSSFYCLEYFPSQMLRTGNNFEFSY
44_2                AHQGCLPPFPADVFMIPQYGYLTLNNG---SQAVGRSSFYCLEYFPSQMLRTGNNFEFSY
29.3\VP1            ARQGCLPPFPADVFMIPQYGYLTLNNG---SQAVGRSSFYCLEYFPSQMLRTGNNFEFSY
29.5\VP1            AHQGCLPPFPADVFMIPQYGYLTLNNG---SQAVGRSSFYCLEYFPSQMLRTGNNFEFSY
42_15               AHQGCPPPFPADVFMIPQYGYLTLNNG---SQAVGRSSFYCLEYFPSQMRRTGNNFEFSY
42_8                AHQGCLPPFPADVFMIPQYGYLTLNNG---SQAVGRSSFYCLEYFPSQMLRTGNNFEFSY
42_13               AHQGCLPPFPADVFMIPQYGYLTLNNG---SQAVGRSSFYCLEYFPSQMLRTGNNFEFSY
42_3A               AHQGCLPPFPADVFMIPQYGYLTLNNG---SQAVGRSSFYCLEYFPSQMLRTGNNFEFSY
42_4                AHQGCLPPFPADVFMIPQYGYLTLNNG---SQAVGRSSFYCLEYFPSQMLRTGNNFEFSY
42_5A               AHQGCLPPFPADVFMIPQYGYLTLNNG---SQSVGRSSFYCLEYFPSQMLRTGNNFEFSY
42_1B               AHQGCLPPFPADVFMIPQYGYLTLNNG---SQAVGRSSFYCLEYFPSQMLRTGNNFEFSY
42_5B               AHQGCLPPFPADVFMIPQYGYLTLNNG---SQAVGRSSFYCLEYFPSQMLRTGNNFEFSY
43_1                AHQGCLPPFPADVFMIPQYGYLTLNNG---SQAVGRSSFYCLEYFPSQMLRTGNNFEFSY
43_12               AHQGCLPPFPADVFMIPQYGYLTLNNG---SQAVGRSSFYCLEYFPSQMLRTGNNFEFSY
43_5                AHQGCLPPFPADVFMIPQYGYLTLNNG---SQAVGRSSFYCLEYFPSQMLRTGNNFEFSY
AAV8                AHQGCLPPFPADVFMIPQYGYLTLNNG---SQAVGRSSFYCLEYFPSQMLRTGNNFQFTY
43_21               AHQGCLPPFPADVFMVPQYGYLTLNNG---SQALGRSSFYCLEYFPSQMLRTGNNFQFSY
43_25               AHQGCLPPFPADVFMVPQYGYLTLNNG---SQALGRSSFYCLEYFPSQMLRTGNNFQFSY
43_23               AHQGCLPPFPADVFMVPQYGYLTLNNG---SQALGRSSFYCLEYFPSQMPRTGNNFQFSY
43_20               AHQGCLPPFPADVFTVPQYGYLTLNNG---SQALGRSSFYCLEYFPSQMLRTGNNFQFSY
AAV_9               AHQGCLPPFPADVFMVPQYGYLTLNNG---SQALGRSSFYCLEYFPSQMLRTGNNFQFSY
24.1                AHQGCLPPFPADVFMIPQYGYLTLNNG---SQSVGRSSFYCLEYFPSQMLRTGNNFEFSY
42.2REAL            AHQGCLPPFPADVFMIPQYGYLTLNNG---SQSVGRSSFYCLEYFPSQMLRTGNNFEFSY
7.2\VP1             AHQGCLPPFPADVFMIPQYGYLTLNNG---SQSVGRSSFYCLEYFPSQMLRTGDNFEFSY
27.3\VP1            AHQGCLPPFPADVFMIPQYGYLTLNNG---SQSVGRSSFCCLEYFPSQMLRTGNNFEFSY
16.3\VP1            AHQGCLPPFPADVFMIPQYGYLTLNNG---SQSMGRSSFYCLEYFPSQMLRTGNNFEFSY
42_10               AHQGCLPPFPADVFMIPQYGYLTLNNG---SQSVGRSSFYCLEYFPSQMLRTGNNFEFSY
42_3B               AHQGCLPPFPADVFMIPQYGYLTLNNG---SQSVGRSSFYCLEYFPSQMLRTGNNFEFSY
42_11               AHQGCLPPFPADVFMIPQYGYLTLNNG---SQSVGRSSFYCLEYFPSQMLRTGNNFEFSY
F1\VP1              AHQGCLPPFPADVFMIPQYGYLTLNNG---SQSVGRSSFYCLEYFPSQMLRTGNNFEFSY
F5\VP1@3            AHQGCLPPFPADVFMIPQYGYLTLNNG---SQSVGRSSFYCLEYFPSQMLRTGNNFEFSY
F3\VP1              AHQGCLPPFPADVFMIPQYGYLTLDNG---SQSVGRSSFYCLEYFPSQMLRTGNNFEFSY
42_6B               AHQGCLPPFPADVFMIPQYGYLTLNNG---SQSVGRSSFYCLEYFPSQMLRTGNNFEFSY
42_12               AHQGCLPPFPADVFMIPQYGYLTLNNG---SQAVGRSSFYCLEYFPSQMLRTGNNFEFSY
AAV5\CAP            GTEGCLPAFPPQVFTLPQYGYATLNRD-NTENPTERSSFFCLEYFPSKMLRTGNNFEFTY
```

FIG. 2G

```
              430        440        450        460        470        480
         ....|....|....|....|....|....|....|....|....|....|....|....|....
C1\VP1   NFGKVPFHSMYAYSQSPDRLMNPLLDQYLWHLQSTTSGETLNQGNAATTFGKIRSGDFAF
C2\VP1   NFEKVPFHSMYAHSQSLDRLMNPLLDQYLWHLQSTTSGETLNQGNAATTFGKIRSGDFAF
C5\VP1@2 NFEKVPFHSMYAHSQSLDGLMNPLLDQYLWHLQSTTSGETLNQGNAATTFGKIRSGDFAF
AAV4\VP1 SFEKVPFHSMYAHSQSLDRLMNPLIDQYLWGLQSTTTGTTLNAGTATTNFTKLRPTNFSN
AAV1     TFEEVPFHSSYAHSQSLDRLMNPLIDQYLYYLNRTQNQSG-SAQNKDLLFSRGSPAGMSV
AAV6\VP1 TFEDVPFHSSYAHSQSLDRLMNPLIDQYLYYLNRTQNQSG-SAQNKDLLFSRGSPAGMSV
A3_3     TFEDVPFHSSYAHSQSLDRLMNPLIDQYLYYLSKTQ-GTSGTTQQSRLQFSQAGPSSMAQ
A3_7     TFEDVPFHSSYAHSQSLDRLMNPLIDQYLYYLSKTQ-GTSGTTQQSRLQFSQAGPSSMAQ
A3_4     TFEDVPFHSSYAHSQSLDRLMNPLIDQYLYYLSKTQ-GTSGTTQQSRLQFSQAGPSSMAQ
A3_5     TFEDVPFHSSYAHSQSLDRLMNPLIDQYLYYLSKTQ-GTSGTTQQSRLQFNQAGPSSMAQ
AAV2     TFEDVPFHSSYAHSQSLDRLMNPLIDQYLYYLSRTN-TPSGTTTQSRLQFSQAGASDIRD
AAV3     TFEDVPFHSSYAHSQSLDRLMNPLIDQYLYYLNRTQGTTSGTTNQSRLLFSQAGPQSMSL
13.3b\VP1 SFEDVPFHSSYAHSQSLDRLMNPLIDQYLYYLARTQSDPGGTAGNRELQFYQGGPSTMAE
AAV7     SFEDVPFHSSYAHSQSLDRLMNPLIDQYLYYLARTQSNPGGTAGNRELQFYQGGPSTMAE
223_4    TFEDVPFHSSYAHSQSLGRLMNPLIDQYLYYLARTQSNAGGTAGNRELQFYQGGPTTMAE
223_5    TFEDVPFHSSYAHSQSLGRLMNPLIDQYLYYLARTQSNAGGTAGNRELQFYQGGPTTMAE
223_10   TFEDVPFHSSYAHSQSLGRLMNPLIDQYLYYLARTQSNAGGTAGNRELQFYQGGPTTMAE
223_2    TFEDVPFHSSYAHSQSLDRLMNPLIDQYLYYLARTQSNAGGTAGNRELQFYQGGPTTMAE
223_7    TFEDVPFHSSYAHSQSLDRLMNPLIDQYLYYLARTQSNAGGTAGNRELQFYQGGPTTMAE
223_6    TFEDVPFHSSYAHSQSLDRLMNPLIDQYLYYLARTQSNAGGTAGNRELQFYQGGPTTMAE
44_1     QFEDVPFHSSYAHSQSLDRLMNPLIDQYLYYLSRTQSTGG-TAGTQQLLFSQAGPNNMSA
44_5     QFEDVPFHSSYAHSQSLDRLMNPLIDQYLYYLSRTQSTGG-TAGTQQLLFSQAGPNNMSA
44_2     QFEDVPFHSSYAHSQSLDRLMNPLIDQYLYYLSRTQSTGG-TAGTQQLLFSQAGPNNMSA
29.3\VP1 QFEDVPFHSSYAHSQSLDRLMNPLIDQYLYYLSRTQSTGG-TAGTQQLLFSQAGPNNMSA
29.5\VP1 QFEDVPFHSSYAHSQSLDRLMNPLIDQYLYYLSRTQSTGG-TAGTQQLLFSQAGPNNMSA
42_15    QFEDVPFHSSYAHSQSLDRLMNPLIDQYLYYLSRTQSTGG-TAGTQQLLFSQAGPNNMSA
42_8     QFEDVPFHSSYAHSQSLDRLMNPLIDQYLYYLSRTQSTGG-TAGTQQLLFSQAGPNNMSA
42_13    QFEDVPFHSSYAHSQSLDRLMNPLIDQYLYYLSRTQSTGG-TAGTQQLLFSQAGPNNMSA
42_3A    QFEDVPFHSSYAHSQSLDRLMNPLIDQYLYYLSRTQSTGG-TAGTQQLLFSQAGPNNMSA
42_4     QFEDVPFHSSYAHSQSLDRLMNPLIDQYLYYLSRTQSTGG-TAGTQQLLFSQAGPNNMSA
42_5A    QFEDVPFHSSYAHSQSLDRLMNPLIDQYLYYLSRTQSTGG-TAGTQQLLFSQAGPNNMSA
42_1B    QFEDVPFHSSYAHSQSLDRLMNPLIDQYLYYLSRTQSTGG-TAGTQQLLFSQAGPNNMSA
42_5B    QFEDVPFHSSYAHSQSLDRLMNPLIDQYLYYLSRTQSTGG-TAGTQQLLFSQAGPNNMSA
43_1     TFEDVPFHSSYAHSQSLDRLMNPLIDQYLYYLSRTQSTGG-TQGTQQLLFSQAGPANMSA
43_12    TFEDVPFHSSYAHSQSLDRLMNPLIDQYLYYLSRTQSTGG-TQGTQQLLFSQAGPANMSA
43_5     TFEDVPFHSSYAHSQSLDRLMNPLIDQYLYYLSRTQSTGG-TQGTQQLLFSQAGPANMSA
AAV8     TFEDVPFHSSYAHSQSLDRLMNPLIDQYLYYLSRTQTTGG-TANTQTLGFSQGGPNTMAN
43_21    TFEDVPFHSSYAHSQSLDRLMNPLIDQYLYYLVRTQTTG--TGGTQTLAFSQAGPSSMAN
43_25    TFEDVPFHSSYAHSQSLDRLMNPLIDQYLYYLVRTQTTG---TGGTQTLAFSQAGPSSMAN
43_23    TFEDVPFHSSYAHSQSLDRLMNPLIDQYLYYLVRTQTTG---TGGTQTLAFSQAGPSSMAN
43_20    TFEDVPFHSSYAHSQSLDRLMNPLIDQYLYYLVRTQTTG---TGGTQTLAFSQAGPSSMAN
AAV_9    TFEDVPFHSSYAHSQSLDRLMNPLIDQYLYYLVRTQTTG--TGGTQTLAFSQAGPSSMAN
24.1     TFEEVPFHSSYVHSQSLDRLMNPLIDQYLYYLARTQST----TGSTRELQFHQAGPNTMAE
42.2REAL TFEEVPFHSSYAHSQSLDRLMNPLIDQYLYYLARTQST---TGSTRELQFHQAGPNTMAE
7.2\VP1  TFEEVPFHSSYAHSQSLDRLMNPLIDQYLYYLARTQST---TGSTRELQFHQAGPNTMAE
27.3\VP1 TFEEVPFHSSYAHSQSLDRLMNPLIDQYLYYLARTQST---TGSTRELQFHQAGPNTVAE
16.3\VP1 TFEEVPFHSSYAHSQSLDRLMNPLIDQYLYYLARTQST---TGSTRELQFHQAGPNTMAE
42_10    TFEEVPFHSSYAHSQSLDRLMNPLIDQYLYYLARTQST---TGSTRELQFHQAGPNTMAE
42_3B    TFEEVPFHSSYAHSQSLDRLMNPLIDQYLYYLARTQST---TGSTRELQFHQAGPNTMAE
42_11    TFEEVPFHSSYAHSQSLDRLMNPLIDQYLYYLARTQST----TGSTRELQFHQAGPNTMAE
F1\VP1   SFEDVPFHSSYAHSQSLDRLMNPLIDQYLYYLARTQST---TGSTRELQFHQAGPNTMAE
F5\VP1@3 SFEDVPFHSSYAHSQSLDRLMNPLIDQYLYYLARTQST----TGSTRELQFHQAGPNTMAE
F3\VP1   SFEDVPFHSSYAHSQSLDRLMNPLIDQYLYYLARTQST---TGSTRELQFHQAGPNTMAE
42_6B    TFEEVPFHSSYAHSQSLDRLMNPLIDQYLYYLARTQST----TGSTRELQFHQAGPNTMAE
42_12    QFEDVPFHSSYAHSQSLDRLTNPLIDQYLYYLARTQST---TGSTRGLQFHQAGPNTMAE
AAV5\CAP NFEEVPFHSSFAPSQNLFKLANPLVDQYLYRFVSTNNTGG--------VQFNKNLAGRYAN
```

FIG. 2H

```
                    490        500        510        520        530        540
                ....|....|....|....|....|....|....|....|....|....|....|....|
    C1\VP1      YRKNWLPGPCVKQQRLSKTASQNYKIPASGGNALLKYDTHYTLNNRWSNIAPGPPMATAG
    C2\VP1      YRKNWLPGPCVKQQRFSKTASQNYKIPASGGNALLKYDTHYTLNNRWSNIAPGPPMATAG
    C5\VP1@2    YRKNWLPGPCVKQQRFSKTASQNYKIPASGGNALLKYDTHYTLNNRWSNIAPGPPMATAG
    AAV4\VP1    FKKNWLPGPSIKQQGFSKTANQNYKIPATGSDSLIKYETHSTLDGRWSALTPGPPMATAG
    AAV1        QPKNWLPGPCYRQQRVSKTKTDN-----NNSNFTWTGASKYNLNGRESIINPGTAMASHK
    AAV6\VP1    QPKNWLPGPCYRQQRVSKTKTDN-----NNSNFTWTGASKYNLNGRESIINPGTAMASHK
    A3_3        QAKNWLPGPSYRQQRMSKTANDN-----NNSEFAWTAATKYYLNGRNSLVNPGPPVASHK
    A3_7        QAKNWLPGPSYRQQRMSKTANDN-----NNSEFAWTAATKYYLNGRNSLVNPGPPMASHK
    A3_4        QAKNWLPGPSYRQQRMSKTANDN-----NNSEFAWTAATKYYLNGRNSLVNPGPPMASHK
    A3_5        QAKNWLPGPSYRQQRMSKTANDN-----NNSEFAWTAATKYYPNGRNSLVNPGPPMASHK
    AAV2        QSRNWLPGPCYRQQRVSKTSADN-----NNSEYSWTGATKYHLNGRDSLVNPGPAMASHK
    AAV3        QARNWLPGPCYRQQRLSKTANDN-----NNSNFPWTAASKYHLNGRDSLVNPGPAMASHK
    13.3b\VP1   QAKNWLPGPCFRQQRVSKTLDQN-----NNSNFAWTGATKYHLNGRNSLVNPGVAMATHK
    AAV7        QAKNWLPGPCFRQQRVSKTLDQN-----NNSNFAWTGATKYHLNGRNSLVNPGVAMATHK
    223_4       QAKNWLPGPCFRQQRVSKTLDQN-----NNSNFAWTGATKYHLNGRNSLVNPGVAMATHK
    223_5       QAKNWLPGPCFRQQRVSKTLDQN-----NNSNFAWTGATKYHLNGRNSLVNPGVAMATHK
    223_10      QAKNWLPGPCFRQQRVSKTLDQN-----NNSNFAWTGATKYHLNXRNSLVNPGVAMATHK
    223_2       QAKNWLPGPCFRQQRVSKTLDQN-----NNSNFAWTGATKYHLNGRNSLVNPGVAMATHK
    223_7       QAKNWLPGPCFRQQRVSKTLDQN-----NNSNFAWTGATKYHLNGRNSLVNPGVAMATHK
    223_6       QAKNWLPGPCFRQQRVSKTLDQN-----NNSNFAWTGATKYHLNGRNSLVNPGVAMATHK
    44_1        QAKNWLPGPCYRQQRVSTTLSQN-----NNSNFAWTGATKYHLNGRDSLVNPGVAMATHK
    44_5        QAKNWLPGPCYRQQRVSTTLSQN-----NNSNFAWTGATKYHLNGRDSLVNPGVAMATHK
    44_2        QAKNWLPGPCYRQQRVSTTLSQN-----NNSNFAWTGATKYHLNGRDSLVNPGVAMATHK
    29.3\VP1    QAKNWLPGPCYRQQRVSTTLSQN-----NNSNFAWTGATKYHLNGRDSLVNPGVAMATHK
    29.5\VP1    QAKNWLPGPCYRQQRVSTTLSQN-----DNSNFAWTGATKYHLNGRDSLVNPGVAMATHK
    42_15       QAKNWLPGPCYRQQRVSTTLSQN-----NNSNFAWTGATKYHLNGRDSLVNPGVAMATHK
    42_8        QAKNWLPGPCYRQQRVSTTLSQN-----NNSNFAWTGATKYHLNGRDSLVNPGVAMATHK
    42_13       QAKNWLPGPCYRQQRVSTTVSQN-----NNSNFAWTGATKYHLNGRDSLVNPGVAMATHK
    42_3A       QAKNWLPGPCYRQQRVSTTLSQN-----NNSNFAWTGATKYHLNGRDSLVNPGVAMATHK
    42_4        QAKNWLPGPCYRQQRVSTTLSQN-----NNSNFAWTGATKYHLNGRDSLVNPGVAMATHK
    42_5A       QAKNWLPGPCYRQQRVSTTLSQN-----NNSNFAWTGATKYHLNGRDSLVNPGVAMATHK
    42_1B       QAKNWLPGPCYRQQRVSTTVSQN-----NNSNFAWTGATKYHLNGRDSLVNPGVAMATHK
    42_5B       QAKNWLPGPCYRQQRVSTTLSQN-----NNSNFAWTGATKYHLNGRDSLVNPGVAMATHK
    43_1        QAKNWLPGPCYRQQRVSTTLSQN-----NNSNFAWTGATKYHLNGRDSLVNPGVAMATHK
    43_12       QAKNWLPGPCYRQQRVSTTLSQN-----NNSNFAWTGATKYHLNGRDSLVNPGVAMATHK
    43_5        QAKNWLPGPCYRQQRVSTTLSQN-----NNSNFAWTGATKYHLNGRDSLVNPGVAMATHK
    AAV8        QAKNWLPGPCYRQQRVSTTTGQN-----NNSNFAWTAGTKYHLNGRNSLANPGIAMATHK
    43_21       QARNWVPGPCYRQQRVSTTTNQS-----NNSNFAWTGAAKFKLNGRDSLMNPGVAMASHK
    43_25       QARNWVPGPCYRQQRVSTTTNQN-----NNSNFAWTGAAKFKLNGRDSLMNPGVAMASHK
    43_23       QARNWVPGPCYRQQRVSTTTNQN-----NNSNFAWTGAAKFKLNGRDSLMNPGVAMASHK
    43_20       QARNWVPGPCYRQQRVSTTTNQN-----NNSNFAWTGAAKFKLNGRDSLMNPGVAMASHK
    AAV_9       QARNWVPGPCYRQQRVSTTTNQN-----NNSNFAWTGAAKFKLNGRDSLMNPGVAMASHK
    24.1        QSKNWLPGPCYRQQRLSKNIDSN-----NNSNFAWTGATKYHLNGRNSLTNPGVAMATNK
    42.2REAL    QSKNWLPGPCYRQQRLSKNIDSN-----NNSNFAWTGATKYHLNGRNSLTNPGVAMATNK
    7.2\VP1     QSKNWLPGPCYRQQRLSKNIDSN-----NNSNFAWTGATKYHLNGRNSLTNPGVAMATNK
    27.3\VP1    QSKNWLPGPCYRQQRLSKNIDSN-----NNSNFAWTGATKYHLNGRNSLTNPGVAMATNK
    16.3\VP1    QSKNWLPGPCYRQQRLSKNIDSN-----NNSNFAWTGATKYHLNGRNSLTNPGVAMATNK
    42_10       QSKNWLPGPCYRQQRLSKNIDSN-----NNSNFAWTGATKYHLNGRNSLTNPGVAMATNK
    42_3B       QSKNWLPGPCYRQQRLSKNIDSN-----NTSNFAWTGATKYHLNGRNSLTNPGVAMATNK
    42_11       QSKNWLPGPCYRRQRLSKDIDSN-----NNSNFAWTGATKYHLNGRNSLTNPGVAMATNK
    F1\VP1      QSKNWLPGPCYRQQGLSKNLDFN-----NNSNFAWTAATKYHLNGRNSLTNPGIPMATNK
    F5\VP1@3    QSKNWLPGPCYRQQRLSKNLDFN-----NNSNFAWTAATKYHLNGRNSLTNPGIPMATNK
    F3\VP1      QSKNWLPGPCYRQQRLSKNLDFN-----NNSNFAWTAATKYHLNGRNSLTNPGIPMATNK
    42_6B       QSKNWLPGPCYRQQRLSKNIDSN-----NNSNFAWTGATKYHLNGRNSLTNPGVAMATNK
    42_12       QSKNWLPGPCYRQQRLSKNIDSN-----NNSNFAWTGATKYHLNGRNSLTNPGVAMATNK
    AAV5\CAP    TYKNWFPGPMGRTQGWNLGSGVN------RASVSAFATTNRMELEGASYQVPPQPNGMTNN
```

FIG. 21

```
                 550        560        570        580        590        600
           ....|....|....|....|....|....|....|....|....|....|....|....|
C1\VP1     PSDGDFS-NAQLIFPGPS--VTGNTTTSAN-NLLFTSEEEIAATNPRDTDMFGQIADNNQ
C2\VP1     PSDGDFS-NAQLIFPGPS--VTGNTTTSAN-NLLFTSEGEIAATNPRDTDMFGQIADNNQ
C5\VP1@2   PSDGDFS-NAQLIFPGPS--VTGNTTTSAN-NLLFTSEEEIAATNPRDTDMFGQIADNNQ
AAV4\VP1   PADSKFS-NSQLIFAGPK--QNGNTATVPG-TLIFTSEEELAATNATDTDMWGNLPGGDQ
AAV1       DDEDKFFPMSGVMIFGKE--SAGASNTALD-NVMITDEEEIKATNPVATERFGTVAVNFQ
AAV6\VP1   DDKDKFFPMSGVMIFGKE--SAGASNTALD-NVMITDEEEIKATNPVATERFGTVAVNLQ
A3_3       DDEEKYFPMHGNLIFGKQ---GTGTTNVDIE-SVLITDEEEIRTTNPVATEQYGQVATNHQ
A3_7       DDEEKYFPMHGNLIFGKQ---GTGTTNVDIE-SVLITDEEEIRTTNPVATEQYGQVATNHQ
A3_4       DDEEKYFPMHGNLIFGKQ---GTGTTNVDIE-SVLITDEEEIRTTNPVATEQYGQVATNHQ
A3_5       DDEEKYFPMHGNLIFGKQ---GTGTTNVDIE-SVLITDEEEIRTTNPVATEQYGQVATNRQ
AAV2       DDEEKFFPQSGVLIFGKQ---GSEKTNVDIE-KVMITDEEEIRTTNPVATEQYGSVSTNLQ
AAV3       DDEEKFFPMHGNLIFGKE--GTTASNAELD-NVMITDEEEIRTTNPVATEQYGTVANNLQ
13.3b\VP1  DDEDRFFPSSGVLIFGKT--GATN-KTTLE-NVLMTNEEEIRPTNPVATEEYGIVSSNLQ
AAV7       DDEDRFFPSSGVLIFGKT--GATN-KTTLE-NVLMTNEEEIRPTNPVATEEYGIVSSNLQ
223_4      DDEERFFPSSGVLIFGKT--GAAN-KTTLE-NVLMTNEEEIRPTNPVATEEYGIVSSNLQ
223_5      DDEERFFPSSGVLIFGKT--GAAN-KTTLE-NVLMTNEEEIRPTNPVATEEYGIVSSNLQ
223_10     DDEERFFPSSGVLIFGKT--GAAN-KTTLE-NVLMTNEEEIRPTNPVATEEYGIVSSNLQ
223_2      DDEERFSPSSGVLIFGKT--GAAN-KTTLE-NVLMTNEEEIRPTNPVATEEYGIVSSNLQ
223_7      DDEERFFPSSGVLIFGKT--GAAN-KTTLE-NVLMTNEEEIRPTNPVATEEYGIVSSNLQ
223_6      DDEERFFPSSGVLIFGKT--GAAN-KTTLE-NVLMTNEEEIRPTNPVATEEYGIVSSNLQ
44_1       DDEERFFPSSGVLMFGKQ--GAGKDNVDYS-SVMLTSEEEIKTTNPVATEQYGVVADNLQ
44_5       DDEERFFPSSGVLMFGKQ--GAGKDNVDYS-SVMLTSEEEIKTTNPVATEQYGVVADNLQ
44_2       DDEERFFPSSGVLMFGKQ--GAGKDNVDYS-SVMLTSEEEIKTTNPVATEQYGVVADNLQ
29.3\VP1   DDEERFFPSSGVLMFGKQ---GAGKGNVDYS-SVMLTSEEEIKTTNPVATEQYGVVADNLQ
29.5\VP1   DDEERFFPSSGVLMFGKQ---GAGKDNVDYS-SVMLTSEEEIKTTNPVATEQYGVVADNLQ
42_15      DDEERFFPSSGVLMFGKQ--GAGKDNVDYS-SVMLTSEEEIKTTNPVATEQYGVVADNLQ
42_8       DDEERFFPSSGVLMFGKQ--GAGKDNVDYS-SVMLTSEEEIKTTNPVATEQYGVVADNLQ
42_13      GDEERFFPSSGVLMFGKQ--GAGKDNVDYS-SVMLTSEEEIKTTNPVATEQYGVVADNLQ
42_3A      DDEERFFPSSGVLMFGKQ---GAGKDNVDYS-SVMLTSEEEIKTTNPVATEQYGVVADNLQ
42_4       DDEERFFPSSGVLMFGKQ---GAGKDNVDYS-SVMLTSEEEIKTTNPVATEQYGVVADNLQ
42_5A      DDEERFFPSSGVLMFGKQ--GAGKDNVDYS-SVMLTSEEEIKTTNPVATEQYGVVADNLQ
42_1B      GDEERFFPSSGVLMFGKQ--GAGKDNVDYS-SVMLTSEEEIKTTNPVATEQYGVVADNLQ
42_5B      DDEERFFPSSGVLMFGKQ--GAGKDNVDYS-SVMLTSEEEIKTTNPVATEQYGVVADNLQ
43_1       DDEERFFPSSGVLMFGKQ--GAGKDNVDYS-SVMLTSEEEIKTTNPVATEQYGVVADNLQ
43_12      DDEERFFPSSGVLMFGKQ--GAGKDNVDYS-SVMLTSEEEIKTTNPVATEQYGVVADNLQ
43_5       DDEERFFPSSGVLMFGKQ--GAGKDNVDYS-SVMLTSEEEIKTTNPVATEQYGVVADNLQ
AAV8       DDEERFFPSNGILIFGKQ---NAARDNADYS-DVMLTSEEEIKTTNPVATEEYGIVADNLQ
43_21      DDDDRFFPSSGVLIFGKQ--GAGNDGVDYS-QVLITDEEEIKATNPVATEEYGAVAINNQ
43_25      DDDDRFFPSSGVLIFGKQ--GAGNDGVDYS-QVLITDEEEIKATNPVATEEYGAVAINNQ
43_23      DDDDRFFPSSGVLIFGKQ--GAGNDGVDYS-QVLITDEEEIKATNPVATEEYGAVAINNQ
43_20      DDDDRFFPSSGVLIFGKQ--GAGNDGVDYS-QVLITDEEEIKATNPVATEEYGAVAINNQ
AAV_9      DDEDRFFPSSGVLIFGKQ--GAGNDGVDYS-QVLITDEEEIKATNPVATEEYGAVAINNQ
24.1       DDEDQFFPINGVLVFGKT--GAAN-KTTLE-NVLMTSEEEIKTTNPVATEEYGVVSSNLQ
42.2REAL   DDEDQFFPINGVLVFGET--GAAN-KTTLE-NVLMTSEEEIKTTNPVATEEYGVVSSNLQ
7.2\VP1    DDEDQFFPINGVLVFGKT--GAAN-KTTLE-NVLMTSEEEIKTTNPVATEEYGVVSSNLQ
27.3\VP1   DDEDQFLPINGVLVFGKT--GAAN-KTTLE-NVLMTSEEEIKTTNPVATEEYGVVSSNLQ
16.3\VP1   DDEGQFFPINGVLVFGKT--GAAN-KTTLE-NVLMTSEEEIKTTNPVATEEYGVVSSNLQ
42_10      DDEDQFFPINGVLVFGKT--GAAN-KTTLE-NVLMTSEEEIKTTNPVATEEYGVVSSNLQ
42_3B      DDEDQFFPINGVLVFGKT--GAAN-KTTLE-NVLMTSEEEIKTTNPVATEQYGVVSSNLQ
42_11      DDEDQFFPINGVLVFGKT--GAAN-KTTLE-NVLMTSEEEIKTTNPVATEEYGVVSSNLQ
F1\VP1     DDEDQFFPINGVLVFGKT--GAAN-KTTLE-NVLMTSEEEIKTTNPVATEEYGVVSSNLQ
F5\VP1@3   DDEDQFFPINGVLVFGKT---GAAN-KTTLE-NVLMTSEEEIKTTNPVATEEYGVVSSNLQ
F3\VP1     DDEDQFFPINGVLVFGKT--GAAN-KTTLE-NVLMTSEEEIKTTNPVATEEYGVVSSNLQ
42_6B      DDEDQFFPINGVLVFGKT---GAAN-KTTLE-NVLMTSEEEIKTTNPVATEEYGVVSSNLQ
42_12      DDEDQFFPINGVLVFGKT--GAAN-KTTLE-NVLMTSEEEIKTTNPVATEEYGVVSSNLQ
AAV5\CAP   LQGSNTYALENTMIFNSQPANPGTTATYLEGNMLITSESETQPVNRVAYNVGGQMATNNQ
```

FIG. 2J

```
                       610        620        630        640        650        660
              ....|....|....|....|....|....|....|....|....|....|....|....|....|
C1\VP1        NATTAPITGNVTAMGVLPGMVWQNRDIYYQGPIWAKIPHADGHFHPSPLIGGFGLKHPPP
C2\VP1        NATTAPITGNVTAMGVLPGMVWQNRDIYYQGPIWAKIPHADGHFHPSPLIGGFGLKHPPP
C5\VP1@2      NATTAPITGNVTAMGVLPGMVWQNRDIYYQGPIWAKIPHADGHFHPSPLIGGFGLKHPPP
AAV4\VP1      SNSNLPTVDRLTALGAVPGMVWQNRDIYYQGPIWAKIPHTDGHFHPSPLIGGFGLKHPPP
AAV1          SSSTDPATGDVHAMGALPGMVWQDRDVYLQGPIWAKIPHTDGHFHPSPLMGGFGLKNPPP
AAV6\VP1      SSSTDPATGDVHVMGALPGMVWQDRDVYLQGPIWAKIPHTDGHFHPSPLMGGFGLKHPPP
A3_3          SQNTTASYGSVDSQGILPGMVWQDRDVYLQGPIWAKTPHTDGHFHPSPLMGGFGLKHPPP
A3_7          SQNTTASYGSVDSQGILPGMVWQDRDVYLQGPIWAKTPHTDGHFHPSPLMGGFGLKHPPP
A3_4          SQDTTASYGSVDSQGILPGMVWQDRDVYLQGPIWAKTPHTDGHFHPSPLMGGFGLKHPPP
A3_5          SQNTTASYGSVDSQGILPGMVWQDRDVYLQGPIWAKTPHTDGHFHPSPLMGGFGLKHPPP
AAV2          RGNRQAATADVNTQGVLPGMVWQDRDVYLQGPIWAKIPHTDGHFHPSPLMGGFGLKHPPP
AAV3          SSNTAPTTGTVNHQGALPGMVWQDRDVYLQGPIWAKIPHTDGHFHPSPLMGGFGLKHPPP
13.3b\VP1     AANTAAQTQVVNNQGALPGMVWQNRDVYLQGPIWAKIPHTDGNFHPSPLMGGFGLKHPPP
AAV7          AANTAAQTQVVNNQGALPGMVWQNRDVYLQGPIWAKIPHTDGNFHPSPLMGGFGLKHPPP
223_4         AASTAAQTQVVNNQGALPGMVWQNRDVYLQGPIWAKIPHTDGNFHPSPLMGGFGLKHPPP
223_5         AASTAAQTQVVNNQGALPGMVWQNRDVYLQGPIWAKIPHTDGNFHPSPLMGGFGLKHPPP
223_10        AASTAAQTQVVNNQGALPGMVWQNRDVYLQGPIWAKIPHTDGNFHPSPLMGGFGLKHPPP
223_2         AASTAAQTQVVNNQGALPGMVWQNRDVYLQGPIWAKIPHTDGNFHPSPLMGGFGLKHPPP
223_7         AASTAAQTQVVNNQGALPGMVWQNRDVYLQGPIWAKIPHTDGNFHPSPLMGGFGLKHPPP
223_6         AASTAAQTQVVNNQGALPGMVWQNRDVYLQGPIWAKIPHTDGNFHPSPLMGGFGLKHPPP
44_1          QQNAAPIVGAVNSQGALPGMVWQNRDVYLQGPIWAKIPHTDGNFHPSPLMGGFGLKHPPP
44_5          QQNAAPIVGAVNSQGALPGMVWQNRDVYLQGPIWAKIPHTDGNFHPSPLMGGFGLKHPPP
44_2          QQNAAPIVGAVNSQGALPGMVWQNRDVYLQGPIWAKIPHTDGNFHPSPLMGGFGLKHPPP
29.3\VP1      QQNAAPIVGAVNSQGALPGMVWQNRDVYLQGPIWAKIPHTDGNFHPSPLMGGFGLKHPPP
29.5\VP1      QQNAAPIVGAVNSQGALPGMVWQNRDVYLQGPIWAKIPHTDGNFHPSPLMGGFGLKHPPP
42_15         QQNAAPIVGAVNSQGALPGMVWQNRDVYLQGPIWAKIPHTDGNFHPSPLMGGFGLKHPPP
42_8          QQNAAPIVGAVNSQGALPGMVWQNRDVYLQGPIWAKIPHTDGNFHPSPLMGGFGLKHPPP
42_13         QQNAAPIVGAVNSQGALPGMVWQNRDVYLQGPIWAKIPHTDGNFHPSPLMGGFGLKHPPP
42_3A         QQNAAPIVGAVNSQGALPGMVWQNRDVYLQGPIWAKIPHTDGNFHPSPLMGGFGLKHPPP
42_4          QQNAAPIVGAVNSQGALPGMVWQNRDVYLQGPIWAKIPHTDGNFHPSPLMGGFGLKHPPP
42_5A         QQNAAPIVGAVNSQGALPGMAWQNRDVYLQGPIWAKIPHTDGNFHPSPLMGGFGLKHPPP
42_1B         QQNAAPIVGAVNSQGALPGMVWQNRDVYLQGPIWAKIPHTDGNFHPSPLMGGFGLKHPPP
42_5B         QQNAAPIVGAVNSQGALPGMVWQNRDVYLQGPIWAKIPHTDGNFHPSPLMGGFGLKHPPP
43_1          QTNGAPIVGTVNSQGALPGMVWQNRDVYLQGPIWAKIPHTDGNFHPSPLMGGFGLKHPPP
43_12         QTNGAPIVGTVNSQGALPGMVWQNRDVYLQGPIWAKIPHTDGNFHPSPLMGGFGLKHPPP
43_5          QTNGAPIVGTVNSQGALPGMVWQNRDVYLQGPIWAKIPHTDGNFHPSPLMGGFGLKHPPP
AAV8          QQNTAPQIGTVNSQGALPGMVWQNRDVYLQGPIWAKIPHTDGNFHPSPLMGGFGLKHPPP
43_21         AANTQAQTGLVHNQGVIPGMVWQNRDVYLQGPIWAKIPHTDGNFHPSPLMGGFGLKHPPP
43_25         AANTQAQTGLVHNQGVIPGMVWQNRDVYLQGPIWAKIPHTDGNFHPSPLMGGFGLKHPPP
43_23         AANTQAQTGLVHNQGVIPGMVWQNRDVYLQGPIWAKIPHTDGNFHPSPLMGGFGLKHPPP
43_20         AANTQAQTGLVHNQGVIPGMVWQNRDVYLQGPIWAKIPHTDGNFHPSPLMGGFGLKHPPP
AAV_9         AANTQAQTGLVHNQGVIPGMVWQNRDVYLQGPIWAKIPHTDGNFHPSPLMGGFGLKHPPP
24.1          SSTAGPQTQTVNSQGALPGMVWQNRDVCLQGPIWAKIPHTDGNFHPSPLMGGFGLKHPPP
42.2REAL      SSTAGPQTQTVNSQGALPGMVWQNRDVYLQGPIWAKIPHTDGNFHPSPLMGGFGLKHPPP
7.2\VP1       SSTAGPQTQTVNSQGALPGMVWQNRDVYLQGPIWAKIPHTDGNFHPSPLMGGFGLKHPPP
27.3\VP1      SSTAGPRTQTVNSQGALPGMVWQNRDVYLQGPIWAEIPHTDGNFHPSPLMGGFGLKHPPP
16.3\VP1      SSTAGPQTQTVNSQGALPGMVWQNRDVYLQGPIWAKIPHTDGNFHPSPLMGGFGLKHPPP
42_10         SSTAGPQTQTVNSQGALPGMVWQNRDVYLQGPIWAKIPHTDGNFHPSPLMGGFGLKHPPP
42_3B         SSTAGPQTQTVNSQGALPGMVWQNRDVYLQGPIWAKIPHTDGNFHPSPLMGGFGLKHPPP
42_11         SSTAGPQTQTVNSQGALPGMVWQNRDVYLQGPIWAKIPHTDGNFHPSPLMGGFGLKHPPP
F1\VP1        PSTAGPQSQTINSQGALPGMVWQNRDVYLQGPIWAKIPHTDGNFHPSPLMGGFGLKHPPP
F5\VP1@3      SSTAGPQSQTINSQGALPGMVWQNRDVYLQGPIWAKIPHTDGNFHPSPLMGGFGLEHPPP
F3\VP1        SSTAGPQSQTINSQGALPGMVWQNRDVYLQGPIWAKIPHTDGNFHPSPLMGGFGLKHPPP
42_6B         SSTAGPQTQTVNSQGALPGMVWQNRDVYLQGPIWAKIPHTDGNFHPSPLMDGFGLKHPPP
42_12         SSTAGPQTQTVNSQGALPGMVWQNRDVYLQGPIWAKIPHTDGNFHPSPLMGGFGLKHPPP
AAV5\CAP      SSTTAPATGTYNLQEIVPGSVWMERDVYLQGPIWAKIPETGAHFHPSPAMGGFGLKHPPP
```

FIG. 2K

```
                        670       680       690       700       710       720
                   ....|....|.... ...|....|....|.... ...|....|....|....|....|
C1\VP1             QIFIKNTPVPANPATTFTAARVDSFITQYSTGQVAVQIEWEIEKERSKRWNPEVQFTSNY
C2\VP1             QIFIKNTPVPANPATTFTAARVDSFITQYSTGQVAVQIEWEIEKERSKRRNPEVQFTSNY
C5\VP1@2           QIFIKNTPVPAYPATTFTAARVDSFITQYSTGQVAVQIEWEIEKERSKRWNPEVQFTSNC
AAV4\VP1           QIFIKNTPVPANPATTFSSTPVNSFITQYSTGQVSVQIDWEIQKERSKRWNPEVQFTSNY
AAV1               QILIKNTPVPANPPAEFSATKFASFITQYSTGQVSVEIEWELQKENSKRWNPEVQYTSNY
AAV6\VP1           QILIKNTPVPANPPAEFSATKFASFITQYSTGQVSVEIEWELQKENSKRWNPEVQYTSNY
A3_3               QILIKNTPVPANPATTFTPGKFASFITQYSTGQVSVEIEWELQKENSKRWNPEIQYTSNY
A3_7               QILIKNTPVPANPATTFTPGKFASFITQYSTGQVSVEIEWELQKENSKRWNPEIQYTSNY
A3_4               QILIKNTPVPANPATTFTPGKFASFITQYSTGQVSVEIEWELQKENSKRWNPEIQYTSNY
A3_5               QILIKNTPVPANPATTFTPGKFASFITQYSTGQVSVEIEWELQKENSKRWNPEIQYTSNY
AAV2               QILIKNTPVPANPSTTFSAAKFASFITQYSTGQVSVEIEWELQKENSKRWNPEIQYTSNY
AAV3               QIMIKNTPVPANPPTTFSPAKFASFITQYSTGQVSVEIEWELQKENSKRWNPEIQYTSNY
13.3b\VP1          QILIKNTPVPANPPEVFTPAKFASFITQYSTGQVSVEIEWELQKENSKRWDPEIQYTSNF
AAV7               QILIKNTPVPANPPEVFTPAKFASFITQYSTGQVSVEIEWELQKENSKRWNPEIQYTSNF
223_4              QILIKNTPVPANPPEVFTPAKFASFITQYSTGQVSVEIEWELQKENSKRWNPEIQYTSNF
223_5              QILIKNTPVPANPPEVFTPAKFASFITQYSTGQVSVEIEWELQKENSKRWNPEIQYTSNF
223_10             QILIKNTPVPANPPEVFTPAKFASFITQYSTGQVSVEIEWELQKENSKRWNPEIQYTSNF
223_2              QILIKNTPVPANPPEVFTPAKFASFITQYSTGQVSVEIEWELQKENSKRWNPEIQYTSNF
223_7              QILIKNTPVPANPPEVFTPAKIASFITQYSTGQVSVEIEWELQKENSKRWNPEIQYTSNF
223_6              QILIKNTPVPANPPEVFTPAKLASFITQYSTGQVSVEIEWELQKENSKRWNPEIQYTSNF
44_1               QILIKNTPVPADPPTTFSQAKLASFITQYSTGQVSVEIEWELQKENSKRWNPEIQYTSNY
44_5               QILIKNTPVPADPPTTFSQAKLASFITQYSTGQVSVEIEWELQKENSKRWNPEIQYTSNY
44_2               QILIKNTPVPADPPTTFSQAKLASFITQYSTGQVSVEIEWELQKENSKRWNPEIQYTSNY
29.3\VP1           QILIKNTPVPADPPTTFSQAKLASFITQYSTGQVSVEIEWELQKENSKRWNPEIQYTSNY
29.5\VP1           QILIKNTPVPADPPTTFSQAKLASFITQYSTGQVSVEIEWELQKENSKRWNPEIQYTSNY
42_15              QILIKNTPVPADPPTTFSQAKLASFITQYSTGQVSVEIEWELQKENSKRWNPEIQYTSNY
42_8               QILIKNTPVPADPPTTFSQAKLASFITQYSTGQVSVEIEWELQKENSKRWNPEIQYTSNY
42_13              QILIKNTPVPADPPTTFSQAKLASFITQYSTGQVSVEIEWELQKENSKRWNPEIQYTSNY
42_3A              QILIKNTPVPADPPTTFSQAKLASFITQYSTGQVSVEIEWELQKENSKRWNPEIQYTSNY
42_4               QILIKNTPVPADPPTTFSQAKPASFITQYSTGQVSVEIEWELQKENSKRWNPEIQYTSNY
42_5A              QILIKNTPVPADPPTTFSQAKLASFITQYSTGQVSVEIEWELQKENSKRWNPEIQYTSNY
42_1B              QILIKNTPVPADPPTTFSQAKLASFITQYSTGQVSVEIEWELQKENSKRWNPEIQYTSNY
42_5B              QILIKNTPVPADPPTTFSQAKLASFITQYSTGQVSVEIEWELQKENSKRWNPEIQYTSNY
43_1               QILVKNTPVPADPPTTFSQAKLASFITQYSTGQVSVEIEWELQKENSKRWNPEIQYTSNY
43_12              QILVKNTPVPADPPTTFSQAKLASFITQYSTGQVSVEIEWELQKENSKRWNPEIQYTSNY
43_5               QILVKNTPVPADPPTTFSQAKLASFITQYSTGQVSVEIEWELQKENSKRWNPEIQYTSNY
AAV8               QILIKNTPVPADPPTTFNQSKLNSFITQYSTGQVSVEIEWELQKENSKRWNPEIQYTSNY
43_21              QILIKNTPVPADPPLTFNQAKLNSFITQYSTGQVSVEIEWELQKENSKRWNPEIQYTSNY
43_25              QILIKNTPVPADPPLTFNQAKLNSFITQYSTGQVSVEIEWELQKENSKRWNPEIQYTSNY
43_23              QILIKNTPVPADPPLTFNQAKLNSFITQYSTGQVSVEIEWELQKENSKRWNPEIQYTSNY
43_20              QILIKNTPVPADPPLTFNQAKLNSFITQYSTGQVSVEIEWELQKENSKRWNPEIQYTSNY
AAV_9              QILIKNTPVPADPPLTFNQAKLNSFITQYSTGQVSVEIEWELQKENSKRWNPEIQYTSNY
24.1               QILIKNTPVPANPPEVFTPAKFASFITQYSTGQVSVEIEWELQKENSKRWNPEIQYTSNY
42.2REAL           QILIKNTPVPANPPEVFTPAKFASFITQYSTGQVSVEIEWELQKENSKRWNPEIQYTSNY
7.2\VP1            QILIKNTPVPANPPEVFTPAKFASFITQYSTGQVSVEIEWELQKENSKRWNPEIQYTSNY
27.3\VP1           QILIKNTPVPANPPEVFTPAKFASFITQYSTGQVSVEIEWELQKENSKRWNPEIQYTSNY
16.3\VP1           QILIKNTPVPANPPGVFTPALFASFITQYSTGQVSVEIEWELQKENSKRWNPEIQYTSNY
42_10              QILIKNTPVPANPPEVFTPAKFASFITQYSTGQVSVEIEWELQKENSKRWNPEIQYTSNY
42_3B              QILIKNTPVPANPPEVFTPAKFASFITQYSTGQVSVEIEWELQKENSKRWNPEIQYTSNY
42_11              QILIKNTPVPANPPEVFTPAKFASFITQYSTGQVSVEIEWELQKENSKRWNPEIQYTSNY
F1\VP1             QILIKNTPVPANPPEVFTPAKFASFITQYSTGQVSVEIEWELQKENSKRWNPEIQYTSNY
F5\VP1@3           QILIKNTPVPANPPEVFTPAKFASFITQYSTGQVSVEIEWELQKENSKRWNPEIQYTSNY
F3\VP1             QILIKNTPVPANPPEVFTPAKFASFITQYSTGQVSVEIEWELQKENSKRWNPEIQYTSNY
42_6B              QILIKNTPVPANPPEVFTPAKFASFITQYSTGQVSVEIEWELQKENSKRWNPEIQYTSNY
42_12              QILIK-------------------------------------------------YTSNY
AAV5\CAP           MMLIKNTPVPGN-ITSFSDVPVSSFITQYSTGQVTVEMEWELKKENSKRWNPEIQYTNNY
```

FIG. 2L

```
                         730       740       750
                 ....|....|....|....|....|....|.
C1\VP1           GNQSSMLWAPDTTGKYTEPRVIGSRYLTNHL
C2\VP1           GNQSSMLWAPDTTGKYTEPRVIGSRYLTNHL
C5\VP1@2         GNQSSMLWAPDTTGKYTEPRVIGSRYLTNHL
AAV4\VP1         GQQNSLLWAPDAAGKYTEPRAIGTRYLTHHL
AAV1             AKSANVDFTVDNNGLYTEPRPIGTRYLTRPL
AAV6\VP1         AKSANVDFTVDNNGLYTEPRPIGTRYLTRPL
A3_3             NKSVNVEFTVDANGVYSEPRPIGTRYLTRNL
A3_7             NKSVNVEFTVDANGVYSEPRPIGTRYLTRNL
A3_4             NKSVNVEFTVDANGVYSEPRPIGTRYLTRNL
A3_5             NKSVNVEFTVDANGVYSEPRPIGTRYLTRNL
AAV2             NKSVNVDFTVDTNGVYSEPRPIGTRYLTRNL
AAV3             NKSVNVDFTVDTNGVYSEPRPIGTRYLTRNL
13.3b\VP1        EKQTGVDFAVDSQGVYSEPRPIGTRYLTRNL
AAV7             EKQTGVDFAVDSQGVYSEPRPIGTRYLTRNL
223_4            DKQTGVDFAVDSQGVYSEP------------
223_5            DKQTGVDFAVDSQGVYSEP------------
223_10           DKQTGVDFAVDSQGVYSEP------------
223_2            DKQTGVDFAVDSQGVYSEP------------
223_7            DKQTGVDFAVDSQGVYSEP------------
223_6            DKQTGVDFAVDSQGVYSEP------------
44_1             YKSTNVDFAVNTDGTYSEPRPIGTRYLTRNL
44_5             YKSTNVDFAVNTDGTYSEPRPIGTRYLTRNL
44_2             YKSTNVDFAVNTDGTYSEPRPIGTRYLTRNL
29.3\VP1         YKSTNVDFAVNTDGTYSEPRPIGTRYLTRNL
29.5\VP1         YKSTNVDFAVNTDGTYSEPRPIGTRYLTRNL
42_15            YKSTNVDFAVNTEGTYSEPRPIGTRYLTRNL
42_8             YKSTNVDFAVNTEGTYSEPRPIGTRYLTRNL
42_13            YKSTNVDFAVNTEGTYSEPRPIGTRYLTRSL
42_3A            YKSTNVDFAVNTEGTYSEPRPIGTRYLTRNL
42_4             YKSTNVDFAVNTEGTYSEPRPIGTRYLTRNL
42_5A            YKSTNVDFAVNTEGTYSEPRPIGTRYLTRNL
42_1B            YKSTNVDFAVNTEGTYSEPRPIGTRYLTRNL
42_5B            YKSTNVDFAVNTEGTYSEPRPIGTRYLTRNL
43_1             YKSTNVDFAVNTEGTYSEPRPIGTRYLTRNL
43_12            YKSTNVDFAVNTEGTYSEPRPIGTRYLTRNL
43_5             YKSTNVDFAVNTEGTYSEPRPIGTRYLTRNL
AAV8             YKSTSVDFAVNTEGVYSEPRPIGTRYLTRNL
43_21            YKSTNVDFAVNTEGVYSEPRPIGTRYLTRNL
43_25            YKSTNVDFAVNTEGVYSEPRPIGTRYLTRNL
43_23            YKSTNVDFAVNTEGVYSEPRPIGTRYLTRNL
43_20            YKSTNVDFAVNTEGVYSEPRPIGTRYLTRNL
AAV_9            YKSTNVDFAVNTEGVYSEPRPIGTRYLTRNL
24.1             AKSNNVEFAVNNEGVYTEPRPIGTRYLTRNL
42.2REAL         AKSNNVEFAVNNEGVYTEPRPIGTRYLTRNL
7.2\VP1          AKSNNVEFAVNNEGVYTEPRPIGTRYLTRNL
27.3\VP1         AKSNNVEFAVNNEGVYTEPRPIGTRYLTRNL
16.3\VP1         AKSNNVEFAVNNEGVYTEPRPIGTRYLTRNL
42_10            AKSNNVEFAVNNEGVYTEPRPIGTRYLTRNL
42_3B            AKSNNVEFAVNNEGVYTEPRPIGTRYLTRNL
42_11            AKSNNVEFAVNNEGVYTEPRPIGTRYLTRNL
F1\VP1           AKSNNVEFAVNPDGVYTEPRPIGTRYLPRNL
F5\VP1@3         AKSNNVEFAVNPDGVYTEPRPIGTRYLTRNL
F3\VP1           AKSNNVEFAVNPDGVYTEPRPIGTRYLTRNL
42_6B            AKSNNVEFAVNNEGVYTEPRPIGTRYLTRNL
42_12            YKSTNVDFAVNTEGTYSEPRPIGTRYLTRNL
AAV5\CAP         NDPQFVDFAPDSTGEYRTTRPIGTRYLTRPL
```

Met Pro Gly Phe Tyr Glu Ile Val Ile Lys Val Pro Ser Asp Leu Asp
1                5                 10                15

Glu His Leu Pro Gly Ile Ser Asp Ser Phe Val Asn Trp Val Ala Glu
         20                25                30

Lys Glu Trp Glu Leu Pro Pro Asp Ser Asp Met Asp Leu Asn Leu Ile
         35                40                45

Glu Gln Ala Pro Leu Thr Val Ala Glu Lys Leu Gln Arg Asp Phe Leu
     50                55                60

Val Gln Trp Arg Arg Val Ser Lys Ala Pro Glu Ala Leu Phe Phe Val
65                70                75                80

Gln Phe Glu Lys Gly Glu Ser Tyr Phe His Leu His Val Leu Val Glu
             85                90                95

Thr Thr Gly Val Lys Ser Met Val Leu Gly Arg Phe Leu Ser Gln Ile
             100               105               110

Arg Glu Lys Leu Val Gln Thr Ile Tyr Arg Gly Val Glu Pro Thr Leu
         115               120               125

Pro Asn Trp Phe Ala Val Thr Lys Thr Arg Asn Gly Ala Gly Gly Gly
         130               135               140

Asn Lys Val Val Asp Glu Cys Tyr Ile Pro Asn Tyr Leu Leu Pro Lys
145               150               155               160

Thr Gln Pro Glu Leu Gln Trp Ala Trp Thr Asn Met Glu Glu Tyr Ile
             165               170               175

Ser Ala Cys Leu Asn Leu Ala Glu Arg Lys Arg Leu Val Ala Gln His
         180               185               190

Leu Thr His Val Ser Gln Thr Gln Glu Gln Asn Lys Glu Asn Leu Asn
         195               200               205

Pro Asn Ser Asp Ala Pro Val Ile Arg Ser Lys Thr Ser Ala Arg Tyr
         210               215               220

FIG. 3B

Met Glu Leu Val Gly Trp Leu Val Asp Arg Gly Ile Thr Ser Glu Lys
225             230             235             240

Gln Trp Ile Gln Glu Asp Gln Ala Ser Tyr Ile Ser Phe Asn Ala Ala
        245             250             255

Ser Asn Ser Arg Ser Gln Ile Lys Ala Ala Leu Asp Asn Ala Gly Lys
        260             265             270

Ile Met Ala Leu Thr Lys Ser Ala Pro Asp Tyr Leu Val Gly Pro Ser
    275             280             285

Leu Pro Ala Asp Ile Lys Thr Asn Arg Ile Tyr Arg Ile Leu Glu Leu
    290             295             300

Asn Gly Tyr Asp Pro Ala Tyr Ala Gly Ser Val Phe Leu Gly Trp Ala
305             310             315             320

Gln Lys Lys Phe Gly Lys Arg Asn Thr Ile Trp Leu Phe Gly Pro Ala
        325             330             335

Thr Thr Gly Lys Thr Asn Ile Ala Glu Ala Ile Ala His Ala Val Pro
        340             345             350

Phe Tyr Gly Cys Val Asn Trp Thr Asn Glu Asn Phe Pro Phe Asn Asp
        355             360             365

Cys Val Asp Lys Met Val Ile Trp Trp Glu Glu Gly Lys Met Thr Ala
    370             375             380

Lys Val Val Glu Ser Ala Lys Ala Ile Leu Gly Gly Ser Lys Val Arg
385             390             395             400

FIG. 3C

Val Asp Gln Lys Cys Lys Ser Ser Ala Gln Ile Asp Pro Thr Pro Val
    405     410     415

Ile Val Thr Ser Asn Thr Asn Met Cys Ala Val Ile Asp Gly Asn Ser
    420     425     430

Thr Thr Phe Glu His Gln Gln Pro Leu Gln Asp Arg Met Phe Lys Phe
    435     440     445

Glu Leu Thr Arg Arg Leu Glu His Asp Phe Gly Lys Val Thr Lys Gln
    450     455     460

Glu Val Lys Glu Phe Phe Arg Trp Ala Ser Asp His Val Thr Glu Val
465     470     475     480

Ala His Glu Phe Tyr Val Arg Lys Gly Gly Ala Ser Lys Arg Pro Ala
    485     490     495

Pro Asp Asp Ala Asp Ile Ser Glu Pro Lys Arg Ala Cys Pro Ser Val
    500     505     510

Ala Asp Pro Ser Thr Ser Asp Ala Glu Gly Ala Pro Val Asp Phe Ala
    515     520     525

Asp Arg Tyr Gln Asn Lys Cys Ser Arg His Ala Gly Met Ile Gln Met
    530     535     540

Leu Phe Pro Cys Lys Thr Cys Glu Arg Met Asn Gln Asn Phe Asn Ile
545     550     555     560

Cys Phe Thr His Gly Val Arg Asp Cys Leu Glu Cys Phe Pro Gly Val
    565     570     575

FIG. 3D

Ser Glu Ser Gln Pro Val Val Arg Lys Lys Thr Tyr Arg Lys Leu Cys
        580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
        610                 615                 620

METHOD FOR DETECTING ADENO-ASSOCIATED VIRUS

CROSS-REFERENCE TO RELATED APPLICATIONS

This is a continuation of U.S. patent application Ser. No. 10/291,583, filed Nov. 12, 2002, now abandoned, which claims the benefit under 35 USC 119(e) of U.S. provisional patent application No. 60/386,675, filed Jun. 5, 2002. U.S. provisional patent application No. 60/377,066, filed May 1, 2002, U.S. provisional patent application No. 60/341,117, filed Dec. 17, 2001, and U.S. provisional patent application No. 60/350,607, filed Nov. 13, 2001. These applications are incorporated by reference herein.

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene therapy. To date, there have been 6 different serotypes of AAVs isolated from human or non-human primates (NHP) and well characterized. Among them, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B.

What are desirable are AAV-based constructs for gene delivery.

SUMMARY OF THE INVENTION

In one aspect, the invention provides a novel method of detecting and identifying AAV sequences from cellular DNAs of various human and non-human primate (NHP) tissues using bioinformatics analysis, PCR based gene amplification and cloning technology, based on the nature of latency and integration of AAVs in the absence of helper virus co-infection.

In another aspect, the invention provides method of isolating novel AAV sequences detected using the above described method of the invention. The invention further comprise methods of generating vectors based upon these novel AAV serotypes, for serology and gene transfer studies solely based on availability of capsid gene sequences and structure of rep/cap gene junctions.

In still another aspect, the invention provides a novel method for performing studies of serology, epidemiology, biodistribution and mode of transmission, using reagents according to the invention, which include generic sets of primers/probes and quantitative real time PCR.

In yet another aspect, the invention provides a method of isolating complete and infectious genomes of novel AAV serotypes from cellular DNA of different origins using RACE and other molecular techniques.

In a further aspect, the invention provides a method of rescuing novel serotypes of AAV genomes from human and NHP cell lines using adenovirus helpers of different origins.

In still a further aspect, the invention provides novel AAV serotypes, vectors containing same, and methods of using same.

These and other aspects of the invention will be readily apparent from the following detailed description of the invention.

BRIEF DESCRIPTION OF THE DRAWINGS

FIGS. 2A through 2M are an alignment of the amino acid sequences of the proteins of the vp1 capsid proteins of previously published AAV serotypes 1 [vp1 capsid proteins of previously published AAV serotypes 1 [SEQ ID NO:64], AAV2 [SEQ ID NO:70], AAV3 [SEQ ID NO: 71], AAV4 [SEQ ID NO:63], AAV5 [SEQ ID NO:114], and AAV6 [SEQ ID NO:65] and novel AAV sequences of the invention, including: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], 42-12 [SEQ ID NO: 113]. Novel serotypes AAV8 [SEQ ID NO:95] and AAV9 [SEQ ID NO:100] are the subject of co-filed patent applications.

FIGS. 3A through 3D provide the amino acid sequences of the AAV7 rep proteins [SEQ ID NO:3].

DETAILED DESCRIPTION OF THE INVENTION

Figure 1B:
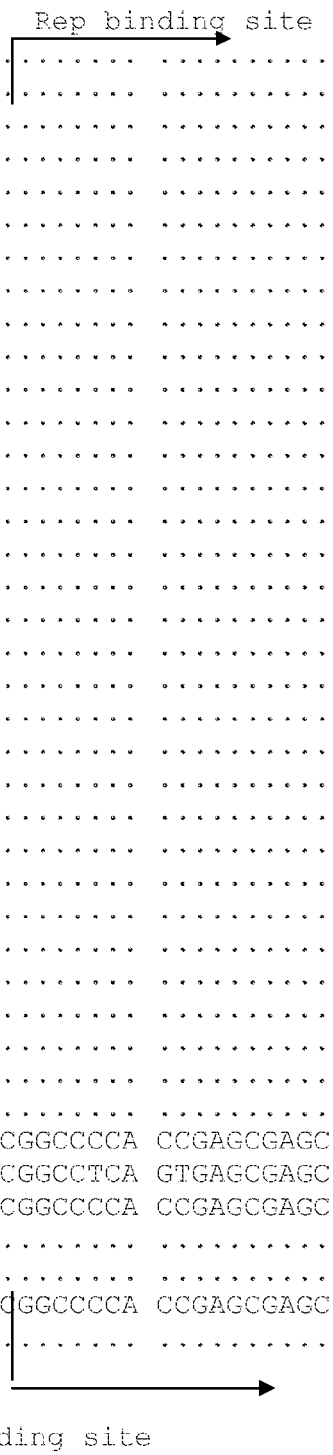
FIGS. 1A through 1AAAR provide an alignment of the nucleic acid sequences encoding at least the cap proteins for the AAV serotypes. The full-length sequences including the ITRs, the rep region, and the capsid region are provided for novel AAV serotype 7 [SEQ ID NO:1], and for previously published AAV1 [SEQ ID NO:6], AAV2 [SEQ ID NO:7]; and AAV3 [SEQ ID NO:8]. Novel AAV serotypes AAV8 [SEQ ID NO:4] and AAV9 [SEQ ID NO:5] are the subject of co-filed applications. The other novel clones of the invention provided in this alignment include: 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], 44.2 [SEQ ID NO: 59]. The nucleotide sequences of the signature regions of AAV10 [SEQ ID NO: 117], AAV11 [SEQ ID NO: 118] and AAV12 [SEQ ID NO:119] are provided in this figure. Critical landmarks in the structures of AAV genomes are shown. Gaps are demonstrated by dots. The 3' ITR of AAV1 [SEQ ID NO:6] is shown in the same configuration as in the published sequences. TRS represents terminal resolution site. Notice that AAV7 is the only AAV reported that uses GTG as the initiation codon for VP3.

In the present invention, the inventors have found a method which takes advantage of the ability of adeno-associated virus (AAV) to penetrate the nucleus, and, in the absence of a helper virus co-infection, to integrate into cellular DNA and establish a latent infection. This method utilizes a polymerase chain reaction (PCR)-based strategy for detection, identification and/or isolation of sequences of AAVs from DNAs from tissues of human and non-human primate origin as well as from other sources. Advantageously, this method is also suitable for detection, identification and/or isolation of other integrated viral and non-viral sequences, as described below.

The invention further provides nucleic acid sequences identified according to the methods of the invention. One such adeno-associated virus is of a novel serotype, termed herein serotype 7 (AAV7). Other novel adeno-associated virus serotypes provided herein include AAV10, AAV11, and AAV12. Still other novel AAV serotypes identified according to the methods of the invention are provided in the present specification. See, Figures and Sequence Listing, which is incorporated by reference.

Also provided are fragments of these AAV sequences. Among particularly desirable AAV fragments are the cap proteins, including the vp1, vp2, vp3, the hypervariable regions, the rep proteins, including rep 78, rep 68, rep 52, and rep 40, and the sequences encoding these proteins. Each of these fragments may be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV cap and/or rep sequences of the invention.

As described herein, alignments are performed using any of a variety of publicly or commercially available Multiple Sequence Alignment Programs, such as Clustal W™ accessible through Web Servers on the internet. Alternatively, Vector NTI® utilities are also used. There are also a number of algorithms known in the art which can be used to measure nucleotide sequence identity, including those contained in the programs described above. As another example, polynucleotide sequences can be compared using Fasta™, a program in GCG Version 6.1. The Fasta™ program provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Similar programs are available for amino acid sequences, e.g., the "Clustal X™" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The term "substantial homology" or "substantial similarity," when referring to amino acids or fragments thereof, indicates that, when optimally aligned with appropriate amino acid insertions or deletions with another amino acid, there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily deter mined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The AAV sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV sequences of the invention.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the terms Acomprising≡ and "including" and their variants are inclusive of other components, elements, integers, steps and the like. Conversely, the term "consisting" and its variants is exclusive of other components, elements, integers, steps and the like.

I. Methods of the Invention

A. Detection of Sequences Via Molecular Cloning

In one aspect, the invention provides a method of detecting and/or identifying target nucleic acid sequences in a sample. This method is particularly well suited for detection of viral sequences which are integrated into the chromosome of a cell, e.g., adeno-associated viruses (AAV) and retroviruses, among others. The specification makes reference to AAV, which is exemplified herein. However, based on this information, one of skill in the art may readily perform the methods of the invention on retroviruses [e.g., feline leukemia virus (FeLV), HTLVI and HTLVII], and lentivirinae [e.g., human immunodeficiency virus (HIV), simian immunodeficiency virus (SIV), feline immunodeficiency virus (FIV), equine infectious anemia virus, and spumaviriral)], among others. Further, the method of the invention may also be used for detection of other viral and non-viral sequences, whether integrated or non-integrated into the genome of the host cell.

As used herein, a sample is any source containing nucleic acids, e.g., tissue, tissue culture, cells, cell culture, and biological fluids including, without limitation, urine and blood. These nucleic acid sequences may be DNA or RNA from plasmids, natural DNA or RNA from any source, including bacteria, yeast, viruses, and higher organisms such as plants or animals. DNA or RNA is extracted from the sample by a variety of techniques known to those of skill in the art, such as those described by Sambrook, Molecular Cloning: A Laboratory Manual (New York: Cold Spring Harbor Laboratory). The origin of the sample and the method by which the nucleic acids are obtained for application of the method of the invention is not a limitation of the present invention. Optionally, the method of the invention can be performed directly on the source of DNA, or on nucleic acids obtained (e.g., extracted) from a source.

The method of the invention involves subjecting a sample containing DNA to amplification via polymerase chain reaction (PCR) using a first set of primers specific for a first region of double-stranded nucleic acid sequences, thereby obtaining amplified sequences.

As used herein, each of the Aregions≡ is predetermined based upon the alignment of the nucleic acid sequences of at least two serotypes (e.g., AAV) or strains (e.g., lentiviruses), and wherein each of said regions is composed of sequences having a 5' end which is highly conserved, a middle which is preferably, but necessarily, variable, and a 3' end which is highly conserved, each of these being conserved or variable relative to the sequences of the at least two aligned AAV serotypes. Preferably, the 5' and/or 3' end is highly conserved over at least about 9, and more preferably, at least 18 base pairs (bp). However, one or both of the sequences at the 5= or 3= end may be conserved over more than 18 bp, more than 25 bp, more than 30 bp, or more than 50 bp at the 5' end. With respect to the variable region, there is no requirement for conserved sequences, these sequences may be relatively conserved, or may have less than 90, 80, or 70% identity among the aligned serotypes or strains.

Each of the regions may span about 100 bp to about 10 kilobase pairs in length. However, it is particularly desirable that one of the regions is a Asignature region≡ i.e., a region which is sufficiently unique to positively identify the amplified sequence as being from the target source. For example, in one embodiment, the first region is about 250 bp in length, and is sufficiently unique among known AAV sequences, that it positively identifies the amplified region as being of AAV origin. Further, the variable sequences within this region are sufficiently unique that can be used to identify the serotype from which the amplified sequences originate. Once amplified (and thereby detected), the sequences can be identified by performing conventional restriction digestion and comparison to restriction digestion patterns for this region in any of AAV1, AAV2, AAV3, AAV4, AAV5, or AAV6, or that of AAV7, AAV10, AAV11, AAV12, or any of the other novel serotypes identified by the invention, which is predetermined and provided by the present invention.

Given the guidance provided herein, one of skill in the art can readily identify such regions among other integrated viruses to permit ready detection and identification of these sequences. Thereafter, an optimal set of generic primers located within the highly conserved ends can be designed and tested for efficient amplification of the selected region from samples. This aspect of the invention is readily adapted to a diagnostic kit for detecting the presence of the target sequence (e.g., AAV) and for identifying the AAV serotype, using standards which include the restriction patterns for the AAV serotypes described herein or isolated using the techniques described herein. For example, quick identification or molecular serotyping of PCR products can be accomplished by digesting the PCR products and comparing restriction patterns.

Thus, in one embodiment, the "signature region" for AAV spans about by 2800 to about 3200 of AAV 1 [SEQ ID NO:6], and corresponding base pairs in AAV 2, AAV3, AAV4, AAV5, and AAV6. More desirably, the region is about 250 bp, located within by 2886 to about 3143 bp of AAV 1 [SEQ ID NO:6], and corresponding base pairs in AAV 2 [SEQ ID NO:7], AAV3 [SEQ ID NO8], and other AAV serotypes. See, FIG. 1. To permit rapid detection of AAV in the sample, primers which specifically amplify this signature region are utilized. However, the present invention is not limited to the exact sequences identified herein for the AAV signature region, as one of skill in the art may readily alter this region to encompass a shorter fragment, or a larger fragment of this signature region.

The PCR primers are generated using techniques known to those of skill in the art. Each of the PCR primer sets is composed of a 5' primer and a 3' primer. See, e.g., Sambrook et al, cited herein. The term "primer" refers to an oligonucleotide which acts as a point of initiation of synthesis when placed under conditions in which synthesis of a primer extension product which is complementary to a nucleic acid strand is induced. The primer is preferably single stranded. However, if a double stranded primer is utilized, it is treated to separate its strands before being used to prepare extension products. The primers may be about 15 to 25 or more nucleotides, and preferably at least 18 nucleotides. However, for certain applications shorter nucleotides, e.g., 7 to 15 nucleotides are utilized.

The primers are selected to be sufficiently complementary to the different strands of each specific sequence to be amplified to hybridize with their respective strands. Therefore, the primer sequence need not reflect the exact sequence of the region being amplified. For example, a non-complementary nucleotide fragment may be attached to the 5' end of the primer, with the remainder of the primer sequence being completely complementary to the strand. Alternatively, non-complementary bases or longer sequences can be interspersed into the primer, provided that the primer sequence has sufficient complementarity with the sequence of the strand to be amplified to hybridize therewith and form a template for synthesis of the extension product of the other primer.

The PCR primers for the signature region according to the invention are based upon the highly conserved sequences of two or more aligned sequences (e.g., two or more AAV serotypes). The primers can accommodate less than exact identity among the two or more aligned AAV serotypes at the 5' end or in the middle. However, the sequences at the 3' end of the primers correspond to a region of two or more aligned AAV serotypes in which there is exact identity over at least five, preferably, over at least nine base pairs, and more preferably, over at least 18 base pairs at the 3' end of the primers. Thus, the 3' end of the primers is composed of sequences with 100% identity to the aligned sequences over at least five nucleotides. However, one can optionally utilize one, two, or more degenerate nucleotides at the 3' end of the primer.

For example, the primer set for the signature region of AAV was designed based upon a unique region within the AAV capsid, as follows. The 5' primer was based upon nt 2867-2891 of AAV2 [SEQ ID NO:7], 5'-GGTAATTCCTCCG-GAAATTGGCATT3'. See, FIG. 1. The 3' primer was designed based upon nt 3096-3122 of AAV2 [SEQ ID NO:7], 5'-GACTCATCAACAACAACTGGGGATTC-3'. However, one of skill in the art may have readily designed the primer set based upon the corresponding regions of AAV 1, AAV3, AAV4, AAV5, AAV6, or based upon the information provided herein, AAV7, AAV10, AAV11, AAV12, or another novel AAV of the invention. In addition, still other primer sets can be readily designed to amplify this signature region, using techniques known to those of skill in the art.

B. Isolation of Target Sequences

As described herein, the present invention provides a first primer set which specifically amplifies the signature region of the target sequence, e.g., an AAV serotype, in order to permit detection of the target. In a situation in which further sequences are desired, e.g., if a novel AAV serotype is identified, the signature region may be extended. Thus, the invention may further utilize one or more additional primer sets.

Suitably, these primer sets are designed to include either the 5' or 3' primer of the first primer set and a second primer unique to the primer set, such that the primer set amplifies a region 5' or 3' to the signature region which anneals to either the 5' end or the 3' end of the signature region. For example, a first primer set is composed of a 5' primer, P1 and a 3' primer P2 to amplify the signature region. In order to extend the signature region on its 3' end, a second primer set is composed of primer P1 and a 3' primer P4, which amplifies the signature region and contiguous sequences downstream of the signature region. In order to extend the signature region on its 5' end, a third primer set is composed of a 5' primer, P5, and primer P2, such that the signature region and contiguous sequences upstream of the signature region are amplified. These extension steps are repeated (or performed at the same time), as needed or desired. Thereafter, the products results from these amplification steps are fused using conventional steps to produce an isolated sequence of the desired length.

The second and third primer sets are designed, as with the primer set for the signature region, to amplify a region having highly conserved sequences among the aligned sequences. Reference herein to the term "second" or "third" primer set is for each of discussion only, and without regard to the order in which these primers are added to the reaction mixture, or used for amplification. The region amplified by the second primer set is selected so that upon amplification it anneals at its 5' end to the 3' end of the signature region. Similarly, the region amplified by the third primer set is selected so that upon amplification it anneals at its 3' end anneals to the 5' end of the signature region. Additional primer sets can be designed such that the regions which they amplify anneal to the either the 5' end or the 3' end of the extension products formed by the second or third primer sets, or by subsequent primer sets.

For example, where AAV is the target sequence, a first set of primers (P1 and P2) are used to amplify the signature region from the sample. In one desirable embodiment, this signature region is located within the AAV capsid. A second set of primers (P1 and P4) is used to extend the 3' end of the signature region to a location in the AAV sequence which is just before the AAV 3' ITR, i.e., providing an extension product containing the entire 3' end of the AAV capsid when using the signature region as an anchor. In one embodiment, the P4 primer corresponds to nt 4435 to 4462 of AAV2 [SEQ ID NO:7], and corresponding sequences in the other AAV serotypes. This results in amplification of a region of about 1.6 kb, which contains the 0.25 kb signature region. A third set of primers (P3 and P2) is used to extend the 5' end of signature region to a location in the AAV sequences which is in the 3' end of the rep genes, i.e., providing an extension product containing the entire 5' end of the AAV capsid when using the signature region as an anchor. In one embodiment, the P3 primer corresponds to nt 1384 to 1409 of AAV2 [SEQ ID NO:7], and corresponding sequences in the other AAV serotypes. This results in amplification of a region of about 1.7 kb, which contains the 0.25 kb signature region. Optionally, a fourth set of primers are used to further extend the extension product containing the entire 5' end of the AAV capsid to also include the rep sequences. In one embodiment, the primer designated P5 corresponds to nt 108 to 133 of AAV2 [SEQ ID NO:7], and corresponding sequences in the other AAV serotypes and is used in conjunction with the P2 primer.

Following completion of the desired number of extension steps, the various extension products are fused, making use of the signature region as an anchor or marker, to construct an intact sequence. In the example provided herein, AAV sequences containing, at a minimum, an intact AAV cap gene are obtained. Larger sequences may be obtained, depending upon the number of extension steps performed.

Suitably, the extension products are assembled into an intact AAV sequence using methods known to those of skill in the art. For example, the extension products may be digested with DraIII, which cleaves at the DraIII site located within the signature region, to provide restriction fragments which are re-ligated to provide products containing (at a minimum) an intact AAV cap gene. However, other suitable techniques for assembling the extension products into an intact sequence may be utilized. See, generally, Sambrook et al, cited herein.

As an alternative to the multiple extension steps described above, another embodiment of the invention provides for direct amplification of a 3.1 kb fragment which allows isolation of full-length cap sequences. To directly amplify a 3.1 kb full-length cap fragment from NHP tissue and blood DNAs, two other highly conserved regions were identified in AAV genomes for use in PCR amplification of large fragments. A primer within a conserved region located in the middle of the rep gene is utilized (AV1ns: 5' GCTGCGTCAACTGGAC-CAATGAGAAC 3', nt of SEQ ID NO:6) in combination with the 3' primer located in another conserved region downstream of the Cap gene (AV2cas: 5' CGCAGAGACCAAAGT-TCAACTGAAACGA 3', SEQ ID NO: 7) for amplification of AAV sequences including the full-length AAV cap. Typically, following amplification, the products are cloned and sequence analysis is performed with an accuracy of 99.9%. Using this method, the inventors have isolated at least 50 capsid clones which have subsequently been characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5). These clones are identified elsewhere in the specification, together with the species of animal from which they were identified and the tissues in that animal these novel sequences have been located.

C. Alternative Method for Isolating Novel AAV

In another aspect, the invention provides an alternative method for isolating novel AAV from a cell. This method involves infecting the cell with a vector which provides helper functions to the AAV; isolating infectious clones containing AAV; sequencing the isolated AAV; and comparing the sequences of the isolated AAV to known AAV serotypes, whereby differences in the sequences of the isolated AAV and known AAV serotypes indicates the presence of a novel AAV.

In one embodiment, the vector providing helper functions provides essential adenovirus functions, including, e.g., E1a, E1b, E2a, E4ORF6. In one embodiment, the helper functions are provided by an adenovirus. The adenovirus may be a wild-type adenovirus, and may be of human or non-human origin, preferably non-human primate (NHP) origin. The DNA sequences of a number of adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified human types [see, e.g., Horwitz, cited above]. Similarly adenoviruses known to infect non-human animals (e.g., chimpanzees) may also be employed in the vector constructs of this invention. See, e.g., U.S. Pat. No. 6,083,716. In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. No. 5,871,982 and U.S. Pat. No. 6,251,677, which describe a hybrid Ad/AAV virus. The selection of the adenovirus type is not anticipated to limit the following invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

In another alternative, infectious AAV may be isolated using genome walking technology (Siebert et al., 1995, *Nucleic Acid Research*, 23:1087-1088, Friezner-Degen et al., 1986, *J. Biol. Chem.* 261:6972-6985, BD Biosciences Clontech, Palo Alto, Calif.). Genome walking is particularly well suited for identifying and isolating the sequences adjacent to the novel sequences identified according to the method of the invention. For example, this technique may be useful for isolating inverted terminal repeat (ITRs) of the novel AAV serotype, based upon the novel AAV capsid and/or rep sequences identified using the methods of the invention. This technique is also useful for isolating sequences adjacent to other AAV and non-AAV sequences identified and isolated according to the present invention. See, Examples 3 and 4.

The methods of the invention may be readily used for a variety of epidemiology studies, studies of biodistribution, monitoring of gene therapy via AAV vectors and vector derived from other integrated viruses. Thus, the methods are well suited for use in pre-packaged kits for use by clinicians, researchers, and epidemiologists.

II. Diagnostic Kit

In another aspect, the invention provides a diagnostic kit for detecting the presence of a known or unknown adeno-associated virus (AAV) in a sample. Such a kit may contain a first set of 5' and 3' PCR primers specific for a signature region of the AAV nucleic acid sequence. Alternatively, or additionally, such a kit can contain a first set of 5' and 3' PCR primers specific for the 3.1 kb fragment which includes the full-length AAV capsid nucleic acid sequence identified herein (e.g., the AV1 ns and AV2cas primers.) Optionally, a kit of the invention may further contain two or more additional sets of 5' and 3' primers, as described herein, and/or PCR probes. These primers and probes are used according to the present invention amplify signature regions of each AAV serotype, e.g., using quantitative PCR.

The invention further provides a kit useful for identifying an AAV serotype detected according to the method of the invention and/or for distinguishing novel AAV from known AAV. Such a kit may further include one or more restriction enzymes, standards for AAV serotypes providing their "signature restriction enzyme digestions analyses", and/or other means for determining the serotype of the AAV detected.

In addition, kits of the invention may include, instructions, a negative and/or positive control, containers, diluents and buffers for the sample, indicator charts for signature comparisons, disposable gloves, decontamination instructions, applicator sticks or containers, and sample preparator cups, as well as any desired reagents, including media, wash reagents and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

The kits provided by the present invention are useful for performing the methods described herein, and for study of biodistribution, epidemiology, mode of transmission of novel AAV serotypes in human and NHPs.

Thus, the methods and kits of the invention permit detection, identification, and isolation of target viral sequences, particularly integrated viral sequences. The methods and kits are particularly well suited for use in detection, identification and isolation of AAV sequences, which may include novel AAV serotypes.

In one notable example, the method of the invention facilitated analysis of cloned AAV sequences by the inventors, which revealed heterogeneity of proviral sequences between cloned fragments from different animals, all of which were distinct from the known six AAV serotypes, with the majority of the variation localized to hypervariable regions of the capsid protein. Surprising divergence of AAV sequences was noted in clones isolated from single tissue sources, such as lymph node, from an individual rhesus monkey. This heterogeneity is best explained by apparent evolution of AAV sequence within individual animals due, in part, to extensive homologous recombination between a limited number of co-infecting parenteral viruses. These studies suggest sequence evolution of widely disseminated virus during the course of a natural AAV infection that presumably leads to the formation of swarms of quasispecies which differ from one another in the array of capsid hypervariable regions. This is the first example of rapid molecular evolution of a DNA virus in a way that formerly was thought to be restricted to RNA viruses.

Sequences of several novel AAV serotypes identified by the method of the invention and characterization of these serotypes is provided.

III. Novel AAV Serotypes

A. Nucleic Acid Sequences

Nucleic acid sequences of novel AAV serotypes identified by the methods of the invention are provided. See, SEQ ID NO:1, 9-59, and 117-120, which are incorporated by reference herein. See also, FIG. 1 and the sequence listing.

For novel serotype AAV7, the full-length sequences, including the AAV 5' ITRs, capsid, rep, and AAV 3' ITRs are provided in SEQ ID NO:1.

For other novel AAV serotypes of the invention, the approximately 3.1 kb fragment isolated according to the method of the invention is provided. This fragment contains sequences encoding full-length capsid protein and all or part of the sequences encoding the rep protein. These sequences include the clones identified below.

For still other novel AAV serotypes, the signature region encoding the capsid protein is provided. For example, the AAV10 nucleic acid sequences of the invention include those illustrated in FIG. 1 [See, SEQ ID NO:117, which spans 255 bases]. The AAV11 nucleic acid sequences of the invention include the DNA sequences illustrated in FIG. 1 [See, SEQ ID NO:118 which spans 258 bases]. The AAV12 nucleic acid sequences of the invention include the DNA sequences illustrated in FIG. 1 [See, SEQ ID NO:119, which consists of 255 bases]. Using the methodology described above, further AAV10, AAV11 and AAV12 sequences can be readily identified and used for a variety of purposes, including those described for AAV7 and the other novel serotypes herein.

Figure 1G:
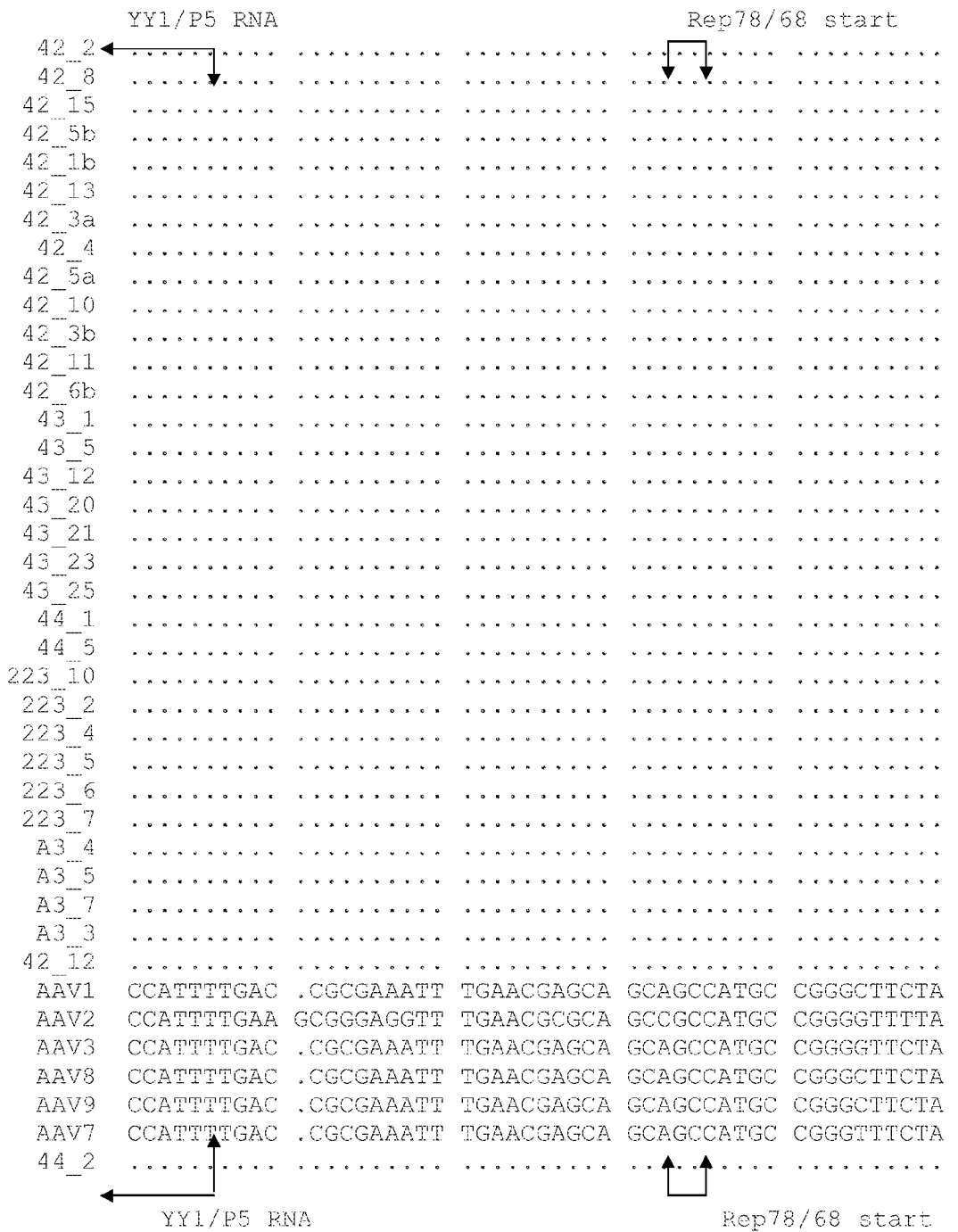
Figure 1R:
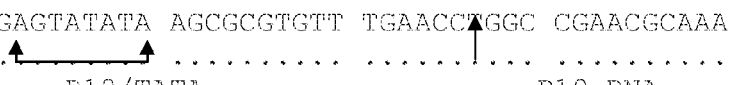

FIG. 1 provides the non-human primate (NHP) AAV nucleic acid sequences of the invention in an alignment with the previously published AAV serotypes, AAV 1 [SEQ ID NO:6], AAV2 [SEQ ID NO:7], and AAV3 [SEQ ID NO:8]. These novel NHP sequences include those provided in the following Table I, which are identified by clone number:

TABLE 1

| AAV Cap Sequence | Clone Number | Source Species | Tissue | SEQ ID NO (DNA) |
|---|---|---|---|---|
| Rh.1 | Clone 9 (AAV9) | Rhesus | Heart | 5 |
| Rh.2 | Clone 43.1 | Rhesus | MLN | 39 |
| Rh.3 | Clone 43.5 | Rhesus | MLN | 40 |
| Rh.4 | Clone 43.12 | Rhesus | MLN | 41 |
| Rh.5 | Clone 43.20 | Rhesus | MLN | 42 |
| Rh.6 | Clone 43.21 | Rhesus | MLN | 43 |
| Rh.7 | Clone 43.23 | Rhesus | MLN | 44 |
| Rh.8 | Clone 43.25 | Rhesus | MLN | 45 |
| Rh.9 | Clone 44.1 | Rhesus | Liver | 46 |
| Rh.10 | Clone 44.2 | Rhesus | Liver | 59 |
| Rh.11 | Clone 44.5 | Rhesus | Liver | 47 |
| Rh.12 | Clone 42.1B | Rhesus | MLN | 30 |
| Rh.13 | 42.2 | Rhesus | MLN | 9 |
| Rh.14 | Clone 42.3A | Rhesus | MLN | 32 |
| Rh.15 | Clone 42.3B | Rhesus | MLN | 36 |
| Rh.16 | Clone 42.4 | Rhesus | MLN | 33 |
| Rh.17 | Clone 42.5A | Rhesus | MLN | 34 |
| Rh.18 | Clone 42.5B | Rhesus | MLN | 29 |
| Rh.19 | Clone 42.6B | Rhesus | MLN | 38 |
| Rh.20 | Clone 42.8 | Rhesus | MLN | 27 |
| Rh.21 | Clone 42.10 | Rhesus | MLN | 35 |
| Rh.22 | Clone 42.11 | Rhesus | MLN | 37 |
| Rh.23 | Clone 42.12 | Rhesus | MLN | 58 |
| Rh.24 | Clone 42.13 | Rhesus | MLN | 31 |
| Rh.25 | Clone 42.15 | Rhesus | MLN | 28 |
| Rh.26 | Clone 223.2 | Rhesus | Liver | 49 |
| Rh.27 | Clone 223.4 | Rhesus | Liver | 50 |
| Rh.28 | Clone 223.5 | Rhesus | Liver | 51 |
| Rh.29 | Clone 223.6 | Rhesus | Liver | 52 |
| Rh.30 | Clone 223.7 | Rhesus | Liver | 53 |
| Rh.31 | Clone 223.10 | Rhesus | Liver | 48 |
| Rh.32 | Clone C1 | Rhesus | Spleen, Duo, Kid & Liver | 19 |
| Rh.33 | Clone C3 | Rhesus | | 20 |
| Rh.34 | Clone C5 | Rhesus | | 21 |
| Rh.35 | Clone F1 | Rhesus | Liver | 22 |
| Rh.36 | Clone F3 | Rhesus | | 23 |
| Rh.37 | Clone F5 | Rhesus | | 24 |
| Cy.1 | Clone 1.3 | Cyno | Blood | 14 |
| Cy.2 | Clone 13.3B | Cyno | Blood | 15 |
| Cy.3 | Clone 24.1 | Cyno | Blood | 16 |
| Cy.4 | Clone 27.3 | Cyno | Blood | 17 |
| Cy.5 | Clone 7.2 | Cyno | Blood | 18 |
| Cy.6 | Clone 16.3 | Cyno | Blood | 10 |
| bb.1 | Clone 29.3 | Baboon | Blood | 11 |
| bb.2 | Clone 29.5 | Baboon | Blood | 13 |
| Ch.1 | Clone A3.3 | Chimp | Blood | 57 |
| Ch.2 | Clone A3.4 | Chimp | Blood | 54 |
| Ch.3 | Clone A3.5 | Chimp | Blood | 55 |
| Ch.4 | Clone A3.7 | Chimp | Blood | 56 |

A novel NHP clone was made by splicing capsids fragments of two chimp adenoviruses into an AAV2 rep construct. This new clone, A3.1, is also termed Ch.5 [SEQ ID NO:20]. Additionally, the present invention includes two human AAV sequences, termed H6 [SEQ ID NO:25] and H2 [SEQ ID NO:26].

The AAV nucleic acid sequences of the invention further encompass the strand which is complementary to the strands provided in the sequences provided in FIG. 1 and the Sequence Listing [SEQ ID NO:1, 9-59, 117-120], nucleic acid sequences, as well as the RNA and cDNA sequences corresponding to the sequences provided in FIG. 1 and the Sequence Listing [SEQ ID NO:1, 9-59, 117-120], and their complementary strands. Also included in the nucleic acid sequences of the invention are natural variants and engineered modifications of the sequences of FIG. 1 and the Sequence Listing [SEQ ID NO:1, 9-59, 117-120], and their complementary strands. Such modifications include, for example, labels which are known in the art, methylation, and substitution of one or more of the naturally occurring nucleotides with a degenerate nucleotide.

Further included in this invention are nucleic acid sequences which are greater than 85%, preferably at least about 90%, more preferably at least about 95%, and most preferably at least about 98 to 99% identical or homologous to the sequences of the invention, including FIG. 1 and the Sequence Listing [SEQ ID NO:1, 9-59, 117-120]. These terms are as defined herein.

Also included within the invention are fragments of the novel AAV sequences identified by the method described herein. Suitable fragments are at least 15 nucleotides in length, and encompass functional fragments, i.e., fragments which are of biological interest. In one embodiment, these fragments are fragments of the novel sequences of FIG. 1 and the Sequence Listing [SEQ ID NO:1, 9-59, 117-120], their complementary strands, cDNA and RNA complementary thereto.

Examples of suitable fragments are provided with respect to the location of these fragments on AAV1, AAV2, or AAV7. However, using the alignment provided herein (obtained using the Clustal W program at default settings), or similar techniques for generating an alignment with other novel serotypes of the invention, one of skill in the art can readily identify the precise nucleotide start and stop codons for desired fragments.

Examples of suitable fragments include the sequences encoding the three variable proteins (vp) of the AAV capsid which are alternative splice variants: vp1 [e.g., nt 825 to 3049 of AAV7, SEQ ID NO: 1]; vp2 [e.g., nt 1234-3049 of AAV7, SEQ ID NO: 1]; and vp 3 [e.g., nt 1434-3049 of AAV7, SEQ ID NO:1]. It is notable that AAV7 has an unusual GTG start codon. With the exception of a few house-keeping genes, such a start codon has not previously been reported in DNA viruses. The start codons for vp1, vp2 and vp3 for other AAV serotypes have been believed to be such that they permit the cellular mechanism of the host cell in which they reside to produce vp1, vp2 and vp3 in a ratio of 10%:10%:80%, respectively, in order to permit efficient assembly of the virion. However, the AAV7 virion has been found to assemble efficiently even with this rare GTG start codon. Thus, the inventors anticipate this it is desirable to alter the start codon of the vp3 of other AAV serotypes to contain this rare GTG start codon, in order to improve packaging efficiency, to alter the virion structure and/or to alter location of epitopes (e.g., neutralizing antibody epitopes) of other AAV serotypes. The start codons may be altered using conventional techniques including, e.g., site directed mutagenesis. Thus, the present invention encompasses altered AAV virions of any selected serotype, composed of a vp 3, and/or optionally, vp 1 and/or vp2 having start codons altered to GTG.

Other suitable fragments of AAV, include a fragment containing the start codon for the AAV capsid protein [e.g., nt 468 to 3090 of AAV7, SEQ ID NO:1, nt 725 to 3090 of AAV7, SEQ ID NO: 1, and corresponding regions of the other AAV serotypes]. Still other fragments of AAV7 and the other novel AAV serotypes identified using the methods described herein include those encoding the rep proteins, including rep 78 [e.g., initiation codon 334 of FIG. 1 for AAV7], rep 68 [initiation codon nt 334 of FIG. 1 for AAV7], rep 52 [initiation codon 1006 of FIG. 1 for AAV7], and rep 40 [initiation codon 1006 of FIG. 1 for AAV7] Other fragments of interest may include the AAV 5' inverted terminal repeats ITRs, [nt 1 to 107 of FIG. 1 for AAV7]; the AAV 3' ITRs [nt 4704 to 4721 of FIG. 1 for AAV7], P19 sequences, AAV P40 sequences, the rep binding site, and the terminal resolute site (TRS). Still other suitable fragments will be readily apparent to those of skill in the art. The corresponding regions in the other novel serotypes of the invention can be readily determined by reference to FIG. 1, or by utilizing conventional alignment techniques with the sequences provided herein.

In addition to including the nucleic acid sequences provided in the figures and Sequence Listing, the present invention includes nucleic acid molecules and sequences which are designed to express the amino acid sequences, proteins and peptides of the AAV serotypes of the invention. Thus, the invention includes nucleic acid sequences which encode the following novel AAV amino acid sequences: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113], and artificial AAV serotypes generated using these sequences and/or unique fragments thereof.

As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

B. AAV Amino Acid Sequences, Proteins and Peptides

The invention provides proteins and fragments thereof which are encoded by the nucleic acid sequences of the novel AAV serotypes identified herein, including, e.g., AAV7 [nt 825 to 3049 of AAV7, SEQ ID NO: 1] the other novel serotypes provided herein. Thus, the capsid proteins of the novel serotypes of the invention, including: H6 [SEQ ID NO: 25], H2 [SEQ ID NO: 26], 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], and 44.2 [SEQ ID NO: 59], can be readily generated using conventional techniques from the open reading frames provided for the above-listed clones.

The invention further encompasses AAV serotypes generated using sequences of the novel AAV serotypes of the invention, which are generated using synthetic, recombinant or other techniques known to those of skill in the art. The invention is not limited to novel AAV amino acid sequences, peptides and proteins expressed from the novel AAV nucleic acid sequences of the invention and encompasses amino acid sequences, peptides and proteins generated by other methods known in the art, including, e.g., by chemical synthesis, by other synthetic techniques, or by other methods. For example, the sequences of any of C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113] by be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The sequences of many of the capsid proteins of the invention are provided in an alignment in FIG. 2 and/or in the Sequence Listing, SEQ ID NO: 2 and 60 to 115, which is incorporated by reference herein. The AAV capsid is composed of three proteins, vp1, vp2 and vp3, which are alternative splice variants. The full-length sequence provided in these figures is that of vp1. Based on the numbering of the AAV7 capsid [SEQ ID NO:2], the sequences of vp2 span amino acid 138-737 of AAV7 and the sequences of vp3 span amino acids 203-737 of AAV7. With this information, one of skill in the art can readily determine the location of the vp2 and vp3 proteins for the other novel serotypes of the invention.

Other desirable proteins and fragments of the capsid protein include the constant and variable regions, located between hypervariable regions (HPV) and the sequences of the HPV regions themselves. An algorithm developed to determine areas of sequence divergence in AAV2 has yielded 12 hypervariable regions (HVR) of which 5 overlap or are part of the four previously described variable regions. [Chiorini et al, *J. Virol,* 73:1309-19 (1999); Rutledge et al, *J. Virol.,* 72:309-319] Using this algorithm and/or the alignment techniques described herein, the HVR of the novel AAV serotypes are determined. For example, with respect to the number of the AAV2 vp1 [SEQ ID NO:70], the HVR are located as follows: HVR1, aa 146-152; HVR2, aa 182-186; HVR3, aa 262-264; HVR4, aa 381-383; HVR5, aa 450-474; HVR6, aa 490-495; HVR7, aa500-504; HVR8, aa 514-522; HVR9, aa 534-555; HVR10, aa 581-594; HVR11, aa 658-667; and HVR12, aa 705-719. Utilizing an alignment prepared in accordance with conventional methods and the novel sequences provided herein [See, e.g., FIG. 2], one can readily determine the location of the HVR in the novel AAV serotypes of the invention. For example, utilizing FIG. 2, one can readily determine that for AAV7 [SEQ ID NO:2]. HVR1 is located at aa 146-152; HVR2 is located at 182-187; HVR3 is located at aa 263-266, HVR4 is located at aa 383-385, HVR5 is located at aa 451-475; HVR6 is located at aa 491-496 of AAV7; HVR7 is located at aa 501-505; HVR8 is located at aa 513-521; HVR9 is located at 533-554; HVR10 is located at aa 583-596; HVR11 is located at aa 660-669; HVR12 is located at aa 707-721. Using the information provided herein, the HVRs for the other novel serotypes of the invention can be readily determined.

In addition, within the capsid, amino acid cassettes of identity have been identified. These cassettes are of particular interest, as they are useful in constructing artificial serotypes, e.g., by replacing a HVR1 cassette of a selected serotype with an HVR1 cassette of another serotype. Certain of these cassettes of identity are noted in FIG. 2. See, FIG. 2, providing the Clustal X alignment, which has a ruler is displayed below the sequences, starting at 1 for the first residue position. The line above the ruler is used to mark strongly conserved positions. Three characters (*, : , .) are used. "*" indicates positions which have a single, fully conserved residue. ":" indicates that a "strong" group is fully conserved "." Indicates that a "weaker" group is fully conserved. These are all the positively scoring groups that occur in the Gonnet Pam250 matrix. The strong groups are defined as a strong score >0.5 and the weak groups are defined as weak score <0.5.

Additionally, examples of other suitable fragments of AAV capsids include, with respect to the numbering of AAV2 [SEQ ID NO:70], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Still other desirable fragments include, for example, in AAV7, amino acids 1 to 184 of SEQ ID NO:2, amino acids 199 to 259; amino acids 274 to 446; amino acids 603 to 659; amino acids 670 to 706; amino acids 724 to 736; aa 185 to 198; aa 260 to 273; aa447 to 477; aa495 to 602; aa660 to 669; and aa707 to 723. Still other desirable regions, based on the numbering of AAV7 [SEQ ID NO:2], are selected from among the group consisting of aa 185 to 198; aa 260 to 273; aa447 to 477; aa495 to 602; aa660 to 669; and aa707 to 723. Using the alignment provided herein performed using the Clustal X program at default settings, or using other commercially or publicly available alignment programs at default settings, one of skill in the art can readily determine corresponding fragments of the novel AAV capsids of the invention.

Other desirable proteins are the AAV rep proteins [aa 1 to 623 of SEQ ID NO:3 for AAV7] and functional fragments thereof, including, e.g., aa 1 to 171, aa 172 to 372, aa 373 to 444, aa 445 to 623 of SEQ ID NO:3, among others. Suitably, such fragments are at least 8 amino acids in length. See, FIG. 3. Comparable regions can be identified in the proteins of the other novel AAV of the invention, using the techniques described herein and those which are known in the art. In addition, fragments of other desired lengths may be readily utilized. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

IV. Production of rAAV with Novel AAV Capsids

The invention encompasses novel, wild-type AAV serotypes identified by the invention, the sequences of which wild-type AAV serotypes are free of DNA and/or cellular material with these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

The molecules of the invention which contain sequences of a novel AAV serotype of the invention include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain sequences encoding a novel AAV capsid of the invention (e.g., AAV7 capsid, AAV 44-2 (rh.10), an AAV10 capsid, an AAV11 capsid, an AAV12 capsid), or a fragment of one or more of these AAV capsids. Alternatively, the vectors may contain the capsid protein, or a fragment thereof, itself.

Optionally, vectors of the invention may contain sequences encoding AAV rep proteins. Such rep sequences may be from the same AAV serotype which is providing the cap sequences. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are expressed from the same source as the cap sequences. In this embodiment, the rep sequences may be fused in frame to cap sequences of a different AAV serotype to form a chimeric AAV vector. Optionally, the vectors of the invention further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV serotype (e.g., AAV7 or another novel AAV). Alternatively, these vectors contain sequences encoding artificial capsids which contain one or more fragments of the AAV7 (or another novel AAV) capsid fused to heterologous AAV or non-AAV capsid proteins (or fragments thereof). These artificial capsid proteins are selected from non-contiguous portions of the AAV7 (or another novel AAV) capsid or from capsids of other AAV serotypes. For example, it may be desirable to modify the coding regions of one or more of the AAV vp1, e.g., in one or more of the hypervariable regions (i.e., HPV1-12), or vp2, and/or vp3. In another example, it may be desirable to alter the start codon of the vp3 protein to GTG. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 7 (or another novel AAV) capsid, or a portion thereof. Such a method involves culturing a host cell which contains a nucleic acid sequence encoding an adeno-associated virus (AAV) serotype 7 (or another novel AAV) capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV7 (or another novel AAV) capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.,* 70:520-532 (1993) and U.S. Pat. No. 5,478,745.

A. The Minigene

The minigene is composed of, at a minimum, a transgene and its regulatory sequences, and 5= and 3=AAV inverted terminal repeats (ITRs). It is this minigene which is packaged into a capsid protein and delivered to a selected host cell.

1. The transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78 (Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner which permits its transcription, translation and/or expression in a cell transfected with the plasmid vector or infected with the virus produced by the invention. As used herein, Aoperably linked≅ sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998);

immunoglobulin heavy chain; T cell receptor α chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5= and 3= ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 µg to about 100 µg DNA, and preferably about 10 to about 50 µg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of the novel AAV capsid protein (e.g., AAV7 or other novel AAV capsid or an artificial capsid protein comprising a fragment of one or more of these capsids) in the host cell and rep sequences of the same serotype as the serotype of the AAV ITRs found in the minigene. The AAV cap and rep sequences may be independently obtained from an AAV source as described above and may be introduced into the host cell in any manner known to one in the art as described above. Additionally, when pseudotyping a novel AAV capsid of the invention, the sequences encoding each of the essential rep proteins may be supplied by the same AAV serotype, or the sequences encoding the rep proteins may be supplied by different AAV serotypes (e.g., AAV1, AAV2, AAV3, AAV4, AAV5, AAV6, or one of the novel serotypes identified herein). For example, the rep78/68 sequences may be from AAV2, whereas the rep52/40 sequences may from AAV1.

In one embodiment, the host cell stably contains the capsid protein under the control of a suitable promoter, such as those described above. Most desirably, in this embodiment, the capsid protein is expressed under the control of an inducible promoter.

In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, Eta, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the λ phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By Adenoviral DNA which expresses the E1a gene products, it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

D. Host Cells And Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The most desirable cells do not carry any adenovirus gene other than E1, E2a and/or E4 ORF6; nor do they contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6. Yet other cell lines can be constructed using the novel AAV rep and/or novel AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

These novel AAV-based vectors which are generated by one of skill in the art are beneficial for gene delivery to selected host cells and gene therapy patients since no neutralization antibodies to AAV7 have been found in the human population. Further, early studies show no neutralizing antibodies in cyno monkey and chimpanzee populations, and less than 15% cross-reactivity of AAV 7 in rhesus monkeys, the species from which the serotype was isolated. One of skill in the art may readily prepare other rAAV viral vectors containing the AAV7 capsid proteins provided herein using a variety of techniques known to those of skill in the art. One may similarly prepare still other rAAV viral vectors containing AAV7 sequence and AAV capsids of another serotype. Similar advantages are conferred by the vectors based on the other novel AAV of the invention.

Thus, one of skill in the art will readily understand that the AAV7 sequences of the invention can be readily adapted for use in these and other viral vector systems for in vitro, ex vivo or in vivo gene delivery. Similarly, one of skill in the art can readily select other fragments of the novel AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

V. Recombinant Viruses and Uses Thereof

Using the techniques described herein, one of skill in the art may generate a rAAV having a capsid of a novel serotype of the invention, or a novel capsid containing one or more novel fragments of an AAV serotype identified by the method of the invention. In one embodiment, a full-length capsid from a single serotype, e.g., AAV7 [SEQ ID NO: 2] can be utilized. In another embodiment, a full-length capsid may be generated which contains one or more fragments of a novel serotype of the invention fused in frame with sequences from another selected AAV serotype. For example, a rAAV may contain one or more of the novel hypervariable region sequences of an AAV serotype of the invention. Alternatively, the unique AAV serotypes of the invention may be used in constructs containing other viral or non-viral sequences.

It will be readily apparent to one of skill in the art one embodiment, that certain serotypes of the invention will be particularly well suited for certain uses. For example, vectors based on AAV7 capsids of the invention are particularly well suited for use in muscle; whereas vectors based on rh.10 (44-2) capsids of the invention are particularly well suited for use in lung. Uses of such vectors are not so limited and one of skill in the art may utilize these vectors for delivery to other cell types, tissues or organs. Further, vectors based upon other capsids of the invention may be used for delivery to these or other cells, tissues or organs.

A. Delivery of Transgene

In another aspect, the present invention provides a method for delivery of a transgene to a host which involves transfecting or infecting a selected host cell with a vector generated with the sequences of the AAV of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences which direct expression thereof and AAV capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W. C. Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with a selected AAV capsid proteins may precede or follow delivery of a gene via a vector with a different serotype AAV capsid protein. Similarly, the delivery of vector with other novel AAV capsid proteins of the invention may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV7 capsid proteins [SEQ ID NO:2], subsequently administered vectors may have capsid proteins selected from among the other serotypes, including AAV1, AAV2, AAV3A, AAV3B, AAV4, AAV6, AAV10, AAV11, and AAV12, or any of the other novel AAV capsids identified herein including, without limitation: A3.1, H2, H6, C1, C2, C5, A3-3, A3-7, A3-4, A3-5, 3.3b, 223.4, 223-5, 223-10, 223-2, 223-7, 223-6, 44-1, 44-5, 44-2, 42-15, 42-8, 42-13, 42-3A, 42-4, 42-5A, 42-1B, 42-5B, 43-1, 43-12, 43-5, 43-21, 43-25, 43-20, 24.1, 42.2, 7.2, 27.3, 16.3, 42.10, 42-3B, 42-11, F1, F5, F3, 42-6B, and/or 42-12.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 ml of solution containing concentrations of from about $1 \times 10^9$ to $1 \times 10^{16}$ genomes virus vector. A preferred human dosage may be about $1 \times 10^{13}$ to $1 \times 10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-I antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce Aself≈-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Alternatively, or in addition, the vectors of the invention may contain AAV sequences of the invention and a transgene encoding a peptide, polypeptide or protein which induces an immune response to a selected immunogen. For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Between the HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. In addition, a variety of modifications to these antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R. Amara, et al, Science, 292:69-74 (6 Apr. 2001). These proteins or subunits thereof may be delivered alone, or in combination via separate vectors or from a single vector.

The papovirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek=s disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, ieporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and *eikenella*; melioidosis; *salmonella; shigella; haemophilus; moraxella; H. ducreyi* (which causes chancroid); *brucella; Franisella tularensis* (which causes tularemia); *yersinia (pasteurella); streptobacillus moniliformis* and *spirillum*; Gram-positive bacilli include *listeria monocytogenes; erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fever, all of which are currently classified as Category A agents; *Coxiella burnetti* (Q fever); *Brucella* species (brucellosis), *Burkholderia mallei* (glanders), *Ricinus communis* and its toxin (ricin toxin), *Clostridium perfringens* and its toxin (epsilon toxin), *Staphylococcus* species and their toxins (enterotoxin B), all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of T cell receptors (TCRs) which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a nucleic acid molecule that encodes at least one of these polypeptides will elicit an immune response that will target T cells involved in scleroderma.

Optionally, vectors containing AAV sequences of the invention may be delivered using a prime-boost regimen. A variety of such regimens have been described in the art and may be readily selected. See, e.g., WO 00/11140, published Mar. 2, 2000, incorporated by reference.

Such prime-boost regimens typically involve the administration of a DNA (e.g., plasmid) based vector to prime the immune system to second, booster, administration with a traditional antigen, such as a protein or a recombinant virus carrying the sequences encoding such an antigen. In one embodiment, the invention provides a method of priming and boosting an immune response to a selected antigen by delivering a plasmid DNA vector carrying said antigen, followed by boosting, e.g., with a vector containing AAV sequences of the invention.

In one embodiment, the prime-boost regimen involves the expression of multiproteins from the prime and/or the boost vehicle. See, e.g., R. R. Amara, Science, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one or example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming vaccine may be administered at various sites in the body in a dose dependent manner, which depends on the antigen to which the desired immune response is being targeted. The invention is not limited to the amount or situs of injection(s) or to the pharmaceutical carrier. Rather, the priming step encompasses treatment regimens which include a single dose or dosage which is administered hourly, daily, weekly or monthly, or yearly. As an example, the mammals may receive one or two priming injection containing between about 10 µg to about 50 µg of plasmid in carrier. A desirable priming amount or dosage of the priming DNA vaccine composition ranges between about 1 µg to about 10,000 µg of the DNA vaccine. Dosages may vary from about 1 µg to 1000 µg DNA per kg of subject body weight. The amount or site of injection is desirably selected based upon the identity and condition of the mammal being vaccinated.

The dosage unit of the DNA vaccine suitable for delivery of the antigen to the mammal is described herein. The DNA vaccine is prepared for administration by being suspended or dissolved in a pharmaceutically or physiologically acceptable carrier such as isotonic saline, isotonic salts solution or other formulations which will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes.

Optionally, the priming step of this invention also includes administering with the priming DNA vaccine composition, a suitable amount of an adjuvant, such as are defined herein.

Preferably, a boosting composition is administered about 2 to about 27 weeks after administering the priming DNA vaccine to the mammalian subject. The administration of the boosting composition is accomplished using an effective amount of a boosting vaccine composition containing or capable of delivering the same antigen as administered by the priming DNA vaccine. The boosting composition may be composed of a recombinant viral vector derived from the same viral source or from another source. Alternatively, the "boosting composition" can be a composition containing the same antigen as encoded in the priming DNA vaccine, but in the form of a protein or peptide, which composition induces an immune response in the host. In another embodiment, the boosting vaccine composition includes a composition containing a DNA sequence encoding the antigen under the control of a regulatory sequence directing its expression in a mammalian cell, e.g., vectors such as well-known bacterial or viral vectors. The primary requirements of the boosting vaccine composition are that the antigen of the vaccine composition is the same antigen, or a cross-reactive antigen, as that encoded by the DNA vaccine.

Suitably, the vectors of the invention are also well suited for use in regimens which use non-AAV vectors as well as proteins, peptides, and/or other biologically useful therapeutic or immunogenic compounds. These regimens are particularly well suited to gene delivery for therapeutic poses and for immunization, including inducing protective immunity. Such uses will be readily apparent to one of skill in the art.

Further, a vector of the invention provides an efficient gene transfer vehicle which can deliver a selected transgene to a selected host cell in vivo or ex vivo even where the organism has neutralizing antibodies to one or more AAV serotypes. In one embodiment, the vector (e.g., an rAAV) and the cells are mixed ex vivo; the infected cells are cultured using conventional methodologies; and the transduced cells are re-infused into the patient. Further, the vectors of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

EXAMPLES

Example 1

PCR Amplification, Cloning and Characterization of Novel AAV Sequences

Tissues from nonhuman primates were screened for AAV sequences using a PCR method based on oligonucleotides to highly conserved regions of known AAVs. A stretch of AAV sequence spanning 2886 to 3143 bp of AAV1 [SEQ ID NO:6] was selected as a PCR amplicon in which a hypervariable region of the capsid protein (Cap) that is unique to each known AAV serotype, which is termed herein a "signature region," is flanked by conserved sequences. In later analysis, this signature region was shown to be located between conserved residues spanning hypervariable region 3.

An initial survey of peripheral blood of a number of non-human primate species revealed detectable AAV in a subset of animals from species such as rhesus macaques, cynomologous macaques, chimpanzees and baboons. However, there were no AAV sequences detected in some other species tested, including Japanese macaques, pig-tailed macaques and squirrel monkeys. A more extensive analysis of vector distribution was conducted in tissues of rhesus monkeys of the University of Pennsylvania and Tulane colonies recovered at necropsy. This revealed AAV sequence throughout a wide array of tissues.

A. Amplification of an AAV Signature Region

DNA sequences of AAV1-6 and AAVs isolated from Goose and Duck were aligned to each other using "Clustal W" at default settings. The alignment for AAV1-6, and including the information for the novel AAV7, is provided in FIG. 1. Sequence similarities among AAVs were compared.

In the line of study, a 257 bp region spanning 2886 bp to 3143 bp of AAV 1 [SEQ ID NO: 6], and the corresponding region in the genomes of AAV 2-6 genomes [See, FIG. 1], was identified by the inventors. This region is located with the AAV capsid gene and has highly conserved sequences among at both 5' and 3' ends and is relatively variable sequence in the middle. In addition, this region contains a DraIII restriction enzyme site (CACCACGTC, SEQ ID NO:15). The inventors have found that this region serves as specific signature for each known type of AAV DNA. In other words, following PCR reactions, digestion with endonucleases that are specific to each known serotypes and gel electrophoresis analysis, this regions can be used to definitively identify amplified DNA as being from serotype 1, 2, 3, 4, 5, 6, or another serotype.

The primers were designed, validated and PCR conditions optimized with AAV1, 2 and 5 DNA controls. The primers were based upon the sequences of AAV2: 5' primer, 1S: by 2867-2891 of AAV2 (SEQ ID NO:7) and 3' primer, 18 as, by 3095-3121 of AAV2 (SEQ ID NO:7).

Cellular DNAs from different tissues including blood, brain, liver, lung, testis, etc. of different rhesus monkeys were studied utilizing the strategy described above. The results revealed that DNAs from different tissues of these monkeys gave rise to strong PCR amplifications. Further restriction analyses of PCR products indicated that they were amplified from AAV sequences different from any published AAV sequences.

PCR products (about 255 bp in size) from DNAs of a variety of monkey tissues have been cloned and sequenced. Bioinformatics study of these novel AAV sequences indicated that they are novel AAV sequences of capsid gene and distinct from each other. FIG. 1 includes in the alignment the novel AAV signature regions for AAV10-12 [SEQ ID NO:117, 118 and 119, respectively]. Multiple sequence alignment analysis was performed using the Clustal W (1.81) program. The percentage of sequence identity between the signature regions of AAV 1-7 and AAV 10-12 genomes is provided below.

TABLE 2

Sequences for Analysis

| Sequence # | AAV Serotype | Size (bp) |
|---|---|---|
| 1 | AAV1 | 258 |
| 2 | AAV2 | 255 |
| 3 | AAV3 | 255 |
| 4 | AAV4 | 246 |
| 5 | AAV5 | 258 |
| 6 | AAV6 | 258 |
| 7 | AAV7 | 258 |
| 10 | AAV10 | 255 |
| 11 | AAV11 | 258 |
| 12 | AAV12 | 255 |

TABLE 3

Pairwise Alignment (Percentage of Identity)

|  | AAV2 | AAV3 | AAV4 | AAV5 | AAV6 | AAV7 | AAV10 | AAV11 | AAV12 |
|---|---|---|---|---|---|---|---|---|---|
| AAV1 | 90 | 90 | 81 | 76 | 97 | 91 | 93 | 94 | 93 |
| AAV2 |  | 93 | 79 | 78 | 90 | 90 | 93 | 93 | 92 |
| AAV3 |  |  | 80 | 76 | 90 | 92 | 92 | 92 | 92 |
| AAV4 |  |  |  | 76 | 81 | 84 | 82 | 81 | 79 |
| AAV5 |  |  |  |  | 75 | 78 | 79 | 79 | 76 |
| AAV6 |  |  |  |  |  | 91 | 92 | 94 | 94 |
| AAV7 |  |  |  |  |  |  | 94 | 92 | 92 |
| AAV10 |  |  |  |  |  |  |  | 95 | 93 |
| AAV11 |  |  |  |  |  |  |  |  | 94 |

Over 300 clones containing novel AAV serotype sequences that span the selected 257 bp region were isolated and sequenced. Bioinformatics analysis of these 300+ clones suggests that this 257 bp region is critical in serving as a good land marker or signature sequence for quick isolation and identification of novel AAV serotype.

B. Use of the Signature Region for PCR Amplification.

The 257 bp signature region was used as a PCR anchor to extend PCR amplifications to 5' of the genome to cover the junction region of rep and cap genes (1398 bp-3143 bp, SEQ ID NO:6) and 3' of the genome to obtain the entire cap gene sequence (2866 bp-4600 bp, SEQ ID NO:6). PCR amplifications were carried out using the standard conditions, including denaturing at 95° C. for 0.5-1 min, annealing at 60-65° C. for 0.5-1 min and extension at 72° C. for 1 min per kb with a total number of amplification cycles ranging from 28 to 42.

Using the aligned sequences as described in "A", two other relative conserved regions were identified in the sequence located in 3' end of rep genes and 5' to the 257 bp region and in the sequence down stream of the 257 bp fragment but before the AAV' 3 ITR. Two sets of new primers were designed and PCR conditions optimized for recovery of entire capsid and a part of rep sequences of novel AAV serotypes. More specifically, for the 5' amplification, the 5' primer, AV1Ns, was GCTGCGTCAACTGGACCAATGAGAAC [nt 1398-1423 of AAV1, SEQ ID NO:6] and the 3' primer was 18 as, identified above. For the 3' amplification, the 5' primer was is, identified above, and the 3' primer was AV2Las, TCGTTTCAGTTGAACTTTGGTCTCTGCG [nt 4435-4462 of AAV2, SEQ ID NO:7].

In these PCR amplifications, the 257 bp region was used as a PCR anchor and land marker to generate overlapping fragments to construct a complete capsid gene by fusion at the DraIII site in the signature region following amplification of the 5' and 3' extension fragments obtained as described herein. More particularly, to generate the intact AAV7 cap gene, the three amplification products (a) the sequences of the signature region; (b) the sequences of the 5' extension; and (c) the sequences of the 3' extension were cloned into a pCR4-Topo [Invitrogen] plasmid backbone according to manufacturer's instructions. Thereafter, the plasmids were digested with DraIII and recombined to form an intact cap gene.

In this line of work, about 80% of capsid sequences of AAV7 and AAV 8 were isolated and analyzed. Another novel serotype, AAV9, was also discovered from Monkey #2.

Using the PCR conditions described above, the remaining portion of the rep gene sequence for AAV7 is isolated and cloned using the primers that amplify 108 bp to 1461 bp of AAV genome (calculated based on the numbering of AAV2, SEQ ID NO:7). This clone is sequenced for construction of a complete AAV7 genome without ITRs.

C. Direct Amplification of 3.1 kb Cap Fragment

To directly amplify a 3.1 kb full-length Cap fragment from NHP tissue and blood DNAs, two other highly conserved regions were identified in AAV genomes for use in PCR amplification of large fragments. A primer within a conserved region located in the middle of the rep gene was selected (AV1ns: 5' GCTGCGTCAACTGGACCAATGAGAAC 3', nt 1398-1423 of SEQ ID NO:6) in combination with the 3' primer located in another conserved region downstream of the Cap gene (AV2cas: 5' CGCAGAGACCAAAGT- TCAACTGAAACGA 3', SEQ ID NO:7) for amplification of full-length cap fragments. The PCR products were Topo-cloned according to manufacturer's directions (Invitrogen) and sequence analysis was performed by Qiagen Genomics™ (Qiagen genomics, Seattle, Wash.) with an accuracy of ≧99.9%. A total of 50 capsid clones were isolated and characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5).

To rule out the possibility that sequence diversity within the novel AAV family was not an artifact of the PCR, such as PCR-mediated gene splicing by overlap extension between different partial DNA templates with homologous sequences, or the result of recombination process in bacteria, a series of experiments were performed under identical conditions for VP1 amplification using total cellular DNAs. First, intact AAV7 and AAV8 plasmids were mixed at an equal molar ratio followed by serial dilutions. The serially diluted mixtures were used as templates for PCR amplification of 3.1 kb VP1 fragments using universal primers and identical PCR conditions to that were used for DNA amplifications to see whether any hybrid PCR products were generated. The mixture was transformed into bacteria and isolated transformants to look for hybrid clones possibly derived from recombination process in bacterial cells. In a different experiment, we restricted AAV7 and AAV8 plasmids with Msp I, Ava I and HaeI, all of which cut both genomes multiple times at different positions, mixed the digestions in different combinations and used them for PCR amplification of VP1 fragments under the same conditions to test whether any PCR products could be generated through overlap sequence extension of partial AAV sequences. In another experiment, a mixture of gel purified 5' 1.5 kb AAV7 VP1 fragment and 3' 1.7 kb AAV8 VP1 fragment with overlap in the signature region was serially diluted and used for PCR amplification in the presence and absence of 200 ng cellular DNA extracted from a monkey cell line that was free of AAV sequences by TaqMan™ analysis. None of these experiments demonstrated efficient PCR-mediated overlap sequence production under the conditions of the genomic DNA Cap amplification (data not shown). As a further confirmation, 3 pairs of primers were designed, which were located at different HVRs, and were sequence specific to the variants of clone 42s from Rhesus macaque F953, in different combinations to amplify shorter fragments from mesenteric lymph node (MLN) DNA from F953 from which clone 42s were isolated. All sequence variations identified in full-length Cap clones were found in these short fragments (data not shown).

Example 2

Adeno-Associated Viruses Undergo Substantial Evolution in Primates During Natural Infections Sequence analysis of selected AAV isolates revealed divergence throughout the genome that is most concentrated in hypervariable regions of the capsid proteins. Epidemiologic data indicate that all known serotypes are endemic to primates, although isolation of clinical isolates has been restricted to AAV2 and AAV3 from anal and throat swabs of human infants and AAV5 from a human condylomatous wart. No known clinical sequalae have been associated with AAV infection.

In an attempt to better understand the biology of AAV, nonhuman primates were used as models to characterize the sequlae of natural infections. Tissues from nonhuman primates were screened for AAV sequences using the PCR method of the invention based on oligonucleotides to highly conserved regions of known AAVs (see Example 1). A stretch of AAV sequence spanning 2886 to 3143 bp of AAV1 [SEQ ID NO:6] was selected as a PCR amplicon in which conserved sequences are flanked by a hypervariable region that is unique to each known AAV serotype, termed herein a "signature region."

An initial survey of peripheral blood of a number of non-human primate species including rhesus monkeys, cynomologous monkeys, chimpanzees, and baboons revealed detectable AAV in a subset of animals from all species. A more extensive analysis of vector distribution was conducted in tissues of rhesus monkeys of the University of Pennsylvania and Tulane colonies recovered at necropsy. This revealed AAV sequence throughout a wide array of tissues.

The amplified signature sequences were subcloned into plasmids and individual transformants were subjected to sequence analysis. This revealed substantial variation in nucleotide sequence of clones derived from different animals. Variation in the signature sequence was also noted in clones obtained within individual animals. Tissues harvested from two animals in which unique signature sequences were identified (i.e., colon from 98E044 and heart from 98E056) were further characterized by expanding the sequence amplified by PCR using oligonucleotides to highly conserved sequences. In this way, complete proviral structures were reconstructed for viral genomes from both tissues as described herein. These proviruses differ from the other known AAVs with the greatest sequence divergence noted in regions of the Cap gene.

Additional experiments were performed to confirm that AAV sequences resident to the nonhuman primate tissue represented proviral genomes of infectious virus that is capable of being rescued and form virions. Genomic DNA from liver tissue of animal 98E056, from which AAV8 signature sequence was detected, was digested with an endonuclease that does not have a site within the AAV sequence and transfected into 293 cells with a plasmid containing an E1 deleted genome of human adenovirus serotype 5 as a source of helper functions. The resulting lysate was passaged on 293 cells once and the lysate was recovered and analyzed for the presence of AAV Cap proteins using a broadly reacting polyclonal antibody to Cap proteins and for the presence and abundance of DNA sequences from the PCR amplified AAV provirus from which AAV8 was derived. Transfection of endonuclease restricted heart DNA and the adenovirus helper plasmid yielded high quantities of AAV8 virus as demonstrated by the detection of Cap proteins by Western blot analysis and the presence of $10^4$ AAV8 vector genomes per 293 cell. Lysates were generated from a large-scale preparation and the AAV was purified by cesium sedimentation. The purified preparation demonstrated 26 nm icosohedral structures that look identical to those of AAV serotype 2. Transfection with the adenovirus helper alone did not yield AAV proteins or genomes, ruling out contamination as a source of the rescued AAV.

To further characterize the inter and intra animal variation of AAV signature sequence, selected tissues were subjected to extended PCR to amplify entire Cap open reading frames.

The resulting fragments were cloned into bacterial plasmids and individual transformants were isolated and fully sequenced. This analysis involved mesenteric lymph nodes from three rhesus monkeys (Tulane/V223—6 clones; Tulane/T612—7 clones; Tulane/F953—14 clones), liver from two rhesus monkeys (Tulane/V251—3 clones; Penn/00E033—3 clones), spleen from one rhesus monkey (Penn/97E043—3 clones), heart from one rhesus monkey (IHGT/98E046—1 clone) and peripheral blood from one chimpanzee (New Iberia/X133—5 clones), six cynomologous macaques (Charles River/A1378, A3099, A3388, A3442, A2821, A3242—6 clones total) and one Baboon (SFRB/8644—2 clones). Of the 50 clones that were sequenced from 15 different animals, 30 were considered non-redundant based on the finding of at least 7 amino acid differences from one another. The non-redundant VP1 clones are numbered sequentially as they were isolated, with a prefix indicating the species of non-human primate from which they were derived. The structural relationships between these 30 non-redundant clones and the previously described 8 AAV serotypes were determined using the SplitsTree program [Huson, D. H. SplitsTree: analyzing and visualizing evolutionary data. *Bioinformatics* 14, 68-73 (1998)] with implementation of the method of split decomposition. The analysis depicts homoplasy between a set of sequences in a tree-like network rather than a bifurcating tree. The advantage is to enable detection of groupings that are the result of convergence and to exhibit phylogenetic relationships even when they are distorted by parallel events. Extensive phylogenetic research will be required in order to elucidate the AAV evolution, whereas the intention here only is to group the different clones as to their sequence similarity.

To confirm that the novel VP1 sequences were derived from infectious viral genomes, cellular DNA from tissues with high abundance of viral DNA was restricted with an endonuclease that should not cleave within AAV and transfected into 293 cells, followed by infection with adenovirus. This resulted in rescue and amplification of AAV genomes from DNA of tissues from two different animals (data not shown).

VP1 sequences of the novel AAVs were further characterized with respect to the nature and location of amino acid sequence variation. All 30 VP1 clones that were shown to differ from one another by greater than 1% amino acid sequence were aligned and scored for variation at each residue. An algorithm developed to determine areas of sequence divergence yielded 12 hypervariable regions (HVR) of which 5 overlap or are part of the 4 previously described variable regions [Kotin, cited above; Rutledge, cited above]. The three-fold-proximal peaks contain most of the variability (HVR5-10). Interestingly the loops located at the 2 and 5 fold axis show intense variation as well. The HVRs 1 and 2 occur in the N-terminal portion of the capsid protein that is not resolved in the X-ray structure suggesting that the N-terminus of the VP1 protein is exposed on the surface of the virion.

Real-time PCR was used to quantify AAV sequences from tissues of 21 rhesus monkeys using primers and probes to highly conserved regions of Rep (one set) and Cap (two sets) of known AAVs. Each data point represents analysis from tissue DNA from an individual animal. This confirmed the wide distribution of AAV sequences, although the quantitative distribution differed between individual animals. The source of animals and previous history or treatments did not appear to influence distribution of AAV sequences in rhesus macaques. The three different sets of primers and probes used to quantify AAV yielded consistent results. The highest levels of AAV were found consistently in mesenteric lymph nodes at an average of 0.01 copies per diploid genome for 13 animals that were positive. Liver and spleen also contained high abundance of virus DNA. There were examples of very high AAV, such as in heart of rhesus macaque 98E056, spleen of rhesus macaque 97E043 and liver of rhesus macaque RQ4407, which demonstrated 1.5, 3 and 20 copies of AAV sequence per diploid genome respectively. Relatively low levels of virus DNA were noted in peripheral blood mononuclear cells, suggesting the data in tissue are not due to resident blood components (data not shown). It should be noted that this method would not necessarily capture all AAVs resident to the nonhuman primates since detection requires high homology to both the oligonucleotides and the real time PCR probe. Tissues from animals with high abundance AAV DNA was further analyzed for the molecular state of the DNA, by DNA hybridization techniques, and its cellular distribution, by in situ hybridization.

The kind of sequence variation revealed in AAV proviral fragments isolated from different animals and within tissues of the same animals is reminiscent of the evolution that occurs for many RNA viruses during pandemics or even within the infection of an individual. In some situations the notion of a wild-type virus has been replaced by the existence of swarms of quasispecies that evolve as a result of rapid replication and mutations in the presence of selective pressure. One example is infection by HIV, which evolves in response to immunologic and pharmacologic pressure. Several mechanisms contribute to the high rate of mutations in RNA viruses, including low fidelity and lack of proof reading capacity of reverse transcriptase and non-homologous and homologous recombination.

Evidence for the formation of quasispecies of AAV was illustrated in this study by the systematic sequencing of multiple cloned proviral fragments. In fact, identical sequences could not be found within any extended clones isolated between or within animals. An important mechanism for this evolution of sequence appears to be a high rate of homologous recombination between a more limited number of parenteral viruses. The net result is extensive swapping of hypervariable regions of the Cap protein leading to an array of chimeras that could have different tropisms and serologic specificities (i.e., the ability to escape immunologic responses especially as it relates to neutralizing antibodies). Mechanisms by which homologous recombination could occur are unclear. One possibility is that + and − strands of different single stranded AAV genomes anneal during replication as has been described during high multiplicity of infections with AAV recombinants. It is unclear if other mechanisms contribute to sequence evolution in AAV infections. The overall rate of mutation that occurs during AAV replication appears to be relatively low and the data do not suggest high frequencies of replication errors. However, substantial rearrangements of the AAV genome have been described during lytic infection leading to the formation of defective interfering particles. Irrespective of the mechanisms that lead to sequence divergence, with few exceptions, vp1 structures of the quasispecies remained intact without frameshifts or nonsense mutations suggesting that competitive selection of viruses with the most favorable profile of fitness contribute to the population dynamics.

These studies have implications in several areas of biology and medicine. The concept of rapid virus evolution, formerly thought to be a property restricted to RNA viruses, should be considered in DNA viruses, which classically have been characterized by serologic assays. It will be important in terms of parvoviruses to develop a new method for describing virus isolates that captures the complexity of its structure and biology, such as with HIV, which are categorized as general families of similar structure and function called Clades. An alternative strategy is to continue to categorize isolates with respect to serologic specificity and develop criteria for describing variants within serologic groups.

Example 3

Vectorology of Recombinant AAV Genomes Equipped with AAV2 ITRs Using Chimeric Plasmids Containing AAV2 Rep and Novel AAV Cap Genes for Serological and Gene Transfer Studies in Different Animal Models Chimeric packaging constructs are generated by fusing AAV2 rep with cap sequences of novel AAV serotypes. These chimeric packaging constructs are used, initially, for pseudotyping recombinant AAV genomes carrying AAV2 ITRs by triple transfection in 293 cell using Ad5 helper plasmid. These pseudotyped vectors are used to evaluate performance in transduction-based serological studies and evaluate gene transfer efficiency of novel AAV serotypes in different animal models including NHP and rodents, before intact and infectious viruses of these novel serotypes are isolated.

A. pAAV2GFP

The AAV2 plasmid which contains the AAV2 ITRs and green fluorescent protein expressed under the control of a constitutitive promoter. This plasmid contains the following elements: the AAV2 ITRs, a CMV promoter, and the GFP coding sequences.

B. Cloning of Trans Plasmid

To construct the chimeric trans-plasmid for production of recombinant pseudotyped AAV7 vectors, p5E18 plasmid (Xiao et al., 1999, *J. Virol* 73:3994-4003) was partially digested with Xho I to linearize the plasmid at the Xho I site at the position of 3169 bp only. The Xho I cut ends were then filled in and ligated back. This modified p5E18 plasmid was restricted with Xba I and Xho I in a complete digestion to remove the AAV2 cap gene sequence and replaced with a 2267 bp Spe I/Xho I fragment containing the AAV7 cap gene which was isolated from pCRAAV7 6-5+15-4 plasmid.

The resulting plasmid contains the AAV2 rep sequences for Rep78/68 under the control of the AAV2 P5 promoter, and the AAV2 rep sequences for Rep52/40 under the control of the AAV2 P19 promoter. The AAV7 capsid sequences are under the control of the AAV2 P40 promoter, which is located within the Rep sequences. This plasmid further contains a spacer 5' of the rep ORF.

C. Production of Pseudotyped rAAV

The rAAV particles (AAV2 vector in AAV7 capsid) are generated using an adenovirus-free method. Briefly, the cis plasmid (pAAV2.1 lacZ plasmid containing AAV2 ITRs), and the trans plasmid pCRAAV7 6-5+15-4 (containing the AAV2 rep and AAV7 cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔF13. Plasmid AdΔ F1 was constructed by cloning Asp700/SalI fragment with a PmeI/SgfI deletion, isolating from pBHG10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 µg of DNA (cis:trans:helper) was transfected onto a 150 mm tissue culture dish. The 293 cells were harvested 72 hours post-transfection, sonicated and treated with 0.5% sodium deoxycholate (37EC for 10 min.) Cell lysates were then subjected to two rounds of a CsCl gradient. Peak fractions containing rAAV vector are collected, pooled and dialyzed against PBS.

Example 4

Creation of Infectious Clones Carrying Intact Novel AAV Serotypes for Study of Basic Virology in Human and NHP Derived Cell Lines and Evaluation of Pathogenesis of Novel AAV Serotypes in NHP and Other Animal Models To achieve this goal, the genome walker system is employed to obtain 5' and 3' terminal sequences (ITRs) and complete construction of clones containing intact novel AAV serotype genomes.

Briefly, utilizing a commercially available Universal Genome Walker Kit [Clontech], genomic DNAs from monkey tissues or cell lines that are identified as positive for the presence of AAV7 sequence are digested with Dra I, EcoR V, Pvu II and Stu I endonucleases and ligated to Genome Walker Adaptor to generate 4 individual Genome Walker Libraries (GWLs). Using DNAs from GWLs as templates, AAV7 and adjacent genomic sequences will be PCR-amplified by the adaptor primer 1 (API, provided in the kit) and an AAV7 specific primer 1, followed by a nested PCR using the adaptor primer 2 (AP2) and another AAV7 specific primer 2, both of which are internal to the first set of primers. The major PCR products from the nested PCR are cloned and characterized by sequencing analysis.

In this experiment, the primers covering the 257 bp or other signature fragment of a generic AAV genome are used for PCR amplification of cellular DNAs extracted from Human and NHP derived cell lines to identify and characterize latent AAV sequences. The identified latent AAV genomes are rescued from the positive cell lines using adenovirus helpers of different species and strains.

To isolate infectious AAV clones from NHP derived cell lines, a desired cell line is obtained from ATCC and screened by PCR to identify the 257 bp amplicon, i.e., signature region of the invention. The 257 bp PCR product is cloned and serotyped by sequencing analysis. For these cell lines containing the AAV7 sequence, the cells are infected with SV-15, a simian adenovirus purchased from ATCC, human Ad5 or transfected with plasmid construct housing the human Ad genes that are responsible for AAV helper functions. At 48 hour post infection or transfection, the cells are harvested and Hirt DNA is prepared for cloning of AAV7 genome following Xiao et al., 1999, J. Virol, 73:3994-4003.

Example 5

Production of AAV Vectors

A pseudotyping strategy similar to that of Example 3 for AAV1/7 was employed to produce AAV2 vectors packaged with AAV1, AAV5 and AAV8 capsid proteins. Briefly, recombinant AAV genomes equipped with AAV2 ITRs were packaged by triple transfection of 293 cells with cis-plasmid, adenovirus helper plasmid and a chimeric packaging construct where the AAV2 rep gene is fused with cap genes of novel AAV serotypes. To create the chimeric packaging constructs, the Xho I site of p5E18 plasmid at 3169 bp was ablated and the modified plasmid was restricted with Xba I and Xho I in a complete digestion to remove the AAV2 cap gene and replace it with a 2267 bp Spe I/Xho I fragment containing the AAV8 cap gene [Xiao, W., et al., (1999) *J Virol*

73, 3994-4003]. A similar cloning strategy was used for creation of chimeric packaging plasmids of AAV2/1 and AAV2/5. All recombinant vectors were purified by the standard CsCl$_2$ sedimentation method except for AAV2/2, which was purified by single step heparin chromatography.

Genome copy (GC) titers of AAV vectors were determined by TaqMan® analysis using probes and primers targeting SV40 poly A region as described previously [Gao, G., et al., (2000) *Hum Gene Ther* 11, 2079-91].

Vectors were constructed for each serotype for a number of in vitro and in vivo studies. Eight different transgene cassettes were incorporated into the vectors and recombinant virions were produced for each serotype. The recovery of virus, based on genome copies, is summarized in Table 4 below. The yields of vector were high for each serotype with no consistent differences between serotypes. Data presented in the table are average genome copy yields with standard deviation ×10$^{13}$ of multiple production lots of 50 plate (150 mm) transfections.

antibodies was determined by assessing the ability of serum to inhibit transduction of 84-31 cells by reporter viruses (AAVCMVEGFP) of different serotypes. Specifically, the reporter virus AAVCMVEGFP of each serotype [at multiplicity of infection (MOI) that led to a transduction of 90% of indicator cells] was pre-incubated with heat-inactivated serum from animals that received different serotypes of AAV or from naïve mice. After 1-hour incubation at 37° C., viruses were added to 84-31 cells in 96 well plates for 48 or 72-hour, depending on the virus serotype. Expression of GFP was measured by FluoroImagin (Molecular Dynamics) and quantified by Image Quant Software. Neutralizing antibody titers were reported as the highest serum dilution that inhibited transduction to less than 50%.

The availability of GFP expressing vectors simplified the development of an assay for neutralizing antibodies that was

TABLE 4

Production of Recombinant Vectors

| | AAV2/1 | AAV2/2 | AAV2/5 | AAV2/7 | AAV2/8 |
|---|---|---|---|---|---|
| CMV LacZ | 7.30 ± 4.33 | 4.49 ± 2.89 | 5.19 ± 5.19 | 3.42 | 0.87 |
| | (n = 9) | (n = 6) | (n = 8) | (n = 1) | (n = 1) |
| CMV EGFP | 6.43 ± 2.42 | 3.39 ± 2.42 | 5.55 ± 6.49 | 2.98 ± 2.66 | 3.74 ± 3.88 |
| | (n = 2) | (n = 2) | (n = 4) | (n = 2) | (n = 2) |
| TBG LacZ | 4.18 | 0.23 | 0.704 ± 0.43 | 2.16 | 0.532 |
| | (n = 1) | (n = 1) | (n = 2) | (n = 1) | (n = 1) |
| Alb A1AT | 4.67 ± 0.75 | 4.77 | 4.09 | 5.04 | 2.02 |
| | (n = 2) | (n = 1) | (n = 1) | (n = 1) | (n = 1) |
| CB A1AT | 0.567 | 0.438 | 2.82 | 2.78 | 0.816 ± 0.679 |
| | (n = 1) | (n = 1) | (n = 1) | (n = 1) | (n = 2) |
| TBG rhCG | 8.51 ± 6.65 | 3.47 ± 2.09 | 5.26 ± 3.85 | 6.52 ± 3.08 | 1.83 ± 0.98 |
| | (n = 6) | (n = 5) | (n = 4) | (n = 4) | (n = 5) |
| TBG cFIX | 1.24 ± 1.29 | 0.63 ± 0.394 | 3.74 ± 2.48 | 4.05 | 15.8 ± 15.0 |
| | (n = 3) | (n = 6) | (n = 7) | (n = 1) | (n = 5) |

Example 6

Serologic Analysis of Pseudotyped Vectors

C57BL/6 mice were injected with vectors of different serotypes of AAVCBA1AT vectors intramuscularly (5×10$^{11}$ GC) and serum samples were collected 34 days later. To test neutralizing and cross-neutralizing activity of sera to each serotype of AAV, sera was analyzed in a transduction based neutralizing antibody assay [Gao, G. P., et al., (1996) *J Virol* 70, 8934-43]. More specifically, the presence of neutralizing antibodies was determined by assessing the ability of serum based on inhibition of transduction in a permissive cell line (i.e., 293 cells stably expressing E4 from Ad5). Sera to selected AAV serotypes were generated by intramuscular injection of the recombinant viruses. Neutralization of AAV transduction by 1:20 and 1:80 dilutions of the antisera was evaluated (See Table 5 below). Antisera to AAV1, AAV2, AAV5 and AAV8 neutralized transduction of the serotype to which the antiserum was generated (AAV5 and AAV8 to a lesser extent than AAV1 and AAV2) but not to the other serotype (i.e., there was no evidence of cross neutralization suggesting that AAV 8 is a truly unique serotype).

TABLE 5

Serological Analysis of New AAV Serotypes.

| | | % Infection on 84-31 cells with AAVCMVEGFP virus: | | | | | | | | |
|---|---|---|---|---|---|---|---|---|---|---|
| | | AAV2/1 Serum dilution: | | AAV2/2 Serum dilution: | | AAV2/5 Serum dilution: | | AAV2/7 Serum dilution: | | AAV2/8 Serum dilution: | |
| Sera: | Vector | 1/20 | 1/80 | 1/20 | 1/80 | 1/20 | 1/80 | 1/20 | 1/80 | 1/20 | 1/80 |
| Group 1 | AAV2/1 | 0 | 0 | 100 | 100 | 100 | 100 | 100 | 100 | 100 | 100 |
| Group 2 | AAV2/2 | 100 | 100 | 0 | 0 | 100 | 100 | 100 | 100 | 100 | 100 |
| Group 3 | AAV2/5 | 100 | 100 | 100 | 100 | 16.5 | 16.5 | 100 | 100 | 100 | 100 |
| Group 4 | AAV2/7 | 100 | 100 | 100 | 100 | 100 | 100 | 61.5 | 100 | 100 | 100 |
| Group 5 | AAV2/8 | 100 | 100 | 100 | 100 | 100 | 100 | 100 | 100 | 26.3 | 60 |

Human sera from 52 normal subjects were screened for neutralization against selected serotypes. No serum sample was found to neutralize AAV2/7 and AAV2/8 while AAV2/2 and AAV2/1 vectors were neutralized in 20% and 10% of sera, respectively. A fraction of human pooled IgG representing a collection of 60,000 individual samples did not neutralize AAV2/7 and AAV2/8, whereas AAV2/2 and AAV2/1 vectors were neutralized at titers of serum equal to 1/1280 and 1/640, respectively.

Example 7

In vivo Evaluation of Different Serotypes of AAV Vectors

In this study, 7 recombinant AAV genomes, AAV2CBhA1AT, AAV2AlbhA1AT, AAV2CMVrhCG, AAV2TBGrhCG, AAV2TBGcFIX, AAV2CMVLacZ and AAV2TBGLacZ were packaged with capsid proteins of different serotypes. In all 7 constructs, minigene cassettes were flanked with AAV2 ITRs. cDNAs of human α-antitrypsin (A1AT) [Xiao, W., et al., (1999) J Virol 73, 3994-4003] β-subunit of rhesus monkey choriogonadotropic hormone (CG) [Zoltick, P. W. & Wilson, J. M. (2000) Mol Ther 2, 657-9] canine factor IX [Wang, L., et al., (1997) Proc Natl Acad Sci USA 94, 11563-6] and bacterial β-galactosidase (i.e., Lac Z) genes were used as reporter genes. For liver-directed gene transfer, either mouse albumin gene promoter (Alb) [Xiao, W. (1999), cited above] or human thyroid hormone binding globulin gene promoter (TBG) [Wang (1997), cited above] was used to drive liver specific expression of reporter genes. In muscle-directed gene transfer experiments, either cytomegalovirus early promoter (CMV) or chicken β-actin promoter with CMV enhancer (CB) was employed to direct expression of reporters.

For muscle-directed gene transfer, vectors were injected into the right tibialis anterior of 4-6 week old NCR nude or C57BL/6 mice (Taconic, Germantown, N.Y.). In liver-directed gene transfer studies, vectors were infused intraportally into 7-9 week old NCR nude or C57BL/6 mice (Taconic, Germantown, N.Y.). Serum samples were collected intraorbitally at different time points after vector administration. Muscle and liver tissues were harvested at different time points for cryosectioning and Xgal histochemical staining from animals that received the lacZ vectors. For the re-administration experiment, C56BL/6 mice initially received AAV2/1, 2/2, 2/5, 2/7 and 2/8CBA1AT vectors intramuscularly and followed for A1AT gene expression for 7 weeks. Animals were then treated with AAV2/8TBGcFIX intraportally and studied for cFIX gene expression.

ELISA based assays were performed to quantify serum levels of hA1AT, rhCG and cFIX proteins as described previously [Gao, G. P., et al., (1996) J Virol 70, 8934-43; Zoltick, P. W. & Wilson, J. M. (2000) Mol Ther 2, 657-9; Wang, L., et al., Proc Natl Acad Sci USA 94, 11563-6]. The experiments were completed when animals were sacrificed for harvest of muscle and liver tissues for DNA extraction and quantitative analysis of genome copies of vectors present in target tissues by TaqMan™ using the same set of primers and probe as in titration of vector preparations [Zhang, Y., et al., (2001) Mol Ther 3, 697-707].

The performance of vectors base on the new serotypes were evaluated in murine models of muscle and liver-directed gene transfer and compared to vectors based on the known serotypes AAV1, AAV2 and AAV5. Vectors expressing secreted proteins (alpha-antitrypsin (A1AT) and chorionic gonadotropin (CG)) were used to quantitate relative transduction efficiencies between different serotypes through ELISA analysis of sera. The cellular distribution of transduction within the target organ was evaluated using lacZ expressing vectors and X-gal histochemistry.

The performance of AAV vectors in skeletal muscle was analyzed following direct injection into the tibialis anterior muscles. Vectors contained the same AAV2 based genome with the immediate early gene of CMV or a CMV enhanced β-actin promoter driving expression of the transgene. Previous studies indicated that immune competent C57BL/6 mice elicit limited humoral responses to the human A1AT protein when expressed from AAV vectors [Xiao, W., et al., (1999) J Virol 73, 3994-4003].

In each strain, AAV2/1 vector produced the highest levels of A1AT and AAV2/2 vector the lowest, with AAV2/7 and AAV2/8 vectors showing intermediate levels of expression. Peak levels of CG at 28 days following injection of nu/nu NCR mice showed the highest levels from AAV2/7 and the lowest from AAV2/2 with AAV2/8 and AAV2/1 in between. Injection of AAV2/1 and AAV2/7 lacZ vectors yielded gene expression at the injection sites in all muscle fibers with substantially fewer lacZ positive fibers observed with AAV2/2 and AAV 2/8 vectors. These data indicate that the efficiency of transduction with AAV2/7 vectors in skeletal muscle is similar to that obtained with AAV2/1, which is the most efficient in skeletal muscle of the previously described serotypes [Xiao, W. (1999), cited above; Chao, H., et al., (2001) Mol Ther 4, 217-22; Chao, H., et al., (2000) Mol Ther 2, 619-23].

Similar murine models were used to evaluate liver-directed gene transfer. Identical doses of vector based on genome copies were infused into the portal veins of mice that were analyzed subsequently for expression of the transgene. Each vector contained an AAV2 based genome using previously described liver-specific promoters (i.e., albumin or thyroid hormone binding globulin) to drive expression of the transgene. More particularly, CMVCG and TBGCG minigene cassettes were used for muscle and liver-directed gene transfer, respectively. Levels of rhCG were defined as relative units (RUs×10$^3$). The data were from assaying serum samples collected at day 28, post vector administration (4 animals per group). As shown in Table 3, the impact of capsid proteins on the efficiency of transduction of A1AT vectors in nu/nu and C57BL/6 mice and CG vectors in C57BL/6 mice was consistent (See Table 6).

TABLE 6

Expression of β-unit of Rhesus Monkey Chorionic Gonadotropin (rhCG)

| Vector | Muscle | Liver |
| --- | --- | --- |
| AAV2/1 | 4.5 ± 2.1 | 1.6 ± 1.0 |
| AAV2 | 0.5 ± 0.1 | 0.7 ± 0.3 |
| AAV2/5 | ND* | 4.8 ± 0.8 |
| AAV2/7 | 14.2 ± 2.4 | 8.2 ± 4.3 |
| AAV2/8 | 4.0 ± 0.7 | 76.0 ± 22.8 |

*Not determined in this experiment.

In all cases, AAV2/8 vectors yielded the highest levels of transgene expression that ranged from 16 to 110 greater than what was obtained with AAV2/2 vectors; expression from AAV2/5 and AAV2/7 vectors was intermediate with AAV2/7 higher than AAV2/5. Analysis of X-Gal stained liver sections of animals that received the corresponding lacZ vectors showed a correlation between the number of transduced cells and overall levels of transgene expression. DNAs extracted from livers of C57BL/6 mice who received the A1AT vectors were analyzed for abundance of vector DNA using real time PCR technology.

The amount of vector DNA found in liver 56 days after injection correlated with the levels of transgene expression (See Table 7). For this experiment, a set of probe and primers targeting the SV40 polyA region of the vector genome was used for TaqMan™ PCR. Values shown are means of three individual animals with standard deviations. The animals were sacrificed at day 56 to harvest liver tissues for DNA extraction. These studies indicate that AAV8 is the most efficient vector for liver-directed gene transfer due to increased numbers of transduced hepatocytes.

TABLE 7

Real Time PCR Analysis for Abundance of AAV Vectors in nu/nu Mouse Liver Following Injection of 1 × 10$^{11}$ Genome Copies of Vector.

| AAV vectors/Dose | Genome Copies per Cell |
| --- | --- |
| AAV2/1AlbA1AT | 0.6 ± 0.36 |
| AAV2AlbA1AT | 0.003 ± 0.001 |
| AAV2/5AlbA1AT | 0.83 ± 0.64 |
| AAV2/7AlbA1AT | 2.2 ± 1.7 |
| AAV2/8AlbA1AT | 18 ± 11 |

The serologic data described above suggest that AAV2/8 vector should not be neutralized in vivo following immunization with the other serotypes. C57BL/6 mice received intraportal injections of AAV2/8 vector expressing canine factor IX (10$^{11}$ genome copies) 56 days after they received intramuscular injections of A1AT vectors of different serotypes. High levels of factor IX expression were obtained 14 days following infusion of AAV2/8 into naïve animals (17±2 µg/ml, n=4) which were not significantly different that what was observed in animals immunized with AAV2/1 (31±23 µg/ml, n=4), AAV2/2 (16 µg/ml, n=2), and AAV2/7 (12 µg/ml, n=2). This contrasts to what was observed in AAV2/8 immunized animals that were infused with the AAV2/8 factor IX vector in which no detectable factor IX was observed (<0.1 µg/ml, n=4).

Oligonucleotides to conserved regions of the cap gene did amplify sequences from rhesus monkeys that represented unique AAVs. Identical cap signature sequences were found in multiple tissues from rhesus monkeys derived from at least two different colonies. Full-length rep and cap open reading frames were isolated and sequenced from single sources. Only the cap open reading frames of the novel AAVs were necessary to evaluate their potential as vectors because vectors with the AAV7 or AAV8 capsids were generated using the ITRs and rep from AAV2. This also simplified the comparison of different vectors since the actual vector genome is identical between different vector serotypes. In fact, the yields of recombinant vectors generated using this approach did not differ between serotypes.

Vectors based on AAV7 and AAV8 appear to be immunologically distinct (i.e., they are not neutralized by antibodies generated against other serotypes). Furthermore, sera from humans do not neutralize transduction by AAV7 and AAV8 vectors, which is a substantial advantage over the human derived AAVs currently under development for which a significant proportion of the human population has pre-existing immunity that is neutralizing [Chirmule, N., et al., (1999) *Gene Ther* 6, 1574-83].

The tropism of each new vector is favorable for in vivo applications. AAV2/7 vectors appear to transduce skeletal muscle as efficiently as AAV2/1, which is the serotype that confers the highest level of transduction in skeletal muscle of the primate AAVs tested to date [Xiao, W., cited above; Chou (2001), cited above, and Chou (2000), cited above]. Importantly, AAV2/8 provides a substantial advantage over the other serotypes in terms of efficiency of gene transfer to liver that until now has been relatively disappointing in terms of the numbers of hepatocytes stably transduced. AAV2/8 consistently achieved a 10 to 100-fold improvement in gene transfer efficiency as compared to the other vectors. The basis for the improved efficiency of AAV2/8 is unclear, although it presumably is due to uptake via a different receptor that is more active on the basolateral surface of hepatocytes. This improved efficiency will be quite useful in the development of liver-directed gene transfer where the number of transduced cells is critical, such as in urea cycle disorders and familial hypercholesterolemia.

Thus, the present invention provides a novel approach for isolating new AAVs based on PCR retrieval of genomic sequences. The amplified sequences were easily incorporated into vectors and tested in animals. The lack of pre-existing immunity to AAV7 and the favorable tropism of the vectors for muscle indicates that AAV7 is suitable for use as a vector in human gene therapy and other in vivo applications. Similarly, the lack of pre-existing immunity to the AAV serotypes of the invention, and their tropisms, renders them useful in delivery of therapeutic molecules and other useful molecules.

Example 9

Tissue Tropism Studies

In the design of a high throughput functional screening scheme for novel AAV constructs, a non-tissue specific and highly active promoter, CB promoter (CMV enhanced chicken β actin promoter) was selected to drive an easily detectable and quantifiable reporter gene, human α anti-trypsin gene. Thus only one vector for each new AAV clone needs to be made for gene transfer studies targeting 3 different tissues, liver, lung and muscle to screen for tissue tropism of a particular AAV construct. The following table summarizes data generated from 4 novel AAV vectors in the tissue tropism studies (AAVCBA1AT), from which a novel AAV capsid clone, 44.2, was found to be a very potent gene transfer vehicle in all 3 tissues with a big lead in the lung tissue particularly. Table 8 reports data obtained (in μg A1AT/mL serum) at day 14 of the study.

TABLE 8

| Vector | Target Tissue | | |
|---|---|---|---|
| | Lung | Liver | Muscle |
| AAV2/1 | ND | ND | 45 ± 11 |
| AAV2/5 | 0.6 ± 0.2 | ND | ND |
| AAV2/8 | ND | 84 ± 30 | ND |
| AAV2/rh.2 (43.1) | 14 ± 7 | 25 ± 7.4 | 35 ± 14 |
| AAV2/rh.10 (44.2) | 23 ± 6 | 53 ± 19 | 46 ± 11 |
| AAV2/rh.13 (42.2) | 3.5 ± 2 | 2 ± 0.8 | 3.5 ± 1.7 |
| AAV2/rh.21 (42.10) | 3.1 ± 2 | 2 ± 1.4 | 4.3 ± 2 |

A couple of other experiments were then performed to confirm the superior tropism of AAV 44.2 in lung tissue. First, AAV vector carried CC10hA1AT minigene for lung specific expression were pseudotyped with capsids of novel AAVs were given to Immune deficient animals (NCR nude) in equal volume (50 μl each of the original preps without dilution) via intratracheal injections as provided in the following table. In Table 9, 50 μl of each original prep per mouse, NCR Nude, detection limit ≧0.033 μg/ml, Day 28

TABLE 9

| Vector | Total GC in 50 μl vector | μg of A1AT/ml with 50 μl vector | μg of A1AT/ml with 1 × 10$^{11}$ vector | Relative Gene transfer as compared to rh.10 (clone 44.2) |
|---|---|---|---|---|
| 2/1 | 3 × 10$^{12}$ | 2.6 ± 0.5 | 0.09 ± 0.02 | 2.2 |
| 2/2 | 5.5 × 10$^{11}$ | <0.03 | <0.005 | <0.1 |
| 2/5 | 3.6 × 10$^{12}$ | 0.65 ± 0.16 | 0.02 ± 0.004 | 0.5 |
| 2/7 | 4.2 × 10$^{12}$ | 1 ± 0.53 | 0.02 ± 0.01 | 0.5 |
| 2/8 | 7.5 × 10$^{11}$ | 0.9 ± 0.7 | 0.12 ± 0.09 | 2.9 |
| 2/ch.5 (A.3.1) | 9 × 10$^{12}$ | 1 ± 0.7 | 0.01 ± 0.008 | 0.24 |
| 2/rh.8 (43.25) | 4.6 × 10$^{12}$ | 26 ± 21 | 0.56 ± 0.46 | 13.7 |
| 2/rh.10 (44.2) | 2.8 × 10$^{12}$ | 115 ± 38 | 4.1 ± 1.4 | 100 |
| 2/rh.13 (42.2) | 6 × 10$^{12}$ | 7.3 ± 0.8 | 0.12 ± 0.01 | 2.9 |
| 2/rh.21 (42.10) | 2.4 × 10$^{12}$ | 9 ± 0.9 | 0.38 ± 0.04 | 9.3 |
| 2/rh.22 (42.11) | 2.6 × 10$^{12}$ | 6 ± 0.4 | 0.23 ± 0.02 | 5.6 |
| 2/rh.24 (42.13) | 1.1 × 10$^{11}$ | 0.4 ± 0.3 | 0.4 ± 0.3 | 1 |

The vectors were also administered to immune competent animals (C57BL/6) in equal genome copies (1×10$^{11}$ GC) as shown in the Table 10. (1×10$^{11}$ GC per animal, C57BL/6, day 14, detection limit ≧0.033 μg/ml)

TABLE 10

| AAV Vector | μg of A1AT/ml with 1 × 10$^{11}$ vector | Relative Gene transfer as compared to rh.10 (clone 44.2) |
|---|---|---|
| 2/1 | 0.076 ± 0.031 | 2.6 |
| 2/2 | 0.1 ± 0.09 | 3.4 |
| 2/5 | 0.0840.033 | 2.9 |

TABLE 10-continued

| AAV Vector | μg of A1AT/ml with 1 × 10$^{11}$ vector | Relative Gene transfer as compared to rh.10 (clone 44.2) |
|---|---|---|
| 2/7 | 0.33 ± 0.01 | 11 |
| 2/8 | 1.92 ± 1.3 | 2.9 |
| 2/ch.5 (A.3.1) | 0.048 ± 0.004 | 1.6 |
| 2/rh.8 (43.25) | 1.7 ± 0.7 | 58 |
| 2/rh.10 (44.2) | 2.93 ± 1.7 | 100 |
| 2/rh.13 (42.2) | 0.45 ± 0.15 | 15 |
| 2/rh.21 (42.10) | 0.86 ± 0.32 | 29 |
| 2/rh.22 (42.11) | 0.38 ± 0.18 | 13 |
| 2/rh.24 (42.13) | 0.3 ± 0.19 | 10 |

The data from both experiments confirmed the superb tropism of clone 44.2 in lung-directed gene transfer.

Interestingly, performance of clone 44.2 in liver and muscle directed gene transfer was also outstanding, close to that of the best liver transducer, AAV8 and the best muscle transducer AAV1, suggesting that this novel AAV has some intriguing biological significance.

To study serological properties of those novel AAVs, pseudotyped AAVGFP vectors were created for immunization of rabbits and in vitro transduction of 84-31 cells in the presence and absence of antisera against different capsids. The data are summarized below:

TABLE 11a

| | Cross-NAB assay in 8431 cells and adenovirus (Adv) coinfection Infection in 8431 cells (coinfected with Adv) with: | | | |
|---|---|---|---|---|
| Serum from rabbit immunized with: | 10$^9$ GC rh.13 AAV2/42.2 | 10$^9$ GC rh.21 AAV2/42.10 | 10$^9$ GC rh.22 AAV2/42.11 | 10$^{10}$ GC rh.24 AAV2/42.13 |
| AAV2/1 | 1/20 | 1/20 | 1/20 | No NAB |
| AAV2/2 | 1/640 | 1/1280 | 1/5120 | No NAB |
| AAV2/5 | No NAB | 1/40 | 1/160 | No NAB |
| AAV2/7 | 1/81920 | 1/81920 | 1/40960 | 1/640 |
| AAV2/8 | 1/640 | 1/640 | 1/320 | 1/5120 |
| Ch.5 AAV2/A3 | 1/20 | 1/160 | 1/640 | 1/640 |

TABLE 11a-continued

Cross-NAB assay in 8431 cells and adenovirus (Adv) coinfection
Infection in 8431 cells (coinfected with Adv) with:

| Serum from rabbit immunized with: | $10^9$ GC rh.13 AAV2/42.2 | $10^9$ GC rh.21 AAV2/42.10 | $10^9$ GC rh.22 AAV2/42.11 | $10^{10}$ GC rh.24 AAV2/42.13 |
|---|---|---|---|---|
| rh.8 AAV2/43.25 | 1/20 | 1/20 | 1/20 | 1/320 |
| rh.10 AAV2/44.2 | No NAB | No NAB | No NAB | 1/5120 |
| rh.13 AAV2/42.2 | 1/5120 | 1/5120 | 1/5120 | No NAB |
| rh.21 AAV2/42.10 | 1/5120 | 1/10240 | 1/5120 | 1/20 |
| rh.22 AAV2/42.11 | 1/20480 | 1/20480 | 1/40960 | No NAB |
| rh.24 AAV2/42.13 | No NAB | 1/20 | 1/20 | 1/5120 |

TABLE 11b

Cross-NAB assay in 8431 cells and Adv coinfection
Infection in 8431 cells (coinfected with Adv) with:

| Serum from rabbit immunized with: | $10^9$ GC rh.12 AAV2/42.1B | $10^{10}$ GC ch.5 AAV2/A3 | $10^{10}$ GC rh.8 AAV2/43.25 | $10^9$ GC rh.10 AAV2/44.2 | $10^9$ GC rh.20 AAV2/42.8.2 |
|---|---|---|---|---|---|
| AAV2/1 | No NAB | 1/20480 | No NAB | 1/80 | ND |
| AAV2/2 | 1/20 | No NAB | No NAB | No NAB | ND |
| AAV2/5 | No NAB | 1/320 | No NAB | No NAB | ND |
| AAV2/7 | 1/2560 | 1/640 | 1/160 | 1/81920 | ND |
| AAV2/8 | 1/10240 | 1/2560 | 1/2560 | 1/81920 | ND |
| ch.5 AAV2/A3 | 1/1280 | 1/10240 | ND | 1/5120 | 1/320 |
| rh.8 AAV2/43.25 | 1/1280 | ND | 1/20400 | 1/5120 | 1/2560 |
| rh.10 AAV2/44.2 | 1/5120 | ND | ND | 1/5120 | 1/5120 |
| rh.13 AAV2/42.2 | 1/20 | ND | ND | No NAB | 1/320 |
| rh.21 AAV2/42.10 | 1/20 | ND | ND | 1/40 | 1/80 |
| rh.22 AAV2/42.11 | No NAB | ND | ND | ND | No NAB |
| rh.24 AAV2/42.13 | 1/5120 | ND | ND | ND | 1/2560 |

TABLE 12

| | Titer of rabbit sera | | Titer after |
|---|---|---|---|
| | Vector | Titer d21 | Boosting |
| ch.5 | AAV2/A3 | 1/10,240 | 1/40,960 |
| rh.8 | AAV2/43.25 | 1/20,400 | 1/163,840 |
| rh.10 | AAV2/44.2 | 1/10,240 | 1/527,680 |
| rh.13 | AAV2/42.2 | 1/5,120 | 1/20,960 |
| rh.21 | AAV2/42.10 | 1/20,400 | 1/81,920 |
| rh.22 | AAV2/42.11 | 1/40,960 | ND |
| rh.24 | AAV2/42.13 | 1/5,120 | ND |

TABLE 13a

Infection in 8431 cells (coinfected with Adv) with GFP

| | $10^9$ GC/well AAV2/1 | $10^9$ GC/well AAV2/2 | $10^9$ GC/well AAV2/5 | $10^9$ GC/well AAV2/7 | $10^9$ GC/well AAV2/8 | $10^9$ GC/well ch.5 AAV2/A3 |
|---|---|---|---|---|---|---|
| # GFU/field | 128 | >200 | 95 | 56 | 13 | 1 |
| | 83 | >200 | 65 | 54 | 11 | 1 |

TABLE 13b

Infection in 8431 cells (coinfected with Adv) with GFP

| | 10⁹ GC/well rh.8 AAV2/43.25 | 10⁹ GC/well rh.10 AAV2/44.2 | 10⁹ GC/well rh.13 AAV2/42.2 | 10⁹ GC/well rh.21 AAV2/42.10 | 10⁹ GC/well rh.22 AAV2/42.11 | 10⁹ GC/well rh.24 AAV2/42.13 | 10⁹ GC/well rh.12 AAV2/42.1B |
|---|---|---|---|---|---|---|---|
| # GFU/field | 3 | 13 | 54 | 62 | 10 | 3 | 18 |
| | 2 | 12 | 71 | 60 | 14 | 2 | 20 |
| | | | 48 | 47 | 16 | 3 | 12 |

Example 10

Mouse Model of Familial Hypercholesterolemia

The following experiment demonstrates that the AAV2/7 construct of the invention delivers the LDL receptor and express LDL receptor in an amount sufficient to reduce the levels of plasma cholesterol and triglycerides in animal models of familial hypercholesterolemia.

A. Vector Construction

AAV vectors packaged with AAV7 or AAV8 capsid proteins were constructed using a pseudotyping strategy [Hildinger M, et al., *J. Virol* 2001; 75:6199-6203]. Recombinant AAV genomes with AAV2 inverted terminal repeats (ITR) were packaged by triple transfection of 293 cells with the cis-plasmid, the adenovirus helper plasmid and a chimeric packaging construct, a fusion of the capsids of the novel AAV serotypes with the rep gene of AAV2. The chimeric packaging plasmid was constructed as previously described [Hildinger et al, cited above]. The recombinant vectors were purified by the standard $CsCl_2$ sedimentation method. To determine the yield TaqMan™ (Applied Biosystems) analysis was performed using probes and primers targeting the SV40 poly(A) region of the vectors [Gao G P, et al., *Hum Gene Ther.* 2000 Oct. 10; 11(15):2079-91]. The resulting vectors express the transgene under the control of the human thyroid hormone binding globulin gene promoter (TBG).

B. Animals

LDL receptor deficient mice on the C57B1/6 background were purchased from the Jackson Laboratory (Bar Harbor, Me., USA) and maintained as a breeding colony. Mice were given unrestricted access to water and obtained a high fat Western Diet (high % cholesterol) starting three weeks prior vector injection. At day −7 as well at day 0, blood was obtained via retroorbital bleeds and the lipid profile evaluated. The mice were randomly divided into seven groups. The vector was injected via an intraportal injection as previously described ([Chen S J et al., *Mol Therapy* 2000; 2(3), 256-261]. Briefly, the mice were anaesthetized with ketamine and xylazine. A laparotomy was performed and the portal vein exposed. Using a 30 g needle the appropriate dose of vector diluted in 100 ul PBS was directly injected into the portal vein. Pressure was applied to the injection site to ensure a stop of the bleeding. The skin wound was closed and draped and the mice carefully monitored for the following day. Weekly bleeds were performed starting at day 14 after liver directed gene transfer to measure blood lipids. Two animals of each group were sacrificed at the time points week 6 and week 12 after vector injection to examine atherosclerotic plaque size as well as receptor expression. The remaining mice were sacrificed at week 20 for plaque measurement and determination of transgene expression.

TABLE 14

| | Vector | dose | n |
|---|---|---|---|
| Group 1 | AAV2/7-TBG-hLDLr | $1 \times 10^{12}$ gc | 12 |
| Group 2 | AAV2/7-TBG-hLDLr | $3 \times 10^{11}$ gc | 12 |
| Group 3 | AAV2/7-TBG-hLDLr | $1 \times 10^{11}$ gc | 12 |
| Group 4 | AAV2/8-TBG-hLDLr | $1 \times 10^{12}$ gc | 12 |
| Group 5 | AAV2/8-TBG-hLDLr | $3 \times 10^{11}$ gc | 12 |
| Group 6 | AAV2/8-TBG-hLDLr | $1 \times 10^{11}$ gc | 12 |
| Group 7 | AAV2/7-TBG-LacZ | $1 \times 10^{11}$ gc | 16 |

C. Serum Lipoprotein and Liver Function Analysis

Blood samples were obtained from the retroorbital plexus after a 6 hour fasting period. The serum was separated from the plasma by centrifugation. The amount of plasma lipoproteins and liver transaminases in the serum were detected using an automatized clinical chemistry analyzer (ACE, Schiapparelli Biosystems, Alpha Wassermann)

D. Detection of Transgene Expression

LDL receptor expression was evaluated by immuno-fluorescence staining and Western blotting. For Western Blot frozen liver tissue was homogenized with lysis buffer (20 mM Tris, pH7.4, 130 mM NaCl, 1% Triton X 100™, proteinase inhibitor (complete, EDTA-free, Roche, Mannheim, Germany). Protein concentration was determined using the Micro BCA Protein™ Assay Reagent Kit (Pierce, Rockford, Ill.). 40 µg of protein was resolved on 4-15% Tris-HCl Ready Gels (Biorad, Hercules, Calif.) and transferred to a nitrocellulose membrane (Invitrogen). To generate Anti-hLDL receptor antibodies a rabbit was injected intravenously with an AdhLDLr prep ($1 \times 10^{13}$ GC). Four weeks later the rabbit serum was obtained and used for Western Blot. A 1:100 dilution of the serum was used as a primary antibody followed by a HRP-conjugated anti-rabbit IgG and ECL chemiluminescent detection (ECL Western Blot Detection Kit, Amersham, Arlington Heights, Ill.).

E. Immunocytochemistry

For determination of LDL receptor expression in frozen liver sections immunohistochemistry analyses were performed. 10 um cryostat sections were either fixed in acetone for 5 minutes, or unfixed. Blocking was obtained via a 1 hour incubation period with 10% of goat serum. Sections were then incubated for one hour with the primary antibody at room temperature. A rabbit polyclonal antibody anti-human LDL (Biomedical Technologies Inc., Stoughton, Mass.) was used diluted accordingly to the instructions of the manufacturer. The sections were washed with PBS, and incubated with 1:100 diluted fluorescein goat anti-rabbit IgG (Sigma, St Louis, Mo.). Specimens were finally examined under fluorescence microscope Nikon Microphot-FXA. In all cases, each incubation was followed by extensive washing with PBS. Negative controls consisted of preincubation with PBS, omission of the primary antibody, and substitution of the primary antibody by an isotype-matched non-immune control antibody. The three types of controls mentioned above were performed for each experiment on the same day.

F. Gene Transfer Efficiency

Liver tissue was obtained after sacrificing the mice at the designated time points. The tissue was shock frozen in liquid nitrogen and stored at −80° C. until further processing. DNA was extracted from the liver tissue using a QIAamp™ DNA Mini Kit (QIAGEN GmbH, Germany) according to the manufacturers protocol. Genome copies of AAV vectors in the liver tissue were evaluated using Taqman analysis using probes and primers against the SV40 poly(A) tail as described above.

G. Atherosclerotic Plaque Measurement

For the quantification of the atherosclerotic plaques in the mouse aorta the mice were anaesthetized (10% ketamine and xylazine, ip), the chest opened and the arterial system perfused with ice-cold phosphate buffered saline through the left ventricle. The aorta was then carefully harvested, slit down along the ventral midline from the aortic arch down to the femoral arteries and fixed in formalin. The lipid-rich atherosclerotic plaques were stained with Sudan IV™ (Sigma, Germany) and the aorta pinned out flat on a black wax surface. The image was captured with a Sony® DXC-960 MD color video camera. The area of the plaque as well as of the complete aortic surface was determined using Phase 3 Imaging Systems™ (Media Cybernetics).

H. Clearance of $I^{125}$ LDL

Two animals per experimental group were tested. A bolus of 1125-labeled LDL (generously provided by Dan Rader, U Penn) was infused slowly through the tail vein over a period of 30 sec (1,000,000 counts of $[I^{125}]$-LDL diluted in 100 µl sterile PBS/animal). At time points 3 min, 30 min, 1.5 hr, 3 hr, 6 hr after injection a blood sample was obtained via the retro-orbital plexus. The plasma was separated off from the whole blood and 10 µl plasma counted in the gamma counter. Finally the fractional catabolic rate was calculated from the lipoprotein clearance data.

I. Evaluation of Liver Lipid Accumulation

Oil Red Staining of frozen liver sections was performed to determine lipid accumulation. The frozen liver sections were briefly rinsed in distilled water followed by a 2 minute incubation in absolute propylene glycol. The sections were then stained in oil red solution (0.5% in propylene glycol) for 16 hours followed by counterstaining with Mayer's hematoxylin solution for 30 seconds and mounting in warmed glycerin jelly solution.

For quantification of the liver cholesterol and triglyceride content liver sections were homogenized and incubated in chloroform/methanol (2:1) overnight. After adding of 0.05% $H_2SO_4$ and centrifugation for 10 minutes, the lower layer of each sample was collected, divided in two aliquots and dried under nitrogen. For the cholesterol measurement the dried lipids of the first aliquot were dissolved in 1% Triton™ X-100 in chloroform. Once dissolved, the solution was dried under nitrogen. After dissolving the lipids in dd$H_2$0 and incubation for 30 minutes at 37° C. the total cholesterol concentration was measured using a Total Cholesterol Kit (Wako Diagnostics). For the second aliquot the dried lipids were dissolved in alcoholic KOH and incubated at 60° C. for 30 minutes. Then 1M $MgCl_2$ was added, followed by incubation on ice for 10 minutes and centrifugation at 14,000 rpm for 30 minutes. The supernatant was finally evaluated for triglycerides (Wako Diagnostics).

All of the vectors pseudotyped in an AAV2/8 or AAV2/7 capsid lowered total cholesterol, LDL and triglycerides as compared to the control. These test vectors also corrected phenotype of hypercholesterolemia in a dose-dependent manner. A reduction in plaque area for the AAV2/8 and AAV2/7 mice was observed in treated mice at the first test (2 months), and the effect was observed to persist over the length of the experiment (6 months).

Example 10

Functional Factor IX Expression and Correction of Hemophilia

A. Knock-Out Mice

Functional canine factor IX (FIX) expression was assessed in hemophilia B mice. Vectors with capsids of AAV1, AAV2, AAV5, AAV7 or AAV8 were constructed to deliver AAV2 5' ITR—liver-specific promoter [LSP]—canine FIX—woodchuck hepatitis post-regulatory element (WPRE)—AAV2 3' ITR. The vectors were constructed as described in Wang et al, 2000, *Molecular Therapy* 2: 154-158), using the appropriate capsids.

Knock-out mice were generated as described in Wang et al, 1997. *Proc. Natl. Acad. Sci. USA* 94: 11563-11566. This model closely mimic the phenotypes of hemophilia B in human.

Vectors of different serotypes (AAV1, AAV2, AAV5, AAV7 and AAV8) were delivered as a single intraportal injection into the liver of adult hemophiliac C57B1/6 mice in a dose of $1 \times 10^{11}$ GC/mouse for the five different serotypes and one group received an AAV8 vector at a lower dose, $1 \times 10^{10}$ GC/mouse. Control group was injected with $1 \times 10^{11}$ GC of AAV2/8 TBG LacZ3. Each group contains 5-10 male and female mice. Mice were bled bi-weekly after vector administration.

1. ELISA

The canine FIX concentration in the mouse plasma was determined by an ELISA assay specific for canine factor IX, performed essentially as described by Axelrod et al, 1990, *Proc. Natl. Acad. Sci. USA*, 87:5173-5177 with modifications. Sheep anti-canine factor IX (Enzyme Research Laboratories) was used as primary antibody and rabbit anti-canine factor IX ((Enzyme Research Laboratories) was used as secondary antibody. Beginning at two weeks following injection, increased plasma levels of cFIX were detected for all test vectors. The increased levels were sustained at therapeutic levels throughout the length of the experiment, i.e., to 12 weeks. Therapeutic levels are considered to be 5% of normal levels, i.e., at about 250 ng/mL.

The highest levels of expression were observed for the AAV2/8 (at $10^{11}$) and AAV2/7 constructs, with sustained superphysiology levels cFIX levels (ten-fold higher than the normal level). Expression levels for AAV2/8 ($10^{11}$) were approximately 10 fold higher than those observed for AAV2/2 and AAV2/8 ($10^{10}$). The lowest expression levels, although still above the therapeutic range, were observed for AAV2/5.

2. In Vitro Activated Partial Thromboplastin Time (aPTT) Assay

Functional factor IX activity in plasma of the FIX knockout mice was determined by an in vitro activated partial thromboplastin time (aPTT) assay—Mouse blood samples were collected from the retro-orbital plexus into ⅟₁₀ volume of citrate buffer. The aPTT assay was performed as described by Wang et al, 1997, *Proc. Natl. Acad. Sci. USA* 94: 11563-11566.

Clotting times by aPTT on plasma samples of all vector injected mice were within the normal range (approximately 60 sec) when measured at two weeks post-injection, and sustained clotting times in the normal or shorter than normal range throughout the study period (12 weeks).

Lowest sustained clotting times were observed in the animals receiving AAV2/8 ($10^{11}$) and AAV2/7. By week 12, AAV2/2 also induced clotting times similar to those for AAV2/8 and AAV2/7. However, this lowered clotting time was not observed for AAV2/2 until week 12, whereas lowered clotting times (in the 25-40 sec range) were observed for AAV2/8 and AAV2/7 beginning at week two.

Immuno-histochemistry staining on the liver tissues harvested from some of the treated mice is currently being performed. About 70-80% of hepatocytes are stained positive for canine FIX in the mouse injected with AAV2/8.cFIX vector.

B. Hemophilia B Dogs

Dogs that have a point mutation in the catalytic domain of the F.IX gene, which, based on modeling studies, appears to render the protein unstable, suffer from hemophilia B [Evans et al, 1989, Proc. Natl. Acad. Sci. USA, 86:10095-10099). A colony of such dogs has been maintained for more than two decades at the University of North Carolina, Chapel Hill. The homeostatic parameters of these dogs are well described and include the absence of plasma F.IX antigen, whole blood clotting times in excess of 60 minutes, whereas normal dogs are 6-8 minutes, and prolonged activated partial thromboplastin time of 50-80 seconds, whereas normal dogs are 13-28 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Four dogs are injected intraportally with AAV.cFIX according to the schedule below. A first dog receives a single injection with AAV2/2.cFIX at a dose of $3.7 \times 10^{11}$ genome copies (GC)/kg. A second dog receives a first injection of AAV2/2.cFIX ($2.8 \times 10^{11}$ GC/kg), followed by a second injection with AAV2/7.cFIX ($2.3 \times 10^{13}$ GC/kg) at day 1180. A third dog receives a single injection with AAV2/2.cFIX at a dose of $4.6 \times 10^{12}$ GC/kg. The fourth dog receives an injection with AAV2/2.cFIX ($2.8 \times 10^{12}$ GC/kg) and an injection at day 995 with AAV2/7.cFIX ($5 \times 10^{12}$ GC/kg).

The abdomen of hemophilia dogs are aseptically and surgically opened under general anesthesia and a single infusion of vector is administered into the portal vein. The animals are protected from hemorrhage in the peri-operative period by intravenous administration of normal canine plasma. The dog is sedated, intubated to induce general anesthesia, and the abdomen shaved and prepped. After the abdomen is opened, the spleen is moved into the operative field. The splenic vein is located and a suture is loosely placed proximal to a small distal incision in the vein. A needle is rapidly inserted into the vein, then the suture loosened and a 5 F cannula is threaded to an intravenous location near the portal vein threaded to an intravenous location near the portal vein bifurcation. After hemostasis is secured and the catheter balloon inflated, approximately 5.0 ml of vector diluted in PBS is infused into the portal vein over a 5 minute interval. The vector infusion is followed by a 5.0 ml infusion of saline. The balloon is then deflated, the callula removed and venous hemostasis is secured. The spleen is then replaced, bleeding vessels are cauterized and the operative wound is closed. The animal is extubated having tolerated the surgical procedure well. Blood samples are analyzed as described. [Wang et al, 2000, *Molecular Therapy* 2: 154-158]

Results showing correction or partial correction are anticipated for AAV2/7.

All publications cited in this specification are incorporated herein by reference. While the invention has been described with reference to a particularly preferred embodiments, it will be appreciated that modifications can be made without departing from the spirit of the invention. Such modifications are intended to fall within the scope of the claims.

The invention claimed is:

1. A method for detecting adeno-associated virus (AAV) nucleotide sequences from an AAV signature region within an AAV capsid gene in a sample from a human or non-human primate, comprising performing a plurality of polymerase chain reactions (PCR) on the sample under conditions that allow for specific amplification of the AAV signature region with a pair of PCR primers consisting of a first PCR primer and a second PCR primer that are designed to amplify an AAV signature region located within the AAV capsid gene in the position of nucleotides 2886 to 3143 of SEQ ID NO:6, wherein the first PCR primer and the second PCR primer form a duplex with AAV sequences which flank said AAV signature region;
wherein the presence of amplicons resulting from the PCR reactions indicates that AAV nucleotide sequences of the AAV signature region have been detected in the sample.

2. The method according to claim 1 further comprising performing digesting reactions on the PCR amplicons resulting from the PCR reactions with one or more restriction enzymes, wherein a restriction enzyme pattern for the PCR amplicons which differ from the restriction enzyme pattern of AAV1, AAV2, AAV3, AAV4, AAV5 and AAV6 indicates the presence of an AAV in the sample that is not AAV1, AAV2, AAV3, AAV4, AAV5 and AAV6.

3. The method of claim 1, wherein when based on the numbering of AAV2 in which said AAV signature region corresponds to nucleotides 2858 to 3012 of SEQ ID NO: 7, the first primer forms a duplex with an AAV sequence of nucleotides 3095 to 3121 SEQ ID NO: 7 and the second primer has an AAV sequence of nucleotides 2867 to 2891 of SEQ ID NO: 7.

4. The method of claim 1, wherein when based on the numbering of AAV2 in which said AAV signature region corresponds to nucleotides 2858 to 3012 of SEQ ID NO: 7 the first primer forms a duplex with an AAV sequence of nucleotides 4435 to 4462 of SEQ ID NO: 7 and the second primer has an AAV sequence of nucleotides 1380 to 1405 of SEQ ID NO: 7 which corresponds to nucleotides 1398 to 1423 of SEQ ID NO: 6.

5. The method of claim 1, further comprising sequencing the PCR amplicons resulting from the PCR reactions, wherein a sequence which is the same as the sequence of AAV1, AAV2, AAV3, AAV4, AAV5 or AAV6 indicates the presence of AAV1, AAV2, AAV3, AAV4, AAV5 or AAV6 in the sample.

6. The method of claim 1 further comprising performing a sequencing reaction on the PCR amplicons resulting from the PCR reactions, wherein a sequence which differs from the sequence of AAV1, AAV2, AAV3, AAV4, AAV5 and AAV6 indicates the presence of an AAV in the sample that is not AAV1, AAV2, AAV3, AAV4, AAV5 and AAV6.

7. The method of claim 1 further comprising performing a digesting reaction on the PCR amplicons resulting from the PCR reactions with one or more restriction enzymes, wherein a restriction enzyme pattern for the PCR amplicons which is the same as the restriction enzyme pattern of AAV1, AAV2, AAV3, AAV4, AAV5 or AAV6 indicates the presence of AAV1, AAV2, AAV3, AAV4, AAV5 or AAV6 in the sample.

8. The method of claim 1, wherein the primer pair has a first primer having a nucleotide sequence comprising the reverse complement of nucleotides 3095 to 3121 of SEQ ID NO: 7.

9. The method of claim 1, wherein the primer pair has a first primer having a nucleotide sequence comprising the reverse complement of nucleotides 4435 to 4462 of SEQ ID NO: 7.

* * * * *

SEQUENCE LISTING

```
<160> NUMBER OF SEQ ID NOS: 120

<210> SEQ ID NO 1
<211> LENGTH: 4721
<212> TYPE: DNA
<213> ORGANISM: Unknown
<220> FEATURE:
<223> OTHER INFORMATION: adeno-associated virus serotype 7

<400> SEQUENCE: 1
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcgaag cgcctccac gctgccgcgt cagcgctgac     180
gtaaatcacg tcatagggga gtggtcctgt attagctgtc acgtgagtgc ttttgcgaca     240
ttttgcgaca ccacgtggcc atttgaggta tatatggccg agtgagcgag caggatctcc     300
attttgaccg cgaaatttga acgagcagca gccatgccgg gtttctacga gatcgtgatc     360
aaggtgccga gcgacctgga cgagcacctg ccgggcattt ctgactcgtt tgtgaactgg     420
gtggccgaga aggaatggga gctgccccg gattctgaca tggatctgaa tctgatcgag     480
caggcacccc tgaccgtggc cgagaagctg cagcgcgact tcctggtcca atggcgccgc     540
gtgagtaagg ccccggaggc cctgttcttt gttcagttcg agaagggcga gagctacttc     600
caccttcacg ttctggtgga gaccacgggg gtcaagtcca tggtgctagg ccgcttcctg     660
```

```
agtcagattc gggagaagct ggtccagacc atctaccgcg gggtcgagcc cacgctgccc    720
aactggttcg cggtgaccaa gacgcgtaat ggcgccggcg gggggaacaa ggtggtggac    780
gagtgctaca tccccaacta cctcctgccc aagacccagc ccgagctgca gtgggcgtgg    840
actaacatgg aggagtatat aagcgcgtgt ttgaacctgg ccgaacgcaa acggctcgtg    900
gcgcagcacc tgacccacgt cagccagacg caggagcaga acaaggagaa tctgaaccccc   960 aattctgacg cgcccgtgat caggtcaaaa acctccgcgc gctacatgga gctggtcggg   1020
tggctggtgg accggggcat cacctccgag aagcagtgga tccaggagga ccaggcctcg   1080
tacatctcct tcaacgccgc ctccaactcg cggtcccaga tcaaggccgc gctggacaat   1140
gccggcaaga tcatggcgct gaccaaatcc gcgcccgact acctggtggg gccctcgctg   1200
cccgcggaca ttaaaaccaa ccgcatctac cgcatcctgg agctgaacgg gtacgatcct   1260
gcctacgccg gctccgtctt tctcggctgg gcccagaaaa agttcgggaa gcgcaacacc   1320
atctggctgt ttgggcccgc caccaccggc aagaccaaca ttgcggaagc catcgcccac   1380
gccgtgccct tctacggctg cgtcaactgg accaatgaga ctttcccctt caacgattgc   1440
gtcgacaaga tggtgatctg gtgggaggag ggcaagatga cggccaaggt cgtggagtcc   1500
gccaaggcca ttctcggcgg cagcaaggtg cgcgtggacc aaaagtgcaa gtcgtccgcc   1560
cagatcgacc ccaccccgt gatcgtcacc tccaacacca acatgtgcgc cgtgattgac   1620
gggaacagca ccaccttcga gcaccagcag ccgttgcagg accggatgtt caaatttgaa   1680
ctcacccgcc gtctggagca cgactttggc aaggtgacga agcaggaagt caaagagttc   1740
ttccgctggg ccagtgatca cgtgaccgag gtggcgcatg agttctacgt cagaaagggc   1800
ggagccagca aaagacccgc ccccgatgac gcggatataa gcgagcccaa gcgggcctgc   1860
ccctcagtcg cggatccatc gacgtcagac gcggaaggag ctccggtgga ctttgccgac   1920
aggtaccaaa acaaatgttc tcgtcacgcg ggcatgattc agatgctgtt tccctgcaaa   1980
acgtgcgaga gaatgaatca gaatttcaac atttgcttca cacacggggt cagagactgt   2040
ttagagtgtt tccccggcgt gtcagaatct caaccggtcg tcagaaaaaa gacgtatcgg   2100
aaactctgcg cgattcatca tctgctgggg cgggcgcccg agattgcttg ctcggcctgc   2160
gacctggtca acgtggacct ggacgactgc gtttctgagc aataaatgac ttaaaccagg   2220 tatgctgcc gatggttatc ttccagattg gctcgaggac aacctctctg agggcattcg   2280
cgagtggtgg gacctgaaac ctggagcccc gaaacccaaa gccaaccagc aaaagcagga   2340
caacggccgg ggtctggtgc ttcctggcta caagtacctc ggacccttca acggactcga   2400 caaggggggag cccgtcaacg cggcggacgc agcggccctc gagcacgaca aggcctacga   2460
ccagcagctc aaagcgggtg acaatccgta cctgcggtat aaccacgccg acgccgagtt   2520
tcaggagcgt ctgcaagaag atacgtcatt tgggggcaac ctcgggcgag cagtcttcca   2580
ggccaagaag cggttctcg aacctctcgg tctggttgag gaaggcgcta agacggctcc   2640
tgcaaagaag agaccggtag agccgtcacc tcagcgttcc cccgactcct ccacgggcat   2700
cggcaagaaa ggccagcagc ccgccagaaa gagactcaat ttcggtcaga ctggcgactc   2760
agagtcagtc cccgacccctc aacctctcgg agaacctcca gcagcgccct ctagtgtggg   2820
atctggtaca gtggctgcag gcggtggcgc accaatggca gacaataacg aaggtgccga   2880
cggagtgggt aatgcctcag gaaattggca ttgcgattcc acatggctgg gcgacagagt   2940
cattaccacc agcaccccgaa cctgggccct gccccaccta caacaaccac tctacaagca   3000
aatctccagt gaaactgcag gtagtaccaa cgacaacacc tacttcggct acagcacccc   3060
```

```
ctgggggtat tttgacttta acagattcca ctgccacttc tcaccacgtg actggcagcg   3120
actcatcaac aacaactggg gattccggcc caagaagctg cggttcaagc tcttcaacat   3180
ccaggtcaag gaggtcacga cgaatgacgg cgttacgacc atcgctaata accttaccag   3240
cacgattcag gtattctcgg actcggaata ccagctgccg tacgtcctcg gctctgcgca   3300
ccagggctgc ctgcctccgt tcccggcgga cgtcttcatg attcctcagt acggctacct   3360
gactctcaac aatggcagtc agtctgtggg acgttcctcc ttctactgcc tggagtactt   3420
cccctctcag atgctgagaa cgggcaacaa ctttgagttc agctacagct cgaggacgt   3480
gccttttccac agcagctacg cacacagcca gagcctggac cggctgatga atcccctcat   3540
cgaccagtac ttgtactacc tggccagaac acagagtaac ccaggaggca cagctggcaa   3600
tcgggaactg cagttttacc agggcgggcc ttcaactatg ccgaacaag ccaagaattg   3660
gttacctgga ccttgcttcc ggcaacaaag agtctccaaa cgctggatc aaaacaacaa   3720
cagcaacttt gcttggactg gtgccaccaa atatcacctg aacggcagaa actcgttggt   3780
taatcccggc gtcgccatgg caactcacaa ggacgacgag gaccgctttt tcccatccag   3840
cggagtcctg attttggaa aaactggagc aactaacaaa actacattgg aaaatgtgtt   3900
aatgacaaat gaagaagaaa ttcgtcctac taatcctgta gccacggaag aatacgggat   3960
agtcagcagc aacttacaag cggctaatac tgcagcccag acacaagttg tcaacaacca   4020
gggagcctta cctggcatgg tctggcagaa ccgggacgtg tacctgcagg gtcccatctg   4080
ggccaagatt cctcacacgg atggcaactt tcacccgtct cctttgatgg gcggcttttgg   4140
acttaaacat ccgcctcctc agatcctgat caagaacact cccgttcccg ctaatcctcc   4200
ggaggtgttt actcctgcca gtttgcttc gttcatcaca cagtacagca ccggacaagt   4260
cagcgtggaa atcgagtggg agctgcagaa ggaaaacagc aagcgctgga acccggagat   4320
tcagtacacc tccaactttg aaaagcagac tggtgtggac tttgccgttg acagccaggg   4380
tgtttactct gagcctcgcc ctattggcac tcgttacctc acccgtaatc tgtaattgca   4440
tgttaatcaa taaaccggtt gattcgtttc agttgaactt tggtctcctg tgcttcttat   4500
cttatcggtt tccatagcaa ctggttacac attaactgct tgggtgcgct tcacgataag   4560
aacactgacg tcaccgcggt acccctagtg atggagttgg ccactccctc tatgcgcgct   4620
cgctcgctcg gtgggcctg cggaccaaag gtccgcagac ggcagagctc tgctctgccg   4680
gcccccaccga gcgagcgagc gcgcatagag ggagtggcca a                     4721
```

<210> SEQ ID NO 2
<211> LENGTH: 737
<212> TYPE: PRT
<213> ORGANISM: Unknown
<220> FEATURE:
<223> OTHER INFORMATION: capsid protein of adeno-associated virus serotpye 7

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
```

```
                65                  70                  75                  80

Gln Gln Leu Lys Ala Gly Asp Asn Pro Tyr Leu Arg Tyr Asn His Ala
                    85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Ala Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495
```

```
Gln Asn Asn Asn Ser Asn Phe Ala Trp Thr Gly Ala Thr Lys Tyr His
                500                 505                 510
Leu Asn Gly Arg Asn Ser Leu Val Asn Pro Gly Val Ala Met Ala Thr
            515                 520                 525
His Lys Asp Asp Glu Asp Arg Phe Phe Pro Ser Ser Gly Val Leu Ile
530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
                565                 570                 575
Glu Tyr Gly Ile Val Ser Ser Asn Leu Gln Ala Ala Asn Thr Ala Ala
            580                 585                 590
Gln Thr Gln Val Val Asn Asn Gln Gly Ala Leu Pro Gly Met Val Trp
        595                 600                 605
Gln Asn Arg Asp Val Tyr Leu Gln Gly Pro Ile Trp Ala Lys Ile Pro
    610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Glu Val Phe Thr Pro Ala Lys Phe Ala Ser Phe Ile
            660                 665                 670
Thr Gln Tyr Ser Thr Gly Gln Val Ser Val Glu Ile Glu Trp Glu Leu
        675                 680                 685
Gln Lys Glu Asn Ser Lys Arg Trp Asn Pro Glu Ile Gln Tyr Thr Ser
    690                 695                 700
Asn Phe Glu Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                725                 730                 735
Leu

<210> SEQ ID NO 3
<211> LENGTH: 623
<212> TYPE: PRT
<213> ORGANISM: Unknown
<220> FEATURE:
<223> OTHER INFORMATION: rep protein of adeno-associated virus serotype
      7

<400> SEQUENCE: 3

Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
                20                  25                  30
Lys Glu Trp Glu Leu Pro Pro Asp Ser Asp Met Asp Leu Asn Leu Ile
            35                  40                  45
Glu Gln Ala Pro Leu Thr Val Ala Glu Lys Leu Gln Arg Asp Phe Leu
        50                  55                  60
Val Gln Trp Arg Arg Val Ser Lys Ala Pro Glu Ala Leu Phe Phe Val
65                  70                  75                  80
Gln Phe Glu Lys Gly Glu Ser Tyr Phe His Leu His Val Leu Val Glu
                85                  90                  95
Thr Thr Gly Val Lys Ser Met Val Leu Gly Arg Phe Leu Ser Gln Ile
                100                 105                 110
Arg Glu Lys Leu Val Gln Thr Ile Tyr Arg Gly Val Glu Pro Thr Leu
```

```
            115                 120                 125
Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
                195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ser
                275                 280                 285

Leu Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
                500                 505                 510

Ala Asp Pro Ser Thr Ser Asp Ala Glu Gly Ala Pro Val Asp Phe Ala
                515                 520                 525

Asp Arg Tyr Gln Asn Lys Cys Ser Arg His Ala Gly Met Ile Gln Met
530                 535                 540
```

```
Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
            565                 570                 575

Ser Glu Ser Gln Pro Val Val Arg Lys Thr Tyr Arg Lys Leu Cys
        580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
    610                 615                 620

<210> SEQ ID NO 4
<211> LENGTH: 4393
<212> TYPE: DNA
<213> ORGANISM: Unknown
<220> FEATURE:
<223> OTHER INFORMATION: adeno-associated virus serotype 8

<400> SEQUENCE: 4
cagagaggga gtggccaact ccatcactag ggtagcgcg  aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccgagtgagc     180
gagcaggatc tccattttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatggcgc gcgtgagta  aggccccgga ggccctcttc tttgttcagt tcgagaaggg     480
cgagagctac tttcacctgc acgttctggt cgagaccacg ggggtcaagt ccatggtgct     540
aggccgcttc ctgagtcaga ttcgggaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca agactcagcc     720
cgagctgcag tgggcgtgga ctaacatgga ggagtatata agcgcgtgct tgaacctggc     780
cgagcgcaaa cggctcgtgg cgcagcacct gacccacgtc agccgacgc  aggagcagaa     840
caaggagaat ctgaaccccc attctgacgc gcccgtgatc aggtcaaaaa cctccgcgcg     900
ctatatggag ctggtcgggt ggctggtgga ccggggcatc acctccgaga agcagtggat     960
ccaggaggac caggcctcgt acatctcctt caacgccgcc tccaactcgc ggtcccagat    1020
caaggccgcg ctggacaatg ccggcaagat catggcgctg accaaatccg cgcccgacta    1080
cctggtgggg ccctcgctgc ccgcggacat tacccagaac cgcatctacc gcatcctcgc    1140
tctcaacggc tacgaccctg cctacgccgg ctccgtcttt ctcggctggg ctcagaaaaa    1200
gttcgggaaa cgcaacacca tctggctgtt tgggcccgcc accaccggca agaccaacat    1260
tgcggaagcc atcgcccacg ccgtgccctt ctacggctgc gtcaactgga ccaatgagaa    1320
cttttccttc aatgattgcg tcgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc caccccgtg  atcgtcacct ccaacaccaa    1500
catgtgcgcc gtgattgacg ggaacagcac caccttcgag caccagcagc ctctccagga    1560
ccggatgttt aagttcgaac tcaccgcgcg tctggagcac gactttggca aggtgacaaa    1620
gcaggaagtc aaagagttct tccgctgggc cagtgatcac gtgaccgagg tggcgcatga    1680
```

```
gttttacgtc agaaagggcg gagccagcaa aagacccgcc cccgatgacg cggataaaag  1740
cgagcccaag cgggcctgcc cctcagtcgc ggatccatcg acgtcagacg cggaaggagc  1800
tccggtggac tttgccgaca ggtaccaaaa caaatgttct cgtcacgcgg gcatgcttca  1860
gatgctgttt ccctgcaaaa cgtgcgagag aatgaatcag aatttcaaca tttgcttcac  1920
acacggggtc agagactgct cagagtgttt ccccggcgtg tcagaatctc aaccggtcgt  1980
cagaaagagg acgtatcgga aactctgtgc gattcatcat ctgctggggc gggctcccga  2040
gattgcttgc tcggcctgcg atctggtcaa cgtggacctg gatgactgtg tttctgagca  2100
ataaatgact taaaccaggt atggctgccg atggttatct tccagattgg ctcgaggaca  2160
acctctctga gggcattcgc gagtggtggg cgctgaaacc tggagcccg aagcccaaag  2220
ccaaccagca aaagcaggac gacggccggg gtctggtgct tcctggctac aagtacctcg  2280
gacccttcaa cggactcgac aagggggagc ccgtcaacgc ggcggacgca gcggccctcg  2340
agcacgacaa ggcctacgac cagcagctgc aggcgggtga caatccgtac ctgcggtata  2400
accacgccga cgccgagttt caggagcgtc tgcaagaaga tacgtctttt ggggcaacc   2460
tcgggcgagc agtcttccag gccaagaagc gggttctcga acctctcggt ctggttgagg  2520
aaggcgctaa cggctcct ggaaagaaga accggtaga gccatcaccc cagcgttctc     2580
cagactcctc tacgggcatc ggcaagaaag gccaacagcc cgccagaaaa agactcaatt  2640
ttggtcagac tggcgactca gagtcagttc cagaccctca acctctcgga gaacctccag  2700
cagcgcccct tggtgtggga cctaatacaa tggctgcagg cggtggcgca ccaatggcag  2760
acaataacga aggcgccgac ggagtgggta gttcctcggg aaattggcat tgcgattcca  2820
catggctggg cgacagagtc atcaccacca gcacccgaac ctgggccctg cccacctaca  2880
acaaccacct ctacaagcaa atctccaacg ggacatcggg aggagccacc aacgacaaca  2940
cctacttcgg ctacagcacc ccctgggggt attttgactt taacagattc cactgccact  3000
tttcaccacg tgactggcag cgactcatca acaacaactg gggattccgg cccaagagac  3060
tcagcttcaa gctcttcaac atccaggtca aggaggtcac gcagaatgaa ggcaccaaga  3120
ccatcgccaa taacctcacc agcaccatcc aggtgtttac ggactcggag taccagctgc  3180
cgtacgttct cggctctgcc caccagggct gcctgcctcc gttcccggcg gacgtgttca  3240
tgattcccca gtacggctac ctaacactca acaacggtag tcaggccgtg ggacgctcct  3300
ccttctactg cctggaatac tttccttcgc agatgctgag aaccggcaac aacttccagt  3360
ttacttacac cttcgaggac gtgcctttcc acagcagcta cgcccacagc cagagcttgg  3420
accggctgat gaatcctctg attgaccagt acctgtacta cttgtctcgg actcaaacaa  3480
caggaggcac ggcaaatacg cagactctgg gcttcagcca aggtgggcct aatacaatgg  3540
ccaatcaggc aaagaactgg ctgccaggac cctgttaccg ccaacaacgc gtctcaacga  3600
caaccgggca aaacaacaat agcaactttg cctggactgc tgggaccaaa taccatctga  3660
atggaagaaa ttcattggct aatcctggca tcgctatggc aacacacaaa gacgacgagg  3720
agcgtttttt tcccagtaac gggatcctga tttttggcaa acaaaatgct gccagagaca  3780
atgcggatta cagcgatgtc atgctcacca gcgaggaaga aatcaaaacc actaaccctg  3840
tggctacaga ggaatacggt atcgtggcag ataacttgca gcagcaaaac acggctcctc  3900
aaattggaac tgtcaacagc cagggggcct acccggtat ggtctggcag aaccgggacg  3960
tgtacctgca gggtcccatc tgggccaaga ttcctcacac ggacggcaac ttccacccgt  4020
ctccgctgat gggcggcttt ggcctgaaac atcctccgcc tcagatcctg atcaagaaca  4080
```

```
cgcctgtacc tgcggatcct ccgaccacct tcaaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcacccgtaa tctgtaattg cctgttaatc aataaaccgg ttgattcgtt tcagttgaac    4380
tttggtctct gcg                                                      4393

<210> SEQ ID NO 5
<211> LENGTH: 4385
<212> TYPE: DNA
<213> ORGANISM: Unknown
<220> FEATURE:
<223> OTHER INFORMATION: adeno-associated virus serotype 9

<400> SEQUENCE: 5
cagagaggga gtggccaact ccatcactag gggtaatcgc gaagcgcctc ccacgctgcc      60
gcgtcagcgc tgacgtagat tacgtcatag gggagtggtc ctgtattagc tgtcacgtga     120
gtgcttttgc gacattttgc gacaccacat ggccatttga ggtatatatg gccgagtgag     180
cgagcaggat ctccattttg accgcgaaat ttgaacgagc agcagccatg ccgggcttct     240
acgagattgt gatcaaggtg ccgagcgacc tggacgagca cctgccgggc atttctgact     300
cttttgtgaa ctgggtggcc gagaaggaat gggagctgcc cccggattct gacatggatc     360
ggaatctgat cgagcaggca cccctgaccg tggccgagaa gctgcagcgc gacttcctgg     420
tccaatggcg ccgcgtgagt aaggcccggg aggccctctt ctttgttcag ttcgagaagg     480
gcgagagcta ctttcacctg cacgttctgg tcgagaccac gggggtcaag tccatggtgc     540
taggccgctt cctgagtcag attcgggaga agctggtcca gaccatctac cgcgggatcg     600
agccgacccT gccCaactgg ttcgcggtga ccaagacgcg taatggcgcc ggcgggggga     660
acaaggtggt ggacgagtgc tacatcccca actacctcct gcccaagact cagcccgagc     720
tgcagtgggc gtggactaac atggaggagt atataagcgc gtgcttgaac ctggccgagc     780
gcaaacggct cgtggcgcag cacctgaccc acgtcagcca gacgcaggag cagaacaagg     840
agaatctgaa ccccaattct gacgcgcccg tgatcaggtc aaaaacctcc gcgcgctaca     900
tggagctggt cgggtggctg gtggaccggg gcatcacctc cgagaagcag tggatccagg     960
aggaccaggc ctcgtacatc tccttcaacg ccgcctccaa ctcgcggtcc cagatcaagg    1020
ccgcgctgga caatgccggc aagatcatgg cgctgaccaa atccgcgccc gactacctgg    1080 taggccttc acttccggtg gacattacgc agaaccgcat ctaccgcatc ctgcagctca    1140
acggctacga ccctgcctac gccggctccg tctttctcgg ctgggcacaa aagaagttcg    1200
ggaaacgcaa caccatctgg ctgtttgggc cggccaccac gggaaagacc aacatcgcag    1260
aagccattgc ccacgccgtg cccttctacg gctgcgtcaa ctggaccaat gagaactttc    1320
ccttcaacga ttgcgtcgac aagatggtga tctggtggga ggagggcaag atgacggcca    1380
aggtcgtgga gtccgccaag gccattctcg gcggcagcaa ggtgcgcgtg gaccaaaagt    1440
gcaagtcgtc cgcccagatc gaccccactc ccgtgatcgt cacctccaac accaacatgt    1500
gcgccgtgat tgacgggaac agcaccacct tcgagcacca gcagcctctc caggaccgga    1560
tgtttaagtt cgaactcacc cgccgtctgg agcacgactt tggcaaggtg acaaagcagg    1620
aagtcaaaga gttcttccgc tgggccatga tcacgtgac cgaggtgcg catgagtttt    1680 acgtcagaaa gggcggagcc agcaaaagac ccgccccga tgacgcggat aaaagcgagc    1740
```

```
ccaagcgggc ctgcccctca gtcgcggatc catcgacgtc agacgcggaa ggagctccgg    1800
tggactttgc cgacaggtac caaaacaaat gttctcgtca cgcgggcatg cttcagatgc    1860
tgcttccctg caaaacgtgc gagagaatga atcagaattt caacatttgc ttcacacacg    1920
gggtcagaga ctgctcagag tgtttccccg gcgtgtcaga atctcaaccg gtcgtcagaa    1980
agaggacgta tcggaaactc tgtgcgattc atcatctgct ggggcgggct cccgagattg    2040
cttgctcggc ctgcgatctg gtcaacgtgg acctggatga ctgtgtttct gagcaataaa    2100
tgacttaaac caggtatggc tgccgatggt tatcttccag attggctcga ggacaacctc    2160
tctgagggca ttcgcgagtg gtgggcgctg aaacctggag ccccgaagcc caaagccaac    2220
cagcaaaagc aggacgacgg ccggggtctg gtgcttcctg gctacaagta cctcggaccc    2280
ttcaacggac tcgacaaggg ggagcccgtc aacgcggcgg acgcagcggc cctcgagcac    2340
ggcaaggcct acgaccagca gctgcaggcg ggtgacaatc cgtacctgcg gtataaccac    2400
gccgacgccg agtttcagga gcgtctgcaa gaagatacgt cttttggggg caacctcggg    2460
cgagcagtct tccaggccaa gaagcgggtt ctcgaacctc tcggtctggt tgaggaaggc    2520
gctaagacgc ctcctggaaa gaagagaccg gtagagccat caccccagcg ttctccagac    2580
tcctctacgg gcatcggcaa gaaaggccaa cagcccgcca gaaaaagact caattttggt    2640
cagactggcg actcagagtc agttccagac cctcaacctc tcggagaacc tccagcagcg    2700
ccctctggtg tgggacctaa tacaatggct gcaggcggtg gcgcaccaat ggcagacaat    2760
aacgaaggcg ccgacggagt gggtaattcc tcgggaaatt ggcattgcga ttccacatgg    2820
ctgggggaca gagtcatcac caccagcacc cgaacctggg cattgcccac ctacaacaac    2880
cacctctaca gcaaatctc caatggaaca tcggaggaa gcaccaacga caacacctac    2940
tttggctaca gcacccctg ggggtatttt gacttcaaca gattccactg ccacttctca    3000
ccacgtgact ggcagcgact catcaacaac aactggggat tccggccaaa gagactcaac    3060
ttcaagctgt tcaacatcca ggtcaaggag gttacgacga acgaaggcac caagaccatc    3120
gccaataacc ttaccagcac cgtccaggtc tttacggact cggagtacca gctaccgtac    3180
gtcctaggct ctgcccacca aggatgcctg ccaccgtttc ctgcagacgt cttcatggtt    3240
cctcagtacg gctacctgac gctcaacaat ggaagtcaag cgttaggacg ttcttctttc    3300
tactgtctgg aatacttccc ttctcagatg ctgagaaccg gcaacaactt tcagttcagc    3360
tacactttcg aggacgtgcc tttccacagc agctacgcac acagccagag tctagatcga    3420
ctgatgaacc ccctcatcga ccagtaccta tactacctgg tcagaacaca gacaactgga    3480 actggggaa ctcaaacttt ggcattcagc caagcaggcc ctagctcaat ggccaatcag    3540
gctagaaact gggtacccgg ccttgctac cgtcagcagc gcgtctccac aaccaccaac    3600
caaaataaca acagcaactt tgcgtggacg ggagctgcta aattcaagct gaacgggaga    3660
gactcgctaa tgaatcctgg cgtggctatg gcatcgcaca aagacgacga ggaccgcttc    3720
tttccatcaa gtggcgttct catatttggc aagcaaggag ccgggaacga tggagtcgac    3780
tacagccagg tgctgattac agatgaggaa gaaattaaag ccaccaaccc tgtagccaca    3840
gaggaatacg gagcagtggc catcaacaac caggccgcta acacgcaggc gcaaactgga    3900
cttgtgcata accaggagt tattcctggt atggtctggc agaacggga cgtgtacctg    3960 cagggcccta tttgggctaa aatacctcac acagatggca actttcaccc gtctcctctg    4020
atgggtggat ttgggactgaa acacccacct ccacagattt aattaaaaaa tacaccagtg    4080
ccggcagatc ctcctcttac cttcaatcaa gccaagctga actctttcat cacgcagtac    4140
```

```
agcacgggac aagtcagcgt ggaaatcgag tgggagctgc agaaagaaaa cagcaagcgc    4200
tggaatccag agatccagta tacttcaaac tactacaaat ctacaaatgt ggactttgct    4260
gtcaatacca aaggtgttta ctctgagcct cgccccattg gtactcgtta cctcacccgt    4320
aatttgtaat tgcctgttaa tcaataaacc ggttaattcg tttcagttga actttggtct    4380
ctgcg                                                                4385

<210> SEQ ID NO 6
<211> LENGTH: 4718
<212> TYPE: DNA
<213> ORGANISM: Unknown
<220> FEATURE:
<223> OTHER INFORMATION: adeno-associated virus serotype 1

<400> SEQUENCE: 6
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcatagggg agtggtcctg tattagctgt cacgtgagtg cttttgcgac     240 atttgcgac accacgtggc catttagggt atatatggcc gagtgagcga gcaggatctc     300
cattttgacc gcgaaatttg aacgagcagc agccatgccg gcttctacg agatcgtgat     360 caaggtgccg agcgacctgg acgagcacct gccgggcatt tctgactcgt tgtgagctg     420 ggtggccgag aaggaatggg agctgccccc ggattctgac atggatctga atctgattga     480
gcaggcaccc ctgaccgtgg ccgagaagct gcagcgcgac ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg ccgcttcct      660 gagtcagatt agggacaagc tggtgcagac catctaccgc gggatcgagc cgaccctgcc     720
caactggttc gcggtgacca agacgcgtaa tggcgccgga gggggaaaca aggtggtgga     780
cgagtgctac atccccaact acctcctgcc caagactcag cccgagctgc agtgggcgtg     840
gactaacatg gaggagtata taagcgcctg tttgaacctg gccgagcgca acggctcgt      900 ggcgcagcac ctgacccacg tcagccagac ccaggagcag aacaaggaga atctgaaccc     960
caattctgac gcgcctgtca tccggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cttccaactc gcggtcccag atcaaggccg ctctggacaa    1140
tgccggcaag atcatggcgc tgaccaaatc cgcgcccgac tacctggtag gccccgctcc    1200
gcccgcggac attaaaacca accgcatcta ccgcatcctg gagctgaacg gctacgaacc    1260
tgcctacgcc ggctcgtct  ttctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggcaagg tcgtggagtc    1500 cgccaaggcc attctcggcg gcagcaaggt gcgcgtggac caaaagtgca gtcgtccgc    1560 ccagatcgac cccaccccg tgatcgtcac ctccaacacc aacatgtgcg ccgtgattga    1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
```

```
tggagccaac aaaagacccg cccccgatga cgcggataaa agcgagccca agcgggcctg   1860
cccctcagtc gcggatccat cgacgtcaga cgcggaagga gctccggtgg actttgccga   1920
caggtaccaa acaaatgtt ctcgtcacgc gggcatgctt cagatgctgt ttccctgcaa   1980
gacatgcgag agaatgaatc agaatttcaa catttgcttc acgcacggga cgagagactg   2040
ttcagagtgc ttccccggcg tgtcagaatc tcaaccggtc gtcagaaaga ggacgtatcg   2100
gaaactctgt gccattcatc atctgctggg gcgggctccc gagattgctt gctcggcctg   2160
cgatctggtc aacgtggacc tggatgactg tgtttctgag caataaatga cttaaaccag   2220
gtatggctgc cgatggttat cttccagatt ggctcgagga caacctctct gagggcattc   2280
gcgagtggtg ggacttgaaa cctggagccc cgaagcccaa agccaaccag caaaagcagg   2340
acgacggccg gggtctggtg cttcctggct acaagtacct cggacccttc aacggactcg   2400
acaaggggga gcccgtcaac gcggcggacg cagcggccct cgagcacgac aaggcctacg   2460
accagcagct caaagcgggt gacaatccgt acctgcggta taaccacgcc gacgccgagt   2520
ttcaggagcg tctgcaagaa gatacgtctt ttgggggcaa cctcgggcga gcagtcttcc   2580
aggccaagaa gcgggttctc gaacctctcg gtctggttga ggaaggcgct aagacggctc   2640
ctggaaagaa acgtccggta gagcagtcgc cacaagagcc agactcctcc tcgggcatcg   2700
gcaagacagg ccagcagccc gctaaaaaga gactcaattt tggtcagact ggcgactcag   2760
agtcagtccc cgatccacaa cctctcggag aacctccagc aaccccgct gctgtgggac   2820 ctactacaat ggcttcaggc ggtggcgcac caatggcaga caataacgaa ggcgccgacg   2880
gagtgggtaa tgcctcagga aattggcatt gcgattccac atggctgggc gacagagtca   2940
tcaccaccag cacccgcacc tgggccttgc ccacctacaa taaccacctc tacaagcaaa   3000
tctccagtgc ttcaacgggg gccagcaacg acaaccacta cttcggctac agcaccccct   3060
gggggtattt tgatttcaac agattccact gccacttttc accacgtgac tggcagcgac   3120
tcatcaacaa caattgggga ttccggccca agagactcaa cttcaaactc ttcaacatcc   3180
aagtcaagga ggtcacgacg aatgatggcg tcacaaccat cgctaataac cttaccagca   3240
cggttcaagt cttctcggac tcggagtacc agcttccgta cgtcctcggc tctgcgcacc   3300
agggctgcct ccctccgttc ccggcggacg tgttcatgat tccgcaatac ggctacctga   3360
cgctcaacaa tggcagccaa gccgtgggac gttcatcctt ttactgcctg gaatatttcc   3420
cttctcagat gctgagaacg ggcaacaact ttaccttcag ctacaccttt gaggaagtgc   3480 cttttccacag cagctacgcg cacagccaga gcctggaccg gctgatgaat cctctcatcg   3540
accaatacct gtattacctg aacagaactc aaaatcagtc cggaagtgcc caaaacaagg   3600
acttgctgtt tagccgtggg tctccagctg gcatgtctgt tcagcccaaa aactggctac   3660 ctggacccg ttatcggcag cagcgcgttt ctaaaacaaa acagacaac aacaacagca   3720 atttacctg gactggtgct tcaaaatata acctcaatgg gcgtgaatcc atcatcaacc   3780
ctggcactgc tatggcctca cacaaagacg acgaagacaa gttctttccc atgagcggtg   3840
tcatgatttt tggaaaagag agcgccggag cttcaaacac tgcattggac aatgtcatga   3900
ttacagacga agaggaaatt aaagccacta cccctgtggc caccgaaaga tttgggaccg   3960
tggcagtcaa tttccagagc agcagcacag accctgcgac cggagatgtg catgctatgg   4020
gagcattacc tggcatggtg tggcaagata gagacgtgta cctgcagggt cccatttggg   4080
ccaaaattcc tcacacagat ggacactttc acccgtctcc tcttatgggc ggctttggac   4140
tcaagaaccc gcctcctcag atcctcatca aaaacacgcc tgttcctgcg aatcctccgg   4200
```

```
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttacttac ccgtccctg taattacgtg     4440 ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                           4718

<210> SEQ ID NO 7
<211> LENGTH: 4675
<212> TYPE: DNA
<213> ORGANISM: adeno-associated virus 2

<400> SEQUENCE: 7
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta gcccgagtg agcacgcagg gtctccattt tgaagcggga    300
ggtttgaacg cgcagccgcc atgccggggt tttacgagat tgtgattaag gtccccagcg    360
accttgacgg gcatctgccc ggcatttctg acagctttgt gaactgggtg gccgagaagg    420
aatgggagtt gccgccagat tctgacatgg atctgaatct gattgagcag gcaccctga    480 ccgtggccga aagctgcag cgcgactttc tgacggaatg gcgccgtgtg agtaaggccc    540
cggaggccct tttctttgtg caatttgaga agggagagag ctacttccac atgcacgtgc    600
tcgtggaaac caccgggtg aaatccatgg ttttgggacg tttcctgagt cagattcgcg    660
aaaaactgat tcagagaatt taccgcggga tcgagccgac ttttgccaaac tggttcgcgg    720 tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca    1020
aggggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagccgtg gaggacattt    1200 ccagcaatcg gatttataaa attttggaac taaacgggta cgatcccaa tatgcggctt    1260 ccgtctttct gggatgggcc acgaaaaagt tcggcaagag gaacaccatc tggctgtttg    1320
ggcctgcaac taccgggaag accaacatcg cggaggccat agcccacact gtgccttct    1380 acgggtgcgt aaactggacc aatgagaact ttccttcaa cgactgtgtc acaagatgg    1440 tgatctggtg ggaggagggg aagatgaccg ccaaggtcgt ggagtcggcc aaagccattc    1500
tcggaggaag caaggtgcgc gtggaccaga atgcaagtc ctcggcccag atagacccga    1560
ctccccgtga tcgtcacctcc aacaccaaca tgtgcgccgt gattgacggg aactcaacga    1620
```

```
ccttcgaaca ccagcagccg ttgcaagacc ggatgttcaa atttgaactc acccgccgtc   1680
tggatcatga ctttgggaag gtcaccaagc aggaagtcaa agacttttc cggtgggcaa    1740 aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg aagctcaaa    2280 cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgta caaagcctac gaccggcagc tcgacagcgg   2460
agacaacccg tacctcaagt acaaccacgc cgacgcggag tttcaggagc gccttaaaga   2520
agatacgtct tttgggggca acctcggacg agcagtcttc caggcgaaaa agagggttct   2580
tgaacctctg ggcctggttg aggaacctgt taagacggct ccgggaaaaa agaggccggt   2640
agagcactct cctgtggagc cagactcctc ctcgggaacc ggaaaggcgg ccagcagcc    2700 tgcaagaaaa agattgaatt ttggtcagac tggagacgca gactcagtac ctgaccccca   2760
gcctctcgga cagccaccag cagcccctc tggtctggga actaatacga tggctacagg    2820
cagtggcgca ccaatggcag acaataacga gggcgccgac ggagtgggta attcctccgg   2880
aaattggcat tgcgattcca catggatggg cgacagagtc atcaccacca gcacccgaac   2940
ctgggccctg cccacctaca caaccacct ctacaaacaa atttccagcc aatcaggagc    3000
ctcgaacgac aatcactact ttggctacag cacccccttgg gggtattttg acttcaacag   3060
attccactgc cacttttcac cacgtgactg gcaaagactc atcaacaaca actggggatt   3120
ccgacccaag agactcaact tcaagctctt taacattcaa gtcaaagagg tcacgcagaa   3180
tgacggtacg acgacgattg ccaataacct taccagcacg gttcaggtgt ttactgactc   3240
ggagtaccag ctcccgtacg tcctcggctc ggcgcatcaa ggatgcctcc cgccgttccc   3300
agcagacgtc ttcatggtgc cacagtatgg atacctcacc ctgaacaacg ggagtcaggc   3360
agtaggacgc tcttcatttt actgcctgga gtactttcct tctcagatgc tgcgtaccgg   3420
aaacaacttt accttcagct cacttttga ggacgttcct ttccacagca gctacgctca    3480
cagccagagt ctggaccgtc tcatgaatcc tctcatcgac cagtacctgt attacttgag   3540
cagaacaaac actccaagtg gaaccaccac gcagtcaagg cttcagtttt ctcaggccgg   3600
agcgagtgac attcgggacc agtctaggaa ctggcttcct ggaccctgtt accgccagca   3660
gcgagtatca aagacatctg cggataacaa caacagtgaa tactcgtgga ctggagctac   3720
caagtaccac ctcaatggca gagactctct ggtgaatccg gccatggcaa gccacaagga   3780
cgatgaagaa aagttttttc ctcagagcgg ggttctcatc tttgggaagc aaggctcaga   3840
gaaaacaaat gtgaacattg aaaaggtcat gattacagac gaagaggaaa tcggaacaac   3900
caatcccgtg gctacggagc agtatggttc tgtatctacc aacctccaga gaggcaacag   3960
acaagcagct accgcagatg tcaacacaca aggcgttctt ccaggcatgg tctggcagga   4020
```

-continued

| | |
|---|---|
| cagagatgtg taccttcagg ggcccatctg ggcaaagatt ccacacacgg acggacattt | 4080 |
| tcacccctct cccctcatgg gtggattcgg acttaaacac cctcctccac agattctcat | 4140 |
| caagaacacc ccggtacctg cgaatccttc gaccaccttc agtgcggcaa agtttgcttc | 4200 |
| cttcatcaca cagtactcca cgggacacgg tcagcgtgga gatcgagtgg gagctgcaga | 4260 |
| aggaaaacag caaacgctgg aatcccgaaa ttcagtacac ttccaactac aacaagtctg | 4320 |
| ttaatcgtgg acttaccgtg gatactaatg gcgtgtattc agagcctcgc cccattggca | 4380 |
| ccagatacct gactcgtaat ctgtaattgc ttgttaatca ataaaccgtt taattcgttt | 4440 |
| cagttgaact ttggtctctg cgtatttctt tcttatctag tttccatggc tacgtagata | 4500 |
| agtagcatgg cgggttaatc attaactaca aggaacccct agtgatggag ttggccactc | 4560 |
| cctctctgcg cgctcgctcg ctcactgagg ccgggcgacc aaaggtcgcc cgacgcccgg | 4620 |
| gctttgcccg gcggcctca gtgagcgagc gagcgcgcag agaggagtg gccaa | 4675 |

<210> SEQ ID NO 8
<211> LENGTH: 4726
<212> TYPE: DNA
<213> ORGANISM: adeno-associated virus 3

<400> SEQUENCE: 8

| | |
|---|---|
| ttggccactc cctctatgcg cactcgctcg ctcggtgggg cctggcgacc aaaggtcgcc | 60 |
| agacggacgt gctttgcacg tccggcccca ccgagcgagc gagtgcgcat agagggagtg | 120 |
| gccaactcca tcactagagg tatggcagtg acgtaacgcg aagcgcgcga agcgagacca | 180 |
| cgcctaccag ctgcgtcagc agtcaggtga ccccttttgcg acagtttgcg acaccacgtg | 240 |
| gccgctgagg gtatatattc tcgagtgagc gaaccaggag ctccattttg accgcgaaat | 300 |
| ttgaacgagc agcagccatg ccgggggttct acgagattgt cctgaaggtc ccgagtgacc | 360 |
| tggacgagcg cctgccgggc atttctaact cgtttgttaa ctgggtggcc gagaaggaat | 420 |
| gggacgtgcc gccggattct gacatggatc cgaatctgat tgagcaggca cccctgaccg | 480 |
| tggccgaaaa gcttcagcgc gagttcctgg tggagtggcg ccgcgtgagt aaggcccgg | 540 |
| aggccctctt ttttgtccag ttcgaaaagg gggagaccta cttccacctg cacgtgctga | 600 |
| ttgagaccat cggggtcaaa tccatggtgg tcggccgcta cgtgagccag attaaagaga | 660 |
| agctggtgac ccgcatctac cgcggggtcg agccgcagct tccgaactgg ttcgcggtga | 720 |
| ccaaaacgcg aaatgcgcc gggggcggga acaaggtggt ggacgactgc tacatcccca | 780 |
| actacctgct ccccaagacc cagcccgagc tccagtgggc gtggactaac atggaccagt | 840 |
| atttaagcgc ctgtttgaat ctcgcggagc gtaaacggct ggtggcgcag catctgacgc | 900 |
| acgtgtcgca gacgcaggag cagaacaaag agaatcagaa ccccaattct gacgcgccgg | 960 |
| tcatcaggtc aaaaacctca gccaggtaca tggagctggt cgggtggctg gtggaccgcg | 1020 |
| ggatcacgtc agaaaagcaa tggattcagg aggaccaggc ctcgtacatc tccttcaacg | 1080 |
| ccgcctccaa ctcgcggtcc cagatcaagg ccgcgctgga caatgcctcc aagatcatga | 1140 |
| gcctgacaaa gacggctccg gactacctgg tgggcagcaa cccgccggag gacattacca | 1200 |
| aaaatcggat ctaccaaatc ctggagctga acgggtacga tccgcagtac gcggcctccg | 1260 |
| tcttcctggg ctgggcgcaa aagaagttcg ggaagaggaa caccatctgg ctcttttggc | 1320 |
| cggccacgac gggtaaaacc aacatcgcgg aagccatcgc ccacgccgtg cccttctacg | 1380 |
| gctgcgtaaa ctggaccaat gagaactttc ccttcaacga ttgcgtcgac aagatggtga | 1440 |
| tctggtggga ggagggcaag atgacggcca aggtcgtgga gagcgccaag gccattctgg | 1500 |

```
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcagccgctg caggaccgga tgtttgaatt tgaacttacc cgccgtttgg   1680
accatgactt tgggaaggtc accaaacagg aagtaaagga cttttttccgg tgggcttccg   1740 atcacgtgac tgacgtggct catgagttct acgtcagaaa gggtggagct aagaaacgcc   1800
ccgcctccaa tgacgcggat gtaagcgagc aaaacggga gtgcacgtca cttgcgcagc   1860
cgacaacgtc agacgcggaa gcaccggcgg actacgcgga caggtaccaa acaaatgtt   1920 ctcgtcacgt gggcatgaat ctgatgcttt ttccctgtaa acatgcgag agaatgaatc   1980 aaatttccaa tgtctgtttt acgcatggtc aaagagactg tggggaatgc ttccctggaa   2040
tgtcagaatc tcaacccgtt tctgtcgtca aaaagaagac ttatcagaaa ctgtgtccaa   2100
ttcatcatat cctgggaagg gcacccgaga ttgcctgttc ggcctgcgat ttggccaatg   2160
tggacttgga tgactgtgtt tctgagcaat aaatgactta accaggtat ggctgctgac   2220 ggttatcttc cagattggct cgaggacaac ctttctgaag gcattcgtga gtggtgggct   2280
ctgaaacctg gagtccctca acccaaagcg aaccaacaac accaggacaa ccgtcggggt   2340
cttgtgcttc cgggttacaa atacctcgga cccggtaacg gactcgacaa aggagagccg   2400
gtcaacgagg cggacgcggc agccctcgaa cacgacaaag cttacgacca gcagctcaag   2460
gccggtgaca acccgtacct caagtacaac cacgccgacg ccgagtttca ggagcgtctt   2520
caagaagata cgtcttttgg gggcaacctt ggcagagcag tcttccaggc caaaaagagg   2580
atccttgagc ctcttggtct ggttgaggaa gcagctaaaa cggctcctgg aaagaagggg   2640
gctgtagatc agtctcctca ggaaccggac tcatcatctg tgttggcaa atcgggcaaa   2700 cagcctgcca gaaaaagact aaatttcggt cagactggag actcagagtc agtcccagac   2760
cctcaacctc tcggagaacc accagcagcc cccacaagtt tgggatctaa tacaatggct   2820
tcaggcggtg gcgcaccaat ggcagacaat aacgagggtg ccgatggagt gggtaattcc   2880
tcaggaaatt ggcattgcga ttcccaatgg ctgggcgaca gagtcatcac caccagcacc   2940
agaacctggg ccctgcccac ttacaacaac catctctaca agcaaatctc cagccaatca   3000
ggagcttcaa cgacaacca ctactttggc tacagcaccc cttgggggta ttttgacttt   3060
aacagattcc actgccactt ctcaccacgt gactggcagc gactcattaa caacaactgg   3120
ggattccggc caagaaaact cagcttcaag ctcttcaaca tccaagttag aggggtcacg   3180
cagaacgatg gcacgacgac tattgccaat aaccttacca gcacggttca agtgtttacg   3240
gactcggagt atcagctccc gtacgtgctc gggtcggcgc accaaggctg tctcccgccg   3300
tttccagcgg acgtcttcat ggtccctcag tatggatacc tcaccctgaa caacggaagt   3360
caagcggtgg gacgctcatc ctttttactgc ctggagtact tcccttcgca gatgctaagg   3420
actggaaata acttccaatt cagctatacc ttcgaggatg tacctttca cagcagctac   3480 gctcacagcc agagtttgga tcgcttgatg aatcctctta ttgatcagta tctgtactac   3540
ctgaacagaa cgcaaggaac aacctctgga caaccaacc aatcacggct gcttttagc    3600 caggctgggc tcagtctat gtctttgcag gccagaaatt ggctacctgg gccctgctac   3660
cggcaacaga gactttcaaa gactgctaac gacaacaaca cagtaacttt ccttggaca    3720 gcggccagca atatcatct caatggccgc gactcgctgg tgaatccagg accagctatg   3780
gccagtcaca aggacgatga agaaaaattt ttccctatgc acggcaatct aatatttggc   3840
aaagaaggga caacggcaag taacgcagaa ttagataatg taatgattac ggatgaagaa   3900
```

```
gagattcgta ccaccaatcc tgtggcaaca gagcagtatg gaactgtggc aaataacttg    3960
cagagctcaa atacagctcc cacgactgga actgtcaatc atcaggggc cttacctggc    4020 atggtgtggc aagatcgtga cgtgtacctt caaggaccta tctgggcaaa gattcctcac    4080
acggatggac actttcatcc ttctcctctg atgggaggct ttggactgaa acatccgcct    4140
cctcaaatca tgatcaaaaa tactccgta ccggcaaatc ctccgacgac tttcagcccg    4200
gccaagtttg cttcatttat cactcagtac tccactggac aggtcagcgt ggaaattgag    4260
tgggagctac agaaagaaaa cagcaaacgt tggaatccag agattcagta cacttccaac    4320
tacaacaagt ctgttaatgt ggactttact gtagacacta atggtgttta tagtgaacct    4380
cgccctattg aacccggta tctcacacga aacttgtgaa tcctggttaa tcaataaacc    4440
gtttaattcg tttcagttga actttggctc ttgtgcactt ctttatcttt atcttgtttc    4500
catggctact gcgtagataa gcagcggcct gcggcgcttg cgcttcgcgg tttacaactg    4560
ctggttaata tttaactctc gccataccte tagtgatgga gttggccact ccctctatgc    4620
gcactcgctc gctcggtggg gcctggcgac caaggtcgc cagacggacg tgctttgcac    4680
gtccggcccc accgagcgag cgagtgcgca tagagggagt ggccaa            4726

<210> SEQ ID NO 9
<211> LENGTH: 3098
<212> TYPE: DNA
<213> ORGANISM: Unknown
<220> FEATURE:
<223> OTHER INFORMATION: AAV serotype, clone 42.2

<400> SEQUENCE: 9
gaattcgccc tttctacggc tgcgtcaact ggaccaatga aactttccc ttcaacgatt      60 gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tcccaccccc gtgatcgtca cttccaacac caacatgtgc gctgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gccccgatg acgcggataa aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaaattca catttgctt cacgcacggg accagagact     660
gttcagaatg tttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgacc gtgtttctga caataaatg acttaaacca     840 ggtatgctg ccgatggtta tcttccagat tggctcgagg acaacctctc tgagggcatt     900
cgcgagtggt gggactgaa acctggagcc ccgaaaccca agccaacca gcaaaagcag     960 gacgacggcc ggggtctggt gcttcctggc tacaagtacc tcggacccct caacggactc    1020
gacaagggag agcggtcaa cgaggcagac gccgcggccc tcgagcacga caaggcctac    1080
gacaagcagc tcgagcaggg ggacaacccg tacctcaagt acaaccacgc cgacgccgag    1140
tttcaggagc gtcttcaaga agatacgtct ttgggggca acctcggcg agcagtcttc    1200 caggccaaga gcgggttct cgaacctctc ggtctggttg aggaaggcgc taagacggct    1260
```

| | |
|---|---|
| cctggaaaga agagacccat agaatccccc gactcctcca cgggcatcgg caagaaaggc | 1320 |
| cagcagcccg ctaaaaagaa gctcaactt gggcagactg gcgactcaga gtcagtgccc | 1380 |
| gaccccaac ctctcggaga acctcccgcc gcgccctcag gtctgggatc tggtacaatg | 1440 |
| gctgcaggcg gtggcgcacc aatggcagac aataacgaag gcgccgacgg agtgggtaat | 1500 |
| gcctccggaa attggcattg cgattccaca tggctgggcg acagagtcat caccaccagc | 1560 |
| acccgcacct gggccctgcc cacctacaac aaccacctct acaagcagat atcaagtcag | 1620 |
| agcggggcta ccaacgacaa ccacttcttc ggctacagca cccctgggg ctattttgac | 1680 |
| ttcaacagat tccactgcca cttctcacca cgtgactggc agcgactcat caacaacaac | 1740 |
| tggggattcc ggcccagaaa gctgcggttc aagttgttca acatccaggt caaggaggtc | 1800 |
| acgacgaacg acggcgttac gaccatcgct aataacctta ccagcacgat tcaggtcttc | 1860 |
| tcggactcgg agtaccaact gccgtacgtc ctcggctctg cgcaccaggg ctgcctccct | 1920 |
| ccgttccctg cggacgtgtt catgattcct cagtacggat atctgactct aaacaacggc | 1980 |
| agtcagtctg tgggacgttc ctccttctac tgcctggagt actttccttc tcagatgctg | 2040 |
| agaacgggca ataactttga attcagctac acctttgagg aagtgccttt ccacagcagc | 2100 |
| tatgcgcaca gccagagcct ggaccggctg atgaatcccc tcatcgacca gtacctgtac | 2160 |
| tacctggccc ggacccagag cactacgggg tccacaaggg agctgcagtt ccatcaggct | 2220 |
| gggcccaaca ccatggccga gcaatcaaag aactggctgc ccggaccctg ttatcggcag | 2280 |
| cagagactgt caaaaacat agacagcaac aacaacagta actttgcctg gaccggggcc | 2340 |
| actaaatacc atctgaatgg tagaaattca ttaaccaacc cgggcgtagc catggccacc | 2400 |
| aacaaggacg acgaggacca gttctttccc atcaacggag tgctggtttt tggcgaaacg | 2460 |
| ggggctgcca acaagacaac gctggaaaac gtgctaatga ccagcgagga ggagatcaaa | 2520 |
| accaccaatc ccgtggctac agaagaatac ggtgtggtct ccagcaacct gcaatcgtct | 2580 |
| acggccggac cccagacaca gactgtcaac agccaggggg ctctgcccgg catggtctgg | 2640 |
| cagaaccggg acgtgtacct gcagggtccc atctgggcca aaattcctca cacggacggc | 2700 |
| aactttcacc cgtctccct gatgggcgga tttggactca acacccgcc tcctcaaatt | 2760 |
| ctcatcaaaa acaccccggt acctgctaat cctccagagg tgtttactcc tgccaagttt | 2820 |
| gcctcattta tcacgcagta cagcaccggc caggtcagcg tggagatcga gtgggaactg | 2880 |
| cagaaagaaa acagcaaacg ctggaatcca gagattcagt acacctcaaa ttatgccaag | 2940 |
| tctaataatg tggaatttgc tgtcaacaac gaagggttt atactgagcc tcgccccatt | 3000 |
| ggcacccgtt acctcacccg taacctgtaa ttgcctgtta atcaataaac cggttaattc | 3060 |
| gtttcagttg aactttggtc tctgcgaagg gcgaattc | 3098 |

<210> SEQ ID NO 10
<211> LENGTH: 3098
<212> TYPE: DNA
<213> ORGANISM: Unknown
<220> FEATURE:
<223> OTHER INFORMATION: AAV serotype, clone 16.3

<400> SEQUENCE: 10

| | |
|---|---|
| gaattcgccc ttcgcagaga ccaaagttca actgaaacga atcaaccggt ttattgatta | 60 |
| acaagtaatt acaggttacg ggtgaggtaa cgggtgccaa tggggcgagg ctcagtataa | 120 |
| accccttcgt tgttgacagc aaattccaca ttattagact tggcataatt tgaggtgtac | 180 |
| tgaatctctg gattccagcg tttgctgttt tctttctgca gttcccactc gatctccacg | 240 |

```
ctgacctggc cggtgctgta ctgcgtgata aatgaggcaa actaggcagg agtaaacacc    300
cctggaggat tagcaggtac cggggtgttt ttgatgagaa tttgaggagg cgggtgtttg    360
agtccaaatc cgcccatcag gggagacggg tgaaagttgc cgtccgtgtg aggaattttg    420
gcccagatgg gaccctgcag gtacacgtcc cggttctgcc agaccatgcc gggcagagcc    480
ccctggctgt tgacagtctg tgtctggggt ccggccgtag acgattgcag gttgctggag    540
accacaccgt attcttctgt agccacggga ttggtggttt tgatctcctc ctcgctggtc    600
attagcacgt tttccagcgt tgtcttgttg gcagcccccg ttttgccaaa aaccagcact    660
ccgttgatgg gaaagaactg gccctcgtcg tccttgttgg tggccatggc tacgcccggg    720
ttggttaatg aatttctacc attcagatgg tatttagtgg ccccggtcca ggcaaagtta    780
ctgttgttgt tgctgtctat gttttttgac agtctctgct gccgataaca gggtccgggc    840
agccagttct ttgattgctc ggccatggtg ttgggcccag cctgatggaa ctgcagctcc    900
cttgtggacc ccgtagtgct ctgggtccgg gccaggtagt acaggtactg gtcgatgagg    960
ggattcatca gccggtccag gctctggctg tgcgcatagc tgctgtggaa aggcacttcc   1020
tcaaaggtgt agctgaattc aaagttattg cccgttctca gcatctgaga aggaaagtac   1080
tccaggcagt agaaggagga acgtcccata gactgactgc cgttgtttag agtcagatat   1140
ccgtactgag gaatcatgaa cacgtccgca gggaacggag ggaggcagcc ctggtgcgca   1200
gagccgagga cgtacggcag ttggtactcc gagtccgaga agacctgaat cgtgctggta   1260
aggttattag cgatggtcgt aacgccgtcg ttcgtcgtga cctccttgac ctggatgttg   1320
aacaacttga accgcagctt tctgggccgg aatccccagt tgttgttgat gagtcgctgc   1380
cagtcacgtg gtgagaagtg gcagtggaat ctgttgaagt caaaatagcc caggggggtg   1440
ctgtagccga agaagtggtt gtcgttggta gccccgctct gacttgatat ctgcttgtag   1500
aggtggttgt tgtaggtggg cagggcccag gtgcgggtgc tggtggtgat gactctgtcg   1560
cccagccatg tggaatcgca atgccaattt ccggaggcat tacccactcc gtcggcgcct   1620
tcgttattgt ctgccattgg tgcgccaccg cctgcagcca ttgtaccaga tcccagacct   1680
gagggcgcgg cgggaggttc tccgagaggt tggggtcgg gcactgactc tgagtcgcca    1740
gtctgcccaa agttgagctt cttttttagcg ggctgctggc cttcttgcc gatgcccgtg    1800 gaggagtcgg gggattctat gggtctcttc tttccaggag ccgtcttagc gccttcctca   1860
accagaccga gaggttcgag aacccgcttc ttggcctgga agactgctcg cccgaggttg   1920 ccccccaaaag acgtatcttc ttgaagacgc tcctgaaact cagcgtcggc gtggttgtac   1980
ttgaggtacg ggttgtcccc ctgctcgagc tgcttgtcgt aggccttgtc gtgctcgagg   2040
gccgcggcgt ctgcctcgtt gaccggctct cccttgtcga gtccgttgaa gggtccgagg   2100
tacttgtagc caggaagcac cagacccegg ccgtcgtcct gcttttgctg gttggctttg   2160
ggtttcgggg ctccaggttt caagtcccac cactcgcgaa tgccctcaga gaggttgtcc   2220
tcgagccaat ctggaagata accatcggca gccatacctg gtttaagtca tttattgctc   2280
agaaacacag tcatccaggt ccacgttgac cagatcgcag gccgagcaag caatctcggg   2340
agcccgcccc agcagatgat gaatggcaca gagtttccga tacgtcctct ttctgacgac   2400
cggttgagat tctgacacgc cggggaaaca ttctgaacag tctctggtcc cgtgcgtgaa   2460
gcaaatgttg aaattctgat tcattctctc gcatgtcttg cagggaaaca gcatctgaag   2520
catgcccgcg tgacgagaac atttgttttg gtacctgtcg gcaaagtcca ccggagctcc   2580
ttccgcgtct gacgtcgatg gatccgcgac tgaggggcag gcccgcttgg gctcgctttt   2640
```

-continued

| | |
|---|---|
| atccgcgtca tcggggcgg gcctcttgtt ggctccaccc tttctgacgt agaactcatg | 2700 |
| cgccacctcg gtcacgtgat cctgcgccca gcggaagaac tctttgactt cctgctttgt | 2760 |
| caccttgcca aagtcctgct ccagacggcg ggtgagttca aatttgaaca tccggtcttg | 2820 |
| taacggctgc tggtgctcga aggtggtgct gttcccgtca atcacggcgc acatgttggt | 2880 |
| gttggaagtg acgatcacgg gggtgggatc gatctgggcg gacgacttgc acttttggtc | 2940 |
| cacgcgcacc ttgctgccgc cgagaatggc cttggcggac tccacgacct tggccgtcat | 3000 |
| cttgccctcc tcccaccaga tcaccatctt gtcgacgcaa tcgttgaagg gaaagttctc | 3060 |
| attggtccag ttgacgcagc cgtagaaagg gcgaattc | 3098 |

<210> SEQ ID NO 11
<211> LENGTH: 3121
<212> TYPE: DNA
<213> ORGANISM: Unknown
<220> FEATURE:
<223> OTHER INFORMATION: AAV serotype, clone 29.3

<400> SEQUENCE: 11

| | |
|---|---|
| gaattcgccc ttcgcagaga ccaaagttca actgaaacga atcaaccggt ttattgatta | 60 |
| acaagcaatt acagattacg ggtgaggtaa cgggtgccga tggggcgagg ctcagaataa | 120 |
| gtgccatctg tgttaacagc aaagtccaca tttgtagatt tgtagtagtt ggaagtgtat | 180 |
| tgaatctctg ggttccagcg tttgctgttt tctttctgca gctcccattc aatttccacg | 240 |
| ctgacctgtc cggtgctgta ctgcgtgatg aacgacgcca gcttagcttg actgaaggta | 300 |
| gttggaggat ccgcgggaac aggtgtattc ttaatcagga tctgaggagg cgggtgtttc | 360 |
| agtccaaagc cccccatcag cggcgaggga tgaaagtttc cgtccgtgtg aggaatcttg | 420 |
| gcccagatag gaccctgcag gtacacgtcc cggttctgcc agaccatgcc aggtaaggct | 480 |
| ccttgactgt tgacgccccc tacaatagga gcggcgtttt gctgttgcag gttatcggcc | 540 |
| accacgccgt actgttctgt ggccactggg ttggtggttt taatttcttc ctcactggtt | 600 |
| agcataacgc tgctatagtc cacgttgcct tttccagctc cctgtttccc aaacattaag | 660 |
| actccgctgg acggaaaaaa tcgctcttcg tcgtccttgt gggttgccat agcgacaccg | 720 |
| ggatttacca gagagtctct gccattcaga tgatacttgg tggcaccggt ccaggcaaag | 780 |
| ttgctgttgt tattttgcga cagtgtcgtg gagacgcgtt gctgccggta gcagggcccg | 840 |
| ggtagccagt ttttggcctg agccgacatg ttattaggcc cggcctgaga aaatagcaac | 900 |
| tgctgagttc ctgcggtacc tcccgtggac tgagtccgag acaggtagta caggtactgg | 960 |
| tcgatgaggg ggttcatcag ccggtccagg ctttggctgt gcgcgtagct gctgtgaaaa | 1020 |
| ggcacgtcct caaactggta gctgaactca agttgttgc ccgttctcag catttgagaa | 1080 |
| ggaaagtact ccaggcagta gaaggaggaa cggcccacgg cctgactgcc attgttcaga | 1140 |
| gtcaggtacc cgtactgagg aatcatgaag acgtccgccg ggaacggagg caggcagccc | 1200 |
| tggcgcgcag agccgaggac gtacgggagc tggtattccg agtccgtaaa gacctgaatc | 1260 |
| gtgctggtaa ggttattggc gatggtcttg gtgccttcat tctgcgtgac ctccttgacc | 1320 |
| tggatgttga agagcttgaa gttgagtctc ttgggccgga atccccagtt gttgttgatg | 1380 |
| agtcgctgcc agtcacgtgg tgagaagtgg cagtggaatc tgttaaagtc aaaataccc | 1440 |
| caggggggtgc tgtagccgaa gtaggtgttg tcgttggtgc ttcctcccga agtccgttg | 1500 |
| gagatttgct tgtagaggtg gttgttgtag gtggggaggg cccaggttcg ggtgctggtg | 1560 |
| gtgatgactc tgtcgcccag ccatgtggaa tcgcaatgcc aatttcctga ggaactaccc | 1620 |

```
actccgtcgg cgccttcgtt attgtctgcc attggagcgc caccgcctgc agccattgta   1680
ccagatccca gaccagaggg gcctgcgggg ggttctccga ttggttgagg gtcgggcact   1740
gactctgagt cgccagtctg cccaaagttg agtctctttt tcgcgggctg ctggcctttc   1800
ttgccgatgc ccgtagtgga gtctggagaa cgctggggtg atggctctac cggtctcttc   1860
tttccaggag ccgtcttagc gccttcctca accagaccga gaggttcgag aacccgcttc   1920
ttggcctgga agactgctcg tccgaggttg cccccaaaag acgtatcttc ttgcagacgc   1980
tcctgaaact cggcgtcggc gtggttatac cgcaggtacg gattgtcacc cgctttgagc   2040
tgctggtcgt aggccttgtc gtgctcgagg gccgctgcgt ccgccgcgtt gacgggctcc   2100
cccttgtcga gtccgttgaa gggtccgagg tacttgtagc caggaagcac cagaccccgg   2160
ccgtcgtcct gcttttgctg gttggctttg gcttcgggg ctccaggttt cagcgcccac    2220
cactcgcgaa tgccctcaga gaggttgtcc tcgagccaat ctggaagata accatcggca   2280
gccatacctg atctaaatca tttattgttc aaagatgcag tcatccaaat ccacattgac   2340
cagatcgcag gcagtgcaag cgtctggcac ctttcccatg atatgatgaa tgtagcacag   2400
tttctgatac gcctttttga cgacagaaac gggttgagat tctgacacgg aaagcactc    2460
taaacagtct ttctgtccgt gagtgaagca gatatttgaa ttctgattca ttctctcgca   2520
ttgtctgcag ggaaacagca tcagattcat gcccacgtga cgagaacatt tgttttggta   2580
cctgtccgcg tagttgatcg aagcttccgc gtctgacgtc gatggctgcg caactgactc   2640
gcgcacccgt ttgggctcac ttatatctgc gtcactgggg gcgggtcttt tcttggctcc   2700
acccttttg acgtagaatt catgctccac ctcaaccacg tgatcctttg cccaccggaa    2760
aaagtctttg acttcctgct tggtgacctt cccaaagtca tgatccagac ggcgggtgag   2820
ttcaaatttg aacatccggt cttgcaacgg ctgctggtgt tcgaaggtcg ttgagttccc   2880
gtcaatcacg gcgcacatgt tggtgttgga ggtgacgatc acgggagtcg ggtctatctg   2940
ggccgaggac ttgcatttct ggtccacgcg caccttgctt cctccgagaa tggctttggc   3000
cgactccacg accttggcgg tcatcttccc ctcctcccac cagatcacca tcttgtcgac   3060
acagtcgttg aagggaaagt tctcattggt ccagttgacg cagccgtaga agggcgaatt   3120
c                                                                   3121
```

<210> SEQ ID NO 12
<211> LENGTH: 3121
<212> TYPE: DNA
<213> ORGANISM: Unknown
<220> FEATURE:
<223> OTHER INFORMATION: AAV serotype, clone 29.4

<400> SEQUENCE: 12

```
gaattcgccc ttctacggct gcgtcaactg gaccaatgag aactttccct tcaacgactg     60
tgtcgacaag atggtgatct ggtgggagga ggggaagatg accgccaagg tcgtggagtc    120
ggccaaagcc attctcggag gaagcaaggt gcgcgtggac cagaaaatgca agtcctcggc   180
ccagatagac ccgactcccg tgatcgtcac ctccaacacc aacatgtgcg ccgtgattga   240
cgggaactca acgaccttcg aacaccagca gccgttgcaa gaccggatgt tcaaatttga   300
actcacccgc cgtctggatc atgactttgg gaaggtcacc aagcaggaag tcaaagactt   360
tttccggtgg gcaaaggatc acgtggttga ggtggagcac gaattctacg tcaaaaaggg   420
tggagccaag aaaagacccg ccccagtga cgcagatata agtgagccca acgggtgcg     480
cgagtcagtt gcgcagccat cgacgtcaga cgcggaagct tcgatcaact acgcagacag   540
```

```
gtaccaaaac aaatgttctc gtcacgcggg catgaatctg atgctgtttc cctgcagaca    600
atgcgagaga atgaatcaga attcaaatat ctgcttcact cacggacaga aagactgttt    660
agagtgcttt cccgtgtcag aatctcaacc cgtttctgtc gtcaaaaagg cgtatcagaa    720
actgtgctac attcatcata tcatgggaaa ggtgccagac gcttgcactg cctgcgatct    780
ggtcgatgtg gatttggatg actgcatctt tgaacaataa atgatttaaa tcaggtatgg    840
ctgccgatgg ttatcttcca gattggctcg aggacaacct ctctgagggc attcgcgagt    900
ggtgggcgct gaaacctgga gccccgaagc ccaaagccaa ccagcaaaag caggacggcg    960
gccggggtct ggtgcttcct ggctacaagt acctcggacc cttcaacgga ctcgacaagg   1020
gggagcccgt caacgcggcg gacgcagcgg ccctcgagca cgacaaggcc tacgaccagc   1080
agctcaaagc gggtgacaat ccgtacctgc ggtataacca cgccgacgcc gagtttcagg   1140
agcgtctgca agaagatacg tcttttgggg gcaacctcgg gcgagcagtc ttccaggcca   1200
agaagcgggt tctcgaacct ctcggtctgg ttgaggaagg cgctaagacg gctcctggaa   1260
agaagagacc ggtagagcca tcaccccagc gttctccaga ctcctctacg ggcatcggca   1320
agaaaggcca gcagcccgcg aaaaagagac tcaactttgg gcagactggc gactcagagt   1380
cagtgcccga ccctcaacca atcggagaac ccccgcaggg ccctctggt ctgggatctg    1440
gtacaatggc tgcaggcggt ggcgctccaa tggcagacaa taacgaaggc gccgacggag   1500
tgggtagttc ctcaggaaat tggcattgcg attccacatg gctgggcgac tgagtcatca   1560
ccaccagcac ccgaacctgg gccctcccca cctacaacaa ccacctctac aagcaaatct   1620
ccaacgggac ttcgggagga agcaccaacg acaacaccta cttcggctac agcaccccct   1680
gggggtattt tgactttaac agattccact gccacttctc accacgtgac tggcagcgac   1740
tcatcaacaa caactgggga ttccggccca agagactcaa cttcaagctc ttcaacatcc   1800
aggtcaagga ggtcacgcag aatgaaggca ccaagaccat cgccaataac cttaccagca   1860
cgattcaggt cttttacggac tcggaatacc agctcccgta cgtcctcggc tctgcgcacc   1920
agggctgcct gcctccgttc ccggcggacg tcttcatgat tcctcagtac gggtacctga   1980
ctctgaacaa tggcagtcag gccgtgggcc gttcctcctt ctactgcctg gagtactttc   2040
cttctcaaat gctgagaacg ggcaacaact ttgagttcag ctaccagttt gaggacgtgc   2100
cttttcacag cagctacgcg cacagccaaa gcctggaccg gctgatgaac cccctcatcg   2160
accagtacct gtactacctg tctcggactc agtccacggg aggtaccgca ggaactcagc   2220
agttgctatt ttctcaggcc gggcctaata acatgtcggc tcaggccaaa aactggctac   2280
ccgggccctg ctaccggcag taacgcgtct ccacgacact gtcgcaaaat aacaacagca   2340
actttgtctg gaccggtgcc accaagtatc atctgaatgg cagagactct ctggtagatc   2400
ccggtgtcgc tatggcaacc cacaaggacg acgaagagcg attttttccg tccagcggag   2460
tcataatgtt tgggaaacag ggagctggaa aagacaacgt ggactatagc agcgtcatgc   2520
taaccagtga ggaagaaatt aaaaccacca cccagtggc cacagaacag tacgcgtgg    2580
tggccgataa cctgcaacag caaaacgccg ctcctattgt aggggccgtc aacagtcaag   2640
gagccttacc tggcatggtc tggcagaacc gggacgtgta cctgcagggt cctacctggg   2700
ccaagattcc tcacacggac ggaaactttc atccctcgcc gctgatggga ggctttggac   2760
tgaaacaccc gcctcctcag atcctgatta agaatacacc tgttcccgcg gatcctccaa   2820
ctaccttcag tcaagctaag ctggcgtcgt tcatcacgca gtacagcacc ggacaggtca   2880
gcgtggaaat tgaatgggag ctgcaggaag aaaacagcaa acgctggaac ccagagattc   2940
```

```
aatacacttc caactactac aaatctacaa atgtggactt tgctgttaac acagatggca    3000
cttattctga gcctcgcccc atcggcaccc gttacctcac ccgtaatctg taattgcttg    3060
ttaatcaata aaccggttga ttcgtttcag ttgaactttg gtctctgcga agggcgaatt    3120
c                                                                    3121
```

<210> SEQ ID NO 13
<211> LENGTH: 3121
<212> TYPE: DNA
<213> ORGANISM: Unknown
<220> FEATURE:
<223> OTHER INFORMATION: AAV serotype, clone 29.5

<400> SEQUENCE: 13

```
gaattcgccc ttcgcgagac caaagttcaa ctgaaacgaa tcaaccggtt tattgattaa     60
caagcaatta cagattacgg gtgaggtaac gggtgccgat ggggcgaggc tcagaataag    120
tgccatctgt gttaacagca aagtccacat ttgtagattt gtagtagttg aagtgtatt    180 gaatctctgg gttccagcgt ttgctgtttt ctttctgcag ctcccattca atttccacgc    240
tgacctgtcc ggtgctgtac tgcgtgatga acgacgccag cttagcttga ctgaaggtag    300
ttggaggatc cgcgggaaca ggtgtattct taatcaggat ctgaggaggc gggtgtttca    360
gtccaaagcc tcccatcagc ggcgagggat gaaagtttcc gtccgtgtga ggaatcttgg    420
cccagatagg accctgcagg tacacgtccc ggttctgcca gaccatgcca ggtaaggctc    480
cttgactgtt gacggcccct acaataggag cggcgttttg ctgttgcagg ttatcggcca    540
ccacgccgta ctgttctgtg gccactgggt tggtggtttt aatttcttcc tcactggtta    600
gcataacgct gctatagtcc acgttgtctt ttccagctcc ctgtttccca acattaaga    660 ctccgctgga cggaaaaaat cgctcttcgt cgtccttgtg ggttgccata gcgacaccgg    720
gatttaccag agagtctctg ccattcagat gatacttggt ggcaccggtc caggcaaagt    780
tgctgttgtc attttgcgac agtgtcgtgg agacgcgttg ctgccggtag cagggcccgg    840
gtagccagtt tttggcctga ccgacatgtt tattaggccc ggcctgagaa atagcaact     900 gctgagttcc tgcggtacct cccgtggact gagtccgaga caggtagtac aggtactggt    960
cgatgagggg gttcatcagc cggtccaggc tttggctgtg cgcgtagctg ctgtgaaaag   1020
gcacgtcctc aaactggtag ctgaactcaa agttgttgcc cgttctcagc atttgagaag   1080
gaaagtactc caggcagtag aaggaggaac ggcccacggc ctgactgcca ttgttcagag   1140
tcaggtaccc gtactgagga atcatgaaga cgtccgccgg gaacggaggc aggcagccct   1200
ggtgcgcaga gccgaggacg tacgggagct ggtattccga gtccgtaaag acctgaatcg   1260
tgctggtaag gttattggcg atggtcttgg tgccttcatt ctgcgtgacc tccttgacct   1320
ggatgttgaa gagcttgaag ttgaggctct ggggccggaa tccccagttg ttgttgatga   1380
gtcgctgcca gtcacgtggt gagaagtggc agtggaatct gttaaagtca aaataccccc   1440
agggggtgct gtagccgaag taggtgttgt cgttggtgct tcctcccgaa gtcccgttgg   1500
agatttgctt gtagaggtgg ttgttgtagg tggggagggc ccaggttcgg gtgctggtgg   1560
tgatgactcc gtcgcccagc catgtggaat cgcaatgcca atttcctgag gaactaccca   1620
ctccgtcggc gccttcgtta ttgtctgcca ttggagcgcc accgcctgca gccattgtac   1680
cagatcccag accagagggg cctgcggggg gttctccgat tggttgaggg tcgggcactg   1740
actctgagtc gccagtctgc ccaaagttga gtctcttttt cgcggggctgc tggcctttct   1800 tgccgatgcc cgtagaggag tctggagaac gctgggggtga tggctctacc ggtctcttct   1860

```
ttccaggagc cgtcttagcg ccttcctcaa ccagaccgag aggttcgaga acccgcttct 1920
tggcctggaa gactgctcgc ccgaggttgc ccccaaaaga cgtatcttct tgcagacgct 1980
cctgaaactc ggcgtcggcg tggttatacc gcaggtacgg attgtcaccc gctttgagct 2040
gctggtcgta ggccttgtcg tgctcgaggg ccgctgcgtc cgccgcgttg acgggctccc 2100
ccttgtcgag tccgttgaag ggtccgaggt acttgtagcc aggaagcacc agaccccggc 2160
cgtcgtcctg cttttgctgg ttggctttgg gcttcggggc tccaggtttc agcgcccacc 2220
actcgcgaat gccctcagag aggttgtcct cgagccaatc tggaagataa ccatcggcag 2280
ccatacctga tttaaatcat ttattgttca aagatgcagt catccaaatc cacattgacc 2340
agatcgcagg cagtgcaagc gtctggcacc tttcccatga tatgatgaat gtagcacagt 2400
ttctgatacg ccttttttgac gacagaaacg ggttgagatt ctgacacggg aaagcactct 2460
aaacagtctt tctgtccgtg agtgaagcag atatttgaat tctgattcat tctctcgcat 2520
tgtctgcagg gaaacagcat cagattcatg cccacgtgac gagaacattt gttttggtac 2580
ctgtctgcgt agttgatcga agcttccgcg tctgacgtcg atggctgcgc aactgactcg 2640
cgcacccgtt tgggctcact tatatctgcg tcactggggg cgggtctttt cttggctcca 2700
ccctttttga cgtagaattc atgctccacc tcaaccacgt gatcctttgc ccaccggaaa 2760
aagtctttga cttcctgctt ggtgaccttc ccaaagtcat gatccagacg gcgggtgagt 2820
tcaaatttga acatccggtc ttgcaacggc tgctggtgtt cgaaggtcgt tgagttcccg 2880
tcaatcacgg cgcacatgtt ggtgttggag gtgacgatca cgggagtcgg gtctatctgg 2940
gccgaggact tgcatttctg gtccacgcgc accttgcttc ctccgagaat ggctttggcc 3000
gactccacga ccttggcggt catcttcccc tcctcccacc agatcaccat cttgtcgaca 3060
cagtcgttga agggaaagtt ctcattggtc cagttgacgc agccgtagaa agggcgaatt 3120
c 3121

<210> SEQ ID NO 14
<211> LENGTH: 3131
<212> TYPE: DNA
<213> ORGANISM: Unknown
<220> FEATURE:
<223> OTHER INFORMATION: AAV serotype, clone 1-3

<400> SEQUENCE: 14
gcggccgcga attcgccctt ggctgcgtca actggaccaa tgagaacttt cccttcaatg 60
attgcgtcga caagatggtg atctggtggg aggagggcaa gatgacggcc aaggtcgtgg 120
agtccgccaa ggccattctc ggcggcagca aggtgcgcgt ggaccaaaag tgcaagtcgt 180
ccgcccagat cgaccccacc cccgtgatcg tcacctccaa caccaacatg tgcgccgtga 240
ttgacgggaa cagcaccacc ttcgagcacc agcagcctct ccaggaccgg atgtttaagt 300
tcgaactcac ccgccgtctg gagcacgact ttggcaaggt gacaaagcag gaagtcaaag 360
agttcttccg ctgggccagt gatcacgtga ccgaggtggc gcatgagttt tacgtcagaa 420
agggcggagc cagcaaaaga cccgcccccg atgacgcgga taaaagcgag cccaagcggg 480
cctgcccctc agtcgcggat ccatcgacgt cagacgcgga aggagctccg gtggactttg 540
ccgacaggta ccaaaacaaa tgttctcgtc acgcgggcat gcttcagatg ctgtttccct 600
gcaaaacgtg cgagagaatg aatcggaatt tcaacatttg cttcacacac ggggtcagag 660
actgctcaga gtgtttcccc ggcgtgtcag aatctcaacc ggtcgtcaga aagaggacgt 720
atcggaaact ccgtgcgatt catcatctgc tggggcgggc tcccgagatt gcttgctcgg 780

```
cctgcgatct ggtcaacgtg gacctggatg actgtgtttc tgagcaataa atgacttaaa    840
ccaggtatgg ctgccgatgg ttatcttcca gattggctcg aggacaacct ctctgagggc    900
attcgcgagt ggtgggcgct gaaacctgga gccccgaagc ccaaagccaa ccagcaaaag    960
caggacgacg gccggggtct ggtgcttcct ggctacaagt acctcggacc cttcaacgga   1020
ctcgacaagg gggagcccgt caacgcggcg gacgcagcgg ccctcgagca cgacaaggct   1080
tacgaccagc agctgcaggc gggtgacaat ccgtacctgc ggtataacca cgccgacgcc   1140
gagtttcagg agcgtctgca agaagatacg tcttttgggg gcaacctcgg gcgagcagtc   1200
ttccaggcca agaagcgggt tctcgaacct ctcggtctgg ttgaggaagg cgctaagacg   1260
gctcctggaa agaagagacc ggtagagcca tcaccccagc gttctccaga ctcctctacg   1320
ggcatcggca agaaaggcca acagcccgcc agaaaaagac tcaattttgg tcagactggc   1380
gactcagagt cagttccaga ccctcaacct ctcggagaac ctccagcagc gccctctggt   1440
gtgggaccta atacaatggc tgcaggcggt ggcgcaccaa tggcagacaa taacgaaggc   1500
gccgacggag tggtagttc ctcgggaaat tggcattgcg attccacatg gctgggcgac   1560
agagtcatca ccaccagcac ccgaacctgg gccctgccca cctacaacaa ccacctctac   1620
aagcaaatct ccaacgggac atcgggagga gccaccaacg acaacaccta cttcggctac   1680
agcaccccct gggggtattt tgactttaac agattccact gccacttttc accacgtgac   1740
tggcagcgac tcatcaacaa caactgggga ttccgaccca agagactcag cttcaagctc   1800
ttcaacatcc aggtcaagga ggtcacgcag aatgaaggca ccaagaccat cgccaataac   1860
ctcaccagca ccatccaggt gtttacggac tcggagtacc agctgccgta cgttctcggc   1920
tctgtccacc agggctgcct gcctccgttc ccggcggacg tgttcatgat tccccagtac   1980
ggctacctaa cactcaacaa cggtagtcag gccgtgggac gctcctcctt ctactgcctg   2040
gaatactttc cttcgcagat gctgagaacc ggcaacaact tccagtttac ttacaccttc   2100
gaggacgtgc cttttccacag cagctacgcc cacagctaga gcttggaccg gctgatgaat   2160
cctctgattg accagtacct gtactacttg tctcggactc aaacaacagg aggcacggca   2220
aatacgcaga ctctgggctt cagccaaggt gggcctaata caatggccaa tcaggcaaag   2280
aactggctgc caggaccctg ttaccgccaa caacgcgtct caacgacaac cgggcaaaac   2340
aacaatagca actttgcctg gactgctggg accaaatacc atctgaatgg aagaaattca   2400
ttggctaatc ctggcatcgc tatggcaaca cacaaagacg acgaggagcg tttttttccc   2460
agtaacggga tcctgatttt tggcaaacaa aatgctgcca gagacaatgc ggattacagc   2520
gatgtcatgc tcaccagcga ggaagaaatc aaaaccacta accctgtggc tacagaggaa   2580
tacggtatcg tggcagataa cttgcagcag caaaacacgg ctcctcaaat tggaactgtc   2640
aacagccagg gggccttacc cggtatggtc tggcagaacc gggacgtgta cctgcagggt   2700
cccatctggg ccaagattcc tcacacggac ggcaacttcc acccgtctcc gctgatgggc   2760
ggctttggcc tgaaacatcc tccgcctcag atcctgatca gaacacgcc tgtacctgcg   2820
gatcctccga ccaccttcaa ccagtcaaag ctgaactctt tcatcacgca atacagcacc   2880
ggacaggtca gcgtggaaat tgaatgggag ctgcagaagg aaaacagcaa gcgctggaac   2940
cccgagatcc agtacacctc caactactac aaatctataa gtgtggactt tgctgttaat   3000
acagaaggcg tgtactctga accccgcccc attggcaccc gttacctcac ccgtaatctg   3060
taattgcctt ttaatcaata aaccggttga ttcgtttcag ttgaactttg gtctctgcga   3120
agggcgaatt c                                                        3131
```

<210> SEQ ID NO 15
<211> LENGTH: 3127
<212> TYPE: DNA
<213> ORGANISM: Unknown
<220> FEATURE:
<223> OTHER INFORMATION: AAV serotype, clone 13-3b

<400> SEQUENCE: 15

| | | | | | | |
|---|---|---|---|---|---|---|
| gcggccgcga | attcgccctt | cgcagagacc | aaagttcaac | tgaaacgaat | caaccggttt | 60 |
| attgattaac | atgcaattac | agattacggg | tgaggtaacg | agtgccaata | gggcgaggct | 120 |
| cagagtaaac | accctggctg | tcaacggcaa | agtccacacc | agtctgcttt | tcaaagttgg | 180 |
| aggtgtactg | aatctccggg | tcccagcgct | tgctgttttc | cttctgcagc | tcccactcga | 240 |
| tttccacgct | gacttgtccg | gtgctgtact | gtgtgatgaa | cgaagcaaac | ttggcaggag | 300 |
| taaacacctc | cggaggatta | gcgggaacgg | gagtgttctt | gatcaggatc | tgaggaggcg | 360 |
| gatgtttaag | tccaaagccg | cccatcaaag | gagacgggtg | aaagttgcca | tccgtgtgag | 420 |
| gaatcttggc | ccagatggga | ccctgcaggt | acacgtcccg | gttctgccag | accatgccag | 480 |
| gtaaggctcc | ctggttgttg | acaacttgtg | tctgggctgc | agtattagcc | gcttgtaagt | 540 |
| tgctgctgac | tatcccgtat | tcttccgtgg | ctacaggatt | agtaggacga | atttcttctt | 600 |
| catttgtcat | taacacattt | tccaatgtag | ttttgttagt | tgctccagtt | tttccaaaaa | 660 |
| tcaggactcc | gctggatggg | aaaaagcggt | cctcgtcgtc | cttgtgagtt | gccatggcga | 720 |
| cgccgggatt | aaccaacgag | tttctgccgt | tcaggtgata | tttggtggca | ccagtccaag | 780 |
| caaagttgct | gttgttgttt | tgatccagcg | ttttggagac | cctttgttgc | cggaagcagg | 840 |
| gtccaggtaa | ccaattcttg | gcttgttcgg | ccatagttga | aggcccgccc | tggtaaaact | 900 |
| gcagttcccg | attgccagct | gtgcctcctg | ggtcactctg | tgttctggcc | aggtagtaca | 960 |
| agtactggtc | gatgagggga | ttcatcagcc | ggtccaggct | ctggctgtgt | gcgtagctgc | 1020 |
| tgtggaaagg | cacgtcctcg | aagctgtagc | tgaactcaaa | gttgttgccc | gttctcagca | 1080 |
| tctgagaggg | gaagtactcc | aggcagtaga | aggaggaacg | tcccacagac | tgactgccat | 1140 |
| tgttgagagt | caggtagccg | tactgaggaa | tcatgaagac | gtccgccggg | aacggaggca | 1200 |
| ggcagccctg | gtgcgcagag | ccgaggacgt | acggcagctg | gtattccgag | tccgagaata | 1260 |
| cctgaatcgt | gctggtaagg | ttattagcga | tggtcgtaac | gccgtcattc | gtcgtgacct | 1320 |
| ccttgacctg | gatgttgaag | agcttgaacc | gcagcttctt | gggccggaat | ccccagttgt | 1380 |
| tgttgatgag | tcgctgccag | tcacgtggtg | agaagtggca | gtggaatctg | ttaaagtcaa | 1440 |
| aataccccca | gggggtgctg | tagccgaagt | aggtgttgtc | gttggtacta | cctgcagttt | 1500 |
| cactggagat | ttgctcgtag | aggtggttgt | tgtaggtggg | cagggccag | gttcgggtgc | 1560 |
| tggtggtaat | gactctgtcg | cccagccatg | tggaatcgca | atgccaattt | cctgaggcat | 1620 |
| tacccactcc | gtcggcacct | tcgttattgt | ctgccattgg | tgcgccaccg | cctgcagcca | 1680 |
| ctgtaccaga | tcccacacta | gagggcgctg | ctggaggttc | tccgagaggt | tgagggtcgg | 1740 |
| ggactgactc | tgagtcgcca | gtctgaccga | aattgagtct | ctttctggcg | gctgctggc | 1800 |
| ccttcttgcc | gatgcccgtg | gaggagtcgg | gggaacgctg | aggtgacggc | tctaccggtc | 1860 |
| tcttcttgc | aggagccgtc | ttagcgcctt | cctcaaccag | accgagaggt | tcgagaaccc | 1920 |
| gcttcttggc | ctggaagact | gctcgcccga | ggttgccccc | aaatgacgta | tcttcttgca | 1980 |
| gacgctcctg | aaactcggcg | tcggcgtggt | tataccgcag | gtacgggttg | tcacccgcat | 2040 |
| tgagctgctg | gtcgtaggcc | ttgtcgtgct | cgagggccgc | tgcgtccgcc | gcgttgacgg | 2100 |

```
gctccccctt gtcgagtccg ttgaagggtc cgaggtactt gtagccagga agcaccagac    2160
cccggccgtt gtcctgcttt tgctggttgg ctttgggttt cggggctcca ggtttcaggt    2220
cccaccactc gcgaatgccc tcagagaggt tgtcctcgag ccaatctgga agataaccat    2280
cggcagccat acctgattta aatcatttat tgttcaaaga tgcagtcatc caaatccaca    2340
ttgaccagat cgcaggcagt gcaagcgtct ggcacctttc ccatgatatg atgaatgtag    2400
cacagtttct gatacgcctt tttgacgaca gaaacgggtt tagattctga cacgggaaag    2460
cactctaaac agtctttctg tccgtgagtg aagcagatat ttgaattctg attcattctc    2520
tcgcattgtc tgcagggaaa cagcatcaga ttcatgccca cgtgacgaga acatttgttt    2580
tggtacctgt ctgcgtagtt gatcgaagct tccgcgtctg acgtcgatgg ctgcgcaact    2640
gactcgcgca cccgtttggg ctcacttata tctgcgtcac tggggcggg tcttttcttg     2700 gctccaccct ttttgacgta gaattcatgc tccacctcaa ccacgtaatc ctttgcccac    2760
cggaaaaagt ctttgacttc ctgcttggtg accttcccaa agtcatgatc cagacggcgg    2820
gtgagttcaa atttgaacat ccggtcttgc aacggctgct ggtgttcgaa ggtcgttgag    2880
ttcccgtcga tcacgcgcca catgttggtg ttggagatga cgatcgcggg agtcgggtct    2940
atctgggccg aggacttgca tttctggtcc acgcgcacct tgcttcctcc gagaatggct    3000
ttggccgact ccacgacctt ggcggtcatc ttcccctcct cccaccagat caccatcttg    3060
tcgacacagt cgttgagggg aaagttctca ttggtccagt tgacgcagcc gtagaaaggg    3120
cgaattc                                                             3127

<210> SEQ ID NO 16
<211> LENGTH: 3106
<212> TYPE: DNA
<213> ORGANISM: Unknown
<220> FEATURE:
<223> OTHER INFORMATION: AAV serotype, clone 24-1

<400> SEQUENCE: 16
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg      180 aggtgtactg aatctctgga ttccagcgtt tgctgttttc tttctgcagt tcccactcga     240
tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
ggtgtttgag tccaaatccg cccatcaggg gagacgggtg aaagttgccg tccgtgtgag    420
gaattttggc ccagatggga ccctgcaggc acacgtcccg gttctgccag accatgccgg     480
gcagagcccc ctggctgttg acagtctgtg tctggggtcc ggccgtagac gattgcaggt    540
tgctggagac cacaccgtat tcttctgtag ccacgggatt ggtggttttg atctcctcct     600
cgctggtcat tagcacgttt tccagcgttg tcttgttggc agccccgtt ttgccaaaaa      660 ccagcactcc gttgatggga aagaactggt cctcgtcgtc cttgttggtg gccatggcta    720
cgcccgggtt ggttaatgaa tttctaccat tcagatggta tttagtggcc ccggtccagg     780
caaagttact gttgttgttg ctgtctatgt tttttgacag tctctgctgc cgataacagg     840
gtccgggcag ccagttcttt gattgctcgg ccatggtgtt gggcccagcc tgatggaact     900
gcagctccct tgtggacccc gtagtgctct gggtccgggc caggtagtac aggtactggt     960
cgatgagggg attcatcagc cggtctaggc tctggctgtg cacatagctg ctgtggaaag   1020
```

```
gcacttcctc aaaggtgtag ctgaattcaa agttattgcc cgttctcagc atctgagaag    1080
gaaagtactc caggcagtag aaggaggaac gtcccacaga ctgactgccg ttgtttagag    1140
tcagatatcc gtactgagga atcatgaaca cgtccgcagg gaacggaggg aggcagccct    1200
ggtgcgcaga gccgaggacg tacggcagtt ggtactccga gtccgagaag acctgaatcg    1260
tgctggtaag gttattagcg atggtcgtaa cgccgtcgtt cgtcgtgacc tccttgacct    1320
ggatgttgaa caacttgaac cgcagctttc tgggccggaa tccccagttg ttgttgatga    1380
gtcgctgcca gtcacgtggt gagaagtggc agtggaatct gttgaagtca aaatagcccc    1440 aggggtgct  gtagctgaag aagtggttgt cgttggtagc cccgctctga cttgatatct    1500
gcttgtagag gtggttgttg taggtgggca gggcccaggt gcgggtgctg gtggtgatga    1560
ctctgtcgcc cagccatgtg aatcgcaat  gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc cgagaggttg ggggtcgggc actgactctg    1740
agtcgccagt ctgcccaaag ttgagcttct ttttagcggg ctgctggcct ttcttgccga    1800
tgcccgtgga ggagtcgggg gattctatgg gtctcttctt tccaggagcc gtcttagcga    1860
cttcctcaac cagaccgaga ggttcgagaa cccgcttctt ggcctggaag actgctcgcc    1920
cgaggttgcc cccaaaagac gtatcttctt gaagacgctc tgaaactcg  gcgtcggcgt    1980 ggttgtactt gaggtacggg ttgtccccct gctcgagctg cttgtcgtag gccttgtcgt    2040
gctcgagggc cgcggcgtct gcctcgttga ccggctctcc cttgtcgagt ccgttgaagg    2100
gtctgaggta cttgtagcca ggaagcacca ccccggcc   gtcgtcctgc ttttgctggt    2160
tggctttggg tttcggggct ccaggtttca agtcccacca ctcgcgaatg ccctcagaga    2220
ggttgtcctc gagccaatct ggaagataac catcggcagc catacctggt ttaagtcatt    2280
tattgctcag aaacacagtc atccaggtcc acgttgacca gatcgcaggc cgagcaagca    2340
atctcgggag cccgccccag cagatgatga atggcacaga gtttccgata cgtcctcttt    2400
ctgacgaccg gttgagattc tgacacgccg gggaaacatt ctgaacagtc tctggtcccg    2460
tgcgtgaagc aaatgttgaa attctgattc actctctcgc atgtcttgca gggaaacagc    2520
atctgaagca tgcccgcgtg acgagaacat ttgttttggt acctgtcggc aaagtccacc    2580
ggagctcctt ccgcgtctga cgtcgatgga ttcgcgactg aggggcaggc ccgcttgggc    2640
tcgcttttat ccgcgtcatc gggggcgggt ctcttgttgg ccccacccct tctgacgtag    2700
aacccatgcg ccacctcggt cacgtgatcc tgcgcccagc ggaagaacct tttgacttcc    2760
tgctttgtca ccttgccaaa gttatgctcc agacggcggg tgggttcaaa tttgaacatc    2820
cggtcctgca acggctgctg gtgctcgaag gtggcgctgt tccgtcaat  cacggcgcac    2880 atgtggtgt  tggaggtgac ggtcacgggg gtggggtcga tctgggcgga cgacttgcac    2940
ttttggtcca cgcgcacctt gctgccgccg agaatggcct tggcggactc cacgaccttg    3000
gccgtcatct tgccctcctc ccaccagatc accatcttgt cggcgcaatc gttgaaggga    3060
aagttctcat tggtccagtt gacgcagccg tagaaagggc gaattc                  3106
```

<210> SEQ ID NO 17
<211> LENGTH: 3102
<212> TYPE: DNA
<213> ORGANISM: Unknown
<220> FEATURE:
<223> OTHER INFORMATION: AAV serotype, clone 27-3

<400> SEQUENCE: 17

-continued

```
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg     180 aggtgtactg aatctctgga ttccagcgtt tgctgttttc tttctgcagt tcccactcga     240
tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
ggtgtttgag tccaaatccg cccatcaggg gagacgggtg aaagttgccg tccgtgtgag     420
gaatttcggc ccagatggga ccctgcaggt acacgtcccg gttctgccag accatgccgg     480
gcagagcccc ctggctgttg acagtctgtg tccggggtcc ggccgtagac gattgcaggt     540
tgctggagac cacaccgtat tcttctgtag ccacgggatt ggtggttttg atctcctcct     600
cgctggtcat tagcacgttt tccagcgttg tcttgttggc agccccgtt ttgccaaaaa     660 ccagcactcc gttgatggga aggaactggt cctcgtcgtc cttgttggtg gccatggcta     720
cgcccgggtt ggttaatgaa tttctaccat tcagatggta tttagtggcc ccggtccagg     780
caaagttact gttgttgttg ctgtctatgt tttttgacag tctctgctgc cgataacagg     840
gtccgggcag ccagttcttt gattgctcgg ccacggtgtt gggcccagcc tgatggaact     900
gcagctccct tgtggacccc gtagtgctct gggtccgggc caggtagtac aggtactggt     960
cgatgagggg attcatcagc cggtccaggc tctggctgtg cgcatagctg ctgtggaaag    1020
gcacttcctc aaaggtgtag ctgaattcaa agttattgcc cgttctcagc atctgagaag    1080
gaaagtactc caggcagcag aaggaggaac gtcccacaga ctgactgccg ttgtttagag    1140
tcagatatcc gtactgagga atcatgaaca cgtccgcagg gaacggaggg aggcagccct    1200
ggtgcgcaga gccgaggacg tacggcagtt ggtactccga gtccgagaag acctgaatcg    1260
tgctggtaag gttattagcg atggtcgtaa cgccgtcgtt cgtcgtgacc tccttgacct    1320
ggatgttgaa caacttgaac cgcagctttc tgggccggaa tccccagttg ttgttgatga    1380
gtcgctgcca gtcacgtggt gagaagtggc agtggaatct gttgaagtca aaatagcccc    1440 aggggtgct gtagccgaag aagtggttgt cgttggtagc cccgctctga cttgatatct    1500
gcttgtagag gtggttgttg taggtgggca gggcccaggt gcgggtgctg gtggtgatga    1560
ctctgtcgcc cagccatgtg gaatcgcaat gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc cgagaggttg gggtcgggc actgactctg    1740 agtcgccagt ctgcccaaag ttgagcttct ttttagcggg ctgctggcct ttcttgccga    1800
tgcccgtgga ggagtcgggg gattctatgg gtctcttctt tccggaagcc gtcttagcgc    1860
cttcctcaac cagaccgaga ggttcgagaa cccgcttctt ggcctggaag actgctcgcc    1920
cgaggttgcc cccaaaagac gtatcttctt gaagacgctc ctgaaactcg gcgtcggcgt    1980
ggttgtactt gaggtacggg ttgtccccct gctcgagctg cttgtcgtag gccttgtcgt    2040
gctcgagggc cgcggcgtct gcctcgttga ccggctctcc cttgtcgagt ccgttgaagg    2100
gtccgaggta cttgtagcca ggaagcacca accccggcc gtcgtcctgc ttttgctggt    2160
tggctttggg tttcggggct ccaggtttca agtcccacca ctcgcgaatg ccctcagaga    2220
ggttgtcctc gagccaatct ggaagataac catcggcagc catacctggt ttaagtcatt    2280
tattgctcag aaacacagtc atccaggtcc acgttgacca gatcgcaggc cgagcaagca    2340
atctcgggag cccgccccag cagatgatga atggcacaga gtttccgata cgtcctcttt    2400
```

```
ctgacgaccg gttgagattc tgacacgccg gggaaacatt ctgaacagtc tctggtcccg    2460
tgcgtgaagc aaatgttgaa attctgattc attctctcgc atgtcttgca gggaaacagc    2520
atctgaagca tgcccgcgtg acgagaacat ttgttttggt acctgtcggc aaagtccacc    2580
ggagctcctt ccgcgtctga cgtcgatgga tccgcgactg aggggcaagc ccgcttgggc    2640
tcgcttttat ccgcgtcatc gggggcgggt ctcttgttgg ctccacccct tctgacgtag    2700
aactcatgcg ccacctcggt cacgtgatcc tgcgcccagc ggaagaactc tttgacttcc    2760
tgctttgtca ccttgccaaa gtcatgctcc agacggcggg tgagttcaaa tttgaacatc    2820
cggtcttgta acggctgctg gtgctcgaag gtggtgctgt tcccgtcaat cacggcgcac    2880
atgttggtgt tggaagtgac gatcacgggg gtgggatcga tctgggcgga cgacttgcac    2940
ttttggtcca cgcgcacctt gctgccgccg agaatggcct tggcggactc cacgaccttg    3000
gccgtcatct tgccctcctc ccaccagatc accatcttgt cgacgcaatc gttgaaggga    3060
aagttctcat tggtccagtt gacgcagccg aagggcgaat tc                      3102

<210> SEQ ID NO 18
<211> LENGTH: 3106
<212> TYPE: DNA
<213> ORGANISM: Unknown
<220> FEATURE:
<223> OTHER INFORMATION: AAV serotype, clone 7-2

<400> SEQUENCE: 18
gcggccgcga attcgccctt cgcagagacc aaagttcaac tgaaacgaat cagccggttt     60
attgattaac aagtaattac aggttacggg tgaggtaacg ggtgccaatg gggcgaggct    120
cagtataaac cccttcgttg ttgacagcaa attccacatt attagacttg cataatttg     180 aggtgtactg aatctctgga ttccagcgtt tgctgttttc tttctgcagt tcccactcga    240
tctccacgct gacctggccg gtgctgtact gcgtgataaa tgaggcaaac ttggcaggag    300
taaacacctc tggaggatta gcaggtaccg gggtgttttt gatgagaatt tgaggaggcg    360
ggtgtttgag tccaaatccg cccatcaggg gagacgggtg aaagttgccg tccgtgtgag    420
gaattttggc ccagatggga ccctgcaggt acacgtcccg gttctgccag accatgccgg    480
gcagagcccc ctggctgttg acagtctgtg tctggggtcc ggccgtagac gattgcaggt    540
tgctggagac cacaccgtat tcttctgtag ccacgggatt ggtggttttg atctcctcct    600
cgctggtcat tagcacgttt tccagcgttg tcttgttggc agccccgtt ttgccaaaaa     660 ccagcactcc gttgatggga aagaactggt cctcgtcgtc cttgttggtg ccatggcta    720 cgcccgggtt ggttaatgaa tttctaccat tcagatggta tttagtgcc ccggtccagg     780 caaagttact gttgttgttg ctgtctatgt tttttgacag tctctgctgc cgataacagg    840
gtccgggcag ccagttcttt gattgctcgg ccatggtgtt gggcccagcc tgatggaact    900
gcagctccct tgtggacccc gtagtgctct gggtccgggc caggtagtac aggtactggt    960
cgatgagggg attcatcagc cggtccaggc tctggctgtg cgcatagctg ctgtggaaag    1020
gcacttcctc aaaggtgtag ctgaattcaa agttatcgcc cgttctcagc atctgagaag   1080
gaaagtactc caggcagtag aaggaggaac gtcccacaga ctgactgccg ttgtttagag   1140
tcagatatcc gtactgagga atcatgaaca cgtccgcagg gaacgagggg aggcagccct   1200
ggtgcgcaga gccgaggacg tacggcagtt ggtactccga gtccgagaag acctgaatcg   1260
tgctggtaag gttattagcg atggtcgtaa cgccgtcgtt cgtcgtgacc tccttgacct   1320
ggatgttgaa caacttgaac cgcagctttc tgggccggaa tccccagttg ttgttgatga   1380
```

```
gtcgctgcca gtcacgtggt gagaagtggc agtggaatct gttgaagtca aatagcccc   1440 aggggtgct gtagccgaag aagtggttgt cgttggtagc cccgctctga cttgatatct   1500
gcttgtagag gtggttgttg taggtgggca gggcccaggt gcgggtgctg gtggtgatga   1560
ctctgtcgcc cagccatgtg gaatcgcaat gccaatttcc ggaggcatta cccactccgt   1620
cggcgccttc gttattgtct gccattggtg cgccaccgcc tgcagccatt gtaccagatc   1680
ccagacctga gggcgcggcg ggaggttctc cgagaggttg ggggtcgggc actgactctg   1740
agtcgccagt ctgcccaaag ttgagcttct ttttagcggg cggctggccg ttcttgccga   1800
tgcccgtgga ggagtcgggg gattctatgg gtctcttctt ccaggagcc gtcttagcgc    1860 cttcctcaac cagaccgaga ggttcgagaa cccgcttctt ggcctggaag actgctcgcc   1920
cgaggttgcc cccaaaagac gtatcttctt gaagacgctc ctgaaactcg gcgtcggcgt   1980
ggttgtactt gaggtacggg ttgtcccccct gctcgagctg cttgtcgtag gccttgtcgt   2040
gctcgagggc cgcggcgtct gcctcgttga ccggctctcc cttgtcgagt ccgttgaagg   2100
gtccgaggta cctgtagcca ggaagcacca gaccccggcc gtcgtcctgc ttttgctggt   2160
tggctttggg tttcgggggct ccaggtttca agtcccacca ctcgcgaatg ccctcagaga   2220
ggttgccctc gagccaatct ggaagataac catcggcagc catacctggt ttaagtcatt   2280
tattgctcag aaacacagtc atccaggtcc acgttggcca gatcgcaggc cgagcaagca   2340
atctcgggag cccgcccag cagatgatga atggcacaga gtttccgata cgtcctcttt    2400
ctgacgaccg gttgagattc tgacacgccg gggaaacatt ctgaacagtc tctggtcccg   2460
tgcgtgaagc aaatgttgaa attctgattc attctctcgc atgtcttgca ggggaacagc   2520
atctgaagca tgcccgcgtg acgagaacat ttgttttggt acctgtcggc aaagtccacc   2580
ggagctcctt ccgcgtctga cgtcgatgga tccgcgactg aggggcaggc ccgcttgggc   2640
tcgcttttat ccgcgtcatc gggggcgggt ctcttgttgg ctccacccct tctgacgtag   2700
aactcatacg ccacctcggt cacgtgatcc tgcgcccagc ggaagaactc tttgacttcc   2760
tgctttgtca ccttgccaaa gtcatgctcc agacggcggg tgagttcaaa tttgaacatc   2820
cggtcttgta acggctgctg gtgctcgaag gtggtgctgt tcccgtcaat cacggcgcac   2880
atgttggtgt tggaagtgac gatcacgggg gtgggatcga tctgggcgga cgacttgcac   2940
ttttggtcca cgcgcacctt gctgccgccg agaatggcct tggcggactc cacgaccttg   3000
gccgtcatcc tgccctcctc ccaccagatc accatcttgt cgacgcaatc gttgaaggga   3060
aagttctcat tggtccagtt gacgcagccg tagaaagggc gaattc                  3106
```

<210> SEQ ID NO 19
<211> LENGTH: 3105
<212> TYPE: DNA
<213> ORGANISM: Unknown
<220> FEATURE:
<223> OTHER INFORMATION: AAV serotype, clone C1

<400> SEQUENCE: 19

```
gaattcgccc ttgctgcgtc aactggacca atgagaactt tcccttcaac gattgcgtcg     60
acaagatggt gatctggtgg gaggagggca agatgaccgc caaggtcgtg gagtccgcca    120
aggccattct gggcggaagc aaggtgcgcg tggaccaaaa gtgcaagtca tcggcccaga   180
tcgaccccac gcccgtgatc gtcacctcca acaccaacat gtgcgccgtg atcgacggga   240
acagcaccac cttcgagcac cagcagccgc tgcaggaccg catgttcaag ttcgagctca   300
cccgccgtct ggagcacgac tttggcaagg tgaccaagca ggaagtcaaa gagttcttcc   360
```

```
gctgggctca ggatcacgtg actgaggtgg cgcatgagtt ctacgtcaga aagggcggag      420
ccaccaaaag acccgccccc agtgacgcgg atataagcga gcccaagcgg gcctgcccct      480
cagttgcgga gccatcgacg tcagacgcgg aagcaccggt ggactttgcg gacaggtacc      540
aaaacaaatg ttctcgtcac gcgggcatgc ttcagatgct gtttccctgc aagacatgcg      600
agagaatgaa tcagaatttc aacgtctgct tcacgcacgg ggtcagagac tgctcagagt      660
gcttccccgg cgcgtcagaa tctcaacccg tcgtcagaaa aagacgtat cagaaactgt       720 gcgcgattca tcatctgctg gggcgggcac ccgagattgc gtgttcggcc cgcgatctcg      780
tcaacgtgga cttggatgac tgtgtttctg agcaataaat gacttaaacc aggtatggct      840
gctgacggtt atcttccaga ttggctcgag gacaacctct ctgagggcat tcgcgagtgg      900
tgggacctga aacctggagc ccccaagccc aaggccaacc agcagaagca ggacgacggc      960
cggggtctgg tgcttcctgg ctacaagtac ctcggaccct tcaacggact cgacaagggg     1020
gagcccgtca acgcggcgga cgcagcggcc ctcgagcacg acaaggccta cgaccagcag     1080
ctcaaagcgg gtgacaatcc gtacctgcgg tataaccacg ccgacgccga gtttcaggag     1140
cgtctgcaag aagatacgtc ttttggggc aacctcgggc gagcagtctt ccaggccaag      1200
aagagggtac tcgaacctct gggcctggtt gaagaaggtg ctaagacggc tcctggaaag     1260
aagagaccgt tagagtcacc acaagagccc gactcctcct caggaatcgg caaaaaggc      1320 aaacaaccag ccaaaaagag actcaacttt gaagaggaca ctggagccgg agacggaccc     1380
cctgaaggat cagataccag cgccatgtct tcagacattg aaatgcgtgc agcaccgggc     1440
ggaaatgctg tcgatgcggg acaaggttcc gatggagtgg gtaatgcctc gggtgattgg     1500
cattgcgatt ccacctggtc tgagggcaag gtcacaacaa cctcgaccag aacctgggtc     1560
ttgcccacct acaacaacca cttgtacctg cggctcggaa caacatcaaa cagcaacacc     1620
tacaacggat tctccacccc ctggggatac tttgacttta acagattcca ctgtcacttc     1680
tcaccacgtg actggcaaag actcatcaac aacaactggg gactacgacc aaaagccatg     1740
cgcgttaaaa tcttcaatat ccaagttaag gaggtcacaa cgtcgaacgg cgagactacg     1800
gtcgctaata accttaccag cacggttcag atatttgcgg actcgtcgta tgagctcccg     1860
tacgtgatgg acgctggaca agagggaagt ctgtctcctt tccccaatga cgtcttcatg     1920
gtgcctcaat atggctactg tggcattgtg actggcgaaa atcagaacca gacggacaga     1980
aatgctttct actgcctgga gtattttcct tcacaaatgc tgagaactgg caataacttt     2040
gaaatggctt acaactttgg gaaggtgccg ttccactcaa tgtatgctta cagccagagc     2100
ccggacagac tgatgaatcc cctcctggac cagtacctgt ggcacttaca gtcgaccacc     2160
tctggagaga ctctgaatca aggcaatgca gcaaccacat ttgaaaaaat caggagtgga     2220
gactttgcct tttacagaaa gaactggctg cctgggcctt gtgttaaaca gcagagactc     2280
tcaaaaactg ccagtcaaaa ttacaagatt cctgccagcg ggcaacgc tctgttaaag      2340 tatgacaccc actataccct aaacaaccgc tggagcaaca tagcgcctgg acctccaatg     2400
gcaacagctg gacttcaga tggggacttc agcaacgccc agctcatctt ccctggacca     2460
tcagtcaccg gaaacacaac aacctcagca acaatctgt tgtttacatc agaagaagaa      2520
attgctgcca ccaacccaag agacacggac atgtttggtc agattgctga caataatcag     2580
aatgctacaa ctgctcccat aaccggcaac gtgactgcta tgggagtgct tcctggcatg     2640
gtgtggcaaa acagagacat ttactaccaa gggccaattt gggccaagat cccacacgcg     2700
gacggacatt ttcatccttc accgctaatt ggcggttttg gactgaaaca tccgcctccc     2760
```

```
cagatattta tcaaaaacac ccccgtacct gccaatcctg cgacaacctt cactgcagcc    2820
agagtggact ctttcatcac acaatacagc accggccagg tcgctgttca gattgaatgg    2880
gaaatcgaaa aggaacgctc caaacgctgg aatcctgaag tgcagtttac ttcaaactat    2940
gggaaccagt cttctatgtt gtgggctccc gatacaactg ggaagtatac agagccgcgg    3000
gttattggct ctcgttattt gactaatcat ttgtaactgc ctagttaatc aataaaccgt    3060
gtgattcgtt tcagttgaac tttggtctct gcgaagggcg aattc                   3105
```

<210> SEQ ID NO 20
<211> LENGTH: 3105
<212> TYPE: DNA
<213> ORGANISM: Unknown
<220> FEATURE:
<223> OTHER INFORMATION: AAV serotype, clone C3

<400> SEQUENCE: 20

```
gaattcgccc ttgctgcgtc aactggacca atgagaactt tcccttcaac gattgcgtcg      60
acaagatggt gatctggtgg gaggagggca agatgaccgc caaggtcgtg gagtccgcca     120
aggccattct gggcggaagc aaggtgcgcg tggaccaaaa gtgcaagtca tcggcccaga     180
tcgaccccac gcccgtgatc gtcacctcca acaccaacat gtgcgccgtg atcgacggga     240
acagcaccac cttcgagcac cagcagccgc tgcaggaccg catgttcaag ttcgagctca     300
cccgccgtct ggagcacgac tttggcaagg tgaccaagca ggaagtcaaa gagttcttcc     360
gctgggctca ggatcacgtg actgaggtgg cgcatgagtt ctacgtcaga aagggcggag     420
ccaccaaaag acccgccccc agtgacgcgg atataagcga gcccaagcgg gcctgcccct     480
cagttgcgga gccatcgacg tcagacgcgg aagcaccggt ggactttgcg gacaggtacc     540
aaaacaaatg ttctcgtcac gcgggcatgc ttcagatgct gttttccctgc aagacatgcg     600 agagaatgaa tcagaatttc aacgtctgct tcacgcacgg ggtcagagac tgctcagagt     660
gcttccccgg cgcgtcagaa tctcaacccg tcgtcagaaa aaagacgtat cagaaactgt     720
gcgcgattca tcatctgctg gggcgggcac ccgagattgc gtgttcggcc tgcgatctcg     780
tcaacgtgga cttggatgac tgtgtttctg agcaataaat gacttaaacc aggtatggct     840
gctgacggtt atcttccaga ttggctcgag acaacctct ctgagggcat cgcgagtgg      900 tgggacctga acctggagc ccccaagctc aaggccaacc agcagaagca ggacgacggc      960
cggggtctgg tgcttcctgg ctacaagtac ctcggaccct ccacggact cgacaagggg    1020 gagcccgtca acgcggcgga cgcagcggcc ctcgagcacg acaaggccta cgaccagcag    1080
ctcaaagcgg gtgacaatcc gtacctgcgg tataaccacg ccgacgccga gtttcaggag    1140
cgtctgcaag aagatacgtc ttttgggggc aacctcgggc gagcagtctt ccaggccaag    1200
aagagggtac tcgaaccact gggcctggtt gaagaaggtg ctaagacggc tcctggaaag    1260
aagagaccgt tagagtcacc acaagagccc gactcctcct caggaatcgg caaaaaggc    1320 aaacaaccag ccaaaaagag actcaacttt gaagaggaca ctggagccgg agacggaccc    1380
cctgaaggat cagataccag cgccatgtct tcagacattg aaatgcgtgc agcaccgggc    1440
ggaaatgctg tcgatgcggg acaaggttcc gatggagtgg gtaatgcctc gggtgattgg    1500
cattgcgatt ccacctggtc tgagggcaag gtcacaacaa cctcgaccag aacctgggtc    1560
ttgcccacct acaacaacca cttgtacctg cggctcggaa caacatcaaa cagcaacacc    1620
tacaacggat tctccacccc ctggggatac tttgacttta acagattcca ctgtcacttc    1680
tcaccacgtg actggcaaag actcatcaac aacaactggg gactacgacc aaaagccatg    1740
```

```
cgcgttaaaa tcttcaatat ccaagttaag gaggtcacaa cgtcgaacgg cgagactacg      1800
gtcgctaata accttaccag cacggttcag atatttgcgg actcgtcgta tgagctcccg      1860
tacgtgatgg acgctggaca agagggaagt ctgcctcctt tccccaatga cgtcttcatg      1920
gtgcctcaat atggctactg tggcattgtg actggcgaaa tcagaaccga acggacaga       1980 aatgctttct actgcctgga gtattttcct tcacaaatgc tgagaactgg caataacttt     2040
gaaatggctt acaactttga aaggtgccg ttccactcaa tgtatgctca cagccagagc      2100
ctggacagac tgatgaatcc cctcctggac cagtacctgt ggcacttaca gtcgaccacc      2160
tctggagaga ctctgaatca aggcaatgca gcaaccacat ttggaaaaat caggagtgga      2220
gactttgcct tttacagaaa gaactggctg cctgggcctt gtgttaaaca gcagagattc      2280
tcaaaaactg ccagtcaaaa ttacaagatt cctgccagcg gggcaacgc tctgttaaag       2340 tatgacaccc actatacctt aaacaaccgc tggagcaaca tagcgcctgg acctccaatg      2400
gcaacagctg gaccttcaga tgggacttc agcaacgccc agctcatctt ccctggacca      2460
tcagtcaccg gaaacacaac aacctcagca acaatctgt tgtttacatc agaaggagaa      2520
attgctgcca ccaacccaag agacacggac atgtttggtc agattgctga caataatcag      2580
aatgctacaa ctgctcccat aaccggcaac gtgactgcta tgggagtgct tcctggcatg      2640
gtgtggcaaa acagagacat ttactaccaa gggccaattt gggccaagat ccacacgcg       2700 gacggacatt ttcatcctc accgctaatt ggcggttttg gactgaaaca tccgcctccc     2760
cagatattta tcaaaaacac ccccgtacct gccaatcctg cgacaacctt cactgcagcc     2820
agagtggact ctttcatcac acaatacagc accggccagg tcgctgttca gattgaatgg    2880
gaaatcgaaa aggaacgctc caaacgccgg aatcctgaag tgcagtttac ttcaaactat    2940
gggaaccagt cttctatgtt gtgggctccc gatacaactg gaagtatac agagccgcgg      3000 gttattggct ctcgttattt gactaatcat ttgtaactgc ctagttaatc aataaaccgt    3060
gtgattcgtt tcagttgaac tttggtctct gcgaagggcg aattc                     3105
```

<210> SEQ ID NO 21
<211> LENGTH: 3105
<212> TYPE: DNA
<213> ORGANISM: Unknown
<220> FEATURE:
<223> OTHER INFORMATION: AAV serotype, clone C5

<400> SEQUENCE: 21

```
gaattcgccc ttcgcagaga ccaaagttca actgaaacga atcacacggt ttattgatta       60
actaggcagt tacaaaatgat tagtcaaata acgagagcca ataacccgcg gctctgtata     120
cttcccagtt gtatcgggag cccacaacat agaagactgg ttcccacagt ttgaagtaaa     180
ctgcacttca ggattccagc gtttggagcg ttccttttcg atttcccatt caatctgaac     240
agcgacctgg ccggtgctgt attgtgtgat gaaagagtcc actctggctg cagtgaaggt    300
tgtcgcagga taggcaggta cggggggtgtt tttgataaat atctggggag gcggatgttt    360
cagtccaaaa ccgccaatta gcggtgaagg atgaaaatgt ccgtccgcgt gtgggatctt    420
ggcccaaatt ggcccttggt agtaaatgtc tctgttttgc cacaccatgc caggaagcac    480
tcccatagca gtcacgttgc cggttatggg agcagttgta gcattctgat tatttgtcagc    540 aatctgacca acatgtccg tgtctcttgg gttggtggca gcaatttctt cttctgatgt     600
aaacaacaga ttgtttgctg aggttgttgt gtttccggtg actgatggtc cagggaagat    660
gagctgggcg ttgctgaagt ccccatctga aggtccagct gttgccattg gaggtccagg    720
```

```
cgctatgttg ctccagcggt tgtttaaggt atagtgggtg tcatacttta acagagcgtt    780
gcccccgctg gcaggaatct tgtaattttg actggcagtt tttgagaatc tctgctgttt    840
aacacaaggc ccaggcagcc agttcttcct gtaaaaggca aagtctccac tcctgatttt    900
tccaaatgtg gttgctgcat tgccttgatt cagagtctct ccagaggtgg tcgactgtaa    960
gtgccacagg tactggtcca ggaggggatt catcagtccg tccaggctct ggctgtgagc   1020
atacattgag tggaacggca ccttctcaaa gttgtaagcc gtttcaaagt tattgccagt   1080
tctcagcatt tgtgaaggaa aatactccag gcagtagaaa gcatttctgt ccgtctggtt   1140
ctgattttcg ccagtcacaa tgccacagta gccatattga ggcaccatga agacgtcatt   1200
ggggaaagga ggcagacttc cctcttgtcc agcgtccatc acgtacggga gctcatacga   1260
cgagtccgca aatatctgaa ccgtgctggt aaggttatta gcgaccgtag tctcgccgtt   1320
cgacgttgtg acctccttaa cttggatatt gaagatttta acgcgcatgg cttttggtcg   1380
tagtccccag ttgttgttga tgagtctttg ccagtcacgt ggtgagaagt gacagtggaa   1440
tctgttaaag tcaaagtatc ccagggggt ggagaatccg ttgtaggtgt gctgtttga    1500
tgttgttccg agccgcaggt acaagtggtt gttgtaggtg ggcaagaccc aggttctggt   1560
cgaggttgtt gtgaccttgc cctcagacca ggtggaatcg caatgccaat cacccgaggc   1620
attacccact ccatcggaac cttgtcccgc atcgacagca tttccgcccg gtgctgcacg   1680
catttcaatg tctgaagaca tggcgctggt atctgatcct tcaggggtc cgtctccggc    1740
tccagtgtcc tcttcaaagt tgagtctctt tttggctggt tgtttgcctt ttttgccgat   1800
tcctgaggag gagtcgggct cttgtggtga ctctaacggt ctcttcttc caggagccgt    1860
cttagcacct tcttcaacca ggcccagagg ttcgagtacc ctcttcttgg cctggaagac   1920
tgctcgcccg aggttgcccc caaaagacgt atcttcttgc agacgctcct gaaactcggc   1980
gtcggcgtgg ttataccgca ggtacggatt gtcacccgct ttgagctgct ggtcgtaggc   2040
cttgtcgtgc tcgagggccg ctgcgtccgc cgcgttgacg ggctccccct tgtcgagtcc   2100
gttgaagggt ccgaggtact cgtagccagg aagcaccaga ccccggccgt cgtcctgctt   2160
ctgctggttg gccttgggct tggggggctcc aggtttcagg tcccaccact cgcgaatgcc   2220
ctcagagagg ttgtcctcga gccaatctgg aagataaccg tcagcagcca tacctggttt   2280
aagtcattta ttgctcagaa acacagtcat ccaagtccac gttgacgaga tcgcaggccg   2340
aacacgcaat ctcgggtgcc cgccccagca gatgatgaat cgcgcacagt ttctgatacg   2400
tctttttcct gacgacgggt tgagattctg acgcgccggg gaagcactct gagcagtctc   2460
tgaccccgtg cgtgaagcag acgttgaaat tctgattcat tctctcgcat gtcttgcagg   2520
gaaacagcat ctgaagcatg cccgcgtgac gagaacattt gttttggtac ctgtccgcaa   2580
ggtccaccgg tgcttccgcg tctgacgtcg atggctccgc aactgagggg caggcccgct   2640
tgggctcgct tatatccgcg tcactggggg cgggtctttt ggtggctccg cccttcctga   2700
cgtagaactc atgcgccacc tcagtcacgt gatcctgagc ccagcggaag aactctttga   2760
cttcctgctt ggtcaccttg ccaaagtcgt gctccagacg gcgggtgagc tcgaacttga   2820
acatgcggtc ctgcagcggc tgctggtgct cgaaggtggt gctgttccg tcgatcacgg    2880
cgcacatgtt ggtgttggag gtgacgatca cgggcgtggg gtcgatctgg gccgatgact   2940
tgcacttttg gtccacgcgc accttgcttc cgcccagaat ggccttggcg gactccacga   3000
ccttggcggt catcttgccc tcctcccacc agatcaccat cttgtcgacg caatcgttga   3060
agggaaagtt ctcattggtc cagttgacgc agcaagggcg aattc             3105
```

<210> SEQ ID NO 22
<211> LENGTH: 3094
<212> TYPE: DNA
<213> ORGANISM: Unknown
<220> FEATURE:
<223> OTHER INFORMATION: AAV serotype, clone F1

<400> SEQUENCE: 22

```
gaattcgccc ttgctgcgtc aactggacca agagaacttt cccttcaacg attgcgtcga      60
caagatggtg atctggtggg aggagggcaa gatgacggcc aaggtcgtgg agtccgccaa     120
agccattctg ggcggaagca aggtgcgcgt cgaccaaaag tgcaagtcct cggcccagat     180
cgatcccacc cccgtgatcg tcacctccaa caccaacatg tgcgccgtga tcgacgggaa     240
cagcaccacc ttcgagcacc agcagccgtt gcaggaccgg atgttcaaat ttgaactcac     300
ccgccgtctg gaacacgact ttggcaaggt gaccaagcag gaagtcaaag agttcttccg     360
ctgggctagt gatcacgtga ctgaggtgac gcatgagttc tacgtcagaa agggcggagc     420
cagcaaaaga cccgcccccg atgacgcgga tataagcgag cccaagcggg cctgtccctc     480
agtcacggac ccatcgacgt cagacgcgga aggagctccg gtggactttg ccgacaggta     540
ccaaaacaaa tgttctcgtc acgcgggcat gcttcagatg ctgtttccct gcaaaacgtg     600
cgagagaatg aatcagaatt caacatttg cttcacgcac ggggtcagag actgtttaga     660
atgtttcccc ggcgtgtcag aatctcaacc ggtcgtcaga aaaagacgt atcggaagct     720
gtgtgcgatt catcatctgc tggggcgggc acccgagatt gcttgctcgg cctgcgacct     780
ggtcaacgtg gacctggacg actgtgtttc tgagcaataa atgacttaaa ccgggtatgg     840
ctgccgatgg ttatcttcca gattggctcg aggacaacct ctctgagggc attcgcgagt     900
ggtgggacct gaaacctgga gccccgaaac ccaaagccaa ccagcaaaag caggacgacg     960
gccgggtgtct ggtgcttcct ggctacaagt acctcggacc cttcaacgga ctcgacaagg    1020
gggagcccgt caacgcggcg gacgcagcgg ccctcgagca cgacaaggcc tacgaccagc    1080
agctcaaagc gggtgacaat ccgtacctgc ggtataacca cgccgacgcc gagtttcagg    1140
agcgtctgca agaagatacg tcatttgggg gcaacctcgg gcgagcagtc ttccaggcca    1200
agaagcgggt tctcgaacct ctcggtctgg ttgaggaagg cgctaagacg gctcctggaa    1260
agaagagacc catagactct ccagactcct ccacgggcat cggcaaaaaa ggccagcagc    1320
ccgctaaaaa gaagctcaat tttggtcaga ctggcgactc agtcagtc cccgacccctc     1380
aacctcttgg agaacctcca gcagcgccct ctagtgtggg atctggtaca atggctgcag    1440
gcggtggcgc accaatggca gacaataacg aaggtgccga cggagtgggt aatgcctcag    1500
gaaattggca ttgcgattcc acatggctgg gcgacagagt catcaccacc agcaccagaa    1560
cctgggccct ccccacctac aacaaccacc tctacaagca atctccagc agcagctcag    1620
gagccaccaa tgacaaccac tacttcggct acagcacccc ctgggggtat tttgacttta    1680
acagattcca ctgccacttc tcaccacgtg actggcagcg actcatcaac aacaactggg    1740
gattccggcc caagaagctg cggttcaagc tcttcaacat ccaggtcaag gaggtcacaa    1800
cgaatgacgg cgtcacgacc atcgctaata accttaccag cacggttcag gtcttctcgg    1860
actcggaata ccagctgccg tacgtcctcg gctctgcgca ccagggctgc ctgcctccgt    1920
tcccggcgga cgtcttcatg attcctcagt acggctacct gactctgaac aacggcagcc    1980
aatcggtggg ccgttcctcc ttctactgcc tggaatattt cccctctcaa atgctgagaa    2040
cgggcaacaa ctttgagttc agttacagct tcgaggacgt gccttttcac agcagctacg    2100
```

```
cgcacagcca gagcctagac cggctgatga accctctcat cgaccagtac ctgtactacc    2160
tggcccggac ccagagcacc acgggttcca ccagggaact gcaatttcat caagctgggc    2220
ccaatactat ggccgagcag tcaaagaact ggctgcctgg accctgctat aggcaacagg    2280
gactgtcaaa gaacttggac tttaacaaca acagcaattt gcctggact gctgccacta     2340 aatatcatct gaatggcaga aactctttga ccaatcctgg cattcccatg caaccaaca     2400 aggatgatga ggaccagttc tttcccatca acggggtact ggttttttggc aagacgggag   2460 ctgccaacaa aactacgctg gaaaacgttc tgatgaccag cgaggaggag atcaagacca    2520
ctaaccctgt ggctacagaa gaatacggtg tggtctccag caacctgcag ccgtctacag    2580
ccgggcctca atcacagact atcaacagcc agggagcact gcctggcatg gtctggcaga    2640
accgggacgt gtatctgcag ggtcccatct gggccaaaat tcctcacacg gatggcaact    2700
ttcacccgtc tcctctgatg ggcggttttg gactcaaaca cccgcctcca cagatcctga    2760
tcaaaaacac acctgtacct gctaatcctc cggaggtgtt tactcctgcc aagtttgcct    2820
ccttcatcac gcagtacagc accggacaag tcagcgtgga aatcgagtgg gagctgcaga    2880
aagaaaacag caagcgctgg aacccagaaa ttcagtatac ttccaattat gccaagtcta    2940
ataatgttga atttgctgtg aaccctgatg tgtttatac tgagcctcgc cccattggca     3000
ctcgttacct cccccgtaat ctgtaattgc ttgttaatca ataaaccggt tgattcgttt    3060
cagttgaact ttggtctctg cgaagggcga attc                               3094
```

<210> SEQ ID NO 23
<211> LENGTH: 3095
<212> TYPE: DNA
<213> ORGANISM: Unknown
<220> FEATURE:
<223> OTHER INFORMATION: AAV serotype, clone F3

<400> SEQUENCE: 23

```
gaattcgccc ttcgcagaga ccaaagttca actgaaacga atcaaccggt ttattgatta    60
acaagcaatt acagattacg ggtgaggtaa cgagtgccaa tggggcgagg ctcagtataa    120
acaccatcag ggttcacagc aaattcaaca ttattagact tggcataatt ggaagtatac    180
tgaatttctg ggttccagcg cttgctgttt tctttctgca gctcccactc gatttccacg    240
ctgacttgtc cggtgctgta ctgcgtgatg aaggaggcaa acttggcagg agtaaacacc    300
tccggaggat tagcaggtac aggtgtgttt ttgatcagga tctgtggagg cgggtgtttg    360
agtccaaaac cgcccatcag aggagacggg tgaaagttgc catccgtgtg aggaattttg    420
gcccagatgg gaccctgcag atacacgtcc cggttctgcc agaccatgcc aggcagtgct    480
ccctggctgt tgatagtctg tgattgaggc ccggctgtag acgactgcag gttgctggag    540
accacaccgt attcttctgt agccacaggg ttagtggtct tgatctcctc ctcgctggtc    600
atcagaacgt tttccagcgt agttttgttg gcagctcccg tcttgccaaa aaccagtacc    660
ccgttgatgg gaaagaactg gtcctcatca tccttgttgg ttgccatggg aatgccagga    720
ttggtcaaag agtttctgcc attcagatga tatttagtgg cagcagtcca ggcaaaattg    780
ctgttgttgt taaagtccaa gttctttgac agtctctgtt gcctatagca gggtccaggc    840
agccagttct tgactgctcg gccatagta ttgggcccag cttgatgaaa ttgcagttcc      900
ctggtggaac ccgtggtgct ctgggtccgg gccaggtagt acaggtactg gtcgatgaga    960
gggttcatca gccggtctag gctctggctg tgcgcgtagc tgctgtggaa aggcacgtcc   1020
tcgaagctgt aactgaactc aaagttgttg cccgttctca gcatttgaga ggggaaatat   1080
```

```
tccaggcagt agaaggagga acggcccacc gattggctgc cgttgtccag agtcaggtag    1140
ccgtactgag gaatcatgaa gacgtccgcc gggaacggag gcaggcagcc ctggtgcgca    1200
gagccgagga cgtacggcag ctggtattcc gagtccgaga agacctgaac cgtgctggta    1260
aggttattag cgatggtcgt gacgccgtca ttcgttgtga cctccttgac ctggatgttg    1320
aggagcttga accgcagctt cttgggccgg aatccccagt tgttgttgat gagtcgctgc    1380
cagtcacgtg gtgagaagtg gcagtggaat ctgttaaagt caaaataccc ccaggggtg     1440 ctgtagccga agtagtggtt gtcattggtg gctcctgagc tgctgctgga gatttgcttg    1500
tagaggtggt tgttgtaggt ggggagggcc caggttctgg tgctggtggt gatgactctg    1560
tcgcccagcc atgtggaatc gcaatgccaa tttcctgagg cattacccac tccgtcggca    1620
ccttcgttat tgtctgccat tggtgcgcca ccgcctgcag ccattgtacc agatcccaca    1680
ctagagggcg ctgctggagg ttctccaaga ggttgagggt cggggactga ctctgagtcg    1740
ccagtctgac caaaattgag cttcttttta gcgggctgct ggccttttttt gccgatgccc    1800 gtggaggagt ctggagagcc tatgggtctc ttctttccag gagccgtctt agcgccttcc    1860
tcaaccagac cgagaggttc gagaacccgc ttcttggcct ggaagactgc tcgcccgagg    1920
ttgcccccaa atgacgtatc ttcttgcaga cgctcctgaa actcggcgtc ggcgtggtta    1980
taccgcaggt acgattgtc acccgctttg agctgctggt cgtaggcctt gtcgtgctcg     2040
agggccgctg cgtccgccgc gttgacgggc tccccttgt cgagtccgtt gaagggtccg      2100
aggtacttgt agccaggaag caccagaccc ggccgtcgt cctgcttttg ctggttggct      2160
ttgggtttcg gggctccagg tttcaggtcc caccactcgc gaatgccctc agagaggttg    2220
tcctcgagcc aatctggaag ataaccatcg gcagccatac ctggtttaag tcatttattg    2280
ctcagaaaca cagtcgtcca ggtccacgtt gaccaggtcg caggccgagc aagcaatctc    2340
gggtgcccgc cccagcagat gatgaatcgc acacagcttc cgatacgtct tttttctgac    2400
gaccggttga gattctgaca cgccggggaa acattctaaa cagtctctga ccccgtgcgt    2460
gaagcaaatg ttgaaattct gattcattct ctcgcacgtt ttgcagggaa acagcacctg    2520
aagcatgccc gcgtgacgag aacatttgtt ttggtacctg tcggcaaagt ccaccggagc    2580
tccttccgcg tctgacgtcg atgggtccgt gactgaggga cgggcccgct tgggctcgct    2640
tatatccgcg tcatcggggg cgggtctttt gctggctccg ccctttctga cgtagaactc    2700
atgcgtcacc tcagtcacgt gatcactagc ccagcggaag aactctttga cttcctgctt    2760
tgtcaccttg ccaaagtcgt gttccagacg gcgggtgagt tcaaatttga acatccggtc    2820
ctgcaacggt tgctggtgct cgaaggtggt gctgttcccg tcgatcacgg cgcacatgtt    2880
ggtgttggag gtgacgatca cggggtggg atcgatctgg gcggacgact tgcacttttg    2940
gtccacgcgc accttgctgc cgccgagaat ggccttggcg gactccacga ccttggccgt    3000
catcttgccc tcctcccacc agatcaccat cttgtcgacg caatcgttga agggaaagtt    3060
ctcattggtc cagttgacgc agcaagggcg aattc                               3095

<210> SEQ ID NO 24
<211> LENGTH: 3095
<212> TYPE: DNA
<213> ORGANISM: Unknown
<220> FEATURE:
<223> OTHER INFORMATION: AAV serotype, clone F5

<400> SEQUENCE: 24
gaattcgccc ttcgcagaga ccaaagttca actgaaacga atcaaccggt ttattgatta    60
```

| | |
|---|---|
| acaagcaatt acagattacg ggtgaggtaa cgagtgccaa tggggcgagg ctcagtataa | 120 |
| acaccatcag ggttcacagc aaattcaaca ttattagact tggcataatt ggaagtatac | 180 |
| tgaatttctg ggttccagcg cttgctgttt tctttctgca gctcccactc gatttccacg | 240 |
| ctgacttgtc cggtgctgta ctgcgtgatg aaggaggcaa acttggcagg agtaaacacc | 300 |
| tccggaggat tagcaggtac aggtgtgttt ttgatcagga tctgtggagg cgggtgttcg | 360 |
| agtccaaaac cgcccatcag aggagacggg tgaaagttgc catccgtgtg aggaattttg | 420 |
| gcccagatgg gaccctgcag atacacgtcc cggttctgcc agaccatgcc aggcagtgct | 480 |
| ccctggctgt tgatagtctg tgattgaggc ccggctgtag acgactgcag gttgctggag | 540 |
| accacaccgt attcttctgt agccacaggg ttagtggtct tgatctcctc ctcgctggtc | 600 |
| atcagaacgt tttccagcgt agttttgttg gcagctcccg tcttgccaaa aaccagtacc | 660 |
| ccgttgatgg gaaagaactg gtcctcatca tccttgttgg ttgccatggg aatgccagga | 720 |
| ttggtcaaag agtttctgcc attcagatga tatttagtgg cagcagtcca ggcaaaattg | 780 |
| ctgttgttgt taaagtccaa gttctttgac agtctctgtt gcctatagca gggtccaggc | 840 |
| agccagttct ttgactgctc ggccatagta ttgggcccag cttgatgaaa ttgcagttcc | 900 |
| ctggtggaac ccgtggtgct ctgggtccgg gccaggtagt acaggtactg gtcgatgaga | 960 |
| gggttcatca gccggtctag gctctggctg tgcgcgtagc tgctgtggaa aggcacgtcc | 1020 |
| tcgaagctgt aactgaactc aaagttgttg cccgttctca gcatttgaga ggggaaatat | 1080 |
| tccaggcagt agaaggagga acggcccacc gattggctgc cgttgttcag agtcaggtag | 1140 |
| ccgtactgag gaatcatgaa gacgtccgcc gggaacggag gcaggcagcc ctggtgcgca | 1200 |
| gagccgagga cgtacggcag ctggtattcc gagtccgaga agacctgaac cgtgctggta | 1260 |
| aggttattag cgatggtcgt gacgccgtca ttcgttgtga cctccttgac ctggatgttg | 1320 |
| aagagcttga accgcagctt cttgggccgg aatcccagt tgttgttgat gagtcgctgc | 1380 |
| cagtcacgtg gtgagaagtg gcagtggaat ctgttaaagt caaaataccc ccaggggtg | 1440 |
| ctgtagccga agtagtggtt gtcattggtg gctcctgagc tgctgctgga gatttgcttg | 1500 |
| tagaggtggt tgttgtaggt ggggagggcc caggttctgg tgctggtggt gatgactctg | 1560 |
| tcgcccagcc atgtggaatc gcaatgccaa tttcctgagg cattacccac tccgtcggca | 1620 |
| ccttcgttat tgtctgccgt tggtgcgcca ccgcctgcag ccattgtacc agatcccaca | 1680 |
| ctagagggcg ctgctggagg ttctccaaga ggttgagggt cggggactga ctctgagtcg | 1740 |
| ccagtctgac caaaattgag cttctttta gcgggctgct ggcctttttt gccgatgccc | 1800 |
| gtggaggagt ctggagagtc tatgggtctc ttctttccag gagccgtctt agcgccttcc | 1860 |
| tcaaccagac cgagaggttc gagaacccgc ttcttggcct ggaagactgc tcgcccgagg | 1920 |
| ttgcccccaa atgacgtatc ttcttgcagg cgctcctgaa actcggcgtc ggcgtggtta | 1980 |
| taccgcaggt acggattgtc acccgctttg agctgctggt cgtaggcctt gtcgtgctcg | 2040 |
| agggccgctg cgtccgccgc gttgacgggc tcccccttgt cgagtccgtt gaagggtccg | 2100 |
| aggtacttgt agccaggaag caccagaccc cggccgtcgt cctgcttttg ctggttggct | 2160 |
| ttgggtttcg gggctccagg tttcaggtcc caccactcgc gaatgccctc agagaggttg | 2220 |
| tcctcgagcc aatctggaag ataaccatcg gcagccatac ctggtttaag ccatttattg | 2280 |
| ctcagaaaca cagtcgtcca ggtccacgtt gaccaggtcg caggccgagc aggcaatctc | 2340 |
| gggtgcccgc cccagcagat gatgaatcgc acacagcttc cgatacgtct tttttctgac | 2400 |
| gaccggttga gattctgaca cgccggggaa acattctaaa cagtctctga ccccgtgcgt | 2460 |

```
gaagcaaatg ttgaaattct gattcattct ctcgcacgtt ttgcaggaa acagcatctg      2520 aagcatgccc gcgtggcgag aacatttgtt ttggtacctg tcggcaaagt ccaccggagc      2580
tccttccgcg tctgacgtcg atgggtccgt gactgaggga caggcccgct tgggctcgct      2640
tatatccgcg tcatcggggg cgggtctttt gctggctccg ccctttctga cgtagaactc      2700
atgcgtcacc tcagtcacgt gatcactagc ccagcggaag aactctttga cttcctgctt      2760
tgtcaccttg ccaaagtcgt gttccagacg gcgggtgagt tcaaatttga acatccggtc      2820
ctgcaacggc tgctggtgct cgaaggtggt gctgttcccg tcgatcacgg cgcgcatgtt      2880
ggtgttggag gtgacgatca cggggtggg atcgatctgg gcggacgact tgcacttttg      2940
gtccacgcgc accttgctgc cgccgagaat ggccttggcg gactccacga ccttggccgt      3000
catcttgccc tcctcccacc agatcaccat cttgtcgacg caatcgttga agggaaagtt      3060
ctcattggtc cagttgacgc agcaagggcg aattc                                3095

<210> SEQ ID NO 25
<211> LENGTH: 3142
<212> TYPE: DNA
<213> ORGANISM: Unknown
<220> FEATURE:
<223> OTHER INFORMATION: AAV serotype, clone H6

<400> SEQUENCE: 25
aaaacgacgg gccagtgatt gtaatacgac tcactatagg gcgaaattga aattagcggc        60
cgcgaattcg cctttcgcag agaccaaagt tcaactgaaa cgaattaaac ggtttattga       120
ttaacaagca attacagatt acgagtcagg tatctggtgc caatggggcg aggctctgaa       180
tacacaccat tagtgtccac agtaaagtcc acattaacag acttgttgta gttggaagtg       240
tactgaattt cgggattcca gcgtttgctg ttctccttct gcagctccca ctcgatctcc       300
acgctgacct gtcccgtgga atactgtgtg atgaaagaag caaacttggc agaactgaag       360
tttgtgggag gattggctgg aacgggagtg ttttgatca tgatctgagg aggcgggtgt       420
ttgagtccaa aacctcccat cagtgggaaa ggatgaaagt gtccatcggt gtgaggaatc       480
ttggcccaaa tgggtccctg caggtacacg tctcgatcct gccacaccat accaggtaac       540
gctccttggt gattgacagt tccagtagtt ggaccagtgt ttgagttttg caaattattt       600
gacacagtcc cgtactgctc cgtagccacg ggattggtgg ccctgatttc ttcttcatct       660
gtaatcatga cattttccaa atccgcgtcg ttggcatttg ttccttgttt accaaatatc       720
agggttccat gcatggggaa aaactttttct tcgtcatcct tgtgactggc catagctggt       780
cctggattaa ccaacgagtc ccggccattt agatgatact ttgtagctgc agtccaggga       840
aagttgctgt tgttgttgtc gtttgcctgt tttgacagac gctgctgtct gtagcaaggt       900
ccaggcagcc agttttttagc ttgaagagac atgttggttg gtccagcttg gctaaacagt       960
agccgagact gctgaagagt tccactattt gtttgtgtct tgttcagata atacaggtac      1020
tggtcgatca gaggattcat cagccgatcc agactctggc tgtgagcgta gctgctgtgg      1080
aaaggcacgt cttcaaaagt gtagctgaac tgaaagttgt ttccagtacg cagcatctga      1140
gaaggaaagt actccaggca gtaaaaggaa gagcgtccta ccgcctgact cccgttgttc      1200
agggtgaggt atccatactg tgggaccatg aagacgtccg ctgaaacgg cgggaggcat      1260 ccttgatgcg ccgagcccag gacgtacggg agctggtact ccgagtcagt aaacacctga      1320
accgtgctgg taaggttatt ggcaatcgtc gtcgtaccgt cattctgcgt gacctctttg      1380
acttgaatat taaagagctt gaagttgagt cttttgggcc ggaatccccg gttgttgttg      1440
```

```
acgagtcttt gccagtcacg tggtgaaaag tggcagtgga atctgttgaa gtcaaaatac    1500
ccccaggggg tgctgtagcc aaagtagtgg ttgtcgttgc tggctcctga ttggctggag    1560
atttgcttgt agaggtggtt gttgtatgtg ggcagggccc aggttcgggt gctggtggtg    1620
atgactctgt cgcccagcca ttgggaatcg caatgccaat ttcctgagga attacccact    1680
ccatcggcac cctcgttatt gtctgccatt ggtgcgccac tgcctgtagc cattgtagta    1740
gatcccagac cagaggggggc tgctggtggc tgtccgagag gctggggggtc aggtacggag    1800 tctgcgtctc cagtctgacc aaaatttaat cttttttcttg caggctgctg gcccgctttt    1860
ccggttcccg aggaggagtc tggctccaca ggagagtgct ctaccggcct cttttttccc     1920
ggagccgtct taacaggctc ctcaaccagg cccagaggtt caagaacccct cttttttcgcc    1980 tggaagactg ctcgtccgag gttgccccca aaagacgtat cttctttaag gcgctcctga    2040
aactctgcgt cggcgtggtt gtacttgagg tacgggttgt ctccgctgtc gagctgccgg    2100
tcgtaggcct tgtcgtgctc gagggccgcg gcgtctgcct cgttgaccgg ctccccctttg    2160 tcgagtccgt tgaagggtcc gaggtacttg tacccaggaa gcacaagacc cctgctgtcg    2220
tccttatgcc gctctgcggg ctttggtggt ggtgggccag gtttgagctt ccaccactgt    2280
cttattcctt cagagagagt gtcctcgagc caatctggaa gataaccatc ggcagccata    2340
cctgatttaa atcatttatt gttcagagat gcagtcatcc aaatccacat tgaccagatc    2400
gcaggcagtg caagcgtctg gcaccttttcc catgatatga tgaatgtagc acagtttctg    2460
atacgccttt ttgacgacag aaacgggttg agattctgac acgggaaagc actctaaaca    2520
gtctttctgt ccgtgagtga agcagatatt tgaattctga ttcattctct cgcattgtct    2580
gcagggaaac agcatcagat tcatgcccac gtgacgagaa catttgtttt ggtacctgtc    2640
cgcgtagttg atcgaagctt ccgcgtctga cgtcgatggc tgcgcaactg actcgcgcgc    2700
ccgtttgggc tcacttatat ctgcgtcact ggggggcgggt cttttcttag ctccacccctt    2760 tttgacgtag aattcatgct ccacctcaac cacgtgatcc tttgcccacc ggaaaaagtc    2820
tttcacttcc tgcttggtga cctttccaaa gtcatgatcc agacggcggg taagttcaaa    2880
tttgaacatc cggtcttgca acggctgctg gtgctcgaag gtcgttgagt tccgtcaat    2940 cacggcgcac atgttggtgt tggaggtgac gatcacggga gtcgggtcta tctgggccga    3000
ggacttgcat ttctggtcca cacgcacctt gcttcctcca agaatggctt tggccgactc    3060
cacgaccttg gcggtcatct tcccctcctc ccaccagatc accatcttgt cgacgcaatg    3120
gtaaaaggaa agttctcatt gg                                             3142

<210> SEQ ID NO 26
<211> LENGTH: 3075
<212> TYPE: DNA
<213> ORGANISM: Unknown
<220> FEATURE:
<223> OTHER INFORMATION: AAV serotype, clone H2

<400> SEQUENCE: 26
tgagaacttt cctttcaacg attgcgtcgg acaagatggt gatctggtgg gaggagggga     60
agatgaccgc caaggtcgtg gagtcggcca agccattctc tggaggaagc aaggtgcgtg    120
tggaccagaa atgcaagtcc tcggcccaga tagacccgac tcccgtgatc gtcacctcca    180
acaccaacat gtgcgccgtg attgacggga actcaacgac cttcgagcac cagcagccgt    240
tgcaagaccg gatgttcaaa tttgaactta cccgccgtct ggatcatgac tttggaaagg    300
tcaccaagca ggaagtgaaa gacttttttcc ggtgggcaaa ggatcacgtg gttgaggtgg    360
```

```
agcatgaatt ctacgtcaaa aagggtggag ctaagaaaag acccgccccc agtgacgcag    420
atataagtga gcccaaacgg gcgcgcgagt cagttgcgca gccatcaacg tcagacgcgg    480
aagcttcgat caactacgcg gacaggtacc aaaaacaaat gttctcgtca cgtgggcatg    540
aatctgatgc tgtttccctg cagacaatgc gagagaatga atcagaattc aaatatctgc    600
ttcactcacg gacagaaaga ctgtttagag tgctttcccg tgtcagaatc tcaacccgtt    660
tctgtcgtca aaaggcgta tcagaaactg tgctacattc atcatatcat gggaaaggtg     720
ccagacgctt gcactgcctg cgatctggtc aatgtggatt tggatgactg catctctgaa    780
caataaatga tttaaatcag gtatggctgc cgatggttat cctccagatt ggctcgagga    840
cactctctct gaagggataa acagtggtg gaagctcaaa cctggcccac caccaccaaa     900
gcccgcagag cggcataagg acgacagcag gggtcttgtg cttcctgggt acaagtacct    960
cggacccttc aacggactcg acaagggga gccggtcaac gaggcagacg ccgcggccct    1020
cgagcacgac aaggcctacg accggcagct cgacagcgga gacaacccgt acctcaagta   1080
caaccacgcc gacgcagagt ttcaggagcg ccttaaagaa gatacgtctt ttgggggcaa   1140
cctcggacga gcagtcttcc aggcgaaaaa gagggttctt gaacctctgg gcctggttga   1200
ggaacctgtt aagacggctc cgggaaaaaa gaggccggta gagcactctc ctgtggagcc   1260
agactcctcc tcgggaaccg gaaaagcggg ccagcggcct gcaagaaaaa gattaaattt   1320
tggtcagact ggagacgcag actccgtacc tgaccccag cctctcggac agccaccagc    1380
agccccctct ggtctgggat ctactacaat ggctacaggc agtggcgcac caatggcaga   1440
caataacgag ggtgccgatg gagtgggtaa ttcctcagga aattggcatt gcgattccca   1500
atggctgggc gacagagtca tcaccaccag cacccgaacc tgggccctgc ccacatacaa   1560
caaccacctc tacaagcaaa tctccagcca atcaggagcc agcaacgaca ccactactt    1620 tggctacagc accccctggg ggtattttga cttcaacaga ttccactgcc actttttcacc   1680 acgtgactgg caaagactca tcaacaacaa ctggggattc cggcccaaaa gactcaactt   1740
caagctcttt aatattcaag tcaaagaggt cacgcagaat gacggtacga cgacgattgc   1800
caataacctt accagcacgg ttcaggtgtt tactgactcg gagtaccagc tcccgtacgt   1860
cctgggctcg gcgcatcaag gatgcctccc gccgtttcca gcggacgtct tcatggtccc   1920
acagtatgga tacctcaccc tgaacaacgg gagtcaggcg gtaggacgct cttccttta    1980 ctgcctggag tactttcctt ctcagatgct gcgtactgga aacaactttc agttcagcta   2040 cactttttgaa gacgtgccctt tccacagcag ctacgctcac agccagagtc tggatcggct   2100
gatgaatcct ctgatcgacc agtacctgta ttatctgaac aagacacaaa caaatagtgg   2160
aactcttcag cagtctcggc tactgtttag ccaagctgga ccaaccaaca tgtctcttca   2220
agctaaaaac tggctgcctg gaccttgcta cagacagcag cgtctgtcaa acaggcaaa    2280 cgacaacaac aacagcaact ttccctggac tgcagctaca aagtatcatc taaatggccg   2340
ggactcgttg gttaatccag gaccagctat ggccagtcac aaggatgacg aagaaaagtt   2400
tttccccatg catggaaccc tgatatttgg taaacaagga caaatgcca acgacgcgga    2460 tttggaaaat gtcatgatta cagatgaaga agaaatcagg gccaccaatc ccgtggctac   2520
ggagcagtac gggactgtgt caaataattt gcaaaactca aacactggtc caactactgg   2580
aactgtcaat cgccaaggag cgttacctgg tatggtgtgg caggatcgag acgtgtacct   2640
gcagggaccc atttgggcca agattcctca caccgatgga cactttcatc cttctccact   2700
gatgggaggt tttggactca aacacccgcc tcctcagatc atgatcaaaa acactcccgt   2760
```

```
tccagccaat cctcccacaa acttcagttc tgccaagttt gcttctttca tcacacagta    2820
ttccacggga caggtcagcg tgggagatcga gtgggagctg cagaaggaga acagcaaacg    2880
ctggaatccc gaaattcagt acacttccaa ctacaacaag tctgttaatg tggactttac    2940
tgtggacact aatggtgtgt attcagagcc tcgccccatt ggcaccagat acctgactcg    3000
taatctgtaa ttgcttgtta atcaataaac cgtttaattc gtttcagttg aactttggtc    3060
tctgcgaagg gcgaa                                                     3075

<210> SEQ ID NO 27
<211> LENGTH: 3128
<212> TYPE: DNA
<213> ORGANISM: Unknown
<220> FEATURE:
<223> OTHER INFORMATION: AAV serotype, clone 42.8

<400> SEQUENCE: 27
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tcccaccccc gtgatcgtca cttccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa agcgagccc aagcgggcct     480 gccccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgccattcat catctgctag ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt     900
cgcgagtggt gggacttgaa acctggagcc ccgaaaccca agccaaccag caaaagcag     960 gacgacggcc ggggtctggt gcttcctggc tacaagtacc tcggacccct caacggactc    1020
gacaaggggg agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga gagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc ccgcaggccc ctctggtctg    1440
ggatctggta caatggctgc aggcggtggc gctccaatgg cagacaataa cgaaggcgcc    1500 gacgagtgg tagttcctc aggaaattgg cattgcgatt ccacatggct gggcgacaga    1560
gtcatcacca ccagcacccg aacctgggcc ctcccacct acaacaacca cctctacaag    1620
caaatctcca cgggacatc gggaggaagc accaacgaca cacctactt cggctacagc    1680 accccctggg ggtattttga ctttaacaga ttccactgcc acttctcacc acgtgactgg    1740
```

```
cagcgactca tcaacaacaa ctggggattc cggcccaaga gactcaactt caagctcttc    1800
aacatccagg tcaaggaggt cacgcagaat gaaggcacca agaccatcgc caataacctt    1860
accagcacga ttcaggtctt tacggactcg gaataccagc tcccgtacgt cctcggctct    1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt ttcacagcag ctacgcgcac agccaaagcc tggaccggct gatgaacccc    2160
ctcatcgacc agtacctgta ctacctgtct cggactcagt ccacgggagg taccgcagga    2220
actcagcagt tgctattttc tcaggccggg cctaataaca tgtcggctca ggccaaaaac    2280
tggctacccg ggccctgcta ccggcagcaa cgcgtctcca cgacactgtc gcaaaataac    2340
aacagcaact ttgcttggac cggtgccacc aagtatcatc tgaatggcag agactctctg    2400
gtaaatcccg gtgtcgctat ggcaacgcac aaggacgacg aagagcgatt ttttccatcc    2460
agcggagtct tgatgtttgg gaaacaggga gctggaaaag acaacgtgga ctatagcagc    2520
gttatgctaa ccagtgagga agaaatcaaa accaccaacc cagtggccac agaacagtac    2580
ggcgtggtgg ccgataacct gcaacagcaa aacgccgctc ctattgtagg ggccgtcaac    2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga aacacccgcc tcctcagatc ctgattaaga atacacctgt tcccgcggat    2820
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgccccatt ggcacccgtt acctcacccg taacctgtaa    3060
ttgcctgtta atcaataaac cggctaattc gtttcagttg aactttggtc tctgcgaagg    3120
gcgaattc                                                            3128
```

<210> SEQ ID NO 28
<211> LENGTH: 3128
<212> TYPE: DNA
<213> ORGANISM: Unknown
<220> FEATURE:
<223> OTHER INFORMATION: AAV serotype, clone 42.15

<400> SEQUENCE: 28

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga ccccaccccc gtgatcgtca cctccaacac caacatgtgc gccgtgattg    240
acgggaacag caccaccttc gagcaccagc agccgttgca ggaccggatg ttcaaatttg    300
aactcacccg ccgtctggag catgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gccccgatg acgcggataa agcgagccc aagcgggcct    480 gccccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcgcggg accagagact    660
```

```
gttcagaatg tttcccgggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccct caacggactc   1020
gacaaggggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga caggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacatc gggaggaagc accaacgaca cacctactt cggctacagc    1680
accccctggg ggtattttga ctttaacaga ttccactgcc acttctcacc acgtgactgg   1740
cagcgactca tcaacaacaa ctgggggattc cggcccaaga gactcaactt caagctcttc   1800
aacatccagg tcaaggaggt cacgcagaat gaaggcacca gaccatcgc caataacctt   1860
accagcacga ttcaggtctt tacggactcg aataccagc tcccgtacgt cctcggctct   1920
gcgcaccagg gctgcccgcc tccgttcccg cggacgtct tcatgattcc tcagtacggg   1980
tacctgactc tgaacaacgg cagtcaggcc gtgggccgtt cctccttcta ctgcctggag   2040
tactttcctt ctcaaatgcg gagaacgggc aacaactttg agttcagcta ccagtttgag   2100
gacgtgcctt ttcacagcag ctacgcgcat agccaaagcc tggaccggct gatgaacccc   2160
ctcatcgacc agtacctgta ctacctgtct cggactcagt ccacgggagg taccgcagga   2220
actcagcagt gctatttttc tcaggccggg cctaataaca tgtcggctca ggccaaaaac   2280
tggctacccg ggccctgcta ccggcagcaa cgcgtctcca cgacactgtc gcaaaataac   2340
aacagcaact tgcttggac cggtgccacc aagtatcatc tgaatggcag agactctctg   2400
gtaaatcccg gtgtcgctat ggcaacgcac aaggacgacg aagagcgatt ttttccatcc   2460
agcggagtct tgatgtttgg gaaacaggga gctggaaaag acaacgtgga ctatagcagc   2520
gttatgctaa ccagtgagga agaaatcaaa accaccaacc cagtggccac agaacagtac   2580
ggcgtggtgg ccgataacct gcaacagcaa acgccgctc ctattgtagg ggccgtcaac   2640
agtcaaggag ccttacctgg catggtctgg cagaaccggg acgtgtacct gcagggtcct   2700
atctgggcca agattcctca cacggacggc aactttcatc cttcgccgct gatgggaggc   2760
tttggactga aacacccgcc tcctcagatc ctgattaaga atacacctgt tccgcgggat   2820
cctccaacta ccttcagtca agccaagctg gcgtcgttca tcacgcagta cagcaccgga   2880
caggtcagcg tggaaattga atgggagctg cagaaagaga acagcaagcg ctggaaccca   2940
gagattcagt atacttccaa ctactacaaa tctacaaatg tggactttgc tgtcaatact   3000
gagggtactt attcagagcc tcgccccatt ggcacccgtt acctcacccg taacctgtaa   3060
```

```
ttgcctgtta atcaataaac cggttaattc gtttcagttg aactttggtc tctgcgaagg    3120
gcgaattc                                                             3128

<210> SEQ ID NO 29
<211> LENGTH: 3197
<212> TYPE: DNA
<213> ORGANISM: Unknown
<220> FEATURE:
<223> OTHER INFORMATION: AAV serotype. clone 42.5b

<400> SEQUENCE: 29
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccacccc gtgatcgtca cctccaacac caacatgtgc gccgtgattg      240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca catttgctt cacgcacggg accagagact      660
gttcagaatg tttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt     900
cgcgagtggt gggacttgaa acctggagcc ccgaaaccca agccaaccca gcaaaagcag    960
gacgacggcc ggggtctggt gcttcctggc tacaagtacc tcggacccct caacggactc    1020
gacaagggag agccggtcaa cgaggcagac gccgcggccc tcgagcacga caaggcctac    1080
gacaagcagc tcgagcaggg ggacaacccg tacctcaagt acaaccacgc cgacgccgag    1140
tttcaggagc gtcttcaaga agatacgtct tttggggca acctcgggcg agcagtcttc    1200
caggccaaga agcgggttct cgaacctctc ggtctggttg aggaaggcgc taagacggct    1260
cctggaaaga gagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc ccgcaggccc ctctggtctg    1440
ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctccccacct acaacaacca cctctacaag    1620
caaatctcca cgggacatc gggaggaagc accaacgaca cacctactt cggctacagc    1680 accccctggg gtattttga ctttaacaga ttccactgcc acttctcacc acgtgactgg    1740
cagcgactca tcaacaacaa ctgggggattc cggcccaaga gactcaactt caagctcttc    1800
aacatccagg tcaaggaggt cacgcagaat gaaggcacca gaccatcgc caataacctt    1860 accagcacga ttcaggtctt tacgactcg gaataccagc tcccgtacgt cctcggctct    1920
gcgcaccagg gctgcctgcc tccgttcccg gcggacgtct tcatgattcc tcagtacggg    1980
```

```
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt tcacagcag ctacgcgcac agccaaagcc tggaccggct gatgaacccc     2160
ctcatcgacc agtacctgta ctacctgtct cggactcagt ccacgggagg taccgcagga    2220
actcagcagt tgctattttc tcaggccggg cctaataaca tgtcggctca ggccaaaaac    2280
tggctacccg ggccctgcta ccggcagcaa cgcgtctcca cgacactgtc gcaaaataac    2340
aacagcaact ttgcttggac cggtgccacc aagtatcatc tgaatggcag agactctctg    2400
gtaaatcccg tgtcgctat ggcaacgcac aaggacgacg aagagcgatt ttttccatcc     2460
agcggagtct tgatgtttgg gaaacaggga gctggaaaag acaacgtgga ctatagcagc    2520
gttatgctaa ccagtgagga gaaaatcaaa accaccaacc cagtggccac agaacagtac    2580
ggcgtggtgg ccgataacct gcaacagcaa acgccgctc ctattgtagg ggccgtcaac     2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga aacacccgcc tcctcagatc ctgattaaga atacacctgt tcccgcggat    2820
cctccaacta ccttcagtca agccaagctg cgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgccccatt ggcacccgtt acctcacccg taacctgtaa    3060
ttgcctgtta atcaataaac cggttaattc gtttcagttg aactttggtc tctgcgaagg    3120
gcgaattcgt ttaaacctgc aggactagtc cctttagtga gggttaattc tgagcttggc    3180
gtaatcatgg gtcatag                                                  3197

<210> SEQ ID NO 30
<211> LENGTH: 2501
<212> TYPE: DNA
<213> ORGANISM: Unknown
<220> FEATURE:
<223> OTHER INFORMATION: AAV serotype, clone 42.1b

<400> SEQUENCE: 30
gaattcgccc ttggctgcgt caactggacc aatgagaact ttcccttcaa cgattgcgtc      60
gacaagatgg tgatctggtg ggaggagggc aagatgacgg ccaaggtcgt ggagtccgcc     120
aaggccattc atcatctgct ggggcgggct cccgagattg cttgctcggc ctgcgatctg     180
gtcaacgtgg acctggatga ctgtgtttct gagcaataaa tgacttaaac caggtatggc     240
tgccgatggt tatcttccag attggctcga ggacaacctc tctgagggca ttcgcgagtg     300
gtgggacttg agacctggag ccccgaaacc caaagccaac cagcaaaagc aggacgacgg     360
ccggggtctg gtgcttcctg gctacaagta cctcggaccc ttcaacggac tcgacaaggg    420
agagccggtc aacagggcag acgccgcggc cctcgagcac gacaaggcct acgacaagca    480
gctcgagcag ggggacaacc cgtacctcaa gtacaaccac gccgacgccg agtttcagga    540
gcgtcttcaa gaagatacgt cttttggggg caacctcggg cgagcagtct tccaggccaa    600
gaagcgggtt ctcgaacctc tcggtctggt tgaggaaggc gctaagacgg ctcctggaaa    660
gaagagaccc atagaatccc ccgactcctc cacgggcatc ggcaagaaag gccagcagcc    720
cgctaaaaag agactcaact ttgggcagac tggcgactca gagtcagtgc ccgaccctca    780
accaatcgga gaaccccccg caggccctc tggtctggga tctggcacaa tggctgcagg    840
```

-continued

```
cggtggcgct ccaatggcag acaataacga aggcgccgac ggagtgggta gttcctcagg       900
aaattggcat tgcgattcca catggctggg cgacagagtc atcaccacca gcacccgaac       960
ctgggccctc cccacctaca acaaccacct ctacaagcaa atctccaacg ggacatcggg      1020
aggaagcacc aacgacaaca cctacttcgg ctacagcacc ccctgggggt attttgactt      1080
taacagattc cactgccact tctcaccacg tgactggcag cgactcatca acaacaactg      1140
gggattccgg cccaagagac tcaacttcaa gctcttcaac atccaggtca aggaggtcac      1200
gcagaatgaa ggcaccaaga ccatcgccaa taacctaacc agcacgattc aggtctttac      1260
ggactcggaa taccagctcc cgtacgtcct cggctctgcg caccagggct gcctgcctcc      1320
gttcccggcg gacgtcttca tgattcctca gtacgggtac ctgactctga acaacggcag      1380
tcaggccgtg ggccgttcct ccttctactg cctggagtac tttccttctc aaatgctgag      1440
aacgggcaac aactttgagt tcagctacca gtttgaggac gtgcctttc acagcagcta      1500 tgcgcacagc caaagcctgg accggctgat gaacccctc atcgaccagt acctgtacta      1560
cctgtctcgg actcagtcca cgggaggtac cgcaggaact cagcagttgc tattttctca      1620
ggccgggcct aataacatgt cggctcaggc caaaaactgg ctaccggc cctgctaccg       1680 gcagcaacgc gtctccacga cagtgtcgca aaataacaac agcaactttg cttggaccgg      1740
tgccaccaag tatcatctga atggcagaga ctctctggta aatcccggtg tcgctatggc      1800
aacgcacaag ggcgacgaag agcgattttt ccatccagc ggagtcttga tgtttgggaa       1860
acagggagct ggaaaagaca acgtagacta tagcagcgtt atgctaacca gtgaggaaga      1920
aatcaaaacc accaacccag tggccacaga acagtacggc gtggtggccg ataacctgca      1980
acagcaaaac gccgctccta ttgtaggggc cgtcaacagt caaggagcct acctggcat       2040 ggtctggcag aaccgggacg tgtacctgca gggtcctatc tgggccaaga ttcctcacac      2100
ggacggcaac tttcatcctt cgccgctgat gggaggcttt ggactgaaac accgcctcc       2160 tcagatcctg attaagaata cacctgttcc cgcggatcct ccaactacct tcagtcaagc      2220
caagctggcg tcgttcatca cgcagtacag caccggacag gtcagcgtgg aaattgaatg      2280
ggagctgcag aaagagaaca gcaagcgctg gaacccagag attcagtata cttccaacta      2340
ctacaaatct acaaatgtgg actttgctgt caatactgag ggtacttatt cagagcctcg      2400
ccccattggc acccgttacc tcacccgtaa cctgtaattg cctgttaatc aataaaccgg      2460
ttgattcgtt tcagttgaac tttggtctca agggcgaatt c                         2501
```

<210> SEQ ID NO 31
<211> LENGTH: 3113
<212> TYPE: DNA
<213> ORGANISM: Unknown
<220> FEATURE:
<223> OTHER INFORMATION: AAV serotype, clone 42.13

<400> SEQUENCE: 31

```
gaattcgccc tttctacggc tgcgtcaact ggaccaatga gaactttccc ttcaacgatt        60
gcgtcgacaa gatggtgatc tggtgggagg agggcaagat gacggccaag gtcgtggagt       120
ccgccaaggc cattctcggc ggcagcaagg tgcgcgtgga ccaaaagtgc aagtcgtccg       180
cccagatcga tccaccccc gtgatcgtca cttccaacac caacatgtgc gccgtgattg       240
acgggaacag caccaccttc gagcaccagc agccgttaca agaccggatg ttcaaatttg       300
aactcacccg ccgtctggag catgactttg gcaaggtgac aaagcaggaa gtcaaagagt       360
tcttccgctg ggcgcaggat cacgtgaccg aggtggcgca tgagttctac gtcagaaagg       420
```

```
gtggagccaa caagagaccc gcccccgatg acgcggataa aagcgagccc aagcgggcct    480
gccccrcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaacca gcaaaagcag    960
gacgacggcc ggggtctggt gcttcctggc tacaagtacc tcggacccct caacggactc    1020
gacaagggg agcccgtcaa cgcggcggac gcagcggccc tcgagcacga caaggcctac    1080
gaccagcagc tcaaagcggg tgacaatccg tacctgcgt ataaccacgc cgacgccgag    1140
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga agagacccat agaatccccc gactcctcca cgggcatcgg caagaaaggc    1320
cagcagcccg ctaaaagaa gctcaacttt gggcagactg gcgactcaga gtcagtgccc    1380
gaccctcaac caatcggaga accccgca ggcccctctg gtctgggatc tggtacaatg    1440
gctgcaggcg gtggcgctcc aatggcagac aataacgaag gcgccgacgg agtgggtagt    1500
tcctcaggaa attggcattg cgattccaca tggctgggcg acagagtcat caccaccagc    1560
acccgaacct gggcccctccc cacctacaac aaccaccet acaagcaaat ctccaacggg    1620
acatcgggag gaagcaccaa cgacaacacc tacttcggct acagcacccc ctggggtat    1680
tttgacttta acagattcca ctgccacttc tcaccacgtg actggcagcg actcatcaac    1740
aacaactggg gattccggcc caagagactc aacttcaagc tcttcaacat ccaggtcaag    1800
gaggtcacgc agaatgaagg caccaagacc atcgccaata accttaccag cacgattcag    1860
gtctttacgg actcggaata ccagctcccg tacgtcctcg gctctgcgca ccagggctgc    1920
ctgcctccgt tccggcgga cgtcttcatg attcctcagt acgggtacct gactctgaac    1980
aacggcagtc aggccgtggg ccgttcctcc ttctactgcc tggagtactt tccttctcaa    2040
atgctgagaa cgggcaacaa ctttgagttc agctaccagt ttgaggacgt gccttttcac    2100
agcagctatg cgcacagcca aagcctggac cggctgatga acccctcat cgaccagtac    2160
ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccggc agcaacgcgt ctccacgaca gtgtcgcaaa ataacaacag caactttgct    2340
tggaccggtg ccaccaagta tcatctgaat ggcagagact ctctggtaaa tcccggtgtc    2400
gctatggcaa cgcacaaggg cgacgaagag cgattttttc catccagcgg agtcttgatg    2460
tttgggaaac agggagctgg aaaagacaac gtggactata gcagcgttat gctaaccagt    2520
gaggaagaaa tcaaaaccac caaccccagtg gccacagaac agtacggcgt ggtggccgat    2580
aacctgcaac agcaaaacgc cgctccrtatt gtagggccg tcaacagtca aggagccrta    2640
cctggcatgg tctggcagaa ccgggacgtg tacctgcagg gtcctatctg ggccaagatt    2700
cctcacacgg acgcaacttt tcatcctccg ccgctgatgg gaggctttgg actgaaacac    2760
ccgcctcctc agatcctgat taagaataca cctgttcccg cggatcctcc aactaccttc    2820
```

| agtcaagcca agctggcgtc gttcatcacg cagtacagca ccggacaggt cagcgtggaa | 2880 |
| attgaatggg agctgcagaa agagaacagc aagcgctgga acccagagat tcagtatact | 2940 |
| tccaactact acaaatctac aaatgtggac tttgctgtca atactgaggg tacttattca | 3000 |
| gagcctcgcc ccattggcac ccgttacctc acccgtagcc tgtaattgcc tgttaatcaa | 3060 |
| taaaccggtt gattcgtttc agttgaactt tggtctctgc gaagggcgaa ttc | 3113 |

<210> SEQ ID NO 32
<211> LENGTH: 3113
<212> TYPE: DNA
<213> ORGANISM: Unknown
<220> FEATURE:
<223> OTHER INFORMATION: AAV serotype, clone 42.3a

<400> SEQUENCE: 32

| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgcgtgga ccaaaagtgc aagtcgtccg | 180 |
| cccagatcga tcccacccccc gtgatcgtca cttccaacac caacatgtgc gccgtgattg | 240 |
| acgggaacag caccaccttc gagcaccagc agccgttaca agaccggatg ttcaaatttg | 300 |
| aactcacccg ccgtctggag catgactttg gcaaggtgac aaagcaggaa gtcaaagagt | 360 |
| tcttccgctg ggcgcaggat cacgtgaccg aggtggcgca tgagttctac gtcagaaagg | 420 |
| gtggagccaa caagagaccc gcccccgatg acgcggataa aagcgagccc aagcgggcct | 480 |
| gccctcagt cgcggatcca tcgacgtcag acgcggaagg agctccggtg gactttgccg | 540 |
| acaggtacca aaacaaatgt tctcgtcacg cgggcatgct tcagatgctg cttccctgca | 600 |
| agacatgcga gagaatgaat cagaatttca gcatttgctt cacgcacggg accagagact | 660 |
| gttcagaatg ttttccccggc gtgtcagaat ctcaaccggt cgtcagaaag aggacgtatc | 720 |
| ggaaactctg tgccattcat catctgctgg ggcgggctcc cgagattgct tgctcggcct | 780 |
| gcgatctggt caacgtggac ctggatgact gtgtttctga gcaataaatg acttaaacca | 840 |
| ggtatggctg ccgatggtca tcttccagat tggctcgagg acaacctctc tgagggcatt | 900 |
| cgcgagtggt gggacttgaa acctggagcc ccgaaaccca agccaaccca gcaaaagcag | 960 |
| gacgacggcc ggggtctggt gcttcctggc tacaagtacc tcggaccctt caacggactc | 1020 |
| gacaaggggg agcccgtcaa cgcggcggac gcagcggccc tcgagcacga caaggcctac | 1080 |
| gaccagcagc tcaaagcggg tgacaatccg tacctgcggt ataaccacgc cgacgccgag | 1140 |
| tttcaggagc gtcttcaaga agatacgtct tttgggggca acctcgggcg agcagtcttc | 1200 |
| caggccaaga agcgggttct cgaacctctc ggtctggttg aggaaggcgc taagacggct | 1260 |
| cctggaaaga gagacccat agaatccccc gactcctcca cgggcatcgg caagaaaggc | 1320 |
| cagcagcccg ctaaaaagaa gctcaacttt gggcagactg gcgactcaga gtcagtgccc | 1380 |
| gaccctcaac caatcggaga acccccgca ggcccctctg gtctgggatc tggtacaatg | 1440 |
| gctgcaggcg gtggcgctcc aatggcagac aataacgaag gcgccgacgg agtgggtagt | 1500 |
| tcctcaggaa attggcattg cgattccaca tagctgggcg acagagtcat caccaccagc | 1560 |
| acccgaacct gggccctccc cacctacaac aaccacctct acaagcaaat ctccaacggg | 1620 |
| acatcgggag gaagcaccaa cgacaacacc tacttcggct acagcacccc ctgggggtat | 1680 |
| tttgacttta acagattcca ctgccacttc tcaccacgtg actggcagcg actcatcaac | 1740 |
| aacagctggg gattccggcc caagagactc aacttcaagc tcttcaacat ccaggtcaag | 1800 |

```
gaggtcacgc agaatgaagg caccaagacc atcgccaata accttaccag cacgattcag    1860
gtctttacgg actcggaata ccagctcccg tacgtcctcg gctctgcgca ccagggctgc    1920
ctgcctccgt tcccggcgga cgtcttcatg attcctcagt acgggtacct gactctgaac    1980
aacggcagtc aggccgtggg ccgttcctcc ttctactgcc tggagtactt ccttctcaa    2040 atgctgagaa cgggcaacaa ctttgagttc agctaccagt ttgaggacgt gccttttcac    2100
agcagctacg cgcacagcca aagcctggac cggctgatga ccccctcat cgaccagtac    2160 ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccggc agcaacgcgt ctccacgaca ctgtcgcaaa ataacaacag caactttgct    2340
tggaccggtg ccaccaagta tcatctgaat ggcagagact ctctggtaaa tcccggtgtc    2400
gctatggcaa cgcacaagga cgacgaagag cgatttttc catccagcgg agtcttgatg    2460
tttgggaaac agggagctgg aaaagacaac gtggactata gcagcgttat gctaaccagt    2520
gaggaagaaa tcaaaaccac caacccagtg gccacagaac agtacggcgt ggtggccgat    2580
aacctgcaac agcaaacgc cgctcctatt gtagggggccg tcaacagtca aggagcctta    2640
cctggcatgg tctggcagaa ccgggacgtg tacctgcagg gtcctatctg gccaagatt    2700 cctcacacgg acggcaactt tcatccttcg ccgctgatgg gaggctttgg actgaaacac    2760
ccgcctcctc agatcctgat taagaataca cctgttcccg cggatcctcc aactaccttc    2820
agtcaagcca gctggcgtc gttcatcacg cagtacagca ccggacaggt cagcgtggaa    2880
attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc acccgtaacc tgtaattgcc tgttaatcaa    3060
taaaccggtt aattcgtttc agttgaactt tggtctctgc gaagggcgaa ttc           3113

<210> SEQ ID NO 33
<211> LENGTH: 2504
<212> TYPE: DNA
<213> ORGANISM: Unknown
<220> FEATURE:
<223> OTHER INFORMATION: AAV serotype, clone 42.4

<400> SEQUENCE: 33
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattcatcat ctgctggggc gggctcccga gattgcttgc tcggcctgcg     180
atctggtcaa cgtggacctg gatgactgtg tttctgagca ataaatgact taaaccaggt     240
atggctgccg atggttatct tccagattgg ctcgaggaca acctctctga gggcattcgc     300
gagtggtggg acttgaaacc tggagccccg aaacccaaag ccaaccagca aaagcaggac     360
gacggcgggg tctggtgct tcctggctac aagtacctcg gacccttcaa cggactcgac     420
aagggagagc cggtcaacga ggcagacgcc gcggccctcg agcacgacaa ggcctacgac     480
aagcagctcg agcagggga caacccgtac ctcaagtaca accacgccga cgccgagttt     540
caggagcgtc ttcaagaaga tacgtctttt ggggcaacc tcgggcgagc agtcttccag     600
gccaagaagc gggttctcga acctctcggt ctggttgagg aaggcgctaa gacggctcct     660
ggaaagaaga gacccataga atcccccgac tcctccacgg gcatcggcaa gaaaggccag     720
cagcccgcta aaaagaagct caactttggg cagactggcg actcagagtc agtgcccgac     780
```

```
cctcaaccaa tcggagaacc ccccgcaggc ccctctggtc tgggatctgg tacaatggct      840
gcaggcggtg gcgctccaat ggcagacaat aacgaaggcg ccgacggagt gggtaatgcc      900
tccggaaatt ggcattgcga ttccacatgg ctgggcgaca gagtcatcac caccagcacc      960
cgcacctggg ccctgcccac ctacaacaac cacctctaca agcagatatc aagtcagagc     1020
ggggctacca acgacaacca cttcttcggc tacagcaccc cctggggcta ttttgacttc     1080
aacagattcc actgccactt ctcatcacgt gactggcagc gactcatcaa caacaactgg     1140
ggattccggc caagagact caacttcaag ctcttcaaca tccaggtcaa ggaggtcacg      1200
cagaatgaag gcaccaagac catcgccaat aaccttacca gcacgattca ggtctttacg     1260
gactcggaat accggctccc gtacgtcctc ggctctgcgc accagggctg cctgcctccg     1320
ttcccggcgg acgtcttcat gattcctcag tacgggtacc tgactctgaa caacggcagt     1380
caggccgtgg gccgttcctc cttctactgc ctggagtact tccttctca aatgctgaga      1440 acgggcaaca actttgagtt cagctaccag tttgaggacg tgccttttca cagcagctac     1500
gcgcacagcc aaagcctgga ccggctgatg aaccccctca tcgaccagta cctgtactac     1560
ctgtctcgga ctcagtccac gggaggtacc gcaggaactc agcagttgct attttctcag     1620
gccgggccta ataacatgtc ggctcaggcc aaaaactggc tacccgggcc ctgctaccgg     1680
cagcaacgcg tctccacgac actgtcgcaa ataacaaca gcaactttgc cttggaccggt    1740 gccaccaagt atcatctgaa tggcagagac tctctggtaa atcccggtgt cgctatggca     1800
acgcacaagg acgacgaaga gcgatttttt ccatccagcg gagtcttgat gtttgggaaa     1860
cagggagctg aaaagacaa cgtggactat agcagcgtta tgctaaccag tgaggaagaa      1920
atcaaaacca ccaacccagt ggccacagaa cagtacggcg tggtggccga taacctgcaa     1980
cagcaaaacg ccgctcctat tgtaggggcc gtcaacagtc aaggagcctt acctggcatg     2040
gtctggcaga accgggacgt gtacctgcag ggtcctatct gggccaagat tcctcacacg     2100
gacggcaact tcatccttc gccgctgatg ggaggctttg gactgaaaca cccgcctcct     2160
cagatcctga ttaagaatac acctgttccc gcggatcctc caactacctt cagtcaagcc     2220
aagccggcgt cgttcatcac gcagtacagc accggacagg tcagcgtgga aattgaatgg     2280
gagctgcaga aagagaacag caagcgctgg aacccagaga ttcagtatac ttccaactac     2340
tacaaatcta caaatgtgga cttttgctgtc aatactgagg gtacttattc agagcctcgc     2400
cccattggca cccgttacct cacccgtaac ctgtaattgc ctgttaatca ataaaccggt     2460
taattcgttt cagttgaact ttggtctctg cgaagggcga attc                     2504
```

<210> SEQ ID NO 34
<211> LENGTH: 3106
<212> TYPE: DNA
<213> ORGANISM: Unknown
<220> FEATURE:
<223> OTHER INFORMATION: AAV serotype, clone 42.5a

<400> SEQUENCE: 34

```
gaattcgccc ttctacggct gcgtcaactg gaccaatgag aactttccct tcaacgattg       60
cgtcgacaag atggtgatct ggtgggagga gggcaagatg acggccaagg tcgtggagtc      120
cgccaaggcc attctcggcg gcagcaaggt gcgcgtggac caaaagtgca gtcgtccgc      180 ccagatcgac cccaccccg tgatcgtcac ctccaacacc aacatgtgcg ccgtgattga      240
cgggaacagc accaccttcg agcaccagca gccgttgcag gaccggatgt tcaaatttga      300
actcacccgc cgtctggagc atgactttgg caaggcgaca aagcaggaag tcaaagagtt      360
```

```
cttccgctgg gcgcaggatc acgtgaccga ggtggcgcat gagttctacg tcagaaaggg    420
tggagccaac aagagacccg cccccgatga cgcggataaa agcgagccca agcgggcccg    480
cccctcagtc gcggatccat cgacgtcaga cgcggaagga gctccggtgg actttgccga    540
caggtaccaa aacaaatgtt ctcgtcacgc gggcatgctt cagatgctgt ttccctgcaa    600
aacatgcgag agaatgaatc agaatttcaa catttgcttc acgcacggga ccagagactg    660
ttcagaatgt ttccccggcg tgtcagaatc tcaaccggtc gtcagaaaga ggacgtatcg    720
gaaactctgt gccattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacggccg gggtctggtg cttcctggct acaagtacct cggacccttc aacggactcg   1020
acaagggaga gccggtcaac gaggcagacg ccgcggccct cgagcacgac aaggcctacg   1080
acaagcagct cgagcagggg gacaacccgt acctcaagta caaccacgcc gacgccgagt   1140
ttcaggagc tcttcaagaa gatacgtctt ttggggggcaa cctcgggcga gcagtcttcc   1200
gggccaagaa gcgggttctc gaacctctcg gtctggttga ggaaggcgct aagacggctc   1260
ctggaaagaa gagacccata gaatccccg actcctccac gggcatcggc aagaaaggcc   1320
agcagcccgc taaaaagaag ctcaactttg gcagactgg cgactcagag tcagtgcccg   1380
accccccaacc tctcggagaa cctcccgccg cgccctcagg tctgggatct ggtacaatgg   1440
ctgcaggcgg tggcgcacca atggcagaca ataacgaagg cgccgacgga gtgggtaatg   1500
cctccggaaa ttggcattgc gattccacat ggctgggcga cagagtcatc accaccagca   1560
cccgcacctg ggccctgccc acctacaaca accacctcta caagcagata tcaagtcaga   1620
gcggggctac caacgacaac cacttcttcg gctacagcac cccctggggc tattttgact   1680
tcaacagatt ccactgccac ttctcaccac gtgactggca gcgactcatc aacaacaacc   1740
ggggattccg gccccagaaag ctgcggttca agttgttcaa catccaggtc aaggaggtca   1800
cgacgaacga cggcgttacg accatcgcta ataaccttac cagcacgatt caggtcttct   1860
cggactcgga gtaccaactg ccgtacgtcc tcggctctgc gcaccagggc tgcctccctc   1920
cgttccctgc ggacgtgttc atgattcctc agtacggata tctgactcta aacaacggca   1980
gtcagtctgt gggacgttcc tccttctact gcctggagta ctttccttct cagatgctga   2040
gaacgggcaa taactttgaa ttcagctacc agtttgagga cgtgccccttt cacagcagct   2100
acgcgcacag ccaaagcctg gaccggctga tgaaccccct catcgaccag tacctgtact   2160
acctgtctcg gactcagtcc acgggaggta ccgcaggaac tcagcagttg ctattttctc   2220
aggccgggcc taataacatg tcggctcagg ccaaaaactg gctacccggg ccctgctacc   2280
ggcagcaacg cgtctccacg acactgtcgc aaaataacaa cagcaacttt gcttggaccg   2340
gtgccaccaa gtatcatctg aatggcagag actctctggt aaatcccggt gtcgctatgg   2400
caacgcacaa ggacgacgaa gagcgatttt ttccatccag cggagtcttg atgtttggga   2460
aacagggagc tggaaaagac aacgtggact atagcagcgt tatgctaacc agtgaggaag   2520
aaatcaaaac caccaaccca gtggccacag aacagtacgg cgtggtggcc gataacctgc   2580
aacagcaaaa cgccgctcct attgtagggg ccgtcaacag tcaaggagcc ttacctggca   2640
tggcctggca gaacgggac gtgtacctgc agggtcctat ctgggccaag attcctcaca   2700
cggacggcaa cttcatcct tcgccgctga tgggaggctt tggactgaaa cacccgcctc   2760
```

-continued

```
ctcagatcct gattaagaat acacctgttc ccgcggatcc tccaactacc ttcagtcaag    2820
ccaagctggc gtcgttcatc acgcagtaca gcaccggaca ggtcagcgtg gaaattgaat    2880
gggagctgca gaaagagaac agcaagcgct ggaacccaga gattcagtat acttccaact    2940
actacaaatc tacaaatgtg actttgctg tcaatactga gggtacttat tcagagcctc     3000
gccccattgg cacccgttac ctcacccgta acctgtaatt gcctgttaat caataaaccg    3060
gttaattcgt ttcagttgaa ctttggtctc tgcgaagggc gaattc                   3106
```

<210> SEQ ID NO 35
<211> LENGTH: 2489
<212> TYPE: DNA
<213> ORGANISM: Unknown
<220> FEATURE:
<223> OTHER INFORMATION: AAV serotype, clone 42.10

<400> SEQUENCE: 35

```
gaattcgccc tttctacggc tgcgtcaact ggaccaatga gaactttccc ttcaacgatt     60
gcgtcgacaa gatggtgatc tggtgggagg agggcaagat gacggccaag gtcgtgaagt    120
ccgccaaggc cattcatcat ctgctggggc gggctcccga gattgcttgc tcggcctgcg    180
atctggtcaa cgtggacctg atgactgtg tttctgagca ataaatgact taaaccaggt     240
atggctgccg atggttatct tccagattgg ctcgaggaca acctctctga gggcattcgc    300
gagtggtggg acttgaaacc tggagccccg aaacccaaag ccaaccagca aaagcaggac    360
gacggccggg gtctggtgct tcctggctac aagtacctcg gacccttcaa cggactcgac    420
aagggagagc cggtcaacga ggcagacgcc gcggccctcg agcacgacaa ggcctacgac    480
aagcagctcg agcaggggga caacccgtac ctcaagtaca accacgccga cgccgagttt    540
caggagcgtc ttcaagaaga tacgtctttt gggggcaacc tcgggcgagc agtcttccag    600
gccaagaagc gggttctcga acctctcggt ctggttgagg aaggcgctaa gacggctcct    660
ggaaagaaga gacccataga atcccccgac tcctccacgg gcatcggcag gaaaggccag    720
cagcccgcta aaaagaagct caactttggg cagactggcg actcagagtc agtgcccgac    780
cctcaaccaa tcggagaacc ccccgcaggc ccctctggtc tgggatctgg tacaatggct    840
gcaggcggtg gcgctccaat ggcagacaat aacgaaggcg ccgacggagt gggtaatgcc    900
tccggaaatt ggcattgcga ttccacatgg ctgggcgaca gagtcatcac caccagcacc    960
cgcacctggg ccctgcccac ctacaacaac cacctctaca agcagatatc aagtcagagc    1020
ggggctacca acgacaacca cttcttcggc tacagcaccc cctggggcta ttttgacttc    1080
aacagattcc actgccactt ctcaccacgt gactggcagc gactcatcaa caacaactgg    1140
ggattccggc ccagaaagct gcggttcaag ttgttcaaca tccaggtcaa ggaggtcacg    1200
acgaacgacg gcgttacgac catcgccaat aaccttacca gcacgattca ggtcttctcg    1260
gactcggagt accaactgcc gtacgtcctc ggctctgcgc accagggctg cctccctccg    1320
ttccctgcgg acgtgttcat gattcctcag tacggatatc tgactctaaa caacggcagt    1380
cagtctgtgg gacgttcctc cttctactgc ctggagtact tccttctca gatgctgaga    1440 acgggcaata actttgaatt cagctacacc tttgaggaag tgcctttcca cagcagctat    1500
gcgcacagcc agagcctgga ccggctgatg aatcccctca tcgaccagta cctgtactac    1560
ctggcccgga cccagagcac tacgggtcc acaagggagc tgcagttcca tcaggctggg    1620
cccaacacca tggccgagca atcaaagaac tggctgcccg accctgtta tcggcagcag    1680 agactgtcaa aaaacataga cagcaacaac aacagtaact ttgcctggac cggggccact    1740
```

```
aaataccatc tgaatggtag aaattcatta accaacccgg gcgtagccat ggccaccaac      1800
aaggacgacg aggaccagtt ctttcccatc aacggagtgc tggttttgg caaaacgggg       1860 gctgccaaca agacaacgct ggaaaacgtg ctaatgacca gcgaggagga gatcaaaacc      1920
accaatcccg tggctacaga agaatacggt gtggtctcca gcaacctgca atcgtctacg      1980
gccggacccc agacacagac tgtcaacagc caggggctc tgcccggcat ggtctggcag       2040
aaccgggacg tgtacctgca gggtcccatc tgggccaaaa ttcctcacac ggacggcaac      2100
tttcacccgt ctcccctgat gggcggattt ggactcaaac accgcctcc tcaaattctc       2160 atcaaaaaca ccccggtacc tgctaatcct ccagaggtgt ttactcctgc caagtttgcc     2220
tcatttatca cgcagtacag caccggccag gtcagcgtgg agatcgagtg ggaactgcag     2280
aaagaaaaca gcaaacgctg gaatccagag attcagtaca cctcaaatta tgccaagtct     2340
aataatgtgg aatttgctgt caacaacgaa ggggtttata ctgagcctcg ccccattggc     2400
acccgttacc tcacccgtaa cctgtaattg cctgttaatc aataaaccgg ttaattcgtt     2460
tcagttgaac tttggtcaag ggcgaattc                                        2489

<210> SEQ ID NO 36
<211> LENGTH: 2495
<212> TYPE: DNA
<213> ORGANISM: Unknown
<220> FEATURE:
<223> OTHER INFORMATION: AAV serotype, clone 42.3b

<400> SEQUENCE: 36
gaattcgccc tttctacggc tgcgtcaact agaccaatga gaactttccc ttcaacgatt      60
gcgtcgacaa gatggtgatc tggtgggagg agggcaagat gacggccaag gtcgtggagt     120
ccgccaaggc cattcatcat ctgctggggc gggctcccga gattgcttgc tcggcctgcg     180
atctggtcaa cgtggacctg gatgactgtg tttctgagca ataaatgact taaaccaggt     240
atggctgccg atggttatct tccagattgg ctcgaggaca acctctctga gggcattcgc     300
gagtggtggg acttgaaacc tggagccccg aaacccaaag ccaaccagca aaagcaggac     360
gacggccggg gtctggtgct tcctggctac aagtacctcg gacccttcaa cggactcgac     420
aagggagagc cggtcaacga ggcagacgcc gcggccctcg agcacgacaa ggcctacgac     480
aagcagctcg agcaggggga caacccgtac ctcaagtaca accacgccga cgccgagttt     540
caggagcgtc ttcaagaaga tacgtctttt gggggcaacc tcgggcgagc agtcttccag     600
gccaagaagc gggttctcga acctctcggt ctggttgagg aaggcgctaa gacggctcct     660
ggaaagaaga gacccataga atccccccgac tcctccacgg gcatcggcaa gaaaggccag     720
cagcccgcta aaaagaagct caactttggg cagactggcg actcagagtc agtgcccgac     780
cctcaaccaa tcggagaacc ccccgcaggc ccctctggtc tgggatctgg tacaatggct     840
gcaggcggtg gcgctccaat ggcagacaat aacgaaggcg ccgacggagt gggtaatgcc     900
tccggaaatt ggcattgcga ttccacatgg ctgggcgaca gagtcatcac caccagcacc     960
cgcacctggg ccctgcccac ctacaacaac cacctctaca gcagatatc aagtcagagc     1020 ggggctacca acgacaacca cttcttcggc tacagcaccc cctgggca tttttgacttc    1080 aacagattcc actgccactt ctcaccacgt gactggcagc gactcatcaa caacaactgg    1140
ggattccggc ccagaaagct gcggttcaag ttgttcaaca tccaggtcaa ggaggtcacg    1200
acgaacgacg gcgttacgac catcgctaat aaccttacca gcacgattca ggtcttctcg    1260
gactcggagt accaactgcc gtacgtcctc ggctctgcgc accagggctg cctccctccg    1320
```

```
ttccctgcgg acgtgttcat gattcctcag tacggatatc tgactctaaa caacggcagt    1380
cagtctgtgg gacgttcctc cttctactgc ctggagtact ttccttctca gatgctgaga    1440
acgggcaata actttgaatt cagctacacc tttgaggaag tgcctttcca cagcagctat    1500
gcgcacagcc agagcctgga ccggctgatg aatcccctca tcgaccagta cctgtactac    1560
ctggcccgga cccagagcac tacggggtcc acaagggagc tgcagttcca tcaggctggg    1620
cccaacacca tggccgagca atcaaagaac tggctgcccg gaccctgtta tcggcagcag    1680
agactgtcaa aaacatagac agcaacaaca ccagtaactt gcctggac cggggccact    1740 aaataccatc tgaatggtag aaattcatta accaacccgg gcgtagccat ggccaccaac    1800
aaggacgacg aggaccagtt ctttcccatc aacggagtgc tggttttggg caaaacgggg    1860
gctgccaaca agacaacgct ggaaaacgtg ctaatgacca cgcgaggagga gatcaaaacc    1920 accaatcccg tggctacaga acagtacggt gtggtctcca gcaacctgca atcgtctacg    1980
gccggacccc agacacagac tgtcaacagc caggggctc tgcccggcat ggtctggcag    2040
aaccgggacg tgtacctgca gggtcccatc tgggccaaaa ttcctcacac ggacggcaac    2100
tttcacccgt ctcccctgat gggcggattt ggactcaaac accgcctcc tcaaattctc    2160 atcaaaaaca ccccggtacc tgctaatcct ccagaggtgt tactcctgc caagtttgcc    2220 tcatttatca cgcagtacag caccggccag gtcagcgtgg agatcgagtg gaactgcag    2280 aaagaaaaca gcaaacgctg gaatccagag attcagtaca cctcaaatta tgccaagtct    2340
aataatgtgg aatttgctgt caacaacgaa ggggtttata ctgagcctcg ccccattggc    2400
acccgttacc tcacccgtaa cctgtaattg cctgttaatc aataaaccgg ttaattcgtt    2460
tcagttgaac tttggtctct gcgaagggcg aattc                              2495
```

<210> SEQ ID NO 37
<211> LENGTH: 3098
<212> TYPE: DNA
<213> ORGANISM: Unknown
<220> FEATURE:
<223> OTHER INFORMATION: AAV serotype, clone 42.11

<400> SEQUENCE: 37

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tcccacccc gtgatcgtca cttccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg gcgcaggat cacgtgaccg aggtggcgca tgagttctac gtcagaaagg     420
gtggagccaa caagagaccc gcccccgatg acgcggataa aagcgagccc aagcgggcct     480 gccctcagt cgcggatcca tcgacgtcag acgcggaagg agctccggtg gactttgccg     540
acaggtacca aaacaaatgt tctcgtcacg cgggcatgct tcagatgctg tttcctgca     600 agacatgcga gagaatgaat cagaatttca acatttgctt cacgcacggg accggagact     660
gttcagaatg ttttcccggc gtgtcagaat ctcaaccggc gtcagaaag aggacgtatc     720 ggaaactctg tgccattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt     900
```

```
cgcgagtggt gggacttgaa acctggagcc ccgaaaccca aagccaacca gcaaaagcag    960
gacgacggcc ggggtctggt gcttcctggc tacaagtacc tcggacccct caacggactc   1020
gacaagggag agccggtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagacccat agaatccccc gactcctcca cgggcatcgg caagaaaggc   1320
cagcagcccg ctaaaaagaa gctcaacttt gggcagactg gcgactcaga gtcagtgccc   1380
gaccctcaac caatcggaga accccccgca ggccctctg gtctgggatc tggtacaatg    1440
gctgcaggcg gtggcgctcc aatggcagac aataacgaag gcgccgacgg agtgggtaat   1500
gcctccggaa attggcattg cgattccaca tggctgggcg acagagtcat caccaccagc   1560
acccgcacct gggccctgcc cacctacaac aaccacctct acaagcagat atcaagtcag   1620
agcggggcta ccaacgacaa ccacttcttc ggctacagca cccccctgggg ctattttgac   1680
ttcaacagat tccactgcca cttctcacca cgtgactggc agcgactcat caacaacaac   1740
tggggattcc ggcccagaaa gctgcggttc aagttgttca acatccaggt caaggaggtc   1800
acgacgaacg acggcgttac gaccatcgct aataacctta ccagcacgat tcaggtcttc   1860
tcggactcgg agtaccaact gccgtacgtc ctcggctctg cgcaccaggg ctgcctccct   1920
ccgttccctg cggacgtgtt catgattcct cagtacggat atctgactct aaacaacggc   1980
agtcagtctg tgggacgttc ctccttctac tgcctggagt actttccttc tcagatgctg   2040
agaacgggca ataactttga attcagctac acctttgagg aagtgccttt ccacagcagc   2100
tatgcgcaca gccagagcct ggaccggctg atgaatcccc tcatcgacca gtacctgtac   2160
tacctggccc ggacccagag cactacgggg tccacaaggg agctgcagtt ccatcaggct   2220
gggcccaaca ccatggccga gcaatcaaag aactggctgc ccggaccctg ttatcggcgg   2280
cagagactgt caaagacat agacagcaac aacaacagta actttgcctg gaccggggcc   2340
actaaatacc atctgaatgg tagaaattca ttaaccaacc cgggcgtagc catggccacc   2400
aacaaggacg acgaggacca gttctttccc atcaacggag tgctggtttt tggcaaaacg   2460
ggggctgcca acaagacaac gctggaaaac gtgctaatga ccagcgagga ggagatcaaa   2520
accaccaatc ccgtggctac agaagaatac ggtgtggtct ccagcaacct gcaatcgtct   2580
acggccggac cccagacaca gactgtcaac agccaggggg ctctgccggg catggtctgg   2640
cagaaccggg acgtgtacct gcagggtccc atctgggcca aaattcctca cacggacggc   2700
aactttcacc cgtctccct gatgggcgga tttggactca acacccgcc tcctcaaatt    2760
ctcatcaaaa acacccccggt acctgctaat cctccagagg tgtttactcc tgccaagttt   2820
gcctcattta tcacgcagta cagcaccggc caggtcagcg tggagatcga gtgggaactg   2880
cagaaagaga acagcaaacg ctggaatcca gagattcagt acacctcaaa ttatgccaag   2940
tctaataatg tggaatttgc tgtcaacaac gaagggggttt atactgagcc tcgcccatt    3000
ggcacccgtt acctcacccg taacctgtaa ttacttgtta atcaataaac cggttgattc   3060
gtttcagttg aactttggtc tctgcgaagg gcgaattc                            3098
```

<210> SEQ ID NO 38
<211> LENGTH: 3276
<212> TYPE: DNA
<213> ORGANISM: Unknown

<220> FEATURE:
<223> OTHER INFORMATION: AAV serotype, clone 42.6a

<400> SEQUENCE: 38

| | | | | | |
|---|---|---|---|---|---:|
| gaattcgccc | ttcgcagaga | ccaaagttca | actgaaacga | attaaccggt | ttattgatta | 60 |
| acaggcaatt | acaggttacg | ggtgaggtaa | cgggtgccaa | tggggcgagg | ctcagtataa | 120 |
| accccttcgt | tgttgacagc | aaattccaca | ttattagact | tggcataatt | tgaggtgtac | 180 |
| tgaatctctg | gattccagcg | tttgctgttt | tctttctgca | gttcccactc | gatctccacg | 240 |
| ctgacctggc | cggtgctgta | ctgcgtgata | aatgaggcaa | acttggcagg | agtaaacacc | 300 |
| tctggaggat | tagcaggtac | cggggtgttt | ttgatgagaa | tttgaggagg | cgggtgtttg | 360 |
| agtccaaatc | cgtccatcag | gggagacggg | tgaaagttgc | cgtccgtgtg | aggaattttg | 420 |
| gcccagatgg | gaccctgcag | gtacacgtcc | cggttctgcc | agaccatgcc | gggcagagcc | 480 |
| ccctggctgt | tgacagtctg | tgtctggggt | ccggccgtag | acgattgcag | gttgctggag | 540 |
| accacaccgt | attcttctgt | agccacggga | ttggtggttt | tgatctcctc | ctcgctggtc | 600 |
| attagcacgt | tttccagcgt | tgtcttgttg | gcagcccccg | ttttgccaaa | aaccagcact | 660 |
| ccgttgatgg | gaaagaactg | gtcctcgtcg | tccttgttgg | tggccatggc | tacgcccggg | 720 |
| ttggttaatg | aatttctacc | attcagatgg | tatttagtgg | ccccggtcca | ggcaaagtta | 780 |
| ctgttgttgt | tgctgtctat | gtttttgac | agtctctgct | gccgataaca | gggtccgggc | 840 |
| agccagttct | ttgattgctc | ggccatggtg | ttgggcccag | cctgatggaa | ctgcagctcc | 900 |
| cttgtggacc | ccgtagtgct | ctgggtccgg | gccaggtagt | acaggtactg | gtcgatgagg | 960 |
| ggattcatca | gccggtccag | gctctggcta | tgcgcatagc | tgctgtggaa | aggcacttcc | 1020 |
| tcaaaggtgt | agctgaattc | aaagttattg | cccgttctca | gcatctgaga | aggaaagtac | 1080 |
| tccaggcagt | agaaggagga | acgtcccaca | gactgactgc | cgttgtttag | agtcagatat | 1140 |
| ccgtactgag | gaatcatgaa | cacgtccgca | gggaacggag | ggaggcagcc | ctggtgcgca | 1200 |
| gagccgagga | cgtacggcag | ttggtactcc | gagtccgaga | agacctgaat | cgtgctggta | 1260 |
| aggttattag | cgatggtcgt | aacgccgtcg | tccgtcgtga | cctccttgac | ctggatgttg | 1320 |
| aacaacttga | accgcagctt | tctgggccgg | aatcccagt | tgttgttgat | gagtcgctgc | 1380 |
| cagtcacgtg | gtgagaagtg | gcagtggaat | ctgttaaagt | caaaataccc | caggggggtg | 1440 |
| ctgtagccga | agtaggtgtt | gtcgttggtg | cttcctcccg | atgtcccgtt | ggagatttgc | 1500 |
| ttgtagaggt | ggttgttgta | ggtggggagg | gcccaggttc | gggtgctggt | ggtgatgact | 1560 |
| ctgtcgccca | gccatgtgga | atcgcaatgc | caatttcctg | aggaactacc | cactccgtcg | 1620 |
| gcgccttcgt | tattgtctgc | cattggagcc | ccaccgcctg | cagccattgt | accagatccc | 1680 |
| agaccagagg | ggcctgcggg | gggttctccg | attggttgag | ggtcgggcac | tgactctgag | 1740 |
| tcgccagtct | gcccaaagtt | gagtctcttt | ttcgcgggct | gctggcctgt | cttgccgatg | 1800 |
| cccgtagagg | agtctggaga | acgctggggt | gatggctcta | ccggtctctt | ctttccagga | 1860 |
| gccgtcttag | cgccttcctc | aaccagaccg | agaggttcga | gaaccccgctt | cttggcctgg | 1920 |
| aagactgctc | gcccgaggtt | gccccaaaa | gacgtatctt | cttgaagacg | ctcctgaaac | 1980 |
| tcggcgtcgg | cgtggttgta | cttgaggtac | gggttgtccc | cctgctcgag | ctgcttgtcg | 2040 |
| taggccttgt | cgtgctcgag | ggccgcgcg | tctgcctcgt | tgaccggctc | tcccttgtcg | 2100 |
| agtccgttga | agggtccgag | gtacttgtag | ccaggaagca | ccagacccg | gccgtcgtcc | 2160 |
| tgcttttgct | ggttggcttt | gggtttcggg | gctccaggtt | tcaagtccca | ccactcgcga | 2220 |
| atgccctcag | agaggttgtc | ctcgagccaa | tctggaagat | aaccatcggc | agccatacct | 2280 |

```
ggtttaagtc atttattgct cagaaacaca gtcatccagg tccacgttga ccagatcgca    2340
ggccgagcaa gcaatctcgg gagcccgccc cagcagatga tgaatggcac agagtttccg    2400
atacgtcctc tttctgacga ccggttgaga ttctgacacg ccggggaaac attctgaaca    2460
gtctctggtc ccgtgcgtga agcaaatgtt gaaattctga ttcattctct cgcatgtctt    2520
gcagggaaac agcatctgaa gcatgcccgc gtgacgagaa cacttgtttt ggtacctgtc    2580
ggcaaagtcc accggagctc cttccgcgtc tgacgtcgat ggatgcaaaa tgtcgcaaaa    2640
gcactcacgt gacagctaat acaggaccac tcccctatga cgtgatttac gtcagcgcta    2700
tgcccgcgtg acgagaacat ttgttttggt acctgtcggc aaagtccacc ggagctcctt    2760
ccgcgtctga cgtcgatgga tccgcgactg aggggcaggc ccgcttgggc tcgcttttat    2820
ccgcgtcatc gggggcgggt ctcttgttgg ctccacccct tctgacgtag aactcatgcg    2880
ccacctcggt cacgtgatcc tgcgcccagc ggaagaactc tttgacttcc tgctttgtca    2940
ccttgccaaa gtcatgctcc agacggcggg tgagttcaaa tttgaacatc cggtcctgca    3000
acggctgctg gtgctcgaag tggtgctgtt cccgtcaat cacggcgcac atgttggtgt    3060
tggaagtgac gatcacgggg gtgggatcga tctgggcgga agacttgcac ttttggtcca    3120
cgcgcacctt gctgccgccg agaatggcct tggcggactc cacgaccttg gccgtcatct    3180
tgccctcctc ccaccagatc accatcttgt cgacgcaatc gttgaaggga aagttctcat    3240
tggtccagtt gacgcagccg tagaaagggc gaattc                             3276
```

<210> SEQ ID NO 39
<211> LENGTH: 3084
<212> TYPE: DNA
<213> ORGANISM: Unknown
<220> FEATURE:
<223> OTHER INFORMATION: AAV serotype, clone 43.1

<400> SEQUENCE: 39

```
gaattcgccc tttctacggc tgcatcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaagttcg     300
aactcacccg ccgtctggag cacgactttg gcaaggtgac caagcaggaa gtcaaagagt     360
tcttccgctg ggcgcaggat cacgtgaccg aggtggcgca tgagttctac gtcagaaagg     420
gcggagccag caaaagaccc gcccccgatg acgcggatat aagcgagccc aagcgggcct     480 gccccctcagt cgcggatcca tcgacgtcag acgcggaagg agctccggtg gactttgccg     540
acaggtacca aaacaaatgt ctcgtcacg cgggcatgct tcagatgctg tttccctgca     600
aaacgtgcga gaaatgaat cagaatttca acatttgctt cacgcacggg gtcagagact     660
gctcagaatg tttccccggt gcatcagaat ctcaaccggt cgtcagaaaa aaacgtatc     720 agaaactgtg tgccattcat catctgctgg ggcgggcacc cgagattgct tgctcggcct     780
gcgatctggt caacgtggac ctggacgact gtgtttctga gcaataaatg acttaaacca     840
ggtatggctg ccgatggtta tcttccagat tggcttgagg acaacctctc tgagggcatt     900
cgcgagtggt gggacctgaa acctggagcc ccgaaaccca agccaaccag caaaagcag     960 gacgacggcc ggggtctggt gcttcctggc tacaagtacc tcggaccctt caacggactc    1020 gacaagggggg agcccgtcaa cgcggcggac gcagcggccc tcgagcacga caaggcctac    1080
```

```
gaccagcagc tcaaagcggg tgacaatccg tacctgcggt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga agagaccggt agagccatca cctcagcgtt cccccgactc ctccacgggc    1320
atcggcaaga aaggccacca gcccgcgaga aagagactga actttgggca gactggcgac    1380
tcggagtcag tccccgaccc tcaaccaatc ggagaaccac cagcaggccc ctctggtctg    1440
ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctgcccacct acaacaacca tctctacaag    1620
caaatctcca acgggacatc gggaggaagc actaacgaca cacctactt tggctacagc     1680 accccctggg ggtattttga cttcaacaga ttccactgcc acttctcacc acgtgactgg    1740
cagcgactca tcaacaataa ctggggattc cggcccaaga gactcaactt caagctcttc    1800
aacatccagg tcaaggaggt cacgcagaat gaaggcacca agaccatcgc caataacctt    1860
accagcacga ttcaggtgtt tacggactcg gaataccagc tcccgtacgt ccccggctct    1920
gcgcaccagg gctgcctccc tccgttcccg gcggacgtct tcatgattcc tcagtacggg    1980
tatctgaccc taaacaatgg cagtcaggct gtgggccgtt cctccttcta ctgcctggaa    2040
tacttcccct tctcaaatgct gaggacgggc aacaactttg aattcagcta ccttcgag     2100 gacgtgcctt tccacagcag ctacgcgcac agccagagcc tggaccggct gatgaaccct    2160
ctcatcgacc agtacctgta ttacttatcc agaactcagt ccacaggagg aactcaaggt    2220
actcagcaat tgttattttc tcaagccggg cccgcaaaca tgtcggctca ggccaagaac    2280
tggctacctg gaccgtgtta ccgtcagcaa cgagtttcca cgacactgtc gcaaaacaac    2340
aacagcaatt ttgcttggac cggtgccacc aagtatcacc tgaatggcag agactccctg    2400
gttaatcccg gcgttgccat ggctacccac aaggacgacg aggagcgctt cttcccgtca    2460
agcggagttc taatgtttgg caagcagggg gctggaaaag acaatgtgga ctacagcagc    2520
gtgatgctca ccagcgaaga agaaattaaa actactaacc cagtggctac agagcagtat    2580
ggtgtggtgg cagacaacct gcagcagacc aacggagctc ccattgtggg aactgtcaac    2640
agccaggggg ccttacctgg tatggtctgg caaaaccggg acgtgtacct gcagggcccc    2700
atctgggcca aaattcctca cacggacggc aactttcatc cttcgccgct gatgggaggc    2760
tttggactga aacacccgcc tcctcagatc ctggtgaaaa acactcctgt tcctgcggat    2820
cctccgacca ccttcagcca ggccaagctg gcttcttta tcacgcagta cagcaccgga    2880
caggtcagcg tggaaatcga atgggagctg cagaaagaaa acagcaagcg ctggaaccca    2940
gagattcagt atacttccaa ctactacaaa tctacaaatg tggactttgc tgtcaatact    3000
gagggtactt attcagagcc tcgccccatt ggcactcgtt atctcacccg taatctgtaa    3060
ttgcttgtta atcaataaac cggt                                          3084

<210> SEQ ID NO 40
<211> LENGTH: 2370
<212> TYPE: DNA
<213> ORGANISM: Unknown
<220> FEATURE:
<223> OTHER INFORMATION: AAV serotype, clone 43.5

<400> SEQUENCE: 40
gaattcgccc tttctacggc tgcgtcaact ggaccaatga gaactttccc ttcaacgatt     60
```

```
gcgtcgacaa gatggtgatc tggtgggagg agggcaagat gacggccaag gtcgtggagt      120
ccgccaaggc cattctcggc ggcagcaagg tgcgcgtgga ccaaaagtgc aagtcgtccg      180
cccagatcga ccccaccccc gtgatcgtca cctccaacac caacatgtgc gccgtgattg      240
acgggaacag caccaccttc gagcaccagc agccgttgca ggaccggatg ttcaagttcg      300
aactcacccg ccgtctggag cacgactttg gcaaggtgac caagcaggaa gtcaaagagt      360
tcttccgctg ggcgcaggat cacgtgaccg aggtggcgca tgagttctac gtcagaaagg      420
gcggagccag caaaagaccc gcccccgatg acgcggatat aagcgagccc aagcgggcct      480
gccccctcagt cgcggatcca tcgacgtcag acgcggaagg agctccggtg gactttgccg      540
acaggtacca aaacaaatgt tctcgtcacg cgggcatgct tcagacgctg tttccctgca      600
aaacgtgcga gagaatgaat cagaatttca acatttgctt cacgcacggg gtcagagact      660
gctcagaatg tttccccggt gcatcagaat ctcaaccggt cgtcagaaaa aaaacgtatc      720
agaaactgtg tgccattcat catctgctgg ggcgggcacc cgagattgct tgctcggcct      780
gcgatctggt caacgtggac ctggacgact gtgtttctga gcaataaatg acttaaacca      840
ggtatggctg ccgatggtta tcttccagat tggcttgagg acaacctctc tgagggcatt      900
cgcgagtggt gggacctgaa acctggagcc ccgaaaccca agccaaccca gcaaaagcag      960
gacgacggcc ggggtctggt gcttcctggc tacaagtacc tcggacccct caacggactc     1020
gacaaggggg agcccgtcaa cgcggcggac gcagcggccc tcgagcacga caaggcctac     1080
gaccagcagc tcaaagcggg tgacaatccg tacctgcgt ataaccacgc cgacgccgag     1140
tttcaggagc gtctgcaaga agatacgtct tttgggggca acctcgggcg agcagtcttc     1200
caggccaaga agcgggttct cgaacctctc ggtctggttg aggaaggcgc taagacggct     1260
cctggaaaga agagaccggt agagccatca cctcagcgtt cccccgactc ctccacgggc     1320
atcggcaaga aaggccacca gcccgcgaga aagagactga actttgggca gactggcgac     1380
tcggagtcag tccccgaccc tcaaccaatc ggagaaccac cagcaggccc tctggtctg      1440
ggatctggta caatggctgc aggcggtggc gctccaatgg cagacaataa cgaaggcgcc     1500
gacggagtgg gtagttcctc aggaaattgg cattgcgatt ccacatggct gggcgacaga     1560
gtcatcacca ccagcacccg aacctgggcc ctgcccacct acaacaacca tctctacaag     1620
caaatctcca acgggacatc gggaggaagc actaacgaca cacctactt tggctacagc     1680
accccctggg ggtattttga cttcaacaga ttccactgcc acttctcacc acgtgactgg     1740
cagcgactca tcaacaataa ctggggattc cggcccaaga gactcaactt caagctcttc     1800
aacatccagg tcaaggaggt cacgcagaat gaaggcacca gaccatcgc caataacctt     1860
accagcacga ttcaggtgtt tacggactcg gaataccagc tcccgtacgt cctcggctct     1920
gcgcaccagg gctgcctccc tccgttcccg gcggacgtct tcatgattcc tcagtacggg     1980
tatctgaccc taaacaatgg cagtcaggct gtgggccgtt cctccttcta ctgcctggaa     2040
tacttccctt ctcaaatgct gaggacgggc aacaactttg aattcagcta caccttcgag     2100
gacgtgcctt tccacagcag ctacgcgcac agccagagcc tggaccggct gatgaaccct     2160
ctcatcgacc agtacctgta ttacttatcc agaactcagt ccacaggagg aactcaaggt     2220
actcagcaat tgttattttc tcaagccggg cccgcaaaca tgtyggctca ggccaagaac     2280
tggctacctg gaccgtgtta ccgtcagcaa cgagtttcca cgacactgtc gcaaaacaac     2340
aacagcaatt ttgctggacc ggtgccacca                                      2370
```

<210> SEQ ID NO 41
<211> LENGTH: 3123
<212> TYPE: DNA
<213> ORGANISM: Unknown
<220> FEATURE:
<223> OTHER INFORMATION: AAV serotype, clone 43.12

<400> SEQUENCE: 41

| | | | | | |
|---|---|---|---|---|---|
| gaattcgccc | ttggctgcgt | caactggacc | aatgagaact | ttcccttcaa | cgattgcgtc | 60 |
| gacaagatgg | tgatctggtg | ggaggagggc | aagatgacgg | ccaaggtcgt | ggagtccgcc | 120 |
| aaggccattc | tcggcggcag | caaggtgcgc | gtggaccaaa | agtgcaagtc | gtccgcccag | 180 |
| atcgacccca | cccccgtgat | cgtcacctcc | aacaccaaca | tgtgcgccgt | gattgacggg | 240 |
| aacagcacca | ccttcgagca | ccagcagccg | ttgcaggacc | ggatgttcaa | gttcgaactc | 300 |
| acccgccgtc | tggagcacga | ctttggcaag | gtgaccaagc | aggaagtcaa | agagttcttc | 360 |
| cgctgggcgc | aggatcacgt | gaccgaggtg | gcgcatgagt | tctacgtcag | aaagggcgga | 420 |
| gccagcaaaa | gacccgcccc | cgatgacgcg | gatataagcg | agcccaagcg | ggcctgcccc | 480 |
| tcagtcgcgg | atccatcgac | gtcagacgcg | gaaggagctc | cggtggactt | gccgacagg | 540 |
| taccaaaaca | aatgttctcg | tcacgcgggc | atgctccaga | tgctgtttcc | ctgcaaaacg | 600 |
| tgcgagagaa | tgaatcagaa | tttcaacatt | tgcttcacgc | acggggtcag | agactgctca | 660 |
| gaatgtttcc | ccggtgcatc | agaatctcaa | ccggtcgtca | gaaaaaaac | gtatcagaaa | 720 |
| ctgtgtgcca | ttcatcatct | gctggggcgg | gcacccgaga | ttgcttgctc | ggcctgcgat | 780 |
| ctggtcaacg | tggacctgga | cgactgtgtt | tctgagcaat | aaatgactta | aaccaggtat | 840 |
| ggctgccgat | ggttatcttc | cagattggct | tgaggacaac | ctctctgagg | gcattcgcga | 900 |
| gtggtgggac | ctgaaacctg | gagccccgaa | acccaaagcc | aaccagcaaa | agcaggacga | 960 |
| cggccggggt | ctggtgcttc | ctggctacaa | gtacctcgga | cccttcaacg | gactcgacaa | 1020 |
| gggggagccc | gtcaacgcgg | cggacgcagc | ggccctcgag | cacgacaagg | cctacgacca | 1080 |
| gcagctcaaa | gcgggtgaca | atccgtacct | gcggtataac | cacgccgacg | ccgagtttca | 1140 |
| ggagcgtctg | caagaagata | cgtcttttgg | gggcaacctc | gggcgagcag | tcttccaggc | 1200 |
| caagaagcgg | gttctcgaac | ctctcggtct | ggttgaggaa | ggcgctaaga | cggctcctgg | 1260 |
| aaagaagaga | ccggtagagc | catcacctca | gcgttccccc | gactcctcca | cgggcatcgg | 1320 |
| caagaaaggc | caccagcccg | cgagaaagag | actgaacttt | gggcagactg | gcgactcgga | 1380 |
| gtcagtcccc | gaccctcaac | caatcggaga | accaccagca | ggcccctctg | gtctgggatc | 1440 |
| tggtacaatg | gctgcaggcg | gtggcgctcc | aatggcagac | aataacgaag | gcgccgacgg | 1500 |
| agtgggtagt | tcctcaggaa | attggcattg | cgattccaca | tggctgggcg | acagagtcat | 1560 |
| caccaccagc | acccgaacct | gggccctgcc | cacctacaac | aaccatctct | acaagcaaat | 1620 |
| ctccaacggg | acatcgggag | gaagcactaa | cgacaacacc | tactttggct | acagcacccc | 1680 |
| ctgggggtat | tttgacttca | acagattcca | ctgccacttc | tcaccacgtg | actggcagcg | 1740 |
| actcatcaac | aataactggg | gattccggcc | caagagactc | aacttcaagc | tcttcaacat | 1800 |
| ccaggtcaag | gaggtcacgc | agaatgaagg | caccaagacc | atcgccaata | accttaccag | 1860 |
| cacgattcag | gtgtttacgg | actcggaata | ccagctcccg | tacgtcctcg | gctctgcgca | 1920 |
| ccagggctgc | ctccctccgt | tcccggcgga | cgtcttcatg | attcctcagt | acgggtatct | 1980 |
| gaccctaaac | aatggcagtc | aggctgtggg | ccgttcctcc | ttctactgcc | tggaatactt | 2040 |
| cccttctcaa | atgctgagga | cgggcaacaa | ctttgaattc | agctacacct | tcgaggacgt | 2100 |
| gcctttccac | agcagctacg | cgcacagcca | gagcctggac | cggctgatga | accctctcat | 2160 |

-continued

```
cgaccagtac ctgtattact tatccagaac tcagtccaca ggaggaactc aaggtactca    2220
gcaattgtta ttttctcaag ccgggcccgc aaacatgtcg gctcaggcca agaactggct    2280
acctggaccg tgttaccgtc agcaacgagt tccacgaca ctgtcgcaaa caacaacag    2340 caattttgct tggaccggtg ccaccaagta tcacctgaat ggcagagact ccctggttaa    2400
tcccggcgtt gccatggcta cccacaagga cgacgaggag cgcttcttcc cgtcaagcgg    2460
agttctaatg tttggcaagc agggggctgg aaaagacaat gtggactaca gcagcgtgat    2520
gctcaccagc gaagaagaaa ttaaaactac taacccagtg ctacagagc agtatggtgt    2580 ggtggcagac aacctgcagc agaccaacgg agctcccatt gtgggaactg tcaacagcca    2640
gggggcctta cctggtatgg tctggcaaaa ccgggacgtg tacctgcagg gccccatctg    2700
ggccaaaatt cctcacacgg acggcaactt tcatccttcg ccgctgatgg gaggctttgg    2760
actgaaacac ccgcctcctc agatcctggt gaaaaacact cctgttcctg cggatcctcc    2820
gaccaccttc agccaggcca agctggcttc ttttatcacg cagtacagca ccggacaggt    2880
cagcgtggaa atcgaatggg agctgcagaa agaaaacagc aagcgctgga acccagagat    2940
tcagtatact tccaactact acaaatctac aaatgtggac tttgctgtca atactgaggg    3000
tacttattca gagcctcgcc ccattggcac tcgttatctc acccgtaatc tgtaattgct    3060
tgttaatcaa taaaccggtt aattcgtttc agttgaactt tggtctctgc gaagggcgaa    3120
ttc                                                                  3123
```

<210> SEQ ID NO 42
<211> LENGTH: 3122
<212> TYPE: DNA
<213> ORGANISM: Unknown
<220> FEATURE:
<223> OTHER INFORMATION: AAV serotype, clone 43.20

<400> SEQUENCE: 42

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgtgtgga ccaaaagtgc aagtcttccg     180
cccagatcga tcccacccc gtgatcgtca cctccaacac caacatgtgc gccgtgattg     240
acgggaacag cgccaccttc gagcaccagc agccgttgca ggaccggatg ttcaaatttg     300
aactcacccg ccgtctggag catgactttg gcaaggtgac gaagcaggaa gtcaaagagt     360
tcttccgctg ggcgcaggat cacgtgaccg aggtggcgca tgagttccac gtcagaaagg     420
gtggagccaa caagagaccc gcccccgatg acgcggatat aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgcgattcat catctgctgg ggcgggctcc cgagattgct tgctcggcct     780
gcgatctggt caacgtggac ctggatgact gtgtttctga gcaataaatg acttaaacca     840
ggtatggctc cgatggtta tcttccgat tggctcgagg acaacctctc tgagggcatt     900
cgcgagtggt gggacttgaa acctggagcc ccgaaaccca agccaaccca gcaaaagcag    960
gacgacggcc ggggtctggt gcttcctggc tacaagtacc tcggaccctt caacggactc    1020 gacaagggg agcccgtcaa cgcggcggac gcagcggccc tcgagcacga caaagcctac    1080
```

```
gaccagcagc tcaaagcggg tgacaatccg tacctgcggt ataatcacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga agagactggt agagcagtcg ccacaagagc cagactcctc ctcgggcatc    1320
ggcaagacag gccagcagcc cgctaaaaag agactcaatt ttggtcagac tggcgactca    1380
gagtcagtcc ccgacccaca acctctcgga gaacctccag cagcccctc aggtctggga     1440 cctaatacaa tggcttcagg cggtggcgct ccaatggcag acaataacga aggcgccgac    1500
ggagtgggta attcctcggg aaattggcat tgcgattcca catggctggg ggacagagtc    1560
atcaccacca gcacccgaac ctgggccctg cccacctaca caaccaccct ctacaagcaa    1620
atctccaacg gcacctcggg aggaagcacc aacgacaaca cctatttggg ctacagcacc    1680 cctgggggt attttgactt caacagattc cactgtcact tttcaccacg tgactggcaa     1740
cgactcatca acaacaattg gggattccgg cccaaaagac tcaacttcaa gctgttcaac    1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttcccggcg gacgtcttca cggttcctca gtacggctat    1980
ttaactttaa acaatggaag ccaagccctg gacgttcct ccttctactg tctggagtat     2040
ttcccatcgc agatgctgag aaccggcaac aactttcagt tcagctacac cttcgaggac    2100 gtgccttttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280 cccggaccttt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatggagca    2580
gtggccatca caaccaggc cgccaatacg caggcgcaga ccggactcgt gcacaaccag    2640
ggggtgattc ccggcatggt gtggcagaat agagacgtgt acctgcaggg tcccatctgg    2700
gccaaaattc ctcacacgga cggcaacttt caccccgtctc ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
agcgtggaaa tcgagtggga gctgcagaaa gaaaacagca acgctggaa tccagagatt    2940 caatacactt ccaactacta caatctcaca aatgtggact ttgctgtcaa cacgaaggaa    3000
gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                  3122
```

<210> SEQ ID NO 43
<211> LENGTH: 3117
<212> TYPE: DNA
<213> ORGANISM: Unknown
<220> FEATURE:
<223> OTHER INFORMATION: AAV serotype, clone 43.21

<400> SEQUENCE: 43

```
gaattcgccc ttggctgcgt caactggacc aatgagaact ttcccttcaa cgattgcgtc    60
gacaagatgg tgatctggtg ggaggagggc aagatgacgg ccaaggtcgt ggagtccgcc   120
aaggccattc tcggcggcag caaggtgcgt gtggaccaaa agtgcaagtc ttccgcccag   180
atcgatccca cccccgtgat cgtcacctcc aacaccaaca tgtgcgccgt gattgacggg   240
aacagcacca ccttcgagca ccagcagccg ttgcaggacc ggatgttcaa atttgaactc   300
acccgccgtc tggagcatga ctttggcaag gtgacgaagc aggaagtcaa agagttcttc   360
cgctgggcgc aggatcacgt gaccgaggtg cgcatgagt tccacgtcag aaagggtgga   420
gccaacaaga gacccgcccc cgatgacgcg gatataagcg agcccaagcg ggcctgcccc   480
tcagtcgcgg atccatcgac gtcagacgcg aaggagctc cggtggactt tgccgacagg   540
taccaaaaca aatgttctcg tcacgcgggc atgcttcaga tgctgtttcc ctgcaagaca   600
tgcgagagaa tgaatcagaa tttcaacatt tgcttcacgc acgggaccag agactgttca   660
gaatgtttcc ccggcgtgtc agaatctcaa ccggtcgtca gaaagaggac gtatcggaaa   720
ctctgtgcga ttcatcatct gctggggcgg gctcccgaga ttgcttgctc ggcctgcgat   780
ctggtcaacg tggacctgga tgactgtgtt tctgagcaat aaatgactta aaccaggtat   840
ggctgccgat ggttatcttc cagattggct cgaggacaac ctctctgagg cattcgcga   900
gtggtgggac ttgaaacctg gagccccgaa acccaaagcc aaccagcaaa gcaggacga   960
cggccggggt ctggtgcttc tggctacaa gtacctcgga cccttcaacg gactcgacaa  1020
gggggagccc gtcaacgcgg cggacgcagc ggccctcgag cacgcaaaag cctacgacca  1080
gcagctcaaa gcgggtgaca atccgtacct gcggtataat cacgccgacg ccgagtttca  1140
ggagcgtctg caagaagata cgtcttttgg gggcaacctc gggcgagcag tcttccaggc  1200
caagaagcgg gttctcgaac ctctcggtct ggttgaggaa ggcgctaaga cggctcctgg  1260
aaagaagaga ccgtagagc agtcgccaca agagccagac tcctcctcgg gcatcggcaa  1320
gacaggccag cagcccgcta aaagagact caattttggt cagactggcg actcagagtc  1380
agtccccgac ccacaacctc tcggagaacc tccagcagcc cctcaggtc tgggacctaa  1440
tacaatggct tcaggcggtg gcgctccaat ggcagacaat aacgaaggcg ccgacggagt  1500
gggtaattcc tcgggaaatt ggcattgcga ttccacatgg ctgggggaca gagtcatcac  1560
caccagcacc cgaacctggg ccctgcccac ctacaacaac cacctctaca gcaaatctc  1620
caacggcacc tcgggaggaa gcaccaacga caacacctat tttggctaca gcaccccctg  1680
ggggtatttt gacttcaaca gattccactg tcacttttca ccacgtgact ggcaacgact  1740
catcaacaac aattgggat tccggcccaa aagactcaac ttcaagctgt tcaacatcca  1800
ggtcaaggaa gtcacgacga acgaaggcac caagaccatc gccaataatc tcaccagcac  1860
cgtgcgggtc tttacggact cggagtacca gttaccgtac gtgctaggat ccgctcacca  1920
gggatgtctg cctccgttcc cggcggacgt cttcatggtt cctcagtacg ctatttaac  1980
tttaaacaat ggaagccaag ccctgggacg ttcctcctc tactgtctgg agtatttccc  2040
atcgcagatg ctgagaaccg gcaacaactt tcagttcagc tacaccttcg aggacgtgcc  2100
tttccacagc agctacgcgc acagccagag cctggacagg ctgatgaatc ccctcatcga  2160
ccagtacctg tactacctgg tcagaacgca acgactgga actggaggga cgcagactct  2220
ggcattcagc caagcgggtc ctagctcaat ggccaaccag gctagaaatt gggtgccgg  2280
acttgctac cggcagcagc gcgtctccac gacaaccaac cagagcaaca acagcaactt  2340
tgcctggacg ggagctgcca agtttaagct gaacggccga gactctctaa tgaatccggg  2400
```

```
cgtggcaatg gcttcccaca aggatgacga cgaccgcttc ttcccttcga gcggggtcct    2460 gattttttggc aagcaaggag ccgggaacga tggagtggat tacagccaag tgctgattac    2520
agatgaggaa gaaatcaagg ctaccaaccc cgtggccaca gaagaatatg gagcagtggc    2580
catcaacaac caggccgcca atacgcaggc gcagaccgga ctcgtgcaca ccagggggt    2640 gattcccggc atggtgtggc agaatagaga cgtgtacctg cagggtccca tctgggccaa    2700
aattcctcac acggacggca actttcaccc gtctccctg atgggcggct ttggactgaa    2760
gcacccgcct cctcaaattc tcatcaagaa cacaccggtt ccagcggacc cgccgcttac    2820
cttcaaccag gccaagctga actctttcat cacgcagtac agcaccggac aggtcagcgt    2880
ggaaatcgag tgggagctgc agaaagaaaa cagcaaacgc tggaatccag agattcaata    2940
cacttccaac tactacaaat ctacaaatgt ggactttgct gtcaacacgg aaggagttta    3000
tagcgagcct cgcccccattg gcacccgtta cctcacccgc aacctgtaat tacatgttaa    3060
tcaataaacc ggttaattcg tttcagttga actttggtct ctgcgaaggg cgaattc      3117
```

<210> SEQ ID NO 44
<211> LENGTH: 3121
<212> TYPE: DNA
<213> ORGANISM: Unknown
<220> FEATURE:
<223> OTHER INFORMATION: AAV serotype, clone 43.23

<400> SEQUENCE: 44

```
gaattcgccc ttctacggct gcgtcaactg gaccaatgag aactttccct tcaacgattg      60
cgtcgacaag atggtgatct ggtgggagga gggcaagatg acggccaagg tcgtggagtc    120
cgccaaggcc attctcggcg gcagcaaggt gcgtgtggac caaaagtgca agtcttccgc    180
ccagatcgat cccaccccccg tgatcgtcac ctccaacacc aacatgtgcg ccgtgattga    240
cgggaacagc accaccttcg agcaccagca gccgttgcag gaccggatgt tcaaatttga    300
actcacccgc cgtctggagc atgactttgg caaggtgacg aagcaggaag tcaaagagtt    360
cttccgctgg gcgcaggatc acgtgaccga ggtggcgcat gagttccacg tcagaaaggg    420
tggcgccaac aagagacccg cccccgatga cgcggatata agcgagccca gcgggcctg    480 cccctcagtc gcggatccat cgacgtcaga gcgcggaagga gctccggtgg actttgccga    540
caggtaccaa aacaaatgtt ctcgtcacgc gggcatgctt cagatgctgt ttccctgcaa    600
gacatgcgag agaatgaatc agaatttcaa catttgcttc acgcacggga ccagagactg    660
ttcagaatgt ttccccggcg tgtcagaatc tcaaccggtc gtcagaaaga ggacgtatcg    720
gaaactctgt gcgattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacgcccg gggtctggtg cttcctggct acaagtacct cggacccttc aacggactcg    1020 acaagggga gcccgtcaac gcggcggacg cagcggccct cgagcacgac aaagcctacg    1080
accagcagct caaagcgggt gacaatccgt acctgcggta taatcacgcc gacgccgagt    1140
ttcaggagcg tctgcaagaa gatacgtcct ttgggggcaa cctcgggcga gcagtcttcc    1200
aggccaagaa gcgggttctc gaacctctcg gtctggttga ggaaggcgct aagacggctc    1260
ctggaaagaa gagaccggta gagcagtcgc cacaagagcc agactcctcc tcgggcatcg    1320
gcaagacagg ccagcagccc gctaaaaaga gactcaattt tggtcagact ggcgactcag    1380
```

```
agtcagtccc cgacccacaa cctctcggag aacctccagc agcccctca ggtctgggac    1440 ctaatacaat ggcttcaggc ggtggcgctc aatggcaga caataacgaa ggcgccgacg    1500
gagtgggtaa ttcctcggga aattggcatt gcgattccac atggctgggg gacagagtca   1560
tcaccaccag cacccgaacc tgggccctgc ccacctacaa caaccacctc tacaagcaaa   1620
tctccaacgg cacctcggga ggaagcacca cgacaacac ctatttggc tacagcaccc     1680 cctggggta ttttgacttc aacagattcc actgtcactt tcaccacgt gactggcaac    1740 gactcatcaa caacaattgg ggattccggc ccaaaagact caacttcaag ctgttcaaca   1800
tccaggtcaa ggaagtcacg acgaacgaag gcaccaagac catcgccaat aatctcacca   1860
gcaccgtgca ggtctttacg gacttggagt accagttacc gtacgtgcta ggatccgctc   1920
accagggatg tctgcctccg ttcccggcgg acgtcttcat ggttcctcag tacggctatt   1980
taactttaaa caatggaagc caagccctgg gacgttcctc cttctactgt ctggagtatt   2040
tcccatcgca gatgccgaga accggcaaca actttcagtt cagctacacc ttcgaggacg   2100
tgccttttca cagcagctac gcgcacagcc agagcctgga caggctgatg aatcccctca   2160
tcgaccagta cctgtactac ctggtcagaa cgcaaacgac tggaactgga gggacgcaga   2220
ctctggcatt cagccaagcg ggtcctagct caatggccaa ccaggctaga aattgggtgc   2280
ccggaccttg ctaccggcag cagcgcgtct ccacgacaac caaccagaac aacaacagca   2340
actttgcctg gacgggagct gccaagttta agctgaacgg ccgagactct ctaatgaatc   2400
cgggcgtggc aatggcttcc cacaaggatg acgacgaccg cttcttccct tcgagcgggg   2460
tcctgatttt tggcaagcaa ggagccggga acgatggagt ggattacagc caagtgctga   2520
ttacagatga ggaagaaatc aaggctacca accccgtggc cacagaagaa tatggagcag   2580
tggccatcaa caaccaggcc gccaatacgc aggcgcagac cggactcgtg cacaaccagg   2640
gggtgattcc cggcatggtg tggcagaata gagacgtgta cctgcagggt cccatctggg   2700
ccaaaattcc tcacacggac ggcaactttc acccgtctcc cctgatgggc ggctttggac   2760
tgaagcaccc gcctcctcaa attctcatca agaacacacc ggttccagcg gacccgccgc   2820
ttaccttcaa ccaggccaag ctgaactctt tcatcacgca gtacagcacc ggacaggtca   2880
gcgtggaaat cgagtgggag ctgcagaaag aaaacagcaa acgctggaat ccagagattc   2940
aatacacttc caactactac aaatctacaa atgtggactt tgctgtcaac acggaaggag   3000
tttatagcga gcctcgcccc attggcaccc gttacctcac ccgcaacctg taattacatg   3060
ttaatcaata aaccggttaa ttcgtttcag ttgaactttg gtctctgcga agggcgaatt   3120
c                                                                   3121
```

<210> SEQ ID NO 45
<211> LENGTH: 3122
<212> TYPE: DNA
<213> ORGANISM: Unknown
<220> FEATURE:
<223> OTHER INFORMATION: AAV serotype, clone 43.25

<400> SEQUENCE: 45

```
gaattcgccc tttctacggc tgcgtcaact ggaccaatga gaactttccc ttcaacgatt    60
gcgtcgacaa gatggtgatc tggtgggagg agggcaagat gacggccaag gtcgtggagt   120
ccgccaaggc cattctcggc ggcagcaagg tgcgtgtgga ccaaaagtgc aagtcttccg   180
cccagatcga tcccaccccc gtgatcgtca cctccaacac caacatgtgc gccgtgattg   240
acgggaacag caccaccttc gagcaccagc agccgttgca ggaccggatg ttcaaatttg   300
```

```
aactcacccg ccgtctggag catgactttg gcaaggtgac gaagcaggaa gtcaaagggt   360
tcttccgctg ggcgcaggat cacgtgaccg aggtggcgca tgagttccac gtgcgagccc   420
aagcgggcct gccccctcagt cgcggatcca tcgacgtcag accagaaagg gtggagccaa   480
caagagaccc gcccccgatg acgcggatat aagcggaagg agctccggtg gactttgccg   540
acaggtacca aaacaaatgt tctcgtcacg cgggcatgct tcagatgctg tttccctgca   600
agacatgcga gagaatgaat cagaatttca acatttgctt cacgcacggg accagagact   660
gttcagaatg tttccccggc gtgtcagaat ctcaaccggt cgtcagaaag gacgtatc    720 ggaaactctg tgcgattcat catctgctgg ggcgggctcc cgagattgct tgctcggcct   780
gcgatctggt caacgtggac ctggatgact gtgtttctga gcaataaatg acttaaacca   840
ggtatggctg ccgatggtta tcttccagat tggctcgagg acaacctctc tgagggcatt   900
cgcgagtggt gggacttgaa acctggagcc cgaaaccca agccaacca gcaaaagcag    960 gacgacggcc ggggtctggt gcttcctggc tacaagtacc tcggacccctt caacggactc  1020 gacaagggg agcccgtcaa cgcggcggac gcagcggccc tcgagcacga caaagcctac   1080
gaccagcagc tcaaagcggg tgacaatccg tacctgcgt ataatcacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagcagtcg ccacaagagc cagactcctc ctcgggcatc   1320
ggcaagacag gccagcagcc cgctaaaaag agactcaatt ttggtcagac tggcgactca   1380
gagtcagtcc ccgacccaca acctctcgga gaacctccag cagcccctc aggtctggga   1440 cctaatacaa tggcttcagg cggtggcgct ccaatggcag acaataacga aggcgccgac   1500
ggagtgggta attcctcggg aaattggcat tgcgattcca catggctggg ggacagagtc   1560
atcaccacca gcacccgaac ctgggccctg cccacctaca caaccaccct ctacaagcaa   1620
atctccaacg gcacctcggg aggaagcacc aacgacaaca cctattttgg ctacagcacc   1680
ccctgggggt attttgactt caacagattc cactgtcact tttcaccacg tgactggcaa   1740
cgactcatca acaacaattg gggattccgg cccaaaagac tcaacttcaa gctgttcaac   1800
atccaggtca aggaagtcac gacgaacgaa ggcaccaaga ccatcgccaa taatctcacc   1860
agcaccgtgc aggtctttac ggactcggag taccagttac cgtacgtgct aggatccgct   1920
caccagggat gtctgcctcc gttcccggcg gacgtcttca tggttcctca gtacggctat   1980
ttaactttaa acaatggaag ccaagccctg gacgttcct ccttctactg tctggagtat   2040
ttcccatcgc agatgctgag aaccggcaac aactttcagt tcagctacac cttcgaggac   2100
gtgcctttcc acagcagcta cgcgcacagc cagagcctgg acaggctgat gaatcccctc   2160
atcgaccagt acctgtacta cctggtcaga acgcaaacga ctggaactgg agggacgcag   2220
actctggcat tcagccaagc gggtcctagc tcaatggcca accaggctag aaattgggtg   2280 cccggaccttt gctaccggca gcagcgcgtc tccacgacaa ccaaccagaa caacaacagc   2340
aactttgcct ggacgggagc tgccaagttt aagctgaacg gccgagactc tctaatgaat   2400
ccgggcgtgg caatggcttc ccacaaggat gacgacgacc gcttcttccc ttcgagcggg   2460
gtcctgattt ttggcaagca aggagccggg aacgatgag tggattacag ccaagtgctg   2520
attacagatg aggaagaaat caaggctacc aaccccgtgg ccacagaaga atatggagca   2580
gtggccatca acaaccaggc cgccaatacg caggcgcaga ccggactcgt gcacaaccag   2640
ggggtgattc ccggcatggt gtggcagaat agagacgtgt acctgcaggg tcccatctgg   2700
```

```
gccaaaattc ctcacacgga cggcaacttt cacccgtctc ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
agcgtggaaa tcgagtggga gctgcagaaa gaaaacagca acgctggaa tccagagatt     2940 caatacactt ccaactacta caaatctaca aatgtggact ttgctgtcaa cacggagggg    3000
gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                  3122

<210> SEQ ID NO 46
<211> LENGTH: 3128
<212> TYPE: DNA
<213> ORGANISM: Unknown
<220> FEATURE:
<223> OTHER INFORMATION: AAV serotype, clone 44.1

<400> SEQUENCE: 46
gaattcgccc tttctacggc tgcgtcaact ggaccaatga gaactttccc ttcaacgatt      60
gcgtcgacaa gatgttgatc tggtgggagg agggcaagat gacggccaag gtcgtggagt     120
ccgccaaggc cattctcggc ggcagcaaag tgcgcgtgga ccaaaagtgc aagccgtccg     180
cccagatcga ccccaccccc gtgatcgtca cctccaacac caacatgtgc gccgtgattg     240
acgggaacag caccaccttc gagcaccagc agccgttgcg ggaccggatg ttcaagtttg     300
aactcacccg ccgtctggag cacgactttg gcaaggtgac aaagcaggaa gtcagagagt     360
tcttccgctg ggcgcaggat cacgtgaccg aggtggcgca cgagttctac gtcagaaagg     420
gtggagccaa caagagaccc gccccgatg acgcggataa agcgagccc agcgggcct      480 gccctcagt cgcggatcca tcgacgtcag acgcggaagg agctccggtg gactttgccg     540
acaggtacca aaacaaatgt tctcgtcacg cgggcatgct tcagatgctg tttccctgca     600
aaacatgcga gagaatgaat cagaatttca acatttgctt cacgcacggg accagagact     660
gttcagaatg tttccccggc gtgtcagaat ctcaaccggt cgtcagaaaa aagacgtatc     720
ggaaactctg tgcgattcat catctgctgg ggcgggcacc cgagattgct tgctcggcct     780
gcgatctggt caacgtggac ctagatgact gtgtttctga gcaataaatg acttaaacca     840
ggtatggctg ccgatggtta tcttccagat tggctcgagg acaacctctc tgagggcatt     900
cgcgagtggt gggacttgaa acctggagcc ccgaaaccca agccaacca gcaaaagcag     960 gacgacggcc ggggtctggt gcttcctggc tacaagtacc tcggacccctt caacggactc    1020 gacaagggg agcccgtcaa cgcggcggac gcagcggccc tcgagcacga caaggcctac    1080
gaccagcagc tcaaagcggg tgacaatccg tacctgcgt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga gagaccggt agagccatca ccccagcgtt ctccagactc ctctacgggc    1320
atcggcaaga aaggccagca gcccgcgaaa aagagactca actttgggca gactggcgac    1380
tcagagtcag tgcccgaccc tcaaccaatc ggagaaccc ccgcaggccc ctctggtctg    1440
ggatctggta caatggctgc aggcggtggc gctccaatgg cagacaataa cgaaggcgcc    1500 gacgagtgg gtagttcctc aggaaattgg cattgcgatt ccacatggct gggcgacaga    1560
gtcatcacca ccagcacccg aacctgggcc ctccccacct acaacaacca cctctacaag    1620
```

| | |
|---|---|
| caaatctcca acgggacttc gggaggaagc accaacgaca acacctactt cggctacagc | 1680 |
| accccctggg ggtattttga ctttaacaga ttccactgcc acttctcacc acgtgactgg | 1740 |
| cagcgactca tcaacaacaa ctggggattc cggcccaaga gactcaactt caagctcttc | 1800 |
| aacatccagg tcaaggaggt cacgcagaat gaaggcacca agaccatcgc caataacctt | 1860 |
| accagcacga ttcaggtctt tacgactcg gaataccagc tcccgtacgt cctcggctct | 1920 |
| gcgcaccagg gctgcctgcc tccgttcccg gcggacgtct tcatgattcc tcagtacggg | 1980 |
| tacctgactc tgaacaatgg cagtcaggcc gtgggccgtt cctccttcta ctgcctggag | 2040 |
| tactttcctt ctcaaatgct gagaacgggc aacaactttg agttcagcta ccagtttgag | 2100 |
| gacgtgcctt ttcacagcag ctacgcgcac agccaaagcc tggaccggct gatgaacccc | 2160 |
| ctcatcgacc agtacctgta ctacctgtct cggactcagt ccacgggagg taccgcagga | 2220 |
| actcagcagt tgctattttc tcaggccggg cctaataaca tgtcggctca ggccaaaaac | 2280 |
| tggctacccg ggccctgcta ccggcagcaa cgcgtctcca cgacactgtc gcaaaataac | 2340 |
| aacagcaact gtaaatcccg tgtcgctat ggcaacccac aaggacgacg aagagcgatt | 2400 |
| ttgcctggac cggtgccacc aagtatcatc tgaatggcag agactctctg ttttccgtcc | 2460 |
| agcggagtct taatgtttgg gaaacaggga gctggaaaag acaacgtgga ctatagcagc | 2520 |
| gttatgctaa ccagtgagga agaaattaaa accaccaacc cagtggccac ggaacagtac | 2580 |
| ggcgtggtgg ccgataacct gcaacagcaa aacgccgctc ctattgtagg ggccgtcaac | 2640 |
| agtcaaggag ccttacctgg catggtctgg cagaaccggg acgtgtacct gcagggtcct | 2700 |
| atctgggcca agattcctca cacggacgga aactttcatc cctcgccgct gatgggaggc | 2760 |
| tttggactga aacacccgcc tcctcagatc ctgattaaga atacacctgt tcccgcggat | 2820 |
| cctccaacta ccttcagtca agctaagctg cgtcgttca tcacgcagta cagcaccgga | 2880 |
| caggtcagcg tggaaattga atgggagctg cagaaagaaa acagcaaacg ctggaaccca | 2940 |
| gagattcaat acacttccaa ctactacaaa tctacaaatg tggacttcgc tgttaacaca | 3000 |
| gatggcactt attctgagcc tcgccccatt ggcacccgtt acctcacccg taatctgtaa | 3060 |
| ttgctcgtta atcaataaac cggttgattc gtttcagttg aactttggtc tctgcgaagg | 3120 |
| gcgaattc | 3128 |

<210> SEQ ID NO 47
<211> LENGTH: 3128
<212> TYPE: DNA
<213> ORGANISM: Unknown
<220> FEATURE:
<223> OTHER INFORMATION: AAV serotype, clone 44.5

<400> SEQUENCE: 47

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaaag tgcgcgtgga ccaaaagtgc aagtcgtccg | 180 |
| cccagatcga ccccaccccc gtgatcgtca cctccaacac caacatgtgc gccgtgattg | 240 |
| acggaacag caccaccttc gagcaccagc agccgttgca ggaccggatg ttcaagtttg | 300 |
| aactcacccg ccgtctggag cacgactttg gcaaggtgac aaagcaggaa gtcagagagt | 360 |
| tcttccgctg ggcgcaggat cacgtgaccg aggtggcgca cgagttctac gtcagaaagg | 420 |
| gtggagccaa caagagaccc gccccgatg acgcggataa aagcgagccc aagcgggcct | 480 |
| gcccctcagt cgcggatcca tcgacgtcag acgcggaagg agctccggtg gactttgccg | 540 |

```
acaggtacca aaacaaatgt tctcgtcacg cgggcatgct tcagatgctg tttccctgca    600
aaacatgcga gagaatgaat cagaatttca acatttgctt cacgcacggg accagagact    660
gttcagaatg tttccccggc gtgtcagaat ctcaaccggt tgtcagaaaa agacgtatc    720 ggaaactctg tgcgattcat catctgctgg ggcgggcacc cgagattgct tgctcggcct    780
gcgatctggt caacgtggac ctagatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccctt caacggactc   1020 gacaaggggg agcccgtcaa cgcggcggac cagcggcccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcggcg agcagtcttc    1200 caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga aaggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacttc gggaggaagc accaacgaca cacctactt cggctacagc    1680 accccctggg ggtattttga ctttaacaga ttccactgcc acttctcacc acgtgactgg   1740
cagcgactca tcaacaacaa ctggggattc cggcccaaga gacccaactt caagctcttc   1800
aacatccagg tcaaggaggt cacgcagaat gaaggcacca agaccatcgc caataacctt   1860
accagcacga ttcaggtctt tacggactcg gaataccagc tcccgtacgt cctcggctct   1920
gcgcaccagg gctgcctgcc tccgttcccg gcggacgtct tcatgattcc tcagtacggg   1980
tacctgactc tgaacaatgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga   2220
actcagcagt tgctatttc tcaggccggg cctaataaca tgtcggctca ggccaaaaac   2280
tggctacccg ggccctgcta ccggcagcaa cgcgtctcca cgacactgtc gcaaaataac   2340
aacagcaact tgcctggac cggtgccacc aagtatcatc tgaatggcag agactctctg   2400
gtaaatcccg tgtcgctat ggcaacccac aaggacgacg aagagcgatt ttttccgtcc   2460
agcggagtct taatgtttgg gaaacaggga gctggaaaag acaacgtgga ctatagcagc   2520
gttatgctaa ccagtgagga agaaattaaa accaccaacc cagtggccac agaacagtac   2580
ggcgtggtgg ccgataacct gcaacagcaa acgccgctc ctattgtagg ggccgtcaac   2640
agtcaaggag ccttacctgg catggtctgg cagaaccggg acgtgtacct gcagggtcct   2700
atctgggcca agattcctca cacggacgga aactttcatc cctcgccgct gatgggaggc   2760
tttggactga aacacccgcc tcctcagatc ctgattaaga atacacctgt tccgcgggat   2820
cctccaacta ccttcagtca agctaagctg gcgtcgttca tcacgcagta cagcaccgga   2880
caggtcagcg tggaaattga atgggagctg cagaaagaaa acagcaaacg ctggaaccca   2940
```

|   |   |   |
|---|---|---|
| gagattcaat acacttccaa ctactacaaa tctacaaatg tggactttgc tgttaacaca | | 3000 |
| gatggcactt attctgagcc tcgccccatt ggcacccgtt acctcacccg taatctgtaa | | 3060 |
| ttgcttgtta atcaataaac cggttgattc gtttcagttg aactttggtc tctgcgaagg | | 3120 |
| gcgaattc | | 3128 |

<210> SEQ ID NO 48
<211> LENGTH: 1933
<212> TYPE: DNA
<213> ORGANISM: Unknown
<220> FEATURE:
<223> OTHER INFORMATION: AAV serotype, clone 223.10
<220> FEATURE:
<221> NAME/KEY: misc_feature
<222> LOCATION: (1302)..(1302)
<223> OTHER INFORMATION: can be a, c, g or t

<400> SEQUENCE: 48

|   |   |   |
|---|---|---|
| caaggcctac gaccagcagc tcaaagcggg tgacaatccg tacctgcggt ataaccacgc | | 60 |
| cgacgccgag tttcaggagc gtcttcaaga agatacgtct tttgggggca acctcgggcg | | 120 |
| agcagtcttc caggccaaaa agcgggttct cgaacctctt ggtctggttg agacgccagc | | 180 |
| taagacggca cctggaaaga agcgaccggt agactcgcca gactccacct cgggcatcgg | | 240 |
| caagaaaggc cagcagcccg cgaaaaagag actcaacttt gggcagactg gcgactcaga | | 300 |
| gtcagtcccc gaccctcaac caatcggaga accaccagca ggcccctctg gtctgggatc | | 360 |
| tggtacaatg gctgcaggcg gtggcgcacc aatggctgac aataacgagg gcgccgacgg | | 420 |
| agtgggtaat gcctcaggaa attggcattg cgattccaca tggctgggcg acagagtcat | | 480 |
| caccaccagc acccgaacct gggccctgcc cacctacaac aaccacctct acaagcaaat | | 540 |
| ctccagtcag tcagcaggga gcaccaacga taacgtctat ttcggctaca gcaccccctg | | 600 |
| ggggtatttt gacttcaaca gattccattg ccacttctca ccacgtgact ggcagcgact | | 660 |
| tatcaacaac aactggggat tccggcccaa gaagctcaac ttcaagctct caacatcca | | 720 |
| ggtcaaggag gtcacgacga atgacggtgt cacaaccatc gctaataacc ttaccagcac | | 780 |
| ggttcaggtc tttcggact cggaatatca actgccgtac gtcctcggct ccgcgcacca | | 840 |
| gggctgcctg cctccgttcc cggcagacgt gttcatgatt ccgcagtacg gatacctgac | | 900 |
| tctgaacaat ggcagccaat cggtaggccg ttcctccttc tactgcctgg agtactttcc | | 960 |
| ttctcagatg ctgagaacgg gcaacaactt caccttagc tacaccttcg aggacgtgcc | | 1020 |
| tttccacagc agctacgcgc acagccagag tctggaccgg ctgatgaatc ccctcatcga | | 1080 |
| ccagtacctg tactacttgg ccagaacaca gagcaacgca ggaggtactg ctggcaatcg | | 1140 |
| ggaactgcag ttttatcagg gcggacctac caccatggcc gaacaagcaa agaactggct | | 1200 |
| gcccggacct tgcttccggc aacagagagt atccaagacg ctggatcaaa ataacaacag | | 1260 |
| caactttgcc tggactggtg ccacaaaata ccatttaaat gnaagaaatt cattggttaa | | 1320 |
| tcccggtgtc gccatggcaa cccacaagga cgacgaggaa cgcttcttcc cttcgagcgg | | 1380 |
| agttctaatt tttggcaaaa ctggagcagc taataaaact acattagaaa acgtgctcat | | 1440 |
| gacaaatgaa gaagaaattc gtcctaccaa cccggtagct accgaggaat acgggattgt | | 1500 |
| aagcagcaac ttgcaggcgg ctagcaccgc agcccagaca caagttgtta caaccaggg | | 1560 |
| agccttacct ggcatggtct ggcagaaccg ggacgtgtac ctgcaaggtc ccatttgggc | | 1620 |
| caagattcct cacacggacg gcaactttca cccgtctcct ctaatgggtg ctttggact | | 1680 |
| gaaacacccg cctccccaga tcctgatcaa aaacacaccg gtacctgcta atcctccaga | | 1740 |

```
agtgtttact cctgccaagt ttgcttcctt catcacgcag tacagcaccg ggcaagtcag    1800
cgttgagatc gagtgggagc tgcagaaaga gaacagcaag cgctggaacc cagagattca    1860
gtacacctcc aactttgaca aacagactgg agtggacttt gctgttgaca gccagggtgt    1920
ttactctgag cct                                                       1933
```

<210> SEQ ID NO 49
<211> LENGTH: 1933
<212> TYPE: DNA
<213> ORGANISM: Unknown
<220> FEATURE:
<223> OTHER INFORMATION: AAV serotype, clone 223.2

<400> SEQUENCE: 49

```
caaggcctac gaccagcagc tcaaagcggg tgacaatccg tacctgcggt ataaccacgc      60
cgacgccgag tttcaggagt gtcttcaaga agatacgtct tttggggca acctcgggcg     120 agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gtcagtcccc gaccctcaac caatcggaga accaccagca ggcccctctg gtctgggatc     360
tggtacaatg gttgcaggcg gtggcgcacc aatggctgac aataacgagg gcgccgacgg     420
agtgggtaat gcctcaggaa attggcattg cgattccaca tggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat tccggcccaa gaagctcaac ttcaagctct caacatcca     720 ggtcaaggag gtcacgacga atgacggtgt cacaaccatc gctaataacc ttaccagcac     780
ggttcaggtc ttttcggact cggaatatca actgccgtac gtcctcggct ccgcgcacca     840
gggctgcctg cctccgttcc cggcagacgt gttcatgatt ccgcagtacg gatacctgac     900
tctgaacaat ggcagccaat cggtaggccg ttcctccttc tactgcctgg agtactttcc     960
ttctcagatg ctgagaacgg gcaacaactt caccttagc tacaccttcg aggacgtgcc    1020
tttccacagc agctacgcgc acagccagag tctggaccgg ctgatgaatc ccctcatcga    1080
ccagtacctg tactacttgg ccagaacaca gagcaacgca ggaggtactg ctggcaatcg    1140
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttctccc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acggggattgt    1500 aagcagcaac ttgcaggcgg ctagcaccgc agcccagaca caagttgtta acaaccaggg    1560
agccttacct ggcatggtct ggcagaaccg ggacgtgtac ctgcaaggtc ccatttgggc    1620
caagattcct cacacggacg gcaactttca cccgtctcct ctaatgggtg gctttggact    1680
gaaacacccg cctccccaga tcctgatcaa aaacacgccg gtacctgcta atcctccaga    1740
agtgtttact cctgccaagt ttgcttcctt catcacgcag tacagcaccg ggcaagtcag    1800
cgttgagatc gagtgggagc tgcagaaaga gaacagcaag cgctggaacc cagagattca    1860
```

```
gtacacctcc aactttgaca aacagactgg agtggacttt gctgttgaca gccagggtgt    1920
ttactctgag cct                                                       1933

<210> SEQ ID NO 50
<211> LENGTH: 1933
<212> TYPE: DNA
<213> ORGANISM: Unknown
<220> FEATURE:
<223> OTHER INFORMATION: AAV serotype, clone 223.4

<400> SEQUENCE: 50
caaggcctac gaccagcagc tcaaagcggg tgacaatccg tacctgcggt ataaccacgc      60
cgacgccgag tttcaggagc gtcttcaaga agatacgtct tttggggca acctcgggcg     120 agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gccagtcccc gaccctcaac caatcggaga accaccagca ggcccctctg gtctgggatc     360
tggtacaatg gctgcaggcg gtggcgcacc aatggctgac aataacgagg cgccgacgg      420 agtgggtaat gcctcaggaa attggcattg cgattccaca cggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat tccggcccaa gaagctcaac ttcaagctct tcaacatcca     720
ggtcaaggag gtcacgacga atgacggcgt cacaaccatc gctaataacc ttaccagcac     780
ggttcaggtc ttttcggact cggaatatca actgccgtac gtcctcggct ccgcgcacca     840
gggctgcctg cctccgttcc cggcagacgt gttcatgatt ccgcagtacg gatacctgac     900
tctgaacaat ggcagccaat cggtaggccg ttcctccttc tactgcctgg agtactttcc     960
ttctcagatg ctgagaacgg gcaacaactt cacctttagc tacaccttcg aggacgtgcc    1020
tttccacagc agctacgcgc acagccagag tctgggccgg ctgatgaatc ccctcatcga    1080
ccagtacctg tactacttgg ccagaacaca gagcaacgca ggaggtactg ctggcaatcg    1140
ggaactgcag ttttatcagg gcggacctac caccatggcc gaacaagcaa agaactggct    1200 gccccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttcttcc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acggattgt      1500 aagcagcaac ttgcaggcgg ctagcaccgc agcccagaca caagttgtta caaccaggg      1560 agccttacct ggcatggtct ggcagaaccg ggacgtgtac ctgcaaggtc ccatttgggc    1620
caagattcct cacacggacg gcaactttca cccgtctcct ctaatgggtg ctttggact      1680 gaaacacccg cctcccccaga tcctgatcaa aaacacaccg gtacctgcta atcctccaga    1740
agtgtttact cctgccaagt ttgcttcctt catcacgcag tacagcaccg gcaagtcag     1800 cgttgagatc gaatgggagc tgcagaaaga aacagcaag cgctggaacc cagagattca     1860
gtacacctcc aactttgaca aacagactgg agtggacttt gctgttgaca gccagggtgt    1920
ttactctgag cct                                                       1933
```

<210> SEQ ID NO 51
<211> LENGTH: 1933
<212> TYPE: DNA
<213> ORGANISM: Unknown
<220> FEATURE:
<223> OTHER INFORMATION: AAV serotype, clone 223.5

<400> SEQUENCE: 51

```
caaggcctac gaccagcagc tcaaagcggg tgacaatccg tacctgcggt ataaccacgc      60
cgacgccgag tttcaggagc gtcttcaaga agatacgtct tttggggggca acctcgggcg    120
agcagtcttc caggccaaaa agcgggttct cgaacctctt ggtctggttg agacgccagc    180
taagacggca cctggaaaga agcgaccggt agactcgcca gactccacct cgggcatcgg    240
caagaaaggc cagcagcccg cgaaaaagag actcaacttt gggcagactg gcgactcaga    300
gccagtcccc gaccctcaac caatcggaga accaccagca ggcccctctg tctgggatc     360
tggtacaatg gctgcaggcg gtggcgcacc aatggctgac aataacgagg cgccgacgg     420
agtgggtaat gcctcaggaa attggcattg cgattccaca cggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcacccctg     600
gggtattttt gacttcaaca gattccattg ccacttctca ccacgtgact ggcagcgact    660
tatcaacaac aactggggat tccggcccaa gaagctcaac ttcaagctct tcaacatcca    720
ggtcaaggag gtcacgacga atgacggcgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt cacctttagc tacaccttcg aggacgtgcc   1020
tttccacagc agctacgcgc acagccagag tctgggccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg ctttggact    1680
gaaacacccg cctcccccaga tcctgatcaa aaacacaccg gtacctgcta atcctccaga   1740
agtgtttact cctgccaagt tgcttccctt catcacgcag tacagcaccg ggcaagtcag   1800
cgttgagatc gaatgggagc tgcagaaaga gaacagcaag cgctggaacc cagagattca   1860
gtacacctcc aactttgaca aacagactgg agtggacttt gctgttgaca gccagggtgt   1920
ttactctgag cct                                                       1933
```

<210> SEQ ID NO 52
<211> LENGTH: 1933

<212> TYPE: DNA
<213> ORGANISM: Unknown
<220> FEATURE:
<223> OTHER INFORMATION: AAV serotype, clone 223.6

<400> SEQUENCE: 52

```
caaggcctac gaccagcagc tcaaagcggg tgacaatccg tacctgcggt ataaccacgc      60
cgacgccgag tttcaggagc gtcttcaaga agatacgtct tttggggggca acctcgggcg    120
agcagtcttc caggccaaaa agcgggttct cgaacctctt ggtctggttg agacgccagc    180
taagacggca cctggaaaga agcgaccggt agactcgcca gactccacct cgggcatcgg    240
caagaaaggc cagcagcccg cgaaaaagag actcaacttt gggcagactg gcgactcaga    300
gtcagtcccc gaccctcaac caatcggaga accaccagca ggcccctctg gtctgggatc    360
tggtacaatg gctgcaggcg gtggcgcacc aatggctgac aatagcgagg gcgccgacgg    420
agtgggtaat gcctcaggaa attggcattg cgattccaca tggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcacccctg    600
ggggtatttt gacttcaaca gattccattg ccacttctca ccacgtgact ggcagcgact    660
tatcaacaac aactggggat tccggcccaa gaagctcaac ttcaagctct tcaacatcca    720
ggtcaaggag gtcacgacga atgacggtgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt caccttttagc tacaccttcg aggacgtgcc   1020
tttccacagc agctacgcgc acagccagag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tccccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaaattc gtcctaccaa cccggtagct accgaggaat acgggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg gctttggact   1680
gaaacacccg cctccccaga tcctgatcaa aaacacaccg gtacctgcta atcctccaga   1740
agtgtttact cctgccaagc ttgcttcctt catcacgcag tacagcaccg gcaagtcag    1800
cgttgagatc gagtgggagc tgcagaaaga aacagcaag cgctggaacc cagagattca   1860
gtacacctcc aactttgaca aacagactgg agtggacttt gctgttgaca gccagggtgt   1920
ttactctgag cct                                                     1933
```

<210> SEQ ID NO 53
<211> LENGTH: 1933
<212> TYPE: DNA
<213> ORGANISM: Unknown
<220> FEATURE:
<223> OTHER INFORMATION: AAV serotype, clone 223.7

<400> SEQUENCE: 53

```
caaggcctac gaccagcagc tcaaagcggg tgacaatccg tacctgcggt ataaccacgc      60
cgacgccgag tttcaggagc gtcttcaaga agatacgtct tttggggca acctcgggcg      120
agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gtcagtcccc gaccctcaac caatcggaga accaccagca ggcccctctg tctgggatc      360
tggtacaatg gctgcaggcg gtggcgcacc aatggctgac aataacgagg cgccgacgg      420
agtgggtaat gcctcaggaa attggcattg cgattccaca tggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat tccggcccaa gaagctcaac ttcaagctct tcaacatcca     720
ggtcaaggag gtcacgacga atgacggcgt cacaaccatc gctaataacc ttaccagcac     780
ggttcaggtc ttttcggacc cggaatatca actgccgtac gtcctcggct ccgcgcacca     840
gggctgcctg cctccgttcc cggcagacgt gttcatgatt ccgcagtacg gatacctgac     900
tctgaacaat ggcagccaat cggtaggccg ttcctccttc tactgcctgg agtactttcc     960
ttctcagatg ctgagaacgg gcaacaactt ccctttagc tacaccttcg aggacgtgcc     1020
tttccacagc agctacgcgc acagccagag tctggaccgg ctgatgaatc ccctcatcga     1080
ccagtacctg tactacttgg ccagaacaca gagcaacgca ggaggtactg ctggcaatcg     1140
ggaactgcag ttttatcagg gcggacctac caccatggcc gaacaagcaa agaactggct     1200
gcccggacct tgcttccggc aacagagagt atccaagacg ctggatcaaa ataacaacag     1260
caactttgcc tggactggtg ccacaaaata ccatttaaat ggaagaaatt cattggttaa     1320
tcccggtgtc gccatggcaa cccacaagga cgacgaggaa cgcttcttcc cttcgagcgg     1380
agttctaatt tttggcaaaa ctggagcagc taataaaact acattagaaa acgtgctcat     1440
gacaaatgaa gaagaaattc gtcctaccaa cccggtagct accgaggaat acgggattgt     1500
aagcagcaac ttgcaggcgg ctagcaccgc agcccagaca caagttgtta acaaccaggg     1560
agccttacct ggcatggtct ggcagaaccg ggacgtgtac ctgcaaggtc ccatttgggc     1620
caagattcct cacacggacg gcaactttca cccgtctcct ctaatgggtg gctttggact     1680
gaaacacccg cctccccaga tcctgatcaa aaacacaccg gtacctgcta atcctccaga     1740
agtgtttact cctgccaaga ttgcttcctt catcacgcag tacagcaccg ggcaagtcag     1800
cgttgagatc gagtgggagc tgcagaaaga aacagcaag cgctggaacc cagagattca     1860
gtacacctcc aactttgaca aacagactgg agtggacttt gctgttgaca gccagggtgt     1920
ttactctgag cct                                                        1933
```

<210> SEQ ID NO 54
<211> LENGTH: 3123
<212> TYPE: DNA
<213> ORGANISM: Unknown
<220> FEATURE:
<223> OTHER INFORMATION: AAV serotype, clone A3.4

<400> SEQUENCE: 54

```
gaattcgccc tttctacggc tgcgtcaact ggaccaatga aaactttccc ttcaacgatt      60
```

```
gcgtcgacaa gatggtgatc tggtgggagg agggaaagat gaccgccaag gtcgtggaat    120
ctgccaaagc cattctgggt ggaagcaagg ttcgtgtgga ccagaaatgc aagtcttcgg    180
cccagatcga cccgactccg gtgattgtca cctctaacac caacatgtgc gccgtgattg    240
acggaaactc gaccaccttc gagcaccagc agccgttgca agaccggatg ttcaaatttg    300
aacttacccg ccgtttggat catgactttg ggaaggtcac caagcaggaa gtcaaagact    360
ttttccggtg ggctcaagat cacgtgactg aggtggagca tgagttctac gtcaaaaagg    420
gtggagccaa gaaaaggccc gcccccgatg atgtatatat aaatgagccc aagcgggcgc    480
gcgagtcagt tgcgcagcca tcgacgtcag acgcggaagc ttcgataaac tacgcgggca    540
ggtaccaaaa caaatgttct cgtcacgtgg gcatgaatct gatgctgttt ccctgtcgac    600
aatgcgaaag aatgaatcag aattcaaata tctgcttcac acacgggcaa aaagactgtt    660
tggaatgctt tcccgtgtca gaatctcaac ccgtttctgt cgtcagaaaa acgtatcaga    720
aactttgtta cattcatcat atcatgggaa aagaaccaga cgcctgcact gcctgcgacc    780
tggtaaatgt ggacttggat gactgtattt ctgagcaata aatgacttaa atcaggtatg    840
gctgctgacg gttatcttcc agattggctc gaggacactc tctctgaagg aatcagacag    900
tggtggaagc tcaaacctgg cccaccaccg ccgaaaccta accaacaaca ccgggacgac    960 agtagggtc ttgtgcttcc tgggtacaag tacctcggac ccttcaacgg actcgacaaa    1020
ggagagccgg tcaacgaggc agacgccgcg gccctcgagc acgacaaagc ctacgaccac    1080
cagctcaagc aaggggacaa cccgtacctc aaatacaacc acgcggacgc tgaatttcag    1140
gagcgtcttc aagaagatac gtctttcggg ggcaacctcg ggcgagcagt cttccaggcc    1200
aaaaagaggg tactcgagcc tcttggtctg gttgaggaag ctgttaagac ggctcctgga    1260 aaaagagac ctatagagca gtcctcctgca gaaccggact cttcctcggg catcggcgaa    1320
tcaggccagc agcccgctaa gaaaagactc aattttggtc agactggcga cacagagtca    1380
gtcccagacc ctcaaccaat cggagaaccc cccgcagccc cctctggtgt gggatctaat    1440
acaatggctt caggcggtgg ggcaccaatg gcagacgata acgaaggcgc cgacggagtg    1500
ggtaattcct cgggaaattg gcattgcgat tccacatgga tgggcgacag agttatcacc    1560
accagcacaa gaacctgggc cctccccacc tacaataatc acctctacaa gcaaatctcc    1620
agcgaatcgg gagccaccaa cgacaaccac tacttcggct acagcacccc ctgggggtat    1680 tttgactttta acagattcca ctgtcacttc tcaccacgtg actggcagcg actcatcaac    1740
aacaactggg gatttagacc caagaaactc aatttcaagc tcttcaacat ccaagtcaag    1800
gaggtcacgc agaatgatgg aaccacgacc atcgccaata accttaccag cacggtgcag    1860
gtcttcacag actctgagta ccagctgccc tacgtcctcg gttcggctca ccagggctgc    1920
cttccgccgt tcccagcaga cgtcttcatg attcctcagt acggctactt gactctgaac    1980
aatggcagcc aagcggtagg acgttcttca ttctactgtc tagagtattt tccctctcag    2040
atgctgagga cggaaacaa cttcacccttc agctacactt ttgaagacgt gccttttcac    2100
agcagctacg cgcacagcca gagtctggat cggctgatga atcctctcat tgaccagtac    2160
ctgtattacc tgagcaaaac tcagggtaca agtggaacaa cgcagcaatc gagactgcag    2220
ttcagccaag ctgggcctag ctccatggct cagcaggcca aaaactggct accgggaccc    2280
agctaccgac agcagcgaat gtctaagacg gctaatgaca caacaacag tgaatttgct    2340 tggactgcag ccaccaaata ttacctgaat ggaagaaatt ctctggtcaa tcccgggccc    2400
ccaatggcca gtcacaagga cgatgaggaa aagtatttcc ccatgcacgg aaatctcatc    2460
```

| | |
|---|---|
| tttggaaaac aaggcacagg aactaccaat gtggacattg aatcagtgct tattacagac | 2520 |
| gaagaagaaa tcagaacaac taatcctgtg gctacagaac aatacggaca ggttgccacc | 2580 |
| aaccatcaga gtcaggacac cacagcttcc tatggaagtg tggacagcca gggaatctta | 2640 |
| cctggaatgg tgtggcagga ccgcgatgtc tatcttcaag gtcccatttg ggccaaaact | 2700 |
| cctcacacgg acggacactt tcatccttct ccgctcatgg gaggctttgg actgaaacac | 2760 |
| cctcctcccc agatcctgat caaaaacaca cctgtgccag cgaatcccgc gaccactttc | 2820 |
| actcctggaa gtttgcttc gttcattacc cagtattcca ccggacaggt cagcgtggaa | 2880 |
| atagagtggg agctgcagaa agaaaacagc aaacgctgga acccagaaat tcagtacacc | 2940 |
| tccaactaca acaagtcggt gaatgtggag tttaccgtgg acgcaaacgg tgtttattct | 3000 |
| gaacccccgcc ctattggcac tcgttacctt acccggaact tgtaatttcc tgttaatgaa | 3060 |
| taaaccgatt tatgcgtttc agttgaactt tggtctctgc gaagggcgaa ttcgcggccg | 3120 |
| cta | 3123 |

<210> SEQ ID NO 55
<211> LENGTH: 3113
<212> TYPE: DNA
<213> ORGANISM: Unknown
<220> FEATURE:
<223> OTHER INFORMATION: AAV serotype, clone A3.5

<400> SEQUENCE: 55

| | |
|---|---|
| gaattcgccc tttctacggc tgcgtcaact ggaccaatga aaactttccc ttcaacgatt | 60 |
| gcgtcgacaa gatggtgatc tggtgggagg agggaaagat gaccgccaag gtcgtggaat | 120 |
| ctgccaaagc cattctgggt ggaagcaagg ttcgtgtgga ccagaaatgc aagtcttcgg | 180 |
| cccagatcga cccgactccg gtgattgtca cctctaacac caacatgtgc gccgtgattg | 240 |
| acggaaactc gaccaccttc gagcaccagc agccgttgca agaccggatg ttcaaatttg | 300 |
| aacttacccg ccgtttggat catgactttg ggaaggtcac caagcaggaa gtcaaagact | 360 |
| ttttccggtg ggctcaagat cacgtgactg aggtggagca tgagttctac gtcaaaaagg | 420 |
| gtggagccaa gaaaaggccc gcccccgatg atgtatatat aaatgagccc aagcgggcgc | 480 |
| gcgagtcagt tgcgcagcca tcgacgtcag acgcggaagc ttcgataaac tacgcggaca | 540 |
| ggtaccaaaa caaatgttct cgtcacgtgg gcatgaatct gatgctgttt ccctgtcgac | 600 |
| aatgcgaaag aatgaatcag aattcaaata tctgcttcac acacgggcaa aaagactgtt | 660 |
| tggaatgctt tcccgtgtca gaatctcaac ccgttcctgt cgtcagaaaa acgtatcaga | 720 |
| aactttgtta cattcatcat atcatgggaa aagtaccaga cgcctgcact gcctgcgacc | 780 |
| tggtaaatgt ggacttggat gactgtattt ctgagcaata aatgacttaa atcaggtatg | 840 |
| gctgctgacg gttatcttcc agattggctc gaggacactc tctctgaagg aatcagacag | 900 |
| tggtggaagc tcaaacctgg cccaccaccg ccgaaaccta accaacaaca ccgggacgac | 960 |
| agtaggggtc ttgtgcttcc tgggtacaag tacctcggac ccttcaacgg actcgacaaa | 1020 |
| ggagagccgg tcaacgaggc agacgccgcg gccctcgagc acgacaaagc ctacgaccac | 1080 |
| cagctcaagc aagggacaa cccgtacctc aaatacaacc acgcggacgc tgaatttcag | 1140 |
| gagcgtcttc aagaagatac gtctttcggg gcaacctcg ggcagcagt cttccaggcc | 1200 |
| aaaaagaggg tactcgagcc tcttggtctg gttgaggaag ctgttaagac ggctcctgga | 1260 |
| aaaaagagac ctagagca gtctcctgca gaaccggact cttcctcggg catcggcaaa | 1320 |
| tcaggccagc agcccgctaa gaaaagactc aattttggtc agactggcga cacagagtca | 1380 |

-continued

```
gtcccagacc ctcaaccaat cggagaaccc cccgcagccc cctctggtgt gggatctaat      1440
acaatggctt caggcggtgg ggcaccaatg gcagacaata cgaaggcgc cgacggagtg       1500 ggtaattcct cgggaaattg gcattgcgat tccacatgga tgggcgacag agttatcacc      1560
accagcacaa gaacctgggc cctccccacc tacaataatc acctctacaa gcaaatctcc     1620
agcgaatcgg gagccaccaa cgacaaccac tacttcggct acagcacccc ctgggggtat     1680
tttgacttta acagattcca ctgtcacttc tcaccacgtg actggcagcg actcatcaat    1740
aacaactggg gatttagacc caagaaactc aatttcaagc tcttcaacat ccaagtcaag     1800
gaggtcacgc agaatgatgg aaccacgacc atcgccaata accttaccag cacggtgcag     1860
gtcttcacag actctgagta ccagctgccc tacgtcctcg gttcggctca ccagggctgc    1920
cttccgccgt tcccagcaga cgtcttcatg attcctcagt acggctactt gactctgaac    1980
aatggcagcc aagcggtagg acgttcttca ttctactgtc tagagtattt tccctctcag    2040
atgctgagga cggaaacaa cttcaccttc agctacactt ttgaagacgt gcctttccac      2100
agcagctacg cgcacagcca gagtctggat cggctgatga atcctctcat tgaccagtac    2160
ctgtattacc tgagcaaaac tcagggtaca agtggaacaa cgcagcaatc gagactgcag    2220
ttcaaccaag ctgggcctag ctccatggct cagcaggcca aaaactggct accgggaccc    2280
agctaccgac agcagcgaat gtctaagacg gctaatgaca caacaacag tgaatttgct      2340 tggactgcag ccaccaaata ttacccgaat ggaagaaatt ctctggtcaa tcccgggccc    2400
ccaatggcca gtcacaagga cgatgaggaa aagtatttcc ccatgcacgg aaatctcatc    2460
tttggaaaac aaggcacagg aactaccaat gtggacattg aatcagtgct tattacagac    2520
gaagaagaaa tcagaacgac taatcctgtg gctacagaac aatacggaca ggttgccacc    2580
aaccgtcaga gtcagaacac cacagcttcc tatggaagtg tggacagcca gggaatctta    2640
cctggaatgg tgtggcagga ccgcgatgtc tatcttcaag gtcccatttg gccaaaaact    2700
cctcacacgg acggacactt tcatccttct ccgctcatgg gaggctttgg actgaaacac    2760
cctcctcccc agatcctgat caaaaacaca cctgtgccag cgaatcccgc gaccactttc    2820
actcctggaa gtttgcttc gttcattacc cagtattcca ccggacaggt cagcgtggaa     2880
atagagtggg agctgcagaa agaaaacagc aaacgctgga acccggaaat tcagtacacc    2940
tccaactaca acaagtcggt gaatgtggag tttaccgtgg acgcaaacgg tgtttattct    3000
gaaccccgcc ctattggcac tcgttacctt acccggaact tgtaatttcc tgttaatgaa     3060
taaaccgatt tatgcgtttc agttgaactt tggtctctgc gaagggcgaa ttc            3113
```

<210> SEQ ID NO 56
<211> LENGTH: 3122
<212> TYPE: DNA
<213> ORGANISM: Unknown
<220> FEATURE:
<223> OTHER INFORMATION: AAV serotype, clone A3.7

<400> SEQUENCE: 56

```
agcggccgcg aattcgccct ttctacggct gcgtcaactg gaccaatgaa aactttccct       60
tcaacgattg cgtcgacaag atggtgatct ggtgggagga gggaaagatg accgccaagg      120
tcgtggaatc tgccaaagcc attctgggtg gaagcaaggt tcgtgtggac cagaaatgca     180
ggtcttcggc ccagatcgac ccgactccgg tgattgtcac ctctaacacc aacatgtgcg     240
ccgtgattga cggaaactcg accaccttcg agcaccagca gccgttgcaa gaccggatgt     300
tcaaatttga acttacccgc cgtttggatc atgactttgg gaaggtcacc aagcaggaag     360
```

| | |
|---|---|
| tcaaagactt tttccggtgg gctcaagatc acgtgactga ggtggagcat gagttctacg | 420 |
| tcaaaaaggg tggagccaag aaaaggcccg cccccgatga tgtatatata aatgagccca | 480 |
| agcgggcgcg cgagtcagtt gcgcagccat cgacgtcaga cgcggaagct tcgataaact | 540 |
| acgcggacag gtaccaaaac aaatgttctc gtcacgtggg catgaatctg atgctgtttc | 600 |
| cctgtcgaca atgcgaaaga atgaatcaga attcaaatat ctgcttcaca cacgggcaaa | 660 |
| aagactgttt ggaatgcttt cccgtgtcag aatctcaacc cgtttctgtc gtcagaaaaa | 720 |
| cgtatcagaa actttgttac attcatcata tcatgggaaa agtaccagac gcctgcactg | 780 |
| cctgcgacct ggtaaatgtg gacttggatg actgtatttc tgagcaataa atgacttaaa | 840 |
| tcaggtatgg ctgctgacgg ttatcttcca gattggctcg aggacactct ctctgaagga | 900 |
| atcagacagt ggtggaagct caaacctggc ccaccaccgc cgaaacctaa ccaacaacac | 960 |
| cgggacgaca gtaggggtct tgtgcttcct gggtacaagt acctcggacc cttcaacgga | 1020 |
| ctcgacaaag gagagccggt caacgaggca gacgccgcgg ccctcgagca cgacaaagcc | 1080 |
| tacgaccacc agctcaagca aggggacaac ccgtacctca aatacaacca cgcggacgct | 1140 |
| gaatttcagg agcgtcttca agaagatacg tctttcgggg gcaacctcgg gcgagcagtc | 1200 |
| ttccaggcca aaagagggt actcgagcct cttggtctgg ttgaggaagc tgttaagacg | 1260 |
| gctcctggaa aaagagacc tatagagcag tctcctgcag aaccggactc ttcctcgggc | 1320 |
| atcggcaaat caggccagca gcccgctaag aaaagactca attttggtca gactggcgac | 1380 |
| acagagtcag tcccagaccc tcaaccaatc ggagaacccc ccgcagcccc ctctggtgtg | 1440 |
| ggatctaata caatggcttc aggcggtggg gcaccaatgg cagacaataa cgaaggcgcc | 1500 |
| gacggagtgg gtaattcctc gggaaattgg cattgcgatt ccacatggat gggcgacaga | 1560 |
| gttatcacca ccagcacaag aacctgggcc ctccccacct acaataatcg cctctacaag | 1620 |
| caaatctcca gcgaatcggg agccaccaac gacaaccact acttcggcta cagcacccccc | 1680 |
| tgggggtatt ttgactttaa cagattccac tgtcacttct caccacgtga ctggcagcga | 1740 |
| ctcatcaaca caactgggg atttagaccc aagaaactca atttcaagct cttcaacatc | 1800 |
| caagtcaagg aggtcacgca gaatgatgga accacgacca tcgccaataa ccttaccagc | 1860 |
| acggtgcagg tcttcacaga ctctgagtac cagctgcccc acgtcctcgg ttcggctcac | 1920 |
| cagggctgcc ttccgccgtt cccagcagac gtcttcatga ttcctcagta cggctacttg | 1980 |
| actctgaaca atggcagcca agcggtagga cgttcttcat tctactgtct agagtatttt | 2040 |
| ccctctcaga tgctgaggac gggaaacaac ttcaccttca gctacacttt tgaagacgtg | 2100 |
| cctttccaca gcagctacgc gcacagccag agtctggatc ggctgatgaa tcctctcatt | 2160 |
| gaccagtacc tgtattacct gagcaaaact cagggtacaa gtggaacaac gcagcaatcg | 2220 |
| agactgcagt tcagccaagc tgggcctagc tccatggctc agcaggccaa aaactggcta | 2280 |
| ccgggaccca gctaccgaca gcagcgaatg tctaagacgg ctaatgacaa caacaacagt | 2340 |
| gaatttgctt ggactgcagc caccaaatat tacctgaatg aagaaattc tctggtcaat | 2400 |
| cccgggcccc caatggccag tcacaaggac gatgaggaaa agtatttccc catgcacgga | 2460 |
| aatctcatct ttggaaaaca aggcacagga actaccaatg tggacattga atcagtgctt | 2520 |
| attacagacg aagaagaaat cagaacaact aatcctgtgg ctacagaaca atacggacag | 2580 |
| gttgccacca accatcagag tcagaacacc acagcttcct atggaagtgt ggacagccag | 2640 |
| ggaatcttac ctgaatggt gtggcaggac cgcgatgtct atcttcaagg tcccatttgg | 2700 |
| gccaaaactc ctcacacgga cggacacttt catccttctc cgctcatggg aggctttgga | 2760 |

```
ctgaaacacc ctcctcccca gatcctgatc aaaaacacac ctgtgccagc gaatcccgcg    2820
accactttca ctcctggaaa gtttgcttcg ttcattaccc agtattccac cggacaggtc    2880
agcgtggaaa tagagtggga gctgcagaaa gaaaacagca acgctggaa cccagaaatt     2940 cagtacacct ccaactacaa caagtcggtg aatgtggagt ttaccgtgga cgcaaacggt    3000
gtttattctg aaccccgccc tattggcact cgttaccttaa cccggaactt gtaatttcct   3060
gttaatgaat aaaccgattt atgcgtttca gttgaacttt ggtctctgcg aagggcgaat    3120
tc                                                                   3122

<210> SEQ ID NO 57
<211> LENGTH: 3123
<212> TYPE: DNA
<213> ORGANISM: Unknown
<220> FEATURE:
<223> OTHER INFORMATION: AAV serotype, clone A3.3

<400> SEQUENCE: 57
gaattcgccc tttctacggc tgcgtcaact ggaccaatga aaactttccc ttcaacgatt      60
gcgtcgacaa gatggtgatc tggtgggagg agggaaagat gaccgccaag gtcgtggaat     120
ctgccaaagc cattctgggt ggaggcaagg ttcgtgtgga ccagaaatgc aagtcttcgg     180
cccagatcga cccgactccg gtgattgtca cctctaacac caacatgtgc gccgtgattg     240
acggaaactc gaccaccttc gagcaccagc agccgttgca agaccggatg ttcaaatttg     300
aacttacccg ccgtttggat catgactttg ggaaggtcac caagcaggaa gtcaaagact     360
ttttccggtg ggctcaagat cacgtgactg aggtggagca tgagttctac gtcaaaaagg     420
gtggagccaa gaaaaggccc gcccccgatg atgtatatat aaatgagccc aagcgggcgc     480
gcgagtcagt tgcgcagcca tcgacgtcag acgcggaagc ttcgataaac tacgcggaca     540
ggtaccaaaa caaatgttct cgtcacgtgg gcatgaatct gatgctgttt ccctgtcgac     600
aatgcgaaag aatgaatcag aattcaaata tctgcttcac acacgggcaa aaagactgtt     660
tggaatgctt tccgtgtca gaatctcaac ccgtttctgt cgtcagaaaa acgtatcaga      720
aactttgtta cattcatcat atcatgggaa agtaccaga cgcctgcact gcctgcgacc      780
tggtaaatgt ggacttggat gactgtattt ctgagcaata aatgactaaa tcaggtatg      840 gctgctgacg gttatcttcc agattggctc gaggacactc tctctgaagg aatcagacag     900
tggtggaagc tcaaacctgg cccaccaccg ccgaaaccta accaacaaa ccgggacgac      960 agtagggtc ttgtgcttcc tgggtacaag tacctcggac ccttcaacgg actcgacaaa     1020
ggagagccgg tcaacgaggc agacgccgcg gccctgagc acgacaaagc ctacgaccac     1080
cagctcaagc aaggggacaa cccgtacctc aaatacaacc acgcggacgc tgaatttcag    1140
gagcgtcttc aagaagatac gtctttcggg ggcaacctcg gcgagcagt cttccaggcc     1200 aaaaagaggg tactcgagcc tcttggtctg gttgaggaag ctgttaagac ggctcctgga    1260
aaaaagagac ctatagagca gtctcctgca gaaccggact cttcctcggg catcggcaaa    1320
tcaggccagc agcccgctaa gaaaagactc aattttggtc agactggcga cacagagtca    1380
gtcccaggcc ctcaaccaat cggagaaccc cccgcagccc cctctggtgt gggatctaat    1440
acaatggctt caggcggtgg ggcaccaatg gcagacaata cgaaggcgc cgacggagtg    1500 ggtaattcct cgggaaattg gcattgcgat tccacatgga tgggcgacag agttatcacc   1560
accagcacaa gaacctgggc cctccccacc tacaataatc acctctacaa gcaaatctcc    1620
agcgaatcgg gagccaccaa cgacaaccac tacttcggct acagcacccc ctgggggtat   1680
```

```
tttgacttta acagattcca ctgtcacttc tcaccacgtg actggcagcg actcatcaac    1740
aacaactggg gatttagacc caagaaactc aatttcaagc tcttcaacat ccaagtcaag    1800
gaggtcacgc agaatgatgg aaccacgacc atcgccaata accttaccag cgcggtgcag    1860
gtcttcacag actctgagta ccagctgccc tacgtcctcg gttcggctca ccagggctgc    1920
cttccgccgt tcccagcaga cgtcttcatg attcctcagt acggctactt gactctgaac    1980
aatggcagcc aagcggtagg acgttcttca ttctactgtc tagagtattt tccctctcag    2040
atgctgagga cgggaaacaa cttcaccttc agctacactt ttgaagacgt gcctttccac    2100
agcagctacg cgcacagcca gagtctggat cggctgatga atcctctcat tgaccagtac    2160
ctgtattacc tgagcaaaac tcagggtaca agtggaacaa cgcagcaatc gagactgcag    2220
ttcagccaag ctgggcctag ctccatggct cagcaggcca aaaactggct accgggaccc    2280
agctaccgac agcagcgaat gtctaagacg ctaatgaca acaacaacag tgaatttgct    2340
tggactgcag ccaccaaata ttacctgaat ggaagaaatt ctctggtcaa tcccgggccc    2400
ccagtggcca gtcacaagga cgatgaggaa aagtatttcc ccatgcacgg aaatctcatc    2460
tttgaaaaac aaggcacagg aactaccaat gtggacattg aatcagtgct tattacagac    2520
gaagaagaaa tcagaacaac taatcctgtg gctacagaac aatacggaca ggttgccacc    2580
aaccatcaga gtcagaacac cacagcttcc tatggaagtg tggacagcca gggaatctta    2640
cctggaatgg tgtggcagga ccgcgatgtc tatcttcaag gtcccatttg gccaaaaact    2700
cctcacacgg acggacactt tcatccttct ccgctcatgg gaggctttgg actgaaacac    2760
cctcctcccc agatcctgat caaaaacaca cctgtgccag cgaatcccgc gaccactttc    2820
actcctggaa agtttgcttc gttcattacc cagtattcca cctgacaggt cagcgtggaa    2880
atagagtggg agctgcagaa agaaaacagc aaacgctgga acccagaaat tcagtacacc    2940
tccaactaca acaagtcggt gaatgtggag tttaccgtgg acgcaaacgg tgtttattct    3000
gaaccccgcc ctattggcac tcgttacctt acccggaact tgtaatttcc tgttaatgaa    3060
taagccgatt tatgcgtttc agttgaactt tggtctctgc gaagggcgaa ttcgtttaaa    3120
cct                                                                  3123
```

<210> SEQ ID NO 58
<211> LENGTH: 2969
<212> TYPE: DNA
<213> ORGANISM: Unknown
<220> FEATURE:
<223> OTHER INFORMATION: AAV serotype, clone 42.12

<400> SEQUENCE: 58

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480
gcccctcagt cgcggatcca tcgacgtcag acgcggaagg agctccggtg gactttgccg     540 acagggtacca aaacaaatgt tctcgtcacg cgggcatgct tcagatgctg tttccctgca     600
```

```
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatc    900
cgcgagtggt gggacttgaa acctggagcc ccgaaaccca agccaaccca gcaaaagcag    960
gacgacggcc ggggtctggt gcttcctggc tacaagtacc tcggacccct caacggactc   1020
gacaagggag agccggtcaa cgaggcagac gccgcggccc tcgagcacga caaggcctac   1080
gacaagcagc tcgagcaggg ggacaacccg tacctcaagt acaaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga caggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500 gacgagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacatc gggaggaagc accaacgaca cacctactt cggctacagc   1680 accccctggg ggtattttga ctttaacaga ttccactgcc acttctcacc acgtgactgg   1740
cagcgactca tcaacaacaa ctggggattc cggcccaaga gactcaactt caagctcttc   1800
aacatccagg tcaaggaggt cacgcagaat gaaggcacca agaccatcgc caataacctt   1860
accagcacga ttcaggtctt tacgactcg gaataccagc tcccgtacgt cctcggctct   1920
gcgcaccagg gctgcctgcc tccgttcccg gcggacgtct tcatgattcc tcagtacggg   1980
tacctgactc tgaacaacgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gacgaacccc   2160
ctcatcgacc agtacctgta ctacctggcc cggacccaga gcactacggg gtccacaagg   2220
gggctgcagt tccatcaggc tgggcccaac accatggccg agcaatcaaa gaactggctg   2280
cccggaccct gttatcggca gcagagactg tcaaaaaaca tagacagcaa caacaacagt   2340
aactttgcct ggaccggggc cactaaatac catctgaatg gtagaaattc attaaccaac   2400
ccgggcgtag ccatggccac caacaaggac gacgaggacc agttctttcc catcaacgga   2460
gtgctggttt ttggcaaaac gggggctgcc aacaagacaa cgctggaaaa cgtgctaatg   2520
accagcgagg aggagatcaa aaccaccaat cccgtggcta cagaagaata cggtgtggtc   2580
tccagcaacc tgcaatcgtc tacgccggga ccccagacac agactgtcaa cagccagggg   2640
gctctgcccg gcatggtctg gcagaaccgg gacgtgtacc tgcagggtcc catctgggcc   2700
aaaattcctc acacggacgg caactttcac ccgtctcccc tgatgggcgg atttggactc   2760
aaacacccgc ctcctcaaat tctcatcaag tatacttcca actactacaa atctacaaat   2820
gtggactttg ctgtcaatac tgagggtact tattcagagc ctcgccccat tggcacccgt   2880
tacctcaccc gtaacctgta attgcctgtt aatcaataaa ccggttaatt cgtttcagtt   2940
gaactttggt ctctgcgaag ggcgaattc                                      2969
```

<210> SEQ ID NO 59
<211> LENGTH: 3129
<212> TYPE: DNA
<213> ORGANISM: Unknown
<220> FEATURE:
<223> OTHER INFORMATION: AAV serotype, clone 44.2

<400> SEQUENCE: 59

| | | | | | |
|---|---|---|---|---|---|
| gaattcgccc | tttctacggc | tgcgtcaact | ggaccaatga | gaactttccc | ttcaacgatt | 60 |
| gcgtcgacaa | gatggtgatc | tggtgggagg | agggcaagat | gacggccaag | gtcgtggagt | 120 |
| ccgccaaggc | cattctcggc | ggcagcaaag | tgcgcgtgga | ccaaaagtgc | aagtcgtccg | 180 |
| cccagatcga | ccccaccccc | gtgatcgtca | cctccaacac | caacatgtgc | gccgtgattg | 240 |
| acgggaacag | caccaccttc | gagcaccagc | agccgttgca | ggaccggatg | ttcaagtttg | 300 |
| aactcacccg | ccgtctggag | cacgactttg | gcaaggtgac | aaagcaggaa | gtcagagagt | 360 |
| tcttccgctg | ggcgcaggat | cacgtgaccg | aggtggcgca | cgagttctac | gtcagaaagg | 420 |
| gtggagccaa | caagagaccc | gcccccgatg | acgcggataa | agcgagccc | aagcgggcct | 480 |
| gcccctcagt | cgcggatcca | tcgacgtcag | acgcggaagg | agctccggtg | gactttgccg | 540 |
| acaggtacca | aaacaaatgt | tctcgtcacg | cgggcatgct | tcagatgctg | tttccctgca | 600 |
| aaacatgcga | gagaatgaat | cagaatttca | acatttgctt | cacgcacggg | accagagact | 660 |
| gttcagaatg | tttccccggc | gtgtcagaat | ctcaaccggt | cgtcagaaaa | aagacgtatc | 720 |
| ggaaactctg | tgcgattcat | catctgctgg | ggcgggcac | ccgagattgc | ttgctcggcc | 780 |
| tgcgatctgg | tcaacgtgga | cctagatgac | tgtgtttctg | agcaataaat | gacttaaacc | 840 |
| aggtatggct | gccgatggtt | atcttccaga | ttggctcgag | gacaacctct | ctgagggcat | 900 |
| tcgcgagtgg | tgggacttga | aacctggagc | cccgaaaccc | aaagccaacc | agcaaaagca | 960 |
| ggacgacggc | cggggtctgg | tgcttcctgg | ctacaagtac | ctcggaccct | tcaacggact | 1020 |
| cgacaagggg | gagcccgtca | acgcggcgga | cgcagcggcc | ctcgagcacg | acaaggccta | 1080 |
| cgaccagcag | ctcaaagcgg | gtgacaatcc | gtacctgcgg | tataaccacc | cgacgccga | 1140 |
| gtttcaggag | cgtctgcaag | aagatacgtc | ttttgggggc | aacctcgggc | gagcagtctt | 1200 |
| ccaggccaag | aagcgggttc | tcgaacctct | cggtctggtt | gaggaaggcg | ctaagacggc | 1260 |
| tcctggaaag | aagagaccgg | tagagccatc | accccagcgt | tctccagact | cctctacggg | 1320 |
| catcggcaag | aaaggccagc | agcccgcgaa | aaagagactc | aactttgggc | agactggcga | 1380 |
| ctcagagtca | gtgcccgacc | ctcaaccaat | cggagaaccc | cccgcaggcc | cctctggtct | 1440 |
| gggatctggt | acaatggctg | caggcggtgg | cgctccaatg | gcagacaata | acgaaggcgc | 1500 |
| cgacggagtg | ggtagttcct | caggaaattg | gcattgcgat | tccacatggc | tgggcgacag | 1560 |
| agtcatcacc | accagcaccc | gaacctgggc | cctccccacc | tacaacaacc | acctctacaa | 1620 |
| gcaaatctcc | aacgggactt | cgggaggaag | caccaacgac | aacacctact | tcggctacag | 1680 |
| caccccctgg | gggtattttg | actttaacag | attccactgc | cacttctcac | cacgtgactg | 1740 |
| gcagcgactc | atcaacaaca | actgggggat | tcggcccaag | agactcaact | tcaagctctt | 1800 |
| caacatccag | gtcaaggagg | tcacgcagaa | tgaaggcacc | aagaccatcg | ccaataacct | 1860 |
| taccagcacg | attcaggtct | ttacggactc | ggaataccag | ctcccgtacg | tcctcggctc | 1920 |
| tgcgcaccag | ggctgcctgc | ctccgttccc | ggcggacgtc | ttcatgattc | ctcagtacgg | 1980 |
| gtacctgact | ctgaacaatg | gcagtcaggc | cgtgggccgt | tcctccttct | actgcctgga | 2040 |
| gtactttcct | tctcaaatgc | tgagaacggg | caacaacttt | gagttcagct | accagtttga | 2100 |

-continued

```
ggacgtgcct tttcacagca gctacgcgca cagccaaagc ctggaccggc tgatgaaccc    2160
cctcatcgac cagtacctgt actacctgtc tcggactcag tccacgggag gtaccgcagg    2220
aactcagcag ttgctatttt ctcaggccgg gcctaataac atgtcggctc aggccaaaaa    2280
ctggctaccc gggccctgct accggcagca acgcgtctcc acgacactgt cgcaaaataa    2340
caacagcaac tttgcctgga ccggtgccac caagtatcat ctgaatggca gagactctct    2400
ggtaaatccc ggtgtcgcta tggcaaccca caaggacgac gaagagcgat tttttccgtc    2460
cagcggagtc ttaatgtttg ggaaacaggg agctggaaaa gacaacgtgg actatagcag    2520
cgttatgcta accagtgagg aagaaattaa aaccaccaac ccagtggcca cagaacagta    2580
cggcgtggtg gccgataacc tgcaacagca aaacgccgct cctattgtag gggccgtcaa    2640
cagtcaagga gccttacctg gcatggtctg gcagaaccgg gacgtgtacc tgcagggtcc    2700
tatctgggcc aagattcctc acacggacgg aaactttcat ccctcgccgc tgatgggagg    2760
ctttggactg aaacacccgc ctcctcagat cctgattaag aatacacctg ttcccgcgga    2820
tcctccaact accttcagtc aagctaagct ggcgtcgttc atcacgcagt acagcaccgg    2880
acaggtcagc gtgaaattga atgggagctg cagaaagaa aacagcaaac gctggaaccc    2940
agagattcaa tacacttcca actactacaa atctacaaat gtggactttg ctgttaacac    3000
agatggcact tattctgagc ctcgccccat cggcacccgt tacctcaccc gtaatctgta    3060
attgcttgtt aatcaataaa ccggttgatt cgtttcagtt gaactttggt ctctgcgaag    3120
ggcgaattc                                                           3129
```

<210> SEQ ID NO 60
<211> LENGTH: 733
<212> TYPE: PRT
<213> ORGANISM: Unknown
<220> FEATURE:
<223> OTHER INFORMATION: capsid protein of AAV serotype, clone C1VP1

<400> SEQUENCE: 60

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Gly Ile Gly Lys
145                 150                 155                 160

Lys Gly Lys Gln Pro Ala Lys Lys Arg Leu Asn Phe Glu Glu Asp Thr
                165                 170                 175
```

-continued

```
Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
        210                 215                 220

Asp Ser Thr Trp Ser Glu Gly Lys Val Thr Thr Ser Thr Arg Thr
225                 230                 235                 240

Trp Val Leu Pro Thr Tyr Asn Asn His Leu Tyr Leu Arg Leu Gly Thr
            245                 250                 255

Thr Ser Asn Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
            325                 330                 335

Ser Ser Tyr Glu Leu Pro Tyr Val Met Asp Ala Gly Gln Glu Gly Ser
        340                 345                 350

Leu Ser Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
        370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Gly Lys Val Pro Phe His Ser Met
            405                 410                 415

Tyr Ala Tyr Ser Gln Ser Pro Asp Arg Leu Met Asn Pro Leu Leu Asp
        420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
        450                 455                 460

Ala Phe Tyr Arg Lys Asn Trp Leu Pro Gly Pro Cys Val Lys Gln Gln
465                 470                 475                 480

Arg Leu Ser Lys Thr Ala Ser Gln Asn Tyr Lys Ile Pro Ala Ser Gly
            485                 490                 495

Gly Asn Ala Leu Leu Lys Tyr Asp Thr His Tyr Thr Leu Asn Asn Arg
        500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
        530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
            565                 570                 575

Ile Ala Asp Asn Asn Gln Asn Ala Thr Thr Ala Pro Ile Thr Gly Asn
        580                 585                 590

Val Thr Ala Met Gly Val Leu Pro Gly Met Val Trp Gln Asn Arg Asp
        595                 600                 605
```

-continued

```
Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
                675                 680                 685

Ser Lys Arg Trp Asn Pro Glu Val Gln Phe Thr Ser Asn Tyr Gly Asn
            690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 61
<211> LENGTH: 733
<212> TYPE: PRT
<213> ORGANISM: Unknown
<220> FEATURE:
<223> OTHER INFORMATION: capsid protein of AAV serotype, clone C2VP1

<400> SEQUENCE: 61

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Leu
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe His Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240
```

-continued

Trp Val Leu Pro Thr Tyr Asn His Leu Tyr Leu Arg Leu Gly Thr
            245             250             255

Thr Ser Asn Ser Asn Thr Tyr Asn Gly Phe Ser Thr Pro Trp Gly Tyr
        260                 265             270

Phe Asp Phe Asn Arg Phe His Cys His Phe Ser Pro Arg Asp Trp Gln
    275                 280             285

Arg Leu Ile Asn Asn Asn Trp Gly Leu Arg Pro Lys Ala Met Arg Val
290                 295             300

Lys Ile Phe Asn Ile Gln Val Lys Glu Val Thr Thr Ser Asn Gly Glu
305             310             315             320

Thr Thr Val Ala Asn Asn Leu Thr Ser Thr Val Gln Ile Phe Ala Asp
            325             330             335

Ser Ser Tyr Glu Leu Pro Tyr Val Met Asp Ala Gly Gln Glu Gly Ser
        340                 345             350

Leu Pro Pro Phe Pro Asn Asp Val Phe Met Val Pro Gln Tyr Gly Tyr
        355                 360             365

Cys Gly Ile Val Thr Gly Glu Asn Gln Asn Gln Thr Asp Arg Asn Ala
        370             375             380

Phe Tyr Cys Leu Glu Tyr Phe Pro Ser Gln Met Leu Arg Thr Gly Asn
385             390             395             400

Asn Phe Glu Met Ala Tyr Asn Phe Glu Lys Val Pro Phe His Ser Met
            405             410             415

Tyr Ala His Ser Gln Ser Leu Asp Arg Leu Met Asn Pro Leu Leu Asp
            420             425             430

Gln Tyr Leu Trp His Leu Gln Ser Thr Thr Ser Gly Glu Thr Leu Asn
        435             440             445

Gln Gly Asn Ala Ala Thr Thr Phe Gly Lys Ile Arg Ser Gly Asp Phe
450                 455             460

Ala Phe Tyr Arg Lys Asn Trp Leu Pro Gly Pro Cys Val Lys Gln Gln
465             470             475             480

Arg Phe Ser Lys Thr Ala Ser Gln Asn Tyr Lys Ile Pro Ala Ser Gly
                485             490             495

Gly Asn Ala Leu Leu Lys Tyr Asp Thr His Tyr Thr Leu Asn Asn Arg
        500             505             510

Trp Ser Asn Ile Ala Pro Gly Pro Pro Met Ala Thr Ala Gly Pro Ser
        515             520             525

Asp Gly Asp Phe Ser Asn Ala Gln Leu Ile Phe Pro Gly Pro Ser Val
    530             535             540

Thr Gly Asn Thr Thr Thr Ser Ala Asn Asn Leu Leu Phe Thr Ser Glu
545             550             555             560

Gly Glu Ile Ala Ala Thr Asn Pro Arg Asp Thr Asp Met Phe Gly Gln
                565             570             575

Ile Ala Asp Asn Asn Gln Asn Ala Thr Thr Ala Pro Ile Thr Gly Asn
            580             585             590

Val Thr Ala Met Gly Val Leu Pro Gly Met Val Trp Gln Asn Arg Asp
        595             600             605

Ile Tyr Tyr Gln Gly Pro Ile Trp Ala Lys Ile Pro His Ala Asp Gly
    610             615             620

His Phe His Pro Ser Pro Leu Ile Gly Gly Phe Gly Leu Lys His Pro
625             630             635             640

Pro Pro Gln Ile Phe Ile Lys Asn Thr Pro Val Pro Ala Asn Pro Ala
            645             650             655

Thr Thr Phe Thr Ala Ala Arg Val Asp Ser Phe Ile Thr Gln Tyr Ser
        660             665             670

```
Thr Gly Gln Val Ala Val Gln Ile Glu Trp Glu Ile Glu Lys Glu Arg
            675                 680                 685

Ser Lys Arg Arg Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 62
<211> LENGTH: 733
<212> TYPE: PRT
<213> ORGANISM: Unknown
<220> FEATURE:
<223> OTHER INFORMATION: capsid protein of AAV serotype, clone C5VP1[@0002]

<400> SEQUENCE: 62

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Glu Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
290                 295                 300
```

```
Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
370                 375                 380

Phe Tyr Cys Leu Glu Tyr Phe Pro Ser Gln Met Leu Arg Thr Gly Asn
385                 390                 395                 400

Asn Phe Glu Thr Ala Tyr Asn Phe Glu Lys Val Pro Phe His Ser Met
                405                 410                 415

Tyr Ala His Ser Gln Ser Leu Asp Gly Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Met Ala Thr Ala Gly Pro Ser
        515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Tyr Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Cys Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

<210> SEQ ID NO 63
<211> LENGTH: 734
<212> TYPE: PRT
<213> ORGANISM: Unknown
<220> FEATURE:
<223> OTHER INFORMATION: capsid protein of AAV serotype, clone AAV4VP1

<400> SEQUENCE: 63

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365
```

-continued

```
Cys Gly Leu Val Thr Gly Asn Thr Ser Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
                420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
                580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 64
<211> LENGTH: 736
<212> TYPE: PRT
<213> ORGANISM: Unknown
<220> FEATURE:
<223> OTHER INFORMATION: capsid protein of AAV serotype, clone AAV1

<400> SEQUENCE: 64

Met Ala Ala Asp Gly Tyr Leu Pro Asp Trp Leu Glu Asp Asn Leu Ser
```

-continued

```
1               5                   10                  15
Glu Gly Ile Arg Glu Trp Trp Asp Leu Lys Pro Gly Ala Pro Lys Pro
                    20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
                420                 425                 430
```

```
Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 65
<211> LENGTH: 736
<212> TYPE: PRT
<213> ORGANISM: Unknown
<220> FEATURE:
<223> OTHER INFORMATION: capsid protein of AAV serotype, clone AAV6VP1

<400> SEQUENCE: 65

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
```

```
                65                  70                  75                  80
Gln Gln Leu Lys Ala Gly Asp Asn Pro Tyr Leu Arg Tyr Asn His Ala
                    85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495
```

```
Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 66
<211> LENGTH: 735
<212> TYPE: PRT
<213> ORGANISM: Unknown
<220> FEATURE:
<223> OTHER INFORMATION: capsid protein of  AAV serotype, clone A3.3

<400> SEQUENCE: 66

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
```

```
              130                 135                 140
Pro Ile Glu Gln Ser Pro Ala Glu Pro Asp Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Gly Pro Gln Pro Ile Gly Glu Pro Pro
                180                 185                 190

Ala Ala Pro Ser Gly Val Gly Ser Asn Thr Met Ala Ser Gly Gly Gly
                195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
        290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Ala Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Ile Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Lys Thr
        435                 440                 445

Gln Gly Thr Ser Gly Thr Thr Gln Gln Ser Arg Leu Gln Phe Ser Gln
450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Leu Asn Gly
                500                 505                 510

Arg Asn Ser Leu Val Asn Pro Gly Pro Val Ala Ser His Lys Asp
                515                 520                 525

Asp Glu Glu Lys Tyr Phe Pro Met His Gly Asn Leu Ile Phe Gly Lys
        530                 535                 540

Gln Gly Thr Gly Thr Thr Asn Val Asp Ile Glu Ser Val Leu Ile Thr
545                 550                 555                 560
```

-continued

```
Asp Glu Glu Glu Ile Arg Thr Thr Asn Pro Val Ala Thr Glu Gln Tyr
                565                 570                 575

Gly Gln Val Ala Thr Asn His Gln Ser Gln Asn Thr Thr Ala Ser Tyr
            580                 585                 590

Gly Ser Val Asp Ser Gln Gly Ile Leu Pro Gly Met Val Trp Gln Asp
        595                 600                 605

Arg Asp Val Tyr Leu Gln Gly Pro Ile Trp Ala Lys Thr Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 67
<211> LENGTH: 735
<212> TYPE: PRT
<213> ORGANISM: Unknown
<220> FEATURE:
<223> OTHER INFORMATION: capsid protein of AAV serotype, clone A3.7

<400> SEQUENCE: 67

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
```

```
                195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn Arg Leu
                245                 250                 255
Tyr Lys Gln Ile Ser Ser Glu Ser Gly Ala Thr Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
                290                 295                 300
Gly Phe Arg Pro Lys Lys Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Ile Pro Gln Tyr Gly Tyr Leu Thr Leu Asn Asn Gly Ser
                370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Lys Thr
                435                 440                 445
Gln Gly Thr Ser Gly Thr Thr Gln Gln Ser Arg Leu Gln Phe Ser Gln
450                 455                 460
Ala Gly Pro Ser Ser Met Ala Gln Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Leu Asn Gly
                500                 505                 510
Arg Asn Ser Leu Val Asn Pro Gly Pro Pro Met Ala Ser His Lys Asp
                515                 520                 525
Asp Glu Glu Lys Tyr Phe Pro Met His Gly Asn Leu Ile Phe Gly Lys
530                 535                 540
Gln Gly Thr Gly Thr Thr Asn Val Asp Ile Glu Ser Val Leu Ile Thr
545                 550                 555                 560
Asp Glu Glu Glu Ile Arg Thr Thr Asn Pro Val Ala Thr Glu Gln Tyr
                565                 570                 575
Gly Gln Val Ala Thr Asn His Gln Ser Gln Asn Thr Thr Ala Ser Tyr
                580                 585                 590
Gly Ser Val Asp Ser Gln Gly Ile Leu Pro Gly Met Val Trp Gln Asp
                595                 600                 605
Arg Asp Val Tyr Leu Gln Gly Pro Ile Trp Ala Lys Thr Pro His Thr
610                 615                 620
```

```
Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 68
<211> LENGTH: 735
<212> TYPE: PRT
<213> ORGANISM: Unknown
<220> FEATURE:
<223> OTHER INFORMATION: capsid protein of AAV serotype, clone A3.4

<400> SEQUENCE: 68

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Glu Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asp Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
```

```
                260                 265                 270
Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Ile Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
            435                 440                 445

Gln Gly Thr Ser Gly Thr Thr Gln Gln Ser Arg Leu Gln Phe Ser Gln
            450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
            485                 490                 495

Asn Ser Glu Phe Ala Trp Thr Ala Ala Thr Lys Tyr Tyr Leu Asn Gly
            500                 505                 510

Arg Asn Ser Leu Val Asn Pro Gly Pro Pro Met Ala Ser His Lys Asp
            515                 520                 525

Asp Glu Glu Lys Tyr Phe Pro Met His Gly Asn Leu Ile Phe Gly Lys
            530                 535                 540

Gln Gly Thr Gly Thr Thr Asn Val Asp Ile Glu Ser Val Leu Ile Thr
545                 550                 555                 560

Asp Glu Glu Ile Arg Thr Thr Asn Pro Val Ala Thr Glu Gln Tyr
            565                 570                 575

Gly Gln Val Ala Thr Asn His Gln Ser Gln Asp Thr Thr Ala Ser Tyr
            580                 585                 590

Gly Ser Val Asp Ser Gln Gly Ile Leu Pro Gly Met Val Trp Gln Asp
            595                 600                 605

Arg Asp Val Tyr Leu Gln Gly Pro Ile Trp Ala Lys Thr Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685
```

| | | | | | | | | | | | | | | | |
|---|---|---|---|---|---|---|---|---|---|---|---|---|---|---|---|
|Glu|Asn|Ser|Lys|Arg|Trp|Asn|Pro|Glu|Ile|Gln|Tyr|Thr|Ser|Asn|Tyr|
| |690| | | |695| | | |700| | | | | | |

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 69
<211> LENGTH: 735
<212> TYPE: PRT
<213> ORGANISM: Unknown
<220> FEATURE:
<223> OTHER INFORMATION: capsid protein of AAV serotype, clone A3.5

<400> SEQUENCE: 69

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu

```
                    325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Ile Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Lys Thr
            435                 440                 445
Gln Gly Thr Ser Gly Thr Thr Gln Gln Ser Arg Leu Gln Phe Asn Gln
            450                 455                 460
Ala Gly Pro Ser Ser Met Ala Gln Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Pro Asn Gly
            500                 505                 510
Arg Asn Ser Leu Val Asn Pro Gly Pro Pro Met Ala Ser His Lys Asp
            515                 520                 525
Asp Glu Glu Lys Tyr Phe Pro Met His Gly Asn Leu Ile Phe Gly Lys
            530                 535                 540
Gln Gly Thr Gly Thr Thr Asn Val Asp Ile Glu Ser Val Leu Ile Thr
545                 550                 555                 560
Asp Glu Glu Glu Ile Arg Thr Thr Asn Pro Val Ala Thr Glu Gln Tyr
                565                 570                 575
Gly Gln Val Ala Thr Asn Arg Gln Ser Gln Asn Thr Thr Ala Ser Tyr
            580                 585                 590
Gly Ser Val Asp Ser Gln Gly Ile Leu Pro Gly Met Val Trp Gln Asp
            595                 600                 605
Arg Asp Val Tyr Leu Gln Gly Pro Ile Trp Ala Lys Thr Pro His Thr
            610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ala Thr Thr Phe Thr Pro Gly Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
            690                 695                 700
Asn Lys Ser Val Asn Val Glu Phe Thr Val Asp Ala Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 70
<211> LENGTH: 735
```

-continued

```
<212> TYPE: PRT
<213> ORGANISM: Unknown
<220> FEATURE:
<223> OTHER INFORMATION: capsid protein of AAV serotype, clone AAV2

<400> SEQUENCE: 70

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
```

```
                385                 390                 395                 400
Gln Met Leu Arg Thr Gly Asn Asn Phe Thr Phe Ser Tyr Thr Phe Glu
                    405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                    485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                    645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                    725                 730                 735

<210> SEQ ID NO 71
<211> LENGTH: 736
<212> TYPE: PRT
<213> ORGANISM: Unknown
<220> FEATURE:
<223> OTHER INFORMATION: capsid protein of  AAV serotype, clone AAV3

<400> SEQUENCE: 71

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30
```

Lys Ala Asn Gln Gln His Gln Asp Asn Arg Arg Gly Leu Val Leu Pro
                35                  40                  45

Gly Tyr Lys Tyr Leu Gly Pro Gly Asn Gly Leu Asp Lys Gly Glu Pro
 50                  55                  60

Val Asn Glu Ala Asp Ala Ala Leu Glu His Asp Lys Ala Tyr Asp
 65              70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
                115                 120                 125

Leu Gly Leu Val Glu Glu Ala Ala Lys Thr Ala Pro Gly Lys Lys Gly
                130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
                210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
                290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser

```
                    450                 455                 460
    Gln Ala Gly Pro Gln Ser Met Ser Leu Gln Ala Arg Asn Trp Leu Pro
    465                 470                 475                 480

Gly Pro Cys Tyr Arg Gln Gln Arg Leu Ser Lys Thr Ala Asn Asp Asn
                        485                 490                 495

Asn Asn Ser Asn Phe Pro Trp Thr Ala Ala Ser Lys Tyr His Leu Asn
                    500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
    545                 550                 555                 560

Thr Asp Glu Glu Glu Ile Arg Thr Thr Asn Pro Val Ala Thr Glu Gln
                    565                 570                 575

Tyr Gly Thr Val Ala Asn Asn Leu Gln Ser Ser Asn Thr Ala Pro Thr
                580                 585                 590

Thr Gly Thr Val Asn His Gln Gly Ala Leu Pro Gly Met Val Trp Gln
                595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
    625                 630                 635                 640

Lys His Pro Pro Pro Gln Ile Met Ile Lys Asn Thr Pro Val Pro Ala
                    645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
    705                 710                 715                 720

Tyr Ser Glu Pro Arg Pro Ile Gly Thr Arg Tyr Leu Thr Arg Asn Leu
                    725                 730                 735

<210> SEQ ID NO 72
<211> LENGTH: 737
<212> TYPE: PRT
<213> ORGANISM: Unknown
<220> FEATURE:
<223> OTHER INFORMATION: capsid protein of AAV serotype, clone 3.3bVP1

<400> SEQUENCE: 72

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Asn Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Ala Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
        210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Glu Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
        370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asp Pro Gly Gly Thr Ala Gly Asn Arg Glu Leu Gln
        450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
```

-continued

```
                515                 520                 525
His Lys Asp Asp Glu Asp Arg Phe Phe Pro Ser Ser Gly Val Leu Ile
530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asp Pro Glu Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 73
<211> LENGTH: 644
<212> TYPE: PRT
<213> ORGANISM: Unknown
<220> FEATURE:
<223> OTHER INFORMATION: capsid protein of AAV serotype, clone 223-4

<400> SEQUENCE: 73

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
                20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
                100                 105                 110

Ala Gly Pro Ser Gly Leu Gly Ser Gly Thr Met Ala Ala Gly Gly Gly
            115                 120                 125

Ala Pro Met Ala Asp Asn Asn Glu Gly Ala Asp Gly Val Gly Asn Ala
130                 135                 140
```

```
Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
    530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575
```

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
        610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 74
<211> LENGTH: 644
<212> TYPE: PRT
<213> ORGANISM: Unknown
<220> FEATURE:
<223> OTHER INFORMATION: capsid protein of AAV serotype, clone 223-5

<400> SEQUENCE: 74

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly

```
                290             295             300
Ser Gln Ser Val Gly Arg Ser Ser Phe Tyr Cys Leu Glu Tyr Phe Pro
305             310             315             320

Ser Gln Met Leu Arg Thr Gly Asn Asn Phe Thr Phe Ser Tyr Thr Phe
            325             330             335

Glu Asp Val Pro Phe His Ser Ser Tyr Ala His Ser Gln Ser Leu Gly
            340             345             350

Arg Leu Met Asn Pro Leu Ile Asp Gln Tyr Leu Tyr Tyr Leu Ala Arg
            355             360             365

Thr Gln Ser Asn Ala Gly Gly Thr Ala Gly Asn Arg Glu Leu Gln Phe
            370             375             380

Tyr Gln Gly Gly Pro Thr Thr Met Ala Glu Gln Ala Lys Asn Trp Leu
385             390             395             400

Pro Gly Pro Cys Phe Arg Gln Gln Arg Val Ser Lys Thr Leu Asp Gln
            405             410             415

Asn Asn Asn Ser Asn Phe Ala Trp Thr Gly Ala Thr Lys Tyr His Leu
            420             425             430

Asn Gly Arg Asn Ser Leu Val Asn Pro Gly Val Ala Met Ala Thr His
            435             440             445

Lys Asp Asp Glu Glu Arg Phe Phe Pro Ser Ser Gly Val Leu Ile Phe
450             455             460

Gly Lys Thr Gly Ala Ala Asn Lys Thr Thr Leu Glu Asn Val Leu Met
465             470             475             480

Thr Asn Glu Glu Glu Ile Arg Pro Thr Asn Pro Val Ala Thr Glu Glu
            485             490             495

Tyr Gly Ile Val Ser Ser Asn Leu Gln Ala Ala Ser Thr Ala Ala Gln
            500             505             510

Thr Gln Val Val Asn Asn Gln Gly Ala Leu Pro Gly Met Val Trp Gln
            515             520             525

Asn Arg Asp Val Tyr Leu Gln Gly Pro Ile Trp Ala Lys Ile Pro His
            530             535             540

Thr Asp Gly Asn Phe His Pro Ser Pro Leu Met Gly Gly Phe Gly Leu
545             550             555             560

Lys His Pro Pro Pro Gln Ile Leu Ile Lys Asn Thr Pro Val Pro Ala
            565             570             575

Asn Pro Pro Glu Val Phe Thr Pro Ala Lys Phe Ala Ser Phe Ile Thr
            580             585             590

Gln Tyr Ser Thr Gly Gln Val Ser Val Glu Ile Glu Trp Glu Leu Gln
            595             600             605

Lys Glu Asn Ser Lys Arg Trp Asn Pro Glu Ile Gln Tyr Thr Ser Asn
610             615             620

Phe Asp Lys Gln Thr Gly Val Asp Phe Ala Val Asp Ser Gln Gly Val
625             630             635             640

Tyr Ser Glu Pro

<210> SEQ ID NO 75
<211> LENGTH: 644
<212> TYPE: PRT
<213> ORGANISM: Unknown
<220> FEATURE:
<223> OTHER INFORMATION: capsid protein of AAV serotype, clone 223-10
<220> FEATURE:
<221> NAME/KEY: MISC_FEATURE
<222> LOCATION: (434)..(434)
<223> OTHER INFORMATION: can be any amino acid

<400> SEQUENCE: 75
```

```
Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
50                      55                  60

Gly Lys Lys Arg Pro Val Asp Ser Pro Asp Ser Thr Ser Gly Ile Gly
65                      70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
                100                 105                 110

Ala Gly Pro Ser Gly Leu Gly Ser Gly Thr Met Ala Ala Gly Gly Gly
            115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
                180                 185                 190

Tyr Phe Gly Tyr Ser Thr Pro Trp Gly Tyr Phe Asp Phe Asn Arg Phe
            195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
                260                 265                 270

Tyr Val Leu Gly Ser Ala His Gln Gly Cys Leu Pro Pro Phe Pro Ala
                275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
            405                 410                 415

Asn Asn Asn Ser Asn Phe Ala Trp Thr Gly Ala Thr Lys Tyr His Leu
```

-continued

```
                420             425             430
Asn Xaa Arg Asn Ser Leu Val Asn Pro Gly Val Ala Met Ala Thr His
            435                 440                 445
Lys Asp Asp Glu Glu Arg Phe Phe Pro Ser Ser Gly Val Leu Ile Phe
450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
                485                 490                 495
Tyr Gly Ile Val Ser Ser Asn Leu Gln Ala Ala Ser Thr Ala Ala Gln
            500                 505                 510
Thr Gln Val Val Asn Asn Gln Gly Ala Leu Pro Gly Met Val Trp Gln
        515                 520                 525
Asn Arg Asp Val Tyr Leu Gln Gly Pro Ile Trp Ala Lys Ile Pro His
    530                 535                 540
Thr Asp Gly Asn Phe His Pro Ser Pro Leu Met Gly Gly Phe Gly Leu
545                 550                 555                 560
Lys His Pro Pro Pro Gln Ile Leu Ile Lys Asn Thr Pro Val Pro Ala
                565                 570                 575
Asn Pro Pro Glu Val Phe Thr Pro Ala Lys Phe Ala Ser Phe Ile Thr
            580                 585                 590
Gln Tyr Ser Thr Gly Gln Val Ser Val Glu Ile Glu Trp Glu Leu Gln
        595                 600                 605
Lys Glu Asn Ser Lys Arg Trp Asn Pro Glu Ile Gln Tyr Thr Ser Asn
    610                 615                 620
Phe Asp Lys Gln Thr Gly Val Asp Phe Ala Val Asp Ser Gln Gly Val
625                 630                 635                 640
Tyr Ser Glu Pro

<210> SEQ ID NO 76
<211> LENGTH: 644
<212> TYPE: PRT
<213> ORGANISM: Unknown
<220> FEATURE:
<223> OTHER INFORMATION: capsid protein of AAV serotype, clone 223-2

<400> SEQUENCE: 76

Lys Ala Tyr Asp Gln Gln Leu Lys Ala Gly Asp Asn Pro Tyr Leu Arg
1               5                   10                  15
Tyr Asn His Ala Asp Ala Glu Phe Gln Glu Cys Leu Gln Glu Asp Thr
            20                  25                  30
Ser Phe Gly Gly Asn Leu Gly Arg Ala Val Phe Gln Ala Lys Lys Arg
        35                  40                  45
Val Leu Glu Pro Leu Gly Leu Val Glu Thr Pro Ala Lys Thr Ala Pro
    50                  55                  60
Gly Lys Lys Arg Pro Val Asp Ser Pro Asp Ser Thr Ser Gly Ile Gly
65                  70                  75                  80
Lys Lys Gly Gln Gln Pro Ala Lys Lys Arg Leu Asn Phe Gly Gln Thr
                85                  90                  95
Gly Asp Ser Glu Ser Val Pro Asp Pro Gln Pro Ile Gly Glu Pro Pro
            100                 105                 110
Ala Gly Pro Ser Gly Leu Gly Ser Gly Thr Met Val Ala Gly Gly Gly
        115                 120                 125
Ala Pro Met Ala Asp Asn Asn Glu Gly Ala Asp Gly Val Gly Asn Ala
    130                 135                 140
```

-continued

```
Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
            165                 170                 175

Tyr Lys Gln Ile Ser Ser Gln Ser Ala Gly Ser Thr Asn Asp Asn Val
        180                 185                 190

Tyr Phe Gly Tyr Ser Thr Pro Trp Gly Tyr Phe Asp Phe Asn Arg Phe
    195                 200                 205

His Cys His Phe Ser Pro Arg Asp Trp Gln Arg Leu Ile Asn Asn Asn
210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
            245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Phe Pro Ala
    275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
            325                 330                 335

Glu Asp Val Pro Phe His Ser Ser Tyr Ala His Ser Gln Ser Leu Asp
            340                 345                 350

Arg Leu Met Asn Pro Leu Ile Asp Gln Tyr Leu Tyr Tyr Leu Ala Arg
            355                 360                 365

Thr Gln Ser Asn Ala Gly Gly Thr Ala Gly Asn Arg Glu Leu Gln Phe
        370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445

Lys Asp Asp Glu Glu Arg Phe Ser Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
            485                 490                 495

Tyr Gly Ile Val Ser Ser Asn Leu Gln Ala Ala Ser Thr Ala Ala Gln
        500                 505                 510

Thr Gln Val Val Asn Asn Gln Gly Ala Leu Pro Gly Met Val Trp Gln
    515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575
```

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
    610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 77
<211> LENGTH: 644
<212> TYPE: PRT
<213> ORGANISM: Unknown
<220> FEATURE:
<223> OTHER INFORMATION: capsid protein of AAV serotype, clone 223-7

<400> SEQUENCE: 77

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
            85                  90                  95

Gly Asp Ser Glu Ser Val Pro Asp Pro Gln Pro Ile Gly Glu Pro Pro
        100                 105                 110

Ala Gly Pro Ser Gly Leu Gly Ser Gly Thr Met Ala Ala Gly Gly Gly
    115                 120                 125

Ala Pro Met Ala Asp Asn Asn Glu Gly Ala Asp Gly Val Gly Asn Ala
130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
            165                 170                 175

Tyr Lys Gln Ile Ser Ser Gln Ser Ala Gly Ser Thr Asn Asp Asn Val
        180                 185                 190

Tyr Phe Gly Tyr Ser Thr Pro Trp Gly Tyr Phe Asp Phe Asn Arg Phe
    195                 200                 205

His Cys His Phe Ser Pro Arg Asp Trp Gln Arg Leu Ile Asn Asn Asn
210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
            245                 250                 255

Leu Thr Ser Thr Val Gln Val Phe Ser Asp Pro Glu Tyr Gln Leu Pro
        260                 265                 270

Tyr Val Leu Gly Ser Ala His Gln Gly Cys Leu Pro Pro Phe Pro Ala
    275                 280                 285

Asp Val Phe Met Ile Pro Gln Tyr Gly Tyr Leu Thr Leu Asn Asn Gly

```
                290                 295                 300
Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
                340                 345                 350

Arg Leu Met Asn Pro Leu Ile Asp Gln Tyr Leu Tyr Tyr Leu Ala Arg
                355                 360                 365

Thr Gln Ser Asn Ala Gly Gly Thr Ala Gly Asn Arg Glu Leu Gln Phe
                370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
                420                 425                 430

Asn Gly Arg Asn Ser Leu Val Asn Pro Gly Val Ala Met Ala Thr His
                435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
                500                 505                 510

Thr Gln Val Val Asn Asn Gln Gly Ala Leu Pro Gly Met Val Trp Gln
                515                 520                 525

Asn Arg Asp Val Tyr Leu Gln Gly Pro Ile Trp Ala Lys Ile Pro His
                530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Ile Ala Ser Phe Ile Thr
                580                 585                 590

Gln Tyr Ser Thr Gly Gln Val Ser Val Glu Ile Glu Trp Glu Leu Gln
                595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 78
<211> LENGTH: 644
<212> TYPE: PRT
<213> ORGANISM: Unknown
<220> FEATURE:
<223> OTHER INFORMATION: capsid protein of AAV serotype, clone 223-6

<400> SEQUENCE: 78

Lys Ala Tyr Asp Gln Gln Leu Lys Ala Gly Asp Asn Pro Tyr Leu Arg
1               5                   10                  15
```

-continued

```
Tyr Asn His Ala Asp Ala Glu Phe Gln Glu Arg Leu Gln Glu Asp Thr
         20                  25                  30

Ser Phe Gly Gly Asn Leu Gly Arg Ala Val Phe Gln Ala Lys Lys Arg
     35                  40                  45

Val Leu Glu Pro Leu Gly Leu Val Glu Thr Pro Ala Lys Thr Ala Pro
 50                  55                  60

Gly Lys Lys Arg Pro Val Asp Ser Pro Asp Ser Thr Ser Gly Ile Gly
 65                  70                  75                  80

Lys Lys Gly Gln Gln Pro Ala Lys Lys Arg Leu Asn Phe Gly Gln Thr
             85                  90                  95

Gly Asp Ser Glu Ser Val Pro Pro Gln Pro Ile Gly Glu Pro Pro
             100                 105                 110

Ala Gly Pro Ser Gly Leu Gly Ser Gly Thr Met Ala Ala Gly Gly Gly
         115                 120                 125

Ala Pro Met Ala Asp Asn Ser Glu Gly Ala Asp Gly Val Gly Asn Ala
     130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445
```

```
Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                    485                 490                 495

Tyr Gly Ile Val Ser Ser Asn Leu Gln Ala Ala Ser Thr Ala Ala Gln
                500                 505                 510

Thr Gln Val Val Asn Asn Gln Gly Ala Leu Pro Gly Met Val Trp Gln
            515                 520                 525

Asn Arg Asp Val Tyr Leu Gln Gly Pro Ile Trp Ala Lys Ile Pro His
        530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
                    565                 570                 575

Asn Pro Pro Glu Val Phe Thr Pro Ala Lys Leu Ala Ser Phe Ile Thr
                580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
        610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 79
<211> LENGTH: 738
<212> TYPE: PRT
<213> ORGANISM: Unknown
<220> FEATURE:
<223> OTHER INFORMATION: capsid protein of AAV serotype, clone 44.1

<400> SEQUENCE: 79

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
```

```
                    165                 170                 175
Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
                210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
                450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
                530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
                580                 585                 590
```

Pro Ile Val Gly Ala Val Asn Ser Gln Gly Ala Leu Pro Gly Met Val
          595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
              645                 650                 655

Pro Ala Asp Pro Pro Thr Thr Phe Ser Gln Ala Lys Leu Ala Ser Phe
              660                 665                 670

Ile Thr Gln Tyr Ser Thr Gly Gln Val Ser Val Glu Ile Glu Trp Glu
          675                 680                 685

Leu Gln Lys Glu Asn Ser Lys Arg Trp Asn Pro Glu Ile Gln Tyr Thr
          690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
              725                 730                 735

Asn Leu

<210> SEQ ID NO 80
<211> LENGTH: 738
<212> TYPE: PRT
<213> ORGANISM: Unknown
<220> FEATURE:
<223> OTHER INFORMATION: capsid protein of AAV serotype, clone 44.5

<400> SEQUENCE: 80

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Pro Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
```

-continued

```
                645                 650                 655
Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 81
<211> LENGTH: 738
<212> TYPE: PRT
<213> ORGANISM: Unknown
<220> FEATURE:
<223> OTHER INFORMATION: capsid protein of AAV serotype, clone 44.2

<400> SEQUENCE: 81

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270
```

```
Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700
```

```
Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 82
<211> LENGTH: 738
<212> TYPE: PRT
<213> ORGANISM: Unknown
<220> FEATURE:
<223> OTHER INFORMATION: capsid protein of AAV serotype, clone 29.3VP1

<400> SEQUENCE: 82

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Thr Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
```

```
                    325                 330                 335
Asn Asn Leu Thr Ser Thr Ile Gln Val Phe Thr Asp Ser Glu Tyr Gln
                340                 345                 350

Leu Pro Tyr Val Leu Gly Ser Ala Arg Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Gly Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 83
<211> LENGTH: 738
<212> TYPE: PRT
<213> ORGANISM: Unknown
<220> FEATURE:
<223> OTHER INFORMATION: capsid protein of AAV serotype, clone 29.5VP1

<400> SEQUENCE: 83

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Gly Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Ser Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

| | | | | | | | | | | | | | | | |
|---|---|---|---|---|---|---|---|---|---|---|---|---|---|---|---|
| Asn | Gly | Ser | Gln | Ala | Val | Gly | Arg | Ser | Ser | Phe | Tyr | Cys | Leu | Glu | Tyr |
| 385 | | | | 390 | | | | 395 | | | | 400 | | | |
| Phe | Pro | Ser | Gln | Met | Leu | Arg | Thr | Gly | Asn | Asn | Phe | Glu | Phe | Ser | Tyr |
| | | | 405 | | | | | 410 | | | | | 415 | | |
| Gln | Phe | Glu | Asp | Val | Pro | Phe | His | Ser | Ser | Tyr | Ala | His | Ser | Gln | Ser |
| | | | 420 | | | | | 425 | | | | | 430 | | |
| Leu | Asp | Arg | Leu | Met | Asn | Pro | Leu | Ile | Asp | Gln | Tyr | Leu | Tyr | Tyr | Leu |
| | | 435 | | | | | 440 | | | | | 445 | | | |
| Ser | Arg | Thr | Gln | Ser | Thr | Gly | Gly | Thr | Ala | Gly | Thr | Gln | Gln | Leu | Leu |
| | 450 | | | | | 455 | | | | | 460 | | | | |
| Phe | Ser | Gln | Ala | Gly | Pro | Asn | Asn | Met | Ser | Ala | Gln | Ala | Lys | Asn | Trp |
| 465 | | | | | 470 | | | | | 475 | | | | | 480 |
| Leu | Pro | Gly | Pro | Cys | Tyr | Arg | Gln | Arg | Val | Ser | Thr | Thr | Leu | Ser |
| | | | | 485 | | | | | 490 | | | | | 495 |
| Gln | Asn | Asp | Asn | Ser | Asn | Phe | Ala | Trp | Thr | Gly | Ala | Thr | Lys | Tyr | His |
| | | | 500 | | | | | 505 | | | | | 510 | | |
| Leu | Asn | Gly | Arg | Asp | Ser | Leu | Val | Asn | Pro | Gly | Val | Ala | Met | Ala | Thr |
| | | | 515 | | | | | 520 | | | | | 525 | | |
| His | Lys | Asp | Asp | Glu | Glu | Arg | Phe | Phe | Pro | Ser | Ser | Gly | Val | Leu | Met |
| | 530 | | | | | 535 | | | | | 540 | | | | |
| Phe | Gly | Lys | Gln | Gly | Ala | Gly | Lys | Asp | Asn | Val | Asp | Tyr | Ser | Ser | Val |
| 545 | | | | | 550 | | | | | 555 | | | | | 560 |
| Met | Leu | Thr | Ser | Glu | Glu | Glu | Ile | Lys | Thr | Thr | Asn | Pro | Val | Ala | Thr |
| | | | | 565 | | | | | 570 | | | | | 575 | |
| Glu | Gln | Tyr | Gly | Val | Val | Ala | Asp | Asn | Leu | Gln | Gln | Asn | Ala | Ala |
| | | | 580 | | | | | 585 | | | | | 590 | | |
| Pro | Ile | Val | Gly | Ala | Val | Asn | Ser | Gln | Gly | Ala | Leu | Pro | Gly | Met | Val |
| | | 595 | | | | | 600 | | | | | 605 | | | |
| Trp | Gln | Asn | Arg | Asp | Val | Tyr | Leu | Gln | Gly | Pro | Ile | Trp | Ala | Lys | Ile |
| | 610 | | | | | 615 | | | | | 620 | | | | |
| Pro | His | Thr | Asp | Gly | Asn | Phe | His | Pro | Ser | Pro | Leu | Met | Gly | Gly | Phe |
| 625 | | | | | 630 | | | | | 635 | | | | | 640 |
| Gly | Leu | Lys | His | Pro | Pro | Pro | Gln | Ile | Leu | Ile | Lys | Asn | Thr | Pro | Val |
| | | | | 645 | | | | | 650 | | | | | 655 | |
| Pro | Ala | Asp | Pro | Pro | Thr | Thr | Phe | Ser | Gln | Ala | Lys | Leu | Ala | Ser | Phe |
| | | | 660 | | | | | 665 | | | | | 670 | | |
| Ile | Thr | Gln | Tyr | Ser | Thr | Gly | Gln | Val | Ser | Val | Glu | Ile | Glu | Trp | Glu |
| | | 675 | | | | | 680 | | | | | 685 | | | |
| Leu | Gln | Lys | Glu | Asn | Ser | Lys | Arg | Trp | Asn | Pro | Glu | Ile | Gln | Tyr | Thr |
| | 690 | | | | | 695 | | | | | 700 | | | | |
| Ser | Asn | Tyr | Tyr | Lys | Ser | Thr | Asn | Val | Asp | Phe | Ala | Val | Asn | Thr | Asp |
| 705 | | | | | 710 | | | | | 715 | | | | | 720 |
| Gly | Thr | Tyr | Ser | Glu | Pro | Arg | Pro | Ile | Gly | Thr | Arg | Tyr | Leu | Thr | Arg |
| | | | | 725 | | | | | 730 | | | | | 735 | |
| Asn | Leu | | | | | | | | | | | | | | |

<210> SEQ ID NO 84
<211> LENGTH: 738
<212> TYPE: PRT
<213> ORGANISM: Unknown
<220> FEATURE:
<223> OTHER INFORMATION: capsid protein of AAV serotype, clone 42.15

<400> SEQUENCE: 84

Met Ala Ala Asp Gly Tyr Leu Pro Asp Trp Leu Glu Asp Asn Leu Ser

-continued

```
1               5               10              15
Glu Gly Ile Arg Glu Trp Trp Asp Leu Lys Pro Gly Ala Pro Lys Pro
                20              25              30
Lys Ala Asn Gln Gln Lys Gln Asp Asp Gly Arg Gly Leu Val Leu Pro
                35              40              45
Gly Tyr Lys Tyr Leu Gly Pro Phe Asn Gly Leu Asp Lys Gly Glu Pro
    50              55              60
Val Asn Ala Ala Asp Ala Ala Leu Glu His Asp Lys Ala Tyr Asp
65              70              75              80
Gln Gln Leu Lys Ala Gly Asp Asn Pro Tyr Leu Arg Tyr Asn His Ala
                85              90              95
Asp Ala Glu Phe Gln Glu Arg Leu Gln Glu Asp Thr Ser Phe Gly Gly
                100             105             110
Asn Leu Gly Arg Ala Val Phe Gln Ala Lys Lys Arg Val Leu Glu Pro
                115             120             125
Leu Gly Leu Val Glu Glu Gly Ala Lys Thr Ala Pro Gly Lys Lys Arg
                130             135             140
Pro Val Glu Pro Ser Pro Gln Arg Ser Pro Asp Ser Ser Thr Gly Ile
145             150             155             160
Gly Lys Thr Gly Gln Gln Pro Ala Lys Lys Arg Leu Asn Phe Gly Gln
                165             170             175
Thr Gly Asp Ser Glu Ser Val Pro Asp Pro Gln Pro Ile Gly Glu Pro
                180             185             190
Pro Ala Gly Pro Ser Gly Leu Gly Ser Gly Thr Met Ala Ala Gly Gly
                195             200             205
Gly Ala Pro Met Ala Asp Asn Asn Glu Gly Ala Asp Gly Val Gly Ser
                210             215             220
Ser Ser Gly Asn Trp His Cys Asp Ser Thr Trp Leu Gly Asp Arg Val
225             230             235             240
Ile Thr Thr Ser Thr Arg Thr Trp Ala Leu Pro Thr Tyr Asn Asn His
                245             250             255
Leu Tyr Lys Gln Ile Ser Asn Gly Thr Ser Gly Gly Ser Thr Asn Asp
                260             265             270
Asn Thr Tyr Phe Gly Tyr Ser Thr Pro Trp Gly Tyr Phe Asp Phe Asn
                275             280             285
Arg Phe His Cys His Phe Ser Pro Arg Asp Trp Gln Arg Leu Ile Asn
                290             295             300
Asn Asn Trp Gly Phe Arg Pro Lys Arg Leu Asn Phe Lys Leu Phe Asn
305             310             315             320
Ile Gln Val Lys Glu Val Thr Gln Asn Glu Gly Thr Lys Thr Ile Ala
                325             330             335
Asn Asn Leu Thr Ser Thr Ile Gln Val Phe Thr Asp Ser Glu Tyr Gln
                340             345             350
Leu Pro Tyr Val Leu Gly Ser Ala His Gln Gly Cys Pro Pro Pro Phe
                355             360             365
Pro Ala Asp Val Phe Met Ile Pro Gln Tyr Gly Tyr Leu Thr Leu Asn
                370             375             380
Asn Gly Ser Gln Ala Val Gly Arg Ser Ser Phe Tyr Cys Leu Glu Tyr
385             390             395             400
Phe Pro Ser Gln Met Arg Arg Thr Gly Asn Asn Phe Glu Phe Ser Tyr
                405             410             415
Gln Phe Glu Asp Val Pro Phe His Ser Ser Tyr Ala His Ser Gln Ser
                420             425             430
```

-continued

```
Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 85
<211> LENGTH: 738
<212> TYPE: PRT
<213> ORGANISM: Unknown
<220> FEATURE:
<223> OTHER INFORMATION: capsid protein of AAV serotype, clone 42.8

<400> SEQUENCE: 85

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser 485                 490                 495
Gln Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 86
<211> LENGTH: 733
<212> TYPE: PRT
<213> ORGANISM: Unknown
<220> FEATURE:
<223> OTHER INFORMATION: capsid protein of AAV serotype, clone 42.13

<400> SEQUENCE: 86

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

```
                                -continued

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Ala Pro Met Ala
            195                 200                 205

Asp Asn Asn Glu Gly Ala Asp Gly Val Gly Ser Ser Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His
    275                 280                 285

Phe Ser Pro Arg Asp Trp Gln Arg Leu Ile Asn Asn Asn Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
            340                 345                 350

Gly Ser Ala His Gln Gly Cys Leu Pro Pro Phe Pro Ala Asp Val Phe
    355                 360                 365

Met Ile Pro Gln Tyr Gly Tyr Leu Thr Leu Asn Asn Gly Ser Gln Ala
    370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
    435                 440                 445

Thr Gly Gly Thr Ala Gly Thr Gln Gln Leu Leu Phe Ser Gln Ala Gly
    450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495

Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Gly Asp Glu
    515                 520                 525

Glu Arg Phe Phe Pro Ser Ser Gly Val Leu Met Phe Gly Lys Gln Gly
    530                 535                 540
```

```
Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Gln Tyr Gly Val
            565                 570                 575

Val Ala Asp Asn Leu Gln Gln Gln Asn Ala Ala Pro Ile Val Gly Ala
                580                 585                 590

Val Asn Ser Gln Gly Ala Leu Pro Gly Met Val Trp Gln Asn Arg Asp
            595                 600                 605

Val Tyr Leu Gln Gly Pro Ile Trp Ala Lys Ile Pro His Thr Asp Gly
            610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
                660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Tyr Lys
            690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Ser Leu
                725                 730

<210> SEQ ID NO 87
<211> LENGTH: 733
<212> TYPE: PRT
<213> ORGANISM: Unknown
<220> FEATURE:
<223> OTHER INFORMATION: capsid protein of AAV serotype, clone 42.3A

<400> SEQUENCE: 87

Met Ala Ala Asp Gly His Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175
```

-continued

```
Ser Val Pro Asp Pro Gln Pro Ile Gly Glu Pro Ala Gly Pro Ser
            180                 185                 190
Gly Leu Gly Ser Gly Thr Met Ala Gly Gly Ala Pro Met Ala
        195                 200                 205
Asp Asn Asn Glu Gly Ala Asp Gly Val Gly Ser Ser Gly Asn Trp
            210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                    245                 250                 255
Ser Asn Gly Thr Ser Gly Gly Ser Thr Asn Asp Asn Thr Tyr Phe Gly
            260                 265                 270
Tyr Ser Thr Pro Trp Gly Tyr Phe Asp Phe Asn Arg Phe His Cys His
            275                 280                 285
Phe Ser Pro Arg Asp Trp Gln Arg Leu Ile Asn Asn Ser Trp Gly Phe
            290                 295                 300
Arg Pro Lys Arg Leu Asn Phe Lys Leu Phe Asn Ile Gln Val Lys Glu
305                 310                 315                 320
Val Thr Gln Asn Glu Gly Thr Lys Thr Ile Ala Asn Asn Leu Thr Ser
                    325                 330                 335
Thr Ile Gln Val Phe Thr Asp Ser Glu Tyr Gln Leu Pro Tyr Val Leu
            340                 345                 350
Gly Ser Ala His Gln Gly Cys Leu Pro Pro Phe Pro Ala Asp Val Phe
            355                 360                 365
Met Ile Pro Gln Tyr Gly Tyr Leu Thr Leu Asn Asn Gly Ser Gln Ala
            370                 375                 380
Val Gly Arg Ser Ser Phe Tyr Cys Leu Glu Tyr Phe Pro Ser Gln Met
385                 390                 395                 400
Leu Arg Thr Gly Asn Asn Phe Glu Phe Ser Tyr Gln Phe Glu Asp Val
                    405                 410                 415
Pro Phe His Ser Ser Tyr Ala His Ser Gln Ser Leu Asp Arg Leu Met
            420                 425                 430
Asn Pro Leu Ile Asp Gln Tyr Leu Tyr Tyr Leu Ser Arg Thr Gln Ser
            435                 440                 445
Thr Gly Gly Thr Ala Gly Thr Gln Gln Leu Leu Phe Ser Gln Ala Gly
        450                 455                 460
Pro Asn Asn Met Ser Ala Gln Ala Lys Asn Trp Leu Pro Gly Pro Cys
465                 470                 475                 480
Tyr Arg Gln Gln Arg Val Ser Thr Thr Leu Ser Gln Asn Asn Asn Ser
                    485                 490                 495
Asn Phe Ala Trp Thr Gly Ala Thr Lys Tyr His Leu Asn Gly Arg Asp
            500                 505                 510
Ser Leu Val Asn Pro Gly Val Ala Met Ala Thr His Lys Asp Asp Glu
        515                 520                 525
Glu Arg Phe Phe Pro Ser Ser Gly Val Leu Met Phe Gly Lys Gln Gly
            530                 535                 540
Ala Gly Lys Asp Asn Val Asp Tyr Ser Ser Val Met Leu Thr Ser Glu
545                 550                 555                 560
Glu Glu Ile Lys Thr Thr Asn Pro Val Ala Thr Glu Gln Tyr Gly Val
                    565                 570                 575
Val Ala Asp Asn Leu Gln Gln Gln Asn Ala Ala Pro Ile Val Gly Ala
            580                 585                 590
Val Asn Ser Gln Gly Ala Leu Pro Gly Met Val Trp Gln Asn Arg Asp
            595                 600                 605
```

```
Val Tyr Leu Gln Gly Pro Ile Trp Ala Lys Ile Pro His Thr Asp Gly
    610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
        675                 680                 685

Ser Lys Arg Trp Asn Pro Glu Ile Gln Tyr Thr Ser Asn Tyr Tyr Lys
    690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 88
<211> LENGTH: 731
<212> TYPE: PRT
<213> ORGANISM: Unknown
<220> FEATURE:
<223> OTHER INFORMATION: capsid protein of AAV serotype, clone 42.4

<400> SEQUENCE: 88

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240
```

-continued

Arg Thr Trp Ala Leu Pro Thr Tyr Asn Asn His Leu Tyr Lys Gln Ile
            245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Ser Arg Asp Trp Gln Arg Leu Ile Asn Asn Trp Gly Phe Arg Pro
290                 295                 300

Lys Arg Leu Asn Phe Lys Leu Phe Asn Ile Gln Val Lys Glu Val Thr
305                 310                 315                 320

Gln Asn Glu Gly Thr Lys Thr Ile Ala Asn Asn Leu Thr Ser Thr Ile
            325                 330                 335

Gln Val Phe Thr Asp Ser Glu Tyr Arg Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ala Val Gly
            370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
            405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ser Arg Thr Gln Ser Thr Gly
            435                 440                 445

Gly Thr Ala Gly Thr Gln Gln Leu Leu Phe Ser Gln Ala Gly Pro Asn
450                 455                 460

Asn Met Ser Ala Gln Ala Lys Asn Trp Leu Pro Gly Pro Cys Tyr Arg
465                 470                 475                 480

Gln Gln Arg Val Ser Thr Thr Leu Ser Gln Asn Asn Asn Ser Asn Phe
            485                 490                 495

Ala Trp Thr Gly Ala Thr Lys Tyr His Leu Asn Gly Arg Asp Ser Leu
            500                 505                 510

Val Asn Pro Gly Val Ala Met Ala Thr His Lys Asp Asp Glu Glu Arg
            515                 520                 525

Phe Phe Pro Ser Ser Gly Val Leu Met Phe Gly Lys Gln Gly Ala Gly
            530                 535                 540

Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
            565                 570                 575

Asp Asn Leu Gln Gln Gln Asn Ala Ala Pro Ile Val Gly Ala Val Asn
            580                 585                 590

Ser Gln Gly Ala Leu Pro Gly Met Val Trp Gln Asn Arg Asp Val Tyr
            595                 600                 605

Leu Gln Gly Pro Ile Trp Ala Lys Ile Pro His Thr Asp Gly Asn Phe
            610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
            645                 650                 655

Phe Ser Gln Ala Lys Pro Ala Ser Phe Ile Thr Gln Tyr Ser Thr Gly
            660                 665                 670

```
Gln Val Ser Val Glu Ile Glu Trp Glu Leu Gln Lys Glu Asn Ser Lys
        675                 680                 685

Arg Trp Asn Pro Glu Ile Gln Tyr Thr Ser Asn Tyr Tyr Lys Ser Thr
        690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
            725                 730

<210> SEQ ID NO 89
<211> LENGTH: 731
<212> TYPE: PRT
<213> ORGANISM: Unknown
<220> FEATURE:
<223> OTHER INFORMATION: capsid protein of AAV serotype, clone 42.5A

<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Arg Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Arg Gly Phe Arg Pro
290                 295                 300
```

```
Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
            325                 330                 335

Gln Val Phe Ser Asp Ser Glu Tyr Gln Leu Pro Tyr Val Leu Gly Ser
        340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ser Arg Thr Gln Ser Thr Gly
        435                 440                 445

Gly Thr Ala Gly Thr Gln Gln Leu Leu Phe Ser Gln Ala Gly Pro Asn
    450                 455                 460

Asn Met Ser Ala Gln Ala Lys Asn Trp Leu Pro Gly Pro Cys Tyr Arg
465                 470                 475                 480

Gln Gln Arg Val Ser Thr Thr Leu Ser Gln Asn Asn Ser Asn Phe
                485                 490                 495

Ala Trp Thr Gly Ala Thr Lys Tyr His Leu Asn Gly Arg Asp Ser Leu
            500                 505                 510

Val Asn Pro Gly Val Ala Met Ala Thr His Lys Asp Asp Glu Glu Arg
    515                 520                 525

Phe Phe Pro Ser Ser Gly Val Leu Met Phe Gly Lys Gln Gly Ala Gly
    530                 535                 540

Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
            565                 570                 575

Asp Asn Leu Gln Gln Gln Asn Ala Ala Pro Ile Val Gly Ala Val Asn
        580                 585                 590

Ser Gln Gly Ala Leu Pro Gly Met Ala Trp Gln Asn Arg Asp Val Tyr
    595                 600                 605

Leu Gln Gly Pro Ile Trp Ala Lys Ile Pro His Thr Asp Gly Asn Phe
    610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
            645                 650                 655

Phe Ser Gln Ala Lys Leu Ala Ser Phe Ile Thr Gln Tyr Ser Thr Gly
        660                 665                 670

Gln Val Ser Val Glu Ile Glu Trp Glu Leu Gln Lys Glu Asn Ser Lys
        675                 680                 685

Arg Trp Asn Pro Glu Ile Gln Tyr Thr Ser Asn Tyr Tyr Lys Ser Thr
    690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
            725                 730
```

<210> SEQ ID NO 90
<211> LENGTH: 733
<212> TYPE: PRT
<213> ORGANISM: Unknown
<220> FEATURE:
<223> OTHER INFORMATION: capsid protein of AAV serotype, clone 42.1B

<400> SEQUENCE: 90

| Met | Ala | Ala | Asp | Gly | Tyr | Leu | Pro | Asp | Trp | Leu | Glu | Asp | Asn | Leu | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Gly | Ile | Arg | Glu | Trp | Trp | Asp | Leu | Arg | Pro | Gly | Ala | Pro | Lys | Pro |
|     |     |     | 20  |     |     |     |     | 25  |     |     |     |     | 30  |     |     |

| Lys | Ala | Asn | Gln | Gln | Lys | Gln | Asp | Asp | Gly | Arg | Gly | Leu | Val | Leu | Pro |
|     |     |     | 35  |     |     |     |     | 40  |     |     |     |     | 45  |     |     |

| Gly | Tyr | Lys | Tyr | Leu | Gly | Pro | Phe | Asn | Gly | Leu | Asp | Lys | Gly | Glu | Pro |
|     |     | 50  |     |     |     |     | 55  |     |     |     |     | 60  |     |     |     |

| Val | Asn | Glu | Ala | Asp | Ala | Ala | Leu | Glu | His | Asp | Lys | Ala | Tyr | Asp |
| 65  |     |     |     | 70  |     |     |     |     | 75  |     |     |     |     | 80  |

| Lys | Gln | Leu | Glu | Gln | Gly | Asp | Asn | Pro | Tyr | Leu | Lys | Tyr | Asn | His | Ala |
|     |     |     |     | 85  |     |     |     |     | 90  |     |     |     |     | 95  |     |

| Asp | Ala | Glu | Phe | Gln | Glu | Arg | Leu | Gln | Glu | Asp | Thr | Ser | Phe | Gly | Gly |
|     |     |     | 100 |     |     |     |     | 105 |     |     |     |     | 110 |     |     |

| Asn | Leu | Gly | Arg | Ala | Val | Phe | Gln | Ala | Lys | Lys | Arg | Val | Leu | Glu | Pro |
|     |     |     | 115 |     |     |     |     | 120 |     |     |     |     | 125 |     |     |

| Leu | Gly | Leu | Val | Glu | Glu | Gly | Ala | Lys | Thr | Ala | Pro | Gly | Lys | Lys | Arg |
|     | 130 |     |     |     |     | 135 |     |     |     |     | 140 |     |     |     |     |

| Pro | Ile | Glu | Ser | Pro | Asp | Ser | Ser | Thr | Gly | Ile | Gly | Lys | Lys | Gly | Gln |
| 145 |     |     |     |     | 150 |     |     |     |     | 155 |     |     |     |     | 160 |

| Gln | Pro | Ala | Lys | Lys | Arg | Leu | Asn | Phe | Gly | Gln | Thr | Gly | Asp | Ser | Glu |
|     |     |     |     | 165 |     |     |     |     | 170 |     |     |     |     | 175 |     |

| Ser | Val | Pro | Asp | Pro | Gln | Pro | Ile | Gly | Glu | Pro | Pro | Ala | Gly | Pro | Ser |
|     |     |     | 180 |     |     |     |     | 185 |     |     |     |     | 190 |     |     |

| Gly | Leu | Gly | Ser | Gly | Thr | Met | Ala | Ala | Gly | Gly | Ala | Pro | Met | Ala |
|     |     | 195 |     |     |     |     | 200 |     |     |     |     | 205 |     |     |

| Asp | Asn | Asn | Glu | Gly | Ala | Asp | Gly | Val | Gly | Ser | Ser | Ser | Gly | Asn | Trp |
|     | 210 |     |     |     |     | 215 |     |     |     |     | 220 |     |     |     |     |

| His | Cys | Asp | Ser | Thr | Trp | Leu | Gly | Asp | Arg | Val | Ile | Thr | Thr | Ser | Thr |
| 225 |     |     |     |     | 230 |     |     |     |     | 235 |     |     |     |     | 240 |

| Arg | Thr | Trp | Ala | Leu | Pro | Thr | Tyr | Asn | Asn | His | Leu | Tyr | Lys | Gln | Ile |
|     |     |     |     | 245 |     |     |     |     | 250 |     |     |     |     | 255 |     |

| Ser | Asn | Gly | Thr | Ser | Gly | Gly | Ser | Thr | Asn | Asp | Asn | Thr | Tyr | Phe | Gly |
|     |     |     | 260 |     |     |     |     | 265 |     |     |     |     | 270 |     |     |

| Tyr | Ser | Thr | Pro | Trp | Gly | Tyr | Phe | Asp | Phe | Asn | Arg | Phe | His | Cys | His |
|     |     | 275 |     |     |     |     | 280 |     |     |     |     | 285 |     |     |     |

| Phe | Ser | Pro | Arg | Asp | Trp | Gln | Arg | Leu | Ile | Asn | Asn | Trp | Gly | Phe |
|     | 290 |     |     |     |     | 295 |     |     |     |     | 300 |     |     |     |

| Arg | Pro | Lys | Arg | Leu | Asn | Phe | Lys | Leu | Phe | Asn | Ile | Gln | Val | Lys | Glu |
| 305 |     |     |     |     | 310 |     |     |     |     | 315 |     |     |     |     | 320 |

| Val | Thr | Gln | Asn | Glu | Gly | Thr | Lys | Thr | Ile | Ala | Asn | Asn | Leu | Thr | Ser |
|     |     |     |     | 325 |     |     |     |     | 330 |     |     |     |     | 335 |     |

| Thr | Ile | Gln | Val | Phe | Thr | Asp | Ser | Glu | Tyr | Gln | Leu | Pro | Tyr | Val | Leu |
|     |     |     | 340 |     |     |     |     | 345 |     |     |     |     | 350 |     |     |

| Gly | Ser | Ala | His | Gln | Gly | Cys | Leu | Pro | Pro | Phe | Pro | Ala | Asp | Val | Phe |
|     |     | 355 |     |     |     |     | 360 |     |     |     |     | 365 |     |     |     |

```
Met Ile Pro Gln Tyr Gly Tyr Leu Thr Leu Asn Asn Gly Ser Gln Ala
            370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
            435                 440                 445

Thr Gly Gly Thr Ala Gly Thr Gln Gln Leu Leu Phe Ser Gln Ala Gly
            450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495

Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Gly Asp Glu
            515                 520                 525

Glu Arg Phe Phe Pro Ser Ser Gly Val Leu Met Phe Gly Lys Gln Gly
            530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
            580                 585                 590

Val Asn Ser Gln Gly Ala Leu Pro Gly Met Val Trp Gln Asn Arg Asp
            595                 600                 605

Val Tyr Leu Gln Gly Pro Ile Trp Ala Lys Ile Pro His Thr Asp Gly
            610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Tyr Lys
            690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 91
<211> LENGTH: 738
<212> TYPE: PRT
<213> ORGANISM: Unknown
<220> FEATURE:
<223> OTHER INFORMATION: capsid protein of AAV serotype, clone 42.5B

<400> SEQUENCE: 91

Met Ala Ala Asp Gly Tyr Leu Pro Asp Trp Leu Glu Asp Asn Leu Ser
```

-continued

```
1               5                   10                  15
Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430
```

-continued

```
Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 92
<211> LENGTH: 738
<212> TYPE: PRT
<213> ORGANISM: Unknown
<220> FEATURE:
<223> OTHER INFORMATION: capsid protein of AAV serotype, clone 43.1

<400> SEQUENCE: 92

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Pro Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
```

485                 490                 495
Gln Asn Asn Asn Ser Asn Phe Ala Trp Thr Gly Ala Thr Lys Tyr His
                 500                 505                 510

Leu Asn Gly Arg Asp Ser Leu Val Asn Pro Gly Val Ala Met Ala Thr
             515                 520                 525

His Lys Asp Asp Glu Glu Arg Phe Phe Pro Ser Ser Gly Val Leu Met
         530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 93
<211> LENGTH: 738
<212> TYPE: PRT
<213> ORGANISM: Unknown
<220> FEATURE:
<223> OTHER INFORMATION: capsid protein of AAV serotype, clone 43.12

<400> SEQUENCE: 93

Met Ala Ala Asp Gly Tyr Leu Pro Asp Trp Leu Glu Asp Asn Leu Ser
1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

```
Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
            195                 200                 205

Gly Ala Pro Met Ala Asp Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540
```

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Thr Asn Gly Ala
                580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 94
<211> LENGTH: 738
<212> TYPE: PRT
<213> ORGANISM: Unknown
<220> FEATURE:
<223> OTHER INFORMATION: capsid protein of AAV serotype, clone 43.5

<400> SEQUENCE: 94

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln

```
                    165                 170                 175
Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
            450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590
```

-continued

```
Pro Ile Val Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
            645                 650                 655

Pro Ala Asp Pro Pro Thr Thr Phe Ser Gln Ala Lys Leu Ala Ser Phe
        660                 665                 670

Ile Thr Gln Tyr Ser Thr Gly Gln Val Ser Val Glu Ile Glu Trp Glu
    675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu
```

<210> SEQ ID NO 95
<211> LENGTH: 738
<212> TYPE: PRT
<213> ORGANISM: Unknown
<220> FEATURE:
<223> OTHER INFORMATION: capsid protein of AAV serotype, clone AAV8

<400> SEQUENCE: 95

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Gly Val Gly Pro Asn Thr Met Ala Ala Gly Gly
    195                 200                 205

Gly Ala Pro Met Ala Asp Asn Asn Glu Gly Ala Asp Gly Val Gly Ser
210                 215                 220
```

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
```

```
                        645                 650                 655
Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 96
<211> LENGTH: 736
<212> TYPE: PRT
<213> ORGANISM: Unknown
<220> FEATURE:
<223> OTHER INFORMATION: capsid protein of AAV serotype, clone 43.21

<400> SEQUENCE: 96

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270
```

-continued

```
Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Gly Thr Lys Thr Ile Ala Asn
                325                 330                 335

Asn Leu Thr Ser Thr Val Arg Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Ser
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700
```

-continued

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 97
<211> LENGTH: 736
<212> TYPE: PRT
<213> ORGANISM: Unknown
<220> FEATURE:
<223> OTHER INFORMATION: capsid protein of AAV serotype, clone 43.25

<400> SEQUENCE: 97

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

-continued

```
            Asn Leu Thr Ser Thr Val Gln Val Phe Thr Asp Ser Glu Tyr Gln Leu
                            340                 345                 350

Pro Tyr Val Leu Gly Ser Ala His Gln Gly Cys Leu Pro Pro Phe Pro
                        355                 360                 365

Ala Asp Val Phe Met Val Pro Gln Tyr Gly Tyr Leu Thr Leu Asn Asn
            370                 375                 380

Gly Ser Gln Ala Leu Gly Arg Ser Ser Phe Tyr Cys Leu Glu Tyr Phe
        385                 390                 395                 400

Pro Ser Gln Met Leu Arg Thr Gly Asn Asn Phe Gln Phe Ser Tyr Thr
                            405                 410                 415

Phe Glu Asp Val Pro Phe His Ser Ser Tyr Ala His Ser Gln Ser Leu
                        420                 425                 430

Asp Arg Leu Met Asn Pro Leu Ile Asp Gln Tyr Leu Tyr Tyr Leu Val
                    435                 440                 445

Arg Thr Gln Thr Thr Gly Thr Gly Thr Gln Thr Leu Ala Phe Ser
                450                 455                 460

Gln Ala Gly Pro Ser Ser Met Ala Asn Gln Ala Arg Asn Trp Val Pro
        465                 470                 475                 480

Gly Pro Cys Tyr Arg Gln Gln Arg Val Ser Thr Thr Thr Asn Gln Asn
                            485                 490                 495

Asn Asn Ser Asn Phe Ala Trp Thr Gly Ala Ala Lys Phe Lys Leu Asn
                        500                 505                 510

Gly Arg Asp Ser Leu Met Asn Pro Gly Val Ala Met Ala Ser His Lys
                    515                 520                 525

Asp Asp Asp Asp Arg Phe Phe Pro Ser Ser Gly Val Leu Ile Phe Gly
            530                 535                 540

Lys Gln Gly Ala Gly Asn Asp Gly Val Asp Tyr Ser Gln Val Leu Ile
        545                 550                 555                 560

Thr Asp Glu Glu Glu Ile Lys Ala Thr Asn Pro Val Ala Thr Glu Glu
                            565                 570                 575

Tyr Gly Ala Val Ala Ile Asn Asn Gln Ala Ala Asn Thr Gln Ala Gln
                        580                 585                 590

Thr Gly Leu Val His Asn Gln Gly Val Ile Pro Gly Met Val Trp Gln
                    595                 600                 605

Asn Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Leu
        625                 630                 635                 640

Lys His Pro Pro Pro Gln Ile Leu Ile Lys Asn Thr Pro Val Pro Ala
                            645                 650                 655

Asp Pro Pro Leu Thr Phe Asn Gln Ala Lys Leu Asn Ser Phe Ile Thr
                        660                 665                 670

Gln Tyr Ser Thr Gly Gln Val Ser Val Glu Ile Glu Trp Glu Leu Gln
                    675                 680                 685

Lys Glu Asn Ser Lys Arg Trp Asn Pro Glu Ile Gln Tyr Thr Ser Asn
            690                 695                 700

Tyr Tyr Lys Ser Thr Asn Val Asp Phe Ala Val Asn Thr Glu Gly Val
        705                 710                 715                 720

Tyr Ser Glu Pro Arg Pro Ile Gly Thr Arg Tyr Leu Thr Arg Asn Leu
                            725                 730                 735

<210> SEQ ID NO 98
<211> LENGTH: 736
<212> TYPE: PRT
<213> ORGANISM: Unknown
```

```
<220> FEATURE:
<223> OTHER INFORMATION: capsid protein of AAV serotype, clone 43.23

<400> SEQUENCE: 98

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Leu Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400
```

```
Pro Ser Gln Met Pro Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 99
<211> LENGTH: 736
<212> TYPE: PRT
<213> ORGANISM: Unknown
<220> FEATURE:
<223> OTHER INFORMATION: capsid protein of AAV serotype, clone 43.20

<400> SEQUENCE: 99

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
```

```
                35                  40                  45
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Leu Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Ser Gly Leu Gly Pro Asn Thr Met Ala Ser Gly Gly Gly
                195                 200                 205

Ala Pro Met Ala Asp Asn Asn Glu Gly Ala Asp Gly Val Gly Asn Ser
                210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Thr Val Pro Gln Tyr Gly Tyr Leu Thr Leu Asn Asn
                370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
                435                 440                 445

Arg Thr Gln Thr Thr Gly Thr Gly Gly Thr Gln Thr Leu Ala Phe Ser
450                 455                 460
```

-continued

```
Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
            485                 490                 495

Asn Asn Ser Asn Phe Ala Trp Thr Gly Ala Ala Lys Phe Lys Leu Asn
        500                 505                 510

Gly Arg Asp Ser Leu Met Asn Pro Gly Val Ala Met Ala Ser His Lys
    515                 520                 525

Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
    595                 600                 605

Asn Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 100
<211> LENGTH: 736
<212> TYPE: PRT
<213> ORGANISM: Unknown
<220> FEATURE:
<223> OTHER INFORMATION: capsid protein of AAV serotype, clone AAV9

<400> SEQUENCE: 100

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
```

-continued

```
            100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
            130                 135                 140
Pro Val Glu Gln Ser Pro Gln Glu Pro Asp Ser Ser Gly Ile Gly
145                 150                 155                 160
Lys Ser Gly Gln Gln Pro Ala Lys Lys Arg Leu Asn Phe Gly Gln Thr
            165                 170                 175
Gly Asp Ser Glu Ser Val Pro Asp Pro Gln Pro Leu Gly Glu Pro Pro
            180                 185                 190
Glu Ala Pro Ser Gly Leu Gly Pro Asn Thr Met Ala Ser Gly Gly Gly
            195                 200                 205
Ala Pro Met Ala Asp Asn Asn Glu Gly Ala Asp Gly Val Gly Asn Ser
            210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Gly Thr Ser Gly Gly Ser Thr Asn Asp Asn
            260                 265                 270
Thr Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Glu Gly Thr Lys Thr Ile Ala Asn
            325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
            355                 360                 365
Ala Asp Val Phe Met Val Pro Gln Tyr Gly Tyr Leu Thr Leu Asn Asn
            370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
            405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Val
            435                 440                 445
Arg Thr Gln Thr Thr Gly Thr Gly Gly Thr Gln Thr Leu Ala Phe Ser
            450                 455                 460
Gln Ala Gly Pro Ser Ser Met Ala Asn Gln Ala Arg Asn Trp Val Pro
465                 470                 475                 480
Gly Pro Cys Tyr Arg Gln Gln Arg Val Ser Thr Thr Thr Asn Gln Asn
            485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
            515                 520                 525
```

-continued

Asp Asp Glu Asp Arg Phe Phe Pro Ser Ser Gly Val Leu Ile Phe Gly
530                535                540

Lys Gln Gly Ala Gly Asn Asp Gly Val Asp Tyr Ser Gln Val Leu Ile
545                550                555                560

Thr Asp Glu Glu Glu Ile Lys Ala Thr Asn Pro Val Ala Thr Glu Glu
            565                570                575

Tyr Gly Ala Val Ala Ile Asn Asn Gln Ala Ala Asn Thr Gln Ala Gln
            580                585                590

Thr Gly Leu Val His Asn Gln Gly Val Ile Pro Gly Met Val Trp Gln
        595                600                605

Asn Arg Asp Val Tyr Leu Gln Gly Pro Ile Trp Ala Lys Ile Pro His
610                615                620

Thr Asp Gly Asn Phe His Pro Ser Pro Leu Met Gly Gly Phe Gly Leu
625                630                635                640

Lys His Pro Pro Pro Gln Ile Leu Ile Lys Asn Thr Pro Val Pro Ala
            645                650                655

Asp Pro Pro Leu Thr Phe Asn Gln Ala Lys Leu Asn Ser Phe Ile Thr
            660                665                670

Gln Tyr Ser Thr Gly Gln Val Ser Val Glu Ile Glu Trp Glu Leu Gln
        675                680                685

Lys Glu Asn Ser Lys Arg Trp Asn Pro Glu Ile Gln Tyr Thr Ser Asn
690                695                700

Tyr Tyr Lys Ser Thr Asn Val Asp Phe Ala Val Asn Thr Glu Gly Val
705                710                715                720

Tyr Ser Glu Pro Arg Pro Ile Gly Thr Arg Tyr Leu Thr Arg Asn Leu
            725                730                735

<210> SEQ ID NO 101
<211> LENGTH: 728
<212> TYPE: PRT
<213> ORGANISM: Unknown
<220> FEATURE:
<223> OTHER INFORMATION: capsid protein of AAV serotype, clone 24.1

<400> SEQUENCE: 101

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Arg Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Val Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu

-continued

```
                    165                 170                 175
Ser Val Pro Asp Pro Gln Pro Leu Gly Glu Pro Ala Ala Pro Ser
            180                 185                 190
Gly Leu Gly Ser Gly Thr Met Ala Ala Gly Gly Ala Pro Met Ala
            195                 200                 205
Asp Asn Asn Glu Gly Ala Asp Gly Val Gly Asn Ala Ser Gly Asn Trp
            210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Ser Tyr Ser
            260                 265                 270
Thr Pro Trp Gly Tyr Phe Asp Phe Asn Arg Phe His Cys His Phe Ser
            275                 280                 285
Pro Arg Asp Trp Gln Arg Leu Ile Asn Asn Asn Trp Gly Phe Arg Pro
            290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
            355                 360                 365
Pro Gln Tyr Gly Tyr Leu Thr Leu Asn Asn Gly Ser Gln Ser Val Gly
            370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Val His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
            435                 440                 445
Gly Ser Thr Arg Glu Leu Gln Phe His Gln Ala Gly Pro Asn Thr Met
            450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
Thr Gly Ala Thr Lys Tyr His Leu Asn Gly Arg Asn Ser Leu Thr Asn
            500                 505                 510
Pro Gly Val Ala Met Ala Thr Asn Lys Asp Asp Glu Asp Gln Phe Phe
            515                 520                 525
Pro Ile Asn Gly Val Leu Val Phe Gly Lys Thr Gly Ala Ala Asn Lys
            530                 535                 540
Thr Thr Leu Glu Asn Val Leu Met Thr Ser Glu Glu Ile Lys Thr
545                 550                 555                 560
Thr Asn Pro Val Ala Thr Glu Glu Tyr Gly Val Val Ser Ser Asn Leu
                565                 570                 575
Gln Ser Ser Thr Ala Gly Pro Gln Thr Gln Thr Val Asn Ser Gln Gly
            580                 585                 590
```

```
Ala Leu Pro Gly Met Val Trp Gln Asn Arg Asp Val Cys Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
                675                 680                 685

Pro Glu Ile Gln Tyr Thr Ser Asn Tyr Ala Lys Ser Asn Asn Val Glu
                690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 102
<211> LENGTH: 728
<212> TYPE: PRT
<213> ORGANISM: Unknown
<220> FEATURE:
<223> OTHER INFORMATION: capsid protein of AAV serotype, clone 42.2REAL

<400> SEQUENCE: 102

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
                180                 185                 190

Gly Leu Gly Ser Gly Thr Met Ala Ala Gly Gly Gly Ala Pro Met Ala
            195                 200                 205

Asp Asn Asn Glu Gly Ala Asp Gly Val Gly Asn Ala Ser Gly Asn Trp
        210                 215                 220

His Cys Asp Ser Thr Trp Leu Gly Asp Arg Val Ile Thr Thr Ser Thr
```

```
              225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Glu Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655
```

-continued

```
Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
            725

<210> SEQ ID NO 103
<211> LENGTH: 728
<212> TYPE: PRT
<213> ORGANISM: Unknown
<220> FEATURE:
<223> OTHER INFORMATION: capsid protein of AAV serotype, clone 7.2VP1

<400> SEQUENCE: 103

Met Ala Ala Asp Gly Tyr Leu Pro Asp Trp Leu Glu Gly Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Arg Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Asn Gly Gln
145                 150                 155                 160

Pro Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
```

```
                      290                 295                 300
Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                    325                 330                 335

Gln Val Phe Ser Asp Ser Glu Tyr Gln Leu Pro Tyr Val Leu Gly Ser
                        340                 345                 350

Ala His Gln Gly Cys Leu Pro Pro Phe Pro Ala Asp Val Phe Met Ile
                355                 360                 365

Pro Gln Tyr Gly Tyr Leu Thr Leu Asn Gly Ser Gln Ser Val Gly
        370                 375                 380

Arg Ser Ser Phe Tyr Cys Leu Glu Tyr Phe Pro Ser Gln Met Leu Arg
385                 390                 395                 400

Thr Gly Asp Asn Phe Glu Phe Ser Tyr Thr Phe Glu Glu Val Pro Phe
                    405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720
```

Thr Arg Tyr Leu Thr Arg Asn Leu
            725

<210> SEQ ID NO 104
<211> LENGTH: 728
<212> TYPE: PRT
<213> ORGANISM: Unknown
<220> FEATURE:
<223> OTHER INFORMATION: capsid protein of AAV serotype, clone 27.3VP1

<400> SEQUENCE: 104

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Ser Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile

```
                355              360              365
Pro Gln Tyr Gly Tyr Leu Thr Leu Asn Asn Gly Ser Gln Ser Val Gly
370              375              380
Arg Ser Ser Phe Cys Cys Leu Glu Tyr Phe Pro Ser Gln Met Leu Arg
385              390              395              400
Thr Gly Asn Asn Phe Glu Phe Ser Tyr Thr Phe Glu Val Pro Phe
            405              410              415
His Ser Ser Tyr Ala His Ser Gln Ser Leu Asp Arg Leu Met Asn Pro
            420              425              430
Leu Ile Asp Gln Tyr Leu Tyr Tyr Leu Ala Arg Thr Gln Ser Thr Thr
            435              440              445
Gly Ser Thr Arg Glu Leu Gln Phe His Gln Ala Gly Pro Asn Thr Val
            450              455              460
Ala Glu Gln Ser Lys Asn Trp Leu Pro Gly Pro Cys Tyr Arg Gln Gln
465              470              475              480
Arg Leu Ser Lys Asn Ile Asp Ser Asn Asn Ser Asn Phe Ala Trp
            485              490              495
Thr Gly Ala Thr Lys Tyr His Leu Asn Gly Arg Asn Ser Leu Thr Asn
            500              505              510
Pro Gly Val Ala Met Ala Thr Asn Lys Asp Asp Glu Asp Gln Phe Leu
            515              520              525
Pro Ile Asn Gly Val Leu Val Phe Gly Lys Thr Gly Ala Ala Asn Lys
530              535              540
Thr Thr Leu Glu Asn Val Leu Met Thr Ser Glu Glu Ile Lys Thr
545              550              555              560
Thr Asn Pro Val Ala Thr Glu Glu Tyr Gly Val Val Ser Ser Asn Leu
            565              570              575
Gln Ser Ser Thr Ala Gly Pro Arg Thr Gln Thr Val Asn Ser Gln Gly
            580              585              590
Ala Leu Pro Gly Met Val Trp Gln Asn Arg Asp Val Tyr Leu Gln Gly
            595              600              605
Pro Ile Trp Ala Glu Ile Pro His Thr Asp Gly Asn Phe His Pro Ser
610              615              620
Pro Leu Met Gly Gly Phe Gly Leu Lys His Pro Pro Gln Ile Leu
625              630              635              640
Ile Lys Asn Thr Pro Val Pro Ala Asn Pro Pro Glu Val Phe Thr Pro
            645              650              655
Ala Lys Phe Ala Ser Phe Ile Thr Gln Tyr Ser Thr Gly Gln Val Ser
            660              665              670
Val Glu Ile Glu Trp Glu Leu Gln Lys Glu Asn Ser Lys Arg Trp Asn
            675              680              685
Pro Glu Ile Gln Tyr Thr Ser Asn Tyr Ala Lys Ser Asn Asn Val Glu
            690              695              700
Phe Ala Val Asn Asn Glu Gly Val Tyr Thr Glu Pro Arg Pro Ile Gly
705              710              715              720
Thr Arg Tyr Leu Thr Arg Asn Leu
                725
```

<210> SEQ ID NO 105
<211> LENGTH: 728
<212> TYPE: PRT
<213> ORGANISM: Unknown
<220> FEATURE:
<223> OTHER INFORMATION: capsid protein of AAV serotype, clone 16.3VP1

<400> SEQUENCE: 105

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
                180                 185                 190

Gly Leu Gly Ser Gly Thr Met Ala Ala Gly Gly Gly Ala Pro Met Ala
            195                 200                 205

Asp Asn Asn Glu Gly Ala Asp Gly Val Gly Asn Ala Ser Gly Asn Trp
            210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
                260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Asn Trp Gly Phe Arg Pro
            290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Met Gly
            370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
```

-continued

```
                420              425              430
Leu Ile Asp Gln Tyr Leu Tyr Tyr Leu Ala Arg Thr Gln Ser Thr Thr
            435              440              445
Gly Ser Thr Arg Glu Leu Gln Phe His Gln Ala Gly Pro Asn Thr Met
        450              455              460
Ala Glu Gln Ser Lys Asn Trp Leu Pro Gly Pro Cys Tyr Arg Gln Gln
465              470              475              480
Arg Leu Ser Lys Asn Ile Asp Ser Asn Asn Ser Asn Phe Ala Trp
                485              490              495
Thr Gly Ala Thr Lys Tyr His Leu Asn Gly Arg Asn Ser Leu Thr Asn
            500              505              510
Pro Gly Val Ala Met Ala Thr Asn Lys Asp Asp Glu Gly Gln Phe Phe
        515              520              525
Pro Ile Asn Gly Val Leu Val Phe Gly Lys Thr Gly Ala Ala Asn Lys
        530              535              540
Thr Thr Leu Glu Asn Val Leu Met Thr Ser Glu Glu Ile Lys Thr
545              550              555              560
Thr Asn Pro Val Ala Thr Glu Glu Tyr Gly Val Val Ser Ser Asn Leu
                565              570              575
Gln Ser Ser Thr Ala Gly Pro Gln Thr Gln Thr Val Asn Ser Gln Gly
            580              585              590
Ala Leu Pro Gly Met Val Trp Gln Asn Arg Asp Val Tyr Leu Gln Gly
                595              600              605
Pro Ile Trp Ala Lys Ile Pro His Thr Asp Gly Asn Phe His Pro Ser
        610              615              620
Pro Leu Met Gly Gly Phe Gly Leu Lys His Pro Pro Gln Ile Leu
625              630              635              640
Ile Lys Asn Thr Pro Val Pro Ala Asn Pro Pro Gly Val Phe Thr Pro
                645              650              655
Ala Leu Phe Ala Ser Phe Ile Thr Gln Tyr Ser Thr Gly Gln Val Ser
            660              665              670
Val Glu Ile Glu Trp Glu Leu Gln Lys Glu Asn Ser Lys Arg Trp Asn
        675              680              685
Pro Glu Ile Gln Tyr Thr Ser Asn Tyr Ala Lys Ser Asn Asn Val Glu
        690              695              700
Phe Ala Val Asn Asn Glu Gly Val Tyr Thr Glu Pro Arg Pro Ile Gly
705              710              715              720
Thr Arg Tyr Leu Thr Arg Asn Leu
                725

<210> SEQ ID NO 106
<211> LENGTH: 728
<212> TYPE: PRT
<213> ORGANISM: Unknown
<220> FEATURE:
<223> OTHER INFORMATION: capsid protein of AAV serotype, clone 42.10

<400> SEQUENCE: 106

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
```

```
Val Asn Glu Ala Asp Ala Ala Leu Glu His Asp Lys Ala Tyr Asp
 65                  70                  75                  80

Lys Gln Leu Glu Gln Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Arg Lys Gly Gln
145                 150                 155                 160

Gln Pro Ala Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
                260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
        450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Asn Ser Asn Phe Ala Trp
```

```
                    485                 490                 495
Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
        530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 107
<211> LENGTH: 728
<212> TYPE: PRT
<213> ORGANISM: Unknown
<220> FEATURE:
<223> OTHER INFORMATION: capsid protein of AAV serotype, clone 42.3B

<400> SEQUENCE: 107

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

Leu Gly Leu Val Glu Glu Gly Ala Lys Thr Ala Pro Gly Lys Lys Arg
    130                 135                 140
Pro Ile Glu Ser Pro Asp Ser Ser Thr Gly Ile Gly Lys Lys Gly Gln
145                 150                 155                 160
Gln Pro Ala Lys Lys Leu Asn Phe Gly Thr Gly Asp Ser Glu
            165                 170                 175
Ser Val Pro Asp Pro Gln Pro Ile Gly Glu Pro Pro Ala Gly Pro Ser
            180                 185                 190
Gly Leu Gly Ser Gly Thr Met Ala Ala Gly Gly Ala Pro Met Ala
            195                 200                 205
Asp Asn Asn Glu Gly Ala Asp Gly Val Gly Asn Ala Ser Gly Asn Trp
            210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
            275                 280                 285
Pro Arg Asp Trp Gln Arg Leu Ile Asn Asn Trp Gly Phe Arg Pro
290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
            355                 360                 365
Pro Gln Tyr Gly Tyr Leu Thr Leu Asn Asn Gly Ser Gln Ser Val Gly
            370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
            435                 440                 445
Gly Ser Thr Arg Glu Leu Gln Phe His Gln Ala Gly Pro Asn Thr Met
450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Thr Ser Asn Phe Ala Trp
                485                 490                 495
Thr Gly Ala Thr Lys Tyr His Leu Asn Gly Arg Asn Ser Leu Thr Asn
            500                 505                 510
Pro Gly Val Ala Met Ala Thr Asn Lys Asp Asp Glu Asp Gln Phe Phe
            515                 520                 525
Pro Ile Asn Gly Val Leu Val Phe Gly Lys Thr Gly Ala Ala Asn Lys
530                 535                 540
Thr Thr Leu Glu Asn Val Leu Met Thr Ser Glu Glu Glu Ile Lys Thr

-continued

```
              545                 550                 555                 560
Thr Asn Pro Val Ala Thr Glu Gln Tyr Gly Val Val Ser Ser Asn Leu
                565                 570                 575
Gln Ser Ser Thr Ala Gly Pro Gln Thr Gln Thr Val Asn Ser Gln Gly
                580                 585                 590
Ala Leu Pro Gly Met Val Trp Gln Asn Arg Asp Val Tyr Leu Gln Gly
                595                 600                 605
Pro Ile Trp Ala Lys Ile Pro His Thr Asp Gly Asn Phe His Pro Ser
610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Pro Glu Val Phe Thr Pro
                645                 650                 655
Ala Lys Phe Ala Ser Phe Ile Thr Gln Tyr Ser Thr Gly Gln Val Ser
                660                 665                 670
Val Glu Ile Glu Trp Glu Leu Gln Lys Glu Asn Ser Lys Arg Trp Asn
                675                 680                 685
Pro Glu Ile Gln Tyr Thr Ser Asn Tyr Ala Lys Ser Asn Asn Val Glu
                690                 695                 700
Phe Ala Val Asn Asn Glu Gly Val Tyr Thr Glu Pro Arg Pro Ile Gly
705                 710                 715                 720
Thr Arg Tyr Leu Thr Arg Asn Leu
                725

<210> SEQ ID NO 108
<211> LENGTH: 728
<212> TYPE: PRT
<213> ORGANISM: Unknown
<220> FEATURE:
<223> OTHER INFORMATION: capsid protein of AAV serotype, clone 42.11

<400> SEQUENCE: 108

Met Ala Ala Asp Gly Tyr Leu Pro Asp Trp Leu Glu Asp Asn Leu Ser
1                   5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
                35                  40                  45
Gly Tyr Lys Tyr Leu Gly Pro Phe Asn Gly Leu Asp Lys Gly Glu Pro
            50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Ile Glu Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Ile Gly Glu Pro Ala Gly Pro Ser
                180                 185                 190
```

```
Gly Leu Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
            245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Asn Trp Gly Phe Arg Pro
            290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
            325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
            370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
            405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Arg Gln
465                 470                 475                 480

Arg Leu Ser Lys Asp Ile Asp Ser Asn Asn Ser Asn Phe Ala Trp
            485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
            565                 570                 575

Gln Ser Ser Thr Ala Gly Pro Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
```

```
                      610                 615                 620
Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                    645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
                    675                 680                 685

Pro Glu Ile Gln Tyr Thr Ser Asn Tyr Ala Lys Ser Asn Asn Val Glu
                690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                    725

<210> SEQ ID NO 109
<211> LENGTH: 729
<212> TYPE: PRT
<213> ORGANISM: Unknown
<220> FEATURE:
<223> OTHER INFORMATION: capsid protein of AAV serotype, clone F1VP1

<400> SEQUENCE: 109

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Ser Val Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255
```

```
Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Trp Gly Phe Arg
290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
                340                 345                 350

Ser Ala His Gln Gly Cys Leu Pro Pro Phe Pro Ala Asp Val Phe Met
            355                 360                 365

Ile Pro Gln Tyr Gly Tyr Leu Thr Leu Asn Asn Gly Ser Gln Ser Val
        370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Thr
        435                 440                 445

Thr Gly Ser Thr Arg Glu Leu Gln Phe His Gln Ala Gly Pro Asn Thr
    450                 455                 460

Met Ala Glu Gln Ser Lys Asn Trp Leu Pro Gly Pro Cys Tyr Arg Gln
465                 470                 475                 480

Gln Gly Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
            500                 505                 510

Asn Pro Gly Ile Pro Met Ala Thr Asn Lys Asp Asp Glu Asp Gln Phe
        515                 520                 525

Phe Pro Ile Asn Gly Val Leu Val Phe Gly Lys Thr Gly Ala Ala Asn
    530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
                565                 570                 575

Leu Gln Pro Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
        595                 600                 605

Gly Pro Ile Trp Ala Lys Ile Pro His Thr Asp Gly Asn Phe His Pro
    610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
```

```
                675                 680                 685
Asn Pro Glu Ile Gln Tyr Thr Ser Asn Tyr Ala Lys Ser Asn Val
    690                 695                 700

Glu Phe Ala Val Asn Pro Asp Gly Val Tyr Thr Glu Pro Arg Pro Ile
705                 710                 715                 720

Gly Thr Arg Tyr Leu Pro Arg Asn Leu
                725

<210> SEQ ID NO 110
<211> LENGTH: 729
<212> TYPE: PRT
<213> ORGANISM: Unknown
<220> FEATURE:
<223> OTHER INFORMATION: capsid protein of AAV serotype, clone F5VP1[@0003]

<400> SEQUENCE: 110

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Gly Ala Pro Thr Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Asn Trp Gly Phe Arg
    290                 295                 300

Pro Lys Lys Leu Arg Phe Lys Leu Phe Asn Ile Gln Val Lys Glu Val
305                 310                 315                 320
```

-continued

```
Thr Thr Asn Asp Gly Val Thr Thr Ile Ala Asn Asn Leu Thr Ser Thr
            325                 330                 335
Val Gln Val Phe Ser Asp Ser Glu Tyr Gln Leu Pro Tyr Val Leu Gly
            340                 345                 350
Ser Ala His Gln Gly Cys Leu Pro Pro Phe Pro Ala Asp Val Phe Met
            355                 360                 365
Ile Pro Gln Tyr Gly Tyr Leu Thr Leu Asn Asn Gly Ser Gln Ser Val
370                 375                 380
Gly Arg Ser Ser Phe Tyr Cys Leu Glu Tyr Phe Pro Ser Gln Met Leu
385                 390                 395                 400
Arg Thr Gly Asn Asn Phe Glu Phe Ser Tyr Ser Phe Glu Asp Val Pro
            405                 410                 415
Phe His Ser Ser Tyr Ala His Ser Gln Ser Leu Asp Arg Leu Met Asn
            420                 425                 430
Pro Leu Ile Asp Gln Tyr Leu Tyr Tyr Leu Ala Arg Thr Gln Ser Thr
            435                 440                 445
Thr Gly Ser Thr Arg Glu Leu Gln Phe His Gln Ala Gly Pro Asn Thr
            450                 455                 460
Met Ala Glu Gln Ser Lys Asn Trp Leu Pro Gly Pro Cys Tyr Arg Gln
465                 470                 475                 480
Gln Arg Leu Ser Lys Asn Leu Asp Phe Asn Asn Asn Ser Asn Phe Ala
            485                 490                 495
Trp Thr Ala Ala Thr Lys Tyr His Leu Asn Gly Arg Asn Ser Leu Thr
            500                 505                 510
Asn Pro Gly Ile Pro Met Ala Thr Asn Lys Asp Asp Glu Asp Gln Phe
            515                 520                 525
Phe Pro Ile Asn Gly Val Leu Val Phe Gly Lys Thr Gly Ala Ala Asn
            530                 535                 540
Lys Thr Thr Leu Glu Asn Val Leu Met Thr Ser Glu Glu Ile Lys
545                 550                 555                 560
Thr Thr Asn Pro Val Ala Thr Glu Glu Tyr Gly Val Val Ser Ser Asn
            565                 570                 575
Leu Gln Ser Ser Thr Ala Gly Pro Gln Ser Gln Thr Ile Asn Ser Gln
            580                 585                 590
Gly Ala Leu Pro Gly Met Val Trp Gln Asn Arg Asp Val Tyr Leu Gln
            595                 600                 605
Gly Pro Ile Trp Ala Lys Ile Pro His Thr Asp Gly Asn Phe His Pro
610                 615                 620
Ser Pro Leu Met Gly Gly Phe Gly Leu Glu His Pro Pro Gln Ile
625                 630                 635                 640
Leu Ile Lys Asn Thr Pro Val Pro Ala Asn Pro Glu Val Phe Thr
            645                 650                 655
Pro Ala Lys Phe Ala Ser Phe Ile Thr Gln Tyr Ser Thr Gly Gln Val
            660                 665                 670
Ser Val Glu Ile Glu Trp Glu Leu Gln Lys Glu Asn Ser Lys Arg Trp
            675                 680                 685
Asn Pro Glu Ile Gln Tyr Thr Ser Asn Tyr Ala Lys Ser Asn Asn Val
            690                 695                 700
Glu Phe Ala Val Asn Pro Asp Gly Val Tyr Thr Glu Pro Arg Pro Ile
705                 710                 715                 720
Gly Thr Arg Tyr Leu Thr Arg Asn Leu
            725
```

-continued

```
<210> SEQ ID NO 111
<211> LENGTH: 729
<212> TYPE: PRT
<213> ORGANISM: Unknown
<220> FEATURE:
<223> OTHER INFORMATION: capsid protein of AAV serotype, clone F3VP1

<400> SEQUENCE: 111

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Gly Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Asn Trp Gly Phe Arg
    290                 295                 300

Pro Lys Lys Leu Arg Phe Lys Leu Leu Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365

Ile Pro Gln Tyr Gly Tyr Leu Thr Leu Asp Asn Gly Ser Gln Ser Val
    370                 375                 380
```

```
Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
            405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Thr
            435                 440                 445

Thr Gly Ser Thr Arg Glu Leu Gln Phe His Gln Ala Gly Pro Asn Thr
450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
            500                 505                 510

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
            530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
                565                 570                 575

Leu Gln Ser Ser Thr Ala Gly Pro Gln Ser Gln Thr Ile Asn Ser Gln
                580                 585                 590

Gly Ala Leu Pro Gly Met Val Trp Gln Asn Arg Asp Val Tyr Leu Gln
                595                 600                 605

Gly Pro Ile Trp Ala Lys Ile Pro His Thr Asp Gly Asn Phe His Pro
610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Ala Lys Ser Asn Asn Val
            690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
                725

<210> SEQ ID NO 112
<211> LENGTH: 735
<212> TYPE: PRT
<213> ORGANISM: Unknown
<220> FEATURE:
<223> OTHER INFORMATION: capsid protein of AAV serotype, clone 42.6B

<400> SEQUENCE: 112

Met Ala Ala Asp Gly Tyr Leu Pro Asp Trp Leu Glu Asp Asn Leu Ser
1               5                   10                  15
```

```
Glu Gly Ile Arg Glu Trp Trp Asp Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Ala Leu Glu His Asp Lys Ala Tyr Asp
 65                  70                  75                  80

Lys Gln Leu Glu Gln Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Arg Lys Leu Arg Phe Lys Leu Phe Asn
305                 310                 315                 320

Ile Gln Val Lys Glu Val Thr Thr Asp Asp Gly Val Thr Thr Ile Ala
                325                 330                 335

Asn Asn Leu Thr Ser Thr Ile Gln Val Phe Ser Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Glu Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445
```

Ala Arg Thr Gln Ser Thr Thr Gly Ser Thr Arg Glu Leu Gln Phe His
    450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
            500                 505                 510

Gly Arg Asn Ser Leu Thr Asn Pro Gly Val Ala Met Ala Thr Asn Lys
        515                 520                 525

Asp Asp Glu Asp Gln Phe Phe Pro Ile Asn Gly Val Leu Val Phe Gly
    530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Asp Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Ala Lys Ser Asn Asn Val Glu Phe Ala Val Asn Asn Glu Gly Val Tyr
705                 710                 715                 720

Thr Glu Pro Arg Pro Ile Gly Thr Arg Tyr Leu Thr Arg Asn Leu
                725                 730                 735

<210> SEQ ID NO 113
<211> LENGTH: 685
<212> TYPE: PRT
<213> ORGANISM: Unknown
<220> FEATURE:
<223> OTHER INFORMATION: capsid protein of AAV serotype, clone 42.12

<400> SEQUENCE: 113

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

```
Lys Gln Leu Glu Gln Gly Asp Asn Pro Tyr Leu Lys Tyr Asn His Ala
                 85                  90                  95

Asp Ala Glu Phe Gln Glu Arg Leu Gln Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
            420                 425                 430

Leu Asp Arg Leu Thr Asn Pro Leu Ile Asp Gln Tyr Leu Tyr Tyr Leu
            435                 440                 445

Ala Arg Thr Gln Ser Thr Thr Gly Ser Thr Arg Gly Leu Gln Phe His
            450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
            500                 505                 510
```

```
Gly Arg Asn Ser Leu Thr Asn Pro Gly Val Ala Met Ala Thr Asn Lys
            515                 520                 525

Asp Asp Glu Asp Gln Phe Phe Pro Ile Asn Gly Val Leu Val Phe Gly
            530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Glu Tyr
                    565                 570                 575

Gly Val Val Ser Ser Asn Leu Gln Ser Ser Thr Ala Gly Pro Gln Thr
                580                 585                 590

Gln Thr Val Asn Ser Gln Gly Ala Leu Pro Gly Met Val Trp Gln Asn
            595                 600                 605

Arg Asp Val Tyr Leu Gln Gly Pro Ile Trp Ala Lys Ile Pro His Thr
            610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Tyr Thr Ser Asn Tyr Tyr Lys
                    645                 650                 655

Ser Thr Asn Val Asp Phe Ala Val Asn Thr Glu Gly Thr Tyr Ser Glu
                660                 665                 670

Pro Arg Pro Ile Gly Thr Arg Tyr Leu Thr Arg Asn Leu
            675                 680                 685

<210> SEQ ID NO 114
<211> LENGTH: 724
<212> TYPE: PRT
<213> ORGANISM: Unknown
<220> FEATURE:
<223> OTHER INFORMATION: capsid protein of AAV serotype, clone AAV5CAP

<400> SEQUENCE: 114

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190
```

-continued

```
Met Ser Ala Gly Gly Gly Pro Leu Gly Asp Asn Gln Gly Ala
        195                 200                 205
Asp Gly Val Gly Asn Ala Ser Gly Asp Trp His Cys Asp Ser Thr Trp
210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
        260                 265                 270
Phe Asp Phe Asn Arg Phe His Ser His Trp Ser Pro Arg Asp Trp Gln
        275                 280                 285
Arg Leu Ile Asn Asn Tyr Trp Gly Phe Arg Pro Arg Ser Leu Arg Val
        290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
        340                 345                 350
Leu Pro Ala Phe Pro Pro Gln Val Phe Thr Leu Pro Gln Tyr Gly Tyr
        355                 360                 365
Ala Thr Leu Asn Arg Asp Asn Thr Glu Asn Pro Thr Glu Arg Ser Ser
        370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
        420                 425                 430
Gln Tyr Leu Tyr Arg Phe Val Ser Thr Asn Asn Thr Gly Gly Val Gln
        435                 440                 445
Phe Asn Lys Asn Leu Ala Gly Arg Tyr Ala Asn Thr Tyr Lys Asn Trp
450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
        500                 505                 510
Asn Asn Leu Gln Gly Ser Asn Thr Tyr Ala Leu Glu Asn Thr Met Ile
        515                 520                 525
Phe Asn Ser Gln Pro Ala Asn Pro Gly Thr Thr Ala Thr Tyr Leu Glu
530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
        580                 585                 590
Gly Ser Val Trp Met Glu Arg Asp Val Tyr Leu Gln Gly Pro Ile Trp
        595                 600                 605
Ala Lys Ile Pro Glu Thr Gly Ala His Phe His Pro Ser Pro Ala Met
610                 615                 620
```

```
Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
        660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 115
<211> LENGTH: 9
<212> TYPE: DNA
<213> ORGANISM: Artificial Sequence
<220> FEATURE:
<223> OTHER INFORMATION: DraIII restriction enzyme site

<400> SEQUENCE: 115 caccacgtc                                                             9

<210> SEQ ID NO 116
<211> LENGTH: 28
<212> TYPE: DNA
<213> ORGANISM: Unknown
<220> FEATURE:
<223> OTHER INFORMATION: AV2cas

<400> SEQUENCE: 116
cgcagagacc aaagttcaac tgaaacga                                        28

<210> SEQ ID NO 117
<211> LENGTH: 255
<212> TYPE: DNA
<213> ORGANISM: Unknown
<220> FEATURE:
<223> OTHER INFORMATION: adeno-associated virus serotype 10

<400> SEQUENCE: 117
ggtaattcct ccggaaattg gcattgcgat tccacatggc tgggcgacag agtcatcacc     60
accagcaccc gaacctgggt cctgcccacc tacaacaacc acatctacaa gcaaatctcc    120
agcgagacag gagccaccaa cgacaaccac tacttcggct acagcacccc ctggggggtat   180 tttgacttta cagattcca  ctgccacttt tcaccacgtg actggcagcg actcatcaac    240
aacaactggg gattc                                                     255

<210> SEQ ID NO 118
<211> LENGTH: 258
<212> TYPE: DNA
<213> ORGANISM: Unknown
<220> FEATURE:
<223> OTHER INFORMATION: adeno-associated virus serotype 11

<400> SEQUENCE: 118
ggtaattcct ccggaaattg gcattgcgat tccacatggc tgggcgacag agtcatcacc     60
accagcaccc gaacctgggc cctgccaacc tacaacaacc acctctacaa acaaatctcc    120
agcgcttcaa cggggccag caacgacaac cactactttg gctacagcac ccctgggg      180
```

```
tattttgact ttaacagatt ccactgccac ttctcaccac gtgactggca gcgactcatc    240
aacaacaact ggggattc                                                  258

<210> SEQ ID NO 119
<211> LENGTH: 255
<212> TYPE: DNA
<213> ORGANISM: Unknown
<220> FEATURE:
<223> OTHER INFORMATION: adeno-associated virus serotype 12

<400> SEQUENCE: 119
ggtaattcct ccggaaattg gcattgcgat tccacatggc tgggcgaccg agtcattacc     60
accagcaccc ggacttgggc cctgcccacc tacaacaacc acctctacaa gcaaatctcc    120
agccaatcgg gtgccaccaa cgacaaccac tacttcggct acagcacccc ttggggtat    180 tttgatttca acagattcca ctgccatttc tcaccacgtg actggcagcg actcatcaac    240
aacaactggg gattc                                                    255

<210> SEQ ID NO 120
<211> LENGTH: 2205
<212> TYPE: DNA
<213> ORGANISM: Unknown
<220> FEATURE:
<223> OTHER INFORMATION: adeno-associated virus serotype, clone A3.1vp1

<400> SEQUENCE: 120
atggctgccg atggttatct tccagattgg ctcgaggaca ctctctctga aggaatcaga     60
cagtggtgga agctcaaacc tggcccacca ccgccgaaac ctaaccaaca caccgggac    120 gacagtaggg gtcttgtgct tcctgggtac aagtacctcg acccttcaa cggactcgac    180 aaaggagagc cggtcaacga ggcagacgcc gcggccctcg agcacgacaa agcctacgac    240
caccagctca gcaagggga caacccgtac ctcaaataca accacgcgga cgctgaattt    300
caggagcgtc ttcaagaaga tacgtctttc ggggggcaacc tcgggcgagc agtcttccag    360
gccaaaaaga gggtactcga gcctcttggt ctggttgagg aagctgttaa gacggctcct    420
ggaaaaaaga gacctataga gcagtctcct gcagaaccgg actcttcctc gggcatcggc    480
aaatcaggcc agcagcccgc taagaaaaga ctcaattttg gtcagactgg cgacacagag    540
tcagtcccag accctcaacc aatcggagaa ccccccgcag cccctctgg tgtgggatct    600 aatacaatgg cttcaggcgg tgggcacca atggcagaca taacgaagg cgccgacgga    660 gtgggtaatt cctcgggaaa ttggcattgc gattccacat ggatgggcga cagagttatc    720
accaccagca aagaacctg gccctcccc acctacaata tcacctcta caagcaaatc    780 tccagcgaat cgggagccac caacgacaac cactacttcg gctacagcac ccctggggg    840 tattttgact ttaacagatt ccactgtcac ttctcaccac gtgactggca gcgactcatc    900
aacaacaact gggattag acccaagaaa ctcaatttca gctcttcaa catccaagtc    960 aaggaggtca cgcagaatga tggaaccacg accatcgcca ataaccttac cagcacggtg   1020
caggtcttca cagactctga gtaccagctg ccctacgtcc tcggttcggc tcaccagggc   1080
tgccttccgc cgttcccagc agacgtcttc atgattcctc agtacggcta cttgactctg   1140
aacaatggca gccaagcgt aggacgttct tcattctact gtctagagta ttttccctct   1200
cagatgctga ggacgggaaa caacttcacc ttcagctaca cttttgaaga cgtgcctttc   1260
cacagcagct acgcgcacag ccagagtctg gatcggctga tgaatcctct cattgaccag   1320
tacctgtatt acctgagcaa aactcagggt acaagtggaa caacgcagca atcgagactg   1380
```

-continued

```
cagttcagcc aagctgggcc tagctccatg gctcagcagg ccaaaaactg gctaccggga    1440
cccagctacc gacagcagcg aatgtctaag acggctaatg acaacaacaa cagtgaattt    1500
gcttggactg cagccaccaa atattacctg aatggaagaa attctctggt caatcccggg    1560
cccccaatgg ccagtcacaa ggacgatgag gaaaagtatt tccccatgca cggaaatctc    1620
atctttggaa aacaaggcac aggaactacc aatgtggaca ttgaatcagt gcttattaca    1680
gacgaagaag aaatcagaac aactaatcct gtggctacag aacaatacgg acaggttgcc    1740
accaaccatc agagtcagaa caccacagct tcctatgaa gtgtggacag ccagggaatc     1800
ttacctggaa tggtgtggca ggaccgcgat gtctatcttc aaggtcccat ttgggccaaa    1860
actcctcaca cggacggaca ctttcatcct tctccgctca tgggaggctt tggactgaaa    1920
caccctcctc cccagatcct gatcaaaaac acacctgtgc cagcgaatcc cgcgaccact    1980
ttcactcctg gaaagtttgc ttcgttcatt acccagtatt ccaccggaca ggtcagcgtg    2040
gaaatagagt gggagctgca gaaagaaaac agcaaacgct ggaacccaga aattcagtac    2100
acctccaact acaacaagtc ggtgaatgtg gagtttaccg tggacgcaaa cggtgtttat    2160
tctgaacccc gccctattgg cactcgttac cttacccgga acttg                    2205
```